US009422557B2

(12) United States Patent
Ader et al.

(10) Patent No.: US 9,422,557 B2
(45) Date of Patent: Aug. 23, 2016

(54) METHODS AND COMPOSITIONS FOR WEED CONTROL

(75) Inventors: Daniel Ader, St. Louis, MO (US); Matt W. Dimmic, Wildwood, MO (US); Zhaolong Li, St. Charles, MO (US); Robert Douglas Sammons, Wentzville, MO (US); Ronak Hasmukh Shah, Jamaica, NY (US); Nengbing Tao, O'Fallon, MO (US); Dafu Wang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 794 days.

(21) Appl. No.: 13/612,941

(22) Filed: Sep. 13, 2012

(65) Prior Publication Data

US 2013/0318658 A1      Nov. 28, 2013

Related U.S. Application Data

(60) Provisional application No. 61/534,073, filed on Sep. 13, 2011.

(51) Int. Cl.
| | | |
|---|---|---|
| *C12N 15/113* | (2010.01) | |
| *A01N 57/24* | (2006.01) | |
| *A01N 35/10* | (2006.01) | |
| *A01H 3/04* | (2006.01) | |
| *C12N 9/00* | (2006.01) | |

(Continued)

(52) U.S. Cl.
CPC .............. *C12N 15/1137* (2013.01); *A01H 3/04* (2013.01); *A01N 35/10* (2013.01); *A01N 57/24* (2013.01); *A01N 65/00* (2013.01); *C12N 9/93* (2013.01); *C12N 15/8218* (2013.01); *C12N 15/8247* (2013.01); *C12N 15/8274* (2013.01); *C12Y 604/01002* (2013.01)

(58) Field of Classification Search
CPC .............................. C12N 12/113; A01N 57/24
See application file for complete search history.

(56) References Cited

U.S. PATENT DOCUMENTS

| | | | |
|---|---|---|---|
| 3,687,808 | A | 8/1972 | Merigan et al. |
| 3,791,932 | A | 2/1974 | Schuurs et al. |
| 3,839,153 | A | 10/1974 | Schuurs et al. |

(Continued)

FOREIGN PATENT DOCUMENTS

| | | |
|---|---|---|
| CN | 101279950 A | 10/2008 |
| CN | 101279951 A | 10/2008 |

(Continued)

OTHER PUBLICATIONS

Bourgeois, Luc, Ian N. Morrison, and David Kelner. "Field and producer survey of ACCase resistant wild oat in Manitoba." Canadian journal of plant science 77.4 (1997): 709-715.*

(Continued)

*Primary Examiner* — Russell Kallis
*Assistant Examiner* — Weihua Fan
(74) *Attorney, Agent, or Firm* — Amanda Carmany-Rampey; David R. Marsh; Arnold & Porter LLP

(57) ABSTRACT

The present invention provides novel compositions for use to enhance weed control. Specifically, the present invention provides for methods and compositions that modulate Acetyl-CoA carboxylase in weed species. The present invention also provides for combinations of compositions and methods that enhance weed control.

28 Claims, 1 Drawing Sheet

(51) Int. Cl.
*C12N 15/82* (2006.01)
*A01N 65/00* (2009.01)

(56) References Cited

U.S. PATENT DOCUMENTS

| | | |
|---|---|---|
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,469,863 A | 9/1984 | Ts'o et al. |
| 4,476,301 A | 10/1984 | Imbach et al. |
| 4,535,060 A | 8/1985 | Comai |
| 4,581,847 A | 4/1986 | Hibberd et al. |
| 4,666,828 A | 5/1987 | Gusella |
| 4,683,202 A | 7/1987 | Mullis |
| 4,761,373 A | 8/1988 | Anderson et al. |
| 4,769,061 A | 9/1988 | Comai |
| 4,801,531 A | 1/1989 | Frossard |
| 4,810,648 A | 3/1989 | Stalker |
| 4,879,219 A | 11/1989 | Wands et al. |
| 4,940,835 A | 7/1990 | Shah et al. |
| 4,971,908 A | 11/1990 | Kishore et al. |
| 5,004,863 A | 4/1991 | Umbeck |
| 5,011,771 A | 4/1991 | Bellet et al. |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Haberlein et al. |
| 5,558,071 A | 9/1996 | Ward et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A * | 11/1999 | Sandbrink ............ A01N 25/00 424/405 |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |

(56) References Cited

U.S. PATENT DOCUMENTS

| | | |
|---|---|---|
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,642,435 B1 | 11/2003 | Rafalski et al. |
| 6,644,341 B1 | 11/2003 | Chemo et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2004/0053289 A1 | 3/2004 | Christian et al. |
| 2004/0055041 A1 | 3/2004 | Labate et al. |
| 2004/0072692 A1 | 4/2004 | Hoffmann et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2005/0005319 A1 | 1/2005 | della-Cioppa et al. |
| 2005/0215435 A1 | 9/2005 | Menges et al. |
| 2006/0009358 A1 | 1/2006 | Kibler et al. |
| 2006/0021087 A1 | 1/2006 | Baum et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffmann et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0205079 A1 | 8/2009 | Kumar et al. |
| 2009/0215628 A1 | 8/2009 | Witschel et al. |
| 2009/0293148 A1 | 11/2009 | Ren et al. |
| 2009/0298787 A1 | 12/2009 | Raemaekers et al. |
| 2009/0307803 A1 | 12/2009 | Baum et al. |
| 2010/0005551 A1 | 1/2010 | Roberts et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0100988 A1 | 4/2010 | Tranel et al. |
| 2010/0152443 A1 | 6/2010 | Hirai et al. |
| 2010/0154083 A1 | 6/2010 | Ross et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0028412 A1 | 2/2011 | Cappello et al. |
| 2011/0035836 A1* | 2/2011 | Eudes et al. .................. 800/278 |
| 2011/0053226 A1 | 3/2011 | Rohayem |
| 2011/0098180 A1 | 4/2011 | Michel et al. |
| 2011/0105327 A1 | 5/2011 | Nelson |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |

(56) References Cited

U.S. PATENT DOCUMENTS

| | | |
|---|---|---|
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2012/0230565 A1 | 9/2012 | Steinberg et al. |
| 2012/0258646 A1 | 10/2012 | Sela et al. |
| 2013/0041004 A1 | 2/2013 | Drager et al. |
| 2013/0047297 A1 | 2/2013 | Sammons et al. |
| 2013/0060133 A1 | 3/2013 | Kassab et al. |
| 2013/0067618 A1 | 3/2013 | Ader et al. |
| 2013/0084243 A1 | 4/2013 | Goetsch et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0296503 A1 | 10/2014 | Avniel et al. |

FOREIGN PATENT DOCUMENTS

| | | | | |
|---|---|---|---|---|
| CN | 201010248213 | * | 12/2010 | ............... A01H 5/00 |
| DE | 10000600 A1 | | 7/2001 | |
| DE | 10116399 A1 | | 10/2002 | |
| DE | 10256353 A1 | | 6/2003 | |
| DE | 10256354 A1 | | 6/2003 | |
| DE | 10256367 A1 | | 6/2003 | |
| DE | 10204951 A1 | | 8/2003 | |
| DE | 10234875 A1 | | 2/2004 | |
| DE | 10234876 A1 | | 2/2004 | |
| DE | 102004054666 A1 | | 5/2006 | |
| DE | 102005014638 A1 | | 10/2006 | |
| DE | 102005014906 A1 | | 10/2006 | |
| DE | 102007012168 A1 | | 9/2008 | |
| DE | 102010042866 A1 | | 5/2011 | |
| EP | 0 804 600 A1 | | 11/1997 | |
| EP | 1 157 991 A2 | | 11/2001 | |
| EP | 1 238 586 A1 | | 9/2002 | |
| EP | 1 416 049 A1 | | 5/2004 | |
| EP | 2 147 919 A1 | | 1/2010 | |
| EP | 2 160 098 B1 | | 11/2010 | |
| EP | 2 530 159 A1 | | 3/2011 | |
| EP | 2 305 813 A2 | | 4/2011 | |
| EP | 2 545 182 A1 | | 1/2013 | |
| JP | 2001253874 A | | 9/2001 | |
| JP | 2002080454 A | | 3/2002 | |
| JP | 2002138075 A | | 5/2002 | |
| JP | 2002145707 A | | 5/2002 | |
| JP | 2002220389 A | | 8/2002 | |
| JP | 2003064059 A | | 3/2003 | |
| JP | 2003096059 A | | 4/2003 | |
| JP | 2004051628 A | | 2/2004 | |
| JP | 2004107228 A | | 4/2004 | |
| JP | 2005008583 A | | 1/2005 | |
| JP | 2005239675 A | | 9/2005 | |
| JP | 2005314407 A | | 11/2005 | |
| JP | 2006232824 A | | 9/2006 | |
| JP | 2006282552 A | | 10/2006 | |
| JP | 2007153847 A | | 6/2007 | |
| JP | 2007161701 A | | 6/2007 | |
| JP | 2007182404 A | | 7/2007 | |
| JP | 2008074840 A | | 4/2008 | |
| JP | 2008074841 A | | 4/2008 | |
| JP | 2008133207 A | | 6/2008 | |
| JP | 2008133218 A | | 6/2008 | |
| JP | 2008169121 A | | 7/2008 | |
| JP | 2009067739 A | | 4/2009 | |
| JP | 2009114128 A | | 5/2009 | |
| JP | 2009126792 A | | 6/2009 | |
| JP | 2009137851 A | | 6/2009 | |
| WO | WO 89/11789 A1 | | 12/1989 | |
| WO | WO 95/34659 A1 | | 12/1995 | |
| WO | WO 95/34668 A2 | | 12/1995 | |
| WO | WO 96/05721 A1 | | 2/1996 | |
| WO | WO 96/33270 A1 | | 10/1996 | |
| WO | WO 96/38567 A2 | | 12/1996 | |
| WO | WO 96/40964 A2 | | 12/1996 | |
| WO | WO 99/24585 A1 | | 5/1999 | |
| WO | WO 99/26467 A1 | | 6/1999 | |
| WO | WO 99/27116 A2 | | 6/1999 | |
| WO | WO 99/32619 A1 | | 7/1999 | |
| WO | WO 99/61631 A1 | | 12/1999 | |
| WO | WO 99/67367 | * | 12/1999 | ............... C12N 9/00 |
| WO | WO 00/32757 A2 | | 6/2000 | |
| WO | WO 00/44914 A1 | | 8/2000 | |
| WO | WO 02/14472 A2 | | 2/2002 | |
| WO | WO 02/066660 A2 | | 8/2002 | |
| WO | WO 03/000679 A2 | | 1/2003 | |
| WO | WO 03/006422 A1 | | 1/2003 | |
| WO | WO 03/013247 A1 | | 2/2003 | |
| WO | WO 03/016308 A1 | | 2/2003 | |
| WO | WO 03/020704 A1 | | 3/2003 | |
| WO | WO 03/022051 A1 | | 3/2003 | |
| WO | WO 03/022831 A1 | | 3/2003 | |
| WO | WO 03/022843 A1 | | 3/2003 | |
| WO | WO 03/029243 A2 | | 4/2003 | |
| WO | WO 03/037085 A1 | | 5/2003 | |
| WO | WO 03/037878 A1 | | 5/2003 | |
| WO | WO 03/045878 A2 | | 6/2003 | |
| WO | WO 03/050087 A2 | | 6/2003 | |
| WO | WO 03/051823 A1 | | 6/2003 | |
| WO | WO 03/051824 A1 | | 6/2003 | |
| WO | WO 03/051846 A2 | | 6/2003 | |
| WO | WO 03/076409 A1 | | 9/2003 | |
| WO | WO 03/077648 A1 | | 9/2003 | |
| WO | WO 03/087067 A1 | | 10/2003 | |
| WO | WO 03/090539 A1 | | 11/2003 | |
| WO | WO 03/091217 A1 | | 11/2003 | |
| WO | WO 03/093269 A2 | | 11/2003 | |
| WO | WO 03/104206 A2 | | 12/2003 | |
| WO | WO 2004/002947 A1 | | 1/2004 | |
| WO | WO 2004/002981 A2 | | 1/2004 | |
| WO | WO 2004/005485 A2 | | 1/2004 | |
| WO | WO 2004/009761 A1 | | 1/2004 | |
| WO | WO 2004/011429 A1 | | 2/2004 | |
| WO | WO 2004/022771 A2 | | 3/2004 | |
| WO | WO 2004/029060 A1 | | 4/2004 | |
| WO | WO 2004/035545 A2 | | 4/2004 | |
| WO | WO 2004/035563 A1 | | 4/2004 | |
| WO | WO 2004/035564 A1 | | 4/2004 | |
| WO | WO 2004/037787 A1 | | 5/2004 | |
| WO | WO 2004/049806 A1 | | 6/2004 | |
| WO | WO 2004/062351 A2 | | 7/2004 | |
| WO | WO 2004/067518 A1 | | 8/2004 | |
| WO | WO 2004/067527 A1 | | 8/2004 | |
| WO | WO 2004/074443 A2 | | 9/2004 | |
| WO | WO 2004/077950 A1 | | 9/2004 | |
| WO | WO 2005/000824 A1 | | 1/2005 | |
| WO | WO 2005/003362 A1 | | 1/2005 | |
| WO | WO 2005/007627 A1 | | 1/2005 | |
| WO | WO 2005/040152 A1 | | 5/2005 | |
| WO | WO 2005/047233 A1 | | 5/2005 | |
| WO | WO 2005/047281 A1 | | 5/2005 | |
| WO | WO 2005/061443 A2 | | 7/2005 | |
| WO | WO 2005/061464 A1 | | 7/2005 | |
| WO | WO 2005/068434 A1 | | 7/2005 | |

(56) References Cited

FOREIGN PATENT DOCUMENTS

| | | |
|---|---|---|
| WO | WO 2005/070889 A1 | 8/2005 |
| WO | WO 2005/089551 A1 | 9/2005 |
| WO | WO 2005/095335 A1 | 10/2005 |
| WO | WO 2005/107437 A2 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/039454 A1 | 4/2007 |
| WO | WO 2007/070389 A2 | 6/2007 |
| WO | WO 2007/071900 A1 | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/096576 A1 | 8/2007 |
| WO | WO 2007/051462 A2 | 10/2007 |
| WO | WO 2007/119434 A1 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/042231 A2 | 4/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/046384 A1 | 4/2009 |
| WO | WO 2009/063180 A1 | 5/2009 |
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/045796 A1 | 4/2011 |
| WO | WO 2011/065451 A1 | 6/2011 |
| WO | WO 2011/067745 A2 | 6/2011 |
| WO | WO 2011/080674 A2 | 7/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/153553 A2 | 10/2013 |
| WO | WO 2013/175480 A1 | 11/2013 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |
| WO | WO 2015/010026 A2 | 1/2015 |

OTHER PUBLICATIONS

Street, 2008, http://biochemistryrevisited.blogspot.com/2008/01/why-is-dna-and-not-rna-stable-storage.html#!/2008/01/why-is-dna-and-not-rna-stable-storage.html.*

Tank mixing benefit, NCSU, 2004, published online at http://www.ncagr.gov/agronomi/pdffiles/Tank_Mixing.pdf.*

Shintani, D., et al. "Antisense expression and overexpression of biotin carboxylase in tobacco leaves." Plant physiology 114.3 (1997): 881-886.*

Kaloumenos NS, Eleftherohorinos IG, 2009, Identification of a johnsongrass (*Sorghum halepense*) biotype resistant to ACCase inhibiting herbicides in northern Greece. Weed Technol 23:470-476.*

Tank Mixing Chemicals Applied to Peanut Crops, published online on Jul. 31, 2004 at www.peanut.ncsu.edu/pdffiles/004993/tank_mixing_chemicals_applied_to_peanut_crops.pdf.*

Alarcón-Reverte et al., "Resistance to ACCase-inhibiting herbicides in the weed *Lolium multiflorum*," Comm. Appl. Biol. Sci., 73(4):899-902 (2008).

Amarzguioui et al., "An algorithm for selection of functional siRNA sequences," Biochemical and Biophysical Research Communications, 316:1050-1058 (2004).

Ambrus et al., "The Diverse Roles of RNA Helicases in RNAi," Cell Cycle, 8(21):3500-3505 (2009).

An et al., "Transient RNAi Induction against Endogenous Genes in *Arabidopsis* Protoplasts Using in Vitro-Prepared Double-Stranded RNA," Biosci Biotechnol Biochem, 69(2):415-418 (2005).

Andersson et al., "A novel selection system for potato transformation using a mutated AHAS gene," Plant Cell Reports, 22(4):261-267 (2003).

Anonymous, "A handbook for high-level expression and purification of 6xHis-tagged proteins," The QIAexpressionist, (2003).

Anonymous, "Agronomy Facts 37: Adjuvants for enhancing herbicide performance," n.p., 1-8, (Jan. 26, 2000), Web, (Jan. 21, 2014).

Anonymous, "Devgen, The mini-Monsanto," KBC Securities (2006).

Anonymous, "Do Monsanto have the next big thing?," Australian Herbicide Resistance Initiative (AHRI), (Apr. 23, 2013) Web. (Jan. 19, 2015).

(56) References Cited

OTHER PUBLICATIONS

Aoki et al., "In Vivo Transfer Efficiency of Antisense Oligonucleotides into the Myocardium Using HVJ-Liposome Method," *Biochem Biophys Res Commun*, 231:540-545 (1997).
Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmymovich, "Using RNA interference to increase crop yield and decrease pest damage," *MMG 445 Basic Biotech.*, 5(1):7-12 (2009).
Australian Patent Examination report No. 1 issued Nov. 11, 2013, in Australian Application No. 2011224570.
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bannerjee et al., "Efficient production of transgenic potato (*S. tuberosum* L. ssp. *andigena*) plants via *Agrobacterium tumefaciens*-mediated transformation," *Plant Sci.*, 170:732 738 (2006).
Baulcombe, "RNA silencing and heritable epigenetic effects in tomato and Arabidopsis," Abstract 13th Annual Fall Symposium, Plant Genomes to Phenomes, Donald Danforth Plant Science Center, 28-30 (2011).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Breaker et al., "A DNA enzyme with Mg2-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Busi et al., "Gene flow increases the initial frequency of herbicide resistance alleles in unselectedpopulations," *Agriculture, Ecosystems and Environments*, Elsevier, Amsterdam, NL, 142(3):403-409 (2011).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chee et al., "Transformation of Soybean (*Glycine max*) by Infecting Germinating Seeds with *Agrobacterium tumefaciens*," *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 50S Ribosomal Subunits of *Arabidopsis* Chloroplasts," *Plant Physiology*, 158:693-707 (2012).
Chinese Office Action issued Aug. 28, 2013 in Chinese Application No. 201180012795.2.
Clough et al., "Floral dip: a simplified method for Agrobacterium-mediated transformation of *Arabidopsis thaliana*," *The Plant Journal*, 16(6):735-743 (1998).
CN101914540 Patent Diclosure, "Introduction of RNA into plant by interference," (2010).
Colbourne et al., "The Ecoresponsive Genome of Daphnia pulex," *Science*, 331(6017):555-561 (2011).
Colombian Office Action issued Aug. 2, 2013 in Application No. 12 152898.
Colombian Office Action issued Feb. 21, 2014 in Application No. 12 152898.
Cooney et al., "Site-Specific Oligonucleotide Binding Represses Transcription of the Human c-myc Gene in Vitro," *Science*, 241:456-459 (1988).
COST Action FA0806 progress report "Plant virus control employing RNA-based vaccines: A novel non-transgenic strategy" (2010).
Coticchia et al., "Calmodulin modulates Akt activity in human breast cancer cell lines," *Breast Cancer Res. Treat*, 115:545-560 (2009).
Dalmay et al., "An RNA-Depenedent RNA Polymerase Gene in *Arabidopsis* is Required for Posttranscriptional Gene Silencing Mediated by a Transgene but Not by a Virus," *Cell*, 101:543-553 (2000).
Database EMBL CBIB Daphnia—XP-002732239 (2011).
Davidson et al., "Engineering regulatory RNAs," *TRENDS in Biotechnology*, 23(3):109-112 (2005).
De Block, et al. "Engineering herbicide resistance in plants by expression of a detoxifying enzyme," *EMBO J.* 6(9):2513-2519 (1987).
De Framond, "MIMI-Ti: A New Vector Strategy for Plant Genetic Engineering," *Nature Biotechnology*, 1:262-269 (1983).
della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Dietemann et al., "*Varroa destructor*: research avenues towards sustainable control," *Journal of Apicultural Research*, 51(1):125-132 (2012).
Du et al., "A systematic analysis of the silencing effects of an active siRNA at all single-nucleotide mismatched target sites," *Nucleic Acids Research*, 33(5):1671-1677 (2005).
Dunoyer et al., "Small RNA Duplexes Function as Mobile Silencing Signals Between Plant Cells," *Science*, 328:912-916 (2010).
Ellington et al., "In vitro selection of RNA molecules that bind specific ligands," *Nature*, 346:818-822 (1990).
Eurasian Office Action issued Feb. 24, 2014, in Application No. 201201264.
European Cooperation in the field of Scientific and Technical Research—Memorandum of Understanding for COST Action FA0806 (2008).
European Supplemental Search Report issued Oct. 8, 2013 in Application No. 11753916.3.
Extended European Search Report dated Jan. 21, 2015, in European Patent Application No. 12 832 415.9.
Extended European Search Report dated Jan. 29, 2015, in European Patent Application No. 12 831 567.8.
Extended European Search Report dated Feb. 2, 2015, in European Patent Application No. 12 830 932.5.
Extended European Search Report dated Feb. 3, 2015, in European Patent Application No. 12 831 945.6.
Extended European Search Report dated Feb. 27, 2015, in European Patent Application No. 12 832 160.1.

(56) References Cited

OTHER PUBLICATIONS

Extended European Search Report dated Mar. 3, 2015, in European Patent Application No. 12 831 166.9.
Extended European Search Report dated Mar. 17, 2015, in European Patent Application No. 12 831 684.1.
Partial Supplementary European Search Report dated Mar. 2, 2015, in European Patent Application No. 12 831 494.5.
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
First Examination Report issued on Apr. 23, 2013, in New Zealand Patent Application No. 601784.
First Examination Report issued on Jul. 28, 2014, in New Zealand Patent Application No. 627060.
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Further Examination Report issued in New Zealand Patent Application No. 601784 on May 16, 2014.
Gaines et al., "Gene amplification confers glyphosate resistance in *Amaranthus palmeri*," *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Gan et al., "Bacterially expressed dsRNA protects maize against SCMV infection," *Plant Cell Rep*, 11:1261-1268 (2010).
Gao et al., "Down-regulation of acetolactate synthase compromises 01-1-mediated resistance to powdery mildew in tomato," *BMC Plant Biology*, 14 (2014).
Garbian et al., "Bidirectional Transfer of RNAi between Honey Bee and *Varroa destructor*: *Varroa* Gene Silencing Reduces *Varroa* Population," 8(12):1-9:e1003035 (2012).
Ge et al., "Rapid vacuolar sequestration: the horseweed glyphosate resistance mechanism," *Pest Management Sci.*, 66:345-348 (2010).
GenBank Accession No. DY640489, PU2_plate27J03 PU2 Prunus persica cDNA similar to expressed mRNA inferred from Prunus persica hypothetical domain/motif containing IPRO11005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
GenBank accession No. AY545657.1, published 2004.
GenBank accession No. GI:186478573, published Jan. 22, 2014.
GenEmbl FJ861243, published Feb. 3, 2010.
Gong et al., "Silencing of Rieske iron—sulfur protein using chemically synthesised siRNA as a potential biopesticide against Plutella xylostella," *Pest Manag Sci*, 67:514-520 (2011).
Gressel et al., "A strategy to provide long-term control of weedy rice while mitigating herbicide resistance transgene flow, and its potential use for other crops with related weeds," *Pest Manag Sci*, 65(7):723-731 (2009).
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hannon, "RNA interference," *Nature*,481:244-251 (2002).
Hardegree, "Drying and storage effects on germination of primed grass seeds," *Journal of Range Management*, 47(3):196-199 (1994).
Harrison et al., "Does Lowering Glutamine Synthetase Activity in Nodules Modigy Nitrogen Metabolism and Growth of *Lotus japonicus*?," *Plant Physiology*, 133:253-262 (2003).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hewezi et al., "Local infiltration of high- and low-molecular-weight RNA from silenced sunflower (*Helianthus annuus* L.) plants triggers post-transcriptional gene silencing in non-silenced plants," *Plant Biotechnology Journal*, 3:81-89 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).
Himber et al., "Transitivity-dependant and -independent cell-to-cell movement of RNA silencing," *The EMBO Journal*, 22(17):4523-4533 (2003).
Hirschberg et al., "Molecular Basis of Herbicide Resistance in *Amaranthus hybridus*," *Science*, 222:1346-1349 (1983).
Hoekema et al., "A binary plant vector strategy based on separation of *vir*- and T-region of the *Agrobacterium tumefaciens* Ti-plasmid," *Nature*, 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.*, 107(2):469-477 (1995).
Hsieh et al., "A library of siRNA duplexes targeting the phosphoinositide 3-kinase pathway: determinants of gene silencing for use in cell-based screens," *Nucleic Acids Res.*, 32(3):893-901 (2004).
Huesken et al., "Design of a genome-wide siRNA library using an artificial neural network," *Nature Biotechnology*, 23(8): 995-1001 (2005).
Hunter et al., "RNA Interference Strategy to suppress Psyllids & Leafhoppers," *International Plant and Animal Genome XIX*, 15-19 (2011).
Ichihara et al., "Thermodynamic instability of siRNA duplex is a prerequisite for dependable prediction of siRNA activities," *Nucleic Acids Res.*, 35(18):e123 (2007).
International Preliminary Report on Patentability issued on Sep. 11, 2014, in International Application No. PCT/IL13/50447.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
International Search Report and the Written Opinion dated Oct. 1, 2013, in International Application No. PCT/IL2013/050447.
International Search Report and the Written Opinion dated Jul. 15, 2014, in International Application No. PCT/US2014/025305.

(56) References Cited

OTHER PUBLICATIONS

International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Feb. 23, 2015, in International Application No. PCT/US2014/063832.
International Search Report dated Mar. 12, 2013, in International Application No. PCT/US 12/54789.
Invitation to Pay Additional Fees dated May 6, 2014, in International Application No. PCT/IL2013/051083.
Invitation to Pay Additional Fees dated May 6, 2014, in International Application No. PCT/IL2013/051085.
Invitation to Pay Additional Fees dated Nov. 25, 2014, in International Application No. PCT/US2014/047204.
Isaacs et al., "Engineered riboregulators enable post-transcriptional control of gene expression," *Nature Biotechnology*, 22(7):841-847 (2004).
Ji et al., "Regulation of small RNA stability: methylation and beyond," *Cell Research*, 22:624-636 (2012).
Jones-Rhoades et al., "MicroRNAs and Their Regulatory Roles in Plants," *Annu. Rev. Plant Biol.*, 57:19-53 (2006).
Josse et al., "A DELLA in Disguise: SPATULA Restrains the Growth of the Developing *Arabidopsis* Seedling," *Plant Cell*, 23:1337-1351 (2011).
Kam et al., "Nanotube Molecular Transporters: Internalization of Carbon Nanotube—Protein Conjugates into Mammalian Cells," *J. Am. Chem. Soc.*, 126(22):6850-6851 (2004).
Katoh et al., "Specific residues at every third position of siRNA shape its efficient RNAi activity," *Nucleic Acids Res.*, 35(4): e27 (2007).
Kertbundit et al., "In vivo random β-glucuronidase gene fusions in *Arabidopsis thaliana*," *Proc. Natl. Acad. Sci. USA.*, 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes Are Able to Penetrate Plant Seed Coat and Dramatically Affect Seed Germination and Plant Growth," *ACS Nano*, 3(10):3221-3227 (2009).
Kirkwood, "Use and Mode of Action of Adjuvants for Herbicides: A Review of some Current Work," *Pestic Sci.*, 38:93-102 (1993).
Klahre et al., "High molecular weight RNAs and small interfering RNAs induce systemic posttranscriptional gene silencing in plants," *Proc. Natl. Acad. Sci. USA*, *PNAS*, 99(18):11981-11986 (2002).
Kronenwett et al., "Oligodeoxyribonucleotide Uptake in Primary Human Hematopoietic Cells is Enhanced by Cationic Lipids and Depends on the Hematopoietic Cell Subset," *Blood*, 91(3):852-862 (1998).
Kumar et al., "Sequencing, De Novo Assembly and Annotation of the Colorado Potato Beetle, *Leptinotarsa decemlineata*, Transcriptome," *PLoS One*, 9(1):e86012 (2014).
Kusaba et al., "*Low glutelin content1*: A Dominant Mutation That Suppresses the *Glutelin* Multigene Family via RNA Silencing ni Rice," *The Plant Cell*, 15(6):1455-1467 (2003).
Kusaba, "RNA interference in crop plants," *Curr Opin Biotechnol*, 15(2):139-143 (2004).
Lavigne et al., "Enhanced antisense inhibition of human immunodeficiency virus type 1 in cell cultures by DLS delivery system," *Biochem Biophys Res Commun*, 237:566-571 (1997).
Lee et al., "Aptamer Database," *Nucleic Acids Research*, 32:D95-D100 (2004).

Lermontova et al., "Reduced activity of plastid protoporphyrinogen oxidase causes attenuated photodynamic damage during high-light compared to low-light exposure," *The Plant Journal*, 48(4):499-510 (2006).
Lesnik et al., "Prediction of rho-independent transcriptional terminators in *Escherichia coli*," *Nucleic Acids Research*, 29(17):3583-3594 (2001).
Li et al., "Establishment of a highly efficient Transformation system for pepper (*Capsicum annuum* L.)," *Plant Cell Reports*, 21: 785-788 (2003).
Li et al., "The FAST technique: a simplified Agrobacterium-based transformation method for transient gene expression analysis in seedlings of Arabidopsis and other plant species," *Plant Methods*, 5(6):1-15 (2009).
Liu et al., "Carbon Nanotubes as Molecular Transporters for Walled Plant Cells," *Nano Letters*, 9(3):1007-1010 (2009).
Liu et al., "Comparative study on the interaction of DNA with three different kinds of surfactants and the formation of multilayer films," *Bioelectrochemistry*, 70:301-307 (2007).
Liu et al., "DNAzyme-mediated recovery of small recombinant RNAs from a 5S rRNA-derived chimera expressed in *Escherichia coli*," *BMC Biotechnology*, 10:85 (2010).
Llave et al., "Endogenous and Silencing-Associated Small RNAs in Plants," *The Plant Cell*, 14:1605-1619 (2002).
Lu et al., "RNA silencing in plants by the expression of siRNA duplexes," *Nucleic Acids Res.*, 32(21):e171 (2004).
Lu et al., "OligoWalk: an online siRNA design tool utilizing hybridization thermodynamics," *Nucleic Acids Research*, 36:W104-W108 (2008).
Luft, "Making sense out of antisense oligodeoxynucleotide delivery: getting there is half the fun," *J Mol Med*, 76:75-76 (1998).
Maas et al., "Mechanism and optimized conditions for PEG mediated DNA transfection into plant protoplasts," *Plant Cell Reports*, 8:148-149 (1989).
Maher III et al., "Inhibition of DNA binding proteins by oligonucleotide-directed triple helix formation," *Science*, 245(4919):725-730 (1989).
Makkouk et al., "Virus Diseases of Peas, Beans, and Faba Bean in the Mediterranean region," *Adv Virus Res*, 84:367-402 (2012).
Mandal et al., "Adenine riboswitches and gene activation by disruption of a transcription terminator," *Nature Struct. Mol. Biol.*, 11(1):29-35 (2004).
Mandal et al., "Gene Regulation by Riboswitches," *Nature Reviews | Molecular Cell Biology*, 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development*, 12:103-128 (2002).
Masoud et al., "Constitutive expression of an inducible β-1,3-glucanase in alfalfa reduces disease severity caused by the oomycete pathogen *Phytophthora megasperma* f. sp *medicaginis*, but does not reduce disease severity of chitincontaining fungi," *Transgenic Research*, 5:313-323 (1996).
Matveeva et al., "Prediction of antisense oligonucleotide efficacy by in vitro methods," *Nature Biotechnology*, 16:1374-1375 (1998).
Meinke, et al., "Identifying essential genes in *Arabidopsis thaliana*," *Trends Plant Sci.*, 13(9):483-491 (2008).
Meins et al., "RNA Silencing Systems and Their Relevance to Plant Development," *Annu. Rev. Cell Dev. Biol.*, 21:297-318 (2005).
Melnyk et al., "Intercellular and systemic movement of RNA silencing signals," *The EMBO Journal*, 30:3553-3563 (2011).
Misawa et al., "Functional expression of the *Erwinia uredovora* carotenoid biosynthesis gene *crtI* in transgenic plants showing an increase of β-carotene biosynthesis activity and resistance to the bleaching herbicide norflurazon," *The Plant Journal*, 4(5):833-840 (1993).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).

(56) References Cited

OTHER PUBLICATIONS

Molnar et al., "Plant Virus-Derived Small Interfering RNAs Originate redominantly from Highly Structured Single-Stranded Viral RNAs," *Journal of Virology*, 79(12):7812-7818 (2005).
Molnar et al., "Small Silencing RNAs in Plants Are Mobile and Direct Epigenetic Modification in Recipient Cells," *Science*, 328:872-875 (2010).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence- Specific Cleavage of Double Helical DNA by Triple Helix Formation," *Science*, 238:645-646 (1987).
Nowak et al., "A new and efficient method for inhibition of RNA viruses by DNA interference," *The FEBS Journal*, 276:4372-4380 (2009).
Office Action dated Feb. 17, 2014, in Mexican Patent Application No. Mx/a/2012/010479.
Office Action issued on Jan. 6, 2015, in Japanese Patent Application No. 2012-557165.
Office Action issued on Nov. 19, 2014, in Eurasian Patent Application No. 201201264/28.
Office Action issued on Nov. 3, 2014, in Chinese Patent Application No. 201180012795.2.
Ongvarrasopone et al., "A Simple and Cost Effective Method to Generate dsRNA for RNAi Studies in Invertebrates," *Science Asia*, 33:35-39 (2007).
Ouellet et al., "Members of the Acetohydroxyacid Synthase Muligene Family of Brassica Napus Have Divergent Patterns of Expression," *The Plant Journal*, Blackwell Scientific Publications, Oxford, GB, 2(3):321-330 (1992).
Paddison et al., "Stable suppression of gene expression by RNAi in mammalian cells," *Proc. Natl Acad. Sci. USA*, 99(3):1443-1448 (2002).
Palauqui et al., "Activation of systemic acquired silencing by localised introduction of DNA," *Current Biology*, 9:59-66 (1999).
Parera et al., "Dehydration Rate after Solid Matrix Priming Alters Seed Performance of Shrunken-2 Corn," *J. Amer. Soc. Hort. Sci.*, 119(3):629-635 (1994).
Paungfoo-Lonhienne et al., "DNA is Taken up by Root Hairs and Pollen, and Stimulates Root and Pollen Tube Growth," *Plant Physiology*, 153:799-805 (2010).
Paungfoo-Lonhienne et al., "DNA uptake by Arabidopsis induces changes in the expression of CLE peptides which control root morphology," *Plant Signaling & Behavior*, 5(9):1112-1114 (2010).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochem. Physiol.*, 84(3):227-235 (2006).
Qiwei," Advance in DNA interference," *Progress in Veterinary Medicine*, 30(1):71-75 (2009).
Rajur et al., "Covalent Protein Oligonucleotide Conjugates for Efficient Delivery of Antisense Molecules," *Bioconjug Chem.*, 8:935-940 (1997).
Reddy et al "Organosilicone Adjuvants Increased the Efficacy of Glyphosate for Control of Weeds in Citrus (*Citrus* spp.)" *HortScience* 27(9):1003-1005 (1992).

Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Ryabov et al., "Cell-to-Cell, but Not Long-Distance, Spread of RNA Silencing That is Induced in Individual Epidermal Cells," *Journal of Virology*, 78(6):3149-3154 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. *Columbia*," Nucleic Acids Research, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Second Chinese Office Action issued in Chinese Patent Application No. 201180012795.2, dated Jun. 10, 2014.
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *Aggregatum*) and carrot (*Daucus carota*)," *Journal of Agricultural Technology*, 7(3):857-867 (2011).
Sharma et al., "A simple and efficient *Agrobacterium*-mediated procedure for transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Silwet L-77 Spray Adjuvant for agricultural applications, product description from Momentive Performance Materials, Inc. (2003).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Stock et al., "Possible Mechanisms for Surfactant-Induced Foliar Uptake of Agrochemicals," *Pestic. Sci.*, 38:165-177 (1993).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "Antisense oligodeoxynucleotide inhibition as a potent strategy in plant biology: identification of SUSIBA2 as a transcriptional activator in plant sugar signalling," *The Plant Journal*, 44:128-138 (2005).
Sun et al., "A Highly efficient Transformation Protocol for Micro-Tom, a Model Cultivar for Tomato Functional Genomics," *Plant Cell Physiol.*, 47(3):426-431 (2006).
Sun et al., "Sweet delivery—sugar translocators as ports of entry for antisense oligodeoxynucleotides in plant cells," *The Plant Journal*, 52:1192-1198 (2007).
Takasaki et al., "An Effective Method for Selecting siRNA Target Sequences in Mammalian Cells," *Cell Cycle*, 3:790-795 (2004).
Temple et al., "Can glutamine synthetase activity levels be modulated in transgenic plants by the use of recombinant DNA technology?" *Transgenic Plants and Plant Biochemistry*, 22:915-920 (1994).

(56) References Cited

OTHER PUBLICATIONS

Temple et al., "Down-regulation of specific members of the glutamine synthetase gene family in Alfalfa by antisense RNA technology," *Plant Molecular Biology*, 37:535-547 (1998).
Templeton et al., "Improved DNA: liposome complexes for increased systemic delivery and gene expression," *Nature Biotechnology*, 15:647-652 (1997).
Tenllado et al., "Crude extracts of bacterially expressed dsRNA can be used to protect plants against virus infection," *BMC Biotechnology*, 3(3):1-11 (2003).
Tenllado et al., "RNA interference as a new biotechnological tool for the control of virus diseases in plants," *Virus Research*, 102:85-96 (2004).
Tepfer, "Risk assessment of virus resistant transgenic plants," *Annual Review of Phytopathology*, 40:467-491 (2002).
The Seed Biology Place, Website Gerhard Leubner Lab Royal Holloway, University of London, <http://www.seedbiology.de/seedtechnology.asp.
Third Party Submission filed on Nov. 29, 2012 in U.S. Appl. No. 13/042,856.
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.* ;573(1-3):127-134 (2004).
Turina et al., "Tospoviruses in the Mediterranean Area," *Advances in Virus Research*, 84:403-437 (2012).
Tuschl, "RNA Interference and Small Interfering RNAs," *ChemBiochem.* 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of *OsDCL2* in Rice Negatively Affects Maintenance of the Endogenous dsRNA Virus, *Oryza sativa* Endornavirus," *Plant and Cell Physiology*, 51(1):58-67 (2010).
van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Vionnet et al., "Systemic Spread of Sequence-Specific Transgene RNA Degradation in Plants is Initiated by Localized Introduction of Ectopic Promoterless DNA," *Cell*, 95:177-187 (1998).

Wakelin et al., "A target-site mutation is present in a glyphosate-resistant *Lolium rigidum* population," *Weed Res. (Oxford)*, 46(5):432-440 (2006).
Walton et al., "Prediction of antisense oligonucleotide binding affinity to a structured RNA target," *Biotechnol Bioeng* 65(1):1-9 (1999).
Wan et al., "Generation of Large Numbers of Independently Transformed Fertile Barley Plants," *Plant Physiol.*, 104:37-48 (1994).
Wardell, "Floral Induction of Vegetative Plants Supplied a Purified Fraction of Deoxyribonucleic Acid from Stems of Flowering Plants," Plant Physiol, 60:885-891 (1977).
Wardell,"Floral Activity in Solutions of Deoxyribonucleic Acid Extracted from Tobacco Stems," *Plant Physiol*, 57:855-861 (1976).
Waterhouse et al., "Virus resistance and gene silencing in plants can be induced by simultaneous expression of sense and antisense RNA," *Proc Natl Acad Sci USA*, 95 13959-13964 (1998).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion dated Sep. 1, 2014, in Singapore Patent Application No. 201206152-9.
Xu et al., Characterization and Functional Analysis of the Calmodulin-Binding Domain of Rac1 GTPase, *Plos One*, 7(8)1-12:e42975 (2012).
Yin et al., "Production of double-stranded RNA for interference with TMV infection utilizing a bacterial prokaryotic expression system," *Appl. Microbiol. Biotechnol.*, 84(2):323-333 (2009).
YouTube video by General Electric Company "Silwet Surfactants," screen shot taken on Jan. 11, 2012 of video of www.youtube.com/watch?v=WBw7nXIMqHk8 (uploaded Jul. 13, 2009).
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "A novel rice gene, NRR responds to macronutrient deficiency and regulates root growth," *Mol Plant*, 5(1):63-72 (2012).
Zhang et al., "*Agrobacterium*-mediated transformation of *Arabidopsis thaliana* using the floral dip method," *Nature Protocols*, 1(2):1-6 (2006).
Zhang et al., "Cationic lipids and polymers mediated vectors for delivery of siRNA," *Journal of Controlled Release*, 123:1-10 (2007).
Zhang et al., "DEG: a database of essential genes," *Nucleic Acids Res.*, 32:D271-D272 (2004).
Zhang et al., "Transgenic rice plants produced by electroporation-mediated plasmid uptake into protoplasts," *The Plant Cell Rep.*, 7:379-384 (1988).
Zhao et al.,"*Phyllotreta striolata* (Coleoptera: Chrysomelidae):Arginine kinase cloning and RNAi-based pest control," *European Journal of Entomology*, 105(5):815-822 (2008).
Zhu et al., "Ingested RNA interference for managing the populations of the Colorado potato beetle, *Leptinotarsa decemlineata*," *Pest Manag Sci*, 67:175-182 (2010).
Agrios, *Plant Pathology* (Second Edition), 2:466-470 (1978).
Bai et al., "Naturally Occurring Broad-Spectrum Powdery Mildew Resistance in a Central American Tomato Accession is Caused by Loss of Mlo Function," *MPMI*, 21(I):30-39 (2008).
Brugière et al., "Glutamine Synthetase in the Phloem Plays a Major Role in Controlling Proline Production," *The Plant Cell*, 11:1995-2011 (1999).

(56) References Cited

OTHER PUBLICATIONS

Campbell et al., "Gene-knockdown in the honey bee mite *Varroa destructor* by a non-invasive approach: studies on a glutathione S-transferase," *Parasites & Vectors*, 3(1):73, pp. 1-10 (2010).
Chang et al., "Cellular Internalization of Fluorescent Proteins via Arginine-rich Intracellular Delivery Peptide in Plant Cells," *Plant Cell Physiol.*, 46(3):482-488 (2005).
Chupp et al., "Chapter 8: White Rust," *Vegetable Diseases and Their Control*, The Ronald Press Company, New York, pp. 267-269 (1960).
Communication pursuant to Article 94(3) EPC dated Jun. 26, 2015, as received in European Patent Application No. 11 753 916.3.
Desai et al., "Reduction in deformed wing virus infection in larval and adult honey bees (*Apis mellifera* L.) by double-stranded RNA ingestion," *Insect Molecular Biology*, 21(4):446-455 (2012).
Emery et al., "Radial Patterning of *Arabidopsis* Shoots by Class III HD-ZIP and KANADI Genes," *Current Biology*, 13:1768-1774 (2003).
Extended European Search Report dated Jun. 29, 2015, in European Patent Application No. 12 831 494.5.
Final Office Action dated Nov. 7, 2013, in U.S. Appl. No. 13/042,856.
First Office Action issued May 27, 2015, in Chinese Patent Application No. 201280054179.8.
International Preliminary Report on Patentability (Chapter II) mailed Jul. 24, 2015, in International Application No. PCT/US2014/047204.
International Search Report and Written Opinion mailed Jul. 8, 2015, in International Application No. PCT/US2015/011408.
International Search Report and Written Opinion mailed Mar. 26, 2015, in International Application No. PCT/US2014/069353.
Jofre-Garfias et al., "*Agrobacterium*-mediated transformation of *Amaranthus hypochondriacus*: light- and tissue-specific expression of a pea chlorophyll a/b-binding protein promoter," Plant Cell Reports, 16:847-852 (1997).
Khan et al., "Matriconditioning of Vegetable Seeds to Improve Stand Establishment in Early Field Plantings," *J. Amer. Soc. Hort. Sci.*, 117(1):41-47 (1992).
Kim et al., "Synthetic dsRNA Dicer substrates enhance RNAi potency and efficacy," *Nature Biotechnology*, 23(2):222-226 (2005).
Leopold et al., "Chapter 4: Moisture as a Regulator of Physiological Reaction in Seeds," *Seed Moisture, CSSA Special Publication No. 14*, pp. 51-69 (1989).
MacKenzie et al., "Transgenic *Nicotiana debneyii* expressing viral coat protein are resistant to potato virus S infection," *Journal of General Virology*, 71:2167-2170 (1990).
Maori et al., "IAPV, a bee-affecting virus associated with Colony Collapse Disorder can be silenced by dsRNA ingestion," *Insect Molecular Biology*, 18(1):55-60 (2009).
Molina et al., "Inhibition of protoporphyrinogen oxidase expression in *Arabidopsis* causes a lesion-mimic phenotype that induces systemic acquired resistance," *The Plant Journal*, 17(6):667-678 (1999).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Mar. 30, 2015, in U.S. Appl. No. 13/583,302.
Non-Final Office Action dated May 15, 2015, in U.S. Appl. No. 14/608,951.
Non-Final Office Action dated May 22, 2015, in U.S. Appl. No. 13/612,985.
Orbović et al., "Foliar-Applied Surfactants and Urea Temporarily Reduce Carbon Assimilation of Grapefruit Leaves," *J. Amer. Soc. Hort. Sci.*, 126(4):486-490 (2001).
Pratt et al., "*Amaranthus rudis* and *A. tuberculatus*, One Species or Two?," *Journal of the Torrey Botanical Society*, 128(3):282-296 (2001).
Restriction Requirement dated Apr. 21, 2015, in U.S. Appl. No. 13/612,954.
Restriction Requirement dated Feb. 12, 2015, in U.S. Appl. No. 13/612,985.
Restriction Requirement dated Mar. 12, 2015, in U.S. Appl. No. 13/612,948.
Restriction Requirement dated May 4, 2015, in U.S. Appl. No. 13/612,929.
Restriction Requirement dated May 5, 2015, in U.S. Appl. No. 13/612,936.
Restriction Requirement dated May 7, 2015, in U.S. Appl. No. 13/612,925.
Restriction Requirement dated May 7, 2015, in U.S. Appl. No. 13/612,995.
Restriction Requirement dated Oct. 2, 2012, in U.S. Appl. No. 13/042,856.
Restriction Requirement dated Oct. 21, 2014, in U.S. Appl. No. 13/583,302.
Riggins et al., "Characterization of de novo transcriptome for waterhemp (*Amaranthus tuberculatus*) using GS-FLX 454 pyrosequencing and its application for studies of herbicide target-site genes," *Pest Manag. Sci.*, 66:1042-1052 (2010).
Rose et al., "Functional polarity is introduced by Dicer processing of short substrate RNAs," *Nucleic Acids Research*, 33(13):4140-4156 (2005).
Rothnie et al., Pararetroviruses and Retroviruses: A Comparative Review of Viral Structure and Gene Expression Strategies, *Advances in Virus Research*, 44:1-67 (1994).
Schweizer et al., "Double-stranded RNA interferes with gene function at the single-cell level in cereals," *The Plant Journal*, 24(6):895-903 (2000).
Senthil-Kumar et al., "A systematic study to determine the extent of gene silencing in *Nicotiana benthamiana* and other *Solanaceae* species when heterologous gene sequences are used for virus-induced gene silencing," *New Phytologist*, 176:782-791 (2007).
Snead et al., "Molecular basis for improved gene silencing by Dicer substrate interfering RNA compared with other siRNA variants," *Nucleic Acids Research*, 41(12):6209-6221 (2013).
Stevens et al., "New Formulation Technology—SILWET® Organosilicone Surfactants Have Physical and Physiological Properties Which Enhance the Performance of Sprays," *Proceedings of the 9th Australian Weeds Conference*, pp. 327-331 (1990).
Sutton et al., "Activity of mesotrione on resistant weeds in maize," *Pest Manag. Sci.*, 58:981-984 (2002).
Taylor, "Seed Storage, Germination and Quality," *The Physiology of Vegetable Crops*, pp. 1-36 (1997).
Tranel et al., "Resistance of weeds to ALS-inhibiting herbicides: what have we learned?," *Weed Science*, 50:700-712 (2002).
Vermeulen et al., "The contributions of dsRNA structure to Dicer specificity and efficiency," *RNA*, 11(5):674-682 (2005).

\* cited by examiner

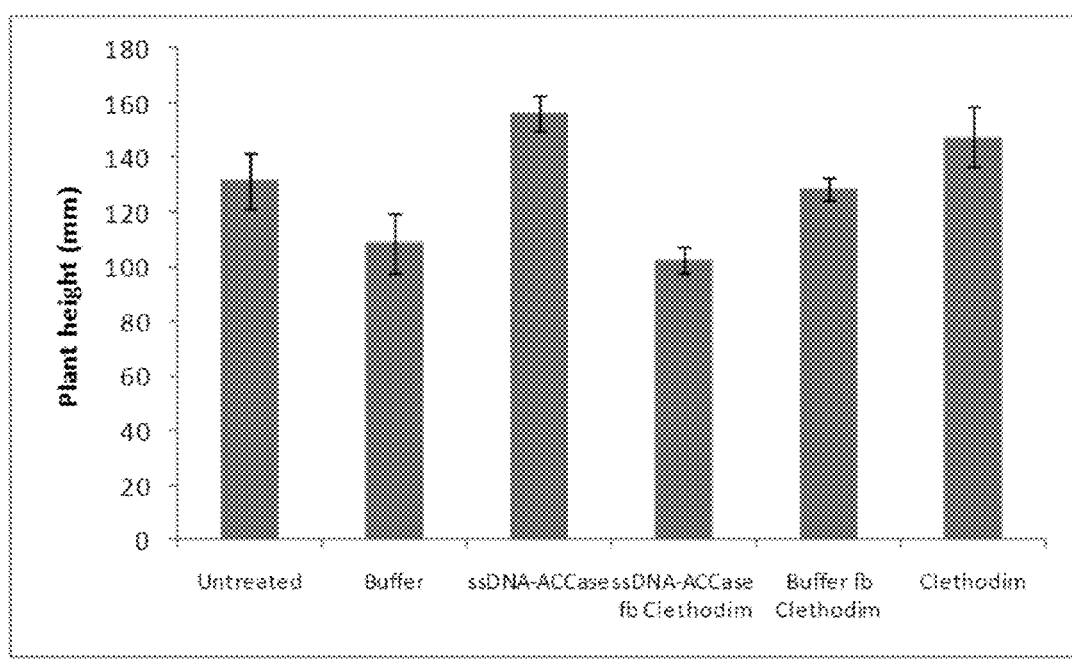

METHODS AND COMPOSITIONS FOR WEED CONTROL

This application claims benefit under 35USC §119(e) of U.S. provisional application Ser. No. 61/534,073 filed Sep. 13, 2011, herein incorporated by reference in it's entirety. The sequence listing that is contained in the file named "40_21(58637)B seq listing.txt", which is 2,094,591 bytes (measured in operating system MS-Windows) and was created on 6 Sep. 2012, is filed herewith and incorporated herein by reference.

FIELD OF THE INVENTION

The invention relates generally to the field of weed management. More specifically, the invention relates to acetyl-CoA carboxylase (ACCase) genes in weedy plants and compositions containing polynucleotide molecules for modulating their expression. The invention further provides methods and compositions useful for weed control.

BACKGROUND OF THE INVENTION

Weeds are plants that compete with cultivated plants in an agronomic environment and cost farmers billions of dollars annually in crop losses and the expense of efforts to keep weeds under control. Weeds also serve as hosts for crop diseases and insect pests. The losses caused by weeds in agricultural production environments include decreases in crop yield, reduced crop quality, increased irrigation costs, increased harvesting costs, reduced land value, injury to livestock, and crop damage from insects and diseases harbored by the weeds. The principal means by which weeds cause these effects are: 1) competing with crop plants for water, nutrients, sunlight and other essentials for growth and development, 2) production of toxic or irritant chemicals that cause human or animal health problem, 3) production of immense quantities of seed or vegetative reproductive parts or both that contaminate agricultural products and perpetuate the species in agricultural lands, and 4) production on agricultural and nonagricultural lands of vast amounts of vegetation that must be disposed of. Herbicide tolerant weeds are a problem with nearly all herbicides in use, there is a need to effectively manage these weeds. There are over 365 weed biotypes currently identified as being herbicide resistant to one or more herbicides by the Herbicide Resistance Action Committee (HRAC), the North American Herbicide Resistance Action Committee (NAHRAC), and the Weed Science Society of America (WSSA).

The Acetyl-CoA carboxylase (ACCase) enzyme catalyzes the biotin-dependent carboxylation of acetyl-CoA to produce malonyl-CoA, this is the first and the committed step in the biosynthesis of long-chain fatty acids. This enzyme is the target of many herbicides that include members of the chemical families of aryloxyphenoxypropionates, cyclohexanediones and phenylpyrazoline.

SUMMARY OF THE INVENTION

In one aspect, the invention provides a method of weedy plant control comprising an external application to a weedy plant of a composition comprising a polynucleotide and a transfer agent, wherein the polynucleotide is essentially identical or essentially complementary to an ACCase gene sequence or fragment thereof, or to the RNA transcript of said ACCase gene sequence or fragment thereof, wherein said ACCase gene sequence is selected from the group consisting of SEQ ID NO:1-92 or a polynucleotide fragment thereof, whereby the weedy plant growth or development or reproductive ability is reduced or the weedy plant is more sensitive to an ACCase inhibitor herbicide relative to a weedy plant not treated with said composition. In this manner, plants that have become resistant to the application of an ACCase inhibitor contanining herbicides may be made more susceptible to the herbicidal effects of an ACCase inhibitor containing herbicide, thus potentiating the effect of the herbicide. The polynucleotide fragment is at least 18 contiguous nucleotides, at least 19 contiguous nucleotides, at least 20 contiguous nucleotides or at least 21 contiguous nucleotides in length and at least 85 percent identical to an ACCase gene sequence selected from the group consisting of SEQ ID NO:1-92 and the transfer agent is an organosilicone composition or compound. The polynucleotide fragment can also be sense or anti-sense ssDNA or ssRNA, dsRNA, or dsDNA, or dsDNA/RNA hybrids. The composition can include more than one polynucleotide fragments, and the composition can include an ACCase inhibitor herbicide and/or other herbicides that enhance the weed control activity of the composition.

In another aspect of the invention, polynucleotide molecules and methods for modulating ACCase gene expression in weedy plant species are provided. The method reduces, represses or otherwise delays expression of an ACCase gene in a weedy plant comprising an external application to a weedy plant of a composition comprising a polynucleotide and a transfer agent, wherein the polynucleotide is essentially identical or essentially complementary to an ACCase gene sequence, represses or otherwise delays, or to the RNA transcript of the ACCase gene sequence, represses or otherwise delays, wherein the ACCase gene sequence is selected from the group consisting of SEQ ID NO:1-92 or a polynucleotide fragment thereof. The polynucleotide fragment fragment is at least 18 contiguous nucleotides, at least 19 contiguous nucleotides, at least 20 contiguous nucleotides at least 21 contiguous nucleotides in length and at least 85 percent identical to an ACCase gene sequence selected from the group consisting of SEQ ID NO:1-92 and the transfer agent is an organosilicone compound. The polynucleotide fragment can also be sense or anti-sense ssDNA or ssRNA, dsRNA, or dsDNA, or dsDNA/RNA hybrids.

In a further aspect of the invention, the polynucleotide molecule containing composition of the invention may be combined with other herbicidal compounds to provide additional control of unwanted plants in a field of cultivated plants.

In a further aspect, the polynucleotide molecule composition may be combined with any one or more additional agricultural chemicals, such as, insecticides, fungicides, nematocides, bactericides, acaricides, growth regulators, chemosterilants, semiochemicals, repellents, attractants, pheromones, feeding stimulants, biopesticides, microbial pesticides or other biologically active compounds to form a multi-component pesticide giving an even broader spectrum of agricultural protection.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein. The invention can be more fully understood from the following description of the figures:

FIG. 1. Treatment of *Amaranthus palmer* with ssDNA trigger polynucleotides and ACCase inhibitor herbicide, clethodim.

DETAILED DESCRIPTION

Provides are methods and compositions containing a polynucleotide that provide for regulation, repression or delay of ACCase (Acetyl-CoA carboxylase) gene expression and enhanced control of weedy plant species and importantly ACCase inhibitor resistant weed biotypes. Aspects of the method can be applied to manage various weedy plants in agronomic and other cultivated environments.

The following definitions and methods are provided to better define the present invention and to guide those of ordinary skill in the art in the practice of the present invention. Unless otherwise noted, terms are to be understood according to conventional usage by those of ordinary skill in the relevant art. Where a term is provided in the singular, the inventors also contemplate aspects of the invention described by the plural of that term.

By "non-transcribable" polynucleotides is meant that the polynucleotides do not comprise a complete polymerase II transcription unit. As used herein "solution" refers to homogeneous mixtures and non-homogeneous mixtures such as suspensions, colloids, micelles, and emulsions.

Weedy plants are plants that compete with cultivated plants, those of particular importance include, but are not limited to important invasive and noxious weeds and herbicide resistant biotypes in crop production, such as, *Amaranthus* species—*A. albus, A. blitoides, A. hybridus, A. palmeri, A. powellii, A. retroflexus, A. spinosus, A. tuberculatus,* and *A. viridis; Ambrosia* species—*A. trifida, A. artemisifolia; Lolium* species—*L. multiflorum, L. rigidium, L perenne; Digitaria* species—*D. insularis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Cassia* species, *Sida* species, *Brachiaria*, species and *Solanum* species.

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridis var, robusta-alba schreiber, Setaria viridis var, robusta-purpurea, Snowdenia polystachea, Sorghum sudanese, Alisma plantago-aquatica, Amaranthus lividus, Amaranthus quitensis, Ammania auriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus difformis, Damasonium minus, Descurainia sophia, Diplotaxis tenuifolia, Echium plantagineum, Elatine triandra var, pedicellata, Euphorbia heterophylla, Fallopia convolvulus, Fimbristylis miliacea, Galeopsis tetrahit, Galium spurium, Helianthus annuus, Iva xanthifolia, Ixophorus unisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubia var, major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suffruticosa, Phalaris minor, Raphanus raphanistrum, Raphanus sativus, Rapistrum rugosum, Rotala indica var, uliginosa, Sagittaria guyanensis, Sagittaria montevidensis, Sagittaria pygmaea, Salsola iberica, Scirpus juncoides var, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenesis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucus carota, Digitaria ischaemum, Echinochloa crus-pavonis, Fimbristylis miliacea, Galeopsis tetrahit, Galium spurium, Limnophila erecta, Matricaria perforate, Papaver rhoeas, Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris.* It is believed that all plants contain a phytoene desaturase gene in their genome, the sequence of which can be isolated and polynucleotides made according to the methods of the present invention that are useful for regulation, suppressing or delaying the expression of the target ACCase gene in the plants and the growth or development of the treated plants.

Some cultivated plants may also be weedy plants when they occur in unwanted environments. For example, corn plants growing in a soybean field. Transgenic crops with one or more herbicide tolerances will need specialized methods of management to control weeds and volunteer crop plants. The present invention enables the targeting of a transgene for herbicide tolerance to permit the treated plants to become sensitive to the herbicide. For example, transgene ACCase DNA sequences in transgenic events that include DAS-40278-9.

A "trigger" or "trigger polynucleotide" is a polynucleotide molecule that is homologous or complementary to a target gene polynucleotide. The trigger polynucleotide molecules modulate expression of the target gene when topically applied to a plant surface with a transfer agent, whereby a plant treated with said composition has its growth or development or reproductive ability regulated, suppressed or delayed or said plant is more sensitive to an ACCase inhibitor herbicide as a result of said polynucleotide containing composition relative to a plant not treated with a composition containing the trigger molecule.

It is contemplated that the composition of the present invention will contain multiple polynucleotides and herbicides that include but not limited to ACCase gene trigger polynucleotides and an ACCase inhibitor herbicide and anyone or more additional herbicide target gene trigger polynucleotides and the related herbicides and anyone or more additional essential gene trigger polynucleotides. Essential genes are genes in a plant that provide key enzymes or other proteins, for example, a biosynthetic enzyme, metabolizing enzyme, receptor, signal transduction protein, structural gene product, transcription factor, or transport protein; or regulating RNAs, such as, microRNAs, that are essential to the growth or survival of the organism or cell or involved in the normal growth and development of the plant (Meinke, et al., Trends Plant Sci. 2008 September; 13(9):483-91). The suppression of an essential gene enhances the effect of a herbicide that affects the function of a gene product different than the suppressed essential gene. The compositions of the present invention can include various trigger polynucleotides that modulate the expression of an essential gene other than ACCase.

Herbicides for which transgenes for plant tolerance have been demonstrated and the method of the present invention can be applied, include but are not limited to: auxin-like herbicides, glyphosate, glufosinate, sulfonylureas, imidazolinones, bromoxynil, delapon, dicamba, cyclohezanedione, protoporphyrionogen oxidase inhibitors, 4-hydroxyphenyl-pyruvate-dioxygenase inhibitors herbicides. For example, transgenes and their polynucleotide molecules that encode proteins involved in herbicide tolerance are known in the art, and include, but are not limited to an 5-enolpyruvylshikimate-3-phosphate synthase (EPSPS), for example, as more fully described in U.S. Pat. No. 7,807,791 (SEQ ID NO:5); U.S. Pat. Nos. 6,248,876 B1; 5,627,061; 5,804,425; 5,633,435; 5,145,783; 4,971,908; 5,3072,910; 5,188,642; 4,940,835; 5,866,775; 6,225,114 B1; 6,130,366; 5,3070, 667; 4,535,060; 4,769,061; 5,633,448; 5,510,471; U.S. Pat. No. Re. 36,449; U.S. Pat. No. RE 37,287 E; and U.S. Pat. No. 5,491,288; tolerance to sulfonylurea and/or imidazolinone, for example, as described more fully in U.S. Pat. Nos. 5,605,011; 5,013,659; 5,141,870; 5,767,361; 5,7307,180; 5,304,732; 4,761,373; 5,3307,107; 5,928,937; and 5,378, 824; and international publication WO 96/33270; tolerance to hydroxyphenylpyruvatedioxygenases inhibitiong herbicides in plants are described in U.S. Pat. Nos. 6,245,968 B1; 6,268,549; and 6,069,115; US Pat. Pub. 20110191897 and U.S. Pat. No. 7,3072,379 SEQ ID NO:3; U.S. Pat. Nos. 7,935,869; 7,304,209, SEQ ID NO:1, 3, 5 and 15; aryloxyalkanoate dioxygenase polynucleotides, which confer tolerance to 2,4-D and other phenoxy auxin herbicides as well as to aryloxyphenoxypropionate herbicides as described, for example, in WO2005/107437; U.S. Pat. No. 7,838,733 SEQ ID NO:5;) and dicamba-tolerance polynucleotides as described, for example, in Herman et al. (2005) J. Biol. Chem. 280: 24759-24767. Other examples of herbicide-tolerance traits include those conferred by polynucleotides encoding an exogenous phosphinothricin acetyltransferase, as described in U.S. Pat. Nos. 5,969,213; 5,489,520; 5,550, 3078; 5,874,265; 5,919,675; 5,561,236; 5,648,477; 5,646, 024; 6,177,616; and 5,879,903. Plants containing an exogenous phosphinothricin acetyltransferase can exhibit improved tolerance to glufosinate herbicides, which inhibit the enzyme glutamine synthase. Additionally, herbicide-tolerance polynucleotides include those conferred by polynucleotides conferring altered protoporphyrinogen oxidase (protox) activity, as described in U.S. Pat. Nos. 6,288,306 B1; 6,282,837 B1; and 5,767,373; and WO 01/12825. Plants containing such polynucleotides can exhibit improved tolerance to any of a variety of herbicides which target the protox enzyme (also referred to as protox inhibitors). Polynucleotides encoding a glyphosate oxidoreductase and a glyphosate-N-acetyl transferase (GOX described in U.S. Pat. No. 5,463,175 and GAT described in U.S. Patent publication 20030083480, dicamba monooxygenase U.S. Patent publication 20030135879, all of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtI) described in Misawa et al, (1993) Plant J. 4:833-840 and Misawa et al, (1994) Plant J. 6:481-489 for norflurazon tolerance; a polynucleotide molecule encoding acetohydroxyacid synthase (AHAS, aka ALS) described in Sathasiivan et al. (1990) Nucl. Acids Res. 18:3078-2193 for tolerance to sulfonylurea herbicides; and the bar gene described in DeBlock, et al. (1987) EMBO J. 6:2513-2519 for glufosinate and bialaphos tolerance. The transgenic coding regions and regulatory elements of the herbicide tolerance genes are targets in which polynucleotide triggers and herbicides can be included in the composition of the present invention.

The composition of the present invention include a component that is an ACCase inhibitor herbicide, which include members of the chemical families of aryloxyphenoxypropionates, cyclohexanediones and phenylpyrazoline that include, but are not limited to an aryloxyphenoxypropionate comprising clodinafop (Propanoic acid, 2-[4-[(5-chloro-3-fluoro-2-pyridinyl)oxy]phenoxy]-,2-propynyl ester, (2R)), cyhalofop (butyl(2R)-2-[4-(4-cyano-2-fluorophenoxy)phenoxy]propionate), diclofop (methyl 2-[4-(2,4-dichlorophenoxy)phenoxy]propanoate), fenoxaprop (ethyl (R)-2-[4-(6-chloro-1,3-benzoxazol-2-yloxy)phenoxy]propionate), fluazifop (2R)-2-[4-[[5-(trifluoromethyl)-2-pyridinyl]oxy]phenoxy]propanoic acid), haloxyfop (2-[4-[[3-chloro-5-(trifluoromethyl)-2-pyridinyl]oxy]phenoxy]propanoic acid), propaquizafop (2-[[(1-methylethylidene)amino]oxy]ethyl (2R)-2-[4-[(6-chloro-2quinoxalinyl)oxy]phenoxy]propanoate) and quizalofop(2R)-2-[4-[(6-chloro-2-quinoxalinyl)oxy]phenoxy]propanoic acid; a cyclohexanedione comprising alloxydim (methyl 2,2-dimethyl-4,6-dioxo-5-[(1E)-1-[(2-propen-1-yloxy)imino]butyl]cyclohexanecarboxylate), butroxydim (2-[1-(ethoxyimino)propyl]-3-hydroxy-5-[2,4, 6-trimethyl-3-(1-oxobutyl)phenyl]-2-cyclohexen-1-one), clethodim (2-[1-[[[(2E)-3-chloro-2-propen-1-yl]oxy]imino] propyl]-5-[2-(ethylthio)propyl]-3-hydroxy-2-cyclohexen-1-one), cycloxydim (2-[1-(ethoxyimino)butyl]-3-hydroxy-5-(tetrahydro-2H-thiopyran-3-yl)-2-cyclohexen-1-one), profoxydim (2-[1-[[2-(4-chlorophenoxy)propoxy]imino]butyl]-3-hydroxy-5-(tetrahydro-2H-thiopyran-3-yl)-2-cyclohexen-1-one), sethoxydim (2-[1-(ethoxyimino)butyl]-5-[2-(ethylthio)propyl]-3-hydroxy-2-cyclohexen-1-one), tepraloxydim (2-[1-[[[(2E)-3-chloro-2-propen-1-yl]oxy] imino]propyl]-3-hydroxy-5-(tetrahydro-2H-pyran-4-yl)-2-cyclohexen-1-one) and tralkoxydim (2-[1-(ethoxyimino) propyl]-3-hydroxy-5-(2,4,6-trimethylphenyl)-2-cyclohexen-1-one); a phenylpyrazoline comprising pinoxaden (8-(2,6-diethyl-4-methylphenyl)-1,2,4,5-tetrahydro-7-oxo-7H-pyrazolo[1,2-d][1,4,5]oxadiazepin-9-yl 2,2-dimethylpropanoate).

Numerous herbicides with similar or different modes of action (herein referred to as co-herbicides) are available that can be added to the composition of the present invention, for example, members of the herbicide families that include but are not limited to amide herbicides, aromatic acid herbicides, arsenical herbicides, benzothiazole herbicides, benzoylcyclohexanedione herbicides, benzofuranyl alkylsulfonate herbicides, carbamate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides. In particular, the rates of use of the added herbicides can be reduced in compositions comprising the polynucleotides of the invention. Use rate reductions of the additional added herbicides can be 10-25 percent, 26-50 percent, 51-75 percent or more can be achieved that enhance the activity of the polynucleotides and herbicide composition and is contemplated as an aspect of the invention. Representative co-herbicides of the families include but are not limited to acetochlor, acifluorfen, acifluorfen-sodium, aclonifen, acrolein, alachlor, alloxydim, allyl alcohol, ametryn, amicarbazone, amidosulfuron, aminopyralid, amitrole, ammonium sulfamate, anilofos, asulam, atraton, atrazine, azimsulfuron, BCPC, beflubutamid, benazolin, benfluralin, benfuresate, bensulfuron, bensulfuron-methyl, bensulide, bentazone, benzfendizone, benzobicyclon, benzofenap, bifenox, bilanafos, bispyribac, bispyribac-sodium, borax, bromacil, bromobutide, bromoxynil, butachlor, butafenacil, butamifos, butralin, butroxydim, butylate, cacodylic acid, calcium chlorate, cafenstrole, carbetamide, carfentrazone, carfentrazone-ethyl, CDEA, CEPC, chlorflurenol, chlorflurenol-methyl, chloridazon, chlorimuron, chlorimuron-ethyl, chloroacetic acid, chlorotoluron, chlorpropham, chlorsulfuron, chlorthal, chlorthal-dimethyl, cinidon-ethyl, cinmethylin, cinosulfuron, cisanilide, clethodim, clodinafop, clodinafop-propargyl, clomazone, clomeprop, clopyralid, cloransulam, cloransulam-methyl, CMA, 4-CPB, CPMF, 4-CPP, CPPC, cresol, cumyluron, cyanamide, cyanazine, cycloate, cyclosulfamuron, cycloxydim, cyhalofop, cyhalofop-butyl, 2,4-D, 3,4-DA, daimuron, dalapon, dazomet, 2,4-DB, 3,4-DB, 2,4-DEB, desmedipham, dicamba, dichlobenil, ortho-dichlorobenzene, para-dichlorobenzene, dichlorprop, dichlorprop-P, diclofop, diclofop-methyl, diclosulam, difenzoquat, difenzoquat metilsulfate, diflufenican, diflufenzopyr, dimefuron, dimepiperate, dimethachlor, dimethametryn, dimethenamid, dimethenamid-P, dimethipin, dimethylarsinic acid, dinitramine, dinoterb, diphenamid, diquat, diquat dibromide, dithiopyr, diuron, DNOC, 3,4-DP, DSMA, EBEP, endothal, EPTC, esprocarb, ethalfluralin, ethametsulfuron, ethametsulfuron-methyl, ethofumesate, ethoxyfen, ethoxysulfuron, etobenzanid, fenoxaprop-P, fenoxaprop-P-ethyl, fentrazamide, ferrous sulfate, flamprop-M, flazasulfuron, florasulam, fluazifop, fluazifop-butyl, fluazifop-P, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, fluoroglycofen, fluoroglycofen-ethyl, flupropanate, flupyrsulfuron, flupyrsulfuron-methyl-sodium, flurenol, fluridone, fluorochloridone, fluoroxypyr, flurtamone, fluthiacet, fluthiacet-methyl, fomesafen, foramsulfuron, fosamine, glufosinate, glufosinate-ammonium, glyphosate, halosulfuron, halosulfuron-methyl, haloxyfop, haloxyfop-P, HC-252, hexazinone, imazamethabenz, imazamethabenz-methyl, imazamox, imazapic, imazapyr, imazaquin, imazethapyr, imazosulfuron, indanofan, iodomethane, iodosulfuron, iodosulfuron-methyl-sodium, ioxynil, isoproturon, isouron, isoxaben, isoxachlortole, isoxaflutole, karbutilate, lactofen, lenacil, linuron, MAA, MAMA, MCPA, MCPA-thioethyl, MCPB, mecoprop, mecoprop-P, mefenacet, mefluidide, mesosulfuron, mesosulfuron-methyl, mesotrione, metam, metamifop, metamitron, metazachlor, methabenzthiazuron, methylarsonic acid, methyldymron, methyl isothiocyanate, metobenzuron, metolachlor, S-metolachlor, metosulam, metoxuron, metribuzin, metsulfuron, metsulfuron-methyl, MK-66, molinate, monolinuron, MSMA, naproanilide, napropamide, naptalam, neburon, nicosulfuron, nonanoic acid, norflurazon, oleic acid (fatty acids), orbencarb, orthosulfamuron, oryzalin, oxadiargyl, oxadiazon, oxasulfuron, oxaziclomefone, oxyfluorfen, paraquat, paraquat dichloride, pebulate, pendimethalin, penoxsulam, pentachlorophenol, pentanochlor, pentoxazone, pethoxamid, petrolium oils, phenmedipham, phenmedipham-ethyl, picloram, picolinafen, pinoxaden, piperophos, potassium arsenite, potassium azide, pretilachlor, primisulfuron, primisulfuron-methyl, prodiamine, profluazol, profoxydim, prometon, prometryn, propachlor, propanil, propaquizafop, propazine, propham, propisochlor, propoxycarbazone, propoxycarbazone-sodium, propyzamide, prosulfocarb, prosulfuron, pyraclonil, pyraflufen, pyraflufen-ethyl, pyrazolynate, pyrazosulfuron, pyrazosulfuron-ethyl, pyrazoxyfen, pyribenzoxim, pyributicarb, pyridafol, pyridate, pyriftalid, pyriminobac, pyriminobac-methyl, pyrimisulfan, pyrithiobac, pyrithiobac-sodium, quinclorac, quinmerac, quinoclamine, quizalofop, quizalofop-P, rimsulfuron, sethoxydim, siduron, simazine, simetryn, SMA, sodium arsenite, sodium azide, sodium chlorate, sulcotrione, sulfentrazone, sulfometuron, sulfometuron-methyl, sulfosate, sulfosulfuron, sulfuric acid, tar oils, 2,3,6-TBA, TCA, TCA-sodium, tebuthiuron, tepraloxydim, terbacil, terbumeton, terbuthylazine, terbutryn, thenylchlor, thiazopyr, thifensulfuron, thifensulfuron-methyl, thiobencarb, tiocarbazil, topramezone, tralkoxydim, tri-allate, triasulfuron, triaziflam, tribenuron, tribenuron-methyl, tricamba, triclopyr, trietazine, trifloxysulfuron, trifloxysulfuron-sodium, trifluralin, triflusulfuron, triflusulfuron-methyl, trihydroxytriazine, tritosulfuron, [3-[2-chloro-4-fluoro-5-(-methyl-6-trifluoromethyl-2,4-dioxo-,2,3,4-t-etrahydropyrimidin-3-yl)phenoxy]-2-pyridyloxy]acetic acid ethyl ester (CAS RN 353292-3-6), 4-[(4,5-dihydro-3-methoxy-4-methyl-5-oxo)-H-,2,4-triazol-ylcarbonyl-sulfamoyl]-5-methylthiophene-3-carboxylic acid (BAY636), BAY747 (CAS RN 33504-84-2), topramezone (CAS RN 2063-68-8), 4-hydroxy-3-[[2-[(2-methoxyethoxy)methyl]-6-(trifluoro-methyl)-3-pyridi-nyl]carbonyl]-bicyclo[3.2]oct-3-en-2-one (CAS RN 35200-68-5), and 4-hydroxy-3-[[2-(3-methoxypropyl)-6-(difluoromethyl)-3-pyridinyl]carbon-yl]-bicyclo[3.2.]oct-3-en-2-one. Additionally, including herbicidal compounds of unspecified modes of action as described in CN101279950A, CN101279951A, DE10000600A1, DE10116399A1, DE102004054666A1, DE102005014638A1, DE102005014906A1, DE102007012168A1, DE102010042866A1, DE10204951A1, DE10234875A1, DE10234876A1, DE10256353A1, DE10256354A1, DE10256367A1, EP1157991A2, EP1238586A1, EP2147919A1, EP2160098A2, JP03968012B2, JP2001253874A, JP2002080454A, JP2002138075A, JP2002145707A, JP2002220389A, JP2003064059A, JP2003096059A, JP2004051628A, JP2004107228A, JP2005008583A, JP2005239675A, JP2005314407A, JP2006232824A, JP2006282552A, JP2007153847A, JP2007161701A, JP2007182404A, JP2008074840A, JP2008074841A, JP2008133207A, JP2008133218A, JP2008169121A, JP2009067739A, JP2009114128A, JP2009126792A, JP2009137851A, US20060111241A1, US20090036311A1, US20090054240A1, US20090215628A1, US20100099561A1, US20100152443A1, US20110105329A1, US20110201501A1, WO2001055066A2, WO2001056975A1, WO2001056979A1, WO2001090071A2, WO2001090080A1, WO2002002540A1, WO2002028182A1, WO2002040473A1, WO2002044173A2, WO2003000679A2, WO2003006422A1, WO2003013247A1, WO2003016308A1, WO2003020704A1, WO2003022051A1, WO2003022831A1, WO2003022843A1, WO2003029243A2, WO2003037085A1, WO2003037878A1, WO2003045878A2, WO2003050087A2, WO2003051823A1, WO2003051824A1, WO2003051846A2, WO2003076409A1, WO2003087067A1, WO2003090539A1, WO2003091217A1, WO2003093269A2, WO2003104206A2, WO2004002947A1, WO2004002981A2, WO2004011429A1, WO2004029060A1, WO2004035545A2, WO2004035563A1, WO2004035564A1, WO2004037787A1, WO2004067518A1, WO2004067527A1, WO2004077950A1, WO2005000824A1, WO2005007627A1, WO2005040152A1, WO2005047233A1, WO2005047281A1, WO2005061443A2, WO2005061464A1, WO2005068434A1, WO2005070889A1, WO2005089551A1, WO2005095335A1, WO2006006569A1, WO2006024820A1, WO2006029828A1, WO2006029829A1, WO2006037945A1, WO2006050803A1, WO2006090792A1, WO2006123088A2, WO2006125687A1, WO2006125688A1, WO2007003294A1, WO2007026834A1, WO2007071900A1, WO2007077201A1, WO2007077247A1, WO2007096576A1, WO2007119434A1, WO2007134984A1, WO2008009908A1, WO2008029084A1, WO2008059948A1, WO2008071918A1, WO2008074991A1, WO2008084073A1, WO2008100426A2, WO2008102908A1, WO2008152072A2, WO2008152073A2, WO2009000757A1, WO2009005297A2, WO2009035150A2, WO2009063180A1, WO2009068170A2, WO2009068171A2, WO2009086041A1, WO2009090401A2, WO2009090402A2, WO2009115788A1, WO2009116558A1, WO2009152995A1, WO2009158258A1, WO2010012649A1, WO2010012649A1, WO2010026989A1, WO2010034153A1, WO2010049270A1, WO2010049369A1, WO2010049405A1, WO2010049414A1, WO2010063422A1, WO2010069802A1, WO2010078906A2, WO2010078912A1, WO2010104217A1, WO2010108611A1, WO2010112826A3, WO2010116122A3, WO2010119906A1, WO2010130970A1, WO2011003776A2, WO2011035874A1, WO2011065451A1, all of which are incorporated herein by reference.

An agronomic field in need of plant control is treated by application of the composition of the present invention directly to the surface of the growing plants, such as by a spray. For example, the method is applied to control weeds in a field of crop plants by spraying the field with the composition. The composition can be provided as a tank mix, a sequential treatment of components (generally the polynucleotide containing composition followed by the herbicide), or a simultaneous treatment or mixing of one or more of the components of the composition from separate containers. Treatment of the field can occur as often as needed to provide weed control and the components of the composition can be adjusted to target specific weed species or weed families through utilization of specific polynucleotides or polynucleotide compositions capable of selectively targeting the specific species or plant family to be controlled. The composition can be applied at effective use rates according to the time of application to the field, for example, preplant, at planting, post planting, post harvest. ACCase inhibitor herbicides can be applied to a field at rates of 10 to 500 g ai/ha (active ingredient per hectare) or more. The polynucleotides of the composition can be applied at rates of 1 to 30 grams per acre depending on the number of trigger molecules needed for the scope of weeds in the field.

Crop plants in which weed control is needed include but are not limited to, i) corn, soybean, cotton, canola, sugar beet, alfalfa, sugarcane, rice, and wheat; ii) vegetable plants including, but not limited to, tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; or, iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e.g., an ornamental flowering plant or shrub or turf grass). The methods and compositions provided herein can also be applied to plants produced by a cutting, cloning, or grafting process (i.e., a plant not grown from a seed) include fruit trees and plants that include, but are not limited to, citrus, apples, avocados, tomatoes, eggplant, cucumber, melons, watermelons, and grapes as well as various ornamental plants.

Pesticidal Mixtures

The polynucleotide compositions may also be used as mixtures with various agricultural chemicals and/or insecticides, miticides and fungicides, pesticidal and biopesticidal agents. Examples include but are not limited to azinphosmethyl, acephate, isoxathion, isofenphos, ethion, etrimfos, oxydemeton-methyl, oxydeprofos, quinalphos, chlorpyrifos, chlorpyrifos-methyl, chlorfenvinphos, cyanophos, dioxabenzofos, dichlorvos, disulfoton, dimethylvinphos, dimethoate, sulprofos, diazinon, thiometon, tetrachlorvinphos, temephos, tebupirimfos, terbufos, naled, vamidothion, pyraclofos, pyridafenthion, pirimiphos-methyl, fenitrothion, fenthion, phenthoate, flupyrazophos, prothiofos, propaphos, profenofos, phoxime, phosalone, phosmet, formothion, phorate, malathion, mecarbam, mesulfenfos, methamidophos, methidathion, parathion, methyl parathion, monocrotophos, trichlorphon, EPN, isazophos, isamidofos, cadusafos, diamidaphos, dichlofenthion, thionazin, fenamiphos, fosthiazate, fosthietan, phosphocarb, DSP, ethoprophos, alanycarb, aldicarb, isoprocarb, ethiofencarb, carbaryl, carbosulfan, xylylcarb, thiodicarb, pirimicarb, fenobucarb, furathiocarb, propoxur, bendiocarb, benfuracarb, methomyl, metolcarb, XMC, carbofuran, aldoxycarb, oxamyl, acrinathrin, allethrin, esfenvalerate, empenthrin, cycloprothrin, cyhalothrin, gamma-cyhalothrin, lambda-cyhalothrin, cyfluthrin, beta-cyfluthrin, cypermethrin, alpha-cypermethrin, zeta-cypermethrin, silafluofen, tetramethrin, tefluthrin, deltamethrin, tralomethrin, bifenthrin, phenothrin, fenvalerate, fenpropathrin, furamethrin, prallethrin, flucythrinate, fluvalinate, flubrocythrinate, permethrin, resmethrin, ethofenprox, cartap, thiocyclam, bensultap, acetamiprid, imidacloprid, clothianidin, dinotefuran, thiacloprid, thiamethoxam, nitenpyram, chlorfluazuron, diflubenzuron, teflubenzuron, triflumuron, novaluron, noviflumuron, bistrifluoron, fluazuron, flucycloxuron, flufenoxuron, hexaflumuron, lufenuron, chromafenozide, tebufenozide, halofenozide, methoxyfenozide, diofenolan, cyromazine, pyriproxyfen, buprofezin, methoprene, hydroprene, kinoprene, triazamate, endosulfan, chlorfenson, chlorobenzilate, dicofol, bromopropylate, acetoprole, fipronil, ethiprole, pyrethrin, rotenone, nicotine sulphate, BT (*Bacillus Thuringiensis*) agent, spinosad, abamectin, acequinocyl, amidoflumet, amitraz, etoxazole, chinomethionat, clofentezine, fenbutatin oxide, dienochlor, cyhexatin, spirodiclofen, spiromesifen, tetradifon, tebufenpyrad, binapacryl, bifenazate, pyridaben, pyrimidifen, fenazaquin, fenothiocarb, fenpyroximate, fluacrypyrim, fluazinam, flufenzin, hexythiazox, propargite, benzomate, polynactin complex, milbemectin, lufenuron, mecarbam, methiocarb, mevinphos, halfenprox, azadirachtin, diafenthiuron, indoxacarb, emamectin benzoate, potassium oleate, sodium oleate, chlorfenapyr, tolfenpyrad, pymetrozine, fenoxycarb, hydramethylnon, hydroxy propyl starch, pyridalyl, flufenerim, flubendiamide, flonicamid, metaflumizole, lepimectin, TPIC, albendazole, oxibendazole, oxfendazole, trichlamide, fensulfothion, fenbendazole, levamisole hydrochloride, morantel tartrate, dazomet, metam-sodium, triadimefon, hexaconazole, propiconazole, ipconazole, prochloraz, triflumizole, tebuconazole, epoxiconazole, difenoconazole, flusilazole, triadimenol, cyproconazole, metconazole, fluquinconazole, bitertanol, tetraconazole, triticonazole, flutriafol, penconazole, diniconazole, fenbuconazole, bromuconazole, imibenconazole, simeconazole, myclobutanil, hymexazole, imazalil, furametpyr, thifluzamide, etridiazole, oxpoconazole, oxpoconazole fumarate, pefurazoate, prothioconazole, pyrifenox, fenarimol, nuarimol, bupirimate, mepanipyrim, cyprodinil, pyrimethanil, metalaxyl, mefenoxam, oxadixyl, benalaxyl, thiophanate, thiophanate-methyl, benomyl, carbendazim, fuberidazole, thiabendazole, manzeb, propineb, zineb, metiram, maneb, ziram, thiuram, chlorothalonil, ethaboxam, oxycarboxin, carboxin, flutolanil, silthiofam, mepronil, dimethomorph, fenpropidin, fenpropimorph, spiroxamine, tridemorph, dodemorph, flumorph, azoxystrobin, kresoxim-methyl, metominostrobin, orysastrobin, fluoxastrobin, trifloxystrobin, dimoxystrobin, pyraclostrobin, picoxystrobin, iprodione, procymidone, vinclozolin, chlozolinate, flusulfamide, dazomet, methyl isothiocyanate, chloropicrin, methasulfocarb, hydroxyisoxazole, potassium hydroxyisoxazole, echlomezol, D-D, carbam, basic copper chloride, basic copper sulfate, copper nonylphenolsulfonate, oxine copper, DBEDC, anhydrous copper sulfate, copper sulfate pentahydrate, cupric hydroxide, inorganic sulfur, wettable sulfur, lime sulfur, zinc sulfate, fentin, sodium hydrogen carbonate, potassium hydrogen carbonate, sodium hypochlorite, silver, edifenphos, tolclofos-methyl, fosetyl, iprobenfos, dinocap, pyrazophos, carpropamid, fthalide, tricyclazole, pyroquilon, diclocymet, fenoxanil, kasugamycin, validamycin, polyoxins, blasticiden S, oxytetracycline, mildiomycin, streptomycin, rape seed oil, machine oil, benthiavalicarbisopropyl, iprovalicarb, propamocarb, diethofencarb, fluoroimide, fludioxanil, fenpiclonil, quinoxyfen, oxolinic acid, chlorothalonil, captan, folpet, probenazole, acibenzolar-S-methyl, tiadinil, cyflufenamid, fenhexamid, diflumetorim, metrafenone, picobenzamide, proquinazid, famoxadone, cyazofamid, fenamidone, zoxamide, boscalid, cymoxanil, dithianon, fluazinam, dichlofluanide, triforine, isoprothiolane, ferimzone, diclomezine, tecloftalam, pencycuron, chinomethionat, iminoctadine acetate, iminoctadine albesilate, ambam, polycarbamate, thiadiazine, chloroneb, nickel dimethyldithiocarbamate, guazatine, dodecylguanidine-acetate, quintozene, tolylfluanid, anilazine, nitrothalisopropyl, fenitropan, dimethirimol, benthiazole, harpin protein, flumetover, mandipropamide and penthiopyrad.

Polynucleotides

As used herein, the term "DNA", "DNA molecule", "DNA polynucleotide molecule" refers to a single-stranded DNA (ssDNA) or double-stranded DNA (dsDNA) molecule of genomic or synthetic origin, such as, a polymer of deoxyribonucleotide bases or a DNA polynucleotide molecule. As used herein, the term "DNA sequence", "DNA nucleotide sequence" or "DNA polynucleotide sequence" refers to the nucleotide sequence of a DNA molecule. As used herein, the term "RNA", "RNA molecule", "RNA polynucleotide molecule" refers to a single-stranded RNA (ssRNA) or double-stranded RNA (dsRNA) molecule of genomic or synthetic origin, such as, a polymer of ribonucleotide bases that comprise single or double stranded regions. Unless otherwise stated, nucleotide sequences in the text of this specification are given, when read from left to right, in the 5' to 3' direction. The nomenclature used herein is that required by Title 37 of the United States Code of Federal Regulations §1.822 and set forth in the tables in WIPO Standard ST.25 (1998), Appendix 2, Tables 1 and 3.

As used herein, "polynucleotide" refers to a DNA or RNA molecule containing multiple nucleotides and generally refers both to "oligonucleotides" (a polynucleotide molecule of typically 50 or fewer nucleotides in length) and polynucleotides of 51 or more nucleotides. Embodiments of this invention include compositions including oligonucleotides having a length of 18-25 nucleotides (18-mers, 19-mers, 20-mers, 21-mers, 22-mers, 23-mers, 24-mers, or 25-mers), for example, oligonucleotides SEQ ID NO:3901-4530 or fragments thereof or medium-length polynucleotides having a length of 26 or more nucleotides (polynucleotides of 26, 27, 28, 29, 30, 307, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), for example, oligonucleotides SEQ ID NO:93-3900 or fragments thereof or long polynucleotides having a length greater than about 300 nucleotides (for example, polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene), for example, polynucleotides of Table 1 (SEQ ID NO:1-93) wherein the selected polynucleotides or fragments thereof are homologous or complementary to SEQ ID NO:1-93 suppresses, represses or otherwise delay the expression of the target ACCase gene. A target gene comprises any polynucleotide molecule in a plant cell or fragment thereof for which the modulation of the expression of the target gene is provided by the methods and compositions of the present invention. Where a polynucleotide is double-stranded, its length can be similarly described in terms of base pairs. Oligonucleotides and polynucleotides of the present invention can be made that are essentially identical or essentially complementary to adjacent genetic elements of a gene, for example, spanning the junction region of an intron and exon, the junction region of a promoter and a transcribed region, the junction region of a 5' leader and a coding sequence, the junction of a 3' untranslated region and a coding sequence.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, for example, US Patent Publication 20110171287, US Patent Publication 20110171176, and US Patent Publication 20110152353, US Patent Publication, 20110152346, US Patent Publication 20110160082, herein incorporated by reference. For example, including but not limited to the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (for example, fluorescein or rhodamine) or other label (for example, biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/ DNA molecule, or combinations thereof. In some embodiments these polynucleotides include chemically modified nucleotides or non-canonical nucleotides. In some embodiments, the oligonucleotides may be blunt-ended or may comprise a 3' overhang of from 1-5 nucleotides of at least one or both of the strands. Other configurations of the oligonucleotide are known in the field and are contemplated herein. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain other embodiments the polynucleotides further includes a promoter, generally a promoter functional in a plant, for example, a pol II promoter, a pol III promoter, a pol IV promoter, or a pol V promoter.

The term "gene" refers to chromosomal DNA, plasmid DNA, cDNA, intron and exon DNA, artificial DNA polynucleotide, or other DNA that encodes a peptide, polypeptide, protein, or RNA transcript molecule, and the genetic elements flanking the coding sequence that are involved in the regulation of expression, such as, promoter regions, 5' leader regions, 3' untranslated regions. Any of the components of the gene are potential targets for the oligonucleotides and polynucleotides of the present invention.

The polynucleotide molecules of the present invention are designed to modulate expression by inducing regulation or suppression of an endogenous ACCase gene in a plant and are designed to have a nucleotide sequence essentially identical or essentially complementary to the nucleotide sequence of an endogenous ACCase gene of a plant or to the sequence of RNA transcribed from an endogenous ACCase gene of a plant, including a transgene in a plant that provides for a herbicide resistant ACCase enzyme, which can be coding sequence or non-coding sequence. Effective molecules that modulate expression are referred to as "a trigger molecule, or trigger polynucleotide". By "essentially identical" or "essentially complementary" is meant that the trigger polynucleotides (or at least one strand of a double-stranded polynucleotide or portion thereof, or a portion of a single strand polynucleotide) are designed to hybridize to the endogenous gene noncoding sequence or to RNA transcribed (known as messenger RNA or an RNA transcript) from the endogenous gene to effect regulation or suppression of expression of the endogenous gene. Trigger molecules are identified by "tiling" the gene targets with partially overlapping probes or non-overlapping probes of antisense or sense polynucleotides that are essentially identical or essentially complementary to the nucleotide sequence of an endogenous gene. Multiple target sequences can be aligned and sequence regions with homology in common, according to the methods of the present invention, are identified as potential trigger molecules for the multiple targets. Multiple trigger molecules of various lengths, for example 18-25 nucleotides, 26-50 nucleotides, 51-100 nucleotides, 101-200 nucleotides, 201-300 nucleotides or more can be pooled into a few treatments in order to investigate polynucleotide molecules that cover a portion of a gene sequence (for example, a portion of a coding versus a portion of a noncoding region, or a 5' versus a 3' portion of a gene) or an entire gene sequence including coding and noncoding regions of a target gene. Polynucleotide molecules of the pooled trigger molecules can be divided into smaller pools or single molecules inorder to identify trigger molecules that provide the desired effect.

The target gene RNA and DNA polynucleotide molecules (Table 1, SEQ ID NO: 1-93) are sequenced by any number of available methods and equipment. Some of the sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies. An ACCase target gene comprising DNA or RNA can be isolated using primers or probes essentially complementary or essentially homologous to SEQ ID NO:1-93 or a fragment thereof. A polymerase chain reaction (PCR) gene fragment can be produced using primers essentially complementary or essentially homologous to SEQ ID NO:1-93 or a fragment thereof that is useful to isolate an ACCase gene from a plant genome. SEQ ID NO: 1-93 or fragments thereof can be used in various sequence capture technologies to isolate additional target gene sequences, for example, including but not limited to Roche NimbleGen® (Madison, Wis.) and Streptavdin-coupled Dynabeads® (Life Technologies, Grand Island, N.Y.) and US20110015084, herein incorporated by reference in its entirety.

Embodiments of functional single-stranded polynucleotides have sequence complementarity that need not be 100 percent, but is at least sufficient to permit hybridization to RNA transcribed from the target gene or DNA of the target gene to form a duplex to permit a gene silencing mechanism. Thus, in embodiments, a polynucleotide fragment is designed to be essentially identical to, or essentially complementary to, a sequence of 18 or more contiguous nucleotides in either the target ACCase gene sequence or messenger RNA transcribed from the target gene. By "essentially identical" is meant having 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the target gene or RNA transcribed from the target gene; by "essentially complementary" is meant having 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene. In some embodiments of this invention polynucleotide molecules are designed to have 100 percent sequence identity with or complementarity to one allele or one family member of a given target gene (coding or non-coding sequence of a gene for of the present invention); in other embodiments the polynucleotide molecules are designed to have 100 percent sequence identity with or complementarity to multiple alleles or family members of a given target gene.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98% or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

"Identity" refers to the degree of similarity between two polynucleic acid or protein sequences. An alignment of the two sequences is performed by a suitable computer program. A widely used and accepted computer program for performing sequence alignments is CLUSTALW v1.6 (Thompson, et al. Nucl. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between a 200 and a 400 amino acid protein, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Trigger molecules for specific gene family members can be identified from coding and/or non-coding sequences of gene families of a plant or multiple plants, by aligning and selecting 200-300 polynucleotide fragments from the least homologous regions amongst the aligned sequences and evaluated using topically applied polynucleotides (as sense or anti-sense ssDNA or ssRNA, dsRNA, or dsDNA) to determine their relative effectiveness in inducing the herbicidal phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the yield/quality phenotype. Once relative effectiveness is determined, the fragments are utilized singly, or again evaluated in combination with one or more other fragments to determine the trigger composition or mixture of trigger polynucleotides for providing the yield/quality phenotype.

Trigger molecules for broad activity can be identified from coding and/or non-coding sequences of gene families of a plant or multiple plants, by aligning and selecting 200-300 polynucleotide fragments from the most homologous regions amongst the aligned sequences and evaluated using topically applied polynucleotides (as sense or antisense ssDNA or ssRNA, dsRNA, or dsDNA) to determine their relative effectiveness in inducing the yield/quality phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the yield/ quality phenotype. Once relative effectiveness is determined, the fragments may be utilized singly, or in combination with one or more other fragments to determine the trigger composition or mixture of trigger polynucleotides for providing the yield/quality phenotype.

Methods of making polynucleotides are well known in the art. Chemical synthesis, in vivo synthesis and in vitro synthesis methods and compositions are known in the art and include various viral elements, microbial cells, modified polymerases, and modified nucleotides. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end in a microbial expression cassette that includes a bacterial T7 polymerase promoter that makes RNA strands that can be assembled into a dsRNA and kits provided by various manufacturers that include T7 RiboMax Express (Promega, Madison, Wis.), AmpliScribe T7-Flash (Epicentre, Madison, Wis.), and TranscriptAid T7 High Yield (Fermentas, Glen Burnie, Md.). dsRNA molecules can be produced from microbial expression cassettes in bacterial cells (Ongvarrasopone et al. ScienceAsia 33:35-39; Yin, Appl. Microbiol. Biotechnol 84:323-333, 2009; Liu et al., BMC Biotechnology 10:85, 2010) that have regulated or deficient RNase III enzyme activity or the use of various viral vectors to produce sufficient quantities of dsRNA. In the present invention, ACCase gene fragments are inserted into the microbial expression cassettes in a position in which the fragments are express to produce ssRNA or dsRNA useful in the methods described herein to regulate expression on a target ACCase gene. In some embodiments design parameters such as Reynolds score (Reynolds et al. Nature Biotechnology 22, 326-330 (2004), Tuschl rules (Pei and Tuschl, Nature Methods 3(9): 670-676, 2006), i-score (Nucleic Acids Res 35: e123, 2007), i-Score Designer tool and associated algorithms (Nucleic Acids Res 32: 936-948, 2004. Biochem Biophys Res Commun 316: 1050-1058, 2004, Nucleic Acids Res 32: 893-901, 2004, Cell Cycle 3: 790-5, 2004, Nat Biotechnol 23: 995-1001, 2005, Nucleic Acids Res 35: e27, 2007, BMC Bioinformatics 7: 520, 2006, Nucleic Acids Res 35: e123, 2007, Nat Biotechnol 22: 326-330, 2004) are known in the art and may be used in selecting polynucleotide sequences effective in gene silencing. In some embodiments the sequence of a polynucleotide is screened against the genomic DNA of the intended plant to minimize unintentional silencing of other genes.

The trigger polynucleotide and oligonucleotide molecule polynucleotide compositions are useful in compositions, such as liquids that comprise these of polynucleotide molecules, at low concentrations, alone or in combination with other components, for example one or more herbicide molecules, either in the same solution or in separately applied liquids that also provide a transfer agent. While there is no upper limit on the concentrations and dosages of polynucleotide molecules that can useful in the methods of this invention, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, or seed. In one embodiment, a useful treatment for herbaceous plants using 25-mer oligonucleotide molecules is about 1 nanomole (nmol) of oligonucleotide molecules per plant, for example, from about 0.05 to 1 nmol per plant. Other embodiments for herbaceous plants include useful ranges of about 0.05 to about 100 nmol, or about 0.1 to about 20 nmol, or about 1 nmol to about 10 nmol of polynucleotides per plant. Very large plants, trees, or vines may require correspondingly larger amounts of polynucleotides. When using long dsRNA molecules that can be processed into multiple oligonucleotides, lower concentrations can be used. To illustrate embodiments of the invention, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e.g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9$^{th}$ Compendium of Herbicide Adjuvants, publicly available on the worldwide web (internet) at herbicide-.adjuvants.com can be used, e.g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL-.REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055,0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, any of the commercially available organosilicone preparations provided such as the following Breakthru S 321, Breakthru S 200 Cat#67674-67-3, Breakthru OE 441 Cat#68937-55-3, Breakthru S 278 Cat #27306-78-1, Breakthru S 243, Breakthru S 233 Cat#134180-76-0, available from manufacturer Evonik Goldschmidt (Germany), Silwet® HS 429, Silwet® HS 312, Silwet® HS 508, Silwet® HS 604 (Momentive Performance Materials, Albany, N.Y.) can be used as transfer agents in a polynucleotide composition. In certain embodiments where an organosilicone preparation is used as a pre-spray treatment of plant leaves or other surfaces, freshly made concentrations in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of a target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

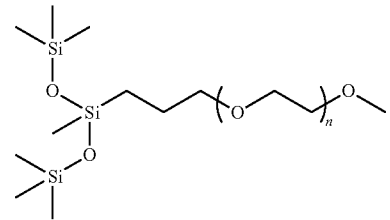

(Compound I: polyalkyleneoxide heptamethyltrisiloxane, average $n$ = 7.5).

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

Compositions include but are not limited components that are one or more polynucleotides essentially identical to, or essentially complementary to an ACCase gene sequence (promoter, intron, exon, 5' untranslated region, 3' untranslated region), a transfer agent that provides for the polynucleotide to enter a plant cell, a herbicide that complements the action of the polynucleotide, one or more additional herbicides that further enhance the herbicide activity of the composition or provide an additional mode of action different from the complementing herbicide, various salts and stabilizing agents that enhance the utility of the composition as an admixture of the components of the composition.

Methods include one or more applications of a polynucleotide composition and one or more applications of a permeability-enhancing agent for conditioning of a plant to permeation by polynucleotides. When the agent for conditioning to permeation is an organosilicone composition or compound contained therein, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods are useful for modulating the expression of an endogenous ACCase gene (for example, U.S. Pat. No. 7,297,541, U.S. Patent Publ. 20110185444, and 20110185445) or transgenic ACCase gene (for example, U.S. Pat. No. 7,3072,379, U.S. Patent Publ. 20110191897) or ACCase inhibitor inactivating genes (U.S. Pat. Nos. 6,268,549; 6,768,044; 7,3072,379; 7,304,209; WO 96/38567, WO 99/24585) in a plant cell. In various embodiments, an ACCase gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species.

An aspect of the invention provides a method for modulating expression of an ACCase gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the target ACCase gene in either anti-sense or sense orientation, whereby the polynucleotide molecules permeate the interior of the plant and induce modulation of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches.

All publications, patents and patent applications are herein incorporated by reference to the same extent as if each individual publication or patent application was specifically and individually indicated to be incorporated by reference.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Polynucleotides Related to the ACCase Gene Sequences

The target ACCase polynucleotide molecule naturally occurs in the genome of *Amaranthus palmeri, Amaranthus rudis, Amaranthsu chlorostachys, Amaranthus thunbergii, Amaranthus graecizans, Amaranthus hybridus, Amaranthus lividus, Amanaranthus spinosus, theophrasti, Ambrosia trifida, Commelina diffusa, Conyza candensis, Lolium multiflorum, Sorghum halepense, Xanthium strumarium, Euphorbia heterophylla, Kochia scoparia* and *Digitaria sanguinalis* and include molecules related to the expression of a polypeptide identified as an ACCase, that include regulatory molecules, cDNAs comprising coding and noncoding regions of an ACCase gene and fragments thereof as shown in Table 1.

Polynucleotide molecules were extracted from these plant species by methods standard in the field, for example, total RNA is extracted using TRIZOL® reagent (Invitrogen Corp. Carlsbad Calif., Cat. No. 15596-018; a monophasic solution of phenol and guanidine isothiocyanate), following the manufacturer's protocol or modifications thereof by those skilled in the art of polynucleotide extraction that may enhance recover or purity of the extracted RNA. Briefly, start with 1 gram of ground plant tissue for extraction. Prealiquot 10 milliliters (mL) TRIZOL® reagent to 15 mL conical tubes. Add ground powder to tubes and shake to homogenize. Incubate the homogenized samples for 5 minutes (min) at room temperature (RT) and then add 3 mL of chloroform. Shakes tubes vigorously by hand for 15-30 seconds(sec) and incubate at RT for 3 min. Centrifuge the tubes at 7,000 revolutions per minute (rpm) for 10 min at 4 degrees C. Transfer the aqueous phase to a new 1.5 mL tube and add 1 volume of cold isopropanol. Incubate the samples for 20-30 min at RT and centrifuge at 10,000 rpm for 10 min at 4 degrees C. Wash pellet with Sigma-grade 80 percent ethanol. Remove the supernatant and briefly air-dry the pellet. Dissolve the RNA pellet in approximately 200 microliters of DEPC treated water. Heat briefly at 65 degrees C. to dissolve pellet and vortex or pipet to resuspend RNA pellet. Adjust RNA concentration to 1-2 microgram/microliter.

DNA was extracted using EZNA SP Plant DNA Mini kit (Omega Biotek, Norcross Ga., Cat#D5511) and Lysing Matrix E tubes (Q-Biogen, Cat#6914), following the manufacturer's protocol or modifications thereof by those skilled in the art of polynucleotide extraction that may enhance recover or purity of the extracted DNA. Briefly, aliquot ground tissue to a Lysing Matrix E tube on dry ice, add 800 µl Buffer SP1 to each sample, homogenize in a bead beater for 35-45 sec, incubate on ice for 45-60 sec, centrifuge at ≥14000 rpm for 1 min at RT, add 10 microliter RNase A to the lysate, incubate at 65° C. for 10 min, centrifuge for 1 min at RT, add 280 µl Buffer SP2 and vortex to mix, incubate the samples on ice for 5 min, centrifuge at ≥10,000 g for 10 min at RT, transfer the supernatant to a homogenizer column in a 2 ml collection tube, centrifuge at 10,000 g for 2 min at RT, transfer the cleared lysate into a 1.5 ml microfuge tube, add 1.5 volumes Buffer SP3 to the cleared lysate, vortex immediately to obtain a homogeneous mixture, transfer up to 650 µl supernatant to the Hi-Bind column, centrifuge at 10,000 g for 1 min, repeat, apply 100 µl 65° C. Elution Buffer to the column, centrifuge at 10,000 g for 5 min at RT.

Next-generation DNA sequencers, such as the 454-FLX (Roche, Branford, Conn.), the SOLiD (Applied Biosystems,), and the Genome Analyzer (HiSeq2000, Illumina, San Diego, Calif.) were used to provide polynucleotide sequence from the DNA and RNA extracted from the plant tissues. Raw sequence data is assembled into contigs. The contig sequence is used to identify trigger molecules that can be applied to the plant to enable regulation of the gene expression. The target DNA sequence isolated from genomic (gDNA) and coding DNA (cDNA) from the various weedy plant species for the ACCase gene and the assembled contigs as set forth in SEQ ID NOs 1-93 and Table 1.

Example 2

Polynucleotides of the Invention Related to the Trigger Molecules

The gene sequences and fragments of Table 1 were divided into 200 polynucleotide (200-mer) lengths with 25 polynucleotide overlapping regions (SEQ ID NO:93-3900). These polynucleotides are tested to select the most efficacious trigger regions across the length of any target sequence. The trigger polynucleotides are constructed as sense or anti-sense ssDNA or ssRNA, dsRNA, or dsDNA, or dsDNA/RNA hybrids and combined with an organosilicone based transfer agent to provide a polynucleotide preparation. The polynucleotides are combined into sets of two to three polynucleotides per set, using 4-8 nmol of each polynucleotide. Each polynucleotide set is prepared with the transfer agent and applied to a plant or a field of plants in combination with a ACCase inhibitor containing herbicide, or followed by a ACCase inhibitor treatment one to three days after the polynucleotide application, to determine the effect on the plant's susceptibility to an ACCase inhibitor. The effect is measured as stunting the growth and/or killing of the plant and is measured 8-14 days after treatment with the polynucleotide set and ACCase inhibitor. The most efficacious sets are identified and the individual polynucleotides are tested in the same methods as the sets are and the most efficacious single 200-mer identified. The 200-mer sequence is divided into smaller sequences of 50-70-mer regions with 10-15 polynucleotide overlapping regions and the polynucleotides tested individually. The most efficacious 50-70-mer is further divided into smaller sequences of 25-mer regions with a 12 to 13 polynucleotide overlapping region and tested for efficacy in combination with ACCase inhibitor treatment. By this method it is possible to identify an oligonucleotide or several oligonucleotides that are the most efficacious trigger molecule to effect plant sensitivity to an ACCase inhibitor or modulation of an ACCase gene expression. The modulation of ACCase gene expression is determined by the detection of ACCase siRNA molecules specific to an ACCase gene or by an observation of a reduction in the amount of ACCase RNA transcript produced relative to an untreated plant or by merely observing the anticipated phenotype of the application of the trigger with the ACCase inhibitor containing herbicide. Detection of siRNA can be accomplished, for example, using kits such as mirVana (Ambion, Austin Tex.) and mirPremier (Sigma-Aldrich, St Louis, Mo.).

The target DNA sequence isolated from genomic (gDNA) and coding DNA (cDNA) from the various weedy plant species for the ACCase gene and the assembled contigs were set forth in SEQ ID NOs: 1-92 and Table 1.

The gene sequences and fragments of Table 1 were compared and 21-mers of contiguous polynucleotides were identified that have homology across the various ACCase gene sequences. The purpose was to identify trigger molecules that are useful as herbicidal molecules or in combination with an ACCase inhibitor herbicide across a broad range of weed species. The sequences, SEQ ID NO:3901-4530 represent the 21-mers that are present in the ACCase gene of at least eight of the weed species of Table 1. It is contemplated that additional 21-mers can be selected from the sequences of Table 1 that are specific for a single weed species or a few weeds species within a genus or trigger molecules that are at least 18 contiguous nucleotides, at least 19 contiguous nucleotides, at least 20 contiguous nucleotides or at least 21 contiguous nucleotides in length and at least 85 percent identical to an ACCase gene sequence selected from the group consisting of SEQ ID NO:1-92 or fragment thereof.

By this method it is possible to identify an oligonucleotide or several oligonucleotides that are the most efficacious trigger molecule to effect plant sensitivity to ACCase inhibitor or modulation of ACCase gene expression. The modulation of ACCase gene expression is determined by the detection of ACCase siRNA molecules specific to ACCase gene or by an observation of a reduction in the amount of ACCase RNA transcript produced relative to an untreated plant or by merely observing the anticipated phenotype of the application of the trigger with the ACCase inhibitor containing herbicide. Detection of siRNA can be accomplished, for example, using kits such as mirVana (Ambion, Austin Tex.) and mirPremier (Sigma-Aldrich, St Louis, Mo.).

The target DNA sequence isolated from genomic (gDNA) and coding DNA (cDNA) from the various weedy plant species for the ACCase gene and the assembled contigs as set forth in SEQ ID NOs 1-92 were divided into fragments as set forth in SEQ ID NOs 3901-4530.

Example 3

Methods Used in the Invention Related to Treating Plants or Plant Parts with a Topical Mixture of the Trigger Molecules Glyphosate-sensitive Palmer amaranth (*A. palmeri* R-22) plants where grown in the greenhouse (30/20 C day/night T; 14 hour photoperiod) in 4 inch square pots containing Sun Gro® Redi-Earth and 3.5 kg/cubic meter Osmocote® 14-14-

14 fertilizer. Palmer amaranth plants at 5 to 10 cm in height were treated with a pool of eight 8 short (21-22mer) single-strand antisense oligo DNA polynucleotides (ssDNA) targeting ACCase shown in Table 2 at 16 nmol, formulated in 10 millimolar sodium phosphate buffer (pH 6.8) containing 2% ammonium sulfate and 0.5% Silwet L-77. Plants were treated manually by pipetting 10 µL of polynucleotide solution on four fully expanded mature leaves, for a total of 40 microliters of solution per plant. Twenty-four and forty-eight hours later, the plants were treated with clethodim (SelectMax®, 0.97 lb ai per gallon; ACCase inhibitor) at 272 g ai/ha, crop oil concentrate (COC) at 1% was added to the herbicide treatments. Four replications of each treatment were conducted. Plant height was determined just before ssDNA treatment and at intervals upto twelve days after herbicide treatments to determine effect of the oligonucleotide and herbicide treatments.

TABLE 2 ssDNA ACCase oligonucleotides

| | | |
|---|---|---|
| OLIGO1 SEQ ID NO: 4531 | gtcttacaagggttctcaa |
| OLIGO2 SEQ ID NO: 4532 | ATCTATGTTCACCTCCCTGTG |
| OLIGO3 SEQ ID NO: 4533 | ATAAACCATTAGCTTTCCcGG |
| OLIGO4 SEQ ID NO: 4534 | TTtATtGgAaCAaGCGgAgTT |
| OLIGO5 SEQ ID NO: 4535 | TATAGCACCACTTCCCGATAG |
| OLIGO6 SEQ ID NO: 4536 | GCACCACGAGGATCACAAGAA |
| OLIGO7 SEQ ID NO: 4537 | CCACCCGAGAAACCTCTCCAA |
| OLIGO8 SEQ ID NO: 4538 | CAGTCTTGaCGAGTGATTCCT |

The results of the treatments are shown in FIG. 1 and demonstrated that plants treated with 16 nmol and the clethodim herbicide caused 22 percent reduction in plant height relative to the untreated control and clethodim alone caused 0 percent reduction in plant height. Surprising result since dicot plants are not normally sensitive to ACCase inhibitor herbicides.

An additional test was conducted to determine which of the ACCase oligonucleotides was responsible for the result. In this test, each oligonucleotide was applied to four plants at 4 nmol (nanomole) per plant, the herbicide was applied 24 hours after the oligonucleotide treatment and the plants were rated for growth effects. This followup test identified that formulated oligo6 (SEQ ID NO:4536) had the largest effect and was able to reduce the plant growth by and average of 40 percent relative to untreated plants. This result provides an opportunity to broaden the spectrum of use for ACCas inhibitor herbicides to include dicot weeds.

Example 4

A Method to Control Weeds in a Field

A method to control weeds in a field comprises the use of trigger polynucleotides that can modulate the expression of an ACCase gene in one or more target weed plant species. An analysis of ACCase gene sequences from seventeen plant species provided a collection of 21-mer polynucleotides that can be used in compositions to affect the growth or develop or sensitivity to ACCase inhibitor herbicide to control multiple weed species in a field. A composition containing 1 or 2 or 3 or 4 or more of the polynucleotides of SEQ ID NO: 3901-4530 would enable broad activity of the composition against the multiple weed species that occur in a field environment.

The method includes creating a composition that comprises components that include at least one polynucleotide of SEQ ID NO: 3901-4530 or any other effective gene expression modulating polynucleotide essentially identical or essentially complementary to SEQ ID NO:1-92 or fragment thereof, a transfer agent that mobilizes the polynucleotide into a plant cell and a ACCase inhibiting herbicide and optionally a polynucleotide that modulates the expression of an essential gene and optionally a herbicide that has a different mode of action relative to an ACCase inhibitor. The polynucleotide of the composition includes a dsRNA, ssDNA or dsDNA or a combination thereof. A composition containing a polynucleotide can have a use rate of about 1 to 30 grams or more per acre depending on the size of the polynucleotide and the number of polynucleotides in the composition. The composition may include one or more additional herbicides as needed to provide effective multi-species weed control. A field of crop plants in need of weed plant control is treated by spray application of the composition. The composition can be provided as a tank mix, a sequential treatment of components (generally the polynucleotide followed by the herbicide), a simultaneous treatment or mixing of one or more of the components of the composition from separate containers. Treatment of the field can occur as often as needed to provide weed control and the components of the composition can be adjusted to target specific weed species or weed families.

TABLE 1

ACCase gene sequences isolated from weedy plant species

| SEQ ID NO | SPECIES | TYPE | LENGTH | SEQ |
|---|---|---|---|---|
| 1 | Abutilon theophrasti | cDNA Contig | 1036 | TTGCTGTAACTGATCTTGCCTGCAGTAAGAAACTGCCTTTA<br>ATTTATTTGGCTGCGAACTCTGGTGCTCGTATTGGGGTAGC<br>TGAAGAAGTCAAAGCCTGCTTTAAAGTTGGTTGGTCTGAT<br>GAATCCAGCCCTGAGCGTGGTTTTCAGTACATTTACATAAC<br>TCCTGAGGATTATACTAGGATTGGATCATCGGTCATTGCAC<br>ATGAGATGAAGCTGGCCAGTGGAGAGAGCAGATGGGTGA<br>TAGATACTATTGTTGGGAAGGAGGATGGTTTGGGGGATC<br>GAGAACTTAACAGGTAGTGGAGCCATTGCTGGTGCATACT<br>CTCGGGCATACAAAGAAACCTTTACCCTAACGTATGTGACT<br>GGTAGAACTGTGGGAATTGGTGCTTATCTTGCTCGTCTTGG<br>CATGCGGTGTATACAAAGACTCGATCAACCCATTATTTTGA<br>CTGGTTTCTCAGCATTGAACAAACTTCTAGGTCGTGAGGTG<br>TATAGCTCCCACATGCAACTTGGTGGACCTAAAATCATGGC<br>AACAAATGGGGTGGTTCATCTCACCGTCTCAGATGATCTTG |

TABLE 1-continued

ACCase gene sequences isolated from weedy plant species

| SEQ ID NO | SPECIES | TYPE | LENGTH | SEQ |
|---|---|---|---|---|
| | | | | AAGGGGTGTCAGCTATTTTGAACTGGATAAGTTGCATACC TCCTCATATTGGTGGTCCACTTCCCATTTTAAACCCATCAGA TCCTCCAGAAAGGCCTGTGGAGTACATCCCGGAAAATTCA TGTGATCCTCGTGCCGCTATTTGTGGTGCTTTAGATAGTAA TGGCAAGTGGAAGGGCGGTATTTTTGACAGGGATAGCTTT GTGGAGACGCTCGAAGGTTGGGCTAGAACAGTTGTCACA GGAAGGGCAAAGCTTGGAGGAATTCCTGCAGGAATAGTT GCAGTTGAGACACAGACGGTGATGCAGGTTATCCCTGCCG ATCCAGGACAACTTGATTCCCATGAAAGAGTTGTCCCTCAA GCTGGACAGGTATGGTTTCCGGATTCTGCTACAAAGACAG CTCAGGCAATAATGGATTTCAACAGGGAAGAGCTTCCACT TTTCATTCTTGCCAATTGGAGAGGCT |
| 2 | Amaranthus graecizans | cDNA Contig | 1479 | ACCACGAGAAGATGCTTTCTTCCTTGCGGTTACAAATCTTG CTTGTGCGAAGAAACTTCCTCTTATTTATCTGGCTGCAAATT CAGGAGCTCGACTTGGTGTTGCCGAAGAGCTAAATCCTG CTTTAAAGTTGGCTGGTCGGATGAGTCAAACCCCGAGAGT GGATTTCAGTATGTCTTCTTAACCCCGGAAGATTACGATCG TATCGGATCGTCAGTCATAGCCCACGAGTTAAAACTCGAA AGTGGAGAAAAAAGATGGGTTATAGACACAGTTGTCGGA AAGGAGGACGGATTAGGTGTCGAGAATCTATCAGGAAGT GGTGCTATAGCCAGTGCATACTCAAGGGCTTACAAGGAAA CATTTACTCTGACTTTTGTAACTGGTAGAACGGTCGGTATT GGTGCCTATCTTGCTCGCCTTGGGATGCGTTGTATACAGAG GCTTGACCAGCCTATAATTCTCACGGGTTTTTCTGCGTTAA ATAAACTTCTTGGTCGGGAGGTTTACAGTTCACACATGCAA CTTGGTGGACCGAAGATTATGGGCACAAACGGGGTAGTTC ATCTTACAGTTTCCGATGATCTTGAAGGCATTTCATCTATCT TGAAGTGGCTGAGCTATGTTCCACCCTATGCAGGTGGTGA ACTTCCGATTTCTCGGTGTTTAGACCCTCCAGAAAGACCCG TTGCGTATTTGCCTGAAAATTCTTGTGATCCTCGTGGTGCT ATATCTGGTACAGTTGACTCCACCGGTAAATGGCATGGGG GTATTTTCGACAAGGATAGTTTTGTGGAAACCTTAGAAGG CTGGGCACGAACAGTTGTCACGGGAAGGGCTAAACTTGG AGGAATTCCAGTTGGGATAGTTGCCGTTGAGACGCAGACT GTTATGCAAGTAATCCCAGCAGATCCCGGTCAACTCGACTC ACACGAGAGAGTCGTACCACAAGCAGGGCAAGTATGGTTC CCAGATTCCGCATCCAAGACAGCACAAGCGCTGATGGATT TCAACCGGGAAGAACTACCACTTTTCATTTTAGCTAATTGG AGAGGTTTCTCGGGTGGACAAAGGGATCTCTTTGAAGGGA TCCTTCAAGCCGGATCCACCATTGTCGAAAATCTTAGGACT TATAATCAACCCGTTTTTGTTTATATACCAATGATGGGGGA GCTTCGAGGAGGCGCATGGGTGGTCGTGGATAGTCGAAT TAATTCCGATCATATAGAAATGTACGCCGACCAAACAGCTA AAGGAAATGTGCTTGAACCCGAAGGAATGATCGAGATTAA GTTCAGAACCAAGGAACTTCTCGAGTGTATGGGAAGGCTT GATCAACAACTCATCGGTCTCAAGGAAAAACTAGCAGAAG CCAAGAGCTCTAATTCCTACGATAAAATCGACCCCCTGCAG CAACAAATAAAAGCCCGCGAGAAGCAACTATTGCCTCTAT ATACTCAGATAGCCACCAAATTTGC |
| 3 | Amaranthus graecizans | cDNA Contig | 638 | AAATATACTCCTTCCCGTGATCGTCAATGGCATCTTTACAC GGTTATTGATAAACCACTCATTCGGAGGATGTTTTTGAGAA CCCTTGTAAGACAACCCATCTCTGAGTTCACAGGCGTCGAA CTAAGCGCTCTTGAAACACAAAAGCCCATCTCTTTTACTTCA AGAAGCATCCTAAGGTCCTTAACAACCGCCATGGAGGAGT TGGAACTCAATGCACATAGTGCTTCATTGAAACCCGATCAC GCTCATATGTACTTGTACATTGTTCGAGAGCAACAAATATA CGATCTTGTGCCATATCACAGGGAGGTGAACATAGATTAC CAACAAGAAGAGGCTTCGGTTCAATTCTTTTTGGAAGAGC TCGCGCATGAAATCCACAGTCTTGCTGGTGTAAGGATGCA TAAACTAAATGTTTGTGAGTGGGAAGTGAAACTTCGGATA TCTTCTCCCGGGAAAGCTAATGGTTTATGGAGGGTGGCGG TTACTAATGTGACTGGTCAGACCTGTTCGGTACATGTTTAT CGTGAATTGGAAGATAGCAACCTACATGAAATGGTCTACC ATTCATTATCCGTTCACGGTCCCCACCATGGGGTACCTGTG AATGCACCCTATCAACCACTAGGTGGCAT |
| 4 | Amaranthus hybridus | cDNA Contig | 2174 | TGAACATAGATTACCAACAAGAAGAGGCTTCGGTTCAATT CTTTTTGGAAGATCTCGCGCATGAAATCCATAGTCTTGCTG GTGTAAGGATGCATAAACTAAATGTTTGTGAGTGGGAAGT GAAACTTCGGATATCATCTCCCGGGAAAGCTAATGGTTTAT GGAGGGTGGCAGTTACTAATGTGACTGGTCATACCTGTTC GGTACATGTTTATCGTGAATTGGAAGATAGCAACCTACAT GAAATGGTCTACCATTCAGTATCTGTTCACGGCCCCCACCA TGGGGTACCTGTGAATGCACCCTATCAACCACTCGGTGGC |

TABLE 1-continued

ACCase gene sequences isolated from weedy plant species

| SEQ ID NO | SPECIES | TYPE | LENGTH | SEQ |
|---|---|---|---|---|
| | | | | ATCTCCCGTAAGCGACTTCAGGCCATGAAGAGTAGCACAA |
| | | | | CATACTGTTACGATTTTCCACTGGCTTTCTCAACTGCCCTGA |
| | | | | AGCAATCATGGGCATCGGAAGCTCCGGATGTCAAGAAACC |
| | | | | CTCGGACAAAGCACTTTTGAAAGTAACCGAGCTAGCATTT |
| | | | | GCTGATCCAAAAGGCACATGGGAACTCCGCTTGTTCCAA |
| | | | | TAAATCGCAAGCCTGGTATGAACGATGTTGGCATGGTAGC |
| | | | | CTGGTACTTGGAAATGTCCACCCCCGAGTTCCCTAACGGAA |
| | | | | GAACAATAATGGTTGTAGCTAATGATGTTACCTTCAAGGCC |
| | | | | GGATCTTTCGGACCACGAGAAGATGCTTTCTTCCTTGCTGT |
| | | | | TACAAATCTTGCTTGCGCGAAGAAACTTCCTCTTATTTATCT |
| | | | | GGCTGCCAATTCAGGAGCTCGACTTGGTGTTGCCGAAGAG |
| | | | | CTAAAATCCTGCTTTAAAGTTGGCTGGTCGGATGAGTCAA |
| | | | | ACCCCGAGAGTGGATTTCAGTATGTCTACTTAACCCCTGAA |
| | | | | GATTACGATCGTATAGGATCGTCAGTCATAGCCCACGAGT |
| | | | | TAAAACTCGAAAGTGGAGAAAAAGATGGGTTATAGACA |
| | | | | CCGTTGTCGGTAAGGAGGACGGATTAGGTGTCGAGAATCT |
| | | | | ATCAGGAAGTGGTGCTATAGCCAGTGCATACTCAAGGGCT |
| | | | | TACAAGGAAACATTTACTCTGACTTTTGTAACCGGTAGAAC |
| | | | | GGTCGGTATTGGTGCCTATCTTGCTCGTCTTGGGATGCGTT |
| | | | | GTATACAGAGGCTTGACCAGCCTATAATTCTCACGGGTTTT |
| | | | | TCTGCGTTAAATAAACTTCTCGGTCGGGAGGTTTACAGTTC |
| | | | | ACACATGCAACTTGGTGGACCGAAGATAATGGGCACAAAC |
| | | | | GGGGTAGTTCATCTTACAGTTTCCGATGATCTTGAAGGCAT |
| | | | | TTCATCTATCTTGAAGTGGCTGAGCTATGTTCCACCCTATTC |
| | | | | AGGTGGTGAACTTCCGATTTCTCGGTGTTTAGACCCTCCCG |
| | | | | AAAGACCGGTTGCGTATTTGCCTGAAAATTGTTGTGATCCT |
| | | | | CGTGGGGCTATATCTGGTACGGTTGACTCCGCCGGTAAAT |
| | | | | GGTTTGGGGGTATTTTCGACAAGGATAGTTTTGTGGAAAC |
| | | | | CTTAGAAGGATGGGCACGAACAGTTGTCACGGGAAGGGC |
| | | | | TAAACTCGGAGGAATTCCAGTTGGCATAGTTGCTGTTGAG |
| | | | | ACACAGACTGTTATGCAAGTAATCCCAGCAGATCCCGGTC |
| | | | | AACTCGACTCACATGAGAGTCGTACCACAAGCAGGGCA |
| | | | | AGTATGGTTCCCAGATTCCGCATCCAAGACAGCACAAGCG |
| | | | | CTGATGGATTTCAACCGGGAAGAACTCCCACTTTTCATTTT |
| | | | | AGCTAATTGGAGAGGTTTCTCGGGTGGACAAAGGGATCTC |
| | | | | TTTGAAGGGATCCTTCAGGCTGGATCCACCATAGTCGAAA |
| | | | | ATCTTAGGACTTATAATCAACCCGTTTTTGTTTATATCCCTA |
| | | | | TGATGGGGGAGCTTCGAGGAGGCGCATGGGTGGTCGTCG |
| | | | | ATAGTCGAATTAATTCCGACCATATAGAAATGTACGCCGAC |
| | | | | CAAACAGCTAAAGGAAATGTGCTTGAACCGGAAGGAATG |
| | | | | ATCGAGATTAAGTTCCGAACCAAGGAACTTCTCGAGTGTAT |
| | | | | GGGAAGGCTTGACCAACAACTCATCGGTCTCAAGGAAAAA |
| | | | | CTAGCCGAAGCCAAGAGCTCTAATTCCTACGATAAAATCG |
| | | | | AGCCCCTGCAGCAACAAATAAAAGCCCGCGAGAAGCAACT |
| | | | | ATTGCCTCTTTATACTCAGATAGCCACCAAATTTGCCGAGT |
| | | | | TGCATGATACGTCTTTAAGGATGGCTGCCAAA |
| 5 | Amaranthus hybridus | cDNA Contig | 530 | CACTCGTCAAGACTGTTCGAGATGCTGCAGGTGAACGGTT |
| | | | | GACCCATAAGTCGGCTTTGGAGTTGATCCGGAAATGGTTC |
| | | | | AATGAGTCAGATATTTCCGGAGAGGCTTCCGATGCTTGGG |
| | | | | CTGATGATGCGACCTTCTTTAAGTGGAAGGACAATACCGC |
| | | | | TAACTACGAGGAGAAGTTGAAAGAGTTGCGGGTTCAGAA |
| | | | | GGTATTGGATCAGCTGTCGAATATTGGAGATTCGGTAACT |
| | | | | AATTTGAGGGCTCTGCCTCAGGGTCTTGCTGCCCTACTTCA |
| | | | | AAAGGTGGATCCATCGAGTCGAGAAGAACTAGTCGAGGA |
| | | | | ACTCCGAAAAGTGCTCACTTGATTTCGCAACCGTTGATGGT |
| | | | | GAAGTGAAACCTTCTTGGTTTCATCATGGTAGAAAATATTA |
| | | | | TTAGGCAAATCTATAATTTTTAGTGACATCAATTGTTTTAGA |
| | | | | CAATAGTATTGAACTAATTTATTTAATTAAATTGTATAAATA |
| | | | | GGAGACCTTGAATTCATTTGAATTAAGTGGCTTATGCTTGC |
| | | | | ATTA |
| 6 | Amaranthus hybridus | cDNA Contig | 527 | TATAGATGAAGTAGTACAGAGTTTGCTGGAATGCCTTGAT |
| | | | | AGTCCCGAACTTCCATTCCTTCAATGGCAAGAATGCTTGTC |
| | | | | TGTGCTGGCAACACGACTTCCCAAAGATCTGAGATACGAA |
| | | | | TTGGAATCAAAATCTAGAGCTTTTGAAGGGATTACCAACAC |
| | | | | CCAGAACGTAGAATTTCCTGCTAAGTTGTTGAAAAGCATTC |
| | | | | TTGAGGACCATTTAAACTCATGCCACGAGAAAGATAAAGG |
| | | | | AGCTCAAGAGAGGCTTATTGAGCCTCTTATGGCTCTTGTAA |
| | | | | AGTCTTACGAAGGTGGGCGAGAAAGTCATGCTCGTTTTAT |
| | | | | TGTTCAATCTTTATTTGAAGAGTATTTATCCGTTGAAGAATT |
| | | | | GTTTAGCGACAATCTCCAGGCTGATGTGATTGAACGTCTCC |
| | | | | GCCTTCAGTATAAGAAGGATCTGCTGAAGATTGTTGACATT |
| | | | | GTACTGTCGCATCAGGGTGTTAAGAATAAAAATAAGCTGA |
| | | | | TTCTACGACTCATGGAACAGCTGGTTTACCCAAATCCCG |

TABLE 1-continued

ACCase gene sequences isolated from weedy plant species

| SEQ ID NO | SPECIES | TYPE | LENGTH | SEQ |
|---|---|---|---|---|
| 7 | Amaranthus lividus | cDNA Contig | 1310 | CGAGAGTGGATTTCAGTATGTCTACTTAACCCCTGAAGATT<br>ACGATCGTATAGGATCGTCAGTCATAGCCCACGAGTTAAA<br>ACTCGAAAGTGGAGAAAAAAGATGGGTTATAGACACCGTT<br>GTCGGTAAGGAGGACGGATTAGGTGTCGAGAATCTATCA<br>GGAAGTGGTGCTATAGCCAGTGCATACTCAAGGGCTTACA<br>AGGAAACATTTACTCTGACTTTTGTAACCGGTAGAACGGTC<br>GGTATTGGTGCCTATCTTGCTCGTCTTGGGATGCGTTGTAT<br>ACAGAGGCTTGACCAGCCTATAATTCTCACGGGTTTTTCTG<br>CGTTAAATAAACTTCTCGGTCGGGAGGTTTACAGTTCACAC<br>ATGCAACTTGGTGGACCGAAGATAATGGGCACAAACGGG<br>GTAGTTCATCTTACAGTTTCCGATGATCTTGAAGGCATTTC<br>ATCTATCTTGAAGTGGCTGAGCTATGTTCCACCCTATTCAG<br>GTGGTGAACTTCCGATTTCTCGGTGTTTAGACCCTCCCGAA<br>AGACCGGTTGCGTATTTGCCTGAAAATTGTTGTGATCCTCG<br>TGGGGCTATATCTGGTACGGTTGACTCCTCCGGTAAATGG<br>TTTGGGGGTATTTTCGACAAGGATAGTTTTGTGGAAACCTT<br>AGAAGGATGGGCACGAACAGTTGTCACGGGAAGGGCTAA<br>ACTCGGAGGAATTCCAGTTGGCATAGTTGCTGTTGAGACG<br>CAGACTGTTATGCAAGTAATCCCAGCAGATCCCGGTCAACT<br>CGACTCACATGAGAGAGTCGTACCACAAGCAGGGCAAGTA<br>TGGTTCCCAGATTCCGCATCCAAGACAGCACAAGCGCTGA<br>TGGATTTCAACCGGGAAGAACTCCCACTTTTCATTTTAGCT<br>AATTGGAGAGGTTTCTCGGGTGGACAAAGGGATCTCTTTG<br>AAGGGATCCTTCAGGCTGGATCCACCATAGTCGAAAATCTT<br>AGGACTTATAATCAACCCGTTTTTGTTTATATCCCTATGATG<br>GGGGAGCTTCGAGGAGGCGCATGGGTGGTCGTCGATAGT<br>CGAATTAATTCCGACCATATAGAAATGTACGCCGATCAAAC<br>AGCTAAAGGAAATGTGCTTGAACCGGAAGGAATGATCGA<br>GATTAAGTTCCGAACCAAGGAACTTCTCGAGTGTATGGGA<br>AGGCTTGACCAACAACTCATCGGTCTCAAGGAAAAACTAG<br>CCGTAGCCAAGAGCTCTAATTCCTACGATAAAATCGAGCCC<br>CTGCAGCAACAAATAAAAGCCCGCGAGAAGCAACTATTGC<br>CTCTTTATACTCAGATAG |
| 8 | Amaranthus lividus | cDNA Contig | 1309 | AAAGCATTCTTGAGGACCATTTAAATTCATGCCACGAGAAA<br>GATAAAGGAGCTCAAGAGAGGCTTATTGAGCCTCTTATGG<br>CTCTTGTAAAGTCTTACGAAGGTGGGCGAGAAAGTCATGC<br>TCGTTTTATTGTTCAATCTTTATTTGAAGAGTATTTATCCGT<br>TGAAGAATTGTTTAGCGACAATCTCCAGGCTGATGTGATT<br>GAACGTCTCCGTCTTCAGTATAAGAAGGATCTGCTGAAGA<br>TTGTTGACATTGTACTGTCGCATCAGGGTGTTAAGAATAAA<br>ATAAGCTGATTCTACGACTCATGGAACAGCTGGTTTACCCA<br>AATCCCGCTGCATACAGGGGGAAACTTATCCGTTTCTCTCA<br>ATTGAACCATACAATGTATTCTGAGTTGGCACTAAAGGCCA<br>GTCAATTGCTTGAACAAACGAAATTGAGTGAGCTCCGTTC<br>GAACATTGCTAGAAACCTCTCTGAGCTAGAAATGTTTACCG<br>AGGATGGCGAAAACATGGATACTCCAAAAAGAAAAAGTG<br>CTATTAATGAACGTATGGAGGCGCTTGTGAGTACTCCTCTA<br>GCTGTCGAAGATGCCCTTGTTGGTTTGTTTGATCATAGTGA<br>TCATACACTTCAGAGGCGGGTTGTTGAGACCTATGTTCGG<br>AGGCTTTATCAGCCTTATCTTGTCAAGGGAAGTGTCAGGAT<br>GCTGTGGCACAGATCAGGCTTCATAGCTTTATGGGAATTT<br>GTTGAGGAGAATATTGACCGAACAAATTTTTCTGATCTGAC<br>TACAAACAGTGGGAACCATAGTGAGCGAAAGTGGGGGGC<br>CATGGTCGTTATTAAAACTCTTCAGTTCTTGCCATCGGTAAT<br>TGCTGCAGCATTGAGAGAAACAACTCATAGTTCCGATCAAT<br>CAACTTCCACTGGCTCTATAGAATCAGTCATCCATGGAAAT<br>ATGCTGCACATTGCACTAGTGGGGGTGAATAACCAGATGA<br>GCTTGTTGCAGGATAGTGGTGATGAAGATCAGGCTCAAGA<br>GAGAATCGATAAGTTGGCCAAAATTCTGAGAGAACAAGAA<br>GTGAGTTCAGCCCTTCGTGCTGTTGGTGTTGGTGTGATTAG<br>TTGCATCATACAGAGAGATGAAGGGCGAACTCCGATGAG<br>GCATTCATTCTATTGGTCAGCAGAAAACAATATTATAGTG<br>AGGAACCTTTACTACGTCATTTGGAACCCCTCTATCTATGT<br>ATCTCGAGCTGGACAAGCTTAAGGGTTATGAAGATATCAA<br>ATATACTCCTTCCCGTGATCGTCAATGGCATCTTTACACGG<br>TTATTGATAAAC |
| 9 | Amaranthus lividus | cDNA Contig | 638 | GGCAGTTACTAATGTGACTGGTCATACCTGTTCGGTACATG<br>TTTATCGTGAATTGGAAGATAGCAACCTACATGAAATGGTC<br>TACCATTCAGTATCTGTTCACGGCCCCCACCATGGGGTACC<br>TGTGAATGCACCCTACCAACCACTCGGTGGCATCTCCCGTA<br>AGCGACTTCAGGCCATGAAGAGTAGCACAACATACTGTTA<br>TGATTTTCCACTGGCTTTCTCAACTGCCCTGAAGCAATCAT<br>GGGCATCGGAAGCTCCGGATGTCAAGAAACCCTCGGACAA<br>AGCACTTTTGAAAGTAACCGAGCTAGCATTTGCTGATCCAA |

TABLE 1-continued

ACCase gene sequences isolated from weedy plant species

| SEQ ID NO | SPECIES | TYPE | LENGTH | SEQ |
|---|---|---|---|---|
| | | | | AAGGCACATGGGGAACTCCGCTTGTTCCAATAAATCGCAA
GCCTGGTATGAACGATGTTGGCATGGTAGCCTGGTACTTG
GAAATGTCCACCCCCGAGTTCCCTAACGGAAGAACAATAA
TGGTTGTAGCTAATGATGTTACCTTCAAGGCCGGATCTTTC
GGACCACGAGAAGATGCTTTCTTCCTTGCTGTTACAAATCT
TGCTTGCGCGAAGAAACTTCCTCTTATTATCTGGCTGCCAA
TTCAGGAGCTCGACTTGGTGTTGCCGAAGAGCTAAAATCC
TGCTTTAAAGTTGGCTGGTCGGATGAGTC |
| 10 | Amaranthus palmeri | cDNA Contig | 4689 | CATAATACATTAAGTCCAGTATCTATACAAGAGATTAAACC
AGCTACAAAAAGCTGATGAGCACAAGATACATCAAACAA
AAACCAGCAGCTGATAGCAGTATTTCCTTTTTCTTAATGGC
AAGAATGCTTGTCTGTGCTGGCAACACGACTCCCCAAGA
TCTGAGATACGAATTGGAATCAAAATCTAGAGCTTTTGAA
GCGATTACCAACACCCCAAACATAGAATTTCCTGCTAAGTT
GTTGAAAAGTATTCTTGAGGACCATTTAAACTCATGCCAAG
AGAAAGATAAAGGAGCTCAAGAGAGGCTTATTGAGCCTCT
TATGGTTCTTGTAAAGTCTTACGAAGGTGGGCGAGAAAGT
CATGCTCGTTTTATTGTTCAATCTTTATTTGAAGAGTATTTA
TCCGTTGAAGAATTGTTTAGCGACAATCTCCAGGCTGATGT
GATTGAACGTCTCCGCCTTCAGTATAAGAAGGATCTGCTG
AAGATTGTTGACATTGTACTGTCGCATCAGGGTGTTAAGA
ATAAAAATAAGCTGATTCTACGACTCATGAACAGCTGGTT
TACCCAAATCCCGCTGCATACAGGGGGCAACTTATCCGTTT
CTCTCAATTGAACCATACAATGTATTCTGAGTTGGCACTAA
AGGCCAGTCAATTGCTTGAACAAACGAAATTGAGTGAGCT
CCGTTCGAACATTGCTAGAAACCTCTCTGAGCTAGAAATGT
TTACCGAGGATGGCGAAAACATGGATACTCCAAAAAGAAA
AAGTGCTATTAATGAACGTATGGAGGCCCTTGTGAGTACT
CCTCTAGCTGTTGAAGATGCCCTTGTCGGTTTGTTTGATCA
TAGTGATCATACACTTCAGAGGCGGGTTGTTGAGACCTAT
GTTCGGAGGCTTTATCAGCCTTATCTTGTCAAGGGAAGTGT
CAGGATGCTGTGGCACAGATCAGGTTTCATAGCTTTATGG
GAATTTGTTGAGGAGAATATTGACCGAACAAATTTTTCNG
ATGATCTGACTACAAACAGTGGGAACCATAGTGAGCGAAA
GTGGGGGCCATGGTCGTTATTAAAACTCTTCAGTTCTTGC
CATCGGTGATTGCTGCAGCATTGAGAGAAACAACTCATAG
TTCCGATCAATCAACTTCCACTGGCTCTATAGAATCAGTCA
TCCATGGAAATATGCTGCACATTGCACTAGTGGGGGTGAA
CAACCAGATGAGCTTGTTGCAGGATAGTGGTGATGAAGAT
CAGGCTCAAGAGAGAATCGATAAATTGGCCAAAATTCTGA
GAGAGCAAGAAGTGAGTTCAGCCCTTCGTGCTGCTGGTGT
TGGTGTGATTAGTTGCATCATACAGAGAGATGAAGGGCGA
ACTCCGATGAGGCATTCATTCTATTGGTCAGCAGAAAAACA
ATATTATAGTGAGGAGCCTTTACTACGTCATTTGGAACCCC
CTCTATCTATGTATCTCGAGCTGGACAAGCTTAAGGGTTAT
GAAGATATCAAATATACTCCTTCCCGTGATCGTCAATGGCA
TCTTTACACGGTTATTGATAAACCATTCATTCGGAGGATGT
TTTTGAGAACCCTTGTAAGACAACCCATCTCTGAGTTCACA
GGCGTCGAACTAAGCGCTCTTGAAACACAAAAGCCTATCT
CTTTCACTTCAAGAAGCATCCTAAGGTCCTTAACAACCGCC
ATGGAGGAGTTGGAGCTCAATGCACATAGTGCTTCACTGA
AACCCGATCACGCTCATATGTACTTGTACATTGTCCGAGAG
CAACAAATATACGATCTTGTGCCATATCACAGGGAGGTGA
ACATAGATCACCAACAAGAAGAGGCTTCGGTTCAATTCTTT
TTGGAAGATCTCGCGCATGAAATCCATAGTCTTGCTGGTGT
AAGGATGCATAAACTAAATGTTTGTGAGTGGGAAGTGAAA
CTTCGGGTATCATCTCCCGGGAAAGCTAATGGTTTATGGA
GGGTGGCAGTTACTAATGTGACTGGTCATACCTGTTCGGT
ACATGTTTATCGTGAATTGGAAGATAGCAACCTACATGAA
ATGGTCTACCATTCAGTATCTGTTCACGGCCCCCACCATGG
GGTACCTGTGAATGCACCCTATCAACCACTCGGTGGCATC
GCCCGTAAGCGACTTCAGGCCATGAAAAGTAGCACAACTT
ACTGTTACGATTTTCCACTGGCTTTCTCAACTGCCCTGAAGC
AATCATGGGCATCGGAAGCTCCGGATGTCAAGAAACCCTC
GGACAAAGCGCTTTTGAAAGTAACCGAGCTTAGCATTTGC
TGATCCAAAAGGCACATGGGGAACTCCGCTTGTTCCAATA
AATCGCAAGCCTGGTATGAACGATGTTGGCATGGTAGCCT
GGTACATGGAAATGTCCACCCCCGAGTTCCCTAACGGAAG
AACAATAATGGTTGTAGCTAATGATGTTACCTTCAAGGCCG
GATCTTTCGGACCACGAGAAGATGCTTTCTTCCTTGCTGTT
ACAAATCTTGCTTGCGCGAAGAAACTTCCTCTTATTTATCTG
GCTGCCAATTCAGGAGCTCGACTTGGTGTTGCCGAAGAGC
TAAAATCCTGCTTTAAAGTTGGCTGGTCGGATGAGTCAAAT
CCCGAGAGTGGATTTCAGTATGTCTACTTAACCCCTGAAGA
TTACGATCGTATAGGATCGTCAGTCATAGCCCACGAGTTAA |

TABLE 1-continued

ACCase gene sequences isolated from weedy plant species

| SEQ ID NO | SPECIES | TYPE | LENGTH | SEQ |
|---|---|---|---|---|
| | | | | AACTCGAAAGTGGAGAAAAAAGATGGGTTATAGATACCGT<br>TGTAGGTAAGGAGGACGGATTAGGTGTTGAGAACCTATC<br>GGGAAGTGGTGCTATAGCCAGTGCATACTCAAGGGCTTAC<br>AAGGAAACATTTACTCTGACTTTTGTAACCGGAAGAACGG<br>TCGGTATTGGTGCCTATCTTGCTCGTCTTGGGATGCGTTGT<br>ATACAGAGGCTTGACCAGCCTATAATTCTCACGGGTTTTTC<br>TGCTTTAAATAAACTTCTCGGCCGGGAGGTTTATAGTTCAC<br>ACATGCAACTTGGTGGACCGAAGATTATGGGCACAAACGG<br>GGTAGTTCATCTTACAGTTTCCGATGATCTTGAAGGCATTT<br>CATCTATCTTGAAGTGGCTGAGCTACGTTCCACCCTATTCA<br>GGTGGTGAACTTCCGATTTCTCGGTGTTTAGACCCTCCAGA<br>AAGACCGGTTGCGTATTTGCCTGAAAATTCTTGTGATCCTC<br>GTGGTGCTATATCTGGTACGGTTGACTCCACCGGTAAATG<br>GTTAGGGGGTATTTTCGACAAAGATAGTTTTGTGGAAACC<br>TTAGAAGGATGGGCGCGAACAGTTGTCACGGGAAGGGCT<br>AAGCTCGGAGGAATTCCAGTTGGCATAGTTGCCGTTGAGA<br>CGCAGACTGTTATGCAAGTAATCCCAGCAGATCCCGGTCA<br>ACTCGACTCACACGAGAGAGTCGTACCACAAGCAGGGCAA<br>GTATGGTTCCCAGATTCGCATCCAAGACAGCACAAGCGC<br>TGATGGATTTCAACCGGGAAGAACTCCCACTTTTCATTTTA<br>GCTAATTGGAGAGGTTTCTCGGGTGGACAAAGGGATCTCT<br>TTGAAGGGATCCTTCAGGCCGGATCCACCATAGTTGAAAA<br>TCTTAGGACTTATAATCAACCCGTTTTTGTTTATATCCCTAT<br>GATGGGGGAGCTTCGAGGAGGCGCATGGGTGGTCGTCGA<br>TAGTCGAATTAATTCCGACCATATAGAAATGTACGCCGACC<br>AAACAGCTAAAGGAAATGTGCTTGAACCGGAAGGAATGA<br>TCGAGATTAAGTTCCGAACCAAGGAACTTCTCGAGTGTAT<br>GGGAAGGCTTGATCAACAACTCATCGGTCTCAAGGAAAAA<br>CTAGCCGAAGCCAAGAGCTCTAATTCCTACAATAAAATCGA<br>GCCCCTGCAGCAACAAATAAAAGCCCGCGAGAAGCAACTA<br>TTGCCTCTATATACTCAAATAGCCACCAAATTTGCCGAGTT<br>GCACGATACGTCTTTAAGGATGGCTGCCAAAGGAGTTATT<br>AGGGACGTCTTGGAATGGAAAAGCTCGCGTTCGTTCTTTT<br>ACAAAAGATTATACAGGAGAGTTATGGAGGAATCACTCGT<br>CAAGACTGTTCGAGATGCTGCAGGTGAACGGTTGACCCAT<br>AAGTCGGCTTTGGAGTTGATCCAAAAATGGTTCAATGAGT<br>CGAATATCTCCGGAGAGGCTTCCGATGCTTGGGCTGATGA<br>TGCGGCCTTCTTTAAGTGGAAGGACGATACCGCCAACTAC<br>GAGGAGAAGTTGAAAGAGTTGCGCGTTCAGAAGGTATTG<br>GATCAGCTGTCGAATATTGGAGATTCGGCAACTAATTTGA<br>GGGCTCTGCCTCAGGGTCTTGCTGCCCTACTTCAAAAGGTG<br>GATCCATCGAGTCGAGAAGAACTAGTCGAGGAACTCCGTA<br>GAGTGCTCACTTGATTTCGCAACCGTTGATGGTGAAGTGA<br>AACCTTCTTGGTTTCATCATGGTAGAAAATATTATTAGGCA<br>AATCTATAATTCTAGTTACATCCATTGTTTTAGACAATAGTA<br>TTGAACTAATTTATTTAATTAAATTGTATAAATAGGAGACC<br>TTGAATTCATTTGAATTAAGTGGCTTATGCTTGCATTATTTT<br>GTATTGAATCAAATAATTATTTACATACTTTTGATTATTAAT<br>AATGGTAAATCCTCAAAATTTGAGGGATTTGTTACCT |
| 11 | Amaranthus palmeri | cDNA Contig | 1582 | GTTGCAGCATTGCATAGCCGTGATTGCAGTGTCCAAAGGC<br>GGCACCAAAAGATCATTGAAGAAGGCCCAATAACGATAGC<br>TCCACCAGAAACGGTGAAGAAGCTTGAGCAAGCAGCTAG<br>AAGATTGGCTTTATGTGTGGGTTATGTTGGCGCAGCTACA<br>GTTGAATATTTATACAGCATGGAAACAGGCGAGTTCCATTT<br>CCTTGAGTTGAATCCTCGGTTACAGGTGGAGCATCCTGTTA<br>CTGAGTGGATTGCTGAGGTAAATCTTCCAGCTGCTCAAGTT<br>GCAGTTGGCATGGGTATCCCACTTTGGCAAATTCCTGAAAT<br>CCGTCGGTTCTATGGAAGGAACATGGTGGGGGTTATGAT<br>ACTTGGATGAGGACATCTGCTTTGGCTACTGCTTTTGATTT<br>TAACGAGGCACAGTCGGTGAAACCTAAAGGTCATTGTATT<br>GCTGCGCGTGTGACAAGTGAGGATCCCGATGACGGTTTTA<br>AGCCTACAAGCGGGAAAGTACAGGAGCTGAGTTTTAAAA<br>GTAAACCGAATGTGTGGGCCTACTTCTCTGTTAAGTCTGGG<br>GGAGGCATTCATGAGTTCTCGGATTCTCAATTTGGCCATGT<br>TTTTGCATTTGGTGAAAACCGAGGTTTGGCCATAGCAAATA<br>TGATTCTTGGATTAAAAGAAATTCAAATTCGTGGAGAAATT<br>CGAACTAATGTTGATTACACCATCGATCTTTTAAATTGTTTG<br>GATTATAGAGAAAACCAAATTCATACAGGTTGGTTGGATA<br>GTAGAATTGCGATGAGGGTCAGAGCTGAAAGGCCACCTT<br>GGTACATCTCTGTTGTGGGAGGAGGGCTTTACAAAGCATC<br>GACTAGTAGTGCAGCGACTGTTTCAGAGTATATAGGCTAT<br>CTTGAAAAAGGTCAAATTCCTCCGAAGCATATATCACTCGT<br>CCACTATGAAGTTGCTCTAAATATCGAGGGGATGAAATAT<br>ACCATTGAGATGATTAGGGGTGGACCAGGAAGCTACAAA<br>ATGTGGTTGAATGGGTCCGTAGTTGAGGCGGAAATACATA |

TABLE 1-continued

ACCase gene sequences isolated from weedy plant species

| SEQ ID NO | SPECIES | TYPE | LENGTH | SEQ |
|---|---|---|---|---|
| | | | | CTTTAAGAGATGGGGGTCTCTTGATGCAGTTGGACGGAAA<br>CAGCCATGTGATATATGCCGAGGAAGAAGCTGCAGGAACT<br>CGCCTTCTGATTGATGGAAGAACTTGTTTGCTTCAGAACGA<br>TCACGATCCTTCAAAGCTAATTGCGGAGACTCCGTGTAAGC<br>TTATGCGGTATTTGGTACCAGATAACAGTCACATAGATGCA<br>GATACTCCGTATGCTGAAGTTGAGGTCATGAAGATGTGTA<br>TGCCTTTGCTTTCCCCTGCATCCGGTGTTTTACAATTTAAGA<br>TGTCCGAAGGTCAAGCTATGCAGGCTGGTGAACTCATAGC<br>TAGTCTAGAGTTGGATGATCCTTCAGCTGTAAGAAAAGCC<br>GAACCTTTCAGTGGAAGCTTTCCTGTCATGGGCTCACCAAC<br>TGCAATATCTGGAAAAGTTCATCAGAGGTGTGCCGCAAGT<br>TTAAATGCCGCTCGGATGATTTTGGCTGGTTATGAACACAA<br>TATAGATGAAGTAGTACAGAGTTTGCTGGAATGCCTTGAT<br>AGTCCCG |
| 12 | Amaranthus palmeri | cDNA Contig | 822 | AGATGTGTATAAGAGACAGTATAATCAAGTTTTTTAGTACC<br>CAAAGCTCTAAATGTTACTTAAAGTTTTGATCTTTTAATGGT<br>TTCTTCTATTTAATCCAATAATTTAAAGTACCCAGATTTCAA<br>TTTTTAGAATAAATTGAGTTTTTGAATTGCCCAAGTTGTAAT<br>TGTTGCTGAATTCTCTTGCTTTGATTTGGGTTTTCTGATTCT<br>ATCCCTTCTGATTCATACAGTTTCAGGAGCAGTGGTCTCAT<br>TTTCGAGCAATACAAAAAGTGCCGTGCTTCTCTAAACAACG<br>ACGATTCAGACATGTCTTCTCCTTCCCACAATAATGAAAAC<br>CCGAACGGACCGATGATGCCACTCCTGAGGAATTCATCTG<br>TAGTATCCATTGTTGATAAGTTCTGTTATGCTCTTGGAGGG<br>ACGCGGCCAATCCATAGTATTTTGATAGCAAACAATGGGA<br>TGGCTGCTGTCAAATTTATAAGAAGTATCCGAACATGGGC<br>TTACGAGACTTTTGGTACTGAGAAGGCTATATTATTGGTAG<br>CCATGGCTACTCCCGAAGACATGAAAATCAATGCCGAGCA<br>TATTCGAATGGCTGATCAGTTTGTTGAAGTCCCCGGAGGA<br>ACTAACAACAATAACTACGCCAATGTGCAGCTCATTGTTGA<br>GTTAGCGGAAGTTACACGAGTTGACGCAGTTTGGCCTGGT<br>TGGGGACATGCATCGGAGATCCCCGAGTTGCCAGATTCAT<br>TAGCTACGAAGGGAATTGTGTTTCTGGGCCCCCCAGCTGC<br>ATCTATGGCTGCTCTTGGAGATAAAATTGGTTCATCATTGA<br>TTGCAC |
| 13 | Amaranthus palmeri | gDNA Contig | 17981 | AAACCAAACCAACCTCCTTAAACTTCTCTTCTTCTACTCACC<br>ATTTTTTCCTCTTTTTATTGATTATTGATTTTAAATATACATT<br>ATATTGTAGGAATTTAATGAAATTTTCATTAAATTCTGATA<br>AAGTTTTGATTTTTTTTAGTGTATGAGATTTTTCAGAAGTAC<br>CCAAATGGTAAATTTCAAGTATAATCAAGTTTTTTAGTACC<br>CAAAGCTCTAAATGTTACTTAAAGTTTTGATCTTTTAATGGT<br>TTCTTGTATTTAATCCAATAATTTAAAGTACCCAGATTTCAA<br>TTTTTAGAATAAATTGAGTTTTTGAATTGCCCAAGTTGTAAT<br>TGTTGCTGAATTCTCTTGCTTTGATTTGGGTTTTCTGATTCT<br>ATCCCTTCTGATTCATACAGGTATTCTGATTTTTTCTTGCTT<br>GATTACTTTTTGTTAGTGTATGGTTGAGCTAATTTAGTTTAT<br>AGTAGTGTGAATTTTATTTTATTTTTTTCAATTTTTTCAATT<br>ATTTCAATTTGTAGAGTAGATTCTCCTATTATGATTTGTTTT<br>TGTAGCTGGGTTTTAATTTTTATTGTCTGATGATTTATCTTA<br>GCAATGTTTTAATGGGTGTGCTGTTTTTCAATTTATAGTGT<br>AATTTAGTTGATTCCTCTTTTCCAATAGAGTGTACAAAACC<br>GACCTGATTAACTGAAACCGAGTATTATCCAACGGGAACA<br>ATCCCTGTTACAAAATTCAAATTAGAATGTCAAGTACCGAA<br>ATCAACCCGACCCCACATATTATACCCGAGATCCACCCGAA<br>CACCCGAATGAACACCTCTGAGATCATAGAGAGGATATAA<br>AGAAAAGTGGAACTAGAATGGGGAATTTAGTTTATTTGAG<br>CTACATTGAGCAAAATTTTTTTTAGTGACTGATTATTGTAGC<br>TGGCTTTTGTTGTATAACTCATCTAAGCAATGTTTTTGATGT<br>GTGTGCAGTAGCATTGGATTGTTTTGATTTTTTGTTATATTG<br>TCTATACAATTCAAATCTTGAATCACACTTGACTTTTAGTTC<br>CATTTTCATCTTCACAAATTCTTGTGAGAGACTGTCAACTGT<br>GAGACGCTCTCTGTACATGGGCTAAATAGCGTAACTAATA<br>CAACTATTAGCATATGAGCTTCTTATTTTGAGGTCGTCTCTC<br>ATAAGAGTAGCTCTCTGTTCTTTATGATTTATGATTCAATG<br>CAAATAAATTATTTACGGCCCGTGTGGTAGGTGGTAATAA<br>ACAATAGTAATGAGAATGAAAAACAAGTGTAATTTTGGTT<br>AAAAAATCTCTTGGTTACGTTGATGGTCATGCTTGTCCAAC<br>TTAAATCATCTCACACTATCATTGGGAGAGGTGGTGTTAG<br>GTGGTAATGAAAATTTGTAAACAAAAAAACTTGTTTGTGAT<br>CAAAGTTTCATTACCATAGGAACGATACGGAACTTTTGATG<br>AAATTTTACACTATAAATCATTTCCATTACCACCATTTAGTA<br>CCTCTAACCAAACGGGACGTTAGAGTTTTGCTTACCTACAA<br>TATCTTCTTAGCTCATAAGCTCAGAACCTTACTTCAATTTTG<br>ACCATATGTTTCTAGCTATACTTTCAGTAAGTATTTAAAAAT |

TABLE 1-continued

ACCase gene sequences isolated from weedy plant species

| SEQ ID NO | SPECIES | TYPE | LENGTH | SEQ |
|---|---|---|---|---|

```
TCATTTTCATTTTATCTATGTATAGTTGCGAATGATGTTTGT
TATAAAGGGTCAATCGAAAAACTTCCTCTTTGTTATTAGTA
ACAAGGGTAAGGTTATGTACATCCAATCCCTCCAAACCCTT
TTTGGGTGGGAGCTACTAATGGCGCTGGGACAATGGAGTT
GTTGTTTGTCGAATTCAAGCGGGGAAGTTTGTTTAGAATG
AATGTTATTTCTAAAAATAGATGGTATAAGTATGTTAATCA
ACAATTAATAATAGAGAACTGTTTTATTGGTGTGATAAACA
GTTTCAGGAGCAGTGGTCTCATTTTCGAGCAATACAAAAA
GTGCCGTGCTTCTCTAAACAACGACGATTCAGACATGACTT
CTCCTTCCCACAATAATGAAAACCCGAACGGACCGATGAT
GCCACTCCTGAGGAATTCATCTGTAGTATCCATTGTTGATA
AGTTCTGTTATGCTCTTGGAGGGACGCGGCCAATCCATAG
TATTTTGATAGCAAACAATGGGATGGCTGCTGTCAAATTTA
TAAGAAGTATCCGAACATGGGCTTACGAGACTTTTGGTAC
TGAGAAGGCTATATTATTGGTAGCCATGGCTACTCCCGAA
GACATGAAAATCAATGCCGAGCATATTCGAATGGCTGATC
AGTTTGTTGAAGTCCCCGGAGGAACTAACAATAATAACTA
CGCCAATGTGCAGCTCATTGTTGAGGTAATGTATCGTGAG
ATTAGAAATTTCTAGCCTGTAATCCATAGTTACATGGAATG
TGGAACATAGCCACGTTCCGCGATTCGGGAACATTCAATCC
CAATCACCATGAAACCCGACCTAAATCACTAAAGGTGACG
TCCCGGTGTAGAACACCTTTTTTTTAAAATGTATTTTTGGCC
TTCATTTACAAATTAAAGGAAAAAGAAAGGAGGAAAAAAC
AAGATGTAACCCAGAAACCTAAACAAATCCACTTGAAAAT
AATTTCTTAAAGCAAATTAATCATTTTAGTTTAATTTTGTTT
CAAATATATATATTATACATAATGTGTCTCATACCCAATCGT
TCTTGAGTAAATCTAGGTTGCGTTCTGTGTTCCCATTCTTGT
TTCCCGTTCGAAACCAAATGTCGTTCAGTTAACAATGCTGT
TATCTGCTTTACTGTGATTTATTAAATGTGTCCTTTGAAAAA
AAGGCAATATCAGAGCGACTCGACGCAGTTTGGCCTGGCC
GGGGACATGCGTAATATGTAATATGAGATTACAAATTTAT
AACCTTTTATATGGTAAAATCTTGTGGTAGGACTAACTTAA
ATCCTTTTTCTTTCAGTTAGCGGAAGTTACACGAGTTGACG
CAGTTTGGCCTGGTTGGGGACATGCATCGGAGATCCCCGA
GCTGCCAGATTCATTAGCTACGAAGGGAATTGTGTTTCTG
GGGCCCCCAGCTGCATCTATGGCTGCTCTTGGAGATAAAA
TTGGTTCATCATTGATTGCACAAGCTGCAGATGTCCCAACT
CTTCCATGGAGTGGTTCTCATGTACGTACTACACGTTTTTTT
TTTCTTTTTTTTTCCTTCCAAATTTCTGATCTTTAGAGTTTT
AGTGATAGATTTATATACGTCTCTATCCCTCAGGTGAAAAT
TCCTGCTGAGAGTTGCCTAGACGTAATTCCCGATGAAGTAT
ATAAAGCGGCATGTGTTTTTACTACAGAGGAAGCAATTGC
TAGCTGTCAAGTTGTTGGTTATCCGGCTATGATCAAAGCTT
CTTGGGGTGGTGGAGGGAAGGGAATAAGAAAGGTAAAAT
TTTTTTGGATGATGATGCTCTTAAAAGACTAAAAGGAGGTT
ACACATATCCCCATTACTTGTTTATCATCAGAAGCAGAGCA
AAAATTGACAAAGATTTAAAGACTCTGTGCAATTTCAAAAA
TATGATATATTTCTAACAACGTATCTTCAAACACTTTAAACA
TACTACCTATTTTAATACTGCGGCCCCTATTTTTTTGAGGCC
GTGTGTGGTCGAACATATTGAATATGCTTAGAACCACTCCT
GTTTATCACTAATATGCCATCTTCCACAGTCGAACCTCTACT
TTGACCCAGATTCCTTGAAAGGGATTTCGATTTAGACTCGA
GCTATGGTCAATTATTAGCAATAGCAAAAGCTTCTTAATAG
TTAATAGATTCTCAAACACTTCCGTCATGCCAACACTTTATG
AAGACTCATGGGTATTCTCTCTTTTAGGTTCATAATGATGA
CGAAGTACGGGCATTATTTAAGCAAGTGCAGGGTGAAGTT
CCCGGCTCACCCATATTTATAATGAAGGTGGCTTCACAGGT
TAGACTTTCTTCAACATTGGTCCGATATTCGAGTAAATTGC
ATTAAAAAAGGTTAAATATACAATTTTTTTGGATAAGTATT
GTATGAGAGACTACTACTAAGATAAAGTATTATTAATATGT
GCAGAGTCGACACTTAGAAGTACAGTTACTGTGTGATGAA
TATGGCAATGTTGCAGCATTGCATAGCCGTGATTGCAGTG
TCCAAAGGCGGCACCAAAAGGTGGGTCTTTGGTAGATTAT
GGTTATGATCTACGGTTTGTTATTGTTTAAGAAAAATATTT
GATTTTAAGCATTATTTAGCTTGCTGGGATTTGAACTTTTCT
GTTCATCATTTTAACTAATCAGATCATTGAAGAAGGCCCAA
TAACAATAGCTCCACCAGAAACGGTGAAGAAGCTTGAGCA
AGCAGCTAGAAGATTGGCTTTATGTGTGGGTTATGTTGGC
GCAGCTACAGTTGAATATTTATACAGCATGGAAACAGGCG
AGTTCCATTTCCTTGAGTTGAATCCTCGGTTACAGGTATGG
AGCTTCCCCAACTTCTTTTAAGTACCCATTATGTAACTGCAT
ATTTATGTAATCCCTCCATTCCAAATTAGTCGCTATGTATTC
CTATGGGGATGTCCCAAATTAGTTGCAACATTTCTGTATAT
GGTAAAGTTTTCCCCTCCAAACCTTAAAACCTAGTTGACCA
TAATCTAACTAAACCCAATTCTTGACCCACTTTGAAAAACA
GGTCAAATGTTGGTGTTTGAACCACCTTTAAACAAATTTAA
```

TABLE 1-continued

ACCase gene sequences isolated from weedy plant species

| SEQ ID NO | SPECIES | TYPE | LENGTH | SEQ |
|---|---|---|---|---|

```
GATTTTGGGTTGGTAATGGCTTATCAGAGATTTGGGTTTTT
GGCATCGGCATTATTTTGGTGTCGATTTGCAAATGATATCC
CGGGATTTCGAACTAGGAGGGGATTCAATTGGTTTTTGAG
GAATTTATGTAATTATTCCTTTAATTAGTGATCATTGAATTG
ATTGTATTTGTGTTGGGGAATTGGACCCGTGAAGAAAAAA
ATGACGGGTTAGCTTTTGGATTAGTGAGTGATTATGTGAG
TTTAATTTGTCTATGAAAGGTCAACTTCAAGCAACATTTTCT
GTTTTAGCTTAGTAATTTTTGGGATGCGATGGAACATTTGA
GCACCTTCTGGATTATCAACAGAAATGATCATCGAAATTGA
TTTTTTTAGTTGTTGACAGTAGAAAAGTATCAGATAAGGTA
GAATAATACAGTATAATCTTTAGTTGCGACAATTTCCAACG
TTTTTATAATAGCTAAAGCTACATTCTCATGTTGCTTGATGA
AAGTGACCGTATTTATTCTGTGTGCTTATACAGGTGGAGCA
TCCTGTTACTGAGTGGATTGCCGAGGTAAATCTTCCAGCTG
CTCAAGTTGCAGTTGGCATGGGTATCCCACTTTGGCAAATT
CCTGGTAAATGTCCAGTACTCTTTTTTCGGTTATGTAACTTA
TATATTATATCTAATTCTTATTTACGAACCGAATTGATCACA
CATTTTTAAAACAGAAATCCGTCGGTTCTATGGGAAGGAA
CATGGTGGGGGTTATGATACTTGGATGAGGACATCTGCTT
TGGCTACTGCTTTTGATTTTAACGAGGCACAGTCGGTGAAA
CCTAAAGGTCATTGTATTGCTGCGCGTGTGACAAGTGAGG
ATCCCGATGACGGTTTTAAGCCTACAAGCGGGAAAGTACA
GGTTAGACCATCCTGGTTTTGTCGATTTACTTCCACAATTG
GTCTTGTTTTGTTTTTGCCTTTGCGGTGAAGAATTTTCTTTA
ATGGGTGCTTTGTTTAGGAGCTGAGTTTTAAAAGTAAACC
GAATGTGTGGGCCTACTTCTCTGTTAAGGTATTTTCCATATT
TCTTTAATTCTTTGATTTTCGCGTTTACAATTTCAGTTCACTC
CATTATGGGCTTGATGATGATAAACACTTTTATTTGCAGTC
TGGGGGAGGCATTCATGAGTTCTCGGATTCTCAATTTGGT
AAGTTAATGGTGCAAACTCTTGTCAGTAATGTTAACTACAG
TTTCACATGATTTACTAATCTCTTCGTGAATTGCGAACTAAA
AAAGAGAATTATTGTCAGTTTTGGGCTATTTTTATTCCATT
TTGAGCCAATGGAAATTCAAAAAGCGAATAGCTAGCGAAT
TTTGTTGATATTCTGGAGGTGTATATTGATGAGAATTTTAC
AAAAAGTTGCTGCTGCTGCACTGTGTTATTTTTTAGAAACA
CTGGGTGACTTTCAATTGTTTGTAAAACTTGCATATTCGAG
TCACAACATGATGTCATAATGAAATGCGAGCGGTTTTTATT
AAATAATAGAGCCATAGTGTAATCGACCAATATTTAGGTG
GTGCAATGACCGCATCACTCCCGTTACCGCATTACCGTTCC
CTACCGCGATCACGATCGTTAGCGCATTTTTACGCTATGAA
TAGACCTTCAGTTCATATTTTATGATGGCTAAAATCAATCA
CTTGGTTAATGGTATATCATATACGAAGGCTAACAAAAGA
ATTTCTTTACAGGCCATGTTTTTGCATTTGGTGAAAACCGA
GGTTTGGCCATAGCAAATATGATTCTTGGATTAAAAGAAAT
TCAAATTCGTGGAGAAATTCGAACTAATGTTGATTACACCA
TCGATCTTTTAAATGTGAGTTTGAATGTAATTTTTGTTGTCT
TTTTTTAGTTTTCGCCTTTCTTCTGTTAAACCTTTGAAGTTCT
CACACTTAACTTTTTTTTCCTCCAGTGTTTGGATTATAGAGA
AAACCAAATTCATACAGGTTGGTTGGATAGTAGAATTGCG
ATGAGGGTTAGAGCCGAAAGGCCACCTTGGTACATCTCTG
TTGTGGGAGGAGGGCTTTACGTATGTACAACTTTTTCATAG
CTATCATTAATTTTTCCGTTGTTATGATCTGTGTTACTTGGA
CTCGGGTTGTTGGATACTGGTATGTGTCCACGTGTCGGAT
ACGTCTAAATATTCAATTTTACGCCTAAAATGAAGTATCTA
AGTGCCATGTCCGAGCATCAAGAATCGGACACGGGTACGT
GAAGCCAAATGAAGAGTCCGAGTAACATAAGTTATGATTA
ATGTTAAATAACTTGTTTTCTTTATCCTCTATATCCAGAAAG
CATCGACTAGTAGTGCAGCGACTGTTTCAGAGTATATAGG
CTATCTTGAAAAAGGTCAAATTCCTCCGAAGGTATGTAACA
TACAATTGGTTGGCGGGTGTTTAGATTAACTTATTCTATTA
ATATCAATTATACTTTCAGTGTTCTGCTTTAATTCTGTTTC
ATGATTGCAGCATATATCACTCGTCCACTATGAAGTTGCTC
TAAATATCGAGGGGATGAAATATACCGTATGTTCCATGCC
ATTCGTACTTTCCTCGTGAATTTTTGTTATGGATGCTATTTT
TGACATTTTCTTTCTAAATATATTTTCTTGAAATTAATGAAC
ATGTCGTTTCGGATTGCCAGATTGAGATGATTAGGGGTGG
ACCAGGAAGCTACAAAATGTGGTTGAATGGGTCCGTAGTT
GAGGCGGAAATACATACTTTAAGAGATGGGGGTCTCTTGA
TGCAGGTATCAAATGTTTTTGATATTTTTTTTCTGATATA
CGGTATTTATATTTTATATCCAAAGCATGGTGATAATACCC
TGGATTTGTAAAGCATTAGATAATATGTTATCAAACAAGTA
GAAGGTAGTTTCGTGAAACCATGAAGCGTTTAGTTTAGAT
TTGAATTTTAATACTTCTACAATGCTTGGGATATTAATCAAT
AATCATGCTTCTAATAGTAAAGAGAAATATTGTCATAGACT
CATAGGTATAATGGCTCGTTAAATCATATGCACTTCTTGTTT
ATGTGAAGTCCGAGTTGGTGTTTGCAATCAACGTTTGAAAT
```

TABLE 1-continued

ACCase gene sequences isolated from weedy plant species

| SEQ ID NO | SPECIES | TYPE | LENGTH | SEQ |
|---|---|---|---|---|

```
CAAGGGCATAGTGCAAAATCTCGAATGTGGTCACTTTTGT
GGTCAATGTAGATGGTTTCATTTCTATCGTGGTATAAATAT
GGGTCGCAGTAATCTTAAGAACCTATATAGTAGACGATAA
CTTGTTATTAAAAGGGTAAAGGCTGCATACATCCGATGTCC
CATTTACCCGGTCTAGATGTGAGCTACTTGGGGTTTTTGTT
ATTGAAGTTAAAGATACAAGAAGGATTATTGCTAAAAAAA
AAAAAGAATATTTGAACTACAAAAAAAGTAATTAGTTTATG
TACTAGTTCGTTCTAGCCCATATAACTCATTTAAAAAAATAT
ATGAAAAAGGGCTTTCAATGTCATGAACGGAAGGGAGGA
AATGGACTGTGGAAGAGTCAACAAAGATTACATATGAATT
CTCTTTTGTTGTTTAAAAAACTTTGAAATTGAAAATTGTTGG
CTTTTTGTTGAAGAAACGATGTGTGTCAGTTGAAAACAGA
ATATTTAAACTACAAAAAAAGCAATTAGTATATACACAATA
CACTTGTTCATTTAAACCCATATAGTACATTTAAATAATTAT
TTGAAAAGGGCTGTTAATGTGTGAAGACTTTCGCTATATTG
ATCTGATTGGATATGTGTAATACCTTGAAACGTCATGCAGT
TGGACGGAAACAGCCATGTGATATATGCCGAGGAAGAAG
CTGCAGGAACTCGCCTTCTGATTGATGGAAGAACTTGTTTG
CTTCAGGTAATGCCGTGTGATTCTCTTTTTTTTTTTTTTTGT
GAATTCTAAACCTTAAAAATCATTCTTCACCGGACATGTTC
ATTTTTCCATATAGAACGATCACGATCCTTCAAAGCTGATT
GCGGAGACTCCGTGTAAGCTTATGCGGTATTTGGTACCAG
ATAACAGTCACATAGATGCAGATACTCCGTATGCTGAAGTT
GAGGTCATGAAGATGTGTATGCCTTTGCTTTCCCCAGCATC
CGGTGTTTTACAATTTAAGATGTCCGAAGGTCAAGCTATGC
AGGTATGCATCATTTTAATCGTAAATTCAGCAACCTCGTTT
ATATTGGATTCTATATATGGTCTTGCTGTGTAGGCTGGTGA
ACTCATAGCTAGTCTAGAGTTGGATGATCCTTCAGCTGTAA
GAAAAGCCGAACCTTTCAGTGGAAGCTTTCCTGCCATGGG
CTCTCCAACTGCAATATCTGGAAAAGTTCATCAGAGGTGTG
CCGCAAGTTTAAATGCCGCTCGGATGATTTTGGCTGGTTAT
GAACACAATATAGATGAAGTAAGTTTCAAACCACCATTTCA
TTTTTCATCAACATAGTTTTTAGGCTAGCCTCTTAATGGGTT
GATGCCATAGTGTAAAAACAAGGCCACATCGCATCACGTC
ACCGCGTTGTTAAGGATTTCAAAAACAACGAACCGATATTT
CCCATGTTGTGGGCCGTACCAAGGGATATCTTATGGTTTTG
ACCGGTATTTAGGCGTTACAATAACCGCATCACTCCCGTTA
CCGCATCATTGTTCTGTTACACTATGGATGCCGAACCTTGA
GATGCATTTCCCATTTTTCAATAGAGCCCCTAGTTTTTTTCT
TCCTGTTTGGAAATTTTTTACATGTGAGCCTTTTATTTTCTC
AGGTAGTACAGAGTTTGCTGGAATGCCTTGATAGTCCCGA
ACTTCCATTCCTTCAATGGCAAGAATGCTTGTCTGTGCTGG
CAACACGACTCCCCAAAGATCTGAGATACGAAGTGTGTAT
TCTATCATCTGTTCTTTATTTAGTTATTTATATTTCCTTATAA
TAATTTTGAACTTTTTCCTCGGAGTTTACAGTTGGAATCAA
AATCTAGAGCTTTTGAAGCGATTACCAACACCCCAAACGTA
GAATTTCCTGCTAAGTTGTTGAAAAGTATTCTTGAGGTTAG
TACCTCACTTTGTTACCTTCTGTAAATTATTCATTCGGCGAG
TTACTCATGTTAGTAACATGTTTATTCTTCGTAGGACCATTT
AAACTCATGCCAAGAGAAAGATAAAGGAGCTCAAGAGAG
GCTTATTGAGCCTCTTATGGTTCTTGTAAAGTCTTACGAAG
GTGGGAGAGAAAGTCATGCTCGTTTTATTGTTCAATCTTTA
TTTGAAGAGTATTTGTCCGTTGAAGAATTGTTTAGCGACAA
TCTCCAGGTTTGTCCATCTATCTAGAGCAATTTGATTATGAT
GTTTTTTTAAAGTTCATAAATTTTAGCTTGGTGCCACACCGT
CAGTGGCTGATGATCGTCGCTTTGTGATCATTAAGCTTTTA
AAAGCTGTCTCCTGTTCTCCATCACTATTTTTAGAAATTTTG
AGTTCTGATGTATATACTCGGTACCCGAGGGACTCTTTGGC
CGCTTTCTTCTTTATGGGTATGAGTTGCCTCCTTCCTTCCCT
CCCCAGATCCTGATCATAGTTTCTATGAGCGGGATACATTG
GGTATGATGATGATGTATATACTCGGTGCTGAGCCAG
CATATGAAAAGCAAACTGTCGTGAATTTATCTTATGTCTTT
AAAGAATACCGAGGCACCTGATTTTACATTTTATCTTTATTT
TTTTCTGTATGAAGAAATAGTAAATTATATTCTTCAATAGTT
GACTCGGAGTGATGTTTGTAATATGTTTAGAAAAAATGTT
GGACTAGAAAGTCAGCGCAGCGCATATATTAGTTTATGAT
TGTGGCTTTAATCAGTTTATGCTTTTGATGTTAATCTTTCCA
GGCTGATGTGATTGAACGTCTCCGCCTTCAGTATAAGAAG
GATCTGCTGAAGATTGTTGACATTGTACTGTCGCATCAGGT
ACGTATTCTTGATTTACTGTTGTTCCTTTTGTTCTCTTCGGC
ATTTCTATTTTTTTTTAATATATTTTATGGTTTTCAGGGTGTT
AAGAATAAAAATAAGCTGATTCTACGACTCATGGAACAGC
TGGTTTACCCAAATCCCGCTGCATACAGGGGGCAACTTATC
CGTTTCTCTCAATTGAACCATACAATGTATTCTGAGGTTGG
TGATCCTCAAACACCCAAAGCTATGTATTTCTCATAATGCTT
AAGTAGAGTAATAATTAATAATTGTCCAATGATTGCAGTTG
```

TABLE 1-continued

ACCase gene sequences isolated from weedy plant species

| SEQ ID NO | SPECIES | TYPE | LENGTH | SEQ |
|---|---|---|---|---|

```
GCACTAAAGGCCAGTCAATTGCTTGAACAAACGAAATTGA
GTGAGCTCCGTTCGAACATTGCTAGAAACCTCTCTGAGCTA
GAAATGTTTACCGAGGATGGTGAAAACATGGATACTCCAA
AAAGAAAAAGTGCTATTAATGAACGTATGGAGGCCCTTGT
GAGTACTCCTCTAGCTGTTGAAGATGCCCTTGTTGGTTTGT
TTGATCATAGTGATCATACACTTCAGAGGCGGGTTGTTGA
GACCTATGTTCGGAGGCTTTATCAGGTGAATACATACTTTA
AATGCGGACTCGGTCCTATTCATTGTAGAAACTTCTCTTGA
TCTTTCTCGAGTCGGGGGACTCTTTGGCCGCACTCTCCTTT
ATGGGTATGAGTTGCCGCCTTCCTTCCCTCCCCAGACCCTG
CACATAGTTTTTCTATGGGAAGGATACTCTGGGTATGATGA
TGATGATTATTATTATCGCTACTTGAACAATTTTTCTTATGT
TATTTAACTCCTTTTTTGTTTTTGGCAACCGCTTTCTCAGCCT
TATCTTGTCAAGGGAAGTGTCAGGATGCTGTGGCACAGAT
CAGGTTTCATAGCTTTATGGGAATTTGTTGAGGAGAATATT
GACCGAACAAATTTTTCTGATGATCTGACTACAAACAGTGG
GAACCATAGTGAGCGAAAGTGGGGGGCCATGGTCGTTAT
TAAAACTCTTCAGTTCTTGCCATCGGTGATTGCTGCAGCAT
TGAGAGAAACAACTCATAGTTCCGATCAATCAACTTCCACT
GGCTCTATAGAATCAGTCATCCATGGAAATATGCTGCACAT
TGCACTAGTGGGGGTGAACAACCAGATGAGCTTGTTGCAG
GATAGGTAAATAAGACTAGCCTGTAACATATGGTGTAATA
ATCTTTATTATGTAACCTTGTGCTTCTAATGTCCTTTAGTTCT
ATGGACTATATTAAAGTACACTTCTTGTTCATGTGATGTTG
ATGTTGATAATTGCTATCGGGTCAATCACAAACAACCTCTT
TGTTATCACTTGAGGTGTTCAAAATAGACCCGATGACTCGA
TATTCATCAGATCTTGTAACTGAACTCGACTTCAAAATGAA
TTTAAAATTATATAAAAATCAATATGGACACAAGACCGGAT
ATCAATCCGACCCGAAATAGTTGACTCGAAATCAACTTGAT
GATCCGAATGAACACCTCTAGTTATCACTAACAAGGGTCA
GATTGCGTACATCAAACCCCTCAAATCCTGCTTAGGTGGGA
GCTTGTCAATGGCTTAGGGGTAACGGGAATGTGTGTGCTA
TGTACATTGTGCATCTATTCTTATACTTATGTTGAGTTTTTT
GGATCAAATATAAAGAACTTAACTTTTGTATTTTCTTGATGT
GGTGTAGTGGTGATGAAGATCAGGCTCAAGAGAGAATCC
ATAAAATTGGCCAAAATTCTGAGAGAGCAAGAAGTGAGTTC
AGCCCCTTCGTGCTGCTGGTGTTGGTGTGATTAGTTGCATCA
TACAGAGAGATGAAGGGCGAACTCCGATGAGGCATTCATT
CTATTGGTCAGCAGAAAAACAATATTATAGTGAGGAGCCT
TTACTACGTCATTTGGAACCCCCTCTATCTATGTATCTCGAG
CTGGTACTAGTCTCTGAACCGATTGCCTTTCTTCTGCTTTGT
TATTCTGTGTGATATTTCGACTTAAGTCTAATTTACATCGTT
TTGTACATTTGTTATCCAAAGCACGTTAAAAGATACTTCCTT
CGTTTTTTTACAAGCACCCAAACACCTTTTTACGCAGCCCAA
TTGGTTTGTCGGGTTGCTTATATATAGAATTATACTCAACTT
AAAAATTATAAAATTTGATATTATGAAAGTATTCGACGTGA
CGAATTAAACAAAATCCCATATGACTATGTTTTTTTCTCGTT
TAATAGCTGTAATATGTAAAATACTATCGAATGATGAATAG
TGTAAAAACTGGTTTGGGTGCAACTAAAAAAATGGAGGAA
GTATAATTATGCAGCCAAAATTGATGGCTTTTAACTTTTCAT
CAAATCAGGACAAGCTTAAGGGTTATGAAGATATCAAATA
TACTCCTTCCCGTGATCGTCAATGGCATCTTTACACAGTTAT
TGATAAACCATTCATTCGGAGGATGTTTTTGAGAACCCTTG
TAAGACAACCCATCTCTGAGTTCACAGGCGTCGAACTAAG
CGCTCTTGAAACACAAAAGCCTATCTCTTTTACTTCAAGAA
GCATCCTAAGGTCCTTAACAACCGCCATGGAGGAGTTGGA
GCTCAATGCACATAGTGCTTCACTGAAACCCGATCACGCTC
ATATGTACTTGTACATTGTTCGAGAGCAACAAATATACGAT
CTTGTGCCATATCACAGGTATCTATTGCTGCGTGCCTCATTT
TTTTTTTTGTTTATTATTGGTCATTAGTACACCTTATTCTTAG
AAGAAACTTTTTTCGGCCAATTATTTCCAGGGAGGTGAACA
TAGATCACCAACAAGAAGAGGCTTCGGTTCAATTCTTTTTG
GAAGATCTCGCGCATGAAATCCATAGTCTTGCTGGTGTAA
GGATGCATAAACTAAATGTTTGTGAGTGGGAAGTGAAACT
TCGGGTATCTTCTCCCGGGAAAGCTAATGGTTTATGGAGG
GTGGCAGTTACTAATGTGACTGGTCATACCTGTTCGGTACA
TGTAAGTCATAAGTTTGAGAACCTCTTTTTTGATCTAGTCAC
AATTTTGATTTTTCACAAATTCTTGTATGAGACGGTCTCACC
GTGAGAATCACCCCATACTTGGATTAAATAGCCGAATAATA
GAAACTTTTAGCATAATGGACCTTTTGTATGAACTCGTCTC
ACGGAGAGAAGGTCTCATACAATAGGGGCAATTAATTTTT
AGCTTTTTATCGGTAAATTTTGCATAGTACATAGTTTTGAAT
TTTGAGAGGTTGAGTCTATGTGACAACGAATATTTAATTGA
GTATAATGTTGTTTAATCCAAATATGATATAAAAGGGTGTG
GCATATGTGATTGAGCATTCTTTTTTCTTTTCTATGGGAAGT
TAAAGGTCTAAACCTTGGTATAATTTCCTTCAATGATGAGC
```

TABLE 1-continued

ACCase gene sequences isolated from weedy plant species

| SEQ ID NO | SPECIES | TYPE | LENGTH | SEQ |
|---|---|---|---|---|

```
AATCAAAGGGTTTCAGACCTGTTTATTTATGACTCGAAAGT
CGAACCCAAACCAGAACCCGAACCCGACTCAACTTGATTTT
TTTGACATGCCTAAATGGAACTACAGATGTATTGGGGAAA
ATAATTAAACTAGAAAATGGGGAAAATAATTAAACTAGAA
AATGGGGAAAACAATTTACCTAGAATATGTTTTCAGCCAAA
ACAAACACTCCCAAATACATTTCTTAGCATCCACAAATGCC
GAGGAATTGCAATGGAACTCCAGTTCCTCGGTTCTTCAACG
TAGAGACGTATATAATTCTTTTTTGCACGATATCATTAAGG
TTAATTGACCTGTTTTTTCTATGAAATATAATTTAATTTTTAT
GCTCTTTAGTTTGTTTTACTACACATGAATAGTTTTGGTTTT
GAGTGATCATTTTCTTACATTATTGATGCCCAGGTTTATCGT
GAATTGGAAGATAGCAACCTTCATGAAATGGTCTACCATTC
AGTATCTGTTCACGGCCCCCACCATGGGGTACCTGTGAAT
GCACCCTATCAACCACTCGGTGGCATCGCCCGTAAGCGAC
TTCAGGCCATGAAAAGTAGCACAACTTACTGTTACGATTTT
CCACTGGTACGGAATTTGAAAATTTCATCACTCCCTCCCCC
GTCTTCCCCTTAATATACTTTGTCGCCCGTTATTTCATATTCC
GTTTTATCAACCATGCAAGGATCTTCCAGGGTTCCGAATTT
CATTTTTTCGTACTTCCAAAGTTTCAGGCAAACTTACTTTTT
TTGACGCTGTTGTTTTCAGGCTTTCTCAACTGCCCTGAAGC
AATCATGGGCATCGGAAGCTCCGGATGTCAAGAAACCCTC
GGACAAAGCGCTTTTGAAAGTAACGGAGTTAGCGTTTGCT
GATCCAAAAGGCACATGGGGAACTCCGCTTGTTCCAATAA
ATCGCAAGCCTGGTATGAACGATGTTGGCATGGTAGCCTG
GTACATGGAAATGTCCACCCCCGAGTTCCCTAATGGAAGA
ACAATAATGGTTGTAGCTAATGATGTTACCTTCAAGGCCG
GATCTTTTGGACCACGAGAAGATGCTTTCTTCCTTGCTGTT
ACAAATCTTGCTTGCGCGAAGAAACTTCCTCTTATTTATCTG
GCTGCCAATTCAGGAGCTCGACTTGGTGTTGCCGAAGAGC
TAAAATCCTGCTTTAAAGTTGGCTGGTCGGATGAGTCAAAT
CCCGAGAGTGGATTTCAGTATGTCTACTTAACCCCTGAAGA
TTACGATCGTATAGGATCGTCAGTCATAGCCCACGAGTTAA
AACTCGAAAGTGGAGAAAAAAGATGGGTTATAGATACCGT
TGTAGGTAAGGAGGACGGATTAGGTGTTGAGAACCTATC
GGGAAGTGGTGCTATAGCCAGTGCATACTCAAGGGCTTAC
AAGGAAACATTTACTCTGACTTTTGTAACCGGAAGAACGG
TCGGTATTGGTGCCTATCTTGCTCGTCTTGGGATGCGTTGT
ATACAGAGGCTTGACCAGCCTATAATTCTCACGGGTTTTTC
TGCGTTAAATAAACTTCTCGGTCGGGAGGTTTATAGTTCAC
ACATGCAACTTGGTGGACCGAAGATTATGGGCACAAACGG
GGTAGTTCATCTTACAGTATCCGATGATCTTGAAGGCATTT
CATCTATCTTGAAGTGGCTGAGCTACGTTCCACCCTATTCA
GGTGGTGAACTTCCGATTTCTCGGTGTTTAGACCCTCCAGG
AAGACCGGTTGCGTATTTGCCTGAAAATTCTTGTGATCCTC
GTGGTGCTATATCTGGTACGGTTGACTCCACCGGTAAATG
GTTTGGGGGTATTTTCGACAAGGATAGTTTTGTGGAAACC
TTAGAAGGATGGGCACAAACAGTTGTCACGGGAAGGGCT
AAACTCGGAGGAATTCCAGTTGGCATAGTTGCCGTTGAGA
CGCAGACTGTTATGCAAGTAATCCCAGCAGATCCCGGTCA
ACTCGACTCACACGAGAGAGTCGTACCACAAGCAGGGCAA
GTATGGTTCCCAGATTCCGCATCCAAGACAGCACAAGCGC
TGATGGATTTCAACCGGGAAGAACTCCCACTTTTCATTCTA
GCTAATTGGAGAGGTTTCTCGGGTGGACAAAGGGATCTCT
TTGAAGGGATCCTTCAGGCCGGATCCACCATAGTTGAAAA
TCTTAGGACTTATAATCAACCCGTTTTTGTTTATATCCCTAT
GATGGGGGAGCTTCGAGGAGGCGCATGGGTGGTCGTCGA
TAGTCGAATTAATTCCGACCATATAGAAATGTACGCCGACC
AAACAGCTAAAGGAAATGTGCTTGAACCGGAAGGAATGA
TTGAGATTAAGTTCCGAACCAAGGAACTTCTCGAGTGTAT
GGGAAGGCTTGATCAACAACTCATCGGTCTCAAGGAAAAA
CTAGCCGAAGCCAAGAGCTCTAATTCCTACAATAAAATCGA
GCCCCTGCAGCAACAAATAAAAGCCCGTGAGAAGCAACTA
TTGCCTCTATATACTCAAATAGCCACCAAATTTGCCGAGTT
GCACGATACGTCTTTAAGGATGGCTGCCAAAGGAGTCATT
AGGGACGTCTTGGAATGGAAAAGCTCGCGTTCGTTCTTTT
ACAAAAGATTATACAGGAGAGTTATGGAGGAATCACTCGT
CAAGACTGTTCGAGATGCTGCAGGTGAACGGTTGACCCAT
AAGTCGGCTTTGGAGTTGATCCAAAAATGGTTCAATGAGT
CGAATATTTCCGGAGAGGCTTCCGATGCTTGGGCTGATGA
TGCGGCCTTCTTTAAGTGGAAGGACAATACCGCCAACTAC
GAGGGAGAAGTTGAAAGAGTTGCGCGTTCAGAAGGTATTG
GATCAGCTGTCGAATATTGGAGATTCGGCAACTAATTTGA
GGGCTCTGCCTCAGGGTCTTGCTGCCCTACTTCAAAAGGTA
ATCTGATTTATTTTATGTACATTCTTTGTTCTTTCTCGTTTGG
GTTGGATGTCGCTTTTGTAACGGGTCGGTCGGATCAATA
TTTTAATGGGCCGGGTCAAGTCATGTCAAATTAAATTGGG
```

TABLE 1-continued

ACCase gene sequences isolated from weedy plant species

| SEQ ID NO | SPECIES | TYPE | LENGTH | SEQ |
|---|---|---|---|---|
| | | | | CTTATGGGCTTTTTGTTTTGAGGTTGTCTCACCGTGAGACG GTCTCATACAAGACGGGCAGAAATCTAAAACAAAAAGTGG TAAAAGGCCCTTTAATGTTCTGACCTGTTATTGACCTGACC CACCGATGACCCATTAAAATGTAACCAGACTCTTGACCCGT CGGGTCAACCCACCCTGTTAAACTCCTTATTCTAATTGCAC ACAAAATCTTTGGGAGATGTTTTGATATCACACCTCAAAAA AACTCGGAAAAACTCCTATTAATTCCTACGATAAACATACA TCCTCGATGCCATGTATATTTTTCGATATCTACTTGTTTTCT ATTGACATTTTGCTACGGAGAAGTGACGTTTTAGATTGAAC GCAGGTGGATCCATCGAGTCGAGAAGAACTAGTCGAGGA ACTCCGAAAAGTGCTCACTTGATTTCGCAACCGTTGATGGT CAAGTGAAACCTTCTTGGTTTCATCATGGTAGAAAATATTA TTAGGCAAATCTATAATTCTAGTTACATCCATTGTTTTAGAC AATAGTATTGAACTAATTTATTTAATTAAATTGTATAAATAG GAGACCTTGAATTCATTTGAATTAAGTGGCTTATGCTTGCA TTATTTTGTATTGAATCAAATAATTATTTACATACTTTTGATT ATTAATAATGGTAAATCCTCAAAATTTGAGGGATTTGTTCC TACAATGAAATCAAGGACAAAATGTATAGTTTGAGGGAAT GGTGCTTGTACACTTGTCTAAACAATAACAGGTGCTCTCTT GAGAGACCGTCTTATGTAAAGACGACTCTCAAAAGTTCAG CCCAAATCTA |
| 14 | Amaranthus palmeri | gDNA Contig | 9312 | ATAGCTCCACCAGAAACGGTGAAGAAGCTTGAGCAAGCA GCTAGAAGATTGGCTTTATGTGTGGGTTATGTTGGCGCAG CTACAGTTGAATATTTATACAGCATGGAAACAGGCGAGTT CCATTTCCTTGAGTTGAATCCTCGGTTACAGGTATGGAGCT TCCCCAACTTCTTTTAAGTACCCATTATGTAACTGCATATTT ATGTAATCCCTCCATTCCAAATTAGTCGCTATGTATTCCTAT GGGGATGTCCCAAATTAGTTGCAACGTTTCTGTAATATGGT AAAGTTTTCCCCTCCAAACCTTAAAACCTAGTTGACCATAAT CTAACTAAACCCAATTCTCGACCCACTTTGAAAAACAGGTC AAATGTTGGTGTTTGAACCACCTTTGAAGAAATTTAAGATT TTGGGTTGGTAATGCTTATTAGAGATTTGGGTTTGTGGCAT CGGCATTATTTTGGTGTCGATTTGCAAATGATATCCCGGGA TTTCGAACTAGGAGGGGATTCAATTGGTTTTTGAGGAATTT ATGTAATTATTCCTTTAATTAGTGATCATTGAATTGATTGTA TTTGTGTTGGGGAATTGGACCCGTGAAGAAAAAAATGACG GGTTAGCTTTTGGATTAGTGAGTGATTATGTGAGTTTAATT TGTCTATGAATGGTCAATTTCAAGCAACATTTTCTGTTTTAG CTTAGTAATTTTTGGGATGCGATTGAACATTTGAGCACCTT CTGGATTATTAACAGAAATGATCATCGAAATTGATTTTTTT AGTTGTTGACAGTAGAATAGTAACAGATAAGGTAGAATAA TACAGTATAATCTTTAGTTGCGACAATTTCCAACGTTTTTAT AATAGCTAAAGCTACATTCTCATGTTGCTTGATGAAAGTGA CTGTATTTATTCCGTGTGCTTATACAGGTGGAGCATCCTGT TACTGAGTGGATTGCCGAGGTAAATCTTCCAGCTGCTCAA GTTGCAGTTGGCATGGGTATCCCACTTTGGCAAATTCCTGG TAAATGTCCAGTACTCTTTTTTCGGTTATGTAACTTATATAT TATATCTAATTCTTATTTACGAACCGAATTGATCACACATTT TTAAAACAGAAATCCGTCGGTTCTATGGGAAGGAACATGG TGGGGGTTATGATACTTGGATGAGGACATCTGCTTTGGCT ACTGCTTTTGATTTTAACGAGGCACAGTCGGTGAAACCTAA AGGTCATTGTATTGCTGCGCGTGTGACAAGTGAGGATCCC GATGACGGTTTTAAGCCTACAAGCGGGAAAGTACAGGTTA GACCATCCTGGTTTTGTCGATTTACTTCCACAATTGGTCTTG TTTTTATTTTGCCTTTGCGGCGAAGAATTTTCTTTAATGGGT GCTTTGTTTAGGAGCTGAGTTTTAAAAGTAAACCGAATGT GTGGGCCTACTTCTCTGTTAAGGTATTTTCCATATTTCTTTA ATTCTTTGATTTTCGCGTTAACAATTTCAGTTCACTCCATTA TGGGTTTGATGATGATAAACACTTTTATTTGCAGTCTGGGG GAGGCATTCATGAGTTCTCGGATTCTCAATTTGGTAAGTTA ATGGTGCAAACTCTTGTCAGTAATGTTAACTCCAGTTTCAC ATGATTTGCTAGTCTTTTTGTGATTTGCGAATCAAAAAAGA GAATTATTGTCGGTTTTGGGCTATTTTTTATTCCATTTGGAG CCAATGGACATTCAAAAAGCAAATAGCTAGCGAATTTTGTT GATATTCTGGAGGTGTATATTGATGAGAATTTTACAATAAA TTGCTGCTGCTGCACTGTGCTATATTTTGGAAACACTGAAT GACTTTCAATTGTTTGTAAAGTTTGCATATTCGAGTCACAA CATGATGTCATAATGAAATGCGAGCGGTTTTATTAAATAA TAGAGCCGTAGTGTAAAAACAAGGCCGCATTGCATCGTGT TGGCTGCATTGTAAAGGTTTTCAAAAACAATGAACTGATAT TTCCCACGTTGTAAAGGCATAAAACATTGCGTTTAGGGAA ATATCAAAGAATATCTTAAGGTTTCAACCGATATTTAGGTG GTGCAATGACCGCATTACTCCCGTTACCGCATTACCGTTCC TTGCTGCGATCACGATCGTTACCGCATTTTTACACTATGAA TAGACCTTCAGTTCATATTTTATGATGGCTAAAATCAATTAC |

TABLE 1-continued

ACCase gene sequences isolated from weedy plant species

| SEQ ID NO | SPECIES | TYPE | LENGTH | SEQ |
|---|---|---|---|---|

```
TTGGTTAAAGGTATATACGAAGGCTAACAAAAGCATTTCTT
TACAGGCCATGTTTTTGCATTTGGTGAAAACCGAGGTTTGG
CCATAGCAAATATGATTCTTGGATTAAAAGAAATTCAAATT
CGTGGAGAAATTCGAACTAATGTTGATTACACCATCGATCT
TTTAAATGTGAGTTTGAATGTAATTCTTGTTGTCTTTTTTA
GTTTTCGCCTTTCTTCTGTTAAACCTTTGAAGTTCTCACACTT
AACTTTTTTTCCTCCAGTGTTTGGATTATAGAGAAAACCA
AATTCATACAGGTTGGTTGGATAGTAGAATTGCGATGAGG
GTCAGAGCTGAAAGGCCACCTTGGTACATCTCTGTTGTGG
GAGGAGGGCTTTACGTATGTACAACTTTTTCACAGCTATCA
TTAATTTTTCCGTTGTTATGATCTGTGTTACTTGGACTCGGG
TTGTTGGATACTGGTATGTGTCCACGTGTCGGATACGTCTA
AATATTCAATTTTACGCCTAAAATGAAGTATCTAAGTGCCA
TGTCCGAGCATCAAGGATCGGACACGGGTACGTGAAGCCA
AATGAAGAGTCCGAGTAACATAAGTTATGATTAATGTTAA
ATAACTTGTTTTCTTTATCCTCTATATCCAGAAAGCATCGAC
TAGTAGTGCAGCGACTGTTTCAGAGTATATAGGCTATCTTG
AAAAAGGTCAAATTCCTCCGAAGGTATGTAACATACAATT
GGTTGGCGGGTGTTTAGATTAACTTATTCTATTAATATCAA
TTATACTTTCAGTGTTCTGCTTTAATTCTGGTTTCATGATTG
CAGCATATATCACTCGTCCACTATGAAGTTGCTCTAAATAT
CGAGGGGATGAAATATACCGTATGTTCCATGCCATTCGTA
CTTTCCTCGTGAATTTTTGTTATGGATGCTATTTTTGACATT
TTCTTTCTAAATATATTTTCTTGAAATTAATGAACATGTCGT
TTCGGATTGCCAGATTGAGATGATTAGGGGTGGACCAGGA
AGCTACAAAATGTGGTTGAATGGGTCCGTAGTTGAGGCGG
AAATACATACTTTAAGAGATGGGGGTCTCTTGATGCAGGT
ATCAAATGTTTTTTGATATTTTTTTTCTGATATACGGTATTT
ATATTTTATATCCAAAGCATGGTGATAATACCCTGGATTTG
TAAAGCATTAGATAATGTGTTATCAAACAAGTAGAATGTA
GTTTTGTGAAATCGTGAAGCGTTTAGTTTAGATTTAAATTT
TAATACTCCTACAATGCTTGGGATATTAATCAATAATCATG
CTTCAAATAGTAAAGAGAAATATTGTCATAGACTCATAGGT
ATAATGGCTCGTTAAATCATATGCACTTCTTGTTTATGTGA
AGTCCGAGTTGGTGTTTGCAATCAACGTTTGAAATCAAGG
GCATAGTGCTAAATCTCGAATGTGGTCACTTTTGTGGTCAA
TGTAGATGGTTTCATTTCTATCGTGGTATAAATATGGGTCG
CAGTAATCTTAAGAACCTATATAGTAGACGATAACTTGTTA
TTAAAAGGGTAAAGGCTGCATACATCCGATGTCCCATTTAC
CCGGTCTAGATGTGAGCTACTTGGGGTTATTGTTATTGAAG
TTAAAGATACAAGAGGGATTACTGTTTGAAAAAACGGAAT
ATTTGAACTACAAAAAAAGTAATTAGTTTAGGTACTAGTTC
GTTCTAGCCCATATAACACATTTTAAAAAAATATATGAAAA
AGGGCTTTCAATGTCATGAACGGAAGGGAGCAAATGGAC
AGTGGAAGAGTCAACAAAGATTACATATGATTTATGAATT
CTCTTTCGTTGTTTAAAAAACTTTGAAATTGAAAATTGTTG
GCTTTTTGTTGAAGAAACGATGTGTGTCAGTTGAAATCAG
AATATTTAAACTACAAAAAAAGCTATTAGTTTATACACAAT
ACACTTGTTCGTTTAAACCCATATAGTACATTTAAATAATTA
TTTGAAAAGGGCTGTTAATGTGTGAAAACTTTCGATATGTT
GATCTGATTGGATATGTGTCATACCTTGAAACGTCATGCAG
TTGGACGGAAACAGCCATGTGATATATGCCGAGGAAGAA
GCTGCAGGAACTCGCCTTCTGATTGATGGAAGAACTTGTTT
GCTTCAGGTAATGCCGTGTGATTCTCTTTTTTTTTTTTTTG
TGAATTCTAAACCTTAAAAATCATTCTCCACCAAACTTGTTC
ATTTTTTCATATAGAACGATCACGATCCTTCAAAGCTGATT
GCGGAGACACCGTGTAAGCTTATGCGGTATTTGGTACCAG
ATAACAGTCACATAGATGCAGATACTCCGTATGCTGAAGTT
GAGGTCATGAAGATGTGTATGCCTTTGCTTTCCCCAGCATC
CGGTGTTTTACAATTTAAGATGTCCGAAGGTCAAGCTATGC
AGGTATGCATCATTTTAATCGTAAATTCAGCAACCTCGTTT
ATATTGGATTCTAAATATGGTCTTGCTGTGTAGGCTGGTGA
ACTCATAGCTAGTCTAGAGTTGGATGATCCTTCAGCTGTAA
GAAAAGCCGAACCTTTCAGTGGAAGCTTTCCTGTCATGGG
CTCACCAACTGCAATATCTGGAAAAGTTCATCAGAGGTGT
GCCGCAAGTTTAAATGCCGCTCGGATGATTTTGGCTGGTTA
TGAACACAATATAGATGAAGTAAGTTTCAAACCACCATTTC
ATTTTTCATCAACATAGTTTTTAGGCTAGCCTCTTAATGGGT
TGATGCCATAGTGTAAAAACAAGGCCACATCGCATCACGT
CACCGCGTTGTAAAGGATTTCAAAAACAACGAACCGATAT
TTCCCACATTGTGGGCTGTATCAAGGGATATTTTATGGTTT
TGACCGGTATTTAGGCGTTACAATAACCGCATCACTCCCGT
TACCGCATCATTGTTCTGTTACCGTGATCATGACCGTTACC
GCATTTTTACACTATGGATGCCGAACCTTGAGATGCATTTC
CCATTTTTCAATAGAGCCCCTAGTTTTTTTCTTCCTGTTTGG
AAATTTTTTACATGTGAGCCTTTTATTTTCTCAGGTAGTACA
```

TABLE 1-continued

ACCase gene sequences isolated from weedy plant species

| SEQ ID NO | SPECIES | TYPE | LENGTH | SEQ |
|---|---|---|---|---|

```
GAGTTTGCTGGAATGCCTTGATAGTCCCGAACTTCCATTCC
TTCAATGGCAAGAATGCTTGTCTGTGCTGGCAACACGACTC
CCCAAAGATCTGAGATACGAAGTGTGTATTCTATCATCTGT
TCTTGATTTAGTTATTTATATTTCCTTATAATAATTTTGAACT
TTTTCCTCGGAATTTACAGTTGGAATCAAAATCTAGAGCTT
TTGAAGCGATTACCAACACCCCAAACATAGAATTTCCTGCT
AAGTTGTTGAAAAGTATTCTTGAGGTTAGTACCTCACTTTG
TTACCTTCTGTAAATTATTCACTCGGCGAGTTACTCATGTTA
GTAACAAGTTTATTCTTCATAGGACCATTTAAACTCATGCC
AAGAGAAAGATAAAGGAGCTCAAGAGAGGCTTATTGAGC
CTCTTATGGTTCTTGTAAAGTCTTACGAAGGTGGGCGAGA
AAGTCATGCTCGTTTTATTGTTCAATCTTTATTTGAAGAGTA
TTTATCCGTTGAAGAATTGTTTAGCGACAATCTCCAGGTTT
GTCCATCTATCTAGAGCAATTTGATTATGATGTTTTTTTAAA
GTTCATAAATTTTAGCTTGGTGCCACACCGTCAGTGGCTGA
TGATCGTCGCTTTGTGATCATTAAGCTTTTAAAAGCTGTCTC
CTGTTCTCCATCACTATTTTTAGAAATTTTGAGTTCTGATGT
ATATACTCGGTACCTGAGGGACTCTTTGGCCGCTTTCTTCTT
TATGGGTATGAATTGCCTCCTTCCTTCCCTCCCCAGATCCTG
ATCATAGTTTCTATGAGCGGGATACATTGGGTATGATGAT
GATTATTATTATTATCGCTATTTGAACAATTTTTCTTATG
TTATTTAACTCCTTTTTGTTTTTGGCAACCGCTTTCTCAGCCT
TATCTTGTCAAGGGAAGTGTCAGGATGCTGTGGCACAGAT
CAGGTTTCATAGCTTTATGGGAATTTGTTGAGGAGAATATT
GACCGAACAAATTTTTCTGATGATCTGACTACAAACAGTGG
GAACCATAGTGAGCGAAAGTGGGGGGCCATGGTCGTTAT
TAAAACTCTTCAGTTCTTGCCATCGGTGATTGCTGCAGCAT
TGAGAGAAACAACTCATAGTTCCGATCAATCAACTTCCACT
GGCTCTATAGAATCAGTCATCCATGGAAATATGCTGCACAT
TGCACTAGTGGGGGTGAACAACCAGATGAGCTTGTTGCAG
GATAGGTATATAAGACTAGCCTGTAACATATGGTGTAATA
ATCTTTATTATGTAACCTGTGCTTCTAATGTCCTTTATTTCT
ATGGACTATATTGAAGTACACTTCTTGTTCATGTGATGTTG
ATGTTGATAATTGCTACCGGGTCAATCGAAAACAACCTCTT
TGTTATCACTTGAGGTGTTCAAAATAGACCCGATGACTCGA
TATTCATCAGATCTTGTAACTGAACTCGACTTCAAAATGAA
TTTAAAATTATATAAAAATCAATATGGACACAAGACCGGAT
ATCAATCCGACCCGAAATAGTTGACTCGAAATCAACTTGAT
GATCCGAATGAACACCTCTAGTTATCACTAACAAGGGTCA
GATTGCGTACATCAAACCCCTCAAATCCTGCTTAGGTGGGA
GCTTGTCAATGGCTTAGGGGTAACGGGAATGTGTGTGCTA
TGTACATTGTGCATCTATTCTTATACTTATGTTGAGTTTTTT
GGATCAAATATAAAGAACTTAACTTTTGTATTTTCTTGATGT
GGTGTAGTGGTGATGAAGATCAGGCTCAAGAGAGAATCC
ATAAATTGGCCAAAATTCTGAGAGAGCAAGAAGTGAGTTC
AGCCCTTCGTGCTGCTGGTGTTGGTGTGATTAGTTGCATCA
TACAGAGAGATGAAGGGCGAACTCCGATGAGGCATTCATT
CTATTGGTCAGCAGAAAAACAATATTATAGTGAGGAGCCT
TTACTACGTCATTTGGAACCCCCTCTATCTATGTATCTCGAG
CTGGTACTAGTCTCTGAACCGATTGCCTTTCTTCTGCTTTGT
TATTCTGTGTGATATTTCGACTTAAGTCTAATTTACATCGTT
TTGTACATTTGTTATCCAAAGCACGTTAAAAGATACTTCCTT
CGTTTTTTTACAAGCACCCAAACACCTTTTTACGCAGCCCAA
TTGGTTTGTCGGGTTGCTTATATATAGAATTATACTCAACTT
AAAAATTATAAAATTTGATATTATGAAAGTATTCGACGTGA
CGAATTAAACAAAATCCCATATGACTATGTTTTTTTCTCGTT
TGATAGCNNNAATATGTAAAATACTATCGAATGATGAATA
GTGTAAAAACTGGTTTGGGTGCAACTAAAAAAAATGGAGGA
AGTATAATTATGCAGCCAAAATTGATGGCTTTTAACTTTTC
ATCAAATCAGGACAAGCTTAAGGGTTATGAAGATATCAAA
TATACTCCTTCCCGTGATCGTCAATGGCATCTTTACACAGTT
ATTGATAAACCATTCATTCGGAGGATGTTTTTGAGAACCCT
TGTAAGACAACCCATCTCTGAGTTCACAGGCGTCGAACTAA
GCGCTCTTGAAACACAAAAGCCTATCTCTTTCACTTCAAGA
AGCATCCTAAGGTCCTTAACAACCGCCATGGAGGAGTTGG
AGCTCAATGCACATAGTGCTTCACTGAAACCCGATCACGCT
CATATGTACTTGTACATTGTCCGAGAGCAACAAATATACGA
TCTTGTGCCATATCACAGGTATCTATTGCTGCGTGCCTCAA
CTTTTTTTGTTTATTATTGGTCATTAGTACACCTTATTCTTAG
AAGAAACTTTTTTCGGCCAATTATTTCCAGGGAGGTGAACA
TAGATCACCAACAAGAAGAGGCTTCAGTTCAATTCTTTTTG
GAAGATCTCGCGCATGAAATCCATAGTCTTGCTGGTGTAA
GGATGCATAAACTAAATGTTTGTGAGTGGGAAGTGAAACT
TCGGGTATCATCTCCCGGGAAAGCTAATGGTTTATGGAGG
GTGGCAGTTACTAATGTGACTGGTCATACCTGTTCGGTACA
TGTAAGTCATAATTTTGAGAACCTCTTTTTTGATCAAGTCAC
```

TABLE 1-continued

ACCase gene sequences isolated from weedy plant species

| SEQ ID NO | SPECIES | TYPE | LENGTH | SEQ |
|---|---|---|---|---|
| | | | | AATTTTAATTTTTCACAAATTCTTGTATGAGACGGTCTCACC<br>GTGAGAAGCGCCCCATACTTGGATTAAATAGCCGAATAAA<br>AGAAACTTTTAGCATAATGGACCTTTTGTATGGACTCGTCT<br>CATGGTGAGAAGGTCTCATACAATAGGGGCAATTAATTTT<br>TAGCTTCTTATCTGTAAATTTTGCATAGTACATAGTTTTGAA<br>TTTTGAGAGGTTGAGTCTATGTGACAACGAATATTTAATTG<br>AGTATAATGTTGTTTAATCCAAATATGATATAAAAGGGTGT<br>GGCATAAGTGATTGAGCATTCTTTTTTCTTTTCAATGGGAA<br>GTTAAAGGTCTAAACCTTGGTATAATTTCCTTCAATGATGA<br>GCAATCAAAGGGATTCTAACCTGTTTATTTATGACTCGAAA<br>GTCGAACCCAAACCAGAACCCGAACCCGACTCAACTTGATT<br>TTTTTGACATGCCTAAATGGAACTACAGATGTATTGGGGA<br>AAATAATTAAACTAGAAAATGGGGAAAATAATTAAACTAG<br>AAAATGGGGAAAACAATTTACCTAGAATATGTTTTCAGCCA<br>AAACAAACACTCCCAAATACATTTCTTAGCATCCACAAATG<br>CCGAGGAATTGCAATGGAACTCCAGTTCCTCGGTTCAACTT<br>AGAGAAGTATATAATTCTTTTTTGCACGATATCATTATGGT<br>TAATTGACCTGTTTTTTCTATGAAATATAATTTAATTTTTAT<br>GCTCTCTAGTTTGTTTTACTACACATGAATAGTTTTGGTTTA<br>GAGTGATCATTTTCTTACAATATTGATGCCCAGGTTTATCG<br>TGAATTGGAAGATAGCAACCTACATGAAATGGTCTACCATT<br>CAGTAT |
| 15 | Amaranthus palmeri | gDNA Contig | 5302 | AACCTTGTGCTTCTAATGTCCTTTATTTCTATGGACTATATT<br>AGAGTACACTTCTTGTTCATGTGATGTTGATGTTGATAATT<br>GCTACCTGGTCAATCACAAACAACCTCTTTGTTATCACTTG<br>AGGTGTTCAAAATAGACCCGATGACTCGATATTCATCAGAT<br>CTTGTAACTGAACTCGACTTCAAAATGAATTTAAAATTATA<br>TAAAAATCAATATGGACACAAGACCGGATATCAATCCGAC<br>CCGAAATAGTTGACTCGAAATCAACTTGATGATCCGAATG<br>AACACCTCTAGTTATCACTTACAAGGGTCAGATTGCGTACA<br>TCAAACCCCTCAAATCCTGCTTAGGTGGGAGCAGTGTCACA<br>TGATTCGCTAGTTAATTCGCATGTCTCGATTCGAGATTCGC<br>TCAAAATGGACCAAAAATGGCCCAAAAACGACCAAAATTC<br>GCTTTTTTCAATTCGCGATTCGCAGAGAGATTAACGAATTA<br>TGTGACAGTGGGTGGGAGCTTGTCAATGGCTTAGGGGTA<br>ACGGAATTGTGTGTGCTATGTATATTGTGCATCTATTCTTAT<br>ACGTATGTTGAGTTTTTTGGATCAAATATAAAGAGCTTATC<br>TTTTGTATTTTCTTGATGTGGTGTAGTGGTGATGAAGATCA<br>GGCTCAAGAGAGAATCGATAAATTGGCCAAAATTCTGAGA<br>GAACAAGAAGTGAGTTCAGCCCTTCGTGCTGCTGGTGTTG<br>GTGTGATAAGTTGCATCATACAGAGAGATGAAGGGCGAA<br>CTCCGATGAGGCATTCATTCTATTGGTCAGCAGAAAAACAA<br>TATTATAGTGAGGAGCCTTTACTACGTCATTTGGAACCCCC<br>TCTATCTATGTATCTCGAGCTGGTACTAGTCTCTGAACCGA<br>TTGCCTTTCTTCTGCTTTGTTATTTTGTGTGATATTTCGACTT<br>AAGTCTAATTTACATCGTTTTGTACATTTGTTATCCAAAGCA<br>CGTTAAAAGATACTTCCTTCGTTTTTTTACAAGCACCCAAAC<br>ACCTTTTTACGCAGTCCAATTGGTTTGTCGGGTTGCTTATAT<br>ATAGAATTTTACTCAACTTAAAATTATAAAATTTGATATTAT<br>GAAAGTATTCGACGAGACGAATAAAACAAAATCCCATATG<br>ACTGTTTTTTCTCGTTTAATAGCTGTAATATGTAAAATACT<br>ATCGAATGATGAATAGTGTAAAAACTGGTTTGGGTGCAAC<br>TAAAAAAATGGAGGAAGTATAATTATGCAGCCAAAACTGA<br>TGGCTTCTAACTTTTCATCAACTCAGGACAAGCTTAAGGGT<br>TATGAAGATATCAAATATACTCCTTCCCGTGATCGTCAATG<br>GCATCTTTACACGGTTATTGATAAACCATTCATTCGGAGGA<br>TGTTTTTGAGAACCCTTGTAAGACAACCCATCTCTGAGTTC<br>ACAGGCGTCGAACTAAGCGCTCTTGAAACACAAAAGCCTA<br>TCTCTTTCACTTCAAGAAGCATCCTAAGGTCCTTAACAACC<br>GCCATGGAGGAGTTGGAGCTCAATGCACATAGTGCTTCAC<br>TGAAACCCGATCACGCTCATATGTACTTGTACATTGTCCGA<br>GAGCAACAAATATACGATCTTGTGCCATATCACAGGTATCT<br>ATTGCTGCGTGCCTCATTTTTTTTGTTTATTATTGGTCATTA<br>GTACACCTTATTCTTAGAAGAAACTTTTTTCGGCCAATTATT<br>TCCAGGGAGGTGAACATAGATCACCAACAAGAAGAGGCTT<br>CGGTTCAATTCTTTTTGGAAGATCTCGCGCATGAAATCCAT<br>AGTCTTGCTGGTGTAAGGATGCATAAACTAAATGTTTGTG<br>AGTGGGAAGTGAAACTTCGGGTATCATCTCCCGGGAAAGC<br>TAATGGTTTATGGAGGGTGGCAGTTACTAATGTGACTGGT<br>CATACCTGTTCGGTACATGTAAGTCATAGTTTTGAGAACCT<br>CTTTTTTGATCTAGTCACAATTTTGATTTTTCACAAATTCTTG<br>TATGAGACGGTCTCACCGTGAGAATCACCCCATACTTGGAT<br>TAAATAGCCGAATAATAGAAACTTTTAGCATAATGGACCTT<br>TTGTATGAACTCGTCTCACGGAGAGAAGGTCTCATACAATA<br>GGGGCAATTAATTTTTAGCTTTTTATCGGTAAATTTTGCATA |

TABLE 1-continued

ACCase gene sequences isolated from weedy plant species

| SEQ ID NO | SPECIES | TYPE | LENGTH | SEQ |
|---|---|---|---|---|

```
GTACATAGTTTTGAATTTTGAGAGGTTGAGTCTACGTGACA
ACGAATATTTAAGTGAGTATAATGTTGTTTAATCCAAATAT
GATATAAAAGGGTGTGGCATATGTGATTGAGCATTCTTTTT
TCTTTTCTATGGGAAGTTAAAGGTCTAAACCTTGGTATAAT
TTCCTTCAATGATGAGCAATCAAAGGGTTTCAGACCTGTTT
ATTTATGACTCGAACCTGAACCCGACTCTACTTGATTTTTTT
GACATGCCTAAATGGAACTACAGATTTATTGGGGAAAATA
ATTAAACTAGAAAATGGGGAAAACAATTTACCTAGAATGC
GTTTTCCGCCAAAACAAACACTCCCAAATACATTTCTTAGC
ATCCACAAATGCCGAGGAATTGCAACGGAACTACCGATCC
TCGGTTCTTCAACGTAGAGACGTATATAATTCTTTTTTGCAC
GATATCATTAAGGTTAATTGACCTGTTTTTTCTATGAAATAT
AATTTAATTTTTATGCTCTTTAGTTTGTTTTACTACACATGA
ATAGTTTTGGTTTTGAGTGATCATTTTCTTACATTATTGATG
CCCAGGTTTATCGTGAATTGGAAGATAGCAACCTTCATGAA
ATGGTCTACCATTCAGTATCTGTTCACGGCCCCCACCATGG
GGTACCTGTGAATGCACCCTATCAACCACTCGGTGGCATC
GCCCGTAAGCGACTTCAGGCCATGAAAAGTAGCACAACTT
ACTGTTACGATTTTCCACTGGTACGGAATTTGAAAATTTCA
TCACTCCCTCCCCCGTCTTCCCCTTAATATACTTTGTCGCCC
GTTATTTCATATTCCGTTTTATCAACCATGCAAGGATCTTCC
AGGGTTCCGAATTTCATTTTTTCGTACTTCCAAAGTTTCAGG
CAAACTTACTTTTTTTGACGCTGTTGTTTTCAGGCTTTCTCA
ACTGCCCTGAAGCAATCATGGGCATCGGAAGCTCCGGATG
TCAAGAAACCCTCGGACAAAGCGCTTTTGAAAGTAACGGA
GTTAGCGTTTGCTGATCCAAAAGGCACATGGGGAACTCCG
CTTGTTCCAATAAATCGCAAGCCTGGTATGAACGATGTTGG
CATGGTAGCCTGGTACATGGAAATGTCCACCCCCGAGTTC
CCTAATGGAAGAACAATAATGGTTGTAGCTAATGATGTTA
CCTTCAAGGCCGGATCTTTTGGACCACGAGAAGATGCTTTC
TTCCTTGCTGTTACAAATCTTGCTTGCGCGAAGAAACTTCCT
CTTATTTATCTGGCTGCCAATTCAGGAGCTCGACTTGGTGT
TGCCGAAGAGCTAAAATCCTGCTTTAAAGTTGGCTGGTCG
GATGAGTCAAATCCCGAGAGTGGATTTCAGTATGTCTACTT
AACCCCTGAAGATTACGATCGTATAGGATCGTCAGTCATA
GCCCACGAGTTAAAACTCGAAAGTGGAGAAAAAAGATGG
GTTATAGATACCGTTGTAGGTAAGGAGGACGGATTAGGTG
TTGAGAACCTATCGGGAAGTGGTGCTATAGCCAGTGCATA
CTCAAGGGCTTACAAGGAAACATTTACTCTGACTTTTGTAA
CCGGAAGAACGGTCGGTATTGGTGCCTATCTTGCTCGTCTT
GGGATGCGTTGTATACAGAGGCTTGACCAGCCTATAATTC
TCACGGGTTTTTCTGCGTTAAATAAACTTCTCGGTCGGGAG
GTTTATAGTTCACACATGCAACTTGGTGGACCGAAGATTAT
GGGCACAAACGGGGTAGTTCATCTTACAGTATCCGATGAT
CTTGAAGGCATTTCATCTATCTTGAAGTGGCTGAGCTACGT
TCCACCCTATTCAGGTGGTGAACTTCCGATTTCTCGGTGTTT
AGACCCTCCAGGAAGACCGGTTGCGTATTTGCCTGAAAAT
TCTTGTGATCCTCGTGGTGCTATATCTGGTACGGTTGACTC
CACCGGTAAATGGTTTGGGGGTATTTTCGACAAGGATAGT
TTTGTGGAAACCTTAGAAGGATGGGCACAAACAGTTGTCA
CGGGAAGGGCTAAACTCGGAGGAATTCCAGTTGGCATAG
TTGCCGTTGAGACGCAGACTGTTATGCAAGTAATCCCAGC
AGATCCCGGTCAACTCGACTCACACGAGAGAGTCGTACCA
CAAGCAGGGCAAGTATGGTTCCCAGATTCTGCATCCAAGA
CAGCACAAGCGCTGATGGATTTCAACCGGGAAGAACTCCC
ACTTTTCATTTTAGCTAATTGGAGAGGTTTCTCGGGTGGAC
AAAGGGATCTCTTTGAAGGGATCCTTCAGGCCGGATCCAC
CATAGTTGAAAATCTTAGGACTTATAATCAACCCGTTTTTG
TTTATATCCCTATGATGGGGAGCTTCGAGGAGGCGCATG
GGTGGTCGTCGATAGTCGAATTAATTCCGACCATATAGAA
ATGTACGCCGACCAAACAGCTAAAGGAAATGTGCTTGAAC
CGGAAGGAATGATTGAGATTAAGTTCCGAACCAAGGAACT
TCTCGAGTGTATGGGAAGGCTTGATCAACAACTCATCGGT
CTCAAGGAAAAACTAGCCGAAGCCAAGAGCTCTAATTCCT
ACAATAAAATCGAGCCCCTGCAGCAACAAATAAAAGCCCG
TGAGAAGCAACTATTGCCTCTATATACTCAAATAGCCACCA
AATTTGCCGAGTTGCACGATACGTCTTTAAGGATGGCTGCC
AAAGGAGTCATTAGGGACGTCTTGGAATGGAAAAGCTCGC
GTTCGTTCTTTTACAAAAGATTATACAGGGAGTTATGGAG
GAATCGCTCGTCAAGACTGTTCGAGATGCTGCAGGTGAAC
GGTTGACCCATAAGTCGGCTTTGGAGTTGATCCAAAAATG
GTTCAATGAGTCGAATATTTCCGGAGAGGCTTCCGATGCTT
GGGCTGATGATGCGGCCTTCTTTAAGTGGAAGGACAATAC
CGCCAACTACGAGGAGAAGTTGAAAGAGTTGCGCGTTCAG
AAGGTATTGGATCAGCTGTCGAATATTGGAGATTCGGCAA
CTAATTTGAGGGCTCTGCCTCAGGGTCTTGCTGCCCTACTT
```

TABLE 1-continued

ACCase gene sequences isolated from weedy plant species

| SEQ ID NO | SPECIES | TYPE | LENGTH | SEQ |
|---|---|---|---|---|
| | | | | CAAAAGGTAATCTGATTTATTTTATGTACATTCTTTGTTCTT<br>TCTC |
| 16 | Amaranthus palmeri | gDNA Contig | 1693 | AAATCATTCCCATTACCGCCATTTAGTACCACTAACCAAAC<br>GGGACGGTAAAGTTTTGCTTACTACAATATCTTCTTAGCTC<br>ATAAGCTCAGAACCTTACTTGAATTTTGACAATGTGTGTCT<br>AGCTATACTTTCAATAAGTATTTAAGAATTCATTTTCTTTTT<br>ATCTATGTAAAGTTGCATATGATGTTTGTTATAAAGGGTCA<br>ATCAAAAAACTATCTCTTTGTTATTAGTAACAAGGGTAACT<br>GGGTAAGGTTATGTACATCCAATCCCTCCAAACCCTTTTTG<br>GGTGGGAGCTACTTAATGGCGCTGGGACAATGGAAGTTTT<br>TGTTTGTCGAATTCAAGCGGGGAAGTTTGTTTAGAATGAA<br>TGTTATTTCTAAAAATAGATGGTATAAGTATGTTAATCAAC<br>AATTAATAATAGAGAACTGTTTTATTGGTGTGATAAACAGT<br>TTCAGGAGCAGTGGTCTCATTTTCGAGCAATACAAAAAGT<br>GCCGTGCTTCTCTAAACAACGACGATTCAGACATGTCTTCT<br>CCTTCCCACAATAATGAAAACCCGAACGGACCGATGATGC<br>CACTCCTGAGGAATTCATCTGTAGTATCCATTGTTGATAAG<br>TTCTGTTATGCTCTTGGAGGGACGCGGCCAATCCATAGTAT<br>TTTGATAGCAAACAATGGGATGGCTGCTGTCAAATTTATAA<br>GAAGTATCCGAACATGGGCTTACGAGACTTTTGGTACTGA<br>GAAGGCTATATTATTGGTAGCCATGGCTACTCCCGAAGAC<br>ATGAAAATCAATGCCGAGCATATTCGAATGGCTGATCAGT<br>TTGTTGAAGTCCCCGGAGGAACTAACAACAATAACTACGC<br>CAATGTGCAGCTCATTGTTGAGGTAATGTATCTTGAGATTA<br>GAAATTTCTAGCCTGTCATCCATAGTTACATGGAATGTGGA<br>ACATAGCCACGTTCCGCGATTCGGGAACATTCATTCCCAAT<br>CACCATGAAACCCGACCTAAATCGCTAAAGGTGACGTCCC<br>GGTGTAGAACACCTTTTTTTAAAATGTATTTTTGGCCTTCA<br>TTTACAAATTGAAGAAAGGAGGAAAAAACAAGATGTAACC<br>CAGAAACCTAAACAAATCCACTTGAAAATAATTTCTTAAAG<br>CAAATTAATCATTTTAGTTTAATTTTGTTTCAAATATATATTT<br>TATACATAATGTATCTCATACCCAATCGTTCTTGAGTAAATC<br>TAGGTTGCGTTCTGTGTTCCCATTCTTGTTTCCTGTTCGAAA<br>CCAAATGTCGTTCAGTTAACAATGCTGTTATCTGCTTTACTG<br>TGATTTATTAAATGTGTCCTTCGAAAAAAGGCAATATCAGA<br>GCGACTTGATGCAGTATGGCCTGGCCGGGGACATGCGTA<br>GTTTGTTATATGAGATTGCAAATTTATAGCCTTTTATATGGT<br>AAAATCTTGTGGTAGGACTAACTTAAATCCTTTTTCTTTCAG<br>TTAGCGGAAGTTACACGAGTTGACGCAGTTTGGCCTGGTT<br>GGGGACATGCATCGGAGATCCCCGAGTTGCCAGATTCATT<br>AGCTACGAAGGGAATTGTGTTTCTGGGCCCCCCAGCTGCA<br>TCTATGGCTGCTCTTGGAGATAAAATTGGTTCATCATTGAT<br>TGCACAAGCTGCAGATGTCCCAACTCTTCCATGGAGTGGTT<br>CTCATGTACGTACTACAC |
| 17 | Amaranthus palmeri | gDNA Contig | 1457 | GGAGACATCTTGTGCCTCTAACCAAACCAAACCAACCTCCT<br>TAAACTTCTCTTCTTCTACTCACCATTTTTTCCTCTTTTTATTG<br>ATTATTGATTATTCATTTTAAATATACATTATATTGTAGGAA<br>TTTAATGAAATTTTCATTAAATTCTGATAAAGTTTTGATTTT<br>TTTTAGTGTATGAGATTTTTCTTAAGTACCCAAATGGTAAA<br>TTTCAAGTATAATCAAGTTTTTTAGTACCCAAAGCTCTAAAT<br>GTTACTTAAAGTTTTGATCTTTTAATGGTTTCTTCTATTTAAT<br>CCAATAATTTAAAGTACCCAGATTTCAATTTTTAGAATAAAT<br>TGAGTTTTTGAATTGCCCAAGTTGTAATTGTTGCTGAATTCT<br>CTTGCTTTGATTTGGGTTTTCTGATTCTATCCCTTCTGATTC<br>ATACAGGTATTCTGATTTTTTCTTGCTTGATTACTTTTTGTTA<br>GTGTATGGTTGAGCTAATTTAGTTTATAGTAGTGTGAATTT<br>TATTTTATTTTTTTTCAATTTTTTCAATTATTTCAATTTGTAG<br>AGTAGATTCTCCTATTATGATTTGTTTTTGTAGCTGGGTTTT<br>AATTTTTATTGTCTGATGATTTATCTTAGCAATGTTTTATTG<br>AAGTGTATTTAGTTGATTCCATTTTTCCAATAGAGTGTACA<br>AAATCGACCTGATTAACTGAAACTGAGTATTATCCAACGG<br>GAACAATCACTGTTACAAAATTCAAATTAGAATGTCAAGTA<br>CCGAAATCAACCCGACCCCACATATTATACCCGAGATCCAC<br>CCGAACACCCGAATGAACACCTCTGAGATCATAGAGAGGA<br>TATAAGAAAAGTGAAACTAGAATGGGGAATTTAGTTTATT<br>TAAGCTACATTGAGCAAAAATTTTTTAGTGACTGATTATT<br>GTAGCTGGCTTTGTTGTATAACTCATCTAAGCAATGTTTTT<br>GATGTGTGTGCAGTAGCATTGGATTGTTTTGATTTTTTTGT<br>TATATTGTCTATACAATTCAATTCTTGAATCACACTTGACTT<br>TTAGTTCCATTTTCATCTTCACAAATTCTTGTGAGAGACGGT<br>CTCAGTGTTAGCGCTCTCTGTACATGGGCTAAATAGCCCA<br>ACTAATACAACTATTAGCATACGAGCTTCTTATTTTGAAGT<br>CATCTCTCATAAGAGTAGCTCTCTATCTTTCGTTGGGTAGA<br>TGGTAATAAACGGTAGTAATGAGGATGAAAAACAAGTGTA |

TABLE 1-continued

ACCase gene sequences isolated from weedy plant species

| SEQ ID NO | SPECIES | TYPE | LENGTH | SEQ |
|---|---|---|---|---|
| | | | | ATTTTGGTTGGAAAATATGTTGGTTACCTTGATGGTCATGC TTGTCCAACTTAAATCATCTTATTTTCTTCTCAAAATTCATTT CAATGCATTACCATTAGGAGAGGTGATATTAGGCGGTAAT GAAATTATGTAAACAAAAAACTTTTTTGTGATTGAAGTTT CATTGCTATAGGAACGATATCGATATGGAACTTTTGATGAA ATTT |
| 18 | Amaranthus palmeri | gDNA Contig | 1175 | TTTTTTTTTCCTTCCAAATTTCTGATCTTTAGAGTTTTAGTGA TAGATTTATATACGTCTCTATCCCTCAGGTGAAAATTCCTGC TGAGAGTTGCCTAGACGTAATTCCCGATGAAGTATATAAA GCGGCATGTGTTTTTACTACAGAGGAAGCAATTGCTAGCT GTCAAGTTGTTGGTTATCCGGCTATGATCAAAGCTTCTTGG GGTGGTGGAGGGAAGGGAATAAGAAAGGTAAAATTTTTT TGGATGATGATGCTCTTAAAAGACTAAAAGGAGGTTACAC ATATCCCCATTACTTGTTTATCATCAGAGGCGGAGCAAAAA TTGACAAAGATTTAAAGGCTGTGTGCAATTTCAAAAAATAT GATATATTTCTAACAACGTATCTTCAAACACTTTAAACATAC TACCTATTCTAATATTGCGGCCCCTATTTTTTTGAGGCCGTG TGTGGTCGAACATATTGAATATGCTTAGAACCACTCCTGTT TATCACTAATATGCCATCTTCCACAATCAAACCTCTACTTTT GACCCAGATTCCTTGAAAGGGATTTCGATTTAGACTCGAG CTATGGTCAATTATTAGCAATAGCAAAAGCTTCTTAATAGT TAATAGATTCTCAAACACTTCCGTCATGCCAACACTTTATGA AGACTCATGGGTATTCTCTCTTTTAGGTTCATAATGATGAC GAAGTACGGGCATTATTTAAGCAAGTGCAGGGTGAAGTTC CCGGCTCACCCATATTTATAATGAAGGTGGCTTCACAGGTT AGACTTTCTTCAACATTGGTCCGATATTCGAGTAAATTGCA TTAAAAAAGGTTAAATATACAATTTTTTTGGATAAGTATTG TATGAGAGACTACTACTAAGATAAAGTATTATTAATATGTG CAGAGTCGACACTTAGAAGTACAGTTACTGTGTGATGAAT ATGGCAATGTTGCAGCATTGCATAGCCGTGATTGCAGTGT CCAAAGGCGGCACCAAAAGGTGGGTCTTTGGTAGATTATG GTTATGATCTACGGTTTCTTATTGTTTAAGAAAAATATTTGA TATTAAGCATTATTTAGCTTGCTGAGATTTGAACTTTTCTGT TCATCATATTAACTAATCAGATCATTGAAGAAGGCCCAATA ACGATAGCTCCACCAGAAACGGTGAAGA |
| 19 | Amaranthus rudis | cDNA Contig | 5038 | AAGAACTTGTTTGCTTCAGAACGATCACGATCCTTCAAAGC TGATTGCGGAGACACCGTGTAAGCTTATGCGGTATTTGGT ACCAGATAACAGTCACATAGATGCAGATACTCCGTATGCT GAAGTTGAGGTCATGAAGATGTGTATGCCTTTGCTTTCCCC TGCATCCGGTGTTTTACAATTTAAGATGTCCGAAGGTCAAG CTATGCAGGCTGGTGAACTCATAGCTAGTCTAGAGTTGGA TGATCCTTCAGCTGTAAGAAAAGCCGAACCTTTCCGTGGAA GCTTTCCTGTCATGGGCGCACCAACTGCAATATCTGGAAAA GTTCATCAGAGGTGTGCCGCAAGTTTAAATGCCACTCGGA TGATTTTGGCTGGTTATGAACACAATATAGATGAAGTAGT ACAGAGTTTGCTGGAATGCCTTGATAGTCCCGAACTTCCAT TCCTTCAATGGCAAGAATGCTTGTCTGTGCTGGCAACACGA CTTCCCAAAGATCTGAGATACGAATTGGAATCAAAATCTAG AGCTTTTGAAGGGATTACCAACACCCAGAACGTAGAATTTC CTGCTAAGTTGTTGAAAAGCATTCTTGAGGACCATTTAAAC TCATGCCACGAGAAAGATAAAGGAGCTCAAGAGAGGCTT ATTGAGCCTCTTATGGCTCTTGTAAAGTCTTACGAAGGTGG GCGAGAAAGTCATGCTCGTTTTATTGTTCAATCTTTATTTGA AGAGTATTTATCCGTTGAAGAATTGTTTAGCGACAATCTCC AGGCTGATGTGATTGAACGTCTCCGCCTTCAGTATAAGAA GGATCTGCTGAAGATTGTTGACATTGTACTGTCGCATCAG GGTGTTAAGAATAAAAATAAGCTGATTCTACGACTCATGG AACAGCTGGTTTACCCAAATCCCGCTGCATACAGGGGGAA ACTTATCCGTTTCTCTCAATTGAACCATACAATGTATTCTGA GTTGGCACTAAAGGCCAGTCAATTGCTTGAACAAACGAAA TTGAGTGAGCTCCGTTCGAACATTGCTAGAAACCTCTCTGA GCTAGAAATGTTTACCGAGGATGGCGAAAACATGGATACT CCAAAAAGAAAAAGTGCTATTAATGAACGTATGGAGGCGC TTGTGAGTACTCCTCAGCTGTCGAAGATGCCCTTGTTGGT TTGTTTGATCATAGTGATCATACACTTCAGAGGCGGGTTGT TGAGACCTATGTTCGGAGGCTTTATCAGCCTTATCTTGTCA AGGGAAGTGTCAGGATGCTGTGGCACAGATCAGGCTTCAT AGCTTTATGGGAATTTGTTGAGGAGAATATTGACCGAACG AATTTTTCTGATCTGACTACAAACAGTGGGAACCATAGTGA GCGAAAGTGGGGGCCATGGTCGTTATTAAAACTCTTCAG TTCTTGCCATCGGTAATTGCTGCAGCATTGAGAGAAACAAC TCATAGTTCCGATCAATCAACTTCCACTGGCTCTATAGAAT CAGTCATCCATGGAAATATGCTGCACATTGCACTAGTCGG GGTGAATAACCAGATGAGCTTGTTGCAGGATAGTGGTGAT |

TABLE 1-continued

ACCase gene sequences isolated from weedy plant species

| SEQ ID NO | SPECIES | TYPE | LENGTH | SEQ |
|---|---|---|---|---|

```
GAAGATCAGGCTCAAGAGAGAATCGATAAGTTGGCCAAA
ATTCTGAGAGAACAAGAAGTGAGTTCAGCCCTTCGTGCTG
TTGGTGTTGGTGTGATTAGTTGCATCATACAGAGAGATGA
AGGGCGAACTCCGATGAGGCATTCATTCTATTGGTCAGCA
GAAAAACAATATTATAGTGAGGAACCTTTACTACGTCATTT
GGAACCCCCTCTATCTATGTATCTCGAGCTGGACAAGCTTA
AGGGTTATGAAGATATCAAATATACTCCTTCCCGTGATCGT
CAATGGCATCTTTACACGGTTATTGATAAACCATTCATTCG
GAGGATGTTTTTGAGAACCCTTGTAAGACAACCCATCTCCG
AGTTCACTGGCGTCGAACTAAGCGCTCTTGAAACACAAAA
GCCTATCTCTTTTACTTCAAGAAGCATCCTAAGGTCATTAAC
AACCGCCATGGAGGAGTTGGAGCTCAATGCACATAGTGCT
TCACTGAAACCCGATCACGCTCATATGTACTTGTACATTGT
CCGAGAGCAACAAATATACGATCTTGTGCCATATAACAGG
GAGGTGAACATAGATTACCAACAAGAAGAGGCTTCGGTTC
AATTCTTTTTGGAAGATCTCGCGCATGAAATCCATAGTCTT
GCTGGTGTAAGGATGCATAAACTAAATGTTTGTGAGTGGG
AAGTGAAACTTCGGATATCATCTCCCGGGAAAGCTAATGG
TTTATGGAGGGTGGCAGTTACTAATGTGACTGGTCATACCT
GTTCGGTACATGTTTATCGTGAATTGGAAGATAGCAACCTA
CATGAAATGGTCTACCATTCAGTATCTGTTCACGGCCCCCA
CCATGGGGTACCTGTGAATGCACCCTATCAACCACTCGGT
GGCATCTCCCGTAAGCGACTTCAGGCCATGAAGAGTAGCA
CAACATACTGTTACGATTTTCCACTGGCTTTCTCAACTGCCC
TGAAGCAATCATGGGCATCGGAAGCTCCGGATGTCAAGAA
ACCCTCGGACAAAGCACTTTTGAAAGTAACCGAGCTAGCA
TTTGCTGATCCAAAAGGCACATGGGGAACTCCGCTTGTTCC
AATAAATCGCAAGCCTGGTATGAACGATGTTGGCATGGTA
GCCTGGTACTTGGAAATGTCCACCCCCGAGTTCCCTAACGG
AAGAACAATAATGGTTGTAGCTAATGATGTTACCTTCAAG
GCCGGATCTTTCGGACCACGAGAAGATGCTTTCTTCCTTGC
TGTTACAAATCTTGCTTGCGCGAAGAAACTTCCTCTTATTTA
TCTGGCTGCCAATTCAGGAGCTCGACTTGGTGTTGCCGAA
GAGCTAAAATCCTGCTTTAAAGTTGGCTGGTCGGATGAGT
CAAACCCCGAGAGTGGATTTCAGTATGTCTACTTAACCCCT
GAAGATTACGATCGTATAGGATCGTCAGTCATAGCCCACG
AGTTAAAACTCGAAAGTGGAGAAAAAAGATGGGTTATAG
ACACCGTTGTCGGTAAGGAGGACGGATTAGGTGTCGAGA
ATCTATCAGGAAGTGGTGCTATAGCCAGTGCATACTCAAG
GGCTTACAAGGAAACATTTACTCTGACTTTTGTAACCGGTA
GAACGGTCGGTATTGGTGCCTATCTTGCTCGTCTTGGGATG
CGTTGTATACAGAGGCTTGACCAGCCTATAATTCTCACGGG
TTTTTCTGCGTTAAATAAACTTCTCGGTCGGGAGGTTTACA
GTTCACACATGCAACTTGGTGGACCGAAGATTAATGGGCA
CAAACGGGGTAGTTCATCTTACAGTTTCCGATGATCTTGAA
GGCATTTCATCTATCTTGAAGTGGCTGAGCTATGTTCCACC
CTATTCAGGTGGTGAACTTCCGATTTCTCGGTGTTTAGACC
CTCCCGAAAGACCGGTTGCGTATTTGCCTGAAAATTGTTGT
GATCCTCGTGGGCTATATCTGGTACGGTTGACTCCGCCG
GTAAATGGTTTGGGGGTATTTTCGACAAGGATAGTTTTGT
GGAAACCTTAGAAGGATGGGCACGAACAGTTGTCACGGG
AAGGGCTAAACTCGGAGGAATTCCAGTTGGCATAGTTGCT
GTTGAGACACAGACTGTTATGCAAGTAATCCCAGCAGATC
CCGGTCAACTCGACTCACATGAGAGTCGTACCACAAGC
AGGGCAAGTATGGTTCCCAGATTCCGCATCCAAGACAGCA
CAAGCGCTGATGGATTTCAACCGGGAAGAACTCCCACTTTT
CATTTTAGCTAATTGGAGAGGTTTCTCGGGTGGACAAAGG
GATCTCTTTGAAGGGATCCTTCAGGCTGGATCCACCATAGT
CGAAAATCTTAGGACTTATAATCAACCCGTTTTTGTTTATAT
ACCTATGATGGGGAGCTTCGAGGAGGGCATGGGTGGTC
GTCGATAGTCGAATTAATTCCGACCATATAGAAATGTACGC
CGACCAAACAGCTAAAGGAAATGTACTTGAACCCGAAGGA
ATGATCGAGATTAAGTTCAGAACCAAGGAACTTCTCGAGT
GTATGGGAAGGCTTGATCAACAACTCATCGGTCTCAAAGA
AAAACTAGCCGAAGCCAAGAGCTCTAATTCCTATGGTAAA
ATCGACCCGCTTCAGCAACAAATAAAAGCCCGCGAGAAGC
AACTATTGCCTCTATATACTCAGATAGCCACCAAATTTGCC
GAGTTGCACGATACGTCTTTAAGGATGGCTGCCAAAGGAG
TCATTAGGGACGTCTTGGAATGGAAAAGCTCGCGTTCTTTC
TTTTACAAACGATTATACAGGAGAGTGATGGAAGAATCGC
TCGTCAAGACCGTTCGAGATGCTGCAGGTGAACGGTTGAC
CCATAAGTCGGCTTTGGAGTTGATCCGGAAATGGTTCAAT
GAGTCGATATTTCCGGAGAGGCTTCCGATGCTTGGGCTGA
TGATGCAGCCTTCTTTAAGTGGAAGGATAATACCGCTAACT
ACGAGGAGAAGTTGAAAGAGTTGCGCGTTCAGAAGGTAT
TGGATCAGCTGTCGAATATTGGAGATTCGGTAACTAATTTG
```

TABLE 1-continued

ACCase gene sequences isolated from weedy plant species

| SEQ ID NO | SPECIES | TYPE | LENGTH | SEQ |
|---|---|---|---|---|
| | | | | AGGGCTCTGCCTCAGGGTCTTGCTGCCCTACTTCAAAAGGT<br>GGATCCATCGAGTCGAGAAGAACTAGTTGAGGAACTCCGA<br>AAAGTGCTCACTTGATTAGCGGCCGTTGATGGTGAAGTGA<br>AACCTTCTTGGTTTCATCATGGTAGAAATTATTATTAGGCA<br>AATCTATAATTCTAGTTACATCAATTGTATTAGACAATAGTA<br>TGAACTAATTTATTTAATTAAATTGTATAAATAGGAAACCTT<br>GAATTCATTTGAATTAATCGGCTTATGCTTGCATTATTTTGT<br>ATTGATTCAATTAATAATTTACATACTTTTGAGTATTAATAA<br>TGGAAAAAAAAAGAAAAAAAAACAAAACATGTCGGCCG<br>CCTCGGTCTCTACTGA |
| 20 | Amaranthus rudis | cDNA Contig | 1529 | CGGTTGCGTATTTGCCGGAAAATTCTTGTGATCCTCGTGGT<br>GCTATATCTGGTACGGTTGACTCCACCGGTAAATGGTTTGG<br>GGGTATCTTCGACAAAGATAGTTTTGTGGAAACCTTAGAA<br>GGCTGGGCACGAACAGTTGTCACGGGAAGGGCTAAACTT<br>GGAGGAATTCCAGTTGGCATAGTTGCCGTTGAGACGCAGA<br>CTGTTATGCAAGTAATCCCAGCAGATCCCGGTCAACTCGAC<br>TCACACGAGAGAGTCGTACCACAAGCAGGGCAAGTATGGT<br>TCCCAGATTCCGCATCCAAGACAGCACAAGCGCTGATGGA<br>TTTCAACCGGGAAGAACTCCCACTTTTCATTTTAGCTAATTG<br>GAGAGGTTTCTCGGGTGGACAAAGGGATCTCTTTGAAGG<br>GATCCTTCAGGCCGGATCCACCATTGTCGAAAATCTTAGGA<br>CTTATAATCAACCCGTTTTTGTTTATATACCTATGATGGGG<br>GAGCTTCGAGGAGGAGCATGGGTGGTCGTCGATAGTCGA<br>ATTAATTCCGACCATATAGAAATGTACGCCGACCAAACAGC<br>TAAAGGAAATGTACTTGAACCCGAAGGAATGATCGAGATT<br>AAGTTCAGAACCAAGGAACTTCTCGAGTGTATGGGAAGGC<br>TTGATCAACAACTCATCGGTCTCAAAGAAAAACTAGCCGA<br>AGCCAAGAGCTCTAATTCCTATGGTAAAATCGACCCGCTTC<br>AGCAACAAATAAAAGCCCGCGAGAAGCAACTATTGCCTCT<br>ATATACTCAGATAGCCACCAAATTTGCCGAGTTGCACGATA<br>CGTCTTTAAGGATGGCTGCCAAAGGAGTCATTAGGGACGT<br>CTTGGAATGGAAAAGCTCGCGTTCTTTCTTTTACAAACGAT<br>TATACAGGAGAGTGATGGAAGAATCGCTCGTCAAGACCGT<br>TCGAGATGCTGCAGGTGAACGGTTGACCCATAAGTCGGCT<br>TTGGAGTTGATCCGGAAATGGTTCAATGAGTCCGATATTTC<br>CGGGAGAGGCTTCTGATGCTTGGGCTGATGATGCAGCCTTC<br>TTTAAATGGAAGGATAATACCGCTAACTACGAGGAGAAGT<br>TGAAAGAGTTGCGCGTTCAGAAGGTATTGGATCAGCTGTC<br>GAATATTGGAGATTCGGTAACTAATTTGAGGGCTCTGCCTC<br>AGGGTCTTGCTGCCCTACTTCAAAAGGTGGATCCATCGAG<br>TCGAGAAGAACTAGTTGAGGAACTCCGAAAAGTGCTCACT<br>TGATTAGCGGCCGTTGATGGTGAAGTGAAACCTTCTTGGT<br>TTCATCATGGTAGAAATTATTATTAGGCAAATCTATAATTCT<br>AGTTACATCAATTGTATTAGACAATAGTATGAACTAATTTA<br>TTTAATTAAATTGTATAAATAGGAAACCTTGAATTCATTTG<br>AATTAATCGGCTTATGCTTGCATTATTTTGTATTGATTCAAT<br>TAATAATTTACATACTTTTGATTATTAATAATGGAAATCCTC<br>AAAGTTTAAGGGGATTGTTTCTAAAAAAAAA |
| 21 | Amaranthus rudis | cDNA Contig | 1103 | GGGGCCATGGTCGTTATTAAAACTCTTCAGTTCTTGCCATC<br>GGTGATTGCCTGCAGCATTGAGAGAAACAACTCATGGTTC<br>AGATCAATCAACTTCCACTGGCTCTATAGAACCAGTCATCC<br>ATGGAAATATGTTGCACATTGCACTAGTCGGGGTGAATAA<br>CCAGATGAGCTTGTTGCAGGATAGTGGTGATGAAGATCAG<br>GCTCAAGAGAGAATCGATAAGTTGGCCAAAATTCTGAGAG<br>AACAAGAAGTAAGTTCAGCCCTTCGTGCTGTTGGTGTTGG<br>TGTGATTAGTTGCATACAGAGAGATGAAGGGCGAACT<br>CCGATGAGGCATTCATTCTATTGGTCAGCAGAAAAACAAT<br>ATTATAGTGAGGAGCCTTTACTACGTCATTTGGAACCCCCT<br>CTGTCTATGTATCTCGAGCTGGACAAGCTTAAGGGTTATGA<br>AGATATCAAATATACTCCTTCCCGTGATCGTCAATGGCATC<br>TTTACACGGTTATTGATAAACCATTCATTCGGAGGATGTTT<br>TTGAGAACCCTTGTAAGACAACCCATCTCCGAGTTCACAGG<br>CGTCGAACTAAGCGCTCTTGAAACACAAAAGCCTATCTCTT<br>TTACTTCAAGAAGCATCCTAAGGTCCTTAACAACCGCCATG<br>GAGGAGTTGGAACTCAATGCACATAGTGCTTCACTGAAAC<br>CCGATCACGCTCATATGTACTTGTACATTGTCCGAGAGCAA<br>CAAATATACGATCTTGTGCCATATCACAGGGAGGTGAACA<br>TAGATTACCAACAAGAAGAGACTTCGGTTCAATTCTTTTTG<br>GAAGATCTCGCGCATGAAATCCACAGTCTTGCTGGTGTAA<br>GGATGCATAAACTAAATGTTTGTGAGTGGGAAGTGAAACT<br>TCGGATATCATCTCCCGGGAAAGCTAATGGTTTATGGAGG<br>GTGGCGGTTACAAATGTGACTGGTCAGACCTGTTCGGTAC<br>ATGTTTACCGTGAATTGGAAGATAACAACCTACATGAAAT<br>GGTCTACCATTCAGTATCCGTTCACGGCCCCCACCATGGGG |

TABLE 1-continued

ACCase gene sequences isolated from weedy plant species

| SEQ ID NO | SPECIES | TYPE | LENGTH | SEQ |
|---|---|---|---|---|
| | | | | TACCTGTGAATGCACCCTATCAACCACTCGGTGGCATCGCC<br>CGTAAGCGAC |
| 22 | Amaranthus<br>rudis | cDNA<br>Contig | 541 | AGATGCTTTCTTTCTTGCAGTTACAAATCTTGCTTGTGCAAA<br>GAAACTTCCTCTTATTTATCTGGCTGCAAATTCAGGAGCTC<br>GACTTGGTGTTGCCGAAGAGCTAAAATCCTGCTTTAAAGTT<br>GGCTGGTCGGATGAGTCAAACCCCGAGAGTGGATTTCAGT<br>ATGTCTACTTAACCCCGGAAGATTACGATCGTATCGGATCG<br>TCAGTCATAGCCCACGAGTTAAAACTCGAAAGTGGAGAAA<br>AAAGATGGGTTATAGACACAGTTGTCGGTAAGGAGGACG<br>GATTAGGTGTCGAGAATTTATCAGGAAGTGGTGCTATAGC<br>AAGTGCATACTCAAGGGCTTACAAGGAAACATTTACTCTG<br>ACTTTTGTAACCGGTAGAACGGTCGGTATTGGTGCCTATCT<br>TGCACGTCTTGGGATGCGTTGTATACAGAGGCTTGACCAG<br>CCTATAATTCTCACGGGTTTTTCTGCGTTAAATAAACTTCTC<br>GGTCGGGAGGTTTACAGTTCACACATGCAACTTGGTGGAC<br>CGAAGATTATGGGC |
| 23 | Amaranthus<br>rudis | gDNA<br>Contig | 1511 | TTTTAAGAACGTAATTTCTTTTTATTTATGAGAAGTTGCAGA<br>TGATGTTTGTTATAAATGGTCAATCGAAAAACTACCTCTTT<br>GTTATCAGTAACAAGGGTAAGGTTGTATATATCCGACTCCT<br>CCAAACTCTTCTTCGGTGGGAGCTACTTAATGTCGCTGGGG<br>CAATGGAAGTTGTTGTTTGTCGAATTTAAGTGGAGAAGTTT<br>GTTTACATTGAATTTTAATTAGATGGTATAAGTATGTTATC<br>AAAGATTATAATTGAAAACTGGTGTGATAAACAGTTTCAG<br>GAGCAGTGGTCTCATTTTCGAGCAATACAAAAAGTGCCGT<br>GCTTCTCTAAACAACGACGATTCAGACATGGCTTCTCATTC<br>CCAAAATAGTGAATACCTGAATGGACCGATGATGCCACTC<br>CTGAGGAATTCATCTGTATTACCCATTGTGGATAAGTTCTG<br>TTATGCTCTTGGAGGGACGCGGCCAATCCATAGTATTTTGA<br>TAGCAAACAATGGGATGGCTGCTGTCAAATTTATAAGAAG<br>TATCCGAACATGGGCTTACGAGACTTTTGGTACAGAGAAG<br>GCTATATTATTGGTAGCCATGGCTACTCCCGAAGACATGAA<br>AATCAATGCCGAGCATATTCGAATGGCTGACCAGTTTGTTG<br>AAGTCCCCGGAGGGACTAACAACAATAACTATGCCAATGT<br>GCAGCTCATTGTTGAGGTAATGTATTGTGAGATTAGAAATT<br>TCTAGCCTATTATCCATAGTTACATGGAACGTGGAACGTAG<br>CCACGTTCCGTGATCCGGGAACATTCATTCCCCAATCACCA<br>CGAAATGCGACCTAAATCGCTCAAGGTGACGTCTCGGTGT<br>AGAACACCTTTTTTAAAATGTATTTTGGCCTTCATTTACAAA<br>TTAAAGAAAAAAGAAAGGAGGAACAAACGAGATGTAACC<br>CAGAAACCTAAAAAAGATCCACTTGAAAATAATTTCTTAAA<br>GCAAATTAATCATTTTAGTTTAATTTTTTTTCAAATATATATT<br>TTATACGTAATGTATCTCGTACCCAATCGAACCTGTCGTTCC<br>AGGTAACAATGCTGTTATCTGCTTTATTGTAATTTATTAAAT<br>GTGTCCTCTGAAAAAATGGCAATATCCGAGCAACTTGACG<br>CAGTTTTGCCTGGCCAGAGACATGCGTAATTTGTTATATGA<br>GATTACAAATTTATAGCCTTTTATATGGTAAAATCTTGTGG<br>TAGGACTAACTTAAATCCTTTTTCTTTCAGTTAGCGGAAGTT<br>ACACGAGTTGACGCAGTTTGGCCTGGTTGGGGACATGCGT<br>CAGAGATCCCCGAGCTGCCAGATTCACTAAGTGCGAAGGG<br>AATTGTGTTTCTAGGGCCCCCAGCTGCATCTATGGCTGCTC<br>TTGGAGATAAAATTGGTTCATCATTGATTGCACAAGCTGCA<br>GATGTCCCAACTCTTCCATGGAGTGGTTCTCATGTACGTAT<br>TACACGTTTTTTCCAAATTTTTGATCATTAGAATTTTAG |
| 24 | Amaranthus<br>rudis | gDNA<br>Contig | 1246 | CATACCAATGTCCGAGCATCAAAAATCGGACACGGGTACG<br>TGAAGCAAATAAAGAGTCCGAGTAACATACTTATGATTA<br>ATGTTAAATAACTTATTGTCTTTATTGTCTATATCCAGAAAG<br>CATCGACTAGTAGTGCAGCGACTGTTTCAGAGTATATAGG<br>CTATCTTGAAAAAGGTCAAATTCCTCCGAAGGTATGCAACA<br>TACCAGTGGTTGGCGGGTGTTTAGATTAACTTATTCTATTT<br>ATATCAATTATACTTTCAGTGTTCTGCTTTAATTCTGGTTTT<br>ATGATTGCAGCATATATCACTCGTCCACTATGAAGTTGCTC<br>TAAATATTGAGGGGATGAAATATACTGTATGTTCCATGCCA<br>CTCGTACTTTCCTCGTGAATTTTGTAATGGATGCTATTTTT<br>GACATTATTCTTTCTAAATATGTTTTCCTGATATTAATGAAC<br>ATGTGGTTTCGGATTGCCAGATTGAGATGATTAGGGGTGG<br>ACCAGGAAGCTACAAAATGTGGTTGAATGGGTCCGTAATT<br>GAGGCGGAAATACATACTTTAAGAGATGGGGGTCTCTTGA<br>TGCAGGTATAACCTGTTTTTTTGGATTTTTTCCGATATACGG<br>TATTTTTATTTTATATGGACCCTGGATTTGAAAAGCATTAG<br>ATAATGTGCTATCGAACAAGTAGAAGGTAGTTTTGTGAGA<br>CCGTGAAGCATTTAGTTAAACCCATTGTTAAGATTACCTTTT<br>AGATTTAGTACTTCTACAATGCTTGGGATATTAATCAATAA<br>TCATGCTTTTAATAATAAAGAGAAATATTGTCATAGACTCA |

TABLE 1-continued

ACCase gene sequences isolated from weedy plant species

| SEQ ID NO | SPECIES | TYPE | LENGTH | SEQ |
|---|---|---|---|---|
| | | | | TAGGTATAATGGCTCGTTAAATTATATGCACTTCTTGTTTAT<br>GTGAAGTTCGAGATGCTGTTTGTAATCAACTTTGGAAATCG<br>AGGGCATAGTGCAAAATCTCGGATGTGGTCACCTTTGATG<br>CAACAATCTCAAAGCCACTTTTGTGGTCAATGTAGATGGTT<br>TCATTTTTATCGTGGTATAAATATGGGTCGCGGTAATCTCA<br>AGAACCCATATAGTAGACGATAACTTGTTATTAAAAGGGA<br>TAAGGCTGCATACATCCGATGTCCCCTTTACCCTGTCTAGA<br>TGTGAGCTACTTGGGGGTTTTCCTATTGAAGTTAAAGATAC<br>AAGAAGGATTTCTGTTAAAAAAAAAGGAATATTTGAACTA<br>CAAAAAAGTAATAAGTTTATATACTAGTTCGTTCTAACCCA<br>TATAGCACATTTTAAAAAA |
| 25 | Amaranthus<br>rudis | gDNA<br>Contig | 780 | TCAGCCTTATCTTGTCAAGGGAAGTGTCAGGATGCTGTGG<br>CACAGATCAGGCTTCATAGCTTTATGGGAATTTGTGGAGG<br>AGAATATTGACCGAACAAATTTTTCTGATGATCTGACTACA<br>AACAGTGAGCGAAAGTGGGGGGCCATGGTCGTTATTAAA<br>ACTCTTCAGTTCTTGCCATCGGTGATTGCTGCAGCATTGAG<br>AGAAACAACTCATGGTTCAGATCAATCAACTTCCACTGGCT<br>CTATAGAACCAGTCATCCATGGAATATGTTGCACATTGCA<br>CTAGTCGGGGTGAATAACCAGATGAGCTTGTTGCAGGATA<br>GGTACGTAAGACTAGCCTGTAACATATGGTTTAATAGTTTT<br>ATTATGTAACCTTGTGCTTTTAATGTCATTTATTTCTAGCCG<br>ATATTACGTAAGACTAGCCGATATTCATCCGATCTTGTAAC<br>TGAACCCGACTTCAAAATCAAATTTAAATTATATATAAATC<br>AACGTGGACATAAGACCCGATTTTAATCTGACCCGAAATCA<br>ACCCAATGACCCGAATGAACACCTATAGTTATCACTAACAA<br>GGGTCAGGTTACGTACATCAAACCCCTCAAATCCTGCTTAG<br>GTGGGAGCTTGTCATTGGCATTGGGGTAACGGGAATGTGT<br>GTGCTATGTACATTGTGCATCTATTCTTATACTTATGTTGTG<br>AGTTTTTTGGATCGAATATAAAGAGCTTATCTTTTGTATTTT<br>CTTGATGTGCTGTAGTGGTGATGAAGATCAGGCTCAAGAG<br>AGAAT |
| 26 | Amaranthus<br>rudis | gDNA<br>Contig | 342 | TTGCTTGAACAAACGAAATTGAGTGAGCTCCGTTCGAACAT<br>TGCTAGAAACCTCTCTGAGCTAGAAATGTTTACCGAGGAT<br>GGCGAAAACATGGATACTCCAAAAGAAAAAGTGCTATTA<br>ATGAACGCATGGAGGCCCTTGTGAGTACTCCTCTAGCTGTT<br>GAAGATGCCCTTGTTGGTTTGTTTGATCACAGTGATCATAC<br>ACTTCAAAGGCGGGTTGTTGAGACCTATGTTCGGAGGCTT<br>TATCAGGTGAATACATACTTAATTGCGGAGTTAGCTTCAGC<br>TTCACTCAGTCCTATTCGTTGCAAGAACTTCTCTTGATCTTT<br>CTCGAGTCGAGGGACT |
| 27 | Amaranthus<br>spinosus | cDNA<br>Contig | 755 | TTCGAGGAGGCGCATGGGTGGTCGTCGATAGTCGAATTAA<br>TTCCGACCATATAGAAATGTACGCCGACCAAACAGCTAAA<br>GGAAATGTGCTTGAACCGGAAGGAATGATCGAGATTAAGT<br>TCCGAACCAAGGAACTTCTCGAGTGTATGGGAAGGCTTGA<br>TCAACAACTCATCGGTCTCAAGGAAAAACTAGCCGAAGCC<br>AAGAGCTCTAATTCCTACAATAAAATTGAGCCCCTGCAGCA<br>ACAAATAAAAGCCCGTGAGAAGCAACTATTGCCTCTATATA<br>CTCAAATAGCCACCAAATTTGCCGAGTTGCACGATACGTCT<br>TTAAGGATGGCTGCCAAAGGAGTCATTAGGGACGTCTTGG<br>AATGGAAAAGCTCGCGTTCGTTCTTTTACAAAAGATTATAC<br>AGGAGAGTTATGGAGGAATCGCTCGTCAAGACTGTTCGAG<br>ATGCTGCAGGTAACGGTTGACCCATAAGTCGGCTTTGGA<br>GTTGATCCAAAAATGGTTCAATGAGTCGAATATTTCCGGA<br>GAGGCTTCCGATGCTTGGGCTGATGATGCGGCCTTCTTTAA<br>GTGGAAGGACAATACCGCCAACTACGAGGAGAAGTTGAA<br>AGAGTTGCGCGTTCAGAAGGTATTGGATCAGCTGTCGAAT<br>ATTGGAGATTCGGCAACTAATTTGAGGGCTCTGCCTCAGG<br>GTCTTGCTGCCCTACTTCAAAAGGTGGATCCATCGAGTCGA<br>GAAGAACTAGTCGAGGAACTCCGAAAAGTG |
| 28 | Amaranthus<br>spinosus | cDNA<br>Contig | 605 | AAGAACGGTCGGTATTGGTGCCTATCTTGCTCGTCTTGGG<br>ATGCGTTGTATACAGAGGCTTGACCAGCCTATAATTCTCAC<br>GGGTTTTTCTGCCTTAAATAAACTTCTCGGCCGGGAGGTTT<br>ATAGTTCACACATGCAACTTGGTGGACCGAAGATTATGGG<br>CACAAACGGGGTAGTTCATCTTACAGTTTCCGATGATCTTG<br>AAGGCATTTCATCTATCTTGAAGTGGCTGAGCTACGTTCCA<br>CCCTATTCAGGTGGTGAACTTCCGATTTCTCGGTGTTTAGA<br>CCCTCCAGAAAGACCGGTTGCGTATTTGCCTGAAAATTCTT<br>GTGATCCTCGTGGTGCTATATCTGGTACGGTTGACTCCACC<br>GGTAAATGGTTTGGGGGTATTTTCGACAAAGATAGTTTTG<br>TGGAAACCTTAGAAGGATGGGCACGAACAGTTGTCACGG<br>GAAGGGCTAAACTCGGAGGAATTCCAGTTGGCATAGTTGC<br>CGTTGAGACGCAGACTGTTATGCAAGTAATCCCAGCAGAT |

TABLE 1-continued

ACCase gene sequences isolated from weedy plant species

| SEQ ID NO | SPECIES | TYPE | LENGTH | SEQ |
|---|---|---|---|---|
| | | | | CCCGGTCAACTCGACTCACACGAGAGAGTCGTACCACAAG<br>CAGGGCAAGTATGGTTCCCAGATTCCGCATCCAAGACAG |
| 29 | Amaranthus spinosus | cDNA Contig | 577 | GAGGTGAACATAGATCACCAACAAGAAGAGGCTTCAGTTC<br>AATTCTTTTTGGAAGATCTCGCGCATGAAATCCATAGTCTT<br>GCTGGTGTAAGGATGCATAAACTAAATGTTTGTGAGTGGG<br>AAGTGAAACTTCGGGTATCATCTCCCGGGAAAGCTAATGG<br>TTTATGGAGGGTGGCAGTTACTAATGTGACTGGTCATACCT<br>GTTCGGTACATGTTTATCGTGAATTGGAAGATAGCAACCTA<br>CATGAAATGGTCTACCATTCAGTATCTGTTCACGGCCCCCA<br>CCATGGGGTACCTGTGAATGCACCCTATCAACCACTCGGT<br>GGCATCGCCCGTAAGCGACTTCAGGCCATGAAAAGTAGCA<br>CAACTTACTGTTACGATTTTCCACTGGCTTTCTCAACTGCCC<br>TGAAGCAATCATGGGCATCGGAAGCTCCGGATGTCAAGAA<br>ACCCTCGGACAAAGCGCTTTTGAAAGTAACCGAGCTTGCA<br>TTTGCGGATCCAAAAGGCACATGGGAACTCCGCTTGTTC<br>CAATAAATCGCAAGCCTGGTATGAACGATGTTGGCATGGT<br>AGCCTGGTACA |
| 30 | Amaranthus thunbergii | cDNA Contig | 1492 | GTGCTATTAATGAACGTATGGAGGCGCTTGTGAGTACTCC<br>TCTAGCTGTCGAAGATGCCCTTGTTGGTTTGTTTGATCATA<br>GTGATCATACACTTCAGAGGCGGGTTGTTGAGACCTATGT<br>TCGGAGGCTTTATCAGCCTTATCTTGTCAAGGGAAGTGTCA<br>GGATGCTGTGGCACAGATCAGGCTTCATAGCTTTATGGGA<br>ATTTGTTGAGGAGAATATTGACCGAACGAATTTTTCTGATC<br>TGACTACAAACAGTGGGAACCATAGTGAGCGAAAGTGGG<br>GGGCCATGGTCGTTATTAAAACTCTTCAGTTCTTGCCATCG<br>GTAATTGCTGCAGCATTGAGAGAAACAACTCATAGTTCCG<br>ATCAATCAACTTCCACTGGCTCTATAGAATCAGTCATCCAT<br>GGAAATATGCTGCACATTGCACTAGTGGGGGTGAATAACC<br>AGATGAGCTTGTTGCAGGATAGTGGTGATGAAGATCAGG<br>CTCAAGAGAGAATCGATAAGTTGGCCAAAATTCTGAGAGA<br>ACAAGAAGTGAGTTCAGCCCTTCGTGCTGTTGGTGTTGGT<br>GTGATTAGTTGCATCATACAGAGAGATGAAGGGCGAACTC<br>CGATGAGGCATTCATTCTATTGGTCAGCAGAAAAACAATAT<br>TATAGTGAGGAACCTTTACTACGTCATTTGGAACCCCTCT<br>ATCTATGTATCTCGAGCTGGACAAGCTTAAGGGTTATGAA<br>GATATCAAATATACTCCTTCCCGTGATCGTCAATGGCATCT<br>TTACACGGTTATTGATAAACCATTCATTCGGAGGATGTTTT<br>TGAGAACCCTTGTAAGACAACCCATCTCCGAGTTCACTGGC<br>GTCGAACTAAGCGCTCTTGAAACACAAAAGCCTATCTCTTT<br>TACTTCAAGAAGCATCCTAAGGTCATTAACAACCGCCATGG<br>AGGAGTTGGAGCTCAATGCACATAGTGCTTCACTGAAACC<br>CGATCACGCTCATATGTACTTGTACATTGTCCGAGAGCAAC<br>AAATATACGATCTTGTGCCATATCACAGGGAGGTGAACAT<br>AGATTACCAACAAGAAGAGGCTTCGGTTCAATTCTTTTTGG<br>AAGATCTCGCGCATGAAATCCATAGTCTTGCTGGTGTAAG<br>GATGCATAAACTAAATGTTTGTGAGTGGGAAGTGAAACTT<br>CGGATATCATCTCCCGGGAAAGCTAATGGTTTATGGAGGG<br>TGGCAGTTACTAATGTGACTGGTCATACCTGTTCGGTACAT<br>GTTTATCGTGAATTGGAAGATAGCAACCTACATGAAATGG<br>TCTACCATTCAGTATCTGTTCACGGCCCCCACCATGGGGTA<br>CCTGTGAATGCACCCTATCAACCACTCGGTGGCATCTCCCG<br>TAAGCGACTTCAGGCCATGAAGAGTAGCACAACATACTGT<br>TACGATTTTCCACTGGCTTTCTCAACTGCCCTGAAGCAATC<br>ATGGGCATCGGAAGCTCCGGATGTCAAGAAACCCTC |
| 31 | Amaranthus thunbergii | cDNA Contig | 1214 | GATGGGTTATAGACACCGTTGTCGGTAAGGAGGACGGATT<br>AGGTGTCGAGAATCTATCAGGAAGTGGTGCTATAGCCAGT<br>GCATACTCAAGGGCTTACAAGGAAACATTTACTCTGACTTT<br>TGTAACCGGTAGAACGGTCGGTATTGTGCCTATCTTGCTC<br>GTCTTGGGATGCGTTGTATACAGAGGCTTGACCAGCCTAT<br>AATTCTCACGGGTTTTCTGCGTTAAATAAACTTCTCGGTCG<br>GGAGGTTTACAGTTCACACATGCAACTTGGTGGACCGAAG<br>ATAATGGGCACAAACGGGGTAGTTCATCTTACAGTTTCCG<br>ATGATCTTGAAGGCATTTCATCTATCTTGAAGTGGCTGAGC<br>TATGTTCCACACTATTCAGGTGGTGAACTTCCGATTTCTCG<br>GTGTTTAGACCCTCCCGAAAGACCGGTTGCGTATTTGCCTG<br>AAAATTGTTGTGATCCTCGTGGGCTATATCTGGTACGGTT<br>GACTCCGCCGGTAAATGGTTTGGGGGTATTTTCGACAAGG<br>ATAGTTTTGTGGAAACCTTAGAAGGATGGGCACGAACAGT<br>TGTCACGGGAAGGGCTAAACTCGGAGGAATTCCAGTTGGC<br>ATAGTTGCTGTTGAGACGCAGACTGTTATGCAAGTAATCCC<br>AGCAGATCCCGGTCAACTCGACTCACATGAGAGAGTCGTA<br>CCACAAGCAGGGCAAGTATGGTTCCCAGATTCCGCATCCA<br>AGACAGCACAAGCGCTGATGGATTTCAACCGGGAAGAACT |

TABLE 1-continued

ACCase gene sequences isolated from weedy plant species

| SEQ ID NO | SPECIES | TYPE | LENGTH | SEQ |
|---|---|---|---|---|
| | | | | CCCACTTTTCATTTTAGCTAATTGGAGAGGTTTCTCGGGTG<br>GACAAAGGGATCTCTTTGAAGGGATCCTTCAGGCTGGATC<br>CACCATAGTCGAAAATCTTAGGACTTATAATCAACCCGTTT<br>TTGTTTATATCCCTATGATGGGGGAGCTTCGAGGAGGCGC<br>ATGGGTGGTCGTCGATAGTCGAATTAATTCCGACCATATA<br>GAAATGTACGCCGACCAAACAGCTAAAGGAAATGTGCTTG<br>AACCGGAAGGAATGATCGAGATTAAGTTCCGAACCAAGG<br>AACTTCTCGAGTGTATGGGAAGGCTTGACCAACAACTCATC<br>GGTCTCAAGGAAAAACTAGCCGAAGCCAAGAGCTCTAATT<br>CCTACGATAAAATCGAGCCCCTGCAGCAACAAATAAAAGC<br>CCGCGAGAAGCAACTATTGCCTCTTTATACTCAGATAGCCA<br>CCA |
| 32 | Amaranthus thunbergii | cDNA Contig | 1121 | TAAGAGATGGGGGTCTCTTGATGCAGTTGGATGGAAACA<br>GCCATGTGATATATGCAGAGGAAGAAGCTGCAGGAACTC<br>GCCTTCTGATTGATGGAAGAACTTGTTTGCTTCAGAACGAT<br>CACGATCCTTCAAAGCTGATTGCGGAGACACCGTGTAAGC<br>TTATGCGGTATTTGGTACCAGATAACAGTCACATAGATGCA<br>GATACTCCGTATGCTGAAGTTGAGGTCATGAAGATGTGTA<br>TGCCTTTGCTTTCCCCTGCATCCGGTGTTTTACAATTTAAGA<br>TGTCCGAAGGTCAAGCTATGCAGGCTGGTGAACTCATAGC<br>TAGTCTAGAGTTGGATGATCCTTCAGCTGTAAGAAAAGCC<br>GAACCTTTCCGTGGAAGCTTTCCTGTCATGGGCGCACCAAC<br>TGCAATATCTGGAAAAGTTCATCAGAGGTGTGCCGCAAGT<br>TTAAATGCCACTCGGATGATTTTGGCTGGTTATGAACACAA<br>TATAGATGAAGTAGTACAGAGTTTGCTGGAATGCCTTGAT<br>AGTCCCGAACTTCCATTCCTTCAATGGCAAGAATGCTTGTC<br>TGTGCTGGCAACACGACTTCCCAAAGATCTGAGATACGAA<br>TTGGAATCAAAATCTAGAGCTTTTGAAGGGATTACCAACAC<br>CCAGAACGTAGAATTTCCTGCTAAGTTGTTGAAAAGCATTC<br>TTGAGGACCATTTAAACTCATGCCACGAGAAAGATAAAGG<br>AGCTCAAGAGAGGCTTATTGAGCCTCTTATGGCTCTTGCAA<br>AGTCTTACGAAGGTGGGCGAGAAAGTCATGCTCGTTTTAT<br>TGTTCAATCTTTATTTGAAGAGTATTTATCCGTTGAAGAATT<br>GTTTAGCGACAATCTCCAGGCTGATGTGATTGAACGTCTCC<br>GCCTTCAGTATAAGAAGGATCTGCTGAAGATTGTTGACATT<br>GTACTGTCGCATCAGGGTGTTAAGAATAAAAATAAGCTGA<br>TTCTACGACTCATGGAACAGCTGGTTTACCCAAATCCCGCT<br>GCATACAGGGGAAACTTATCCGTTTCTCTCAATTGAACCA<br>TACAATGTATTCTGAGTTGGCACTAAAGGCCAGTCAATTGC<br>TTGAACAAACGAAATTGAGTGAGCTC |
| 33 | Amaranthus viridis | cDNA Contig | 5705 | AGGCACAGTCGGTGAAACCTAAAGGTCATTGTATTGCTGC<br>GCGTGTGACAAGTGAGGATCCCGATGACGGTTTTAAGCCT<br>ACAAGCGGGAAAGTACAGGAGCTGAGTTTTAAAAGTAAA<br>CCGAATGTGTGGGCCTACTTCTCTGTTAAGTCTGGGGGAG<br>GCATTCATGAGTTCTCGGATTCTCAATTTGGCCATGTTTTTG<br>CATTTGGTGAAAACCGAGGTTTGGCCATAGCAAATATGAT<br>TCTTGGATTAAAAGAAATTCAAATTCGTGGAGAAATTCGA<br>ACTAATGTTGATTACACCATCGATCTTTTAAATTGTTTGGAT<br>TATAGAGAAAACCAAATTCATACAGGTTGGTTGGATAGTA<br>GAATTGCGATGAGGGTCAGAGCCGAAAGGCCACCTTGGT<br>ACATCTCTGTTGTGGGAGGAGGGCTTTACAAAGCATCGAC<br>TAGTAGTGCAGCGACTGTTTCAGAGTATATAGGCTATCTTG<br>AAAAAGGTCAAATTCCTCCGAAGCATATATCACTCGTCCAC<br>TATGAAGTTGCTCTAAATATCGAGGGGATGAAATATACCA<br>TTGAGATGATTAGGGGTGGACCAGGAAGCTACAAAATGT<br>GGTTGAATGGGTCCGTAGTTGAGGCGGAAATACATACTTT<br>AAGAGATGGGGGTCTCTTGATGCAGTTGGATGGAAACAG<br>CCATGTGATATATGCTGAGGAAGAAGCTGCAGGAACTCGC<br>CTTCTGATTGATGGAAGAACTTGTTTGCTTCAGAACGATCA<br>CGATCCTTCAAAGCTGATTGCGGAGACACCGTGTAAGCTT<br>ATGCGGTATTTGGTACCAGATAACAGTCACATAGATGCAG<br>ATACTCCGTATGCTGAAGTTGAGGTCATGAAGATGTGTAT<br>GCCTTTGCTTTCCCCTGCATCCGGTGTTTTACAATTTAAGAT<br>GTCCGAAGGTCAAGCTATGCAGGCTGGTGAGCTCATAGCT<br>AGTCTAGAGTTGGATGATCCTTCAGCTGTAAGAAAAGCCG<br>AACCTTTCCGTGGAAGCTTTCCTGTCATGGGCGCACCAACT<br>GCAATATCTGGAAAAGTTCATCAGAGGTGTGCCGCAAGTT<br>TAAATGCCACTCGGATGATTTTGGCTGGTTATGAACACAAT<br>ATAGATGAAGTAGTACAGAGTTTGCTGGAATGCCTTGATA<br>GTCCCGAACTTCCATTCCTTCAATGGCAAGAATGCTTGTCT<br>GTGCTGGCAACACGACTTCCCAAAGATCTGAGATACGAAT<br>TGGAATCAAAATCTAGAGCTTTTGAAGGGATTACCAACAC<br>CCAGAACGTAGAATTTCCTGCTAAGTTGTTGAAAAGCATTC<br>TTGAGGACCATTTAAACTCATGCCACGAGAAAGATAAAGG |

TABLE 1-continued

ACCase gene sequences isolated from weedy plant species

| SEQ ID NO | SPECIES | TYPE | LENGTH | SEQ |
|---|---|---|---|---|

```
AGCTCAAGAGAGGCTTATTGAGCCTCTTATGGCTCTTGTAA
AGTCTTACGAAGGTGGGCGAGAAAGTCATGCTCGTTTTAT
TGTTCAATCTTTATTTGAAGAGTATTTATCCGTTGAAGAATT
GTTTAGCGACAATCTCCAGGCTGATGTGATTGAACGTCTCC
GTCTTCAGTATAAGAAGGATCTGCTGAAGATTGTTGACATT
GTACTGTCGCATCAGGGTGTTAAGAATAAAATAAGCTGAT
TCTACGACTCATGGAACAGCTGGTTTACCCAAATCCCGCTG
CATACAGGGGGCAAACTTATCCGTTTCTCTCAATTGAACCA
TACAATGTATTCTGAGTTGGCACTAAAGGCCAGTCAATTGC
TTGAACAAACGAAATTGAGTGAGCTCCGTTCGAACATTGCT
AGAAACCTCTCTGAGCTAGAAATGTTTACCGAGGATGGCG
AAAACATGGATACTCCAAAAAGAAAAAGTGCTATTAATGA
ACGTATGGAGGCGCTTGTGAGTACTCCTCTAGCTGTCGAA
GATGCCCTTGTTGGTTTGTTTGATCATAGTGATCATACACTT
CAGAGGCGGGTTGTTGAGACCTATGTTCGGAGGCTTTATC
AGCCTTATCTTGTCAAGGGAAGTGTCAGGATGCTGTGGCA
CAGATCAGGCTTCATAGCTTTATGGGAATTTGTTGAGGAG
AATATTGACCGAACAAATTTTTCTGATCTGACTACAAACAG
TGGGAACCATAGTGAGCGAAAGTGGGGGGCCATGGTCGT
TATTAAAACTCTTCAGTTCTTGCCATCGGTAATTGCTGCAG
CATTGAGAGAAACAACTCATAGTTCCGATCAATCAACTTCC
ACTGGCTCTATAGAATCAGTCATCCATGGAAATATGCTGCA
CATTGCACTAGTGGGGGTGAATAACCAGATGAGCTTGTTG
CAGGATAGTGGTGATGAAGATCAGGCTCAAGAGAGAATC
GATAAGTTGGCCAAAATTCTGAGAGAACAAGAAGTGAGTT
CAGCCCTTCGTGCTGTTGGTGTTGGTGTGATTAGTTGCATC
ATACAGAGAGATGAAGGGCGAACTCCGATGAGGCATTCAT
TCTATTGGTCAGCAGAAAAACAATATTATAGTGAGGAACC
TTTACTACGTCATTTGGAACCCCCTCTATCTATGTATCTCGA
GCTGGACAAGCTTAAGGGTTATGAAGATATCAAATATACT
CCTTCCCGTGATCGTCAATGGCATCTTTACACGGTTATTGA
TAAACCATTCATTCGGAGGATGTTTTTGAGAACCCTTGTAA
GACAACCCATCTCCGAGTTCACTGGCGTCGAACTAAGCGCT
CTTGAAACACAAAAGCCTATCTCTTTTACTTCAAGAAGCAT
CCTAAGGTCATTAACAACCGCCATGGAGGAGTTGGAGCTC
AATGCACATAGTGCTTCACTGAAACCCGATCACGCTCATAT
GTACTTGTACATTGTCCGAGAGCAACAAATATACGATCTTG
TGCCATATCACAGGGAGGTGAACATAGATTACCAACAAGA
AGAGGCTTCGGTTCAATTCTTTTTGGAAGATCTCGCGCATG
AAATCCATAGTCTTGCTGGTGTAAGGATGCATAAACTAAAT
GTTTGTGAGTGGGAAGTGAAACTTCGGATATCATCTCCCG
GGAAAGCTAATGGTTTATGGAGGGTGGCAGTTACTAATGT
GACTGGTCATACCTGTTCGGTACATGTTTATCGTGAATTGG
AAGATAGCAACCTACATGAAATGGTCTACCATTCAGTATCT
GTTCACGGCCCCCACCATGGGGTACCTGTGAATGCACCCT
ATCAACCACTCGGTGGCATCTCCCGTAAGCGACTTCAGGCC
ATGAAGAGTAGCACAACATACTGTTACGATTTTCCACTGGC
TTTCTCAACTGCCCTGAAGCAATCATGGGCATCGGAAGCTC
CGGATGTCAAGAAACCCTCGGACAAAGCACTTTTGAAAGT
AACCGAGCTAGCATTTGCTGATCCAAAAGGCACATGGGGA
ACTCCGCTTGTTCCAATAAATCGCAAGCCTGGTATGAACGA
TGTTGGCATGGTAGCCTGGTACTTGGAAATGTCCACCCCC
GAGTTCCCTAACGGAAGAACAATAATGGTTGTAGCTAATG
ATGTTACCTTCAAGGCCGGATCTTTCGGACCACGAGAAGA
TGCTTTCTTCCTTGCTGTTACAAATCTTGCTTGCGCGAAGAA
ACTTCCTCTTATTTATCTGGCTGCCAATTCAGGAGCTCGACT
TGGTGTTGCCGAAGAGCTAAAATCCTGCTTTAAAGTTGGCT
GGTCGGATGAGTCAAACCCCGAGAGTGGATTTCAGTATGT
CTACTTAACCCCTGAAGATTACGATCGTATAGGATCGTCAG
TCATAGCCCACGAGTTAAAACTCGAAAGTGGAGAAAAAAG
ATGGGTTATAGACACCGTTGTCGGTAAGGAGGACGGATTA
GGTGTCGAGAATCTATCAGGAAGTGGTGCTATAGCCAGTG
CATACTCAAGGGCTTACAAGGAAACATTTACTCTGACTTTT
GTAACCGGTAGAACGGTCGGTATTGGTGCCTATCTTGCTC
GTCTTGGGATGCGTTGTATACAGAGGCTTGACCAGCCTAT
AATTCTCACGGGTTTTTCTGCGTTAAATAAACTTCTCGGTC
GGGAGGTTTACAGTTCACACATGCAACTTGGTGGACCGAA
GATAATGGGCACAAACGGGGTAGTTCATCTTACAGTTTCC
GATGATCTTGAAGGCATTTCATCTATCTTGAAGTGGCTGAG
CTATGTTCCACCCTATTCAGGTGGTGAACTTCCGATTTCTCG
GTGTTTAGACCCTCCCGAAAGACCGGTTGCGTATTTGCCTG
AAAATTGTTGTGATCCTCGTGGGGCTATATCTGGTACGGTT
GACTCCGCCGGTAAATGGTTTGGGGTATTTTCGACAAGG
ATAGTTTTGTGGAAACCTTAGAAGGATGGGCACGAACAGT
TGTCACGGGAAGGGCTAAACTCGGAGGAATTCCAGTTGGC
ATAGTTGCTGTTGAGACGCAGACTGTTATGCAAGTAATCCC
```

TABLE 1-continued

ACCase gene sequences isolated from weedy plant species

| SEQ ID NO | SPECIES | TYPE | LENGTH | SEQ |
|---|---|---|---|---|
| | | | | AGCAGATCCCGGTCAACTCGACTCACATGAGAGAGTCGTA |
| | | | | CCACAAGCAGGGCAAGTATGGTTCCCAGATTCCGCATCCA |
| | | | | AGACAGCACAAGCGCTGATGGATTTCAACCGGGAAGAACT |
| | | | | CCCACTTTTCATTTTAGCTAATTGGAGAGGTTTCTCGGGTG |
| | | | | GACAAAGGGATCTCTTTGAAGGGATCCTTCAGGCTGGATC |
| | | | | CACCATAGTCGAAATCTTAGGACTTATAATCAACCCGTTT |
| | | | | TTGTTTATATCCCTATGATGGGGAGCTTCGAGGAGGCGC |
| | | | | ATGGGTGGTCGTCGATAGTCGAATTAATTCCGACCATATA |
| | | | | GAAATGTACGCCGACCAAACAGCTAAAGGAAATGTGCTTG |
| | | | | AACCGGAAGGAATCGAGATTAAGTTCCGAACCAAGG |
| | | | | AACTTCTCGAGTGTATGGGAAGGCTTGACCAACAACTCATC |
| | | | | GGTCTCAAGGAAAAACTAGCCGAAGCCAAGAGCTCTAATT |
| | | | | CCTACGATAAAATCGAGCCCCTGCAGCAACAAATAAAAGC |
| | | | | CCGCGAGAAGCAACTATTGCCTCTTTATACTCAGATAGCCA |
| | | | | CCAAATTTGCCGAGTTGCATGATACGTCTTTAAGGATGGCT |
| | | | | GCCAAAGGAGTCATTAGGGACGTCTTGGAATGGAAAAGCT |
| | | | | CGCGTTCGTTCTTTTACAAAAGATTATACAGGAGAGTTATG |
| | | | | GAGGAATCACTCGTCAAGACTGTTCGAGATGCTGCAGGTG |
| | | | | AACGGTTGACCCATAAGTCGGCTTTGGAGTTGATCCGGAA |
| | | | | ATGGTTCAATGAGTCAGATATTTCCGGAGAGGCTTCCGAT |
| | | | | GCTTGGGCTGATGATGCGACCTTCTTTAAGTGGAAGGACA |
| | | | | ATACCGCTAACTACGAGGAGAAGTTGAAAGAGTTGCGGGT |
| | | | | TCAGAAGGTATTGGATCAGCTGTCGAATATTGGAGATTCG |
| | | | | GTAACTAATTTGAGGGCTCTGCCTCAGGGTCTTGCTGCCCT |
| | | | | ACTTCAAAAGGTGGATCCATCGAGTCGAGAAGAACTAGTC |
| | | | | GAGGAACTCCGAAAAGTGCTCACTTGATTTCGCAACCGTT |
| | | | | GATGGTGAAGTGAAACCTTCTTGGTTTCATCATGGTAGAA |
| | | | | AATATTATTAGGCAAATCTATAATTTTAGTGACATCAATTG |
| | | | | TTTTAGACAATAGTATTGAACTAATTTATTTAATTAAATTGT |
| | | | | ATAAATAGGAGACCTTGAATTCATTTGAATTAAGTGGCTTA |
| | | | | TGCTTGCATTATTTGTATTGAATCAAATAATTATTTACATAC |
| 34 | Ambrosia trifida | cDNA Contig | 2186 | CAGTTGGAATGGGAATTCCACTTTGGCAAATACCAGAAAT |
| | | | | TAGACGGTTTTATGGGATGGATAATAGTGGAGGTTATGAT |
| | | | | GCTTGGAGAAAAACATCGGCTCTTGCAACCCCTTTTGACTT |
| | | | | TGACCAAGCAGAGTCAATTAGACCAAGGGGTCATTGTATT |
| | | | | GCTGTTCGTGTAACGAGTGAGGATCCAGATGATGGTTTTA |
| | | | | AGCCACCGGTGGAAAAGTACAGGAACTAGTTTTAAAAGCA |
| | | | | AGCCAAATGTGTGGGCATACTTTTCTGTCAAGTCTGGAGG |
| | | | | AGGCATTCATGAATTTTCGGATTCCCAATTTGGTCATGTTTT |
| | | | | TGCATTTGGAGAGTCAAGAACGTTGGCTATTGCAAATATG |
| | | | | GTTCTTGGGCTGAAGGAAATCCAAATTCGTGGAGAAATTC |
| | | | | GTACTAATGTTGATTATACAATCGATCTATTACATGCTCTG |
| | | | | GATTATAGAGAAAACAAAATCCATACAGGTTGGTTAGATA |
| | | | | GCCGAATTGCTATGCGGGTTAGAGCAGAAAGGCCCCCATG |
| | | | | GTACCTTTCAGTAGTTGGTGGAGCTCTTTATAAAGCTGCTG |
| | | | | CTAGAAGTGCTTTACATGGTTTCTGACTATGTTGGTTATCTT |
| | | | | GAAAAGGGTCAAATCCCTCCTAAGCATATATCATTGGTCAA |
| | | | | CTCTCAAGTTTCTTTGAATATTGAGGGTAGTAAGATACACG |
| | | | | ATTGATATGCTGAAAAGAGGACCAGGAAGTTACAGACTGA |
| | | | | GAATGAATCAATCTGAAATTGAAGCAGAAATACATACTCT |
| | | | | ACGTGATGGGGGTTTACTGATGCAGTTGGATGGAAATAGT |
| | | | | CATATTATATACGCAGAGGAAGAAGCAGCTGGTACTCGTC |
| | | | | TTCTAATTGATGGACGAACTTGCTTGCTTCAGAATGATCAT |
| | | | | GATCCTTCCAAATTGGTGGCGGAAACACCATGCAAGCTTCT |
| | | | | AAGATATTTAGTCTCAGATGGTAGCCATGTTGATGCTGACA |
| | | | | CACCTTATGTTGAGGTTGAAGTGATGAAAATGTGTATGCC |
| | | | | ACTTCTTTCGCCGGCTTCTGGAGTTATACAATTTAAAATGTC |
| | | | | CGAAGGTCAAGCCATGCAGGCTGGTGAGCTTATAGCAAGA |
| | | | | CTAGATCTTGATGATCCGTCAGCTGTAAGAAAAGCAGAGC |
| | | | | CCTTTCCTGGAAGCTTTCCTGTTCTGGGCCCACCGACCGCC |
| | | | | ATTTCAGATAAAGTTCATCTGAAATGTGCTGCAACTCTGAA |
| | | | | TGCTGCTCGGATGATTCTTGCTGGCTATGATGACAACATTG |
| | | | | ATGATGTTGTACAAAATCTGCTTCTTTGTCTGGATAGCCCG |
| | | | | GAGCTTCCTTTCCTACAATGGCAAGAATGCTTCGCAGTATT |
| | | | | AGCAAATCGACTTGATAAAGATCTAAGAAACAAGCTAGAA |
| | | | | TCAAAGTTTAAGGAGTACGAAGGAATTTCCACTCAACAAG |
| | | | | CTATCGACTTCCCCGCCAAAGTTTTACGGAACATTCTAGAA |
| | | | | ACTCACCTCGGATCTTGCTCAGAAAAAGAGAAGGTGGCCC |
| | | | | AGGAAAGACTCATTGAACCGTTAATGAGTCTCGTTAAGTC |
| | | | | ATATGACGGTGGTAGAGAGAGTCATGCACGCGGGATTGTT |
| | | | | CATGCTCTTTTTGAAGAGTATTTATCTGTTGAAGAATTATTT |
| | | | | AGTGACAATATTCAGGCTGATGTAATCGAACGTCTACGACT |
| | | | | CCAATACAACAAAGATCTCTTGAGGATTGTTGACATTGTGC |
| | | | | TTTCCCATCAGGGAGTTAGGAGTAAAAACAAGCTGATACT |
| | | | | ACGACTGATGGAGCATTTGGTCTACCCTAATCCAGCTCCTT |

TABLE 1-continued

ACCase gene sequences isolated from weedy plant species

| SEQ ID NO | SPECIES | TYPE | LENGTH | SEQ |
|---|---|---|---|---|
| | | | | ATAGAGAGAAACTCATACGGTTTTCTGCACTCAACCACACA<br>AGTTATTCTGAGTTAGCATTGAAGGCAAGTCAATTGCTGG<br>AACAAACTAAATTAAGTGAACTTCGTTCAAGTATTGCAAGA<br>AGTCTATCTGAATTAGAAATGTTTACCGAAGAAGGTGAGA<br>ATATCGATACCCCTAAAAGAAAAGTGCAATTAACGAAAG<br>AATGGAGGATATCGTGAGTGCTCCTTTGGCGGTTGAAGAT<br>GCCCTTGTTGGTCTTTTTGACCATAGTGATCACACCCTTCAA<br>AGGCGTGTTGTTGAGACCTATGTTAGAAGATTATATCAGC<br>CATATCTGGTGAAGGGGAGTGTTAGAATGCAATGGCACAG<br>ATTGGGACTTATTGCATCATGGCAATTCGTGGAAGGG |
| 35 | Ambrosia trifida | cDNA Contig | 1838 | TAATCCTGAAGATTACAGTCGAATCAAATCGTCAGTGATTG<br>CACATGAATTTTGTCTGGAGAGTGGTGAAACCAGATGGAT<br>TATTGATACAATTGTAGGAAAGGAAGACGGATTAGGGGTT<br>GAGAATTTAAGCGGTAGCGGGGCCATTGCTGGTGCGTTTT<br>CGAAAGCATATAAAGAAACGTTCACCTTAACATATGTGAC<br>GGGAAGAACCGTTGGGATAGGAGCTTATTTGGCCCGTTTG<br>GGAATGAGGTGCATACAACGGACCGACCAACCAATAATCT<br>TGACCGGGTTTTCGGCCCTGAACAAGCTTTTGGGCCGAGA<br>GGTTTACAGCTCGCAAATGCAACTTGGAGGGCCGAAGATC<br>ATGGGGACAAACGGTGTTGTTCATTTAACGGTTTCTGACG<br>ATCTGGAAGGCGTTATGGCAATCATAAATTGGTTGAGCTTT<br>GTTCCACCGTATGTTGGTGGCCCGCTTCCTGTTTTGGCAGC<br>AGTGGACCCGGTAGACCGGCCTGTGGAGTACCAGCCTGA<br>AAACTCGTGTGATCCTCGTGCGGCTGTTTGTGGTACAGTG<br>GATGGGAATGGGAAATGGTTAGGAGGGATTTTCGATAGA<br>GACAGTTTTGTGGAAACATTGGAGGGTTGGGCTAGGACG<br>GTTGTAACGGGCCGGGCCAAACTTGGTGGGATCCCCGTAG<br>GGGTTATTGCTGTCGAGACGCAAACAGTGATGCAAATAAT<br>ACCTGCGGATCCTGGGCAGCTCGACTCACACGAACGTGTT<br>GTCCCGCAAGCTGGGCAGGTGTGGTTCCCTGATTCTGCTA<br>GCAAAACTGCTCAAGCTTTAATGGATTTTAACCGCGAAGA<br>GCTTCCGCTGTTCATCATGGCGAACTGGCGGGGGTTTTCTG<br>CTGGTCAACGGGATCTTTTTGAAGGAATTTTACAGGCGGG<br>ATCGACAATTGTTGAGAACCTTAGAACGTATAAACAGCCG<br>GTTTTCGTTTACATCCCGAAAACCGGCGAGCTTCGTGGCG<br>GCGCGTGGGTGGTTGTTGACAGTCGAATCAACTCGGACCA<br>TATAGAAATGTATGCAGAAACAACCGCAAAAGGAAATGTT<br>CTTGAACCCGAAGGTATGATTGAAATTAAGTTCCGAAACA<br>AGGAATTGTTAGAATGTATGAACCGACTGGACCCGCAAAT<br>CCGAAACCTCAAACAAAAATTACAAGAAACAAAATACGAC<br>CAAACAATCACCGACCAGATAAAAGCCCGTGAGAAGCAAC<br>TTCTGCCCATTTACACTCAGATCGCCACCAAGTTCGCGGAG<br>CTTCACGACACATCTTTCCGAATGGCTGAAAAAGGCGTGG<br>TGAAAAAGGTTGTTGACTGGAACATTTCTCGGTTTTTCTTC<br>TACAAAAGGCTCCGCCGTCGGCTCGCAGAAGCTTCTTTAAT<br>AAATACCACACGTGATGCCGCCGGTGACACACTTACCTACA<br>ATGCTGCTTATGATATGATCAAGAAATGGTTTTTGGCCACG<br>AAGACGGAAGAAGTTTGGCTTGATGATGATGTGTTTTTCA<br>CATGGAAAGATGACCCGTCTAATTACACCGATAAGTTAGC<br>CACATTACGTACACAGAAGGTTTCGAATCAGCTATTAAAGT<br>TTGGTGGTTCACCGTCTGATCTGGAAGCTTTACCGCAGGG<br>GCTTGCTGCACTTCTGCAAGAGGTGGATCCAGCGACTAAA<br>AGTAAACTAATTGAAGACATCCGGCGTGTCATTGAGACTT<br>GGCCGGCTAAATGAGAAGCCATTCGGGCAATGTATACTAT<br>TTAGAACTACTACATGTAAGAATATTTATTTTCCTTGAATAT<br>TTTTGTAAATAAATCACACATTTCCAATC |
| 36 | Ambrosia trifida | cDNA Contig | 818 | GCAGATTATTCCTGCAGATCCTGGGCAACTTGATTCACATG<br>AACGGGTGGTCCCACAAGCTGGGCAGGTGTGGTTCCCGG<br>ACTCTGCTAGTAAAACGGCTCAAGCTATAATGGATTTTAAC<br>CGAGAAGAGCTCCCTCTTTTCATTATGGCCAACTGGCGGG<br>GGTTTTCAGCGGGTCAACGTGACCTTTTTGAAGGGATTTTA<br>CAGGCGGGATCCACAATTGTTGAGAATCTGAGAACGTATA<br>AACAGCCGTTTTCGTTTACATTCCAAAAACCGGTGAACTTC<br>GTGGTGGTGCATGGGTGGTTGTGGATAGTCGGATCAATTC<br>AGACCATATTGAAATGTATGCAGAAACCACTGCCAGAGGA<br>AATGTTCTTGAACCCAAGGAATGATTGAAATCAAATTCCGA<br>AATAAAGAATTGTTGGACTGCATGAGCCGACTCGATCCAC<br>AAATCCAAATTCTTAAAGGAAAACTTAAAGAGTCCAAATAC<br>GATCAAAGAATCGGCGACCAGATAAAAGCCCGTGAGAGA<br>CAGCTTTTACCAATATACACTCAGATCGCCACGAAATTCGC<br>TGAGCTTCATGACACATCGTTCCGAATGGCTGAAAAAGGG<br>GTGGTAAAAGAAGTGGTTGACTGGAAAGCTTCTCGGTTTT<br>TCTTCTACAAAAGGCTGCGGCGTAGGCTGGGGAGGCTTC<br>TTTGATAAGTAGCATGCGTGATGCTGCGGGTGGGACGCTG |

TABLE 1-continued

ACCase gene sequences isolated from weedy plant species

| SEQ ID NO | SPECIES | TYPE | LENGTH | SEQ |
|---|---|---|---|---|
| | | | | TCGTACAAGTCGGCTTATGATATGATTAAGAAATGGTTTCT<br>GGAGAGCAAAGGGGAAGCAGAGTTGTGGGTTGATGATGA<br>TGCTTTTTTCACA |
| 37 | Ambrosia<br>trifida | cDNA<br>Contig | 505 | TTGATTGCTCNGTTTGGCAGTGGAAGCATGTCAGAAGCTC<br>AAAGACTGCCTTTAAATGGAAGCAGCTTAAACTACAACATT<br>TCCTTGAGGTCTTCTGCAGCTAGATCTGCTGCCATTGATGA<br>GTTTTGTTATGCACTTGGTGGAAATAGGCCCATTCATAATA<br>TTCTTGTTGCAAACAATGGAATGGCTGCTGTTAAGTTTATA<br>ACAAGTGTCAGAACATGGAGCTACGAAACATTTGGTTCAG<br>AAAAAGCTATTTCATTGGTCGCCATGGCTACTCCAGAAGAT<br>ATGAGGATAAATGCAGAGCATATTAGAATCGCTGATCAGT<br>TTGTTGAAGTCCCTGGTGGTACAAATAATAATAATTATGCT<br>AATGTGCAACTCATTGTAGAGACTGCTGAGATAACACATG<br>TCGATGCGGTTTGGCCTGGTTGGGGTCCATGCATCTGAAA<br>TCCCTGAACTACCAGATGCATTGGAGGCTAAAGGAATTAT<br>ATTTCTTGGGCCACCTGCT |
| 38 | Ambrosia<br>trifida | gDNA<br>Contig | 4795 | AAATACCATTTCTTACATTATGAGGCAAATAAAAAAAAATA<br>TCAGTTACTTCTAAAAGTTCATTTCATTAAATAAACAAATTA<br>TCAAACAGCGTTCTTACGTTGGTCATTTTCTGTGCATAATGT<br>TCTTTTTGCTTGCTATTTTATAAAGTGGAACTGATTGTTATA<br>AATAGCTGTTATATTTTACTTTCTATGAGATGCATACATATG<br>ATATTTTTAGTGTTTTGAAATCGTAAATATGATTTTATGAAA<br>TGTTGAGGTTTTGGAAGGATTATAAGACTTGCCCAAAGGT<br>TTGTTTTCATTATCTAACATATTGACTTGAATTGCACTTTTG<br>TAGGAGCTTAGTTTCAAAAGCAAGCCAAATGTGTGGGCAT<br>ACTTTTCTGTCAAGGTAAATTTATATTTACATATTTTGATGC<br>AATTTCCCAATTCAAAAATATAAATATATTTTTATTTAAAAA<br>TTGCAGTCCGGAGGAGGCATTCATGAATTCTCAGATTCTCA<br>ATTTGGTAAGAAAACTGAATCTTGTTTGGTTTTAGTTTTTAA<br>CAGTCATACTGCTGGTGTAGTTGGCTTTACACGATTCTTTG<br>CTAAAGCATTCGTTATCTTATTTAATTATTATTTTGTACGCTT<br>TAGGTCATGTTTTTGCATTTGGAGAGTCAAGAGCACTGGC<br>CATTGCAAATATGGTTCTTGGGTTGAAAGAAATCCAAATTC<br>GTGGTGAAATCCGTACTAATGTTGATTATACAATCGACTTA<br>TTACATGTGAGCATCTTGGTTCTTTTGCTCCCTTTGTTCCAA<br>ATTTTATTGCCTACAAAAAGTACTCCATAATTTAAGAAATG<br>CACAAGCAAATCAGATTTTAATCAGCAGAGTGCCAGTTTAC<br>CCTGAATGCATCTAAAATACGGTAAAATTTTAAGATAAGTG<br>TAATCAAGGGTGAAACTAGAAAACTAATAAATTACAACAT<br>TTCATTTCTAGAACAGGACAGTTATTATGATACAAATTAAA<br>AAAGAAAAGTAGACAAATTTTGAGACGGGTCGACTGTCAT<br>GAAGTTAATAGATTACATACGTTTTTTTTACAGAATTACTTA<br>TGTACATGCTTCATATTGAGAAATTGATTAAATTTACAAAT<br>TCTTTATTTCTTGTACATTAGCTTTATGATTTTGATTCTTTTA<br>CACTTAATAATTTTATTATTATTATTTCTACATTTGTAGGCTC<br>CGGATTATAGCGAAAACAAAATCCATACAGGTTGGTTAGA<br>TAGCCGAATTGCTATGCGGGTTAGAGCAGAAAGGCCCCCA<br>TGGTACCTTTCAGTAGTTGGTGGAGCTCTTTATGTAAGTGG<br>TTTGTTAATAATACTTTTCCTTTTCTATATTCACCACCGTTTA<br>ATGTACTCTTGTCTTACTGTTGATTTTTGTTGACCTCAGAAA<br>GCTGCTGCTAGAAGTGCAGCCATGGTATCAGATTATGTTG<br>GTTATCTTGAAAAGGGTCAAATCCCTCCTAAGGTATTTTGA<br>CTTAGCATTGACCTTTATGTTGACCTCAGAATGCCCTTTGCT<br>TAATTTTTTTTCTTTTCTTGAAGCATATATCATTGGTCAACT<br>CTCAAGTTTCTTTGAATATTGAGGGTAGTAAGTACACGGTA<br>AGTAATAACATAAATTTCTGTTCTTGATCTCTGTTTTTTTTA<br>ATTATTATTTTTTCTTCTAATTTATGTGTTTGTTTTTTGTAAGA<br>TTGATATGGTAAAAAAAGGACCAGGAAGTTACAGATTAAA<br>AATGAATCACTCTGAGATTGAAGCAGAAATACATACTCTAC<br>GCGATGGGGTTTGTTAATGCAGGTAAACATTTTTGTTTAT<br>TTTTCAAGTTAAAGTCCTATGGGTATGGGATACATGATTTG<br>CTTCATAAATAAAATCAAAAGATACAATATTTACAGTCATG<br>CAAATTTGTTACATTTTTACATGTATTTACACATTTGTTTGTC<br>ACATGCCTATATTTATATAATATTGATTGGATAATTTAATAT<br>TGTAGTTGGATGGAAATAGCCATATTATATATGCAGAGGA<br>AGAAGCTGCCGGTACTCGACTCCTAATTGATGGACGAACT<br>TGCTTGCTTCAGGTGTCAACAACTACTTCTTTTTGTTGTTGT<br>TTACTTCTTTTTGTTGTTGTTGTTATTATTATTATTATTTATT<br>ATAGATGTGGCTGTTTCTATGCATTTACTTTTGAGTTGATTG<br>ATTTAGGTCATATGTTATCTTTAATGGGTAAAAAAGTTTAG<br>CCTAAAACGAGACGGGTCAGTTGGATCCATTAGGTTGAAA<br>GTCACCTGTAGTTTATCTATTACGCATAATGTGATTAGACC<br>ACCTGATTGCATTAAAAAAAATATAAAACCCTCATTTCAAT<br>CCAAACGGACTCGTTTAGACAATCTTCCATTTTTGACCAAT |

TABLE 1-continued

ACCase gene sequences isolated from weedy plant species

| SEQ ID NO | SPECIES | TYPE | LENGTH | SEQ |
|---|---|---|---|---|
| | | | | ACCCGCCCATTATCCCACATCTGTTTGTTATTCACTAATTTG<br>TTCTATATTTGGTTTAATTTGTTGTTAGAATGATCATGATCC<br>TTCCAAGTTGATGGCAGAAACGCCATGCAAGCTTCTAAGA<br>TACTTAGTGTCTGATGGTAGCCATGTTGATGCTGACACACC<br>TTATGTTGAGGTTGAAGTGATGAAAATGTGTATGCCACTTC<br>TTTCGCCGGCTTCTGGAGTTATACAATTTAAAATGTCCGAA<br>GGTCAAGCCATGCAGGTTAGATTTAAATATCTTCTTAATAT<br>TTATTGTTTTTGCGAAATATATACAAAAATTTCCTTTTACGA<br>ACATTAATGAAAAATCAATTCTGAATCTACATGAGAATTTA<br>ATTTATTTATTTTTTTATATATGGACATCTTTTCTGAGTAAA<br>ATTTTGGCATTGTAGTTGTTTTTTCTTTATTTTATAACTCTAA<br>CTTTTTCAAAAAGGTAATATCTAAGATATTTAGAGGCATAA<br>TGAGTCACTTTTTACAATTAATATTATTCCCAATTGTTTCAG<br>TTACAAATATTATATTGGTACGTCAGTGCTCGATTTTTTGTT<br>GTTTACACAAATTCTCTCCATAATACAATCATATCTTTATCT<br>TCTATACAGCATGCATACATGGGATGCACTTTTTGTCCTAA<br>ATTTTGAACATATGAATGTTTTTATATGTAGGCTGGTGAGC<br>TTATAGCAAGACTAGATCTTGATGATCCGTCAGCTGTAAGA<br>AAAGCAGAGCCCTTTCCTGGAAGCTTTCCTGTTCTGGGCCC<br>ACCGACCGCCATTTCAGATAAAGTTCATCTGAAATGTGCTG<br>CAACTCTGAATGCTGCTCGGATGATTCTTGCTGGCTATGAT<br>GACAACATTGATGAAGTAATCTTGTTTTTATTTTATTCTTTT<br>TGCCATTTAAATAACCCATATGAAATATTTTAATCAACTAAT<br>CACAACTTTATGTAGTGGTGAAAAATTTAACCCACAATTTA<br>TGAACGGGTCGACTTGGGTTATGTTGATCCATAAGTGGTC<br>AAACACAAAAATAGAAATGCTCAAAAGATAATGGTCATAT<br>GGGTCAAGTCAGCCAAAGTGTATTCTTATGCATAAAACCTC<br>CTAAATCATTTTTATTCAAAAAAATTAACTTCTTTTAATAAT<br>ATAAATTTTGGAATAGTATTTGATATGCTAATTATATATAA<br>CTAAATTTAGTTTTTGAACAAGTGTTAAGGGTCAAGCAAGC<br>CTAACTTGCTTTGATTGACACAAAATTATGCATTATTCCATA<br>CCGGTTTTGACTCGTGACCCATCCCGCCAAGTCGTTCTTTTT<br>TCTCACCATTAGCTTAGTTCTTCAATGAGCTTACTTTCTTTTA<br>AATTTTTCTTTTTGTTATTTATAACATGTTTAATCTTTGATTT<br>TAGGTTGTGCAAAACCTGCTTCTTTGTCTGGATAGTCCTGA<br>GCTTCCTTTCCTTCAATGGCAAGAATGCTTTGCAGTTCTAG<br>CAAATCGACTTCCTAAAGATCTAAGAAACAAGGCAAATTA<br>ATGTCTTATAATCATGTTGTTTATTTAAGTTATTATTGTAAC<br>ATTTTTTTTCTAATTTTTAATTCTTCTATAACAGTTGGAGTCG<br>AAGTTTAAGGAGTACGAAGGAATTTCCACCCAACAAGCTA<br>TCGAATTCCCCGCCAAAGTGTTACGGGCCATTCTAGAAGTT<br>AGTTTACGATCAAATACTTATAATTTGACTTTTTTCGTATTT<br>AAATATTTAGTTTACTTTATACTATACTTTTGTAATGTTTAT<br>GGTTAGACGCACCTTGGATCTTGCTTAGAAAAAGAGAAAG<br>TTGCCCAAGAAAGACTCATTGAACCGTTGATGAGTCTTGTT<br>AAGTCATATGAAGGTGGCAGAGAGAGTCATGCACGTGGG<br>ATTGTTCATGCACTTTTTGAAAAATATTTATCCATTGAAGAA<br>TTATTTAGTGACAATATTCAGGTGAAGTTTTTAACTGATTA<br>GTATAAAAAATGCAAAATTTCATATATAAACTTTATAGTAT<br>CATATTTATTTTTTCAAATTTCCATGGTGAAACAAATAACGA<br>ATGCAAAAGCAATGTTATTACTGTGAATCATGTCTACACAT<br>AATGCTCTTATAAGTAATTAATTTGCATGCACTTTAACATCA<br>TACTCTTTCATGTTGAGTAAATTTTTCTTAAATGTAAAATGA<br>AATTTTTTTCTTTAGGCTGATGTAATCGAACGTCTACGACTC<br>CAATACAACAAAGATCTCTTGAGGATTGTTGACATTGTGCT<br>TTCCCATCAGGTATATATGTTATTTTTAGAGGTTGCAAAAT<br>GGACTGTGGGATGGGTTTGTCAACGGGTCAAAATTTGCCA<br>TTTTGCTAAGGGTTGATACCGGTTGGGTTGGGTTGGGTT |
| 39 | Ambrosia<br>trifida | gDNA<br>Contig | 4587 | TTTTCAAAAAAAAAAATTAAAAAAAAAAATAGTGTCTACT<br>TCTTTTTTGTATTAAATTTATTTGCACATAACTCTTTTATAAA<br>GCAAGTCATGTTTGTACATTTTAACTTCAAAGACTCATGAC<br>ACGAAAATAAAACGAATAAGTTAAATTTGTTTACATATAT<br>TGTGCTACATTTACATATATACTTGTTATCCAATAGTTAATT<br>ATGATGATTTACATTTTTAATTATTTGTGTTCAAAGTTTGTT<br>TAAACTCACTGGATAATCTTGGGAGTTAAGGCAAGTATGG<br>CATTGAAAAGTAGAACCCTGGGCCCTGAAACAGCGATTGA<br>AAAAAAGCAGTGGCGATGGGTCGAACTGGTCAATTCAAA<br>GGGTCCCTTTATCAGCAAATTACTTGGACAATTTTGACTTTT<br>ACTTTGACCTCTTCCAATAATATAGCTTTTTTTTATTCCTTCT<br>AATTTTAACTACAAATATACATGTTTGTTTTTCTACACACTT<br>TCAACATCTGTACATTTCTATCAGTTTGTCTACAGTATATAA<br>TCGCAAGAATATTTCGACTTATAATCATAGATATTCTGTTTG<br>CACTTATAGCATGCAAAATACAGATGCATAGAATTTGCATA<br>CGCCTAAAAGTGCAGAGAAAAATCATGTGAACATTCTTAT<br>GTCCGTTTTATAAATGTTGCTCACAAATAGACAAAAATATT |

TABLE 1-continued

ACCase gene sequences isolated from weedy plant species

| SEQ ID NO | SPECIES | TYPE | LENGTH | SEQ |
|---|---|---|---|---|

```
ACTGTTTTTTGTTATACTATGTAGAAAAAGTCATGCAAAT
CACATACATATGGATTGTTTTATAACAATTACAAATTGTGT
GCAGGAGAGTTGACGTAGATTCTGGGACCGAAGAGGGTG
TGGTTGAGGCACTTTTGGTGAAGTTGGCTCGTGAGATACA
CACAATGGTTGGTATAAAAATGCACCGGTTAGGTGTTTTTG
AGTGGGAGGTTAAGCTTCGCATGGTGTCTTCTGGTCAAGC
CAATGGTGCCTGGAGGGTGGTGGTCACTAATGTGACCGGT
CATACGTGTATTGTACATGTAAGTTAAAAGGCCATTTTAGA
CATTTCAACAATAGGTAAACTCTTTTTGCTCATACATGCTTA
ATGTTACTCTTTGCGATTTTCATTTAGGTCTATCGGGAAATC
GAGGATAATGTTGAACACAAGGTAGTTTATCATGCTACCTC
GACATCAAGCCCCTTACATGGTGTATCTGTGAACACACCAT
TTCAGCCTTTGAAATTACTCGATCAGAAACGTCTTTTGGCC
CGTAAAAGCAATACTACTTACTGCTATGACTTTGCACTGGT
AAAATTGCCATTTTGCCCTTCTACTTTTAATGCATGCATGTT
CTTTTATTTAAAAGTAGTAAAATTACCATTCTGCCCTTTCGA
ACTTGGATTATGGTTAATTCTTACGGATCTTGCTTTTGTATC
CGCAGGCATTTGAAGCAGCCCTTGAGAATATCTGGTCATT
GAAACTCCCAGGTGTCAACAAGCCCGTTGGTAAGCTTGTA
AATGTGACAGAGCTCGCATTTGCTGACCCGAGAGGCTCAT
GGGGTACACCGCTTGTGCAAATAAACCGTGAGCCGGGCCA
GAACAATGCGGGCATGGTGGCTTGGACCATGGACCTCTGC
ACACCTGAGTTTCCTCATGGAAGGACAATTTTGGTAGTTGC
AAACGATGTCACGTTTAAAAATGGGTCTTTCGGCCCGATTG
AGGACGCGTTTTTCGAGGCGGTCACCGAACTTGCCTGTTCC
AAGAAACTGCCACTCATTTACCTGGCAGCGAACTCGGGGG
CCCGAATTGGGGCGGCTGAGGAGGTTAGATCTTGCTTTAG
AATTGGGTGGTCCGATGAATCGAACCCTGATTCAGGGTTC
CAGTATTTGTACCTAACTCCTGAAGATTACAGTCGAATCAA
ATCGTCAGTGATTGCACATGAATTTTGTTTGGAGAGTGGT
GAAACCAGATGGATTATTGATACAATTGTAGGAAAGGAAG
ACGGATTAGGGGTTGAGAATTTAAGCGGTAGCGGGGCCA
TTGCTGGTGCGTTTTCGAAAGCATATAAAGAAACGTTCACC
TTAACATATGTGACGGGAAGAACCGTTGGGATAGGAGCTT
ATTTGGCCCGTTTGGGAATGAGGTGCATACAACGGACCGA
CCAACCAATAATCTTGACCGGGTTTTCGGCCCTGAACAAGC
TTTTGGGCCGAGAGGTTTACAGCTCGCAAATGCAACTTGG
AGGGCCGAAGATCATGGGGACAAACGGTGTTGTTCATTTA
ACGGTTTCTGACGATCTGGAAGGCGTTATGGCAATCATAA
ATTGGTTGAGCTTTGTTCCACCGTATGTTGGTGGCCCGCTT
CCTGTTTTGGCAGCAGTGGACCCGGTAGACCGGCCTGTGG
AGTACCAGCCTGAAAACTCGTGTGATCCTCGTGCGGCTGTT
TGTGGTACAGTGGATGGGAATGGGAAATGGTTAGGAGGG
ATTTTCGATAGAGACAGTTTTGTGGAAACATTGGAGGGTT
GGGCTAGGACGGTTGTAACGGGCCGGGCCAAACTTGGTG
GGATCCCCGTAGGGGTTATTGCTGTCGAGACGCAAACAGT
GATGCAAATAATACCTGCGGATCCTGGGCAGCTCGACTCA
CACGAACGTGTTGTCCCGCAAGCTGGGCAGGTGTGGTTCC
CTGATTCTGCTAGCAAAACTGCTCAAGCTTTAATGGATTTT
AACCGCGAAGAGCTTCCGCTGTTCATCATGGCGAACTGGC
GGGGGTTTTCTGCTGGTCAACGGGATCTTTTTGAAGGAAT
TTTACAGGCGGGATCGACAATTGTTGAGAACCTTAGAACG
TATAAACAGCCGGTTTTCGTTTACATCCCGAAAACCGGCGA
GCTTCGTGGCGGCGCGTGGGTGGTTGTTGACAGTCGAATC
AACTCGGACCATATAGAAATGTATGCAGAAACAACCGCAA
AAGGAAATGTTCTTGAACCTGAAGGTATGATTGAAATTAA
GTTCCGAAACAAAGAATTGTTAGAATGTATGAACCGACTG
GACCCGCAAATCCGAAACCTCAAACAAAAATTACAAGAAA
CAAAATACGACCAAACAATCACCGACCAGATAAAAGCCCG
TGAGAAGCAACTTCTGCCCATTTACACTCAGATCGCCACCA
AGTTCGCGGAGCTTCACGACACATCTTTCCGAATGGCTGA
AAAAGGGGTGGTAAAAGAAGAAGTGGTGGTTGACTGGAA
AGCTTCTTCTCGGTTTTTCTTCTACAAAAGGCTGCGGCGTA
GGCTGGGGGAGGCTTCTTTGATAAGTAGCATGCGTGATGC
TGCTGGTGACACGCTTACCTACAATGCTGCTTATGATATGA
TCAAGAAATGGTTTTGGAGAGCAAAGGGGAAGCAGAGT
TGTGGGTTGATGATGATGCTTTTTTCACATGGAAAGATGAC
CCGTCTAATTACACTGATAAGTTAGCCACATTACGTACACA
GAAGATATCAAATCAGTTATTAAAGATTGGTGGTTCACCGT
CCGATCTGGAAGCTTTACCGCAGGGGCTTGCTGCACTTCTG
CAAGAGGTAACTGTTGTTTCTTGAATCTTGACGACTACATT
CCTTTCACCATTTTGCAAGTCGAGAATAAGATTGTTTTTAAT
GTCGTTTTGTTTGTTGTGTTTCAGGTGGATCCAGCGACTAA
AAGTAAACTAATTGAAGACATCCGGCGTGTCATTGAGACT
TGGCCGGCTAAATGAGAAGCCATTCGGGCAATGTATACTA
TTTAGAACTACTACATGTAAGAATATTTATTTTCCTTGAATA
```

TABLE 1-continued

ACCase gene sequences isolated from weedy plant species

| SEQ ID NO | SPECIES | TYPE | LENGTH | SEQ |
|---|---|---|---|---|
| | | | | TTTTTGTAAATAAATCACACATTTCGAATCATATCAAATAAT |
| | | | | TATTCATTGTAGTCTTTTCTGTAATCGGTATTTGCGATATCT |
| | | | | ATGTTTGAGTATTTATTAACTAATTATACAAATCTTTGTTGG |
| | | | | GCTTTGCACTTTCTGGATCAACAACTCAGACCTCGTGATCA |
| | | | | AGCTTTGGTGAACATGAATGAACTGCATCTGCAACAGTGA |
| | | | | GAAAAATCTTGTTTTCCCCAATCAAGTCGGGGAAACCTGAT |
| | | | | GCGTATAGCTTGTCTAGCACTTGTTGACCCGGGTTCGCAAG |
| | | | | AATAAGCTGTCAAACCAAAATATTATTGTTTTAGCACGCAA |
| | | | | TTGCGGAAATTATTATGAAAACTTTTTATCCGTTGTTAACC |
| | | | | GTATAATAAATGAGTTGATGATATGTGTAGTAGTGTTTAAT |
| | | | | CGCATAAAATTACATGTTTTGTTCTCAACTGGTTTTGGCAC |
| | | | | GTTTACTTGTAATATTATAAACAGTATTGCTGCTGCTTACTT |
| | | | | GGACATCTCTCTTTTGCAGACTACGGTATAACTCTTCCAAG |
| | | | | GCATGGATTCCACTTGTGTCGATATCAGTAACCGCTGCAGT |
| | | | | TAGAGAACACTCTTTAAACAAAGTATTCGCCCCGCTCATTA |
| | | | | AATATTCATGACTGACTATAGGAAATAGAAGAGCTTCTTTC |
| | | | | TTACGTGACAATTCCACTATCAAGAACTGAATTTTGGGTTG |
| | | | | AAAAGTTGCTGCTTTTAGATTATCTTCTTCCTCAGCTAGCCA |
| | | | | TCTTAATATCCTGCAACGAATTATAGCTTTCAAGGATGGAA |
| | | | | ACATACATACATACATAGTTAAACTCC |
| 40 | Ambrosia trifida | gDNA Contig | 2723 | ATGGGGACAAACGGTGTTGTTCATTTAACGGTTTCTGACG |
| | | | | ATCTGGAAGGCGTTATGGCAATCATAAATTGGTTGAGCTTT |
| | | | | GTTCCACCGTATGTTGGTGGCCCGCTTCCTGTTTTGGCAGC |
| | | | | AGTGGACCCGGTAGACCGGCCTGTGGAGTACCAGCCTGA |
| | | | | AAACTCGTGTGATCCTCGTGCGGCTGTTTGTGGTACAGTG |
| | | | | GATGGGAATGGGAAATGGTTAGGAGGGATTTTCGATAGA |
| | | | | GACAGTTTTGTGGAAACATTGGAGGGTTGGGCTAGGACG |
| | | | | GTTGTAACGGGCCGGGCCAAACTTGGTGGGATCCCCGTAG |
| | | | | GGGTTATTGCTGTCGAGACGCAAACAGTGATGCAAATAAT |
| | | | | ACCTGCGGATCCTGGGCAGCTCGACTCACACGAACGTGTT |
| | | | | GTCCCGCAAGCTGGGCAGGTGTGGTTCCCTGATTCTGCTA |
| | | | | GCAAAACTGCTCAAGCTTTAATGGATTTTAACCGCGAAGA |
| | | | | GCTTCCGCTGTTCATCATGGCGAACTGGCGGGGGTTTTCTG |
| | | | | CTGGTCAACGGGATCTTTTTGAAGGAATTTTACAGGCGGG |
| | | | | ATCGACAATTGTTGAGAACCTTAGAACGTATAAACAGCCG |
| | | | | GTTTTCGTTTACATCCCGAAAACCGGCGAGCTTCGTGGCG |
| | | | | GCGCGTGGGTGGTTGTTGACAGTCGAATCAACTCGGACCA |
| | | | | TATAGAAATGTATGCAGAAACAACCGCAAAAGGAAATGTT |
| | | | | CTTGAACCCGAAGGTATGATTGAAATTAAGTTCCGAAACA |
| | | | | AGGAATTGTTAGAATGTATGAACCGACTGGACCCGCAAAT |
| | | | | CCGAAACCTCAAACAAAAATTACAAGAAACAAAATACGAC |
| | | | | CAAACAATCACCGACCAGATAAAAGCCCGTGAGAAGCAAC |
| | | | | TTCTGCCCATTTACACTCAGATCGCCACCAAGTTCGCGGAG |
| | | | | CTTCACGACACATCTTTCCGAATGGCTGAAAAAGGCGTGG |
| | | | | TGAAAAAGGTTGTTGACTGGAACATTTCTCGGTTTTCTTC |
| | | | | TACAAAAGGCTGCGGCGTAGGCTGGGGGAGGCTTCTTTG |
| | | | | ATAAGTAGCATGCGTGATGCTGCGGGTGGGACGCTGTCGT |
| | | | | ACAAGTCGGCTTATGATATGATTAAGAAATGGTTTCTGGA |
| | | | | GAGCAAAGGGGAAGCAGAGTTGTGGGTTGATGATGATGC |
| | | | | TTTTTTCACATGGAAAGATGAACCAAAGAACTACAGGCAC |
| | | | | AAGTTAAGTGAGTTACGTGCACGCAAGGTTGCAAATGAGT |
| | | | | TATTAAAGATTGGTGGTTCAGCGTCGGATGTGGAAGCGTT |
| | | | | GGCGCAGGGGCTGGCTGCACTTCTAAAAGAGGTAACTGTT |
| | | | | GTTTCTTGAATCTTGACGACTACATTCCTTTCACCATTTTGC |
| | | | | AAGTCGAGAATAAGATTGTTTTTAATGTCGTTTTGTTTGTT |
| | | | | GTGTTTCAGGTGGATCCAGCGACTAAAAGTAAACTAATTG |
| | | | | AAGACATCCGGCGTGTCATTGAGACTTGGCCGGCTAAATG |
| | | | | AGAAGCCATTCGGGCAATGTATACTATTTAGAACTACTACA |
| | | | | TGTAAGAATATTTATTTTCCTTGAATATTTTTGTAAATAAAT |
| | | | | CACACATTTCCAATCATATCAAATAATTATTCATTGTAGTCT |
| | | | | TTTCTGTAATCGGTATTTGCGATATCTATGTTTGAGTATTTG |
| | | | | TGAACCTTTTATTAACTAATTATACAAATCTTTGTTGGGCTT |
| | | | | TGCACTTTCTGGATCAACAACTCAGACCTCGTGATCAAGCT |
| | | | | TTGGTGAACATGAATGAACTGCATCTGCAACAGTGAGAAA |
| | | | | AATCTTGTTTTCCCCAATCAAGTCGGGGAAACCTGATGCGT |
| | | | | ATAGCTTGTCTAGCACTTGTTGACCCGGGTTCGCAAGAATA |
| | | | | AGCTGTCAAACCAAAATATTATTGTTTTAGCACGCAATTGC |
| | | | | GGAAATTATTATGAAAACTTTTTATCCGTTGTTAACGTATA |
| | | | | ATAAATGAGTTGATGATATGTGTAGTAGTGTTTAATCGCAT |
| | | | | AAAATTACATGTTTTGTTCTCAACTGGTTTTGGCACGTTTAC |
| | | | | TTGTAATATTATAAACAGTATTGCTGCTGCTTACTTGGACA |
| | | | | TCTCTCTTTTGCAGACTACGGTATAACTCTTCCAAGGCATG |
| | | | | GATTCCACTTGTGTCGATATCAGTAACCGCTGCAGTTAGAG |
| | | | | AACACTCTTTAAACAAAGTATTCGCCCCGCTCATTAAATAT |
| | | | | AGGAAATAGAAGAGCTTCTTTCCTTACGTGACAATTCCACTA |

TABLE 1-continued

ACCase gene sequences isolated from weedy plant species

| SEQ ID NO | SPECIES | TYPE | LENGTH | SEQ |
|---|---|---|---|---|
| | | | | TCAAGAACTGAATTTTGGGTTGAAAAGTTGCTGCTTTTAGA<br>TTATCTTCTTCCTCAGCTAGCCATCTTAATATCCTGCAACGA<br>ATTATAGCTTTCAAGGATGGAAACCTACATACACACATAGT<br>TAAAATCCGATGGTTTGTACCTTTCTTTGATGTAATTTGAAT<br>TTGAGAAATAAATAGCAGAATCAATCCTAACAATTACAACA<br>CCCGGAATTTTATTCGCTTCTGGATACTGTCCGATATTCCG<br>GTACACGCTGGTCATCGGAATCTTCCCAAGAAGCGCGGTT<br>CGTGGGCGTGTAACTTGCAGAAGAATCTTAGCAAAAGATA<br>TCGCCACCTGATTCAACAATCTTATTAAACAAAAGCTCAAA<br>ATTGACCTAAAAACAATGTTTTCATAACCAGTTCAATGGTT<br>GGGCCCAAATGCCATCATAAATAATTTATTTATTTATATGA<br>ATAATATATAAACTATAAAGTAAGTAGTAAATGGATCACTA<br>AATGAT |
| 41 | Ambrosia trifida | gDNA Contig | 2408 | GTTGACCTGAAACATGTTTTTGTTTTCAAAAGTTTTAGATA<br>ATTTGTTAGTCAAATATGATGAAATATACAAATTATTATTTC<br>AATAATAATCCAGTTTTTTTAAAAAGATATAGGTGATATGT<br>GTACAGTAAAAAGATACAATTTGGTAGGTATTTCACAAGTT<br>CAGGCGCTAGAAACATGTCCTTTTAAGATTTTGTTCTGCCT<br>TGTACCTTTTGAACGTTTAAAGCAGAACCCGACTCGACCCA<br>TTCATGAGTAAATGGGTTGAAATTGCCGTCTCTAGTTTTTC<br>TGGTTTTATGTTTCCACTTATTAATATTAAATAAAATTTATT<br>CTGAAGTCGATATTTTAAATTTAACAGGGAGTTAGGAGTA<br>AAAACAAGCTGATACTACGACTGATGGAGCATTTGGTCTA<br>CCCTAATCCAGCTCCTTATAGAGAGAAACTCATACGGTTTT<br>CTGCACTCAACCACACAAGTTATTCTGAGGTCAATATCGTC<br>ATTTAACATACTCAAAGGCTCTAACTAACTACTTTTTTTAT<br>TGGCATATTTAACTTCATTATCATTAATTTAACAGTTAGCAT<br>TGAAGGCAAGTCAATTGCTGGAACAAACTAAATTAAGTGA<br>ACTTCGTTCAAGTATTGCAAGAAGTCTATCTGAATTAGAAA<br>TGTTTACCGAAGAAGGTGAGAATATCGATACCCCTAAAAG<br>AAAAAGTGCAATTAACGAAAGAATGGAGGATATCGTGAG<br>TGCTCCTTTGGCGGTTGAAGATGCCCTTGTTGGTCTTTTTG<br>ACCATAGTGATCACACCCTTCAAAGGCGTGTTGTTGAGACC<br>TATGTCAGAAGATTATACCAGGTATGCAGTTGGTTTTTCTC<br>TTAAACATATACTATCTATCCATTTAAGTCGCCATTGACTAA<br>TACAGCTCAATAAAAAAAGTTAAAAGGATGGATGTGATTA<br>ATTTGTAAATATCAAAATCAAGTCTATTGTATATTGATATTT<br>GGTATGATAAACAAGGGGCAAATGAGTAATTGTACCTTGT<br>AATTCTATTTTCAGCCATATCTTGTGAAGGGGAGTGTTAGA<br>ATGCAATGGCACAGATTGGGACTTATTGCATCATGGCAAT<br>TCGTGGAAGGGCATACTGAGGAATTGAATGCTTCTGGACC<br>ATTGGTTGATAGGAAATGGGGAGCTATGGTTATTATTAAA<br>TCTCTTCAATTTTTGCCCGATGTGATAAGTGCAGCTCTTAAA<br>GAAACGACTCAAACTGGGTCAGCAGGTCATACTATTACTA<br>ACCATGGTAACATGATGCACATTGCATTGGCCGGCATCAA<br>CAACCAAATGAGTTTGCTTCAAGACAGGTTTGACCATACAA<br>GTCAACATCATCATGTTTGGTTATAAATCAATTTATAAAAAT<br>TCATTATCTCTAGAATTGAAACCAAATTATATTTATATATTT<br>GATATTAACTAATACGCGCATATTTTCTTATAAACTGCAGT<br>GGTGATGAGGACCAGGCCCAAGAAAGAGTCAATCGGTTA<br>GCAAAAATATTAAAGGACAAAGAACTAAGCTCGAGTCTAA<br>AAAACGCAGGGTATGATGTTATAAGTTGTATAATACAAAG<br>AGACGAAGGTAGGGGCCCAATGAGACATTCATTTCATTGG<br>TCAGAAAGTAATCGTTATTATGTCGAAGAGCCATTATTGCG<br>CCATGTGGAACCTCCATTATCTATTTACCTTGAACTGGTTTG<br>TACTCATAGCCCGCTTCATTTTGTTTCCATTTCTTTAAATAGT<br>AATAATACTAAGGACAAATGTCCACAAAAAGTGAAATCGA<br>GTCAGCTTTTAGCACATTAGGCTTCCACGTTATCGTTTTTAC<br>ATGATTGGATGCCATGTCAGCAGTTTTAAGCATTTTGTATG<br>CCGTGTCAACTTATGCAACCTAACTCTTTGCAGTAACACAC<br>ATTAAAGTGTTGCAATAGCGACACATTTTAGAAGAGAAGT<br>AAATTTTATAAATACTCATAATTTTAGAAGGTTTCGGTAAA<br>AAAGTATTAGTTTCCAGAAAGGTCTAAAATTATTTATGTCA<br>CTATATATCTTGGCATTTTTATCCACACTCAGTGACCAGTTT<br>TGTTGTGTTGCTAAATTTCAATTTTGGTGCAGCGACCCTCTT<br>TTAAAGACTTAGTGAACAACGGGGACATTCGATTACCATTT<br>AATGACATATTCCCTAATATTAGAAGAAAAGTTATATAAAT<br>TTCCATGTATTATAAATTGGTTATTTTTTCAGGATAAACTGA<br>AGGGCTATGAGAATATACAGTACACTCCATCGCGCGACAA<br>ACAATGGCACATGTATACGGTTGATGCGAAACCACTTCCG<br>GTTCGCAGAATGTTTCTTCGAGCACTTGTAAGACAACCAAC<br>AAAAGAATGGTTTTCGCCCTCGGGATACCATGATTC |

TABLE 1-continued

ACCase gene sequences isolated from weedy plant species

| SEQ ID NO | SPECIES | TYPE | LENGTH | SEQ |
|---|---|---|---|---|
| 42 | Ambrosia trifida | gDNA Contig | 1771 | TGGCGGCCGTAAAGTTTATAAGAAGTGTGAGAACATGGA GTTATGAAACATTTGGTTCAGAAAAAGCAATTTTGTTGGTA GCCATGGCGACTCCGGAGGATATGAGGATAAATGCAGAG CATATTAGAATTGCTGATCAATTTGTGGAAGTCCCAGGTG GTACAAATAATAATAATTATGCAAACGTGCAACTCATTGTG GAGGTATATAGGTTTCATACATATATAATTTATTTAGGCAT CAACTGATGTATTTTATGAACCACCATACACGCCATTTTATT GCAAAGTAACCATTGTTCTTTAGAACAGTCTTATTTTGACTT TTCGGTCAAATTATCTGTTTATAAACGTTCATTCCTGCAACG ATAAGTCAGATATGATGGTTCAAGAAGTCGGTCACTAAAC AAGGGTTGGATTTACCTTCACTTATTCAGAAGTCCTTAAAA TATTACATTTGCTCTCTACAAAGTATTTTTTACTATGAATTTT CAAGTGGACTACATCAATTTTGTAATTAATACGAAATTACA AATGTGTGTAACTTTTGATGAAAAATCCTACTTTGACATAC CTAACTATATCCTTAAGTTATAACATTGATATTGCAATGCTT AACTTTTGAGGAAAATCATTACCTACATCATGTTTAATGAT TGCAGACTGCTGAGATAACACATGTTGATGCTGTTTGGCCT GGTTGGGGTCATGCATCTGAAATCCCGGAACTACCAGATG CATTGGAGGCTAAAGGAATTATATTTCTTGGGCCACCTGCT GCTTCCATGGCAGCTTTAGGAGATAAAATCGGTTCATCGTT GATTGCACTAGCAGCTGATGTGCCAACACTTCCATGGAGT GGCTCTCATGTAAGTTTTGCCACTTTTATAGTCAGTCCTTTT TAGTTTTTTCAGAAAAAAAAAACTCATTTCATACCTCTTGTT TTTCAAAAAACTGGTTCCTAATGCTACTTATTTTTTAAAAAC TGCATCTTTACTAGTCTTTATAACACCTCATCTTTTTAGCTC GTATTCTTTTACAATTGCACCTATAAACCTCAAAAATCTCAT CTTTATTCTGCTTATTATATAAAATATCCTGCTTTAGGTGAA AATTCCTGTGGAAAGCTGTTTGGCCACAATCCCAGATGAT GTATATAGAAAAGCTTGTGTATCTACAACTGAAGAAGCAA TTGCTAGCTGTCAGTTTATTGGTTATCCGGCTATGATCAAG GCATCATGGGCGGAGGTGGCAAAGGCATAAGAAAGGTT TGTTTCCTTCAACTTGACCTTTAAAAGTCAATAAACTAGTTT TGACCTCAAAGCACTTATTTATTTTTGTTAATTTAGGTGCAT AATGATGAAGAAGTCAAGGCACTTTTCAAGCAAGTTCAAG GTGAAGTGCCAGGTTCACCTATATTCATTATGAAAGTTGCC TCCCAGGTGAGAAAACGTTTGAATAACTCATCTGATCTTAA TGTGTGACTTAAAACTTATTATAACACTATTTAAATATTATT TTAAAACCAGAGCCGGCATCTAGAAGTTCAGCTACTGTGT GATCAGCATGGCAATGTAGCAGCCTTACATAGTCGTGATT GCAGTGTTCAAAGACGACACCAAAAGGTAGTCTGAGAATC GCAGTCTTTCTAAAAAATAACAAATCTTGATTTTAATATAAT TTTTTATATTTTTTAAGATTATCGAGGAGGGTCCAATTACC GTAGCTCCACCTGACACAATAAAGAAGCTTGAGCAAGCAG CAAGAAGA |
| 43 | Ambrosia trifida | gDNA Contig | 1320 | CATGATGAGTGATGACATATGTGGTCTTTCACTCTAATTCT TGCAATTGTCGATGCTTTCGACTCTTGTCTTCTTTACGGTAA TTAGTCTTCTTCCCCTTTCCCCCAAATTTAAAAAAGAAACTA AAGTTTGATAGCTCTGTTTGGCAGTGGAAGCATGTCAGAA GCTCAAAGACTGCCTTTAAATGGAAGCAGCTTAAACTACA ACATTTCCTTGAGGTCTTCTGCAGCTAGATCTGCTGCCATT GATGAGTTTTGTTATGCACTTGGTGGAAATAGGCCCATTCA TAATATTCTTGTTGCAAACAATGGAATGGCGGCAGTAAAG CTTATAAGAAATGTGAGAACATGGAGGTATGAAACATTTG GTTCAGAAAAAGCAATTTTGTTGGTAGCCATGGCTACCCC GGAGGATATGAGGATAAATGCAGAGCATATTAGAATTGTT GGTCAATTTGTAGAAGTGCCTGGTGGAACAAATAATGATA ATAATGCAAACGTGCAACTCATTGTAGAGGTATATAGGTTT CATACATATATAATTTATTTAGGCATCAACTGATGTATTTTA TGAACCACCATACACGCCATTTTATTGCAAAGTAACCATTG TTCTTTAGAACAGTCTTATTTTGACTTTTCGGTCAAATTATC TGTTTATAAACGTTCATTCCTGCAACGATAAGTCAGATATG ATGGTTCAAGAAGTCGGTCACTAAACAAGGGTTGGATTTA CCTTCACTTATTCAGAAGTCCTTAAAATATTACATTTGCTCT CTACAAAGTATTTTTTACTATGAATTTTCAAGTGGACTACAT CAATTTTGTAATTAATACGAAATTACAAATGTGTGTAACTT TTGATGAAAAATCCTACTTTGACATACCTAACTATATCCTTA AGTTATAACATTGATATTGCAATGCTTAACTTTTGAGGAAA ATCATTACCTACATCATGTTTAATGATTGCAGACTGCTGAG ATAACACATGTCGATGCGGTTTGGCCTGGTTGGGGTCATG CATCTGAAATCCCTGAACTACCAGACGCATTGGAGGCCAA AGGAATTGTATTTCTTGGCCCCCTGCTTCATCCATGGCGG CTTTAGGAGATAAAATTGGTTCTTCTTTGATTGCACAAGCG GCTGCTGTACCAACACTTCCATGGAGTGGTTCTCATGTAAA TATTGCCACTTTTATAGTCGGTCCTTTTTAGTTTTTTCAGAA |

TABLE 1-continued

ACCase gene sequences isolated from weedy plant species

| SEQ ID NO | SPECIES | TYPE | LENGTH | SEQ |
|---|---|---|---|---|
| | | | | AAAAAAAACTCATTTCATACCTCTTGTTTTTCAAAAAACTGG
TTCCTAATGCTACTTATTTTTTAAAAACTGCATCTTTATTTTA
TTTTTTT |
| 44 | *Conyza canadensis* | cDNA Contig | 7026 | ATGAATTTTCGGGCATTTGATCTGAAGCTCAACATTTTTCT
GGGCGATTCAAATAAGCGTTTTACTGTTACAAAAAGTTTCG
TCTCAACGGGTGACCACTACACGACTTCTGATAACACCAAT
CCGACCAGTCTTACAAAGGTGAAGGTGAAGAAACATGTGA
AGAGGGATAAATTTGGAGAAAGAATGGCATCACTAAAAC
AGATAGTGTCACCCTATGGCAAGGATTTTGCTAAACATAGT
TGTAAGGGTTATAGTTACAACACAATAGAATGGAGTCTAG
ACTTGGACCATTGTGTTTTAGAGAAGAAGGGAATCGAACG
CAAAGTTTGCGTTGTGATAGTCAGGAGACAGAAAGGGCA
ATTTGTTTCTGTTCTTTTTAAGTTAGATAGTGGCACCATGTC
AGAAGCTCAAAGAATGCTTCTAAGTGGAAGTTTCAATTATT
ATGGTAATGGCATTGTAAATGGGGCGATTTCACTGAGGTC
TTCTGCTAGTAGATCTGCAATTGATGAATTTTGTAATGCAC
TTGGAGGCACCAGGCCAATCCAAAGTATTTTAATTGCAAAT
AATGGAATGGCGGCTGTAAAGTTTATAAGAAGTGTGAGG
ACATGGAGTTATGAAACATTTGGCTCAGATAAAGCTATTTT
GCTGGTAGCCATGGCTACACCGGAAGATATGAGGATAAAT
GCCGAGCATATTAGAATCGCTGATCAGTTTGTTGAAGTCCC
TGGTGGTACAAATAATAATAATTATGCGAATGTGCAACTCA
TTGTAGAGACTGCTGAGATAACACATGTTGATGCTGTTTG
GCCTGGTTGGGGCCATGCATCCGAAATCCCTGAGCTGCCT
GATGCATTGGAAGCAAAAGGTATTGTATTTCTTGGGCCAC
CAGCTTCCTCCATGGCAGCTTTAGGTGATAAAATTGGTTCT
TCTTTGATTGCACAAGCTGCTGATGTACCGACACTTCCTTG
GAGCGGTTCTCATGTAAAAATTCCTGTGGATAGCTGTTTGG
ACACACTCCCGGATGATGTATATAGAAAAGCGTGTGTGCA
TACAACAGAAGAAGCAATTGCTAGTTGTCAAGTTGTTGGT
TATCCAGCAATGATTAAGGCATCATGGGGTGGAGGTGGCA
AAGGCATAAGAAAGGTGCATAATGACGAAGAAGTCAAGG
CACTTTTTAAGCAAGTTCAGGGTGAAGTGCCTGGTTCCCCT
ATTTTCATTATGAAAGTTGCTTCTCAGAGCCGACATCTAGA
AGTGCAGCTACTATGCGATCAACATGGGAATGTAGCAGCT
TTGCATAGTCGTGATTGCAGTGTTCAAAGGCGACATCAAA
AGATTATTGAAGAGGGGCCAATAACCATAGCTCCACATGA
CACAATAAAGAAGCTTGAGCAAGCGGCGAGAAGATTAGC
AAAGTCGGTTAATTATGTTGGAGCAGCCACTGTAGAGTAT
TTGTATAGCATGGAAACTGGAGACTATTACTTTTTGGAGCT
CAATCCCCGGTTACAGGTTGAGCATCCAGTCACAGAGTGG
ATAGCGGAAATCAATCTACCTGCAGCACAAGTTGCGGTTG
GAATGGGCATTCCTCTTTGGCAAATACCAGAAATAAGACG
ATTTTATGGAATGGACAATAGTGGAGGATACGATGCTTGG
AGGAGAACATCTGCTCTTGCAACTCCATTTGACTTTGACAA
GGCAGAGTCTATCAGCCCAAAAGGTCATTGTATTGCTGTA
CGTGTAACAAGTGAGGACCCAGATGATGGATTTAAGCCCA
CTAGTGGAAAAGTTCAGGAGCTAAGTTTTAAAAGCAAGCC
AAATGTCTGGGCATACTTTTCTGTCAAGTCCGGAGGAGGC
ATTCATGAATTCTCAGATTCTCAATTTGGCCACGTTTTTGCA
TTTGGCGAGTCAAGACCTTTGGCTATTGCAAATATGGTTCT
TGGGCTGAAGGAAATTCAAATTCGTGGCGAGATCCGTACG
AATGTTGATTATACAATTGATCTGTTACATGCTCCTGATTAT
AGAGAAAATAAAATACATACCGGTTGGTTAGATAGCCGAA
TTGCTATGAGGGTTAGAGCAGAAAGGCCCCCTTGGTATCT
TTCAGTAGTTGGGGGAGCACTTTATAAAGCTGCTGCTAGA
AGTGCAGCCATGGTCTCGGACTATGTTGGTTACCTTGAAA
AGGGCCAAATCCCTCCTAAGCATATATCATTGGTCAACTCA
CAAGTTTCTTTGAATATTGAGGGCAGCAAATACACGATTGA
TATGGTAAAAAGAGGGCCAGGAAGTTACAGATTGAGAAT
GAATCAATCCGAGATTGAAGCAGAGATACATACACTACGT
GACGGAGGCTTATTGATGCAGTTGGATGGGAATAGTCATA
TATTATACGCCGAGGAAGAAGCTGCCGGTACTCGCTTGCT
TATTGATGGACGGACTTGCTTGCTTCAGAATGATCATGATC
CTTCCAAGTTGATGGCTGAAACACCATGCAAACTTCTAAGG
TACTTGGTCTCAGATGATAGCCATGTTAATGCTGACACACC
GTATGCTGAGGTTGAAGTTATGAAGATGTGTATGCCACTC
CTTTCACCGGCTGCTGGAGTTATACAATTCAAGATGTCAGA
AGGTCAAGCCATGCAGGCTGGTGAGCTTATAGCAAGGCTA
GATCTTGACGATCCGTCAGCTGTAAGAAAAGCAGAGCCTT
TCAATGGAAACTTTCCTCTTCTTGGGCCTCCAACGGCCATG
TCAGACAAAGTGCATCAGAAGTGTGCTGCAACTTTAAATG
CTGCTCGAATGATTCTCGCAGGCTATGATCATAACATTGAT
GAATTGGAATCCAAGTTTAAGGAGTACGAAGGAATTTCCA
CACAACAAACTATTGACTTTCCTGCTAGAGTTCTACGGGTC |

TABLE 1-continued

ACCase gene sequences isolated from weedy plant species

| SEQ ID NO | SPECIES | TYPE | LENGTH | SEQ |
|---|---|---|---|---|

```
ATTCTTGAAACCCATCTTGGATCTTGCTCAGAAAAAGAAAA
GGGAGCCCAAGAAAGGCTCGTTGAGCCATTAATGGGTCTT
GTAAAGTCATATGAAGGGGGAAGAGAAAGTCATGCACGT
GGGATCGTTCATGCTCTATTTGATGAATATTTATCTGTTGA
AGAGTTGTTCAGCGACAACATTCAGGCTGATGTAATCGAA
CGTCTTCGACAACTATACAAGAAAGATCTCTTGAGGATTGT
CGACATTGTCCTTTCCCATCAGGGTGTTAGGAGTAAAAACA
AATTGATACTACGGCTGATGGAGCATTTGGTTTACCCCAAT
CCGGCTGCGTATAGGGAGAAACTGATACGATTTTCTCAAC
TTAACCACACAAGTTATTCTGAGTTAGCACTGAAGGCAAGT
CAACTTTTAGAACAAACTAAACTAAGTGAACTTCGTTCAAG
CATTGCGCGAAGTCTTTCTGAATTAGAGATGTTTACTGAAG
AAGGTGAAAATATGGATACCCCTAAGAGGAAGAGTGCCAT
TAATGAAAGAATGGAGGATATTGTGAGTGCTCCATTGGCA
GTTGAAGATGCCCTTGTTGGTCTTTTTGACCATAGCGATCA
CACCCTTCAAAGGCGTGTTGTTGAGACCTATGTTCGAAGAT
TATATCAGCCATATCTCGTGAAGGGGAGTGTTAGAATGCA
GTGGCACAGATCCGGACTCATCGCTACATGGCAATTTATA
GAAGGACTCATTGGAGAAGTTAATGTGCCTGACTATGAAC
AGAATGAAGCTCCCTTGGAAGACAAGAAATGGGGAGCTA
TGGTTATTATTAAATCTCTTCAATTTTTGCCTGATGTCATAA
GTGCATCTCTTAAAGAAACGAGTCATAACCTTCCCAGAACA
AGTCAGAATGGGTTTGCTGGTCATAGTAACCATGGTAATA
TGATGCACATTGCTTTGGCCGGCATAAATAACCAGATGAG
TTTGCTTCAAGACAGTGGTGATGAGGATCAGGCTCAAGAG
AGAGTCAACAGGTTAGCAAAAATACTCAAAGATAAAGAAG
TAAGCTCGAGTCTTAAAAACGCAGGGTATGGAGTGATCAG
TTGTATAATACAAAGAGATGAAGGGAGAGGCCCCATGAG
ACACTCATTTCACTGGTCAGAAGAGAATCATTATTATATTG
AAGAGCCATTATTGCGTCACTTGGAGCCTCCATTATCGACA
TATCTTGAACTGGACAAACTTAAGGGCTATGATAATATAAA
GTACACTCCGTCGCGTGACCGTCAATGGCACATGTATACTG
TTGATGCTAAACCACTTCCGGTACAAAGAATGTTTCTTAGA
ACTCTTATAAGGCATCCAACAAAGGAATGGTTCTCGCCCTC
AGGTTACCAAGGTTCAGAAGATGAGGGCCCACGGTCTCAG
TTAAATCTCCCTTTTACATCAAGGAGCATCTTGAGATCATTA
GTGACGGCTATGGAGGAGTTGGAACTTCATGTTCATAATG
CTACTGTCAAGTCTGACCATGCTCATATGTACCTATATGTAT
TGAAGGAGCAACAAATTGGTGATCTTGTTCCATACACAAC
GAGAGTGGATGTAGATTCTGGGACAGAAGATTGCGTGGT
TGAGACACTTTTGGTAAGGCTGGCTCGTGAAATCCATTCAA
TGGTTGGTGTAAAGATGCACCGGTTGGGAGTTTTTGAGTG
GGAGGTGAAGCTTTGCATGGCATCATCGGGTCAAGCCAAC
GGTGCGTGGAGGGTTGTGGTCACAAATGTGACTGGTCATA
CCTGCGTTGTGCATGTATATCGTGAACTGGAAGATACTGG
TTTGCACAAGGTGTATCATGCTACCTCTACATTGGGTCCTTT
GCATGGCGTACCTGTGAATACACCCTTTCAGCCTTTAGGAT
TACTTGATCAGAAGCGTCTTTTGGCAAGGAAAAGCAATAC
TACGTACTGCTACGACTTTGCACTGGCATTTGAAGCAGCTC
TTGAGAATATCTGGGCGTCGAAAGTCGTAAGTGATAGCAG
GCCTAAGGGTAAACTTGTGAATGTGACGGAGCTCATGTTT
GCTGAGCCAAGTGGCTCATGGGGAACTCCCCTTGTTGCAG
TAAATCGTGAGCCAGGGCAAAACAAGGTGGGCATGGTGG
CGTGGACTATGGACCTCTGCACTCCTGAGTTTCCTGATGGA
AGAACGATTTTGGTAGTAGCAAACGATGTTACGTTCAAAA
ATGGATCTTTTGGTCCTCTTGAGGATGCCTTTTTTGAGGCA
GTTACTGATCTCGCTTGTGCCAAGAAACTGCCACTAATATA
CTTGGCAGCAAACTCGGGGGCCCGTATCGGAGCGGCTGA
GGAAGTCAGATCTTGCTTTAGAATTGGGTGGTCTGATGAG
TCGACTCCTGAATCGGGATTCCAGTATTTGTATCTTACTCCT
GAAGATTATACCCACATCAAATCATCTGTAATAGCTCATGA
GGTTCATCTATCAAATGGCGAAACAAGATATGTCATCGATA
CTATTGTGGGAAAAGAAGACGGACTCGGGGTTGAAAATTT
GAGTGGTAGCGGGGCAATTGCTGGTGCCTATTCGAAAGCA
TATAAGGAAACGTTTACATTAACATATGTTACTGGAAGAAC
AGTTGGGATAGGCGCATATCTGGCACGTCTTGGGATGCGG
TGCATACAGCGGCTTGATCAACCGATTATATTAACGGGTTT
TTCTGCACTGAACAAGCTTTTGGGCCGAGAGGTTTATAGCT
CACAGATGCAACTAGGTGGGCCTAAAATTATGGCTACGAA
TGGTGTTGTCCATTTAACGGTGTCCGATGATCTCGAAGGTG
TCTCAGCTATCTTGAATTGGTTGAGCTTTGTTCCACCTTATG
TCGGTGGCCCACTTCCTGTTTTAGCACCTGTGGATCCACCA
GAAAGGCCCGTTGAGTACCTCCCTGAAAACTCATGTGATCC
TCGGGCAGCTATTTGTGGGGTCGTGGATAGCAACGGTGAA
TGGGCTGGTGGGATTTTCGATAGAGACAGTTTTGTGGAGA
CATTGGAAGGTTGGGCGAGGACAGTCGTAACGGGTCGTG
```

TABLE 1-continued

ACCase gene sequences isolated from weedy plant species

| SEQ ID NO | SPECIES | TYPE | LENGTH | SEQ |
|---|---|---|---|---|
| | | | | CCAAACTTGGCGGGATCCCAGTCGGGATCGTTGCTGTTGA GACACAAACAGTGATGCAAGAAATACCTGCAGATCCCGGG CAGCTTGATTCACACGAACGTGTTGTTCCTCAAGCAGGTCA GGTCTGGTTCCCGGATTCCGCCAGCAAAACAGCTCAGGCA TTGATGGATTTCAACCGAGAAGAGCTCCCACTTTTCATCAT GGCTAACTGGCGAGGCTTTTCTGCAGGTCAGCGGGATCTT TTTGAAGGGATTTTACAAGCAGGGTCAACAATTGTTGAGA ATCTCAGAACATATAACCAGCCTGTTTTTGTATACATCCCG AAAACTGGGAGAACTTCGTGGCGGTGCATGGGTGGTTGTCG ACAGTCGAATCAATTCAGATCATATAGAAATGTATGCAGA AACCACAGCAAAAGGAAATGTCCTTGAACCTGAAGGTATG ATTGAGATTAAGTTCCGAAACAAAGAATTGATAGACTGTA TGGGTCGTCTAGATCCACAGATTCGAAGCCTTAAAGAAAG ACTTCGAGAAACAAAGTACGATCAAACGATCGTCCAACAG ATAAAATCTCGTGAAAAACAGCTTTTACCGATTTACACTCA AATTGCTACCAAATTCGCTGAACTTCATGACACATCATTGC GAATGGCTGAAAAAGGTGTGGTCAAACAAGTTGTTGACTG GAAAGTATCTCGGTTTTTCTTTTACAAAAGGCTTCGTCGTA GGCTCGCAGAGGCTTCCTTGATCAGTAGTGCTCGTGAAGC TGCTGGTGATACTCTTTCCTACAAGTCTGCTCATGAGTTGA TTAAGAAATGGTTTTTGGAATCGAAAACTGAAGATTTATG GCTTAGTGATGATGCTTTTTTCACTTGGAAAGACAATCTGA TGAACTATAATGACAAGTTAGCCAAGCTACGTACTCAGAA GCTCTTGGATCAGTTATTAAAGATTGGTAATTCACCATTGG ATCTACAAGCTTTACCACAAGGCCTCGCCGCACTTTTGCAA GAGGTGAACAAACTCTCTTTTATTTTCCCTTAG |
| 45 | Conyza canadensis | cDNA Contig | 6912 | ATGAATTTTCGGGCATTTGATCTGAAGCTCAACATTTTTCC GGGCGATTCAAATAAGCGTTTTACTGTTACAAAAAGTTTCG TCTCAACGGGTGACCACTACACGACTTCTGATAACACCAAT CCGACCAGTCTTACAAAGGTGAAGGTGAAGAAACATGTGA AGAGGGATAAATTTGGAGAAAGAATGGCATCACTAAAAC AGATAGTGTCACCCTATGGCAAGGAGTCTAGACTTGGACC ATTGTGTTTTAGAGAAGAAGGGAATCGAACGCAAAGTGGC ACCATGTCAGAAGCTCAAAGAATGCTTCTAAGTGGAAGTT TCAATTATTATGGTAATGGCATTGTAAATGGGGCGATTTCA CTGAGGTCTTCTGCTAGTAGATCTGCAATTGATGAATTTTG TAATGCACTTGGAGGCACCAGGCCAATCCAAAGTATTTTAA TTGCAAATAATGGAATGGCGGCTGTAAAGTTTATAAGAAG TGTGAGGACATGGAGTTATGAAACATTTGGCTCAGATAAA GCTATTTTGCTGGTAGCCATGGCTACACCGGAAGATATGA GGATAAATGCCGAGCATATTAGAATCGCTGATCAGTTTGTT GAAGTCCCTGGTGGTACAAATAATAATAATTATGCGAATG TGCAACTCATTGTAGAGACTGCTGAGATAACACATGTTGAT GCTGTTTGGCCTGGTTGGGGCCATGCATCCGAAATCCCTG AGCTGCCTGATGCATTGGAAGCAAAAGGTATTGTATTTCTT GGGCCACCAGCTTCCTCCATGGCAGCTTTAGGTGATAAAA TTGGTTCTTCTTTGATTGCACAAGCTGCTGATGTACCGACA CTTCCTTGGAGCGGTTCTCATGTAAAAATTCCTGTGGATAG CTGTTTGGACACACTCCCGGATGATGTATATAGAAAAGCG TGTGTGCATACAACAGAAGAAGCAATTGCTAGTTGTCAAG TTGTTGGTTATCCAGCAATGATTAAGGCATCATGGGGTGG AGGTGGCAAAGGCATAAGAAAGGTGCATAATGACGAAGA AGTCAAGGCACTTTTTAAGCAAGTTCAGGGTGAAGTGCCT GGTTCCCCTATTTTCATTATGAAAGTTGCTTCTCAGAGCCG ACATCTAGAAGTGCAGCTACTATGCGATCAACATGGGAAT GTAGCAGCTTTGCATAGTCGTGATTGCAGTGTTCAAAGGC GACATCAAAAGATTATTGAAGAGGGGCCAATAACCATAGC TCCACATGACACAATAAAGAAGCTTGAGCAAGCGGCGAGA AGATTAGCAAAGTCGGTTAATTATGTTGGAGCAGCCACTG TAGAGTATTTGTATAGCATGGAAACTGGAGACTATTACTTT TTGGAGCTCAATCCCCGGTTACAGGTTGAGCATCCAGTCAC AGAGTGGATAGCGGAAATCAATCTACCTGCAGCACAAGTT GCGGTTGGAATGGGCATTCCTCTTTGGCAAATACCAGAAA TAAGACGATTTTATGGAATGGACAATAGTGGAGGATACGA TGCTTGGAGGAGAACATCTGCTCTTGCAACTCCATTTGACT TTGACAAGGCAGAGTCTATCAGCCCAAAAGGTCATTGTATT GCTGTACGTGTAACAAGTGAGGACCCAGATGATGGATTTA AGCCCACTAGTGGAAAAGTTCAGGAGCTAAGTTTTAAAAG CAAGCCAAATGTCTGGGCATACTTTTCTGTCAAGTCCGGAG GAGGCATTCATGAATTCTCAGATTCTCAATTTGGCCACGTT TTTGCATTTGGCGAGTCAAGACCTTTGGCTATTGCAAATAT GGTTCTTGGGCTGAAGGAAATTCAAATTCGTGGCGAGATC CGTACGAATGTTGATTATACAATTGATCTGTTACATGCTCC TGATTATAGAGAAAATAAAATACATACCGGTTGGTTAGAT AGCCGAATTGCTATGAGGGTTAGAGCAGAAAGGCCCCCTT |

TABLE 1-continued

ACCase gene sequences isolated from weedy plant species

| SEQ ID NO | SPECIES | TYPE | LENGTH | SEQ |
|---|---|---|---|---|

```
GGTATCTTTCAGTAGTTGGGGGAGCACTTTACAAAGCTGC
TGCTAGAAGTGCAGCCATGGTCTCGGACTATGTTGGTTAC
CTTGAAAAGGGCCAAATCCCTCCTAAGCATATATCATTGGT
CAACTCACAAGTTTCTTTGAATATTGAGGGCAGCAAATACA
CGATTGATATGGTAAAAGAGGGCCAGGAAGTTACAGATT
GAGAATGAATCAATCCGAGATTGAAGCAGAGATACATACA
CTACGTGACGGAGGCTTATTGATGCAGTTGGATGGGAATA
GTCATATATTATACGCCGAGGAAGAAGCTGCCGGTACTCG
CTTGCTTATTGATGGACGGACTTGCTTGCTTCAGAATGATC
ATGATCCTTCCAAGTTGATGGCTGAAACACCATGCAAACTT
CTAAGGTACTTGGTCTCAGATGATAGCCATGTTAATGCTGA
CACACCGTATGCTGAGGTTGAAGTTATGAAGATGTGTATG
CCACTCCTTTCACCGGCTGCTGGAGTTATACAATTCAAGAT
GTCAGAAGGTCAAGCCATGCAGGCTGGTGAGCTTATAGCA
AGGCTAGATCTTGACGATCCGTCAGCTGTAAGAAAAGCAG
AGCCTTTCAATGGAAACTTTCCTCTTCTTGGGCCTCCAACG
GCCATGTCAGACAAAGTGCATCAGAAGTGTGCTGCAACTT
TAAATGCTGCTCGAATGATTCTCGCAGGCTATGATCATAAC
ATTGATGAATTGGAATCCAAGTTTAAGGAGTACGAAGGAA
TTTCCACACAACAAACTATTGACTTTCCTGCTAGAGTTCTAC
GGGTCATTCTTGAAACCCATCTTGGATCTTGCTCAGAAAAA
GAAAAGGGAGCCCAAGAAAGGCTCGTTGAGCCATTAATG
GGTCTTGTAAAGTCGTATGAAGGGGGAAGAGAAAGTCAT
GCACGTGGGATCGTTCATGCTCTATTTGATGAATATTTATC
TGTTGAAGAGTTGTTCAGCGACAACATTCAGGCTGATGTA
ATCGAACGTCTTCGACAACTATACAAGAAAGATCTCTTGAG
GATTGTCGACATTGTCCTTTCCCATCAGGGTGTTAGGAGTA
AAAACAAATTGATACTACGGCTGATGGAGCATTTGGTTTAC
CCCAATCCGGCTGCGTATAGGGAGAAACTGATACGATTTT
CTCAACTTAACCACACAAGTTATTCTGAGTTAGCACTGAAG
GCAAGTCAACTTTTAGAACAAACTAAACTAAGTGAACTTCG
TTCAAGCATTGCGCGAAGTCTTTCTGAATTAGAGATGTTTA
CTGAAGAAGGTGAAAATATGGATACCCCTAAGAGGAAGA
GTGCCATTAATGAAAGAATGAGGATATTGTGAGTGCTCC
ATTGGCAGTTGAAGATGCCCTTGTTGGTCTTTTTGACCATA
GCGATCACACCCTTCAAAGGCGTGTTGTTGAGACCTATGTT
CGAAGATTATATCAGCCATATCTCGTGAAGGGGAGTGTTA
GAATGCAGTGGCACAGATCCGGACTCATCGCTACATGGCA
ATTTATAGAAGGACTCATTGGAGAAGTTAATGTGCCTGAC
TATGAACAGAATGAAGCTCCCTTGGAAGACAAGAATGGG
GAGCTATGGTTATTATTAAATCTCTTCAATTTTTGCCTGATG
TCATAAGTGCATCTCTTAAAGAAACGAGTCATAACCTTCCC
AGAACAAGTCAGAATGGGTTTGCTGGTCATAGTAACCATG
GTAATATGATGCACATTGCTTTGGCCGGCATAAATAACCAG
ATGAGTTTGCTTCAAGACAGTGGTGATGAGGATCAGGCTC
AAGAGAGAGTCAACAGGTTAGCAAAAATACTCAAAGATAA
AGAAGTAAGCTCGAGTCTTAAAAACGCAGGGTATGGAGT
GATCAGTTGTATAATACAAAGAGATGAAGGGAGAGGCCC
CATGAGACACTCATTTCACTGGTCAGAAGAGAATCATTATT
ATATTGAAGAGCCATTATTGCGTCACTTGGAGCCTCCATTA
TCGACATATCTTGAACTGGACAAACTTAAGGGCTATGATAA
TATAAAGTACACTCCGTCGCGTGACCGTCAATGGCACATGT
ATACTGTTGATGCTAAACCACTTCCGGTACAAAGAATGTTT
CTTAGAACTCTTTATAAGGCATCCAACAAAGGAATGGTTCTC
GCCCTCAGGTTACCAAGGTTCAGAAGATGAGGGCCCACGG
TCTCAGTTAAATCTCCCTTTTACATCAAGGAGCATCTTGAG
ATCATTAGTGACGGCTATGGAGGAGTTGGAACTTCATGTT
CATAATGCTACTGTCAAGTCTGACCATGCTCATATGTACCT
ATATGTATTGAAGGAGCAACAAATTGGTGATCTTGTTCCAT
ACACAACGAGAGTGGATGTAGATTCTGGGACAGAAGATT
GCGTGGTTGAGACACTTTTGGTAAGGCTGGCTCGTGAAAT
CCATTCAATGGTTGGTGTAAAGATGCACCGGTTGGGAGTT
TTTGAGTGGGAGGTGAAGCTTTGCATGGCATCATCGGGTC
AAGCCAACGGTGCGTGGAGGGTTGTGGTCACAAATGTGA
CTGGTCATACCTGCGTTGTGCATGTATATCGTGAACTGGAA
GATACTGGTTTGCACAAGGTGTATCATGCTACCTCTACATT
GGGTCCTTTGCATGGCGTACCTGTGAATACACCCTTTCAGC
CTTTAGGATTACTTGATCAGAAGCGTCTTTTGGCAAGGAAA
AGCAATACTACGTACTGCTACGACTTTGCACTGGCATTTGA
AGCAGCTCTTGAGAATATCTGGGCGTCGAAAGTCGTAAGT
GATAGCAGGCCTAAGGGTAAACTTGTGAATGTGACGGAG
CTCATGTTTGCTGAGCCAAGTGGCTCATGGGAACTCCCCT
TGTTGCAGTAAATCGTGAGCCAGGGCAAAACAAGGTGGG
CATGGTGGCGTGGACTATGGACCTCTGCACTCCTGAGTTTC
CTGATGGAAGAACGATTTTGGTAGTAGCAAACGATGTTAC
GTTCAAAAATGGATCTTTTGGTCCTCTTGAGGATGCCTTTTT
```

TABLE 1-continued

ACCase gene sequences isolated from weedy plant species

| SEQ ID NO | SPECIES | TYPE | LENGTH | SEQ |
|---|---|---|---|---|
| | | | | TGAGGCAGTTACTGATCTCGCTTGTGCCAAGAAACTGCCA
CTAATATACTTGGCAGCAAACTCGGGGGCCCGTATCGGAG
CGGCTGAGGAAGTCAGATCTTGCTTTAGAATTGGGTGGTC
TGATGAGTCGACTCCTGAATCGGGATTCCAGTATTTGTATC
TTACTCCTGAAGATTATACCCACATCAAATCATCTGTAATA
GCTCATGAGGTTCATCTATCAAATGGCGAAACAAGATATG
TCATCGATACTATTGTGGGAAAAGAAGACGGACTCGGGGT
TGAAAATTTGAGTGGTAGCGGGGCAATTGCTGGTGCCTAT
TCGAAAGCATATAAGGAAACGTTTACATTAACATATGTTAC
TGGAAGAACAGTTGGGATAGGCGCATATCTGGCACGTCTT
GGGATGCGGTGCATACAGCGGCTTGATCAACCGATTATAT
TAACGGGTTTTTCTGCACTGAACAAGCTTTTGGGCCGAGA
GGTTTATAGCTCACAGATGCAACTAGGTGGGCCTAAAATT
ATGGCTACGAATGGTGTTGTCCATTTAACGGTGTCCGATG
ATCTCGAAGGTGTCTCAGCTATCTTGAATTGGTTGAGCTTT
GTTCCACCTTATGTCGGTGGCCCACTTCCTGTTTTAGCACCT
GTGGATCCACCAGAAAGGCCCGTTGAGTACCTCCCTGAAA
ACTCATGTGATCCTCGGGCAGCTATTTGTGGGGTCGTGGA
TAGCAACGGTGAATGGGCTGGTGGGATTTTCGATAGAGAC
AGTTTTGTGGAGACATTGGAAGGTTGGGCGAGGACAGTC
GTAACGGGTCGTGCCAAACTTGGCGGGATCCCAGTCGGG
ATCGTTGCTGTTGAGACACAAACAGTGATGCAAGAAATAC
CTGCAGATCCCGGGCAGCTTGATTCACACGAACGTGTTGTT
CCTCAAGCAGGTCAGGTCTGGTTCCCGGATTCCGCCAGCA
AAACAGCTCAGGCATTGATGGATTTCAACCGAGAAGAGCT
CCCACTTTTCATCATGGCTAACTGGCGAGGCTTTTCTGCAG
GTCAGCGGGATCTTTTTGAAGGGATTTTACAAGCAGGGTC
AACAATTGTTGAGAATCTCAGAACATATAACCAGCCTGTTT
TTGTATACATCCCGAAAACTGGAGAACTTCGTGGTGGTGC
ATGGGTGGTTGTCGACAGTCGAATCAATTCAGATCATATA
GAAATGTATGCAGAAACCACAGCAAAAGGAAATGTCCTTG
AACCTGAAGGTATGATTGAGATTAAGTTCCGAAACAAAGA
ATTGATAGACTGTATGGGTCGTCTAGATCCACAGATTCGA
AGCCTTAAAGAAAGACTTCGAGAAACAAAGTACGATCAAA
CGATCGTCCAACAGATAAAATCTCGTGAAAAACAGCTTTTA
CCGATTTACACTCAAATTGCTACCAAATTCGCTGAACTTCAT
GACACATCATTGCGAATGGCTGAAAAAGGTGTGGTCAAAC
AAGTTGTTGACTGGAAAGTATCTCGGTTTTTCTTTTACAAA
AGGCTTCGTCGTAGGCTCGCAGAGGCTTCCTTGATCAGTA
GTGCTCGTGAAGCTGCTGGTGATACTCTTTCCTACAAGTCT
GCTCATGAGTTGATTAAGAAATGGTTTTTGGAATCGAAAA
CTGAAGATTTATGGCTTAGTGATGATGCTTTTTTCACTTGG
AAAGACAATCTGATGAACTATAATGACAAGTTAGCCAAGC
TACGTACTCAGAAGCTCTTGGATCAGTTATTAAAGATTGGT
AATTCACCATTGGATCTACAAGCTTTACCACAAGGCCTCGC
CGCACTTTTGCAAGAGGTGAACAAACTCTCTTTTATTTTCCC
TTAG |
| 46 | Conyza canadensis | cDNA Contig | 6654 | ATGCCAGAAGCTCAAAGAATGCCTCTAAATGGAAGCCTTA
ATCTTGGTAATGGTTATGTAAATGGGGCCATTTCATTGAGG
TCTTCTGCTAGCAGATCTGCCATTGATGAATTTTGTAATGC
ACTTGGGGGGAATAGGCCAATCCATAGTATTTTAATTGCA
AACAATGGAATGGCTGCTGTAAAGTTTATAAGAAGTGTGA
GGACATGGAGTTATGAAACGTTTGGTTCAGAAAAAGCAAT
TTTGTTGGTAGCCATGGCTACACCTGAGGATATGAGGATT
AATGCCGAGCATATTAGAATTGCTGATCAGTTTGTTGAAGT
CCCAGGTGGTACAAATAATAATAATTATGCTAATGTGCAGC
TCATCGTGGAGACTGCTGAGATAACACATGTTGATGCTGTT
TGGCCTGGTTGGGGTCATGCCTCTGAAATTCCTGAATTACC
TGATGCATTGGACGCAAAGGGAATTGTATTTCTTGGGCCG
CCGGCTTCATCCATGGCGGCTTTAGGAGACAAAATCGGCT
CTTCTTTAATTGCACAAGCTGCTGACGTGCCAACACTTCCTT
GGAGTGGTTCTCATGTGAAAATTTCTGCAGAGAGCTGCTT
AGACACAATTCCAGATGACGTATATAGAAAAGCTTGTGTC
CATACAACCGAGGAAGCAGTTGCTTCTTGTCAAGTTATTGG
TTATCCTGCTATGATCAAGGCATCATGGGCGGTGGTGGC
AAAGGCATAAGAAAGGTGCATAGTGATGAAGAAGTCAAG
ACACTTTTTAAGCAAGTTCAGGGTGAAGTCCCTGGTTCCCC
CATATTTATTATGAAGTTGCTTCCCAGAGCCGACATCTAG
AAGTACAACTCCTCTGTGATCAGCATGGCAATGTAGCGGC
TTTACATAGTCGGGATTGCAGTGTTCAAAGGCGGCATCAA
AAGATTATCGAGGAGGGGCCAATAACCATAGCCCCCCCTG
ACACAATAAAAAAATTGGAGCAAGCGGCAAGAAGATTAG
CCAAATCGGTCAATTATGTTGGAGCTGCAACTGTAGAGTA
TTTGTACAGTATGGAAACCGGAGATTATTACTTTTTGGAGC
TCAATCCCCGTTTACAGGTTGAGCATCCTGTCACTGAGTGG |

TABLE 1-continued

ACCase gene sequences isolated from weedy plant species

| SEQ ID NO | SPECIES | TYPE | LENGTH | SEQ |
|---|---|---|---|---|

```
ATAGCGGAAGTTAATCTACCTGCAGCACAAGTTGCGGTTG
GAATGGGCATTCCACTTTGGCAAATTCCCGAAATAAGACG
GTTTTATGGAAAGGAAAACGGTGGAGGGTATGATGCTTG
GAGGAGAACATCGGTTCTTGCAACCCCATTTGATTTTGATC
GCGCCGAGTCAGTTAGGCCGAAGGGTCATTGTGTTGCTGT
ACGTGTAACAAGTGAAGATCCGGATGATGGTTTTAAGCCC
ACCAGTGGAAAAGTTCAGGAGCTAAGTTTTAAAAGCAAGC
CAAACGTATGGGCATACTTTTCTGTCAAGTCTGGAGGAGG
CATTCATGAATTCTCAGATTCTCAATTCGGTCATGTTTTTGC
ATTTGGAGAGTCAAGAACATTGGCTATTGCAAATATGGTT
CTTGGGCTAAAGGAAATTCAAATTCGTGGCGAAATGCGCA
CTAATGTTGATTATACAATTGATTTATTACATGCTCCAGATT
ATAGAGAAAACAAAATACACACGGGTTGGTTAGATAGCCG
AATTGCGATGCGGGTTAGAGCAGAAAGGCCTCCTTGGTAT
CTTTCGGTAGTGGGGGAGCTCTTTACAAAGCCGCTGCTA
GAAGTGCAGCCATGGCCTCTGACTATGTTGGTTATCTTGAA
AAGGGGCAAATCCCTCCAAAGCATTTATCACTAGTCAACTC
TCAAGTTACTTTGAATATTGAGGGGAGCAGATACACAATT
GATATGGTAAAAGAGGACCTGGAGGTTATAGATTGAAA
ATGAACCAATCTGAGATTGAAGCAGAAATACATACTCTAC
GTGACGGGGTTTATTGATGCAGTTGGATGGGAATAGTCA
TATTATATATGCTGAAGAAGAAGCCGCTGGTACTCGTCTCC
TCATTGATGGACGGACATGTTTGCTTCAGAATGATCATGAT
CCTTCCAAGCTGGTGGCCGAAACACCATGCAAACTTCTAAG
ATACTTAGTCTCAGATAGTAGCCATGTCGATGCTGACACAC
CTTATGCTGAGGTGGAGGTAATGAAGATGTGTATGCCGCT
ACTTTCGCCGGCTTCTGGAGTTATACAGTTTAAGATGTCTG
AAGGTCAAGCAATGCATGCTGGTGAGCTAATAGCAAGGCT
TGATCTTGATGACCCATCAGCAGTAAGAAAAGCAGAGCCT
TTCCATGGAACTTTTCCTCTTCTTGGGTCTTCAACTGCCATG
TCAGATAAAGTTCATCAAAAGTGTGCTACAACTCTAAGTGC
CGCTCGAATGATTCTTGCAGGCTATGATCACGATATTGATG
AATTGGAAACAAAATTTAAGGAGTACGAAGGAATTTCCAC
CCAACAAGCTATTGATTTCCCCGCCAAATTATTATGGGGAA
TTCTTGAAACACATCTTGAATTGTGCTCGGAAAAGGAAAG
GGGAGCCCAAGAAAGGCTTGCTGAGCCATTAATGAGTCTT
GTCAAGTCCTATGAAGGTGGCAGAGAGAGTCATGCACGT
GGGATCGTTCATGCTCTTTTTGAAGCATATTTATCTGTTGA
AGAGCTATTTAGCGACAACATTCAGGCTGATGTAATTGAA
CGTCTTAGACAACAATACAAGAAGGATCTGTCGAGGGTTG
TTGACATCGTGATTTCACATCAGGGTGTTAAGACTAAAAAC
AAACTGATACTACGACTGATGGAGCATTTGGTTTACCCTAA
TCCAGCCGCCTATAGGGAAAATCTGATACGGTTTTCTCAAT
TGAACCACACTAGTTATTCTGAGTTAGCATTGAAGGCAAGT
CAGCTGCTAGAACAGACTAAACTGAGTGAACTTCGTTCAA
GCATAGCTAGAAGTCTTTCTGAGTTAGAGATGTTTACCGAA
GAAGGTGAGAATATAGATACCCCTAAGAGGAAGAGTGCC
ATTGATGAAAGAATGGAGGATATTGTGAGTGCTCCTTTGG
CGGTCGAAGATGCCCTTGTTGGTCTTTTTGATCACAGTGAT
CACACCCTTCAAAGGCGTGTTGTTGAGACCTATGTTCGAAG
GCTATATCAGCCATATCTCGTGAAGAGGAGTGTTAAGATG
CAGTGGCACAGATCCGGACTTATTGCTTCATGGCAATTCAT
GGAAGGACACGCTGAAGCTGTTAATGTGTCTGATTATGAA
ACTATTGATACACAATTGGTAGATAAGAAATGGGGAGCTA
TGGTTATTATTAGATCTCTTCAATTTTTACCTGATGTCATAA
GTGCAGCTCTTAAAGAAACTACTTATAAACATCATGGCACA
AGTCAAAATGGGGATGCCAATCCAAGTTATCAAGGTTATA
TGATGCATATTGCATTGGTAGGCATCAACAACCAAATGAG
TTTGCTTCAAGACAGTGGTGATGAGGATCAGGCTCAAGAG
AGAGTCAACAAGTTAGCAAAAATACTCAAAGATAAAGAAA
TAAGTGTGAAACTAAAAAATGCAGGATATGAAGTTGTAAG
TTGCATAATACAAAGAGACGAAGGTAGAGGCCCGGTGAG
ACACTCATTTCACTGGTCAGAAAAGAATCGTTATTATATCG
AAGAGCCATCATTGCGTCATTTGGAGCCTCCATTATCGATT
TATCTTGAACTGGACAAGCTTAAGGGCTATGAGAATGTAA
AGTACACTCCATCACGTGACCGTCAATGGCACATGTATACT
GTTGATGCTAAACCACTTCCGGTTCAAAGAATGTTTCTTAG
AACGCTTGTAAGGCACCCGACAAAAGAATGGTTCTTGCCC
TCAGGATACCAAGATTCGGAAGTTGTGACCCACGGTCTC
AGTTAACTTTACCTTTTACATCAAGGAGCATCTTGAGATCTT
TAGTGACCGCCATGGAGGAGTTGGAACTTCATGTTCATAA
TGCTATAGTCAAGTCGGACCATGCTCATATGTACCTCTATA
TATTGAAAGAACAACAAATAAATGATCTTGTTCCATATACT
AAGAGAGTGGATGTAGATTCTGGTAAAGAAGAAGGTGTG
GTTGAGACGCTTTTGGTGAAGTTGGTCCGTGAACTTCATTC
GATGGTTGGGGTAAAGATGCACCGGTTAGGTGTTTTTGAG
```

TABLE 1-continued

ACCase gene sequences isolated from weedy plant species

| SEQ ID NO | SPECIES | TYPE | LENGTH | SEQ |
|---|---|---|---|---|
| | | | | TGGGAGGTGAAGCTTTGTATGGTATCATCTGGTGAAGCCA<br>ACGGTGTTTGGAGGGTGGTGGTCACAAATGTGACTGGGC<br>ATACCTGCAATGTACATGTGTATCGGGAAGTAGAAGATAC<br>TGTTAAACACAAGGCAGTGTATCATGCTCCCTCTACATTGG<br>GACCTTTACATGGTGTGCTGGTGAACACACCCTTTCAGCCT<br>CTGGGATTACTCGATCAGAAGCGTCTTGTCGCCAGGAAAA<br>GCAATACTACTTACTGCTACGACTTTGCACTGGCATTTGAA<br>GCAGCCCTTGAGAATATCTGGTCATCAAAACTGCCTGGTGT<br>AAGCAGGCCCAAGGGCAAACTTGTAAATGCGATGGAGCTT<br>GTGTTTGCTGACCGAAGAGGTTTATGGGGCACTCCACTTG<br>TGCCAGTAACGCGCGAGCCTGGACAAAATAATGTGGGAAT<br>GGTAGCGTGGACTATGGACCTCTGCACACCAGAATTTCCT<br>GATGGTAGGACGATTTTAGTTGTTTCAAATGACGTCACATT<br>TAAAAACGGATCTTTTGGTCCTATCGAGGATGCGTTTTTTG<br>AGGCAGTCACTGAGCTTGCTTGTGCCAAAAAACTGCCGCT<br>CATTTACCTGGCGGCAAACTCAGGGGCCCGTATCGGGGTG<br>GCCGAAGAGGTCAGATCCAGCTTTAGAATTGGGTGGTCTG<br>ATGAGTCAACTCCCGACTCCGGCTTTCAGTATTTGTATCTA<br>ACTCCCGAAGATTACTCTCGTTTGGAATCATCAGTAATAGC<br>ACATGAAATTCGTCTATCCAGTGGTGAAACAAGATGGGTC<br>ATTGATACTATTGTCGGGAAGAGGATGGATTAGGGGTTG<br>AGAATTTGAGTGGTAGTGGGGCGATTGCTGGGGCTTTTTC<br>GAAGGCATATAAAGAAACTTTTACTTTAACCTACGTGACTG<br>GAAGAACTGTTGGGATAGGTGCATATCTGGCCCGTCTTGG<br>GATGCGATGCATACAAAGGCTTGATCAACCGATTATTTTAA<br>CTGGGTTTTCTGCACTAAACAAGCTTTTGGGCCGAGAGGTT<br>TATAGTTCGCAGATGCAACTTGGTGGACCTAAAATTATGG<br>CCACGAATGGCGTTGTTCATCAAACTGTATCTGATGATTTG<br>GAAGGTGTCTCGGCTATCTTGAACTGGTTGAGCTATGTTCC<br>GCCTTACGTTGGCGGTCCACTTCCTGTTTTGCCACCCATGG<br>ATCCACCAGACAGGCCCGTCGAGTACCTGCCTGAAAACTC<br>ATGTGATCCTAGGGCAGCCATTTGTGGGACCGTGGATGGT<br>AACGGGAAATGGGTTGGTGGATTTTCGACAGAAACAGTT<br>TTGTGGAGACGTTGGAAGGTTGGGCAAGGACAGTTGTAA<br>CAGGTCGGGCGAAACTCGGTGGAATCCCTGTGGGGGTTG<br>TTGCTGTCGAGACACAAACGATGATGCAAGTTATACCTGC<br>GGATCCTGGGCAGCTCGATTCACATGAACGTGTAGTTCCTC<br>AAGCTGGGCAGGTCTGGTTCCCGGATTCTGCTAGTAAGAC<br>AGCTCAAGCGCTGATGGATTTTAATCGAGAAGAGCTCCCC<br>CTTTTCATTATGGCAAACTGGCGAGGGTTTTCAGCCGGTCA<br>ACGTGACCTTTTTGAAGGGATTCTACAAGCGGGATCGACA<br>ATTGTAGAGAATCTTAGAACCTATAAACAGCCAGTTTTTGT<br>CTACATTCCAAAAACAGGTGAGCTTCGAGGTGGTGCATGG<br>GTGGTCGTTGACAGTCGAATCAATTCAGACCATATAGAAA<br>TGTATGCAGAAACAACTGCGAAAGGAAATGTTCTTGAACC<br>CGAAGGTATGATTGAAATAAAGTTCCGAAATAAAGAGCTG<br>GTAGACTGCATGGGTCGATTGGACCCACTAATTTGCAATCT<br>AAAAGAAAAACTTAAAGAAACGAAGCTCGATCAAGCAATC<br>ACCCAGCAGATAAAAGCCCGTGAGAAACAGCTTTTACCAA<br>TTTACACTCAAATCGCTACAAAGTTTGCTGAACTTCATGAC<br>ACATCATTCCGAATGGCTGAAAAAGGTGTTGTCAAAAAGG<br>TTGTTGACTGGGCAATTTCCCGGTTTTTCTTCTACAAAAGA<br>CTCCAGCGTAGGCTGGCCGAGGCTTCTCTAATCAAGAGTG<br>CTCGTGATGCTGCTGGTGACACGCTTTCACACAAATCTGCT<br>CATGAAATGATCAAAAAATGGTTTTTGGACACAAAAAGTG<br>AAGATATGTGGGTGAATGACGACGCCTTTTTCACATGGAA<br>AGATGATCCATTGAACTATACTAGCAAATTAGCCGATCTAC<br>GTACACAGAAGATATCAAATCAGTTATTAAAGATTGGCAG<br>TTCACCTTCCGATCTGCAAGCTTTACCACAGGGACTCGCTG<br>CACTTTTGCAAGAGGTGAATCCTGCAGCCAAAAATAAATT<br>GATTGAAGAACTCAGGCGGATAATTGAGTAG |
| 47 | Conyza<br>canadensis | cDNA<br>Contig | 4804 | CTACTTTCGCCGGCTTCTGGAGTTATACAGTTTAAGATGTC<br>TGAAGGTCAAGCAATGCATGCTGGTGAGCTAATAGCAAGG<br>CTTGATCTTGATGACCCATCAGCAGTAAGAAAAGCAGAGC<br>CTTTCCATGGAACTTTTCCTCTTCTTGGGTCTTCAACTGCCA<br>TGTCAGATAAAGTTCATCAAAAGTGTGCTACAACTCTAAGT<br>GCCGCTCGAATGATTCTTGCAGGCTATGATCACGATATTGA<br>TGAAGTTGTCAAAAACCTTCTTCGTTGTCTAGATAATCCCA<br>AGCTACCTTTCCTCCAGTGGCAAGAATGCTTTGCAGTTCTA<br>GCCAATCGTCTCCCTAAAGATCTAAGAAACAAGTTGGAATC<br>CAAGTTTAAGGAGTACGAAGGAATTTCCACACAACAAACT<br>ATTGACTTTCCTGCTAGAGTTCTACGGGTCATTCTTGAAAC<br>CCATCTTGGATCTTGCTCAGAAAAGAAAAGGGAGCCCAA<br>GAAAGGCTCGTTGAGCCATTAATGGGTCTTGTAAAGTCAT<br>ATGAAGGGGGAAGAGAAAGTCATGCACGTGGGATCGTTC |

TABLE 1-continued

ACCase gene sequences isolated from weedy plant species

| SEQ ID NO | SPECIES | TYPE | LENGTH | SEQ |
|---|---|---|---|---|

ATGCTCTATTTGATGAATATTTATCTGTTGAAGAGTTGTTCA
GCGACAACATTCAGGCTGATGTAATCGAACGTCTTCGACA
ACTATACAAGAAAGATCTCTTGAGGATTGTCGACATTGTCC
TTTCCCATCAGGGTGTTAGGAGTAAAAACAAATTGATACTA
CGGCTGATGGAGCATTTGGTTTACCCCAATCCGGCTGCGT
ATAGGGAGAAACTGATACGATTTTCTCAACTTAACCACACA
AGTTATTCTGAGTTAGCACTGAAGGCAAGTCAACTTTTAGA
ACAAACTAAACTAAGTGAACTTCGTTCAAGCATTGCGCGA
AGTCTTTCTGAATTAGAGATGTTTACTGAAGAAGGTGAAA
ATATGGATACCCCTAAGAGGAAGAGTGCCATTAATGAAAG
AATGGAGGATATTGTGAGTGCTCCATTGGCAGTTGAAGAT
GCCCTTGTTGGTCTTTTTGACCATAGCGATCACACCCTTCAA
AGGCGTGTTGTTGAGACCTATGTTCGAAGATTATATCAGCC
ATATCTCGTGAAGGGGAGTGTTAGAATGCAGTGGCACAGA
TCCGGACTCATCGCTACATGGCAATTTATAGAAGGACTCAT
TGGAGAAGTTAATGTGCCTGACTATGAACAGAATGAAGCT
CCCTTGGAAGACAAGAAATGGGGAGCTATGGTTATTATTA
AATCTCTTCAATTTTTGCCTGATGTCATAAGTGCATCTCTTA
AAGAAACGAGTCATAACCTTCCCAGAACAAGTCAGAATGG
GTTTGCTGGTCATAGTAACCATGGTAATATGATGCACATTG
CTTTGGCCGGCATAAATAACCAGATGAGTTTGCTTCAAGAC
AGTGGTGATGAGGATCAGGCTCAAGAGAGAGTCAACAGG
TTAGCAAAAATACTCAAAGATAAAGAAGTAAGCTCGAGTC
TTAAAAACGCAGGGTATGGAGTGATCAGTTGTATAATACA
AAGAGATGAAGGGAGAGGCCCCATGAGACACTCATTTCAC
TGGTCAGAAGAGAATCATTATTATATTGAAGAGCCATTATT
GCGTCACTTGGAGCCTCCATTATCGACATATCTTGAACTGG
ACAAACTTAAGGGCTATGATAATATAAAGTACACTCCGTCG
CGTGACCGTCAATGGCACATGTATACTGTTGATGCTAAACC
ACTTCCGGTACAAAGAATGTTTCTTAGAACTCTTATAAGGC
ATCCAACAAAGGAATGGTTCTCGCCCTCAGGTTACCAAGG
TTCAGAAGATGAGGGCCCACGGTCTCAGTTAAATCTCCCTT
TTACATCAAGGAGCATCTTGAGATCATTAGTGACGGCTAT
GGAGGAGTTGGAACTTCATGTTCATAATGCTACTGTCAAG
TCTGACCATGCTCATATGTACCTATATGTATTGAAGGAGCA
ACAAATTGGTGATCTTGTTCCATACACAACGAGAGTGGAT
GTAGATTCTGGGACAGAAGATTGCGTGGTTGAGACACTTT
TGGTAAGGCTGGCTCGTGAAATCCATTCAATGGTTGGTGT
AAAGATGCACCGGTTGGGAGTTTTTGAGTGGGAGGTGAA
GCTTTGCATGGCATCATCGGGTCAAGCCAACGGTGCGTGG
AGGGTTGTGGTCACAAATGTGACTGGTCATACCTGCGTTG
TGCATGTATATCGTGAACTGGAAGATACTGGTTTGCACAA
GGTGTATCATGCTACCTCTACATTGGGTCCTTTGCATGGCG
TACCTGTGAATACACCCTTTCAGCCTTTAGGATTACTTGATC
AGAAGCGTCTTTTGGCAAGGAAAAGCAATACTACGTACTG
CTACGACTTTGCACTGGCATTTGAAGCAGCTCTTGAGAATA
TCTGGGCGTCGAAAGTCGTAAGTGATAGCAGGCCTAAGG
GTAAACTTGTGAATGTGACGGAGCTCATGTTTGCTGAGCC
AAGTGGCTCATGGGGAACTCCCCTTGTTGCAGTAAATCGT
GAGCCAGGGCAAAACAAGGTGGGCATGGTGGCGTGGACT
ATGGACCTCTGCACTCCTGAGTTTCCTGATGGAAGAACGAT
TTTGGTAGTAGCAAACGATGTTACGTTCAAAAATGGATCTT
TTGGTCCTCTTGAGGATGCCTTTTTTGAGGCAGTTACTGAT
CTCGCTTGTGCCAAGAAACTGCCACTAATATACTTGGCAGC
AAACTCGGGGCCCGTATCGGAGCGGCTGAGGAAGTCAG
ATCTTGCTTTAGAATTGGGTGGTCTGATGAGTCGACTCCTG
AATCGGGATTCCAGTATTTGTATCTTACTCCTGAAGATTAT
ACCCACATCAAATCATCTGTAATAGCTCATGAGGTTCATCT
ATCAAATGGCGAAACAAGATATGTCATCGATACTATTGTG
GGAAAAGAAGACGGACTCGGGGTTGAAAATTTGAGTGGT
AGCGGGGCAATTGCTGGTGCCTATTCGAAAGCATATAAGG
AAACGTTTACATTAACATATGTTACTGGAAGAACAGTTGG
GATAGGCGCATATCTGGCACGTCTTGGGATGCGGTGCATA
CAGCGGCTTGATCAACCGATTATATTAACGGGTTTTCTGC
ACTGAACAAGCTTTTGGGCCGAGAGGTTTATAGCTCACAG
ATGCAACTAGGTGGGCCTAAAATTATGGCTACGAATGGTG
TTGTCCATTTAACGGTGTCCGATGATCTCGAAGGTGTCTCA
GCTATCTTGAATTGGTTGAGCTTTGTTCCACCTTATGTCGGT
GGCCCACTTCCTGTTTTAGCACCTGTGGATCCACCAGAAAG
GCCCGTTGAGTACCTCCCTGAAAACTCATGTGATCCTCGGG
CAGCTATTTGTGGGGTCGTGGATAGCAACGGTGAATGGGC
TGGTGGGATTTTCGATAGAGACAGTTTTGTGGAGACATTG
GAAGGTTGGGCGAGGACAGTCGTAACGGGTCGTGCCAAA
CTTGGCGGGATCCCAGTCGGGATCGTTGCTGTTGAGACAC
AAACAGTGATGCAAGAAATACCTGCAGATCCCGGGCAGCT
TGATTCACACGAACGTGTTGTTCCTCAAGCAGGTCAGGTCT

TABLE 1-continued

ACCase gene sequences isolated from weedy plant species

| SEQ ID NO | SPECIES | TYPE | LENGTH | SEQ |
|---|---|---|---|---|
| | | | | GGTTCCCGGATTCCGCCAGCAAAACAGCTCAGGCATTGAT<br>GGATTTCAACCGAGAAGAGCTCCCACTTTTCATCATGGCTA<br>ACTGGCGAGGCTTTTCTGCAGGTCAGCGGGATCTTTTTGA<br>AGGGATTTTACAAGCAGGGTCAACAATTGTTGAGAATCTC<br>AGAACATATAACCAGCCTGTTTTTGTATACATCCCGAAAAC<br>TGGAGAACTTCGTGGCGGTGCATGGGTGGTTGTCGACAGT<br>CGAATCAATTCAGATCATATAGAAATGTATGCAGAAACCA<br>CAGCAAAAGGAAATGTCCTTGAACCTGAAGGTATGATTGA<br>GATTAAGTTCCGAAACAAAGAATTGATAGACTGTATGGGT<br>CGTCTAGATCCACAGATTCGAAGCCTTAAAGAAAGACTTC<br>GAGAAACAAAGTACGATCAAACGATCGTCCAACAGATAAA<br>ATCTCGTGAAAAACAGCTTTTACCGATTTACACTCAAATTG<br>CTACCAAATTCGCTGAACTTCATGACACATCATTGCGAATG<br>GCTGAAAAGGTGTGGTCAAACAAGTTGTTGACTGGAAAG<br>TATCTCGGTTTTTCTTTTACAAAAGGCTTCGTCGTAGGCTCG<br>CAGAGGCTTCCTTGATCAGTAGTGCTCGTGAAGCTGCTGG<br>TGATACTCTTTCCTACAAGTCTGCTCATGAGTTGATTAAGA<br>AATGGTTTTTGGAATCGAAAACTGAAGATTTATGGCTTAGT<br>GATGATGCTTTTTTCACTTGGAAAGACAATCTGATGAACTA<br>TAATGACAAGTTAGCCAAGCTACGTACTCAGAAGCTCTTG<br>GATCAGTTATTAAAGATTGGTAATTCACCATTGGATCTACA<br>AGCTTTACCACAAGGCCTCGCCGCACTTTTGCAAGAGGTG<br>GATCCAGTGACCAAAAATAAACTAGTCGAAGAACTCTTGC<br>GCGTAATTAAGTAGGTAATTATACACAAAGCTCATCAGATT<br>CTTTCTTTGTTTGTCAAAGTGAGAAGCCTTTTGAGCAGTGT<br>ACATTATAAGTAGGTGTCATAAGAAAACAGGCTCAAAATA<br>GTTTAAAGTATATGAGGTTTACCATGTTCAGATTGTTTTATT<br>TTTCTTCATAAATTGTATAATACCATCACATTTCTATCGCAT<br>TTTTTATATATCTATATATAAATGGTCA |
| 48 | Conyza canadensis | cDNA Contig | 454 | GGTCATTGTGTTGCTGTACGTGTAACAAGTGAAGATCCGG<br>ATGATGGTTTTAAGCCCACCAGTGGAAAAGTTCAGGAGCT<br>AAGTTTTAAAAGCAAGCCAAACGTATGGGCATACTTTTCTG<br>TCAAGTCTGGAGGAGGCATTCATGAATTCTCAGATTCTCAA<br>TTCGGTCATGTTTTTGCATTTGGAGAGTCAAGAACATTGGC<br>TATTGCAAATATGGTTCTTGGGCTAAAGGAAATTCAAATTC<br>GTGGCGAGATGCGCACTAATGTTGATTATACAATTGATTTA<br>TTACATGCTCCAGATTATAGAGAAAACAAAATACACATACC<br>GGTTGGTTAGATAGCCGAATTGCTATGAGGGTTAGAGCAG<br>AAAGGCCCCCTTGGTATCTTTCAGTAGTTGGGGGAGCACT<br>TTATAAAGCTGCTGCTAGAAGTGCAGCCATGGTCTCGGAC<br>TATGTTGG |
| 49 | Conyza canadensis | gDNA Contig | 19367 | TTTGGTGGTGGTTTCGTGGTCTAATTCGAAGAAACGAGTG<br>AGATATCGGTATTTTAAGTTTTCCGGCGAACTTTCCGATGA<br>AAGTTAGCCGGAGAAGATGAAGATGATGACAACAGAAA<br>TTAAATTTCATTTTTTGTCCCTGAACTTGTCACTTTTCGCACT<br>TTAAGTCCCTCACGTGTTTTGCACGTGTGGGACTTAACGGC<br>TGAAACTTAACACCGTTTGGCGAGGGACGTCGATTGCAAA<br>AATCTGTCAAGTTTAGGGTCAAAATTGTAATTTTTTCATTTT<br>AGGGATGAAAAGTGAAAAACGCGCCAAGTTTAGGGACGA<br>AAAATGTAATTTACTCTAAGTATTATGTAATTTGTTTTGTTA<br>TTAATAAAACATATAAATTAAAAAAAGGTTAGTTATTTAAA<br>GTTTATAAATGTTAAGGATAAATTATTAAAANNTGAAGAA<br>AAGGTTGGGAGTTTTGGTTGCCACTAGAAAAAGGTTGAAA<br>AAAAGGTTGGAGGGTTGAAATGAGGTGGAGTAATTTGAT<br>TGGGTATTTAAAGGGAGATGAGAGGGTTGAACCCTCGGCT<br>CCGTCCCCCCTTATAGGACACCTTGTTCATGAGGATACTTT<br>GATATTTTAATGGGGAAATGATAAATTCTTTTAAATTAACC<br>TAAAAATCATTCTAAAACTATAAGAAGATGATATGTGATAT<br>CTACTAATTCTCTTCTCTACTCTCGCCCTTTTTTCACATATAA<br>TCATCTCATTATTAAGAACATTTTTAGGTTATTTAGTTAAAA<br>GAATGAATCATTTCTCATTTTAATATAAATGGTTAATTTGAA<br>TTGACATCAATCACTGGCGAGAAACACAAAGGTAAAAGAG<br>TAGTGAACACGAAGGTAAAAGAGTAGTAAATTACCAATCA<br>TATCCTTCCTCCTTTATATTTTGATGGAACAAACACAAATTT<br>ATTTTAGAATTTTTTAAAAAAATATATTAAACCGGGTAGAA<br>CATAATCATTATTATTGTTACACGAAATTTATTGTACACCGT<br>GTTAGCTGGTTACAGTAGTATTAATTAATTGGTCAAATATA<br>TGTGCATTAAAATCAGGAACACATTTATAACAAACATAGCG<br>AGATTTTAGGAGAACTTTAATTGAAAATTTTACCATTACAG<br>TAATTAATTAACTTAAACACATACAAAACCCTATACATTATT<br>TACATTGTCTACATTTCATTACTGTTGTTGGTTTCTGATCGA<br>ATGCCATGAATTTTCGGGCATTTGATCTGAAGCTCAACATT<br>TTTCTGGGCGATTCAAATAAGCGTTTTACTGTTACAAAAAG<br>TTTCGTCTCAACGGGTGACCACTACACGACTTCTGATAACA |

TABLE 1-continued

ACCase gene sequences isolated from weedy plant species

| SEQ ID NO | SPECIES | TYPE | LENGTH | SEQ |
|---|---|---|---|---|

```
CCAATCCGACCAGTCTTACAAAGGTGAAGGTGAGCGTCAA
TATTTAGTTTAATCTCATCGTCTGTGTTTTAAGCTTTTTTGA
GGTCTAAACCTTTTTGGTCAGCAAAATTTGAAAATTCTTTTA
ATATGTTAACTTCTTTTGGAAGCTTTAGAGATTTATATATTC
TTAATCCATAATAATCTATAATTCTATATTTCTTTACTCCTCT
ATAAAGCATATTGCTTTTTTTATTTTTGGAAATTAAGCATTT
TTTAAAATATTTTCATAATACCCTTACACCCCTACCTTCTTTC
TAATCATTACACGCTCTCCTCGACCTTCTATCACCCTCCGCC
GCCGCCCTCCTTCTCCACCACCGCCCTCGATCTCCACCACCG
CCTCCCTTTTATATTGTCATCGCCTTTTAGCCGTTGCAACGC
GCGGACACTATGCTCGTATTAAAAGTAGTAACGTAATAAA
CATAAAGTTTACGTAAAGTTTATATATTTCATTATTTTGTTA
TGATTTTGTACTGATGAATATATATTTAAGCTAAAATCATTC
ACTCTAGAGTGTAAGTCGAACGGGTCCAAACTGAACTAAA
CTATTTGTCTATGGTAGTCAAATTCTTAATCTTTTTGGTATC
GATCGTTGTGTAGTGTTGCACACCTCACTTGATATTAGTTTT
ATGTGATTATATATGGTTAATTTAATTTTTCTTTGATTTTTG
ATCATGGTCTTAAATATTATTAAAGGTGAAGAAACATGTGA
AGAGGGATAAATTTGGAGAAAGAATGGCATCACTAAAAC
AGATAGTGTCACCCTATGGCAAGGTTAGTCCTTCTTTAAGT
TTATTAATTATATGTAATTTGTTTGATTAGGTATATCATATA
TGTATACTAGTTGTTTTGATTTCCAATCTATACAAGTAGGAT
TTTGCTAAACATAGTTGTAAGGGTTATAGTTACAACACAAT
AGAATGGTATACATACATTATACATATATAAAGATATATAA
CTGTTTATTAATAATAATCTTTAACCGTCATGTAAACCAATT
TACTTTGCTTTATCCATATCCTTAAAGGCTATGAATAGCATA
GTCGATGTAAGTATATGGTTGCTTAGACGGTGTGTTAATGT
TGATCTTACAGGAGTCTAGACTTGGACCATTGTGTTTTAGA
GAAGAAGGGAATCGAACGCAAAGGTAAAACTTCCTTTATT
TTTAAGAGCATAGTTATAATATCATTCAAATTTAACCAACA
ATTTCTGTTACATACATCGAAATAGGCTTGATTACTCATACC
TATAGAGATGAGTGACATGTGTGTATGAAGATTTATATATT
GAATTGTAGGATATCATTTTCCCATTTCTAATGTACTAGTTA
ATTATGGTTTGCGGTTTTTTCTTTGTTGTATGTCCATTACA
AAATTACAGTTGGACATCTTCTTGGTGGAATTCAGATGATA
TAAAATAGTTAATTTTACCAAACACTACATCATTGGTAGAG
AGAAATTAGAACGTAGATAAATGGTTTGTAAGTTTCAAAA
GAGATACTCGTATTACATAAAATGTTGTCTTTTGCAATTCG
CAGATTTCCAATTACAACAGATTTGACACAATGTTCTATTAT
TTGTTAATCCAACCATGAACCACTAATAAAACAGTACAAAC
ATCTTGAATAAAAAAAGCCACCAATACATTATTGATTGTT
GTATGCTTTTTGTCTCCATATAATGACCAGTAATATCAAAA
AACATGTATTTTATTCTTATTCTAGCTTAAAAAGGTTCAAAA
ATGCACATCCAACTTTCTCTCTTCTTTCCAATCATAGCTTTTC
AAATTAAAAGCATACACGTAAAAGAAACATATGGATGTAG
ATTGATATGTGTGGGGGGTAGTTGGTTAACCATGTCAC
GTGCTCTGCATCACCTCCCATCCTTGGACCCCAATTTGTTTT
TTGTACCTACTACATATTTAAGTAACTTTATGGCACCTCACC
AAAAACCAACCAAACAAACCAAACTCCCAACTATACATCAC
TTAATTGCACACACACATATACCTCAACAAGTACTTACATCT
CTCCCAGATTTCTGTCATTCCAATTTTCTTGTTTTTAATCACA
ATTTTGTTGTTGTTGTCAATGTCTGTCTCTTTTCAAACCAGC
TAAAAAAAGAAGCAAATTCTTGATTTGATTCAGCTGTTGTT
CCACTTGTTTATGGTTAGTCTTTCTCATTCTTTCACCCCCCAA
GTTTAAATCTTTGAGTTAATTTCTTCAAATTCCTGTGTTTTTT
GAACCGGGTTTTTATCAGTTTTGTTGAGTTTAGCAAAAAAG
TAGAGTTGGGTATGTAAAGATTGAATCTTTTTACTGGGTTT
ATGTAATTTCTTTGAAATTTATAAGTTTCTTGCAATGGGTAT
ATGATTTTCTATTAATTGAAGTGGTTAATAACAGGATTTGG
TGAGTAAAGTTTGAATCTTTCGAGTTATGGATTTATGTCAT
ACCTTTTCTTGCCCTTCAAAATAAAGTCAAAGCTTTAGTTTT
GTGATTTGACTTTGGTATGCTGTTGCTCCCATGAATATTTTC
ATGCTGTTTGTAAATTGTAATATATATTTTGATAAATTCAAT
TTTGTTATATTTGTTTCCTGATAAAGTTTTAATGTGATTAGT
GATTACTTCAATTTGATGAGTTCAATAATAATAAGAAATTT
AGAACTTTGAACCTCGTATTTCTAATTCGAGGTTTCCTAGCT
CTATGTAAACCCCACTATATTCTCCATTATAACATACGTTTA
TGTGTTACTTTATTTAGACATTTTAATATTTGACTCAATTAT
AACATAGGTTCAGCTGAAAATTTAATTTCTTTGTTAGTGAA
TTGTTGTGACTTTTTTTTTGGTAGTTTGCGTTGTGATAGTC
AGGAGACAGAAAGGGCAATTTGTTTCTGTTCTTTTTAAGTT
AGATAGGTGACCATTTCGGTAGATACTAGATAGTGCAAAG
ATATAGTGTTTTTTGTAAGTACCAAGTACTTTATGAACTTAC
CCAATGATAACAACTTTTGATGGTTCAGTGGTTCAGCCTTC
TCTTTGTCCCTAGACTAATTAGTCCAATCTATCTCTCAGTAT
ATATTTTTTAGGTATTGACATATTTTATGATATTGGCAAGTT
```

TABLE 1-continued

ACCase gene sequences isolated from weedy plant species

| SEQ ID NO | SPECIES | TYPE | LENGTH | SEQ |
|---|---|---|---|---|

```
GGTAGTTTACTTTCAACTTTTAAGCAATATATGGACATATC
CACATATATCAGTTCCATATTACTAGCATGTATCCTATTCTG
GGTTAGTATGCTACAAAAAGGGTTTACATGTCAAATGCAG
AATTGTTCAAAGAAAACGAGTTGTTAGACCTAATAAGTCA
AAGTAATGCTTACTCTACACTTTGCTTACTGTTTGGCAGTG
GCACCATGTCAGAAGCTCAAAGAATGCTTCTAAGTGGAAG
TTTCAATTATTATGGTAATGGCATTGTAAATGGGGCGATTT
CACTGAGGTCTTCTGCTAGTAGATCTGCAATTGATGAATTT
TGTAATGCACTTGGAGGCACCAGGCCAATCCAAAGTATTTT
AATTGCAAATAATGGAATGGCGGCTGTAAAGTTTATAAGA
AGTGTGAGGACATGGAGTTATGAAACATTTGGCTCAGATA
AAGCTATTTTGCTGGTAGCCATGGCTACACCGGAAGATAT
GAGGATAAATGCCGAGCATATTAGAATCGCTGATCAGTTT
GTTGAAGTCCCTGGTGGTACAAATAATAATAATTATGCGA
ATGTGCAACTCATTGTAGAGGTATGTAGCTTATATACGTGG
ATCCTACATCATGATTTATAAGCTTTAAATGATCTATTTTA
TGAAACATTGTGCATTTAATGATGCCTGAAAAGATTATGTT
TCCAAGACTTATTTTGCTTAACTTGTTGGATCAAAATGTTG
ATCTGCTTCCATGAATATAGTAATTCGAATATGTTGGTTTA
ATCTTCACTTTCAAAAAAAAAAAAAAATACTTCTTTTTATGT
TAGCATTTGAGTTTGAATCTCAAGAGAACTTATTTCACTTTT
GAAATCGATATGGATGTGTTGAACATGTAATTGATAATCA
GCAACATTTTAAAATTTATTAGAAAATGACGAGGGATGCCT
CTTCAGGCTACGCGGCGAGCCTTTGGCTCTAATGTAAGCG
GCCTAACCGGTATACCCGGGTCTCTTCTGAGATCTTTGGGT
CACCTTACCACTAGACCCCCTTGGAGAAGGTTTTAAAAAGT
ATTAGAAAGTATATAAATATAAAATAGAAACGATATGTAA
AATTTTAAAAATATGTTTCATTGAGTTATCTTACACCTGACT
ATTTGATATTGAGCATTAATACGAGTTTGATGGAAAATATA
AAATAATTAATATTTAGCTATCATCATCAATTCCTTTAAAAT
GGTTCATTTATGATTTATGACTTCAGACTGCTGAGATAACA
CATGTTGATGCTGTTTGGCCTGGTTGGGGCCATGCATCCG
AAATCCCTGAGCTGCCTGATGCATTGGAAGCAAAAGGTAT
TGTATTTCTTGGGCCACCAGCTTCCTCCATGGCAGCTTTAG
GTGATAAAATTGGTTCTTCTTTGATTGCACAAGCTGCTGAT
GTACCGACACTTCCTTGGAGCGGTTCTCATGTAAGATTTTT
TTTACTATTGTAGTCTTTGTCACATCAACAATGATCCTTATA
CTTTTAACTCCATAAAGATTGCATCGTTCTATCTCATATTCT
CTATAATCTAAAAAAATTCTATATTCCTCTTATTTGTGAAAA
GTCTGAACTTCATAACAAAATCACATCTTGTACCTCTTATAT
ATTAAACTGCATCTTTATGCCTCTAATTTATTGGAAACAAG
ATCTTTAAATCCTTTAAAGGTTGCATCTTTATACCTCTTATTC
TGTAGAAATTACATTTCATACCACTTGTTCTTTGCAATTTCG
CATAGATATTAATGCCTACTCTTTAAAAGATACTTTTCTACT
TCTTTACCTCTATAATCACATCTTTGTACCTTTCACCTCTCCA
GTCTTCTTACTCTCTACAGTCACATTTTTAGGTAAAAATTCC
TGTGGATAGCTGTTTGGACACACTCCCGGATGATGTATATA
GAAAAGCGTGTGCATACAACAGAAGAAGCAATTGCTAG
TTGTCAAGTTGTTGGTTATCCAGCAATGATTAAGGCATCAT
GGGGTGGAGGTGGCAAAGGCATAAGAAAGGTTTGATTCT
TTACAATTGGGAAATTATTTCTTCTCCTCAAAGTATACGGC
AAACTTTTAAAACCAATTACCTATTGAAACTTTAGGTGCAT
AATGACGAAGAAGTCAAGGCACTTTTTAAGCAAGTTCAGG
GTGAAGTGCCTGGTTCCCCTATTTTCATTATGAAAGTTGCT
TCTCAGGTAGGACAATGTTGTAATTGTTATTATTTTCCCAAT
TTCAACTCAAAACCCATTATCATTATAATAATATGTTGATTT
CTTGTATATACAGAGCCGACATCTAGAAGTGCAGCTACTAT
GCGATCAACATGGGAATGTAGCAGCTTTGCATAGTCGTGA
TTGCAGTGTTCAAAGGCGACATCAAAAGGTAAGTTCATGT
TTGTCCTTTTTACTTTCTTTTTATCCTGTTTTGTAACTCTAATT
TTATTTAATACTTGATATGTCAAGATTATTGAAGAGGGGCC
AATAACCATAGCTCCACATGACACAATAAAGAAGCTTGAG
CAAGCGGCGAGAAGATTAGCAAAGTCGGTTAATTATGTTG
GAGCAGCCACTGTAGAGTATTTGTATAGCATGGAAACTGG
AGACTATTACTTTTTGGAGCTCAATCCCCGGTTACAGGTGC
TTGCAATTTCTGTTTTGTGGGTCCTAGTTATGTGTCCTAAGA
AGTAAGATGAAATGGTGGGCTCCAAGATGGTTATGATTTG
TTTTCTGAAGCTATGTATGTGGAACCTTTCTTTAGGTTGAG
CATCCAGTCACAGAGTGGATAGCGGAAATCAATCTACCTG
CAGCACAAGTTGCGGTTGGAATGGGCATTCCTCTTTGGCA
AATACCAGGTTAGATATCAAAAGTTCGTTTTTTGTTGACTA
TCATAGTTGGTCTTTTGCTACAATGCAACCATCATGTCAACT
ATTTTCTTAATTGCTCTACATGCTTGTTGGCTTAGAAATAA
GACGATTTTATGGAATGGACAATAGTGGAGGATACGATGC
TTGGAGGAGAACATCTGCTCTTGCAACTCCATTTGACTTTG
ACAAGGCAGAGTCTATCAGCCCAAAAGGTCATTGTATTGC
```

TABLE 1-continued

ACCase gene sequences isolated from weedy plant species

| SEQ ID NO | SPECIES | TYPE | LENGTH | SEQ |
|---|---|---|---|---|

```
TGTACGTGTAACAAGTGAGGACCCAGATGATGGATTTAAG
CCCACTAGTGGAAAAGTTCAGGTTTGGAAGCAGACTAACA
TATACCATATACCCCTACAAATATAATATATATCCTTTTTTTT
TTTTTTTTACCATATTGATCGAATTCCACTTTTAGGAGCTAA
GTTTTAAAAGCAAGCCAAATGTCTGGGCATACTTTTCTGTC
AAGGTACGCTGGGTTCAAACCTTTTTTTTTTTTTTGAACTT
CCAATTGACATATTCTAAATGTTTGAACATTGCAGTCCGG
AGGAGGCATTCATGAATTCTCAGATTCTCAATTTGGTAAAG
ACGACTGGATCTTGTTTGGTTGAAATATCTTGAATACTCAC
TTATTGGTGTAGTTCAAGTTTACATTCTTGGTCAAAACGTTC
ATGTTCTCATTTTAATTCTGTATCTATCTTAGGCCACGTTTTT
GCATTTGGCGAGTCAAGACCTTTGGCTATTGCAAATATGGT
TCTTGGGCTGAAGGAAATTCAAATTCGTGGCGAGATCCGT
ACGAATGTTGATTATACAATTGATCTGTTACATGTGAGCAT
TTTGGGGTTTCACAGCTAACAAATTTCTTATTTTGTTTACCA
TAATGAGTTACTTCATGGCGATATAAGGGGTGAGCCATGG
AGCAAGTGCCATGTATCTTAACAGATAAATTGTTATGTTCA
TGTTTGGCGAGTACTTACACATTTGAGAATGTCGAGAATTT
GATTATATTTCACCAAACGTTCTTATTGCTTCACCTAAAATG
TGAACGTTTTCTTACATGCTTAGTTTTTATTCCTTTTTCTATA
CTTGTAGGCTCCTGATTATAGAGAAAATAAAATACATACCG
GTTGGTTAGATAGCCGAATTGCTATGAGGGTTAGAGCAGA
AAGGCCCCCTTGGTATCTTTCAGTAGTTGGGGGAGCACTTT
ATGTAAGTACAAAATACCTCTTTCTTTCTATATTCGTCATTT
TTAAAGTACTTTTACTTACCATTGATGTTTGTTAACTTCAGA
AAGCTGCTGCTAGAAGTGCAGCCATGGTCTCGGACTATGT
TGGTTACCTTGAAAAGGGCCAAATCCCTCCTAAGGTTTGTC
AGATATTTAGTATTTTTTTTAATTTTTAAGAGTTGGTTCTC
GTAATGTTTACATTGATGATCAGTATTTGTCTGTTTTCTTAC
TTTCAGCATATATCATTGGTCAACTCACAAGTTTCTTTGAAT
ATTGAGGGCAGCAAATACACGGTAAATAACAAGATAACTG
CCTATCGTTATTCGTTCATAAAAATGGTTGTTCTTGAAGTTT
TCTTTTGTGTGTTTTTTTTCTTCTGATTTTTTTCTTTTTATTTG
TTAGATTGATATGGTAAAAAGAGGGCCAGGAAGTTACAGA
TTGAGAATGAATCAATCCGAGATTGAAGCAGAGATACATA
CACTACGTGACGGAGGCTTATTGATGCAGGTACTTAATCC
ATACGCTCTATTTTTCTTTCTATTTGGTTTATTCTGTCAAATT
TTCTTTTTATTTGGTTTATTCTGTCAAAATTTCTTTTTATTTG
GTTTATTCCGTAGTTAGTTTGTGATTAACTGATTACTATATT
AAGTCATTGGTTGGTATGTATACATATAAAACTCGAATATA
AGCATTTTAATGATGCCAAACCTATATGTAGTTTTACTCTTT
AGGATTTCATGATATACCTAGGAAATCCCTCGTGTCTTTGT
GGCAGCTAGCAAGTTGAAGATTAATAATATCAATAAAGAA
ATTCAGAGAATTTAATGCAGCATGTTCTAAGGGAGTGTTC
GGGGATGCATTCTGAAAATAATTATGTGATATTTAGTAAAA
TTGCAATTAAACGTGGTGCAAGAAATAGTGTTTGGATATG
CTTCTGCTATAAAGTTCTGGCAATCGCTGTATTGAGTGTTT
GACGGATTATGTCTATTTAAGAAGGTGGTAGATAAACTAA
AAGTATACATGGTTAGTGGTGCTGTAAGCATTTGCCATCAA
AAAGTAGGTAGATAAAGGAAGAGTGCTATAAGTAGTTTTA
TGCTACTTTTTGGTTATCGAGTTCGTTGCAGCTAGTATCAA
ACTAATTCTTTAACTATCGTAGCTGTAATAGGTCACCCTGA
ACATTTCAATTTATTGCAACCTTAAGTTACATCATTTGATAA
TCATGTTCAAGACACATTCTTATTTTATACTCTGATATCATA
TGATTTGTGGTTGGTTGATTCAATGATGTAGTTGGATGGG
AATAGTCATATATTATACGCCGAGGAAGAAGCTGCCGGTA
CTCGCTTGCTTATTGATGGACGGACTTGCTTGCTTCAGGTG
CGAACAACTAGTTCTTTTCTTGAACTTTATTTAGAGGTTGCC
ATTTCAACCATTTATCTATGATGGGACAATTTAAACAATGT
TTTACCCTTAATGGTGTATTCAAATGGGTCAACAGTGACCC
AAAGTACATTCTCACTGGAGCAAACTGCCTGTATCATTTTT
TTTTGTGAGGTTCATTGTTTTTGAATAATATTGTGTTAATTT
TCATATTTAGTAGACTAAAGTAATTATGTAAGTTGTTGTGA
ACCCGTTCGATCTGCTCAGGTTATACTCGACCGGTTGCAAT
CCTCCTAATTTGCCACCTTTACTATTACTTACTATTTGGGTT
ACCTGTTTATAGAATGATCATGATCCTTCCAAGTTGATGGC
TGAAACACCATGCAAACTTCTAAGGTACTTGGTCTCAGATG
ATAGCCATGTTAATGCTGACACACCGTATGCTGAGGTTGA
AGTTATGAAGATGTGTATGCCACTCCTTTCACCGGCTGCTG
GAGTTATACAATTCAAGATGTCAGAAGGTCAAGCCATGCA
GGTTAGCATGTCACTTTTTCCCCATTTTTAAGAAGTATTTAC
ATTGTTCAGTTTTTCCGAACATCCAAGAATAAAGCTCTTGG
TTCTATGTTTTTGCCAACTACTTACAGCTATTTATATTTACAT
GTTAATAAAATGTTCTATCGATTGACTTCTTGAGTCATTGT
GCTTATCGCAACTCAATCTTCGTTATTGTACAGTGATTTTTT
AAATGTAATACTGCCAACTTTTTGAATAAATCGTATCAAAT
```

TABLE 1-continued

ACCase gene sequences isolated from weedy plant species

| SEQ ID NO | SPECIES | TYPE | LENGTH | SEQ |
|---|---|---|---|---|

GTAATCTTTAAGCTATATAACAAACATATGAATTTCGATTTC
CAAATAATATCTACAGTTCACAAACAAATGCTTGTTTCCTGT
TTGTTAATACCATTTTTGTCTTCTCTAAATCATACATACCAA
AACCAAAATTGTTGATCATTTCTGATGAATATAAATCTTTGT
ATATGTAGGCTGGTGAGCTTATAGCAAGGCTAGATCTTGA
CGATCCGTCAGCTGTAAGAAAAGCAGAGCCTTTCAATGGA
AACTTTCCTCTTCTTGGGCCTCCAACGGCCATGTCAGACAA
AGTGCATCAGAAGTGTGCTGCAACTTTAAATGCTGCTCGA
ATGATTCTCGCAGGCTATGATCATAACATTGATGAAGTAAC
TTGTTTGCCATTTACTGATTTCAAATTTTCTGAAAGATTATT
CTGTTAACAGTTCTGATCTTTGATCGTAGGTTGTGCAAAAC
TTGCTTCGTTGTCTTGATAGTCCCGAGCTTCCTTTCCTTCAG
TGGCAAGAATGCTTTGCAGTTCTAGCAAATCGTCTCCCTAA
AGATCTAAGAAACAAGGCAAATTGATATTTTACCCTTTTTT
TTTTCTTTTCAAGCAGTTAACATTGGGATTATTTTTCTAAAT
TCAATATGTTTTGTATATTCAGTTGGAATCCAAGTTTAAGG
AGTACGAAGGAATTTCCACACAACAAACTATTGACTTTCCT
GCTAGAGTTCTACGGGTCATTCTTGAAGTTAGTTGTGATCA
GTAGTTTTCTTTATAAGTCCTTTCTTTGATTTAAAGACATAA
TTTAGTTATATGTTACCTTTGTAATGTTTTCGTTCAGACCCA
TCTTGGATCTTGCTCAGAAAAAGAAAAGGGAGCCCAAGAA
AGGCTCGTTGAGCCATTAATGGGTCTTGTAAAGTCATATG
AAGGGGGAAGAGAAAGTCATGCACGTGGGATCGTTCATG
CTCTATTTGATGAATATTTATCTGTTGAAGAGTTGTTCAGC
GACAACATTCAGGTGCGTTTGTTAGGATCGCCGATCCAGT
ATTTTGGATTTTCGATAGGGCATGCACTTGCATTACCATAG
TCAGTTTATATTTTATTTCATCTTGTTACACGACAACAAAGT
ACCTTTTTTCAAAGTATAAAACTGCACAGGTTATGTGCTCC
CAAAGGGTTTTTTAATACTTTGATCTATGTGGAAATGGTAT
AAGAGTTTTAATCATTTTGACATTAATGTCTGGATAAATTT
GTTACGGGTTAAACCAATCAATCTAAGCCAAACCAAAAGTT
ACCTGCAAAAGCTATTACCTAACCCACCCATTTTGCCACCTC
TGTTGGTTTTCTTTAGGTCTACTAATGGTTATCGAGTAAATT
ATATTATAACATAAGTAGTAAACCAAAATCCTGTACCTTTT
AGGCTGATGTAATCGAACGTCTTCGACAACTATACAAGAA
AGATCTCTTGAGGATTGTCGACATTGTCCTTTCCCATCAGG
TACACATGTTTTTTGGTTTTTGTTCTCCCCTTTAATGTGTATT
TTATACCGATCATTAATATATGTCCATGCAGGGTGTTAGGA
GTAAAAACAAATTGATACTACGGCTGATGGAGCATTTGGT
TTACCCCAATCCGGCTGCGTATAGGGAGAAACTGATACGA
TTTTCTCAACTTAACCACACAAGTTATTCTGAGGTCATCATC
GTCATATATATACACTGTTACAATTTTGATCATCTCAATCAC
TTTTCTGTTAGTACTGAGTTTATGTTAATTGATTATTATTAA
TAGTTAGCACTGAAGGCAAGTCAACTTTTAGAACAAACTA
AACTAAGTGAACTTCGTTCAAGCATTGCGCGAAGTCTTTCT
GAATTAGAGATGTTTACTGAAGAAGGTGAAAATATGGATA
CCCCTAAGAGGAAGAGTGCCATTAATGAAAGAATGGAGG
ATATTGTGAGTGCTCCATTGGCAGTTGAAGATGCCCTTGTT
GGTCTTTTTGACCATAGCGATCACACCCTTCAAAGGCGTGT
TGTTGAGACCTATGTTCGAAGATTATATCAGGTTTTTACCTT
TCATTTCTGCATCAACAGAGTTGTCAATTTGTTGTCATAGA
AAATTGAAGGTGTTTGATCAGATTGTTTTAAATAAAATGTG
GTTTAATATATGCATACATCTTTAAAAAAAGAAACGACATG
TATTTATTGGTAAAAAACTAAAACATCAAATCAAGTGTGGA
TTTTATACTGTTTTTTTACAAAACTTTGTAAACTGATTATATG
TTGTTTACTTGAACAGATAAATGTTTTAAACTATTAAGAAT
ATTTAAAAGATGGAATAAGAATAAATTTAAAGTCATTTCTG
AGTTGTGGCCCTTGAGAATAGCTGTTCATGTAGTTAGTAG
ACCTATTTGACTTTTTTCTAAAATGTATACTACACTGTTTATT
AATGCCTACTCAAATGAATCGGGTTGTCTAAAATAAAACAT
CACTTATAACAACAATAAAAGAAGCAAAGCAGTCATTTTA
GTTTGCACTTTTGCAATTCTCTTGGTAGGAAGAAATCTAAT
ATGATTTTAACTGACCATGCTTCTCATATCTGTATCAGCCAT
ATCTCGTGAAGGGGAGTGTTAGAATGCAGTGGCACAGATC
CGGACTCATCGCTACATGGCAATTTATAGAAGGACTCATTG
GAGAAGTTAATGTGCCTGACTATGAACAGAATGAAGCTCC
CTTGGAAGACAAGAAATGGGGAGCTATGGTTATTATTAAA
TCTCTTCAATTTTTGCCTGATGTCATAAGTGCATCTCTTAAA
GAAACGAGTCATAACCTTCCCAGAACAAGTCAGAATGGGT
TTGCTGGTCATAGTAACCATGGTAATATGATGCACATTGCT
TTGGCCGGCATAAATAACCAGATGAGTTTGCTTCAAGACA
GGTATGTGATGATAATGTTACATGAAAAGATACCATCAAA
CCTGCTTTATGATCTTTGTGTCATGCTCAAGAAACAAATA
ACTGGATAAATATAAAAACTGAGACCCATCATCATTCGATG
ATGCATGCCATGTTAACAGTCGGTAGATTTGATGGCTTATT
CATTAGCTGGTGACATATATTTGCCCTGTTGATGTTATGTTC

TABLE 1-continued

ACCase gene sequences isolated from weedy plant species

| SEQ ID NO | SPECIES | TYPE | LENGTH | SEQ |
|---|---|---|---|---|

```
ACTTGTTATGTGATGAACTGTAGTGGTGATGAGGATCAGG
CTCAAGAGAGAGTCAACAGGTTAGCAAAAATACTCAAAGA
TAAAGAAGTAAGCTCGAGTCTTAAAAACGCAGGGTATGGA
GTGATCAGTTGTATAATACAAAGAGATGAAGGGAGAGGC
CCCATGAGACACTCATTTCACTGGTCAGAAGAGAATCATTA
TTATATTGAAGAGCCATTATTGCGTCACTTGGAGCCTCCAT
TATCGACATATCTTGAACTGGTTTGTGCTCAAAAGACCCTT
CATAATTTTTCAATTCATTAATAATATTATAATACTAATGAA
GTTGTAAATGTATTGCTTATGCAGGACAAACTTAAGGGCT
ATGATAATATAAAGTACACTCCGTCGCGTGACCGTCAATG
GCACATGTATACTGTTGATGCTAAACCACTTCCGGTACAAA
GAATGTTTCTTAGAACTCTTATAAGGCATCCAACAAAGGAA
TGGTTCTCGCCCTCAGGTTACCAAGGTTCAGAAGATGAGG
GCCCACGGTCTCAGTTAAATCTCCCTTTTACATCAAGGAGC
ATCTTGAGATCATTAGTGACGGCTATGGAGGAGTTGGAAC
TTCATGTTCATAATGCTACTGTCAAGTCTGACCATGCTCATA
TGTACCTATATGTATTGAAGGAGCAACAAATTGGTGATCTT
GTTCCATACACAACGTAAGTATTCATGTCATCTTCATGAATT
TTTTTTTATCATATGCACTCATTTAACAATGGTAATATGTTG
TGAACAGGAGAGTGGATGTAGATTCTGGGACAGAAGATT
GCGTGGTTGAGACACTTTTGGTAAGGCTGGCTCGTGAAAT
CCATTCAATGGTTGGTGTAAAGATGCACCGGTTGGGAGTT
TTTGAGTGGGAGGTGAAGCTTTGCATGGCATCATCGGGTC
AAGCCAACGGTGCGTGGAGGGTTGTGGTCACAAATGTGA
CTGGTCATACCTGCGTTGTGCATGTAAGTCATTAGATAGGA
TTATAGACATTTCAGCAATACCCCTCAAACATGCTTTTACCT
AAAGTCAATTGCTGCAATTTTGATTTAGGTATATCGTGAAC
TGGAAGATACTGGTTTGCACAAGGTGTATCATGCTACCTCT
ACATTGGGTCCTTTGCATGGCGTACCTGTGAATACACCCTT
TCAGCCTTTAGGATTACTTGATCAGAAGCGTCTTTTGGCAA
GGAAAAGCAATACTACGTACTGCTACGACTTTGCACTGGT
ATAACTATCATTTTGCTCTTTCAATGCTTGATGGTCACCTAA
ATTTGATTGTACAGAAACACTTATTACCATATCTATATTTCC
AGGCATTTGAAGCAGCTCTTGAGAATATCTGGGCGTCGAA
AGTCGTAAGTGATAGCAGGCCTAAGGGTAAACTTGTGAAT
GTGACGGAGCTCATGTTTGCTGAGCCAAGTGGCTCATGGG
GAACTCCCCTTGTTGCAGTAAATCGTGAGCCAGGGCAAAA
CAAGGTGGGCATGGTGGCGTGGACTATGGACCTCTGCACT
CCTGAGTTTCCTGATGGAAGAACGATTTTGGTAGTAGCAA
ACGATGTTACGTTCAAAAATGGATCTTTTGGTCCTCTTGAG
GATGCCTTTTTTGAGGCAGTTACTGATCTCGCTTGTGCCAA
GAAACTGCCACTAATATACTTGGCAGCAAACTCGGGGGCC
CGTATCGGAGCGGCTGAGGAAGTCAGATCTTGCTTTAGAA
TTGGGTGGTCTGATGAGTCGACTCCTGAATCGGGATTCCA
GTATTTGTATCTTACTCCTGAAGATTATACCCACATCAAATC
ATCTGTAATAGCTCATGAGGTTCATCTATCAAATGGCGAAA
CAAGATATGTCATCGATACTATTGTGGGAAAAGAAGACGG
ACTCGGGGTTGAAAATTTGAGTGGTAGCGGGGCAATTGCT
GGTGCCTATTCGAAAGCATATAAGGAAACGTTTACATTAAC
ATATGTTACTGGAAGAACAGTTGGGATAGGCGCATATCTG
GCACGTCTTGGGATGCGGTGCATACAGCGGCTTGATCAAC
CGATTATATTAACGGGTTTTCTGCACTGAACAAGCTTTTG
GGCCGAGAGGTTTATAGCTCACAGATGCAACTAGGTGGGC
CTAAAATTATGGCTACGAATGGTGTTGTCCATTTAACGGTG
TCCGATGATCTCGAAGGTGTCTCAGCTATCTTGAATTGGTT
GAGCTTTGTTCCACCTTATGTCGGTGGCCCACTTCCTGTTTT
AGCACCTGTGGATCCACCAGAAAGGCCCGTTGAGTACCTC
CCTGAAAACTCATGTGATCCTCGGGCAGCTATTTGTGGGG
TCGTGGATAGCAACGGTGAATGGGCTGGTGGGATTTTCGA
TAGAGACAGTTTTGTGGAGACATTGGAAGGTTGGGCGAG
GACAGTCGTAACGGGTCGTGCCAAACTTGGCGGGATCCCA
GTCGGGATCGTTGCTGTTGAGACACAAACAGTGATGCAAG
AAATACCTGCAGATCCCGGGCAGCTTGATTCACACGAACG
TGTTGTTCCTCAAGCAGGTCAGGTCTGGTTCCCGGATTCCG
CCAGCAAAACAGCTCAGGCATTGATGGATTTCAACCGAGA
AGAGCTCCCACTTTTCATCATGGCTAACTGGCGAGGCTTTT
CTGCAGGTCAGCGGGATCTTTTTGAAGGGATTTTACAAGC
AGGGTCAACAATTGTTGAGAATCTCAGAACATATAACCAG
CCTGTTTTTGTATACATCCCGAAAACTGGAGAACTTCGTGG
CGGTGCATGGGTGGTTGTCGACAGTCGAATCAATTCAGAT
CATATAGAAATGTATGCAGAAACCACAGCAAAAGGAAATG
TCCTTGAACCTGAAGGTATGATTGAGATTAAGTTCCGAAAC
AAAGAATTGATAGACTGTATGGGTCGTCTAGATCCACAGA
TTCGAAGCCTTAAAGAAAGACTTCGAGAAACAAAGTACGA
TCAAACGATCGTCCAACAGATAAAATCTCGTGAAAAACAG
CTTTTACCGATTTACACTCAAATTGCTACCAAATTCGCTGAA
```

TABLE 1-continued

ACCase gene sequences isolated from weedy plant species

| SEQ ID NO | SPECIES | TYPE | LENGTH | SEQ |
|---|---|---|---|---|
| | | | | CTTCATGACACATCATTGCGAATGGCTGAAAAAGGTGTGG
TCAAACAAGTTGTTGACTGGAAAGTATCTCGGTTTTTCTTTT
ACAAAAGGCTTCGTCGTAGGCTCGCAGAGGCTTCCTTGAT
CAGTAGTGCTCGTGAAGCTGCTGGTGATACTCTTTCCTACA
AGTCTGCTCATGAGTTGATTAAGAAATGGTTTTTGGAATCG
AAAACTGAAGATTTATGGCTTAGTGATGATGCTTTTTTCAC
TTGGAAAGACAATCTGATGAACTATAATGACAAGTTAGCC
AAGCTACGTACTCAGAAGCTCTTGGATCAGTTATTAAAGAT
TGGTAATTCACCATTGGATCTACAAGCTTTACCACAAGGCC
TCGCCGCACTTTTGCAAGAGGTGAACAAACTCTCTTTTATT
TTCCCTTAGAACTATTTAATTTAATTATCTATGAATGCGCAA
AAACAACAGTTTTATTTAAATATTTTTCTTTCACTATGCTGC
AGGTGGATCCAGTGACCAAAAATAAACTAGTCGAAGAACT
CTTGCGCGTAATTAAGTAGGTAATTATACACAAAGCTCATC
AGATTCTTTCTTTGTTTGTCAAAGTGAGAAGCCTTTTGAGC
AGTGTACATTATAAGTAGGTGTCATAAGAAAACAGGCTCA
AAATAGTTTAAAGTATATGAGGTTTACCATGTTCAGATTGT
TTTATTTTTCTTCATAAATTGTATAATACCATCACATTTCTAT
CGCATTTTTTATATATCTATATATAAATGGTCATTTTTTATTT
TATTTTATTTTTATAAAAGGTTCTCTTTGACCATCTTTGTGTT
TCCTTTTGGCTCTTCTTGTCCATCTTCAGTTCTTCTCCTTCCT
TCGCTTTCTTTTCGTCTCTTGAGTTATCTTTTCTTTATCTTCTC
ATCGTGTACGGATTACGTTGATATGAGCACATATGGCAAA
GTTGATTCAGATAACTCCACAACAAATTTTCACTTGATTTTT
GAATGTTTATAAGCTTACAATACATCCATGCACTCATGTTC
ATCTGCTAAATGTACTAGTACATAATCAAGTTAAAAACTTC
AACCCAAGAACACTATTCCACTAAAAATTTCGGCATGATCT
CATCATAAAATCTACAATCATTGTTTATTGTCAACCATCAAA
GACCTGTAGAATACTAATGAACAATTGCAACAAGTGAACA
GTTTGCCCCTTGTTACCGTTGAATGAATATTTCAAAGATCA
TGATCGAGCCTCGATCTTGACCAGCACTGAAACATTATAAA
AACAACTTCCATTTTAAATGTTTGTCTAATATAGGGAAGTG
AGAGTCAGGTAGCCCACAATGTTTTAGACCCCAGAGCTAC
TTGTTCTGGCTGTGGGGTTAAATATAGTTATATAGACTTAT
GTTAAGTGCAGGCATTACACACTTTTTTGCATTATATGTTTA
CGCGCAGATATATGTATTTGTGACCAGTTAAACCGGTGTG
CTTCTCTTTTCTGTGTAATGAGCTCTGTTATGCAGTTTCGGG
TTTGAGTCGCTTTGTGATAATTTTGTATGTGTTACTGGCCC
GGCCAGATAAATGATCGGTTGATATAGGCTGGTTCTAGTC
ACACTAGACGCTGATTAGTGGTAGGCTTCGATGTATAAAT
CAAAGTTATAGCTACATTCAAATCATTATTATAATTATTTCT
ATTTCATTCAAAGTAGGAAGATTATATCATACATAAATATG
ACACACAGGATGAATTTCATAAACTTCAATTCTACTTTTCAT
TAAAAGCTTAATTTATCTAGTTGCCCGGTTTCCCATTCTTCT
TCCCGTTGCCGCCACCAGGCCTTTTACTCCACCATGGCCAC
CCCCTCCTTCCCCAACCACCAAATGGATATCCACCCCAGAT
ACCTGGCCATCCACCACCTGGCCAAAATCCGCCACCAGGA
AAATATCCACCACCTGGCCAATAACCCCCATAATACGGATA
TGATGGGTCATAGCCCCCTCCATATCCTTTACCTCTTCCTGG
TCCACCGTACCCTCCATATCCATCACCCGAATCATAACCTCC
CCCTCCACCATATCTGCCACCATGATCTTTTCCACGTCCTTC
ATCATAACCACCATCTTCTCCACCATGATCTTTTCCACGTCC
TTCATCGTCGTCCCCTTTGCCTTCATGATCACCATCTTCACC
ACCATGATCTTCTCCAGGTTCATCATCATCATGGTCATCGCC
TTTTCCCCCTTCATCACCATGATCTCTTCCTGGTCCATCTTGT
CCACCACCTTCATGATCACCACCTTCATCACCATGATCTTGT
CCAGGTCCATCATCATCATGGTCACCACCTTTTCCCCCTTCG
CCACCATGATCTCTTCCTGGTCCATCTTGTCCGCCACCTTCA
TGATCACCGCCTTCACCA |
| 50 | Conyza canadensis | gDNA Contig | 17803 | CATAATACTCTTACACCCCTACCTTCTTTCTAATCATTACAC
GCTCTCCTCGACCTTCTATCACCCTCCGCCGCCGCCCTCCTT
CTCCACCACCGCCCTCGATCTCCACCACCGCTCCCTTTTAT
ATTGTCATCGCCTTTTAGCCGTTGCAACGCGCGGACACTAT
GCTCGTATTAAAAGTAGTAACGTAATAAACATAAAGTTTAC
GTAAAGTTTATATATTTCATTATTTTGTTATGATTTTGTACT
GATGAATATATATTTAAGCTAAAATCATTCACTCTAGAGTG
TAAGTCGAACGGGTCCAAACTGAACTAAACTATTTGTCTAT
GGTAGTCAAATTCTTAATCTTTTTGGTATCGATCGTTGTGTA
GTGTTGCACACCTCACTTGATATTAGTTTTATGTGATTATAT
ATGGTTAATTTAATTTTTCTTTGATTTTTTGATCATGGTCTTA
AATATCATTAAAGGTGAAGAAACATGTGAAGAGGGATAA
ATTTGGAGAAAGAATGGCATCACTAAAACAGATAGTGTCA
CCCTATGGCAAGGTTAGTCCTTCTTTAAGTTTATTAATTATA
TGTAATTTGTTTGATTAGGTATATCATATATGTATACTAGTT
GTTTTGATTTCCAATCTATACAAGTAGGATTTTGCTAAACAT |

TABLE 1-continued

ACCase gene sequences isolated from weedy plant species

| SEQ ID NO | SPECIES | TYPE | LENGTH | SEQ |
|---|---|---|---|---|
| | | | | AGTTGTAAGGGTTATAGTTACAACACAATAGAATGGTATA |
| | | | | CATACATTATATATATAAAGATATATAACTGTTTATTAAT |
| | | | | AATAATCTTTAACCGTCATGTAAACCAATTTACTTTGCTTTA |
| | | | | TCCATATCCTTAAAGGCTATGAATAGCATAGTCGATGTAAG |
| | | | | TATATGGTTGCTTAGACGGTGTGTTAATGTTGATCGTACAG |
| | | | | GAGTCTAGACTTGGACCATTGTGTTTTAGAGAAGAAGGGA |
| | | | | ATCGAACGCAAAGGTAAAACTTCCTTTATTTTTAAGAGCAT |
| | | | | AGTTATAATATCATTCAAATTTAACCAACAATTTCTGTTACA |
| | | | | TACATCGAAATAGGCTTGATTACTCATACCTATAGAGATGA |
| | | | | GTGACATGTGTGTATGAAGATTTATATATTGAATTGTAGGA |
| | | | | TATCATTTTCCCATTTCTAATGTACTAGTTAATTATGGTTTG |
| | | | | CGGTTTTTTTCTTTGTTGTATGTCCATTACAAAATTACAGTT |
| | | | | GGACATCTTCTTGGTGGAATTCAGATGATATAAAATAGTTA |
| | | | | ATTTTACCAAACACTACATCATTGGTAGAGAGAAATTAGAA |
| | | | | CGTAGATAAATGGTTTGTAAGTTTCAAAAGAGATACTCGTA |
| | | | | TTACATAAAATGTTGTCTTTTGCAATTCGCAGATTTCCAATT |
| | | | | ACAACAGATTTGACACAATGTTCTATTATTTGTTAATCCAAC |
| | | | | CATGAACCACTAATAAAACAGTACAAACATCTTGAATAAAA |
| | | | | AAAAGCCACCAATACATTATTGATTGTTGTATGCTTTTTGTC |
| | | | | TCCATATAATGACCAGTAATATCAAAAAACATGTATTTTATT |
| | | | | CTTATTCTAGCTTAAAAAGGTTCAAAAATGCACATCCAACT |
| | | | | TTCTCTCTTCTTTCCAATCATAGCTTTTCAAATTAAAAGCAT |
| | | | | ACACGTAAAAGAAACATATGGATGTAGATTGATATGTGTG |
| | | | | TGGGGGGTAGTTGGTTAACCATGTCACGTGCTCTGCATCA |
| | | | | CCTCCCATCCTTGGACCCCAATTTGTTTTTTGTACCTACTAC |
| | | | | ATATTTAAGTAACTTTATGGCACCTCACCAAAAACCAACCA |
| | | | | AACAAACCAAACTCCCAACTATACATCACTTAATTGCACAC |
| | | | | ACACATATACCTCAACAAGTACTTACATCTCTCCCAGATTTC |
| | | | | TGTCATTCCAATTTTCTTGTTTTTAATCACAATTTTGTTGTTG |
| | | | | TTGTCAATGTCTGTCTCTTTTCAAACCAGCTAAAAAAAGAA |
| | | | | GCAAATTCTTGATTTGATTCAGCTGTTGTTCCACTTGTTTAT |
| | | | | GGTTAGTCTTTCTCATTCTTTCACCCCCCAAGTTTAAATCTTT |
| | | | | GAGTTAATTTCTTCAAATTCCTGTGTTTTTTGAACCGGGTTT |
| | | | | TTATCAGTTTTGTTGAGTTTAGCAAAAAAGTAGAGTTGGGT |
| | | | | ATGTAAAGATTGAATCTTTTTACTGGGTTTATGTAATTTCTT |
| | | | | TGAAATTTATAAGTTTCTTGCAATGGGTATATGATTTTCTAT |
| | | | | TGATTGAAGTGGTTAATAACAGGATTTGGTGAGTAAAGTT |
| | | | | TGAATCTTTCGAGTTATGGATTTATGTCATACCTTTTCTTGC |
| | | | | CCTTCAAAATAAAGTCAAAGCTTTAGTTTTGTGATTTGACTT |
| | | | | TGGTATCCCTTCAAAATAAAGTCAAAGCTTTAGTTTTGTGA |
| | | | | TTTGACTTTGGTATGCTGTTGCTCCCATGAATATTTTCATGC |
| | | | | TGTTTGTAAATTGTAATATATATTTTGATAAATTCAATTTTG |
| | | | | TTATATTTGTTTCCTGATAAAGTTTTAATGTGATTAGTGATT |
| | | | | ACTTCAATTTGATGAGTTCAATAATAATAAGAAATTTAGAA |
| | | | | CTTTGAACCTCGTAGTTCTAATTCGAGGTTTCCTAGCTCTAT |
| | | | | GTAAACCCCACTATATTCTCCATTATAACATACGTTTATGTG |
| | | | | TTACTTTATTTAGACATTTTAATATTGACTCAATTATAACAT |
| | | | | AGGTTCAGCTGAAAATTTAATTTCTTTGTTAGTGAATTGTT |
| | | | | GTGACTTTTTTTTTGGTAGTTTGCGTTGTGATAGTCAGGA |
| | | | | GACAGAAAGGGCAATTTGTTTCTGTTCTTTTTAAGTTAGAT |
| | | | | AGGTGACCATTTCGGTAGATACTAGATAGTGCAAAGATAT |
| | | | | AGTGTTTTTTGTAAGTACCAAGTACTTTATGAACTTACCCA |
| | | | | ATGATAACAACTTTTGATGGTTCAGTGGTTCAGCCTTCTCTT |
| | | | | TGTCCCTAGACTAATTAGTCCAATCTATCTCTCAGTATATAT |
| | | | | TTTTTAGGTATTGACATATTTTATGATATTGGCAAGTTGGT |
| | | | | AGTTTACTTTCAACTTTTAAGCAATATATGGACATATCCACA |
| | | | | TATATCAGTTCCATATTACTAGCATGTATCCTATTCTGGGTT |
| | | | | AGTATGCTACAAAAAGGGTTTACATGTCAAATGCAGAATT |
| | | | | GTTCAAAGAAAACGAGTTGTTAGACCTAATAAGTCAAAGT |
| | | | | AATGCTTACTCTACACTTTGCTTACTGTTTGGCAGTGGCAC |
| | | | | CATGTCAGAAGCTCAAAGAATGCTTCTAAGTGGAAGTTTC |
| | | | | AATTATTATGGTAATGGCATTGTAAATGGGGCGATTTCACT |
| | | | | GAGGTCTTCTGCTAGTAGATCTGCAATTGATGAATTTTGTA |
| | | | | ATGCACTTGGAGGCACCAGGCCAATCCAAAGTATTTTAATT |
| | | | | GCAAATAATGGAATGGCGGCTGTAAAGTTTATAAGAAGTG |
| | | | | TGAGGACATGGAGTTATGAAACATTTGGCTCAGATAAAGC |
| | | | | TATTTTGCTGGTAGCCATGGCTACACCGGAAGATATGAGG |
| | | | | ATAAATGCCGAGCATATTAGAATCGCTGATCAGTTTGTTGA |
| | | | | AGTCCCTGGTGGTACAAATAATAATAATTATGCGAATGTGC |
| | | | | AACTCATTGTAGAGGTATGTAGCTTATATACGTGGATCCTA |
| | | | | CATCATGATTTATAAGCTTTAAAATGATCTATTTTATGAAAC |
| | | | | ATTGTGCATTTAATGATGCCTGAAAAGATTATGTTTCCAAG |
| | | | | ACTTATTTTGCTTAACTTGTTGGATCAAATGTTGATCTGCT |
| | | | | TCCATGAATATAGTAATTCGAATATGTTGGTTTAATCTTCAC |
| | | | | TTTCAAAAAAAAAAAAAATACTTTCAACTTTTTATGTTAGC |
| | | | | ATTGAGTTTGAATCTCAAGAGAACTTATTTCACTTTTGAAA |

TABLE 1-continued

ACCase gene sequences isolated from weedy plant species

| SEQ ID NO | SPECIES | TYPE | LENGTH | SEQ |
|---|---|---|---|---|

```
TCGATATGGATGTGTTGAACATGTAATTGATAATCAGCAAC
ATTTTAAAATTTATTAGAAAATGACGAGGGATGCCTCTTCA
GGCTACGCGGCGAGCCTTTGGCTCTAATGTAAGCGGCCTA
ACCGGTATACCCGGGTCTCTTCTGAGATCTTTGGGTCACCT
TACCACTAGACCCCCTTGGAGAAGGTTTTAAAAAGTATTAG
AAAGTATATAAATATAAAATAGAAACGATATGTAAAATTTA
AAAAATATGTTTCATTGAGTTATCTTACACCTGACTATTTGA
TATTGAGCATTAATACGAGTTTGATGGAAAATATAAAATAA
TTAATATTTAGCTATCATCATCAATTCCTTTAAAATGGTTCA
TTTATGATTTATGACTTCAGACTGCTGAGATAACACATGTT
GATGCTGTTTGGCCTGGTTGGGCCATGCATCCGAAATCC
CTGAGCTGCCTGATGCATTGGAAGCAAAAGGTATTGTATT
TCTTGGGCCACCAGCTTCCTCCATGGCAGCTTTAGGTGATA
AAATTGGTTCTTCTTTGATTGCACAAGCTGCTGATGTACCG
ACACTTCCTTGGAGCGGTTCTCATGTAAGATTTTTTTACTA
TTGTAGTCTTTGTCACATCAACAATGATCCTTATACTTTTAA
CTCCATAAAGATTGCATCGTTCTATCTCATATTCTCTATAAT
CTAAAAAAATTCTATATTCCTCTTATTTGTGAAAAGTCTGAA
CTTCATAACAAAATCACATCTTGTACCTCTTATATATTAAAC
TGCATCTTTATGCCTCTAATTTATTGGAAACAAGATCTTTAA
ATCCTTTAAAGGTTGCATCTTTATACCTCTTATTCTGTAGAA
ATTACATTTCATACCACTTGTTCTTTGCAATTTCGCATAGAT
ATTAATGCCTACTCTTTAAAAGATACATTTTCTACTTCTTTA
CCTCTATAATCACATCTTTGTACCTTTCACCTCTCCAGTCTTC
TTACTCTCTACAGTCACATTTTTAGGTAAAAATTCCTGTGGA
TAGCTGTTTGGACACACTCCCGGATGATGTATATAGAAAA
GCGTGTGTGCATACAACAGAAGAAGCAATTGCTAGTTGTC
AAGTTGTTGGTTATCCAGCAATGATTAAGGCATCATGGGG
TGGAGGTGGCAAAGGCATAAGAAAGGTTTGATTCTTTACA
ATTGGGAAATTATTTCTTCTCCTCAAAGTATACGGCAAACT
TTTAAAACCAATTACCTATTGAAACTTTAGGTGCATAATGA
CGAAGAAGTCAAGGCACTTTTTAAGCAAGTTCAGGGTGAA
GTGCCTGGTTCCCCTATTTTCATTATGAAAGTTGCTTCTCAG
GTAGGACAATGTTGTAATTGTTATTATTTTCCCAATTTCAAC
TCAAAACCCATTATCATTATAATAATATGTTGATTTCTTGTA
TATACAGAGCCGACATCTAGAAGTGCAGCTACTATGCGAT
CAACATGGGAATGTAGCAGCTTTGCATAGTCGTGATTGCA
GTGTTCAAAGGCGACATCAAAAGGTAAGTTCATGTTTGTC
CTTTTTACTTTCTTTTTATCCTGTTTTGTAACTCTAATTTTATT
TAATACTTGATATGTCAAGATTATTGAAGAGGGGCCAATA
ACCATAGCTCCACATGACACAATAAAGAAGCTTGAGCAAG
CGGCGAGAAGATTAGCAAAGTCGGTTAATTATGTTGGAGC
AGCCACTGTAGAGTATTTGTATAGCATGGAAACTGGAGAC
TATTACTTTTTGGAGCTCAATCCCCGGTTACAGGTGCTTGC
AATTTCTGTTTTGTGGGTCCTAGTTATGTGTCCTAAGAAGT
AAGATGAAATGGTGGGCTCCAAGATGGTTATGATTTGTTT
TCTGAAGCTATGTATGTGGAACCTTTCTTTAGGTTGAGCAT
CCAGTCACAGAGTGGATAGCGGAAATCAATCTACCTGCAG
CACAAGTTGCGGTTGGAATGGGCATTCCTCTTTGGCAAAT
ACCAGGTTAGATATCAAAAGTTCGTTTTTTGTTGACTATCA
TAGTTGGTCTTTTGCTACAATGCAACCATCATGTCAACTATT
TTCTTAATTTCTCTACATGTCTTGTTGGCTTAGAAATAAGAC
GATTTTATGGAATGGACAATAGTGGAGGATACGATGCTTG
GAGGAGAACATCTGCTCTTGCAACTCCATTTGACTTTGACA
AGGCAGAGTCTATCAGCCCAAAAGGTCATTGTATTGCTGT
ACGTGTAACAAGTGAGGACCCAGATGATGGATTTAAGCCC
ACTAGTGGAAAAGTTCAGGTTTGGAAGCAGACTAACATAT
ACCATATACCCCTACAAATATAATATATATCCTTTTTTTTTT
TTTTTACCATATTGATCGAATTCCACTTTTAGGAGCTAAGTT
TTAAAAGCAAGCCAAATGTCTGGGCATACTTTTCTGTCAAG
GTACGCTGGGTTCAAACCTTTTTTTTTTTTTTGAACTTCCA
ATTGACATATTCTAAAATGTTTGAACATTGCAGTCCGGAGG
AGGCATTCATGAATTCTCAGATTCTCAATTTGGTAAAGACG
ACTGGATCTTGTTTGGTTGAAATATCTTGAATACTCACTTAT
TGGTGTAGTTCAAGTTTACATTCTTGGTCAAAACGTTCATG
TTCTCATTTTAATTCTGTATCTATCTTAGGCCACGTTTTGCA
TTTGGCGAGTCAAGACCTTTGGCTATTGCAAATATGGTTCT
TGGGCTGAAGGAAATTCAAATTCGTGGCGAGATCCGTACG
AATGTTGATTATACAATTGATCTGTTACATGTGAGCATTTT
GGGGTTTCACAGCTAACAAATTTCTTATTTTGTTTACCATAA
TGAGTTACTTCATGCGATATAAGGGGTGAGCCATGGAGC
AAGTGCCATGTATCTTAACAGATAAATTGTTATGTTCATGT
TTGGCGAGTACTTACACATTTGAGAATGTCGAGAATTTGAT
TATATTTCACCAAACGTTCTTATTGCTTCACCTAAAATGTGA
ACGTTTTCTTACATGCTTAGTTTTTATTCCTTTTTCTATACTT
GTAGGCTCCTGATTATAGAGAAAATAAAATACATACCGGT
```

TABLE 1-continued

ACCase gene sequences isolated from weedy plant species

| SEQ ID NO | SPECIES | TYPE | LENGTH | SEQ |
|---|---|---|---|---|

```
TGGTTAGATAGCCGAATTGCTATGAGGGTTAGAGCAGAAA
GGCCCCCTTGGTATCTTTCAGTAGTTGGGGGAGCACTTTAC
GTAAGTACAAAATACCTCTTTCTTTCTATATTCGTCATTTTT
AAAGTACTTTTACTTACCATTGATGTTTGTTAACTTCAGAAA
GCTGCTGCTAGAAGTGCAGCCATGGTCTCGGACTATGTTG
GTTACCTTGAAAAGGGCCAAATCCCTCCTAAGGTTTGTCAG
ATATTTTAGTATTTTTTTTTAATTTTTAAGAGTTGGTTCTCGT
AATGTTTACATTGATGATCAGTATTTGTCTGTTTTCTTACTT
TCAGCATATATCATTGGTCAACTCACAAGTTTCTTTGAATAT
TGAGGGCAGCAAATACACGGTAAATAACAAGATAACTGCC
TATCGTTATTCGTTCATAAAAATGGTTGTTCTTGAAGTTTTC
TTTTGTGTGTTTTTTTTCTTCTGATTTTTTTCTTTTTATTTGTT
AGATTGATATGGTAAAAAGAGGGCCAGGAAGTTACAGATT
GAGAATGAATCAATCCGAGATTGAAGCAGAGATACATACA
CTACGTGACGGAGGCTTATTGATGCAGGTACTTAATCCATA
CGCTCTATTTTTCTTTCTATTTGGTTTATTCTGTCAAATTTTC
TTTTTATTTGGTTTATTCTGTCAAAATTTCTTTTTATTTGGTT
TATTCCGTAGTTAGTTTGTGATTAACTGATTACTATATTAAG
TCATTGGTTGGTATGTATACATATAAAACTCGAATATAAGC
ATTTTAATGATGCCAAACCTATATGTAGTTTTACTCTTTAGG
ATTTCATGATATACCTAGGAAATCCCTCGTGTCTTTGTGGC
AGCTAGCAAGTTGAAGATTAATAATATCAATAAAGAAATT
CAGAGAATTTAATGCAGCATGTTCTAAGGGAGTGTTCGGG
GATGCATTCTGAAAATAATTATGTGATATTTAGTAAAATTG
CAATTAAACGTGGTGCAAGAAATAGTGTTTGGATATGCTT
CTGCTATAAAGTTCTGGCAATCGCTGTATTGAGTGTTTGAC
GGATTATGTCTATTTAAGAAGGTGGTAGATAAACTAAAAG
TATACATGGTTAGTGGTGCTGTAAGCATTTGCCATCAAAAA
GTAGGTAGATAAAGGAAGAGTGCTATAGGTAGTTTTATGC
TACTTTTTGGTTATCGAGTTCGTTGCAGCTAGTATCAAACT
AATTCTTTAACTATCGTAGCTGTAATAGGTCACCCTGAACA
TTTCAATTTATTGCAACCTTAAGTTACATCATTTGATAATCA
CGTTCAAGACACATTCTTATTTTATACTCTGATATCATATGA
TTTGTGGTTGGTTGATTCAATGATGTAGTTGGATGGGAAT
AGTCATATATTATACGCCGAGGAAGAAGCTGCCGGTACTC
GCTTGCTTATTGATGGACGGACTTGCTTGCTTCAGGTGCGA
ACAACTAGTTCTTTTCTTGAACTTTATTTAGAGGTTGCCATT
TCAACCATTTATCTATGATGGGACAATTTAAACAATGTTTT
ACCCTTAATGGTGTATTCAAATGGGTCAACAGTGACCCAAA
GTACATTCTCACTGGAGCAAACTGCCTGTATCATTTTTTTT
GTGAGGTTCATTGTTTTTGAATAATATTGTGTTAATTTTCAT
ATTTAGTAGACTAAAGTAATTATGTAAGTTGTTGTGAACCC
GTTCGATCTGCTCAGGTTATACTCAACCGGTTGCAATCCTC
CTAATTTGCCACCTTTACTATTACTTACTATTTGGGTTACCT
GTTTATAGAATGATCATGATCCTTCCAAGTTGATGGCTGAA
ACACCATGCAAACTTCTAAGGTACTTGGTCTCAGATGATAG
CCATGTTAATGCTGACACACCGTATGCTGAGGTTGAAGTTA
TGAAGATGTGTATGCCACTCCTTTCACCGGCTGCTGGAGTT
ATACAATTCAAGATGTCAGAAGGTCAAGCCATGCAGGTTA
GCATGTCACTTTTTCCCCATTTTTAAGAAGTATTTACATTGT
TCAGTTTTTCCGAACATCCAAGAATAAAGCTCTTGGTTCTA
TGTTTTTGCCAACTACTTACAGCTATTTATATTTACATGTTA
ATAAAATGTTCTATCGATTGACTTCTTGAGTCATTGTGCTTA
TCGCAACTCAATCTTCGTTATTGTACAGTGATTTTTTAAATG
TAATACTGCCAACTTTTTGAATAAATCGTATCAAATGTAATC
TTTAAGCTATATAACAAACATATGAATTTCGATTTCCAAATA
ATATCTACAGTTCACAAACAAATGCTTGTTTCCTGCTTGTTA
ATACCATTTTTGTCTTCTCTAAATCATACATACCAAAACCAA
AATTGTTGATCATTTCTGATGAATATAAATCTTTGTATATGT
AGGCTGGTGAGCTTATAGCAAGGCTAGATCTTGACGATCC
GTCAGCTGTAAGAAAAGCAGAGCCTTTCAATGGAAACTTT
CCTCTTCTTGGGCCTCCAACGGCCATGTCAGACAAAGTGCA
TCAGAAGTGTGCTGCAACTTTAAATGCTGCTCGAATGATTC
TCGCAGGCTATGATCATAACATTGATGAAGTAACTTGTTTG
CCATTTACTGATTTCAAATTTTCTGAAAGATTATTCTGTTAA
CAGTTCTGATCTTTGATCGTAGGTTGTGCAAAACTTGCTTC
GTTGTCTTGATAGTCCCGAGCTTCCTTTCCTTCAGTGGCAA
GAATGCTTTGCAGTTCTAGCAAATCGTCTCCCTAAAGATCT
AAGAAACAAGGCAAATTGATATTTTACCCTTTTTTTTTCTT
TTCAAGCAGTTAACATTGGGATTATTTTTCTAAATTCAATAT
GTTTTGTATATTCAGTTGGAATCCAAGTTTAAGGAGTACGA
AGGAATTTCCACACAACAAACTATTGACTTTCCTGCTAGAG
TTCTACGGGTCATTCTTGAAGTTAGTTGTGATCAGTAGTTT
TCTTTATAAGTCCTTTCTTTGATTTAAAGACATAATTTAGTT
ATATGTTACCTTTGTAATGTTTTCGTTCAGACCCATCTTGGA
TCTTGCTCAGAAAAGAAAAGGGAGCCCAAGAAAGGCTC
```

TABLE 1-continued

ACCase gene sequences isolated from weedy plant species

| SEQ ID NO | SPECIES | TYPE | LENGTH | SEQ |
|---|---|---|---|---|

GTTGAGCCATTAATGGGTCTTGTAAAGTCGTATGAAGGGG
GAAGAGAAAGTCATGCACGTGGGATCGTTCATGCTCTATT
TGATGAATATTTATCTGTTGAAGAGTTGTTCAGCGACAACA
TTCAGGTGCGTTTGTTAGGATCGCCGATCCAGTATTTTGGA
TTTTCGATAGGGCATGCACTTGCATTACCATAGTCAGTTTA
TATTTTATTTCATCTTGTTACACGACAACAAAGTACCTTTTT
TCAAAGTATAAAACTGCACAGGTTATGTGCTCCCAAAGGG
TTTTTTAATACTTTGATCTATGTGGAAATGGTATAAGAGTTT
TAATCATTTTGACATTAATGTCTGGATAAATTTGTTACGGG
TTAAACCAATCAATCTAAGCCAAACCAAAAGTTACCTGCAA
AAGCTATTACCTAACCCACCCATTTTGCCACCTCTGTTGGTT
TTCTTTAGGTCTACTAATGGTTATCGAGTAAATTATATTATA
ACATAAGTAGTAAACCAAAATCCTGTACCTTTTAGGCTGAT
GTAATCGAACGTCTTCGACAACTATACAAGAAAGATCTCTT
GAGGATTGTCGACATTGTCCTTTCCCATCAGGTACACATGT
TTTTTGGTTTTTGTTCTCCCCTTTAATGTGTATTTTATACCGA
TCATTAATATATGTCCATGCAGGGTGTTAGGAGTAAAAAC
AAATTGATACTACGGCTGATGGAGCATTTGGTTTACCCCAA
TCCGGCTGCGTATAGGGAGAAACTGATACGATTTTCTCAA
CTTAACCACACAAGTTATTCTGAGGTCATCATCGTCATATA
TATACACTGTTACAATTTTGATCATCTCAATCACTTTTCTGTT
AGTACTGAGTTTATGTTAATTGATTATTATTAATAGTTAGC
ACTGAAGGCAAGTCAACTTTTAGAACAAACTAAACTAAGT
GAACTTCGTTCAAGCATTGCGCGAAGTCTTTCTGAATTAGA
GATGTTTACTGAAGAAGGTGAAAATATGGATACCCCTAAG
AGGAAGAGTGCCATTAATGAAAGAATGGAGGATATTGTG
AGTGCTCCATTGGCAGTTGAAGATGCCCTTGTTGGTCTTTT
TGACCATAGCGATCACACCCTTCAAAGGCGTGTTGTTGAG
ACCTATGTTCGAAGATTATATCAGGTTTTTACCTTTCATTTC
TGCATCAACAGAGTTGTCAATTTGTTGTCATAGAAAATTAA
AGGTGTTTGATCAGATTGTTTTAAATAAAATGTGGTTTAAT
ATATGCATACATCTTTAAAAAAAGAAACGACATGTATTTAT
TGGTAAAAAACTAAAACATCAAATCAAGTGTGGATTTTATA
CTGTTTTTTACAAAACTTTGTAAACTGATTATATGTTGTTTA
CTTGAACAGATAAATGTTTTAAACTATTAAGAATATTTAAA
AGATGGAATAAGAATAAATTTAAAGTCATTTCTGAGTTGTG
GCCCTTGAGAATAGCTGTTCATGTAGTTAGTAGACCTATTT
GACTTTTTTCTAAAATGTATACTACACTGTTTATTAATGCCT
ACTCAAATGAATCGGGTTGTCTAAAATAAAACATCACTTAT
AACAACAATAAAAGAAGCAAAGCAGTCATTTTAGTTTGCA
CTTTTGCAATTCTCTTGGTAGGAAGAAATCTAATATGATTTT
AACTGACCATGCTTCTCATATCTGTATCAGCCATATCTCGTG
AAGGGGAGTGTTAGAATGCAGTGGCACAGATCCGGACTC
ATCGCTACATGGCAATTTATAGAAGGACTCATTGGAGAAG
TTAATGTGCCTGACTATGAACAGAATGAAGCTCCCTTGGAA
GACAAGAAATGGGGAGCTATGGTTATTATTAAATCTCTTCA
ATTTTTGCCTGATGTCATAAGTGCATCTCTTAAAGAAACGA
GTCATAACCTTCCCAGAACAAGTCAGAATGGGTTTGCTGG
TCATAGTAACCATGGTAATATGATGCACATTGCTTTGGCCG
GCATAAATAACCAGATGAGTTTGCTTCAAGACAGGTATGT
GATGATAATGTTACATGAAAAGATACCATCAAACCTGCTTT
ATGATCTTTGTGTCATGCTCAAGAAACAAAATAACTGGATA
AATATAAAAACTGAGACCCATCATCATTCGATGATGCATGC
CATGTTAACAGTCGGTAGATTTGATGGCTTATTCATTAGCT
GGTGACATATATTTGCCCTGTTGATGTTATGTTCACTTGTTA
TGTGATGAACTGTAGTGGTGATGAGGATCAGGCTCAAGA
GAGAGTCAACAGGTTAGCAAAAATACTCAAAGATAAAGAA
GTAAGCTCGAGTCTTAAAAACGCAGGGTATGGAGTGATCA
GTTGTATAATACAAAGAGATGAAGGGAGAGGCCCCATGA
GACACTCATTTCACTGGTCAGAAGAGAATCATTATTATATT
GAAGAGCCATTATTGCGTCACTTGGAGCCTCCATTATCGAC
ATATCTTGAACTGGTTTGTGCTCAAAAGACCCTTCATAATTT
TTCAATTCATTAATAATATTATAATACCAATGAAGTTGTAAA
TGTATTGCTTATGCAGGACAAACTTAAGGGCTATGATAATA
TAAAGTACACTCCGTCGCGTGACCGTCAATGGCACATGTAT
ACTGTTGATGCTAAACCACTTCCGGTACAAAGAATGTTTCT
TAGAACTCTTATAAGGCATCCAACAAAGGAATGGTTCTCGC
CCTCAGGTTACCAAGGTTCAGAAGATGAGGGCCCACGGTC
TCAGTTAAATCTCCCTTTTACATCAAGGAGCATCTTGAGAT
CATTAGTGACGGCTATGGAGGAGTTGGAACTTCATGTTCA
TAATGCTACTGTCAAGTCTGACCATGCTCATATGTACCTAT
ATGTATTGAAGGAGCAACAAATTGGTGATCTTGTTCCATAC
ACAACGTAAGTATTCATGTCATCTTCATGAATTTTTTTTTAT
CATATGCACTCATTTAACAATGGTAATATGTTGTGAACAGG
AGAGTGGATGTAGATTCTGGGACAGAAGATTGCGTGGTT
GAGACACTTTTGGTAAGGCTGGCTCGTGAAATCCATTCAAT

TABLE 1-continued

ACCase gene sequences isolated from weedy plant species

| SEQ ID NO | SPECIES | TYPE | LENGTH | SEQ |
|---|---|---|---|---|

```
GGTTGGTGTAAAGATGCACCGGTTGGGAGTTTTTGAGTGG
GAGGTGAAGCTTTGCATGGCATCATCGGGTCAAGCCAACG
GTGCGTGGAGGGTTGTGGTCACAAATGTGACTGGTCATAC
CTGCGTTGTGCATGTAAGTCATTAGATAGGATTATAGACAT
TTCAGCAATACCCCTCAAACATGCTTTTACCTAAAGTCAATT
GCTGCAATTTTGATTTAGGTATATCGTGAACTGGAAGATAC
TGGTTTGCACAAGGTGTATCATGCTACCTCTACATTGGGTC
CTTTGCATGGCGTACCTGTGAATACACCCTTTCAGCCTTTA
GGATTACTTGATCAGAAGCGTCTTTTGGCAAGGAAAAGCA
ATACTACGTACTGCTACGACTTTGCACTGGTATAACTATCA
TTTTGCTCTTTCAATGCTTGATGGTCACCTAAATTTGATTGT
ACAGAAACACTTATTACCATATCTATATTTCCAGGCATTTGA
AGCAGCTCTTGAGAATATCTGGGCGTCGAAAGTCGTAAGT
GATAGCAGGCCTAAGGGTAAACTTGTGAATGTGACGGAG
CTCATGTTTGCTGAGCCAAGTGGCTCATGGGGAACTCCCCT
TGTTGCAGTAAATCGTGAGCCAGGGCAAAACAAGGTGGG
CATGGTGGCGTGGACTATGGACCTCTGCACTCCTGAGTTTC
CTGATGGAAGAACGATTTTGGTAGTAGCAAACGATGTTAC
GTTCAAAAATGGATCTTTTGGTCCTCTTGAGGATGCCTTTTT
TGAGGCAGTTACTGATCTCGCTTGTGCCAAGAAACTGCCA
CTAATATACTTGGCAGCAAACTCGGGGGCCCGTATCGGAG
CGGCTGAGGAAGTCAGATCTTGCTTTAGAATTGGGTGGTC
TGATGAGTCGACTCCTGAATCGGGATTCCAGTATTTGTATC
TTACTCCTGAAGATTATACCCACATCAAATCATCTGTAATA
GCTCATGAGGTTCATCTATCAAATGGCGAAACAAGATATG
TCATCGATACTATTGTGGGAAAAGAAGACGGACTCGGGGT
TGAAAATTTGAGTGGTAGCGGGGCAATTGCTGGTGCCTAT
TCGAAAGCATATAAGGAAACGTTTACATTAACATATGTTAC
TGGAAGAACAGTTGGGATAGGCGCATATCTGGCACGTCTT
GGGATGCGGTGCATACAGCGGCTTGATCAACCGATTATAT
TAACGGGTTTTTCTGCACTGAACAAGCTTTTGGGCCGAGA
GGTTTATAGCTCACAGATGCAACTAGGTGGGCCTAAAATT
ATGGCTACGAATGGTGTTGTCCATTTAACGGTGTCCGATG
ATCTCGAAGGTGTCTCAGCTATCTTGAATTGGTTGAGCTTT
GTTCCACCTTATGTCGGTGGCCCACTTCCTGTTTTAGCACCT
GTGGATCCACCAGAAAGGCCCGTTGAGTACCTCCCTGAAA
ACTCATGTGATCCTCGGGCAGCTATTTGTGGGGTCGTGGA
TAGCAACGGTGAATGGGCTGGTGGGATTTTCGATAGAGAC
AGTTTTGTGGAGACATTGGAAGGTTGGGCGAGGACAGTC
GTAACGGGTCGTGCCAAACTTGGCGGGATCCCAGTCGGG
ATCGTTGCTGTTGAGACACAAACAGTGATGCAAGAAATAC
CTGCAGATCCCGGGCAGCTTGATTCACACGAACGTGTTGTT
CCTCAAGCAGGTCAGGTCTGGTTCCCGGATTCCGCCAGCA
AAACAGCTCAGGCATTGATGGATTTCAACCGAGAAGAGCT
CCCACTTTTCATCATGGCTAACTGGCGAGGCTTTTCTGCAG
GTCAGCGGGATCTTTTTGAAGGGATTTTACAAGCAGGGTC
AACAATTGTTGAGAATCTCAGAACATATAACCAGCCTGTTT
TTGTATACATCCCGAAAACTGGAGAACTTCGTGGTGGTGC
ATGGGTGGTTGTCGACAGTCGAATCAATTCAGATCATATA
GAAATGTATGCAGAAACCACAGCAAAAGGAAATGTCCTTG
AACCTGAAGGTATGATTGAGATTAAGTTCCGAAACAAAGA
ATTGATAGACTGTATGGGTCGTCTAGATCCACAGATTCGA
AGCCTTAAAGAAAGACTTCGAGAAACAAAGTACGATCAAA
CGATCGTCCAACAGATAAAATCTCGTGAAAAACAGCTTTTA
CCGATTTACACTCAAATTGCTACCAAATTCGCTGAACTTCAT
GACACATCATTGCGAATGGCTGAAAAAGGTGTGGTCAAAC
AAGTTGTTGACTGGAAAGTATCTCGGTTTTTCTTTTACAAA
AGGCTTCGTCGTAGGCTCGCAGAGGCTTCCTTGATCAGTA
GTGCTCGTGAAGCTGCTGGTGATACTCTTTCCTACAAGTCT
GCTCATGAGTTGATTAAGAAATGGTTTTTGGAATCGAAAA
CTGAAGATTTATGGCTTAGTGATGATGCTTTTTTCACTTGG
AAAGACAATCTGATGAACTATAATGACAAGTTAGCCAAGC
TACGTACTCAGAAGCTCTTGGATCAGTTATTAAAGATTGGT
AATTCACCATTGGATCTACAAGCTTTACCACAAGGCCTCGC
CGCACTTTTGCAAGAGGTGAACAAACTCTCTTTTATTTTCCC
TTAGAACTATTTAATTTAATTATCTATGAATGCGCAAAAAC
AACAGTTTTATTTAAATATTTTTCTTTCACTATGCTGCAGGT
GGATCCAGTGACCAAAAATAAACTAGTCGAAGAACTCTTG
CGCGTAATTAAGTAGGTAATTATACACAAAGCTCATCAGAT
TCTTTCTTTGTTTGTCAAAGTGAGAAGCCTTTTGAGCAGTG
TACATTATAAGTAGGTGTCATAAGAAAACAGGCTCAAAAT
AGTTTAAAGTATATGAGGTTTACCATGTTCAGATTGTTTTA
TTTTTCTTCATAAATTGTATAATACCATCACATTTCTATCGC
ATTTTTTATATATCTATATATAAATGGTCATTTTTTATTTTAT
TTTATTTTTATAAAAGGTTCTCTTTGACCATCTTTGTGTTTCC
TTTTGGCTCTTCTTGTCCATCTTCAGTTCTTCTCCTTCCTTCG
```

TABLE 1-continued

ACCase gene sequences isolated from weedy plant species

| SEQ ID NO | SPECIES | TYPE | LENGTH | SEQ |
|---|---|---|---|---|
| | | | | CTTTCTTTTCGTCTCTTGAGTTATCTTTTCTTTATCTTCTCATC<br>GTGTACGGATTACGTTGATATGAGCACATATGGCAAAGTT<br>GATTCAGATAACTCCACAACAAATTTTCACTTGATTTTTGAA<br>TGTTTATAAGCTTACAATACATCCATGCACTCATGTTCATCT<br>GCTAAATGTACTAGTACATAATCAAGTTAAAAACTTCAACC<br>CAAGAACACTATTCCACTAAAAATTTCGGCATGATCTCATC<br>ATAAAATCTACAATCATTGTTTATTGTCAACCATCAAAGAC<br>CTGTAGAATACTAATGAACAATTGCAACAAGTGAACAGTTT<br>GCCCCTTGTTACTGTTGAATGAATATTTCAAAGATCATGAT<br>CGAGCCTCGATCTTGACCAGCACTGAAACATTATAAAAACA<br>ACTTCCATTTTAAATGTTTGTCTAATATAGGGAAGTGAGAG<br>TCAGGTAGCCCACAATGTTTTAGACCCCAGAGCTACTTGTT<br>CTGGCTGTGGGGTTAAATATAGTTATATAGACTTATGTTAA<br>GTGCAGGCATTACACACTTTTTTGCATTATATGTTTACGCG<br>CAGATATATGTATTTGTGACCAGTTAAACCGGTGTGCTTCT<br>CTTTTCTGTGTAATGAGCTCTGTTATGCAGTTTCGGGTTTG<br>AGTCGCTTTGTGATAATTTTGTATGTGTTACTGGCCCGGCC<br>AGATAAATGATCGGTTGATATAGGCTGGTTCTAGTCACACT<br>AGACGCTGATTAGTGGTTAGGCTTCGATGTATAAATCAAA<br>GTTATAGCTACATTCAAATCATTATTATAATTATTTCTATTTC<br>ATTCAAAGTAGGAAGATTATATCATACATAAATATGACACA<br>GAGGATGAATTTCATAAACTTCAATTCTACTTTTCATTAAAA<br>GCTTAATTTATCTAGTTGCCCGGTTTCCCATTCTTCTTCCCG<br>TTGCCGCCACCAGGCCTTTTACTCCACCATGGCCACCCCCT<br>CCTTCCCCAACCACCAAATGGATATCCACCCCAGATACCTG<br>GCCATCCACCACCTGGCCAAAATCCGCCACCAGGAAAATA<br>TCCACCACCTGGCCAATAACCCCCATAATACGGATATGATG<br>GGTCATAGCCCCCTCCATATCCTTTACCTCTTCCTGGTCCAC<br>CGTACCCTCCATATCCATCACCCGAATCATAACCTCCCCCTC<br>CACCATATCTGCCACCATGATCTTTTCCACGTCCTTCATCAT<br>AACCACCATCTTCTCCACCATGATCTTTTCCACGTCCTTCAT<br>CGTCGTCCCCTTTGCCTTCATGATCACCATCTTCACCACCAT<br>GATCTTCTCCAGGTTCATCATCATCATGGTCATCGCCTTTTC<br>CCCCTTCATCACCATGATCTCTTCCTGGTCCATCTTGTCCAC<br>CACCTTCATGATCACCACCTTCATCACCATGATCTTGTCCAG<br>GTCCATCATCATCATGGTCACCACCTTTTCCCCCTTCGCCAC<br>CATGATCTCTTCCTGGTCCATCTTGTCCGCCACCTTCATGAT<br>CACCGCCTTCACCA |
| 51 | Conyza canadensis | gDNA Contig | 16098 | AGTAGAGTCTAGATTAAAATTTCATATACGATTGATATTAT<br>AAAGTGAATAATAGTAGCCTTGACGAGTCAAAGAGATATC<br>ACAGAGAGATATTAGAATCCGGACATTACTAACGGCATAG<br>GATTAACGGAATTTGTGGTTTTAAAACAGTAATTATCTAAG<br>AAATATGAAACAAGAAGTTATATATTCGAATAAACTTGGAT<br>ACAATAATTTGATTACATGTTAGTTCAACCATAATCAAATA<br>CTCGAAAGTCGTAATACACTACCAATATCTTGATTCATATC<br>ATTTGCATTGACTAAATCACTAAAATCATCATTAAATTACAA<br>CAAAAATATTATGTATTGGACTATTGGGGGTGGGGTGGGG<br>TAGGGTAGGGTAGGGGGTTTGGTTACCCATCTCACGTGGC<br>ATGCATCACCTCTCATATTTATATGCAGGCATACTAAACAAA<br>CCAAATACCCAACAAAAAACACCCATATTTCAGCAATTCCA<br>ACTTTCTTGCAACAACGTTATTATTATTTTATCTTGTAAATT<br>CTTGATTGATTCAACTGCTTTTCCACTTGTTCATGGTTAGTC<br>TTTCTCATTCTTTATATTTTGAAAAAAAGATGATTTTTAGTG<br>ATTAAAGATTGAATCTTTTTTCTAAGTTTATGTCATTTCTTG<br>AAATTTTTGTGCTTCTAGAATTGGGTTACTGTGTTATATGA<br>ATTTAATAAGTAAAAAAGATGATTTTAGTGATTAAAGACTG<br>AATCTTTTTTCTAAGTTTATGTCATTTCTTGAAATTCTTGTGC<br>TTCTTGAACTGGGTTTACTGTGTTATATGAATTTAACAAGT<br>AAAAAAGATGATTTTAGTGATTAAAGATTGAATTATTTTAC<br>TGGGTGTAATGTCATTTCTTAAAATTCTTGTGTTTCTTGAAT<br>TATTATGAATTTAAGTAGTAAGTATACAAAAGATGATTTAC<br>TGGGGTAAAGGTTGAATCATTTTACTGGGTGTTATGTCATT<br>TTGTGAAATACTTGTGATTTTTGAATTGGGTTTACTGGGTT<br>TTATGAATTCAAGTAGTAGTGCAAAAAAATGATGAAGAGG<br>GTGTTGGAAAGATTAACTCATTACTGAATTTAGGAAAGCC<br>AAATAATGAGAGATTAGTGTTTGGCAGAACAAATGAATTT<br>TCTGGGTCTTGAACATAGTTTGAAAAAGCATGCTGGGACA<br>TGTTTTTCCAAAAATGCTATTTTGTAAACAAAATTTCAAACT<br>CCTCCTTTGCAGTTAAAGATTGAATCTTTCTTACCGGGTATA<br>TGTCGTTTCTTGAAATTCGTGTCTTTCTTGAATTGGGTTTAC<br>TGTTTAACGATTAAACTTTGAGACTTTTTACTATGTTTATGT<br>TAATTTCTTTCTCTCAATGTTGTGATTTGACTTTGGAATGCT<br>GTCTAATTAACTATAGTTTTGTTGATTTTGACATTTTTTTG<br>GCATATGGGTATGCATCTTAGGAGGATCTTTTATGTGTTTT<br>GTTGGGTTACATTTGTTTGATAAGATTTTGGATTAATCAAG |

TABLE 1-continued

ACCase gene sequences isolated from weedy plant species

| SEQ ID NO | SPECIES | TYPE | LENGTH | SEQ |
|---|---|---|---|---|

```
TGGACATGATGAAACTTTATGTGATGAAATAATATAAAAAT
CCCAATATAGAATTAAACACAGAATTAAAAAGTAGATATG
ATGCGCACATTCCGCCTTTTTGATCCCACAAGTAACTTTTAG
ATTGGATCACTGACTATAAAATATTCCACATCATTCTATAAA
AAATCAGAATTCTGGATTATAAAATACACATTGGTATCCAT
TTTTTGAAGCACCAAAGTTTGATCCCTTTGTGATACTTCATA
TTCAGTTTCACGTGGTTATTAATTTATTATCTGAAATTGTAA
TTTTCATTTGAATTCGCCTGTTTGATTTACAAAATTTGAGTT
GCAAGTTCTGTTTTTATCCCCCTTAAGTTTGCTTCAAGAAAA
TAGTTAAGATTATTAAAGAAGAAAAAACCCAGTTGTTTGAC
CATTTAGGAATTTAAGTAATGCTGAACTAAACTTTGATTGG
TCTACTTGGCAGTGGAACCATGCCAGAAGCTCAAAGAATG
CCTCTAAATGGAAGCCTTAATCTTGGTAATGGTTATGTAAA
TGGGGCCATTTCATTGAGGTCTTCTGCTAGCAGATCTGCCA
TTGATGAATTTTGTAATGCACTTGGGGGGAATAGGCCAAT
CCATAGTATTTTAATTGCAAACAATGGAATGGCTGCTGTAA
AGTTTATAAGAAGTGTGAGGACATGGAGTTATGAAACGTT
TGGTTCAGAAAAAGCAATTTTGTTGGTAGCCATGGCTACA
CCTGAGGATATGAGGATTAATGCCGAGCATATTAGAATTG
CTGATCAGTTTGTTGAAGTCCCAGGTGGTACAAATAATAAT
AATTATGCTAATGTGCAGCTCATCGTGGAGGTAAGTATGG
ATCCGACACTCGTTTATTTACATACCACTAAGTGACTGACTT
TATGAGCCGGGTCATATTTGGCTTTTTATCGCACATCAGCT
GTAGCTGTTTTGTATATGCCGAAAGACCAGTATATTGGGT
GATCACTATCAATTTTCTTTAGAAGTTTGAGTTTGTGTCTGA
TTATTTCAGACTGCTGAGATAACACATGTTGATGCTGTTTG
GCCTGGTTGGGGTCATGCCTCTGAAATTCCTGAATTACCTG
ATGCATTGGACGCAAAGGGAATTGTATTTCTTGGGCCGCC
GGCTTCATCCATGGCGGCTTTAGGAGACAAAATCGGCTCT
TCTTTAATTGCACAAGCTGCTGACGTGCCAACACTTCCTTG
GAGTGGTTCTCATGTAAAATTTTCCACCATTGTTTTATTACT
TTTACCATTACAGTGAGCTTGACACCTCTTATTTTTCAAAAT
TGGAGATTAATGCCCCTCAGCTATAAGAATTTGGATATTTA
TACCTTCTGATTTCCAACCAACATATCTATGTGTTTTTGAAA
ATCATACGTGTATCTATACCTCTTACTCTTAAATAATCTAAT
CCTTTTTTTTTCTTTGTTCAAAATCACACAAATATGTTGCTCA
TTTGTCAAATTTATATCTTTCAGGTGAAAATTTCTGCAGAG
AGCTGCTTAGACACAATTCCAGATGACGTATATAGAAAAG
CTTGTGTCCATACAACCGAGGAAGCAGTTGCTTCTTGTCAA
GTTATTGGTTATCCTGCTATGATCAAGGCATCATGGGGCG
GTGGTGGCAAAGGCATAAGAAAGGTGTGCTTCCTTACATT
TGAGAATAATTTTTATGTGAAGTTGTCAAAGGTGTAGAAT
GAAGTGATAACACATTAATCTGTAGGTGCATAGTGATGAA
GAAGTCAAGACACTTTTTAAGCAAGTTCAGGGTGAAGTCC
CTGGTTCCCCCATATTTATTATGAAAGTTGCTTCCCAGGTG
AGAAAACATTCTAATATCTTTCTAACCGTAATATGCATTTAT
CATTTTTTCTTTCTAAAAGCATTTTTTGTCATTTATCATTTGT
TGTCGGAAAATAGAGCCGACATCTAGAAGTACAACTCCTC
TGTGATCAGCATGGCAATGTAGCGGCTTTACATAGTCGGG
ATTGCAGTGTTCAAAGGCGGCATCAAAAGGTTCACCCAAT
TCAATTGTTTAATTCATTTTTTCCTTTTTATCTTGTTTTTAATC
TTTTTTTTTTGGATAATTTCAAGATTATCGAGGAGGGGCCA
ATAACCATAGCCCCCCCTGACACAATAAAAAAATTGGAGC
AAGCGGCAAGAAGATTAGCCAAATCGGTCAATTATGTTGG
AGCTGCAACTGTAGAGTATTTGTACAGTATGGAAACCGGA
GATTATTACTTTTTGGAGCTCAATCCCCGTTTACAGGTGCA
AGTGTTTTTTTGGTGCTGTATATTGGAGGACACTAGATGT
GATTCATTCTCAGTCATATCTGACACCTTTTTATTAGGTTGA
GCATCCTGTCACTGAGTGGATAGCGGAAGTTAATCTACCT
GCAGCACAAGTTGCGGTTGGAATGGGCATTCCACTTTGGC
AAATTCCCGGTAATATGTCAGAATAAGCCATAAATGTAATG
AACGGTTGACAATTGTTGGCCATCATACTTGTCTACCTAGC
ACTTGTCATTGAAATTTATAAAAAAGACCTGTCTATTTAGG
AGTATCTTTTGAACCTTTTTTCTTTGCTTTAGAAATAAGAC
GGTTTTATGGAAAGGAAAACGGTGGAGGGTATGATGCTT
GGAGGAGAACATCGGTTCTTGCAACCCCATTTGATTTTGAT
CGCGCCGAGTCAGTTAGGCCGAAGGGTCATTGTGTTGCTG
TACGTGTAACAAGTGAAGATCCGGATGATGGTTTTAAGCC
CACCAGTGGAAAAGTTCAGGTTTTTGAAAAGACTTATGCA
CCCTTACGAAAATACCAAATATTATAAGTATTGATTATATA
GCATACTGATTGACAACTTTTTAGGAGCTAAGTTTTAAAAG
CAAGCCAAACGTATGGGCATACTTTTCTGTCAAGGTACTCT
TGTCTCCCATTTATAGACATTTATGTAACTGCTTGATTGCCA
AACTACATTTTTTTACTTGCTAACACCTTGGACTCTTGCAGT
CTGGAGGAGGCATTCATGAATTCTCAGATTCTCAATTCGGT
AAAGGCCGAATCTTGTTTGGGTTCTGTTTAAATGTTTGAAT
```

TABLE 1-continued

ACCase gene sequences isolated from weedy plant species

| SEQ ID NO | SPECIES | TYPE | LENGTH | SEQ |
|---|---|---|---|---|

```
CTCCAATTGTTAGCGTAGTTAAATTTTATGAGAATCACTGC
CAAGATGTTTTTTTCTCATTTTAGTTTTTTACATACCTCAGGT
CATGTTTTTGCATTTGGAGAGTCAAGAACATTGGCTATTGC
AAATATGGTTCTTGGGCTAAAGGAAATTCAAATTCGTGGC
GAAATGCGCACTAATGTTGATTATACAATTGATTTATTACA
TGTGAGCAACTTGGCCTTCAAAGTTAAATTCGTTTTGATAA
TATTCATTTACTTCAAATAAATTACATTTTTTCTTTGTAATCT
TCAAAATATATAAATTTATAAAGTACACACATCACATTGGG
CGAAGAAAAGTACACTCCATAAAGTTTAGAATTTTTTTAAA
AAAATTTTCATTCTTTTTTCTTATTCTTACACTTATTAGTGTG
AACTTTCACATTCTTGATTTTTCTTTCTTATTTCTGCACATGT
AGGCTCCAGATTATAGAGAAAACAAAATACACACGGGTTG
GTTAGATAGCCGAATTGCGATGCGGGTTAGAGCAGAAAG
GCCTCCTTGGTATCTTTCGGTAGTGGGGGGAGCTCTTTACG
TAAGTCATTTCATATCACAATGTGGTTTCTCTATTACTTATC
ATCTTTTGAAGCACTTCCACTTACCATCGGCTTTTGTCGACC
TCAGAAAGCCGCTGCTAGAAGTGCAGCCATGGCCTCTGAC
TATGTTGGTTATCTTGAAAAGGGGCAAATCCCTCCAAAGG
TATCATGCATTCCGAAATTTAGAACTTGGGTTTTGTTTTTAT
AAAAATTGGTTAAAAGTCGTTATGTTTGTTTTACTTATTAAT
GTTTCATTACTTGCAGCATTTATCACTAGTCAACTCTCAAGT
TACTTTGAATATTGAGGGGAGCAGATACACAGTGAGTAAC
AAGATACACAAGCTACTAGGATTTTTTTTGTGTGTATATTA
ATTCATCTTTTCTGATTCTCGTATTTGTTGTTAGATTGATAT
GGTAAAAAGAGGACCTGGAGGTTATAGATTGAAAATGAA
CCAATCTGAGATTGAAGCAGAAATACATACTCTACGTGAC
GGGGGTTTATTGATGCAGGTATGTAATTCATAATGATTCAT
TTTCGTTTTCTGGGTTTATTTAGAACTGTACAATGTGTATCA
TATAAAATGCATCTTAACATTGGGGTGCATCTGTGAATCAA
AATGATAATCACTATAATGTTACATAAATTGTTACTATTTAA
GAAAAATGGGTATAACTGAATATACCAGAAATTATGTTTTA
CCGATTGATAATCAGTTTTCTTGCAGTTAGTTACAAACTGA
TAGTCGTAGCTGAAATGGGTCACCCAAACACTTGAAAGTG
ATTACTGCGACTTGAAGTTGCATTAATTGGATAATCACTTT
CAAAGCGAATTGTTATATACACCAATAACACAATGATATCT
AACTGGTTGATTTAATGTGGTAGTTGGATGGGAATAGTCA
TATTATATATGCTGAAGAAGAAGCCGCTGGTACTCGTCTCC
TCATTGATGGACGGACATGTTTGCTTCAGGTGCCAACAACT
TTTTTTGTTAACTTTTGCTGTAGTGGTGGCAACATTTACTCA
TCTATTTTTAAATTAGTCAGTTTGAGTCATATTTAAGATCTA
AAGTGTCAAACGGGTTAAATAGAAAAAACTGAAGGAAACT
GGTCAAATAGGCGGTAAGTGGCCTGTGTGTATTCAACACA
CATAACCTTCCAAATTATTTTTGTTGGAAATATATCATTCT
TATATCATATTCGGAGGACTAGTTTACATAAATAATTTTACT
TTTTATACAAAAAGTGTTTGTGTTCAATCCAAAATCAACCC
AACCTGTACTGTACAAAATTACCTGTTTTGACCTGAACCAG
ATCTGTTACCCAGCCTGATGGGATATCTCAATTTGTCACCTT
TACCATATCCTTGCTTGTGTGGATTTTAAGTTTGCATTACTT
CTTTTTAGAATGATCATGATCCTTCCAAGCTGGTGGCCGAA
ACACCATGCAAACTTCTAAGATACTTAGTCTCAGATAGTAG
CCATGTCGATGCTGACACACCTTATGCTGAGGTGGAGGTA
ATGAAGATGTGTATGCCGCTACTTTCGCCGGCTTCTGGAGT
TATACAGTTTAAGATGTCTGAAGGTCAAGCAATGCATGTTA
GCCCTTTTTCTCTATTTTTTATTCCATTTTCGTCTTCTTCAAAT
CATACACCGTGGACCCACGAAACAAAGAAAGTTTATTTATT
TGAGCTGTTATGAATGACTTCATTTGTAGGCTGGTGAGCTA
ATAGCAAGGCTTGATCTTGATGACCCATCAGCAGTAAGAA
AAGCAGAGCCTTTCCATGGAACTTTTCCTCTTCTTGGGTCTT
CAACTGCCATGTCAGATAAAGTTCATCAAAAGTGTGCTACA
ACTCTAAGTGCCGCTCGAATGATTCTTGCAGGCTATGATCA
CGATATTGATGAAGTAATCTTTTCGCCGTATAAGGATTTTA
CAGTTTCAAAAAGAAGTTGTTCTTCTGTTAACAAGTTTAAC
CTTTTATTGTAGGTTGTCAAAAACCTTCTTCGTTGTCTAGAT
AATCCCAAGCTACCTTTCCTCCAGTGGCAAGAATGCTTTGC
AGTTCTAGCCAATCGACTTCCTAAAGATTTAAAAAACAAGG
CAAATTTACATCTTATAATTCTTATCTATTTTTCTTTTCTTTCA
AATTGGAACATTGAAATGTATTTTTCTAATTCTGTTATTTGT
ATATTCAGTTGGAAACAAAATTTAAGGAGTACGAAGGAAT
TTCCACCCAACAAGCTATTGATTTCCCCGCCAAATTATTATG
GGGAATTCTTGAAGTTAGTTTGCGATTAATAATTTTTTTTAT
TATACACATACACTTTTTCATATTTAAAGATGTAATATGGTA
ATGCTATCTGCACAGACACATCTTGAATTGTGCTCGGAAAA
GGAAAGGGGAGCCCAAGAAAGGCTTGCTGAGCCATTAAT
GAGTCTTGTCAAGTCCTATGAAGGTGGCAGAGAGAGTCAT
GCACGTGGGATCGTTCATGCTCTTTTTGAAGCATATTTATC
TGTTGAAGAGCTATTTAGCGACAACATTCAGGTGCGTTTTT
```

TABLE 1-continued

ACCase gene sequences isolated from weedy plant species

| SEQ ID NO | SPECIES | TYPE | LENGTH | SEQ |
|---|---|---|---|---|

```
TTCTGCTGTGTTGATCCATGTTTTTTTTTGGGATTTCTGAT
CGGGCATGTACTACCATAACAGTTCTTTCTATTTTATCTTTT
TACACTACACAGCCCAATTTTTTTCAAGGTTAACACATTCCC
ACCTTAGCTTTAAAAACCTATTTACCTATGACCGGGTCGGC
AAAAGTTATCCCTTTATTTCAAACTTTGAAACTGGTAAAAA
GTCAACCAAAGTGTAGTTATTAATTCATTAAACCCTTTGAA
TTACTTTTCCAAAACTTGGATTATTATAAAATAAAGTTTCTG
GGCAATAGTGTTTCCGGTCAACCAACCTGTTCAAAAAATGA
CATGATTTGACTTGTTTCTGGACATGATATAATGTTTCAGG
CTGATGTAATTGAACGTCTTAGACAACAATACAAGAAGGA
TCTGTCGAGGGTTGTTGACATCGTGATTCACATCAGGTAT
GTTAATTCCACTGTTTTGTATCTTCCATTCTAATTGTTTAAGT
TAACAACCTATTTTATGTCGACACAGGGTGTTAAGACTAAA
AACAAACTGATACTACGACTGATGGAGCATTTGGTTTACCC
TAATCCAGCCGCCTATAGGGAAAATCTGATACGGTTTTCTC
AATTGAACCACACTAGTTATTCTGAGGTCAATATTGTCATT
TGACATACTCATACCAGTTTGAATATTTTTCCGAATCTTTTT
TATGCTAATACTAGTTTGTGTTTCTCATTTCTTGTTAATAGT
TAGCATTGAAGGCAAGTCAGCTGCTAGAACAGACTAAACT
GAGTGAACTTCGTTCAAGCATAGCTAGAAGTCTTTCTGAGT
TAGAGATGTTTACCGAAGAAGGTGAGAATATAGATACCCC
TAAGAGGAAGAGTGCCATTGATGAAAGAATGGAGGATAT
TGTGAGTGCTCCTTTGGCGGTCGAAGATGCCCTTGTTGGTC
TTTTTGATCACAGTGATCACACCCTTCAAAGGCGTGTTGTT
GAGACCTATGTTCGAAGGCTATATCAGGTATTTTTGCTTCT
CTCATATAAAATAATTAATTTGTATCACATAACTGGAGTCT
GCATTATAACTGAAGCAAATTTCTTGGAATGTTATAAAGAT
GAAATCATAGTTATAGTTTCAATTAAAGGCATTATTGGTAA
CACTTACATTGTATGCATCATTTTGGTAGTGTGAGCAGAGT
AGTGATTTTCATGGCAATTAAAAATTAAAATGCTTTGTTTC
ATCTCTTACTGAATTACACTGTTGTTCACAAAACTACTTAAA
TTGATTTTCATCTGAACTTTTTGTGCCAAATACCTTGGTTTT
TCTATCCAGATTTACTTTTGTCTTTTTTACCCAACAAGGCCA
GAGCAATGATCTTGATTTAGGTACACAAGATTCTTGTGTTA
AAGGAGTCCTACATTTGATTAATGATCAACATATTTTTCAA
ATACCACAATTTATATTGTAATACAGGGTGTGTATTTTGAC
TTCAGACCTTTTTCAGCTATTTTTGTAGTAGGCAGAAAGTT
GTTAACTGAATTAATATAAAAATATATATAAAAAGTGAAG
AAATGTGTTTGAGTATTGTAATGTATACTCTATGTTTAGCT
GGCTGGAAATGTTCCACTATCTTGTATATGTCTACTACACT
CTTCATGAATTGCTAAAGAAAAGAATTTTGTGATGTAAATA
TATATTCAGTTATTTACACTTCTTACGGGCCAAAGTCACGT
GAGGTTTACTGACCACTCACTTCATATCTGTTATCAGCCAT
ATCTCGTGAAGAGGAGTGTTAAGATGCAGTGGCACAGATC
CGGACTTATTGCTTCATGGCAATTCATGGAAGGACACGCT
GAAGCTGTTAATGTGTCTGATTATGAAACTATTGATACACA
ATTGGTAGATAAGAAATGGGGAGCTATGGTTATTATTAGA
TCTCTTCAATTTTTACCTGATGTCATAAGTGCAGCTCTTAAA
GAAACTACTTATAAACATCATGGCACAAGTCAAATGGGG
ATGCCAATCCAAGTTATCAAGGTTATATGATGCATATTGCA
TTGGTAGGCATCAACAACCAAATGAGTTTGCTTCAAGACA
GGTATACAATGTTTCATGTTGATCTTATGTATCGAATTTGTA
AAATACCATTTGCTACAAAAAGTTGAAATAAAGCAACTTAT
TGTACCCAAGTTGTTTATGTGTACTGATGCTAGAGTGTCAA
AACAGACAGGTTGGATAGCATGCCTAAACTGATTTGGGTC
AAAACGGGCCAGATTAAATCTGCTCCCATTTGTATTAAAAT
CTTTCTATTTTACAAGTACTTAATGTAATATTGGATGCTTAC
AACGACTATATTATATCCTTTATTAACTTTTAGCTTAGTACA
AACATACATATAATATTCCCTGTATTAACTCTTAGCTAAGTA
CTTAATGTATTTTGGATGCTTACAACAACTATCATATTACCT
GTTTGACCTGTTATCAACTAAGTACAAACATACATATAAAT
GGCTGTGATAACTAGGTGACCAACCTTAAATTACCAAAAA
GGTACTTGTTGTATTTTTCATCAAACTAACCATCTCATGACA
TTATGTCATTATGATATGCCATGGTATAGGGATAAAAATG
GAAAAATGGGCCTAGTATCAGGCCATGATATTTGCCATGT
TTACCAAAGGATAAGTTTGATGGATATAATTTTTTTTCCCC
GATGATCTGAAATTAATGGACATGTTATCTTTTTAACTGCA
GTGGTGATGAGGATCAGGCTCAAGAGAGAGTCAACAAGT
TAGCAAAAATACTCAAAGATAAAGAAATAAGTGTGAAACT
AAAAAATGCAGGATATGAAGTTGTAAGTTGCATAATACAA
AGAGACGAAGGTAGAGGCCCGGTGAGACACTCATTTCACT
GGTCAGAAAAGAATCGTTATTATATCGAAGAGCCATCATT
GCGTCATTTGGAGCCTCCATTATCGATTTATCTTGAACTGG
TTTGTACTCTTAACACGCCTGAATACGTTCTTGATAACGAA
AGAACAATAATTCATAAATGTATTATTTGTTTAGGACAAGC
TTAAGGGCTATGAGAATGTAAAGTACACTCCATCACGTGA
```

TABLE 1-continued

ACCase gene sequences isolated from weedy plant species

| SEQ ID NO | SPECIES | TYPE | LENGTH | SEQ |
|---|---|---|---|---|

```
CCGTCAATGGCACATGTATACTGTTGATGCTAAACCACTTC
CGGTTCAAAGAATGTTTCTTAGAACGCTTGTAAGGCACCC
GACAAAAGAATGGTTCTTGCCCTCAGGATACCAAGATTCG
GAAGTTGTGGACCCACGGTCTCAGTTAACTTTACCTTTTAC
ATCAAGGAGCATCTTGAGATCTTTAGTGACCGCCATGGAG
GAGTTGGAACTTCATGTTCATAATGCTATAGTCAAGTCGGA
CCATGCTCATATGTACCTCTATATATTGAAAGAACAACAAA
TAAATGATCTTGTTCCATATACTAAGTAAGCATTGCCATCCT
CTTTCTGAGACATTATATATGTATGGATAATATTATAATTTC
ACAAGTTGTAAACAGGAGAGTGGATGTAGATTCTGGTAAA
GAAGAAGGTGTGGTTGAGACGCTTTTGGTGAAGTTGGTCC
GTGAACTTCATTCGATGGTTGGGGTAAAGATGCACCGGTT
AGGTGTTTTTGAGTGGGAGGTGAAGCTTTGTATGGTATCA
TCTGGTGAAGCCAACGGTGTTTGGAGGGTGGTGGTCACAA
ATGTGACTGGGCATACCTGCAATGTACATGTAAGTCATTAA
ACGGACTTTTTAGACATTTGACCATACTCGATATCTTTTACC
TACAATGAATTTTTGAAATTTGTATATAGGTGTATCGGGAA
GTAGAAGATACTGTTAAACACAAGGCAGTGTATCATGCTC
CCTCTACATTGGGACCTTTACATGGTGTGCTGGTGAACACA
CCCTTTCAGCCTCTGGGATTACTCGATCAGAAGCGTCTTGT
CGCCAGGAAAAGCAATACTACTTACTGCTACGACTTTGCAC
TGGTAAAATCCCCGTTCTTCCCTTTTAAGTCAGATATGCATT
TGCTATACTATTTTTTACAAAGTACTGGTTCTTATTGATCAT
ACTTGTATGTGCAGGCATTTGAAGCAGCCCTTGAGAATATC
TGGTCATCAAAACTGCCTGGTGTAAGCAGGCCCAAGGGCA
AACTTGTAAATGCGATGGAGCTTGTGTTTGCTGACCGAAG
AGGTTTATGGGGCACTCCACTTGTGCCAGTAACGCGCGAG
CCTGGACAAAATAATGTGGGAATGGTAGCGTGGACTATGG
ACCTCTGCACACCAGAATTTCCTGATGGTAGGACGATTTTA
GTTGTTTCAAATGACGTCACATTTAAAAACGGATCTTTTGG
TCCTATCGAGGATGCGTTTTTTGAGGCAGTCACTGAGCTTG
CTTGTGCCAAAAAACTGCCGCTCATTTACCTGGCGGCAAAC
TCAGGGGCCCGTATCGGGGTGGCCGAAGAGGTCAGATCC
AGCTTTAGAATTGGGTGGTCTGATGAGTCAACTCCCGACTC
CGGCTTTCAGTATTTGTATCTAACTCCCGAAGATTACTCTCG
TTTGGAATCATCAGTAATAGCACATGAAATTCGTCTATCCA
GTGGTGAAACAAGATGGGTCATTGATACTATTGTCGGGAA
AGAGGATGGATTAGGGGTTGAGAATTTGAGTGGTAGTGG
GGCGATTGCTGGGGCTTTTTCGAAGGCATATAAAGAAACT
TTTACTTTAACCTACGTGACTGGAAGAACTGTTGGGATAG
GTGCATATCTGGCCCGTCTTGGGATGCGATGCATACAAAG
GCTTGATCAACCGATTATTTTAACTGGGTTTTCTGCACTAA
ACAAGCTTTTGGGCCGAGAGGTTTATAGTTCGCAGATGCA
ACTTGGTGGACCTAAAATTATGGCCACGAATGGCGTTGTT
CATCAAACTGTATCTGATGATTTGGAAGGTGTCTCGGCTAT
CTTGAACTGGTTGAGCTATGTTCCGCCTTACGTTGGCGGTC
CACTTCCTGTTTTGCCACCCATGGATCCACCAGACAGGCCC
GTCGAGTACCTGCCTGAAAACTCATGTGATCCTAGGGCAG
CCATTTGTGGGACCGTGGATGGTAACGGGAAATGGGTTG
GTGGGATTTTCGACAGAAACAGTTTTGTGGAGACGTTGGA
AGGTTGGGCAAGGACAGTTGTAACAGGTCGGGCGAAACT
CGGTGGAATCCCTGTGGGGGTTGTTGCTGTCGAGACACAA
ACGATGATGCAAGTTATACCTGCGGATCCTGGGCAGCTCG
ATTCACATGAACGTGTAGTTCCTCAAGCTGGGCAGGTCTG
GTTCCCGGATTCTGCTAGTAAGACAGCTCAAGCGCTGATG
GATTTTAATCGAGAAGAGCTCCCCCTTTTCATTATGGCAAA
CTGGCGAGGGTTTTCAGCCGGTCAACGTGACCTTTTTGAA
GGGATTCTACAAGCGGGATCGACAATTGTAGAGAATCTTA
GAACCTATAAACAGCCAGTTTTTGTCTACATTCCAAAAACA
GGTGAGCTTCGAGGTGGTGCATGGGTGGTCGTTGACAGTC
GAATCAATTCAGACCATATAGAAATGTATGCAGAAACAAC
TGCGAAAGGAAATGTTCTTGAACCCGAAGGTATGATTGAA
ATAAAGTTCCGAAATAAAGAGCTGGTAGACTGCATGGGTC
GATTGGACCCACTAATTTGCAATCTAAAAGAAAAACTTAAA
GAAACGAAGCTCGATCAAGCAATCACCCAGCAGATAAAAG
CCCGTGAGAAACAGCTTTTACCAATTTACACTCAAATCGCT
ACAAAGTTTGCTGAACTTCATGACACATCATTCCGAATGGC
TGAAAAAGGTGTTGTCAAAAAGGTTGTTGACTGGGCAATT
TCCCGGTTTTCTTCTACAAAAGACTCCAGCGTAGGCTGGC
CGAGGCTTCTCTAATCAAGAGTGCTCGTGATGCTGCTGGT
GACACGCTTTCACACAAATCTGCTCATGAAATGATCAAAAA
ATGGTTTTTGGACACAAAAAGTGAAGATATGTGGGTGAAT
GACGACGCCTTTTTCACATGGAAAGATGATCCATTGAACTA
TACTAGCAAATTAGCCGATCTACGTACACAGAAGATATCAA
ATCAGTTATTAAAGATTGGCAGTTCACCTTCCGATCTGCAA
GCTTTACCACAGGGACTCGCTGCACTTTTGCAAGAGGTAA
```

TABLE 1-continued

ACCase gene sequences isolated from weedy plant species

| SEQ ID NO | SPECIES | TYPE | LENGTH | SEQ |
|---|---|---|---|---|
| | | | | ACCATAATATCCCGATTACCTGCCGTTTTAAAATTCATAAAT<br>TTCACTGTTTTGTTTAACTTTGTTGTGTTCTTCTATGATGTA<br>GGTGAATCCTGCAGCCAAAAATAAATTGATTGAAGAACTC<br>AGGCGGATAATTGAGTAGGAATCGATAGGTAACTATTATC<br>AAGGAGTTCTTCATTATAAATTTTGCCAGCAGTTTGAGATT<br>TTTCCAGCCAAATGAGAAGCCTTTGAACCTGTGTACATTAA<br>GGTGTTGATAGGGAGATAGAGTAAAGATAGTATAAATTGT<br>AATTAGTGTTCACAAGAACTTTACATTAGAATCATTATATAT<br>CATGGTCAATTCTTTTAACAAACATAATTCAAATTCATATTC<br>TGATATTCATATGTTGAAACAATTGCTTTTCTTTTTGATTTTT<br>TTGTTCTCTTTTCCCTTCGGTTTCTGTTTCTTTACTTTACTTTC<br>TCGTTTGCGTTCTTCTTTTTCCTTTCTCTCAAGTTCTTCTCTTT<br>CCTTTGCTTTTTTCTTCTTTCTTTCGAGTTCTTCTTTTTTCCTT<br>AACTTATCTTTCTCGTGTTTTACCTTCTCTTTCTCGTGTTTTA<br>CCTTCTCTTTCATTTTCTTTTTCATTTTCTTCTTCTCTTTTCGT<br>AGGAGTATCCGCTTGATGATGTTCATACACATTCTTACTTT<br>GGAATTATTGTCTGCAAATGTCAAATCAATAGAGAACTATG<br>TAGATATGCTTTAAATGGCATATACTTCTTTTTGTTTTTGTC<br>AATTATTTATTTATAGGTGCATACATAGTGTTTATCAACATT<br>GTAGGAAATGACAAAAGTTTGTTTTTCAAACGGGCAAACC<br>AGATTCTCGTTGTAATCAACTGTAACAATGTAGGATTGTGT<br>TTGTCCGTCGACCAAATGTTGCAAGTTCGATCAATATCTGT<br>ACGAACGTTTCAATCAACACATCGAAGAATAATTGAATATA<br>ATCCAAGTTAATGTTGAAAAGCAACAAGATAACAATATA<br>AGATTGGTGGTCCTGTTCAGAAAATGGTATTTATGTTTAAC<br>TGTGTATGAAGTAAAACAAACATATGATTGAGATTTTAATT<br>CTCAACATCAATTTCAACACTAACATAAGTTCATTACTAAG<br>ATATAGTTTTCCATTATTAGCTTAGACTTCTGTCATAAAAAA<br>CGGACATCAAGTAAATGTAGAAAAATGTAGCGTCATATGT<br>CTTTACACGGATTCAAACCATTATACAACTTACAAACTGTT<br>GACGGTTATATCATGTGCAATTGTCTAACAGAATCCAAAAG<br>CGTAAAAAAAGAGGCAAAATTGCAGTTTCCTACATTGTTC<br>TCTTTATCTCCAAGCCCTAGTCATTTCATGTATAAACAATCT<br>AACAAACAAGCTTATTCTGTAAAAAATCCAACAATTCTGAT<br>TTCATATATAGGTTGAGTACATATGGGGATTCTAACTAGTG<br>AGTAGTGACTCTAAACTTTAATTCTTCTTGCACTTCACATTT<br>TACTGATGAGGTCAGACCTCATGAGCAGACTTTGATGAAC<br>ATGTATGAACAGCATCTGCAACTGTGAGAAAAATCTTGTTT<br>TCGCCAATCAAGTCAGGGAAATCCGCTGCATATAGCTTGTC<br>TAGGACGAGTTGCCCGGGGTTTGCAAGAACAAGCTGCCAT<br>GTCAATTTAGTTTTTAGTCCTTGAGATGGCATTACAACACA<br>TGCAATTTATTATTTATACACACTTAGAACCATTTGTTAATA<br>AATTGGAGACTGTTTTACTAACCTGAACATCTCTCTTTTGCA<br>AACTTCTGTGTAACTCTTCAAAGGCATGGATTCCACTGGTG<br>TCAATATCAGTAACAGCTGCAATTAGGCAACCATACGTTAG<br>AGAGAAAAGTTTCAATGACCCAAAATGTAAAGGTAACCAT<br>GGTAAAAGCTAGTTTCTTACGCGACATTTCAACTATTAAGA<br>ATTGAATATTTGGTAGGTATGCTGCTTTTAGATTTTCTTCTT<br>CCTCAGTTAGCCATCTCAATATCCTGCAAATAAAGTGCTCG<br>ATTTATTACTTGAAAATGATCTGCTGGATAATCTATATAGTT<br>CAAGATTCTTAAAATAATTCACAGTTTGCAGAAAAAAATGT<br>ACCTTTCTTTGATGTAGTTGGAGTTGGAAA |
| 52 | *Euphorbia heterophylla* | cDNA Contig | 2292 | CCGGAAGGAAAATCTTGATAGTAGCGAACGACGTGACCTT<br>CAAAGCCGGGTCTTTCGGCCCGAGAGAGGATGCATTCTTT<br>TCCGCCATAACCGATCTTGCATGCACCAAAAAGCTCCCTTT<br>AGTCTACCTGGCAGCAAACTCTGGTGCTCGTATAGGTGTT<br>GCCGAGGAAGTCAAGTCTTGCTTTAAAGTCGGTTGGTCAG<br>ATGAGTCATCTCCCGAGCGTGGTTTCCAGTACGTATATTTG<br>ACTCCCGAGGATTATGTAACCATTGGATCATCGGTGATAG<br>CACACGAGCTGAATCAGAATGGAGAAACACGGTGGGTCA<br>TAGATGCCATTGTTGGGAAAGAGGATGGCTTAGGTGTCGA<br>AAATTTATCGGGAAGTGGAGCCATTGCTAGTGCATACTCA<br>AGGGCATATAAGGAAACCTTCACATTGACATACGTAACTG<br>GAAGAACAGTGGGAATCGGTGCTTACCTGGCACGCCTCGG<br>GATGAGATGCATACAACGGCTCGATCAACCGATCATCTTG<br>ACCGGGTTCTCCGCGTTAAACAAACTCCTCGGCCGTGAAG<br>TGTATAGCTCTCACATGCAACTCGGCGGTCCGAAAATTATG<br>GCCACCAATGGGGTAGTCCATCGCACCGTCTCCGATGACC<br>TCGAAGGTATTTCGGAAATCCTGAAATGGCTAAGCTGTATT<br>CCCCCTCAAAGCGGCGGGGCAATTCCGGTATTTCCTTCTCC<br>GGATCCTCCGGAGCGACCCGTGGAGTACTTCCCAGAAACA<br>TCGTGCGACCCGCGGGCGGCCATCTCGGGTACAATGGACG<br>GCAGCGGGAAGAAGTGGCTCGGGGGTATTTTCGACAAAG<br>ACAGCTTCGTGGAGACACTGGAAGGGTGGGCGAGGACCG<br>TGGTGACCGGGCGGGCAAAGCTCGGGGGGATTCCGGTTG |

TABLE 1-continued

ACCase gene sequences isolated from weedy plant species

| SEQ ID NO | SPECIES | TYPE | LENGTH | SEQ |
|---|---|---|---|---|
| | | | | GGATAATAGCCGTCGAGACTCAAACCGTGATGCAAGTGAT
CCCCGCCGACCCGGGCCAGCTGGACTCGCACGAGCGGGTC
GTGCCCCAGGCGGGTCAAGTATGGTTCCCAGATTCGGCGA
ATAAAACCGCCAAGCGATTATGGATTTCAACCGAGAGAA
GCTCCCGCTCTTTATCCTCGCCAACTGGCGAGGCTTCTCGG
GCGGCCAACGAGACCTCTTCGAAGGTATCCTTCAGGCGGG
GTCCACCATAGTGGAAAACTTAAGGACATATAACCAACCG
GTTTTCGTATACATCCCTATGATGGGCGAGCTTCGTGGTGG
GGCCTGGGTTGTTGTGGACAGTCAGATAAATTCTGACCAC
ATCGAGATGTACGCTGATCGGACGGCTAAAGGCAACGTCC
TTGAACCGGAAGGAATAATCGAGATCAAGTTTAGAACAAA
GGAGTTGCTCGATTGCATGAATCGACTCGACCCAAAGCTG
ATATCTTTTAAAACCAAACTAACCGAAGCGAAGAATAGTG
GGACCTACGGGATGGTCGATTCCGTACAACAGCAGATAAA
ATCCCGGGAAAAGCAACTTCTGCCGCTATACACACAAATC
GCCACACGATTCGCCGAGCTTCACGACTCGGCTTTACGAAT
GGCGGCAAAGGGGGTGATTCGAGAAGTTGTCGACTGGGG
GATTTCACGATCTTACTTCTACAAAAGGTTAAGAAGGAGA
ATCGCCGAGGCTTCGTTGGTGAACACCGTGAAAGATGCAG
CGGGTGATAAGCTCCAGCATAAGTCGGCTATGGAGTTGGT
CAAAAACTGGTTTCTGGACTCGAAAGGCGATTGGGAAAAC
GATGAAGCTTTCTATGCTTGGAAGGATAATCCCGCGAATT
ACGAGGAAAAGCTACAGGAGTTACGGGTCCAGAAGGTGT
TGCTTCAGTTAACTAACATTGGCGAGTCTTTGTCGGATTTG
AAAGCTTTACCTCAAGGTCTTGCTGCCCTTCTAAATAAGGT
GGAGCCATCGAGCCGAGGGGCGTTGATCGATGAGCTTCG
GAAGGTGCTTAATTGATTTTCGGTAAGTGTTTCTCGGCTAC
TAAATATGTTTTACTTTGGCTTCAGTCTCTGGGTAGTTTGAA
TCAATAGAAAATGCCAATGTGAAAATACCCAGTAATATATT
TGATAAGTGTAAATGTAACTATTATTATATTTAAGTGAATA
GGGGGAATTAGTTCATATGATTATTGTTGTTATAAACAAAT
CAGAGATAGAGAGCTATATTTATTATTATATTTGCGAAT
TAAAGTTATTAGGAGTAGTATAATTTGGCGGTTGTTGCATT
TTACGTGTAATGATCTGAATGTTGTTTGTTCGTGATTATTG |
| 53 | Euphorbia heterophylla | cDNA Contig | 1338 | TTGACGGGAGGACTTGCTTGCTACAGAATGATCATGATCC
GTCAAAGTTAGTGGCAGAGACGCCATGCAAACTTCTGAGA
TATTTGGTTTCAGATGGTAGTCATATTGAAGCTGATGCTCC
ATATGCAGAGGTTGAAGTTATGAAGATGTGCATGCCTCTT
CTTTCACCTGCTTCTGGAGTTGTCCATTTTAAAATGTCTGAA
GGTCAAGCAATGCAGGCTGGGGAGCTCATTGCAAGGCTT
GATCTTGATGATCCTTCTGCTGTAAGAAGGCAGAACCTTTT
CATGGGAGATTCCCGCTACTTGGCTCTCCTACTGCTATTTCT
GGTAAAGTTCATCAGAGATGTGCTGCAAGTCTAAATGCAG
CCCGTATGATTCTCGCTGGCTACGATCATAATATTGATGAA
GTAGTGCAAAACTTGCTCAATTGCCTTGATAGTCCTGAACT
CCCTTTCCTTCAGTGGCAAGAGTGCTTGTCTGTTCTAGCAA
CTCGCCTTCCCAAGGATCTTAGGAGCGAGTTGGAATCAAA
ATACACAGAGTTTGAAGGAATTTCGAGCTCCCAGAACATT
GACTTCCCTGCCAAACTGTTAAGGGGTGTCCTCGAGGCAC
ACCTGAAATCCTGTCCTGAGAAAGAAAAAGGAGCGTTGGA
AAGGCTTGTTGAACCTTTGATGAGTCTTGTAAAGTCTTATG
AGGGAGGACGTGAGAGTCATGCTCGAGTGATCGTCCAATC
ACTTTTTGAAGAGTATTTATCTGTAGAAGAATTATTTAGTG
ACAACATCCAGGCTGATGTGATTGAACGTCTCAGACTTCAA
TATAAGAAAGACCTTTTGAAGATAGTGGACATTGTCCTTTC
TCATCAGGGTGTTAAGAGTAAAAATAAGCTGATACTACGG
CTCATGGAACAACTTGTTTACCCCAACCCTGCTGCATATAG
GGATAAACTCATTCGGTTCTCTCAGCTTAACCACACCAGCT
ATTCCGAGTTGGCATTGAAGGCAAGTCAACTCCTAGAACA
AACCAAACTGAGTGAACTCCGTTCCACTATTGCTAGAAGCC
TTTCGGAATTGGAGATGTTTACCGAGGATGGTGAAAATAT
GGATACTCCCAAAAGGAAAAGTGCCATTAATGAACGTATG
GAGGATCTTGTGAGTGCTCCTTTGGCTGTTGAAGATGCTTT
AGTGGGTCTTTTCGAGCACAGTGATCACACCCTTCAAAGG
CGAGTGGTGGAAACTTATGTTCGTAGGCTATATCAGCCCT
ATCTGGTCAAAGGTAGTGTCAGGATGCAGTGGCATAGATT
TGGTCTTATTGCTACATGGGAATTCTTGGGAGAGCATATCGG |
| 54 | Euphorbia heterophylla | cDNA Contig | 1250 | TAATATGATGCACATAGCATTGGTAGGCATCAATAATCAG
ATGAGCTTACTACAGATAGTGGTGATGAGGATCAGGCAC
AAGAGAGAATTAACAAGTTAGCCAAGATTCTCAAAGAACA
GGAACTAGGTTCCAGTTTGAGCTTGTCAGGCGTTGGAGTT
ATTAGCTGTATCATACAGAGGGATGAAGGGAGAGCCCCTA
TGAGGCACTCCTTTCACTGGTCAGAGGAAAAGCTTTATATG
AGGAAGAACCTCTATTGCGACATTTGGAACCTCCACTATCC |

TABLE 1-continued

ACCase gene sequences isolated from weedy plant species

| SEQ ID NO | SPECIES | TYPE | LENGTH | SEQ |
|---|---|---|---|---|
| | | | | ATCTACCTTGAACTGGACAAACTTAAAGGCTATGACAATAG<br>ACAATATACTCAGTCAAGGGACAGACAATGGCACATGTAC<br>ACTGTTGTAGACAAACCAGTTCCAATCCAGAGGATGTTTCT<br>AAGAACCCTTGTGAGACAGCCCACAAGTACTTCATATCAA<br>GGTCTTGGCGCCGAAGCACCCAATGTGCAGTGGGCCATGT<br>CCTTTACGTCAAAGAGCATTTTGAGGTCCTTAGTAGCTGCA<br>ATGGAGGAACTGGAGCTTCACGTGCACACTGTCAAATCTG<br>ACCATGCTCATATGTACCTCTGCATATTGAGGGAGCAACG<br>GATAGAAGATCTTGTTCCATACACGAAGAAAACCGATGTA<br>GATGCCAACCAAGAAGAGCTGCGGTAGCAAGAATCTTG<br>GAAGAACTAGCGAGGAAGATACATGCGTCGGTTGGAGTC<br>AGAATGCATAGGTTAAATGTTTGCGAGTGGGAAGTGAAGC<br>TATGGATGACATCATCTGGACAGGCAAATGGTGCTTGGAG<br>AGTTGTCACAACAAATGTGACTGGGCATACCTGTGCTGTG<br>CATATATATCGGGAACTTGGGGACGACAGCAAACACGAAG<br>TGGTTTACCATTCGATCTCTCCAAGAGGCCCACTGCATAGC<br>ATGCCAGTGAATGCTGTTTATCAGCCCTTGGGAGTTCTCGA<br>TCGAAAACGTTTGTTGGCAAGGAAGAGCAACACCACTTAC<br>TGCTATGATTTTCCACTGGCGTTTGAGACAGCCATCGAACA<br>ATTATGGGAATCTCAATCACCAGGGACTGAAAGAAGCAAA<br>GAAAACGTCCTAAAAGTCTCGGAGCTTGTTTTTGCCGATCA<br>GAAAGGTACCTGGGGAACTCCACTTGTTCATGCAGAACGG<br>CCAGCTGGGCTTAATGACGTGGGCATGGTAGCATGGTGCA<br>TGGAAATGTTCACCCCGGAATGCCCTTCCGGAAGGAAATC<br>TTG |
| 55 | Euphorbia heterophylla | cDNA Contig | 959 | TCGCTCATAATCGCTTGATCGCAGTCCTATTCGAGTTCAATT<br>TTTTTGAGATTCCGCTTATATTTTCAGAATGTTGGAGACAC<br>AGAGGAGGCAGCCGTTAGCAGTAGGGGTTACTCGTGGGA<br>ATGATTTCACCAATGGTGTGCTTACGATGAGAAGCCCTGCT<br>ACAATATCAGAAGTAGATCAATTTTGCCGTGCTCTTGGAG<br>GAAAGAGACCGATCCACAGTATATTAATTGCAAACAATGG<br>AATGGCAGCTGTCAAGTTTATACGAAGTGTTAGGACATGG<br>GCTTATGAAACTTTTGGCACTGAAAAGGCTATCTTGTTGGT<br>GGCCATGGCAACTCCAGAAGACATGAGGATCAATGCAGA<br>GCATATTAGAATAGCTGATCAGTTTGTGGAAGTTCCTGGG<br>GGGACAAACAATAACAATTATGCCAATGTGCAACTCATTGT<br>TGAGATGGCAGAGGTCACCCATGTTGATGCAGTTTGGCCT<br>GGTTGGGGACATGCATCTGAAAACCCAGAGCTTCCAGATG<br>CACTAACTGCAAAGGGAATCGTATTTCTTGGGCCCCCAGCT<br>GCGTCCATGGGAGCTTTGGGTGATAAAATTGGATCCTCTTT<br>GATTGCGCAAGCAGCAGATGTTCCTACTCTTCCATGGAGT<br>GGCTCTCATGTGAAAATTCCTCCAGAAAGTTGTTTGATTAC<br>CATCCCCGATGACATATATAGAGAAGCATGTGTTCACACAA<br>CAGAGGAAGCTATTGCAAGCTGCCAAGTTGTTGGTTACCC<br>TGCTATGATAAAGGCATCATGGGGCGGTGGTGGTAAAGG<br>CATAAGAAAGGTTCATAATGATGATGAAGTTAGGGCATTG<br>TTTAAACAAGTTCAGGGTGAAGTTCCAGGATCACCCATATT<br>TATAATGAAGGTTGCTTCCCAGAGTCGACATTTAGAAGTCC<br>AATTGCTCTGCGATCAATATGGAAATGTAG |
| 56 | Euphorbia heterophylla | cDNA Contig | 935 | CCAATTACCGTTGCACCATTGGTGACTGTAAAAAAACTAGA<br>GCAGGCAGCTCGAAGGTTAGCGAAATCTGTGAATTATGTG<br>GGCGCTGCTACTGTTGAGTATTTGTACAGTATGGAAACTG<br>GCGAGTACTATTTTCTAGAGCTCAACCCTCGGTTACAGGTG<br>GAGCATCCTGTCACAGAGTGGATTGCTGAAATAAATTTGC<br>CTGCTGCCCAAGTAGCTGTTGGGATGGGAATTCCTCTGTG<br>GCAAATTCCTGAGATTAGGCGATTTTATGGAATGGAACAT<br>GGTGGAGGATATGATGCTTGGAGGAAAACTTCAGTGGCT<br>GCTACGCCTTTTGATTTTGACAAGGTAGACTCTACAAAGCC<br>AAAAGGTCATTGTGTAGCTGTACGTGTGACAAGTGAGGAT<br>CCAGATGACGGTTTCAAGCCTACTAGTGGAAAAGTACTGG<br>AGCTGAGTTTTAAAAGCAAGCCAAATGTGTGGGCTTATTTC<br>TCTGTGAAGTCTGGTGGAGGCATTCATGAATTCTCAGATTC<br>ACAATTTGGACATGTTTTTGCATTTGGGGAGTCCAGAGCTT<br>TGGCAATAGCTAATATGGTTCTTGGGCTGAAGGAAATACA<br>GATAAGAGGAGAAATCCGCACCAATGTTGACTACTCTGTT<br>GACCTTTTACATGCTTCAGATTATAGGGAAAATAAAATTCA<br>CACAGGTTGGTTGGACAGTAGAATAGCTATGAGGGTTAGA<br>GCAGAAAGACCTCCTTGGTACCTCTCTGTTGTTGGAGGGG<br>CACTATATAAAGCATCTGCTAGCAGCGCAGCTATGGTTTCT<br>GATTATGTTGGTACCTTGAAAAGGGCAAATCCCTCCCAA<br>GCACATATCACTTGTGAACTCTCAAGTTTCATTGAACATCG<br>AAGGAAGCAAATATACGATTGACATGGTTAGAGGGGGGC<br>CAGGGAG |

TABLE 1-continued

ACCase gene sequences isolated from weedy plant species

| SEQ ID NO | SPECIES | TYPE | LENGTH | SEQ |
|---|---|---|---|---|
| 57 | Euphorbia heterophylla | gDNA Contig | 12503 | TTTTCAGGTTTGTTTGTTTCGATTTTCCGATTGTGTTTTTGA GTCGCTGTTGCTTGATTTCTGCTGCTGTTACTGCTGGTTGA CTCTTCTAGTGTGTTGATTGAGATTTGTTAGTTTGATTCGAC TTCGATTTTGGAATCGGATTTTTGAACTTGGAGTTGTAAGT GTTTTGAAGCGTGTTTTTCGGCGTTTTAGTTGCGTTTTTCTT ATGGATCCGATTCTTTTATATGAATGCGGCGTTTGGCGCTG AGCAACATGAATTGGAATAAACTTGTGGTATTTTGCTCTTT TTCTATATATTAGTCTAATTCAACTTCGATTATGGAATCTGA TTTTTGAATTTGGAGTATATGTAGTATATTTAAACATGTTTT TCGGTGTTATCATTGTGTATTTTTTATGGATCCTGTGCATCG GAGATGCGTTTATATGAATACTGTGTTTGGTGCTGAGCAA CATAAATTGGATTATACTTGTCGAAAATAATTCTCGTAATA AGGTTCAAGGTATCTAGAAGTCTACCTGAAGTGATATAGT GGACCATGCGGATTTGATTCTTTGAGTTGTTTTTCTTCAAGT CAAAGATCCTGTTATATTTAATTATTTCTTTTGATTTATGAA ATGAGTAATTAAGCAAGTGGTATGCTCAATTCGTTGAAAAT ATTATGTATTGAAAAGGATTTGAAGGTTACGAACTGGATTT TCAACTCGAATGAGTTTTTTTTTGTGCAGAATGTTGGAGAC ACAGAGGAGGCAGCCGTTAGCAGTAGGGGTTACTCGTGG GAATGATTTCACCAATGGTGTGCTTACGATGAGAAGCCCT GCTACAATATCAGAAGTAGATCAATTTTGCCGTGCTCTTGG AGGAAAGAGACCGATCCACAGTATATTAATTGCAAACAAT GGAATGGCAGCTGTCAAGTTTATACGAAGTGTTAGGACAT GGGCTTATGAAACTTTTGGCACTGAAAAGGCTATCTTGTTG GTGGCCATGGCAACTCCAGAAGACATGAGGATCAATGCAG AGCATATTAGAATAGCTGATCAGTTTGTGGAAGTTCCTGG GGGGACAAACAATAACAATTATGCCAATGTGCAACTCATT GTTGAGGTGTGTAAGTTCATAACCTTTTAGCATATTGGATA GCTTATGTTGTGTTAGTCTAAAGTTCGATAATTCTAAGCAT ATAATGATATTAAATGTGTTTAAGGATTTCTCAGTAATAGG AATTTGTAAATCTTTTCTGTCAATGGGTTTTACAGAAATTCA TAAATTATAATGTAATCTAGAAGCTTTGAAATTGTATTTTTG CACATCTCAGAAGATTATGAAGTAATAGGCTGGTATACAG TGAATTTCATTATTGCAAGATATTGTTGTTATGTGCTCACTC AAGAGCATTCTTTTCAATTTGGCAATGTGAAAAGGTTCAGT TAGAAATATCACTTGTTACCCTTGTTGTTTGCATAACTAAGT TTGATTTTGTGTCCAGATGGCAGAGGTCACCCATGTTGATG CAGTTTGGCCTGGTTGGGGACATGCATCTGAAAACCCAGA GCTTCCAGATGCACTAACTGCAAAGGGAATCGTATTTCTTG GGCCCCCAGCTGCGTCCATGGGAGCTTTGGGTGATAAAAT TGGATCCTCTTTGATTGCGCAAGCAGCAGATGTTCCTACTC TTCCATGGAGTGGCTCTCATGTAAGTAATGCTCTTCTCAAG CTGTTCTTTCATTTTCTGTAGTCATTCCAATCTAAGATATCA TGATCTTCCTTATAGGTGAAAATTCCTCCAGAAAGTTGTTT GATTACCATCCCCGATGACATATATAGAGAAGCATGTGTTC ACACAACAGAGGAAGCTATTGCAAGCTGCCAAGTTGTTGG TTACCCTGCTATGATAAAGGCATCATGGGGCGGTGGTGGT AAAGGCATAAGAAAGGTTTGGCTTCGATATAACAAATTTC CGAGTGTAGTGTTCAAGTCTGTAGTGTACGATGGCTGAGT TTTGTTTTCTTGGATTATCTAGGTTCATAATGATGATGAAGT TAGGGCATTGTTTAAACAAGTTCAGGGTGAAGTTCCAGGA TCACCCATATTTATAATGAAGGTTGCTTCCCAGGTTAGGAT ATTATCTAGCTTCTAATTTGATACAAGAGATTTTACTTTGTG ATTCTTGACGCGTGAATCGAATTCTGATGATCTATTTGATTT TCCTTATGTAGAGTCGACATTTAGAAGTCCAATTGCTCTGC GATCAATATGGAAATGTAGCAGCTTTGCATAGCCGTGATT GTAGTGTTCAAAGGCGGCATCAAAAGGCATGTTTATTTCTC TCAAGTAATTTTGATTTTGTCTGCTTAGTGAAATTGACCAT GAAAGTATAAGCTTAGTGTGAAGAGCCTGAGGCTCTGACC ACATGCATGTTGAGAATGAGCCAGTGACTTTTAATCAGTG GCTCAACCATTAATTTCTCCCCTTCCAAATTTCAACTGTTTG TACATCTATCTAGTATCTACTACATGGGTTATGCATTTCAAA AAAGGCCTAACTTGTGTTGAGATGTGAAACAGATAATTGA GGAGGGTCCAATTACCGTTGCACCATTGGTGACTGTAAAA AAACTAGAGCAGGCAGCTCGAAGGTTAGCGAAATCTGTGA ATTATGTGGGCGCTGCTACTGTTGAGTATTTGTACAGTATG GAAACTGGCGAGTACTATTTTCTAGAGCTCAACCCTCGGTT ACAGGTATAAATGAATATAGTTTGTAGGGATGTGAAGTTG TTATGCTCTATAGTAGTAATGATATCTAAAATGCTTAAATTT TATGTTGCTCAATTGATGACAATTGGATAAACCGTATTCAC TTGGGAAAAACCATCCTGAATATAGTTCGTACCTCATTCAC CTTGCGTACTACTGATATTGATCCTATGAATCTGTTTTTTAA AATATCTTTGTTTCTGTAATAAATTGTTCTTTGACTTTTCTAA TGATCTTTAATCTACATCCTAATCTGGATGTAGGTGGAGCA TCCTGTCACAGAGTGGATTGCTGAAATAAATTTGCCTGCTG CCCAAGTAGCTGTTGGGATGGGAATTCCTCTGTGGCAAAT |

TABLE 1-continued

ACCase gene sequences isolated from weedy plant species

| SEQ ID NO | SPECIES | TYPE | LENGTH | SEQ |
|---|---|---|---|---|

```
TCCTGGTATGACCGCAAAAGTTGGAAATTCGCATTCTCTTG
CTCATTAGACATGTTTCTTTGACATTCTGTTCATTTTTATTCA
GAGATTAGGCGATTTTATGGAATGGAACATGGTGGAGGA
TATGATGCTTGGAGGAAAACTTCAGTGGCTGCTACGCCTTT
TGATTTTGACAAGGTAGACTCTACAAAGCCAAAAGGTCATT
GTGTAGCTGTACGTGTGACAAGTGAGGATCCAGATGACG
GTTTCAAGCCTACTAGTGGAAAAGTACTGGTAAGGTTTTCA
GGTTGACTATTCTAATTTGAATTTCCTTCTATTCCAAAATTC
CTTATCCTGTAATGAACTTGTACTTTTATTGTCTTGCACAGG
AGCTGAGTTTTAAAAGCAAGCCAAATGTGTGGGCTTATTTC
TCTGTGAAGGTGACTTTTTGCTGCTCTCTTTCTTTGGAACAT
GTTTATGTTGACACAATTGGTTTCTGACTTAATAACTTCATT
CTGATTTGTAGTCTGGTGGAGGCATTCATGAATTCTCAGAT
TCACAATTTGGTAAGTAATAATTGCTAAATAATCACACTTC
ATGGATAATAATGAAAGAAGTTTGTGAGATGAGTTATCC
AATCTGCTGCAAATTAATGGTTCTTTTTTATCTTCTTGTGAC
ATTTTTTTTAACAAAAGCTACAGTCTGCTTTTCAGTTTAGTC
TTTTCCGTTTGTTACATTTGCTATCGAAAGCACTCATGATTG
TCGTAATCTTTCCTTAGGACATGTTTTTGCATTTGGGGAGT
CCAGAGCTTTGGCAATAGCTAATATGGTTCTTGGGCTGAA
GGAAATACAGATAAGAGGAGAAATCCGCACCAATGTTGAC
TACTCTGTTGACCTTTTACATGTAAACTATCTTAGCTGTTGA
TGTTCCCTTTATACATCATGTAAACTTTCACGAGGAACATG
AACACGAGTTGACATGCTATGCAGGCTTCAGATTATAGGG
AAAATAAAATTCACACAGGTTGGTTGGACAGTAGAATAGC
TATGAGGGTTAGAGCAGAAAGACCTCCTTGGTACCTCTCT
GTTGTTGGAGGGGCACTATATGTAAGTTGTCACGATTTCAC
ATGAGAGGATGACTGTATACTTTTGGAATGCTTTATTATGT
CTTTCAGAACTTGCCACTTAAGTGTTCAATTTTTTGTTTGCA
CCAGAAAGCATCTGCTAGCAGCGCAGCTATGGTTTCTGATT
ATGTTGGTTACCTTGAAAAGGGCCAAATCCCTCCCAAGGTA
CATCAAAAGTATATTTGTACAATTGTATATGTTTCTTATTCA
GCCGATTATGTTGATGTTGATGTTGATGTTAGTTGATCTTG
TTTTCAGCACATATCACTTGTGAACTCTCAAGTTTCATTGAA
CATCGAAGGAAGCAAATATACGGTATGGTACCTTTCATATT
AGTATCTTAAATGAATAAATTTTAGTTTGGTGATGGATGCC
ATTTACGTTTGTAAAATCATTGCTAGATTGACATGGTTAGA
GGGGGGCCAGGGAGCTATAGATTGAGGATGAATGGATCG
GAGATAGAGGCAGAAATTCATACACTGCGTGATGGAGGTT
TATTGATGCAGGCAAGTTGACTCATTAACCATGGCTGTTGT
AAACTAATAATTTTCGTCCTTTTTATCATTTAATATTTGCTTT
AGTCGACCCTCCATGCTTTGGAGACCATAACAGACTCTATT
CTGTTTCTTCACAGTTAGACGGAAACAGTCATGTAATATAT
GCTGAAGAAGAAGCAGCCGGAACTCGCCTTCTAATTGACG
GGAGGACTTGCTTGCTACAGAATGATCATGATCCGTCAAA
GTTAGTGGCAGAGACACCATGCAAACTTCTGAGATATTTG
GTTTCAGATGGTAGTCATATTGAAGCTGATGCTCCATATGC
AGAGGTTGAAGTTATGAAGATGTGCATGCCTCTTCTTTCAC
CTGCTTCTGGAGTTGTCCATTTTAAAATGTCTGAAGGTCAA
GCAATGCAGGTGTGTTTGATTTCACAAACACGTGCTTTTGG
GCTTGATAAGTACTTTTTAGTTTTATATGAATAGTCAGTTTT
GATGTGAATCTAAGAAGTTTTCATGTAGGCTGGGGAGCTC
ATTGCAAGGCTTGATCTTGATGATCCTTCTGCTGTAAGAAA
GGCAGAGCCTTTTCATGGGAGATTCCCGCTACTTGGCTCTC
CGACTGCTATTTCTGGTAAAGTTCATCAGAGATGTGCTGCA
AGTTTGAATGCAGCCCGTATGATTCTTGCTGGCTATGATCA
TAATATTGATGAAGTAAGTTGCAAGCTGGCTAGTTTCAACA
TGAACTTAATTGATGAATTAATTGTTCATTCTATATTTTGTT
GATTGTGTAATTTCATAACAAAATAATGAACTATGCATTTG
GTTTATTATACTGACAATTATTTGTTGAAATCTGATGTAATA
TCTCAATGACATCTATAGGTAGTGCAAAACTTGCTCAATTG
CCTTGACAGTCCTGAACTCCCTTTCCTTCAGTGGCAAGAGT
GCTTGTCTGTTCTAGCAACTCGCCTTCCCAAGGATCTTAGA
AGCGAGGTGAATAATTTTCTGTAATTTTTTCATGACCACA
TAGTCTTCTTGCTCACAATTTGATATTGGCAATTTGTATAGT
TGGAATCAAAATACACAGAGTTTGAAGGAATTTCAAGCTC
CCAGAACATTGACTTCCCTGCCAAACTGTTAAGGGGTGTCC
TCGAGGTGGGTTCCTTATTGCATGGCTCTCTTGGAATTTCT
CATTATCTGTTTTTTTTGCTGTTTAATGAGATGTGTATGCTT
TTCCTCCAGGCACACCTGAAATCCTGTCCTGAGAAAGAAAA
AGGGAGCCCTGGAAAGGCTTGTTGAACCTTTGATGAGTCTT
GTAAAGTCTTATGAGGGAGGACGTGAGAGTCATGCTCGA
GTGATCGTCCAATCACTTTTTGAAGAGTATTTATCTGTAGA
AGAATTATTTAGTGACAACATCCAGGTTAGCTTCTTCCTAT
CAAACATAATATGGAATTATTTTGGATTCTGAAAGTCTTCC
CTCTTTGGCATCTTTTAGAAAAATTAAGCATAATACTAGGTA
```

TABLE 1-continued

ACCase gene sequences isolated from weedy plant species

| SEQ ID NO | SPECIES | TYPE | LENGTH | SEQ |
|---|---|---|---|---|

```
CTATATCCATTATTCTTTATAATCATGAAATTTAATTTTTACA
GAAGAAAAGTGGAATTTCTATATATATTTAAACCAAGCTG
GCAAGCTTTGAATTCAATCCTGTTGTTTATTGTTTTATCCAA
CATGCCAAAAATATTAGGAACTTCATGTGACTACTTGTATC
ATTCTTATTCTGTAATTACAGTAAAGTAACTTGTCATATCCT
AATGTTATAACTCGTAACATTCTTCTTTAGGCTGATGTGATT
GAACGTCTCAGACTTCAATATAAGAAAGACCTTTTGAAGAT
AGTGGACATTGTCCTTTCTCATCAGGTATCTGATTTTCGGTT
TTAATTTTTATCTCGGGTTTTCTAAAATAGAATTCTGAGTTT
GTGGAAATAACTACCGTATTTGTTGGTTTATAGGGTGTTAA
GAGTAAAAATAAGCTGATACTACGGCTCATGGAACAACTT
GTTTACCCCAACCCTGCTGCATATAGGGATAAACTCATTCG
GTTCTCTCAGCTTAACCACACCAGCTATTCCGAGGTTGGCA
GCTATACTTGGTCCATCTGTAATTTCATAAAGTTGTTGCTCT
GTTTCCTTTTGTTCACAAGTTCATTTTTGAGAGTTTTCCATA
GGATGGTGACTGACAGGAAGAGGATTCTAATGTTTTCTCT
TGGAGGATTTTTTCTGTATTTTCATTTCTTGTCGGTCATTGA
TTAATTCCGTTTCTGGTATCAGTATCATCAAAATGTTGTCTT
TTTCTGTATACTGATGCTGAATTATGTGAACAGTTGGCATT
GAAGGCAAGTCAACTCCTAGAACAAACCAAACTGAGTGAA
CTCCGTTCCACTATTGCTAGAAGCCTTTCGGAATTGGAGAT
GTTTACCGAGGATGGTGAAAATATGGATACTCCCAAAAGG
AAAAGTGCCATTAATGAACGTATGGAGGATCTTGTGAGTG
CTCCTTTGGCTGTTGAAGATGCTTTAGTGGGTCTTTTCGAG
CACAGTGATCACACCCTTCAAAGGCGAGTGGTGGAAACTT
ATGTTCGTAGGCTATATCAGGTACTGTGTTGTAGAAACTTA
AAACTTTTATCTGGTGATCAAACACTAGACGAAACTTGATC
TTGATCAACTGTTTGTCTACCGCACCAGCCCTATCTGGTCA
AAGGTAGTGTCAGGATGCAGTGGCATAGATTTGGTCTTAT
TGCTACATGGGAATTCTTGGGAGAGCATATCGGGAGAAAG
AATGGATCTGAAGGTCAAATGTCAGATGAACCAGAGGCTA
AAAAACAGTCTAATAAGAGATGGGGAGCAATGGTTATCAT
CAGATCTCTGCAGTTTTTGCCTTCAGTTATTGGTGCTGCATT
AAGGGAAACAAATCAAAGCCTTAATGAGTCCATTCCAAGT
GGATTAGTAAAATCAGCGAGCTTTGGTAATATGATGCACA
TAGCATTGGTAGGCATCAATAATCAGATGAGCTTACTACA
GGATAGGTAACTTCCTTCGGTACTATAAATATAAGCGTTTAT
TTTAATCATAAAAATTAGTAGCATTTTACATTCTATTATTCA
TTGTAAGATCTCAAGTCTTCTTAATCATTTCTGCATTTGAAA
CCTTGATAGATCTGGATAGATTCCTTATTTTTGTTTAAAATT
TATGATAGAGTTACCTGGTCTCGAACCCTTAAAACATGCAC
ATATATTGGCTTGCCAAACATAAGTTATTTTGCGTTGTCAA
TTTCGATTATTGACGGTCAGCTTGTTAATGCTCCTAACTGG
CACCATCTATGACATTTTGCAGTGGTGATGAGGATCAGGC
ACAAGAGAGAATTAACAAGTTAGCCAAAATTCTCAAAGAA
CAGGAACTAGGTTCCAGTTTGAGCTTGTCAGGCGTTGGAG
TTATTAGCTGTATCATACAGAGGGATGAAGGGAGAGCCCC
TATGAGGCACTCCTTTCACTGGTCAGAGGAAAAGCTTTATT
ATGAGGAAGAACCTCTATTGCGACATTTGGAACCTCCACTA
TCCATCTACCTTGAACTGGTTTGTCACCTATCGCAGTGTTTC
AATACATTTTTTTGGCAGAAACCTTTATTGAGCCCCTGAAC
TTACCAGTTTTATTCTCAAGTTATTATTTGACTACATTAAAT
ACTTAATTACTATTGATTCCACATTATGACCTTGCAATATAA
TTACAAGTGTTACGTTTTATTGATAAAATTATAACTGTTGCT
ATTTTGTTTTACATATATCAAGGACTGCACTATAGTAAAAA
AATGAGGACTCGATAGGATTGGAAAGTTCAGGGGCTTACT
AATTGTTTGAGCGGAAAAAAATATATATAAATGTGAAATT
GGATAATTCTATATCATTCATCTGAAGCTTATTATGGCCTTT
TTTTGATCCAGGACAAACTTAAAGGCTATGACAATAGACA
ATATACTCAGTCAAGGGACAGACAATGGCACATGTACACT
GTTGTAGACAAACCAGTTCCAATCCAGAGGATGTTTCTAAG
AACCCTTGTGAGACAGCCCACAAGTACTTCATATCAAGGTC
TTGGCGCCGAAGCACCCAATGTGCAGTGGGCCATGTCCTT
TACGTCAAAGAGCATTTTGAGGTCCTTAGTAGCTGCAATG
GAGGAACTGGAGCTTCACGTGCACACTGTCAAATCTGACC
ATGCTCATATGTACCTCTGCATATTGAGGGAGCAACGGAT
AGAAGATCTTGTTCCATACACGAAGTAATTATATCAATCTT
TATGATTTATTGTGTACTTGGCACCATAACTTTATGTGTACT
CACTATGAGACTCCATCTCCAGGAAAACCGATGTAGATGC
CAACCAAGAAGAAGCTGCGGTAGCAAGAATCTTGGAAGA
ACTAGCGAGGAAGATACATGCGTCGGTTGGAGTCAGAAT
GCATAGGTTAAATGTTTGCGAGTGGGAAGTGAAGCTATGG
ATGACATCATCTGGACAGGCAAATGGTGCTTGGAGAGTTG
TCACAACAAATGTGACTGGGCATACCTGTGCTGTGCATGT
AAGTATCTGCGCATCTTATTTCAAGAAAATGTCTTTCCCTTC
CATGCATTCCTTATTAGTCGACTTAGTAATGGGGAATGTCG
```

TABLE 1-continued

ACCase gene sequences isolated from weedy plant species

| SEQ ID NO | SPECIES | TYPE | LENGTH | SEQ |
|---|---|---|---|---|

```
AGAAGTGTTGGATGGTTACCAATGTGAGTACCATCACTGT
TTAGATTAAAATTGACCATTGCTTTAGCAATACAATAATGA
ATCTAATTGTGGCATGGGAGGCTTTTCTATGTGTGATCCAT
GGAAAAACTTGTATATAGTTCCTTAGTAGGTTTGAGTTGTT
TTCATTTTTCTTTTATCACATTGTAATTGTATTGGTGATTGAT
ACGAAAATTAGATATATCGGGAACTTGGGGACGAGAGCA
AACATGAAGTGGTGTACCATTCAATCTCTCCAAGAGGCCCA
CTGCATAGCATGCCAGTGAATGCTGTTTATCAGCCCTTGGG
AGTTCTCGATCGAAAACGTTTGTTGGCAAGGAAGAGCAAC
ACCACTTACTGCTATGATTTTCCACTGGTTAGTATTTCTATA
ATCATTAATCAAACATCAGTTTTTTATTGGGGATAATTAA
AATCAAATAATTTTTCCTGGCCTCATCCTTTTCAGGCGTTCG
AGACAGCCATCGAACAATTATGGGAATCTCAATCACCAGG
GACTGAAAGAAACAAAGAAAAAGTCCTAAAAGTCTCGGA
GCTTGTTTTTGCCGATCAGAAAGGTACCTGGGGAACTCCA
CTTGTTCATGCAGAACGGCCAGCTGGGCTTAACGACGTGG
GCATGGTAGCATGGTGCATGGAAATGTTCACCCCGGAATG
CCCTTCCGGAAGGAAAATCTTGATAGTAGCGAACGACGTG
ACCTTCAAAGCCGGGTCTTTCGGCCCGAGAGAGGATGCAT
TCTTTTCCGCCATAACCGATCTTGCATGCACCAAAAAGCTC
CCTTTAGTCTACCTGGCAGCAAACTCTGGTGCTCGTATAGG
TGTTGCCGAGGAAGTCAAGTCTTGCTTTAAAGTCGGTTGG
TCAGATGAGTCATCTCCCGAGCGTGGTTTCCAGTACGTATA
TTTGACTCCCGAGGATTATGTAACCATTGGATCATCGGTGA
TAGCACACGAGCTGAATCAGAATGGAGAAACACGGTGGG
TCATAGATGCCATTGTTGGGAAAGAGGATGGCTTAGGTGT
CGAAAATTTATCGGGAAGTGGAGCCATTGCTAGTGCATAC
TCAAGGGCATATAAGGAAACCTTCACATTGACATACGTAA
CTGGAAGAACAGTGGGAATCGGTGCTTACCTGGCACGCCT
CGGGATGAGATGCATACAACGGCTCGATCAACCGATCATC
TTGACCGGGTTCTCCGCGTTAAACAAACTCCTCGGCCGTGA
AGTGTATAGCTCTCACATGCAACTCGGCGGTCCGAAAATTA
TGGCCACCAATGGGGTAGTCCATCGCACCGTCTCCGATGA
CCTCGAAGGTATTTCGGAAATCCTGAAATGGCTAAGCTGT
ATTCCCCCTCAAAGCGGCGGGGCAATTCCGGTATTTCCTTC
TCCGGATCCTCCGGAGCGACCCGTGGAGTACTTCCCAGAA
ACATCGTGCGACCCGCGGGCGGCCATCTCGGGTACAATGG
ACGGCAGCGGGAAGAAGTGGCTCGGGGGTATTTTCGACA
AAGACAGCTTCGTGGAGACACTGGAAGGGTGGGCGAGGA
CCGTGGTGACCGGGCGGGCAAAGCTCGGGGGGATTCCGG
TTGGGATAATAGCCGTCGAGACTCAAACCGTGATGCAAGT
GATCCCCGCCGACCCGGGCCAGCTGGACTCGCACGAGCG
GGTCGTGCCCCAGGCGGGTCAAGTATGGTTCCCAGATTCG
GCGAATAAAACCGCCCAAGCGATTATGGATTTCAACCGAG
AAGAGCTCCCGCTCTTTATCCTCGCCAACTGGCGAGGCTTC
TCGGGCGGCCAACGAGACCTCTTCGAAGGTATCCTACAGG
CGGGGTCCACCATAGTGGAAAACTTAAGGACATATAACCA
ACCGGTTTTCGTATACATCCCTATGATGGGCGAGCTTCGTG
GTGGGGCCTGGGTTGTTGTGGACAGTCAGATAAATTCCGA
CCACATCGAGATGTACGCTGATCGGACGGCTAAAGGCAAC
GTCCTTGAACCGGAAGGAATAATCGAGATCAAGTTTAGAA
CAAAGGAGTTGCTCGATTGCATGAATCGACTCGACCCAAA
GCTGATATCTTTAAAAACCAAACTAACCGAAGCGAAGAAT
AGTGGGACCTACGGGATGGTCGATTCCGTACAACAGCTGA
TAAAATCCCGGGAAAAGCAACTTCTGCCGCTTTACACGCAA
ATCGCCACACGATTCGCCGAGCTTCACGACTCGGCTTTACG
AATGGCGGCAAAGGGGGTGATTCGAGAAGTTGTCGACTG
GGGGATTTCACGATCTTACTTCTACAAAAGGTTAAGAAGG
AGAATCGCCGAGGCTTCGTTGGTGAACACCGTGAAAGATG
CAGCGGGTGATAAGCTCCAGCATAAGTCGGCTATGGAGTT
GGTCAAAAACTGGTTTCTGGACTCGAAAGGCGATTGGGAA
AACGATGAAGCTTTCTATGCTTGGAAGGATAATCCCGCGA
ATTACGAGGAAAAGCTACAGGAGTTACGGGTCCAGAAGG
TGTTGCTTCAGTTAACTAACATTGGCGAGTCTTTGTCGGAT
TTGAAAGCTTTACCTCAAGGTCTTGCTGCCCTTCTAAATAA
GGTAATTTTTTGGGTTTTTTCTTCCAGGAATATTGTTTATTT
AGACGATCGAGTCGGATGTTATGTAATACTTTATGTTTGAT
GTAGGTGGAGCCATCGAGCCGAGGGGCGTTGATCGATGA
GCTTCGGAAGGTGCTTAATTGATTTTCGGTAAGTGTTTCTC
GGCTACTAAATATGTTTTACTTTGGCTTCAGTCTCTGGGTA
GTTTGAATCAATAGAAAATGCCAATGTGAAAATACCCAGT
AATATATTTGATAAGTGTAAATGTAACTATTATTATATTTAA
GTGAATAGGGGGAATTAGTTCATATGATTATTGTTGTTATA
AACAAATCAGAGATAGAGAGAGCTATATTTATTATTATATT
TGCGAATTAAAGTTATTAGGAGTAGTATAATTTGGCGGTT
GTTGCATTTTACGTGTAATGATCTGAATGTTGTTTGTTCGT
```

TABLE 1-continued

ACCase gene sequences isolated from weedy plant species

| SEQ ID NO | SPECIES | TYPE | LENGTH | SEQ |
|---|---|---|---|---|
| | | | | GATTATTGAATAAAAGGGCATCAAATGCCATAATTTATCTT |
| | | | | TCTTTGTTAACAAGATTTTAATTAGTTTTTTTTAATTATTAGT |
| | | | | ATGTTTTGTATAATTTATATT |
| 58 | *Euphorbia heterophylla* | gDNA Contig | 5227 | TATATAAATGTGAAATTGGATAATTCTATATCATTCATCTG |
| | | | | AAGCTTATTATGGCCTTTTTTGATCCAGGACAAACTTAAAG |
| | | | | GCTATGACAATAGACAATATACTCAGTCAAGGGACAGACA |
| | | | | ATGGCACATGTACACTGTTGTAGACAAACCAGTTCCAATCC |
| | | | | AGAGGATGTTTCTAAGAACCCTTGTGAGACAGCCCACAAG |
| | | | | TACTTCATATCAAGGTCTTGGCGCCGAAGCACCCAATGTGC |
| | | | | AGTGGGCCATGTCCTTTACGTCAAAGAGCATTTTGAGGTCC |
| | | | | TTAGTAGCTGCAATGGAGGAACTGGAGCTTCACGTGCACA |
| | | | | CTGTCAAATCTGACCATGCTCATATGTACCTCTGCATATTG |
| | | | | AGGGAGCAACGGATAGAAGATCTTGTTCCATACACGAAGT |
| | | | | AATTATATCAATCTTTATGATTTATCGTGTACTTGGCACCAT |
| | | | | AACTTTATGTGTACTCACTATGAGACTCCATCTCCAGGAAA |
| | | | | ACCGATGTAGATGCCAACCAAGAAGAAGCTGCGGTAGCA |
| | | | | AGAATCTTGGAAGAACTAGCGAGGAAGATACATGCGTCG |
| | | | | GTTGGAGTCAGAATGCATAGGTTAAATGTTTGCGAGTGGG |
| | | | | AAGTGAAGCTATGGATGACATCATCTGGACAGGCAAATGG |
| | | | | TGCTTGGAGAGTTGTCACAACAAATGTGACTGGGCATACC |
| | | | | TGTGCTGTGCATGTAAGTATCTGCGCATCTTATTTCAAGAA |
| | | | | AATGTCTTTCCCTTCCATGCATTCCTTATTAGTCGACTTAGT |
| | | | | AATGGGGAATGTCGAGAAGTGTTGGATGGTTACCAATGTG |
| | | | | AGTACCATCACTGTTTAGATTAAAATTGACCATTGCTTTAG |
| | | | | CAATACAATAATGAATCTAATTGTGGCATGGGAGGCTTTTC |
| | | | | TATGTGTGATCCATGGAAAAACTTGTATATAGTTCCTTAGT |
| | | | | AGGTTTGAGTTGTTTTCATTTTTCTTTTATCACATTGTAATT |
| | | | | GTATTGGTGATTGATACGAAAATTAGATATATCGGGAACT |
| | | | | TGGGGACGACAGCAAACACGAAGTGGTTTACCATTCGATC |
| | | | | TCTCCAAGAGGCCCACTGCATAGCATGCCAGTGAATGCTG |
| | | | | TTTATCAGCCCTTGGGAGTTCTCGATCGAAAACGTTTGTTG |
| | | | | GCAAGGAAGAGCAACACCACTTACTGCTATGATTTTCCACT |
| | | | | GGTTAGTATTTATATAATCATTAATCAAACATCAGTTTTTTT |
| | | | | ATTGGGGATAACTAAAATCAAATAATTTTTCCTGGCCTCAT |
| | | | | CCTTTTCAGGCGTTCGAGACAGCCATCGAACAATTATGGG |
| | | | | AATCTCAATCACCAGGGACTGAAAGAAACAAAGAAAAAGT |
| | | | | CCTAAAAGTCTCGGAGCTTGTTTTTGCCGATCAGAAAGGTA |
| | | | | CCTGGGGAACTCCACTTGTTCATGCAGAACGGCCAGCTGG |
| | | | | GCTTAACGACGTGGGCATGGTAGCATGGTGCATGGAAAT |
| | | | | GTTCACCCCAGAATGCCCTTCCGGAAGGAAAATCTTGATA |
| | | | | GTAGCGAACGACGTGACCTTCAAAGCCGGGTCTTTCGGTC |
| | | | | CAAGAGAGGATGCATTCTTTTCCGCCATAACCGATCTGGCA |
| | | | | TGCACCAAAAAGCTCCCTTTAGTCTACCTGGCAGCAAACTC |
| | | | | TGGTGCTCGTATAGGTGTTGCCGAGGAAGTCAAGTCTTGC |
| | | | | TTTAAAGTCGGTTGGTCAGATGAGTCATCTCCCGAGCGTG |
| | | | | GTTTCCAGTACGTATATTTGACTCCCGAGGATTATGCAACC |
| | | | | ATTGGATCATCGGTGATAGCACACGAGCTGAATCAGAATG |
| | | | | GAGAAACACGGTGGGTCATAGATGCCATTGTTGGGAAAG |
| | | | | AGGATGGCTTAGGTGTCGAAAATTTATCGGGAAGTGGAG |
| | | | | CCATTGCTAGTGCATACTCAAGGGCATATAAGGAAACCTTC |
| | | | | ACATTGACATACGTAACTGGAAGAACAGTGGGAATCGGTG |
| | | | | CTTACCTGGCACGCCTCGGGATGAGATGCATACAACGGCT |
| | | | | CGATCAACCGATCATCTTGACCGGGTTCTCCGCGTTAAACA |
| | | | | AACTCCTCGGCCGTGAAGTGTATAGCTCTCACATGCAACTC |
| | | | | GGCGGTCCGAAAATTATGGCCACCAATGGGGTAGTCCATC |
| | | | | GCACCGTCTCCGATGACCTCGAAGGTATTTCGGAAATCCTG |
| | | | | AAATGGCTAAGCTGTATTCCCCCTCAAAGCGGCGGGGCAA |
| | | | | TTCCGGTATTTCCTTCTCCGGATCCTCCGGAGCGACCCGTG |
| | | | | GAGTACTTCCCAGAAACATCGTGCGACCCGCGGGCGGCCA |
| | | | | TCTCGGGTACAATGGACGGCAGCGGGAAGAAGTGGCTCG |
| | | | | GGGGTATTTTCGACAAAGACAGCTTCGTGGAGACACTGGA |
| | | | | AGGGTGGGCGAGGACCGTGGTGACCGGGCGGGCAAAGC |
| | | | | TCGGGGGATTCCGGTTGGGATAATAGCCGTCGAGACTCA |
| | | | | AACCGTGGTGCAAGTGATCCCCGCCGACCCGGGCCAGCTG |
| | | | | GACTCGCACGAGCGGGTCGTGCCCCAGGCGGGTCAAGTA |
| | | | | TGGTTCCCAGATTCGGCGAATAAAACCGCCCAAGCGATTA |
| | | | | TGGATTTCAACCGAGAAGAGCTCCCGCTCTTTATCCTCGCC |
| | | | | AACTGGCGAGGCTTCTCGGGCGGCCAACGAGACCTCTTCG |
| | | | | AAGGTATCCTACAGGCGGGGTCCACCATAGTGGAAACTT |
| | | | | AAGGACATATAACCAACCGGTTTCGTATACATCCCTATGA |
| | | | | TGGGCGAGCTTCGTGGTGGGGCCTGGGTTGTTGTGGACA |
| | | | | GTCAGATAAATTCTGACCACATCGAGATGTACGCTGATCG |
| | | | | GACGGCTAAAGGCAACGTCCTTGAACCGGAAGGAATAATC |
| | | | | GAGATCAAGTTTAGAACAAAGGAGTTGCTCGATTGCATGA |
| | | | | ATCGACTCGACCCAAAGCTGATATCTTTAAAAACCAAACTA |

TABLE 1-continued

ACCase gene sequences isolated from weedy plant species

| SEQ ID NO | SPECIES | TYPE | LENGTH | SEQ |
|---|---|---|---|---|
| | | | | ACCGAAGCGAAGAATAGTGGGACCTACGGGATGGTCGAT<br>TCCGTACAACAGCTGATAAAATCCCGGGAAAAGCAACTTC<br>TGCCGCTTTACACGCAAATCGCCACACGATTCGCCGAGCTT<br>CACGACTCGGCTTTACGAATGGCGGCAAAGGGGGTGATTC<br>GAGAAGTTGTCGACTGGGGGATTTCACGATCTTACTTCTAC<br>AAAAGGTTAAGAAGGAGAATCGCCGAGGCTTCGTTGGTG<br>AACACCGTGAAAGATGCAGCGGGTGATAAGCTCCAGCATA<br>AGTCGGCTATGGAGTTGGTCAAAAACTGGTTTCTGGACTC<br>GAAAGGCGATTGGGAAAACGATGAAGCTTTCTATGCTTGG<br>AAGGATAATCCCGCGAATTACGAGGAAAAGCTACAGGAG<br>TTACGGGTCCAGAAGGTGTTGCTTCAGTTAACTAACATTGG<br>CGAGTCTTTGTCGGATTTGAAAGCTTTACCTCAAGGTCTTG<br>CTGCCCTTCTAAATAAGGTAATTTTTTGGGTTTTTTCTTCCA<br>GGAATATTGTTTATTTAGACGATCGGAGTCGGATGTTATGT<br>AACACTTTATGTTTGATGTAGGTGGAGCCATCGAGCCGAG<br>GGGCGTTGATCGATGAGCTTCGGAAGGTGCTTAATTGATT<br>TTCGGTAAGTGTTTCTCGGCTACTAAATATGTTTTACTTTGG<br>CTTCAGTCTCTGGGTAGTTTGAATCAATAGAAAATGCCAAT<br>GTGAAAATACCCAGTAATATATTTGATAAGTGTAAATGTAA<br>CTATTATTATATTTAAGTGAATAGGGGGAATTAGTTCATAT<br>GATTATTGTTGTTATAAACAAATCAGAGATAGAGAGAGCT<br>ATATTTATTATTATATTTGCGAATTAAAGTTATTAGGAGTA<br>GTATAATTTGGCGGTTGTTGCATTTTACGTGTAATGATCTG<br>AATGTTGTTTGTTCGTGATTATTGAATAAAAGGGCATCAAA<br>TGCCATAATTTATCTTTCTTTGTTAACAAGATTTTAATTAGT<br>TTTTTTTAATTATTAGTATGTTTTGTATAATTTATATTTGACT<br>AATTAATGAGTTCTTTCTGAATTTATACCAAAATTTCAATAT<br>AATACTGAATTTAAAACTTGAGTCTAGATTACCAACAAGGT<br>GTAGCTCAGTTGGCAACGCAGGCTGGGTAAGTTGGAGGA<br>GAACAATGTTTGAATCCTACTAAATACACTTGTTGGGAGG<br>GGTGATGAGCCTTAACTGTGATTAAGTCCCGAACAAGATT<br>ATCTCAATGGTGATACTTGTAATTATTACCAAAAAAAACTT<br>GAGTCTACGATGCAAATATGTATTATCTAGGCATGGTCTAA<br>TTAGATTTAAATATGGGCTGATTGGATTTAAATTTCTCTTTT<br>TTTAGTACGATCTTATTAATTCAAATTAGAGTCCATTACATT<br>TCTAATGGATGAGAAACCACGTCCTCCTCTATGTCAAAGAA<br>ATAGATGTCTTGGCTAATAAATGGACAACTTGATTCGTAGA<br>CCTATTAACAAAAACAACTTTTAAACCTAAAAAAGAGGTCA<br>TGAGTATTTTGCAATCGAAAATAGTGAAACCTATTGACGAA<br>TGAAGAGGAGAGTTGATCAGAGCATATAGCTCGAGAATG<br>ACACTATCCAAGCCTTGGCTCTTTAGTCAACTGAGCGCCTC<br>TCTGCAACTCATAGCCTCTACTAGAAGAACATCTTGCATGA<br>GAGAGGATTGGGCTGCTACAAATCTACCCATATAATCTCG<br>AATTACACAGCCATTCATCTACCATTCTCAAACACACTAGC<br>ACGTTACATTTAAATCCAATGTTGTTTTAGCTTTGGATGTTT<br>TGTGTGTCATTAATGTTTGTTGTCTGCCATTCACTGAGGAA<br>CCCCAAACTGTGCCTAATAACTTGGGAATCAATTCGAAAAC<br>GTTGATTCCAAGCCCAGCTATTCCTTCTGGGACCATATAGT<br>GCACAAAATCAAATCCACCAATCTGTGATGGAAGCTATCG<br>AATATGGCCACCCATTGCTGCAAATGCCCGACCATAACGC<br>GAGAGCAAATGGTCAGGTAACGAGGGCGTGATAAGTCAA<br>TGTGTCGTGTCAGCCCCATCACTGCATATAGAACCAACATG<br>GTCGATCATAATATGCTTATCTTGAAGCCTAACCAACGTTG<br>GTAATGGGAGTCCCACCATCGCTACTTTCCAAAAAAAGAT<br>GAGTACATGAGCTGGGAATTGGATGTCCCGAATTTTTAGA<br>TTAAATATATCAACATTATAAATTTCTTTTTTTTTTTTATAA<br>ATTAACATTATAAATTCAATCAAAATGATAATCGTTCTATG<br>AT |
| 59 | *Euphorbia heterophylla* | gDNA Contig | 4102 | ATGTTAGTTGATCTTGTTTTCAGCACATATCACTTGTGAACT<br>CTCAAGTTTCATTGAACATCGAAGGAAGCAAATATACGGT<br>ATGGTACCTTTCATATTAGTATCTTAAATGAATAAATTTTAG<br>TTTGGTGATGGATGCCATTTACGTTTGTAAAATCATTGCTA<br>GATTGACATGGTTAGAGGGGGGCCAGGGAGCTATAGATT<br>GAGGATGAATGGATCGGAGATAGAGGCAGAAATTCATAC<br>ACTGCGTGATGGAGGTTTATTGATGCAGGCAAGTTGACTC<br>ATTAACCATGGCTGTTGTAAACTAATAATTTTCGTCCTTTTT<br>ATCATTTAATATTTGCTTTAGTCGACCCTCCATGCTTTGGAG<br>ACCATAACAGACTCTATTCTGTTTCTTCACAGTTAGACGGA<br>AACAGTCATGTAATATATGCTGAAGAAGAAGCAGCCGGAA<br>CTCGCCTTCTAATTGACGGGAGGACTTGCTTGCTACAGAAT<br>GATCATGATCCGTCAAAGTTAGTGGCAGAGACGCCATGCA<br>AACTTCTGAGATATTTGGTTTCAGATGGTAGTCATATTGAA<br>GCTGATGCTCCATATGCAGAGGTTGAAGTTATGAAGATGT<br>GCATGCCTCTTCTTTCACCTGCTTCTGGAGTTGTCCATTTTA<br>AAATGTCTGAAGGTCAAGCAATGCAGGTGTGTTTGATTTC |

TABLE 1-continued

ACCase gene sequences isolated from weedy plant species

| SEQ ID NO | SPECIES | TYPE | LENGTH | SEQ |
|---|---|---|---|---|
| | | | | ACAAACACATGCTTTTGGGCTTGATAAGTACATTTTGGTTT |
| | | | | TATATGAATAGTCAGTTTTGATGTGAATCTAAGAAGTTTTC |
| | | | | ATGTAGGCTGGGGAGCTCATTGCAAGGCTTGATCTTGATG |
| | | | | ATCCTTCTGCTGTAAGAAAGGCAGAGCCTTTTCATGGGAG |
| | | | | ATTCCCGCTACTTGGCTCTCCGACTGCTATTTCTGGTAAAGT |
| | | | | TCATCAGAGATGTGCTGCAAGTTTGAATGCAGCCCGTATG |
| | | | | ATTCTTGCTGGCTATGATCATAATATTGATGAAGTAAGTTG |
| | | | | CAAGCTGGCTAGTTTCAACATGAACTTAATTGATGAATTAA |
| | | | | TTGTTCATTCTATATTTTGTTGATTGTGTAATTTCATAACAA |
| | | | | AATAATGAACTGTGCATTTGGTTTATTATATTGACAATTATT |
| | | | | TGTTGAAATCTGATGTAATATCTCAATGACATCTATAGGTA |
| | | | | GTGCAAAACTTGCTCAATTGCCTTGACAGTCCTGAACTCCC |
| | | | | TTTCCTTCAGTGGCAAGAGTGCTTGTCTGTTCTAGCAACTC |
| | | | | GCCTTCCCAAGGATCTTAGAAGCGAGGTGAATAATTTTTCT |
| | | | | GTAATTTTTTCATGACCACATAGTCTTCTTGCTCACAATTTG |
| | | | | ATATTGGCAATTTGTATAGTTGGAATCAAAATACACAGAGT |
| | | | | TTGAAGGAATTTCAAGCTCCCAGAACATTGACTTCCCTGCC |
| | | | | AAACTGTTAAGGGGTGTCCTCGAGGTGGGTTCCTTATTGC |
| | | | | ATGGCTCTCTTGGAATTTCTCATTATCTGTTTTTTTTGCTGTT |
| | | | | TAATGAGATGTGTATGCTTTTCCTCCAGGCACACCTGAAAT |
| | | | | CCTGTCCTGAGAAAGAAAAAGGAGCCCTGGAAAGGCTTGT |
| | | | | TGAACCTTTGATGAGTCTTGTAAAGTCTTATGAGGGAGGA |
| | | | | CGTGAGAGTCATGCTCGAGTGATCGTCCAATCACTTTTTGA |
| | | | | AGAGTATTTATCTGTAGAAGAATTATTTAGTGACAACATCC |
| | | | | AGGTTAGCTTCTTCCTATCAAACATAATATGGAATTATTTTG |
| | | | | GATTCTGAAAGTCTTCCCTCTTTGGCATCTTTTAGAAAATTA |
| | | | | AGCATAATACTGGGTACTATATCCATTATTCTTTATAATCAT |
| | | | | GAAATTTATTCTTACAGAAGAAAAGTGGAATTTCTATATAT |
| | | | | ATTTAAACCAAGCTGGCAAGCTTTGAATTCAATCCTGTTGT |
| | | | | TTATTGTTTTATCCAACATGCCAAAAATATTAGGAACTTCAT |
| | | | | GTGACTACTTGTATCATTCTTATTCTGTAATTACAGTAAAGT |
| | | | | AACTTGTCATATCCTAATGTTATAACTCGTAACATTCTTCTT |
| | | | | TAGGCTGATGTGATTGAACGTCTCAGACTTCAATATAAGAA |
| | | | | AGACCTTTTGAAGATAGTGGACATTGTCCTTTCTCATCAGG |
| | | | | TATCTGATTTTCGGTTTTAATTTTTATCTCGGGTTTTCTAAA |
| | | | | ATAGAATTCTGAGTTTGTGGAAATAACTACCGTATTTGTTG |
| | | | | GTTTATAGGGTGTTAAGAGTAAAATAAGCTGATACTACG |
| | | | | GCTCATGGAACAACTTGTTTACCCCAACCCTGCTGCATATA |
| | | | | GGGATAAACTCATTCGGTTCTCTCAGCTTAACCACACCAGC |
| | | | | TATTCCGAGGTTGGCAGCTATACTTGGTCCATCTGTAATTT |
| | | | | CATAAAGTTGTTGCTCTGTTTCCTTTTGTTCACAAGTTCATT |
| | | | | TTTGAGAGTTTTCCATAGGATGGTGACTGACAGGAAGAGG |
| | | | | ATTCTAATGTTTTCTCTTGGAGGATTTTTTCTGTATTTTCATT |
| | | | | TCTTGTCGGTCATTGATTAATTCCGTTTCTGGTATCAGTATC |
| | | | | ATCAAAATGTTGTCTTTTTCTGTATACTGATGCTGAATTATG |
| | | | | TGAACAGTTGGCATTGAAGGCAAGTCAACTCCTAGAACAA |
| | | | | ACCAAACTGAGTGAACTCCGTTCCACTATTGCTAGAAGCCT |
| | | | | TTCGGAATTGGAGATGTTTACAGAGGATGGTGAAAATATG |
| | | | | GATACTCCCAAAAGGAAAGTGCCATTAATGAACGTATGG |
| | | | | AGGATCTTGTGAGTGCTCCTTTGGCTGTTGAAGATGCTTTA |
| | | | | GTGGGTCTTTTCGAGCACAGTGATCACACCCTTCAAAGGC |
| | | | | GAGTGGTGGAAACTTATGTTCGTAGGCTATATCAGGTACT |
| | | | | GTGTTGTAGAAACTTAAAACTTTTATCTGGTGATCAAACAC |
| | | | | TAGACGAAACTTGATCTTGATCAACTGTTTGTCTACCGCAC |
| | | | | CAGCCCTATCTGGTCAAAGGTAGTGTCAGGATGCAGTGGC |
| | | | | ATAGATTTGGTCTTATTGCTACATGGGAATTCTTGGGAGAG |
| | | | | CATATCGGGAGAAAGAATGGATCTGAAGGTCAAATGTCAG |
| | | | | ATGAACCAGAGGCTAAAAAACAGTCTAATAAGAGATGGG |
| | | | | GAGCAATGGTTATCATCAGATCTCTGCAGTTTTTGCCTTCA |
| | | | | GTTATTGGTGCTGCATTAAGGGAAACAAATCAAAGCCTTA |
| | | | | ATGAGTCCATTCCAAGTGGATTAGTAAAATCAGCGAGCTTT |
| | | | | GGTAATATGATGCACATAGCATTGGTAGGCATCAATAATC |
| | | | | AGATGAGCTTACTACAGGATAGGTAACTTCCTTCGGTACTA |
| | | | | TAATATAAGCGTTTATTTTAATCATAAAAATTAGTAGCATTT |
| | | | | TACATTCTATTATTCATTGTAAGATCTCAAGTCTTCTTAATC |
| | | | | ATTTCTGCATTTGAAACCTTGATAGATCTGGATAGATTCCTT |
| | | | | ATTTTTGTTTAAAATTTATGATAGAGTTACCTGGTCTCGAAC |
| | | | | CCTTAAAACATGCACATATATTGGCTTGCCAAACATAAGTT |
| | | | | ATTTTGCGTTGTCAATTTCGATTATTGACAGTCATCTTGTTA |
| | | | | ATGCTCCTAACTGGCACCATCTATGACATTTTGCAGTGGTG |
| | | | | ATGAGGATCAGGCACAAGAGAGAATTAACAAGTTAGCCA |
| | | | | AGATTCTCAAAGAACAGGAACTAGGTTCCAGTTTGAGCTT |
| | | | | GTCAGGCGTTGGAGTTATTAGCTGTATCATACAGAGGGAT |
| | | | | GAAGGGAGAGCCCCTATGAGGCACTCCTTTCACTGGTCAG |
| | | | | AGGAAAAGCTTTATTATGAGGAAGAACCTCTATTGCGACA |
| | | | | TTTGGAACCTCCACTATCCATCTACCTTGAACTGGTTTGTCA |

TABLE 1-continued

ACCase gene sequences isolated from weedy plant species

| SEQ ID NO | SPECIES | TYPE | LENGTH | SEQ |
|---|---|---|---|---|
| | | | | CCTATCGCAGTGTTTCAATACATTTTTTTGGCAGAAACCTTT<br>ATTGAGCCCCTGAACTTACCAGTTTTATTCTCAAGTTATTAT<br>TTGACTACATTAAATACTTGAATTACTATTGAATCCACATTA<br>CGACCTTGAAAACGTTTTATTGATAAAATTATAACTGTTGC<br>TATTTTGTTTTACATATATCAAGGACTGCACTATAGTAAAA<br>AAATGAGGACTCGATATGATTGGAAAGTTCAGGGGCTTAC<br>TAATTGTTTGAGCGGAAAAAAATATATATAAATGTGAAATT<br>GGATAA |
| 60 | Euphorbia heterophylla | gDNA Contig | 1523 | AAAATATCTTTGTTTCTGTAATAAATTGTTCTTTGACTTTTCT<br>AATGATCTTTAATCTACATCCTAATCTGGATGTAGGTGGAG<br>CATCCCGTCACAGAGTGGATTGCTGAAATAAATTTGCCTGC<br>TGCCCAAGTAGCTGTTGGGATGGGAATTCCTCTGTGGCAA<br>ATTCCTGGTATGACCGCAAAAGTTGGAAATTCACATTTTCT<br>TGCTCATTAGACATGTTTCTTTGACATTCTGTTGATTTTTAA<br>TCAGAGATTAGGCGATTTTATGGAATGGAACATGGTGGAG<br>GATATGATGCTTGGAGGAAAACTTCAGTGGCTGCTACGCC<br>TTTTGATTTTGACAAGGTAGACTCTACAAAGCCAAAAGGTC<br>ATTGTGTAGCTGTACGTGTGACAAGTGAGGATCCAGATGA<br>CGGCTTTAAGCCTACTAGTGGAAAAGTACTGGTAAGGTTT<br>TCAGGTTGACTATTCTAATTTGAATTTCCTTCTATTCCAAAA<br>TTCCTTATCCTGTAATGAACTTGTACTTTTATTGTCTTGCAC<br>AGGAGCTGAGTTTTAAAAGCAAGCCAAATGTGTGGGCTTA<br>TTTTCTCTGTGAAGGTGACTTTTTGCTGCTCTCTTTCTTTGGA<br>ACATGTTTATGTTGACACAATTGGTTTCTGACTTAATAACTT<br>CATTCTGATTTGTAGTCTGGTGGAGGCATTCATGAATTCTC<br>AGATTCACAATTTGGTAAGTAATAATTGCTAAATAATCACA<br>CTTCATGGATAATAATGAAAAGAAGTTTGTGAGATGAGTT<br>ATCCAATCTGCTGCAAATTAATGGTTCTTTTTTATCTTCTTG<br>TGACATTTTTTTAACAAAAGCTACAGTCTGCTTTTCAGTTT<br>AGTCTTTTCCGTTTGTTACATTTGCTATCGAAAGCACTCATG<br>ATTGTCGTAATCTTTCCTTAGGACATGTTTTTGCATTTGGGG<br>AGTCCAGAGCTTTGGCAATAGCTAATATGGTTCTTGGGCT<br>GAAGGAAATACAGATAAGAGGAGAAATCCGCACCAATGT<br>TGACTACTCTGTTGACCTTTTACATGTAAACTATCTTAGCTG<br>TTGATGTTCCCTTTATACATCATGTAAACTTTCACGAGGAA<br>CATGAACACGAGTTGACATGCTATGCAGGCTTCAGATTATA<br>GGGAAAATAAAATTCACACAGGTTGGTTGGACAGTAGAAT<br>AGCTATGAGGGTTAGAGCAGAAAGACCTCCTTGGTACCTC<br>TCTGTTGTTGGAGGGGCACTATATGTAAGTTGTCACGATTT<br>CACATGAGAGGATGACTGTATACTTTTGGAATGCTTTATTA<br>TGTCTTTCAGAACTTGCCACTTAAGTGTTCAATTTTTTGTTT<br>GCACCAGAAAGCATCTGCTAGCAGCGCAGCTATGGTTTCT<br>GATTATGTTGGTTACCTTGAAAAGGGCCAAATCCCTCCCAA<br>GGTACATCAAAAGTATATTTGTACAATTGTATATGTTTCTTA<br>TTCAGCCGATTATGTTGATGTTGATGTTAGTTGATCTTGTTT<br>TCAG |
| 61 | Xanthium strumarium | cDNA Contig | 1349 | GTTGTTGTCAAGTCTCTATTTGAGGAGTATCTGTCTGTTGA<br>AGAACTCTTCAATGATAACCTTCAGTCTGATGTTATAGAGC<br>GTCTACGTCTTCAACATGCAAAAGACCTTGAGAAGGTTGTA<br>CACATTGTGTTCTCGCACCAGGGTGTGAGAAACAAAAATA<br>AATTAATACTACGGCTTATGGAAGCATTAGTATATCCAAAC<br>CCATCTGCTTACAGAGACCAGTTGATTCGCTTCTCTGCCTT<br>GAACCATACATCTTATTCTGAGTTGGCACTTAAAGCAAGCC<br>AACTTCTAGAGCATACTAAATTGAGTGAACTTCGAACAAGC<br>ATAGCAAGAAGCCTTTCAGAGTTGGAGATGTTTACTGAGG<br>AAGGAGAACGGGTGTCAACACCTAGGAGAAAGATGGCAA<br>TAAATGAGAGGATGGAAGATTTAGTATGTGCTCCACTGGC<br>AGTTGAAGATGCTCTTGTAGCTTTGTTTGATCACAGCGATC<br>CTACACTTCAGCGGAGGGTTGTTGAGACATATATACGTCG<br>ATTGTATCAGCCCTACCTTGTAAGTGGAAGTATCCGGATGC<br>AATGGCACCGAGCTGGCTTAATTGCTTTATGGGAGTTCTCT<br>GAAGAGCATCTTAAGCAAAGAAATGGGCACGATGTGCTTG<br>TACAGCAAGTAGAGAATCCCATTGAGAAGAGATGGGGTG<br>TCATGGTTGTAATCAAGTCTCTTCAGTTTCTAGCAACTGCA<br>ATTGATGCTGCACTGAAGGAGACCTCGCAATATAGAGCAG<br>GTGCTGTAAGTGTCTCGAATGGTAACCATGTAAATTCAAAT<br>CAAAGCAATATGCTGCATATTGCTTTGGTTGGTATCAATAA<br>TCAGATGAGTACTCTCCAAGACAGTGGTGACGAGGATCAA<br>GCACAGGAAAGGATCAACAAACTATCCAAAATTTTGAAGG<br>ATAATACTATTACATCGCAACTTAATGGTGCTGGTGTTAAG<br>GTCGTCAGTTGCATTATCCAAAGAGATGAAGGGCGTCCAC<br>CAATGCGACACTCCTTCCATTGGTCTGTTGACAAGCTTTATT<br>ATGAGGAGGATCCAATGCTCCGCCACGTGGAACCACCATT<br>GTCTACATTCCTTGAGCTGGACAAAGTAAATTTGGAGGGT |

TABLE 1-continued

ACCase gene sequences isolated from weedy plant species

| SEQ ID NO | SPECIES | TYPE | LENGTH | SEQ |
|---|---|---|---|---|
| | | | | TACACTGAAGTAAAATACACCCCATCACGTGATCGTCAGTG<br>GCATATTTACACACTTATCAAGAACAAGAAAGATCAGAGA<br>TTAAACGACCAGAGGATGTTCCTTCGTACCATAGTCAGACA<br>ACAAAGCGCAACAAATGGTTTCCTGTCAGGAAATATTGAC<br>AATGAAGTAGGCCGCACTCAAGCTTCGTCATTCACATCACA<br>CAGCATCCTCAG |
| 62 | Commelina<br>diffusa | cDNA<br>Contig | 7098 | ATGACACTGATTAAATATCTATGTAGAACGCCTGAAGCCCA<br>GAAGGGAGCAGTTATGGCAGATGTCTGGCAAGATCATGG<br>GATTTTAAATGGGACAGTTCAAGTCAAACATGCAGCTACA<br>ACGTCTGAAGTTGATGATTTCTGTTATGCACTTGGTGGAAA<br>GAGACCTATTCGCAGCATATTGATTGCTAATAATGGAATG<br>GCTGCTGTCAAATTCATGCGTAGTATTAGAACCTGGGCTTA<br>CGAAACATTTGGATCAGAAAAGGCAATTTTGTTGGTTGCG<br>ATGGCAACTCCAGAAGACTTGAGGATAAATGCCGAGCACA<br>TTAGAATTGCTGATCAATTTGTAGAGGTTCCCGGTGGAACC<br>AATAATAACAATTATGCAAATGTTCAACTCATTGTGGAGCT<br>GGCCGAAATAACACGTGTTTCTGCAGTTTGGCCTGGATGG<br>GGCCATGCATCCGAGAATCCCGAACTTCCAGATGCCCTGA<br>ATGCAAAGGGAATAATCTTTCTCGGGCCTCCAGCTGCGCC<br>AATGTCAGCACTAGGTGATAAAATTGGTTCTTCTCTAATTG<br>CTCAGGCAGCAGGTGTACCAACTCTTCCGTGGAGTGGCTC<br>ACATGTCAAAATTTCAGCGGAAAGTTGTATGGACACAATA<br>CCCGAAGAGATATACAAGCAGGCTTGTGTTTATACAACAG<br>AAGAAGCAGTGGCCAGCTGCCAGGTAGTTGGCTATCCTGC<br>CATGATAAAGGCATCTTGGGGCGGTGGTGGTAAAGGAAT<br>AAGAAAGGTTCACAATGACGATGAAGTGAGAGCTCTCTTC<br>AAACAAGTGCAAGGAGAAGTTCCAGGATCTCCAATATTTA<br>TAATGAAAGTGGCATCACAGAGTCGTCACTTGGAAGTTCA<br>GTTGCTTTGTGATGAATATGGCAATGTTGCTGCTCTTCACA<br>GTCGAGATTGCAGTGTTCAAAGGCGACACCAAAAGATCAT<br>CGAAGAAGGTCCGATCACGGTGGCCCCTCCTGAGACAGTC<br>AAACAACTTGAGCAGGCAGCAAGAAGGCTTGCTAAGTGTG<br>TTGGTTATGTTGGTGCTGCTACTGTTGAATATCTCTACAGT<br>ATGGAAACTGGTGACTACTATTTCCTAGAACTGAACCCTCG<br>ATTACAGGTTGAGCATCCTGTAACTGAGTGGATAGCTGAA<br>GTCAGCTTGCCTGCGGCTCAAGTTTCAGTTGGTATGGGCAT<br>ACCACTATGGCAAATTCCAGAAATCAGAAGATTTTATGGA<br>AAGGAGCATGGTGGAGGATATGATGCTTGGAGGAAGACA<br>TCACTTTCTGCAAGTCCTTTTGACTTTGACAAAGCAGAGTC<br>TACAAGGCCAAGAGGTCATTGTGTAGCTGTTCGTGTGACG<br>AGTGAAGATCCAGATGATGGCTTCAAGCCCACCAGTGGCA<br>AAGTGCAGGAGCTAAATTTTAAAAGCAAGCCTAATGTGTG<br>GGCATACTTCTCTGTTAAGTCTGGTGGTGGCATCCATGAAT<br>TTTCTGATTCTCAATTTGGACATGTTTTTGCATTTGGGGAAT<br>CTAGAGCCTTGGCGATAGCTAACATGGTTCTTGGACTGAA<br>GGAGATCCAAATTCGTGGGGAAATTCGAACAAATGTTGAT<br>TACACAATTGATCTATTAAATGCATCAGAATACAGAGACAA<br>CAAAATCCACACTGGTTGGCTGGATAGCAGAATAGCAATG<br>AGGGTCAGAGCTGAGAGGCCTCCATGGTACCTTTCAGTTG<br>TTGGAGGAGCTCTTTATAAAGCAACAACTAGCAGTGCTGC<br>CATTGTTTCCGAATATGTTGGTTATCTTGGTAAAGGTCAAA<br>TCCCACCAAAGATTGAAATGGTTCGAGGTGGACCTGGTAG<br>TTATAAATTAAAAATGAATGGTTCAGAGATTGAAGCTGAA<br>ATTCATACTCTCCGTGATGGTGGACTTCTGATGCAGCTAGT<br>TTCAGTGGCAAAGCAAGCATTCCAATATGCTAAGCCTGTTA<br>ACAGTATTGATGCTGCTGTAAAATTGCCCCGTATGAATTTC<br>CAGTCTTCTTCATACTCTATTTTTCTTAATAAGATAATGTAC<br>CGACAACTTGATGATGGAAGCTTTTTGGATGGAAACAGCC<br>ATGTGATATATGCTGAAGAGGAGGCTGCTGGTACACGCCT<br>TCTTATCGATGGAAGGACTTGCTTGTTACAGAATGATCATG<br>ATCCATCGAAATTGATTGCGGAGACACCATGCAAACTTCTT<br>CGCTACTTGATTGCTGATGGAGAGCATCTTGATGCTGATGC<br>ACCATATGCAGAGGTCGAAGTAATGAAGATGTGCATGCCC<br>CTTTTGTTACCTGCTTCTGGAGTTATTCATTTTGTGATGTCT<br>GAAGGTCAGGCTATGCAGGCTGGTGACCTCATAGCAAGG<br>CTCGACTTAGACGATCCATCTGCTGTAAGAAGAGCTGAAC<br>CATTCAATGGTACATTCCCTAAAGTAGGTCCTCCCACTGCA<br>GTTTCTGACAGAGTTCACCAGAGATGTGCTGCAAGTTTGA<br>ATGCTGCACGCATGATTCTTGCAGGATATGAACATAATATT<br>AATGAAGTTGTTCAAGAGTTACTACATTGTTTGGATAGTCC<br>GGAGCTTCCTTTTCTACAGTGGCAGGAAAGTATGTCTGTAT<br>TGGCAACTCGCCTGCCGAAAGAACTTAAAAATGAGTTGGA<br>TTCTAAATACAAAGTATTTGAAACAAACTCAAACGTTCAAA<br>AGAATGTGGAATTCCTGCCAAGCTTCTGAGTGGAGTTATT<br>GAGAGCTATCTCTCATCTTGTAGTGAGAAAGATAAGGCGG |

TABLE 1-continued

ACCase gene sequences isolated from weedy plant species

| SEQ ID NO | SPECIES | TYPE | LENGTH | SEQ |
|---|---|---|---|---|

```
CACAGGAAAGGCTTGTGGAACCACTTCTGAGCCTTGCGAA
GTCATACGAAGGTGGAAGAGAAAGCCATGCTCGTGTAATT
GTGCATTCTCTTTTTGAAGAGTACTTATCTGTTGAAGAGTT
ATTCAGTGATAGCATTCAGGCCGATGTCATAGAACGCCTAC
GACTTCAATACCAGAAGGATCTTCTGAAAGTTGTAGACATA
GTGCTGTCTCATCAGGGTGTTAGAAGTAAAAATAAGCTGA
TACTGAGGTTGATGGAAGCATTGGTCTATCCTAATCCTGCT
GCCTATCGGGAACAACTGATTCGCTTCTCTGCTCTTAACCA
TACCACTTACTCCGAGTTAGCATTGAAAGCCAGTCAACTCC
TTGAACAAACTAAATTGAGTGAGCTTCGAACAAGCATTGC
CAGAAGCCTTTCCGAGCTAGAAATGTTTACAGAAGAAGGT
GAACGTCTATCTACACCGAGAAGGAAAAGTGCTATCAATG
AGAGGATGGAGGATCTTGTAAGTGCTACGCTGGCCGTTGA
AGATGCACTTGTGTCTTTGTTTGATCACACTGATCCAACTG
TTCAGAGACGAGTGATGGAAACATATGTCCGAAGATTGTA
CCAGCCCTACCTTGTGAAGGATAGTGTCCGAATGCAGTGG
CACCGTTCTGGTTTGATCGCGACATGGGAATTCACCGAAG
AACATATTGAGAAAAAGAATGATTCTTCTACACAAGATAA
GTCATTTATGGAGAAACATTGTCAAAAGAGATGGGGAGCT
ATGGTTATCGTCAAATCTCTCCAGTTTCTTCCAGCAGCAATT
AGTGCAGCATTGAAGGAAACCAGTCATCTGTCATCTGATA
CTGATCATGATACAGTATCTAATGGGCTTCCTCAACATGCT
AGTCAAGGCAATATGCTTCATGTTGCATTGGTTGGCATTAA
CAATCAAATGAGTACACTTCAGGATAGTGGAGATGAGGAT
CAGGCTCAGGAGAGGATACACAAGCTTGCCAAGATTCTAA
AAGATAACAAGGTAGCGACTGAACTTTCCAATGCTGGAGT
CCGAGTTGTTAGCTGTATTATACAAAGAGATGAAGGACGA
ACACCTATGCGTCACTCCTTCCATTGGTCTGCCGATAAGCA
ATGCTATGAAGAAGAACCCTTGCTTCGTCATCTGGAACCTC
CTCTGTCTACTTTCCTTGAATTGGATAAGCTGAAAGGCTAC
AAAAATATACAATACACACCATCACGGGATCGCCAGTGGC
ATATGTACACAGTTCAAGAAACTAAACCACTTAATCAGAG
GATGTTTCTGAGGACCCTTGTCAGACAACCAAGGATAAAT
AATGGATTTTCATCAAACCAGCTTCCCGAATTAGAAACTAG
ACATGATTTATCCTTTACATCAGTCAGCTTGTTGAGATCTTT
GATGGCAGCATTGGAAGAGTTAGAACTACATGTCCATAGC
GAAACAATCAGATCTGATCATTCTCACATGTATCTCTGCAT
ATTACAAGAACAACAACTCTCCGATCTTTTACCTCGTTCAG
GTACTCTTGATCCTGATGCCTATCAGAATGAAAGTCAAGTG
TCCCTGCTTTTAAAAGATATGGCTGTCAGGATTCATGAGAT
AGTTGGTGTAAGGATGCATCGTCTTACTGTTATTGAGTGG
GAGGTAAAGCTCTGGTTGGGTTCTGATGGTGTTGCTGGTG
GTTCTTGGAGGGTTGTGGTGACAAATGTTACTGGACGTAC
ATGTAATGTCCATATTTACCGAGAATTGGAGGACAGCAAA
TCACATGAAGTGGTCTATCACTCTGCAGCTTCAGTCACAGG
ACCTCTCCATGGTATGCCGTTGATTGCTAGATATCAGCCAC
TTAGTGTTATTGATAAAAAACGATGGGTGGCAAGAAGGAG
CAACACTACTTATTGCTATGACTTTCCACTGGCGTTTGAGA
CAGCACTGAAGCAGTCATGGGCTTCTTATAGTGATACTAAA
GCACCAGAAAGCAAAGCTCTTCTCCAAGTTCAAGAACTTAT
GTTTGTTGACAAAAAGGGATCATGGGGTACTCCTGTTGAA
CCTGTATGCTGCCCACCTGGTCTCAGTGATATTGGCATGGT
TGCTTGGTCAATGGAAATGTACACACCAGAATTTCCCGAA
GGAAGGAAGATTGTTGTTGTAGCCAATGATTTGACTTTCA
AAGCAGGCTCCTTTGGGCCTCGTGAAGATGCATTTTTCCAT
GCTGTAACCAATTATGCATGTGATAAGAGGCTCCCTCTAAT
CTATTTGGCAGCAAATTCTGGCGCCAGGATTGGTGCTGCT
GAAGAGGTCAAGTCTTGCTTTAAGGTTGGATGGTCTGATG
AGTCGAGTCCAGAACGTGGTTTTCAGTATGTGTATCTGACA
CAGGAGGACTATAACCGTATTGGTTCATCTGTTATTGCACA
TGAACTGAAGCTTGAAAGTGGTGAGATCAGATGGGTGATC
GACACAATTGTTGGCAAAGATGATGACTTGGGTGTTGAGA
ACCTCACTGGCAGTGGTGCAATTGCCGGTGCTTATTCCAG
GGCTTATAACGAGGTATTTACTCTTACATATGTGACTGGAC
GTACTGTAGGAATCGGAGCCTATCTTGCTCGGCTTGGCAT
GAGGTGTATCCAGAGGCTAGACCAGCCTATAATCCTAACA
GGGTTTTCTACACTCAACAAGTTGCTTGGCCGTGAGGTGTA
CAGCTCACACATGCAACTAGGTGGCCCGAAGATCATGGCT
ACAAATGGTGTTGTTCATCTGACGGTATCAGATGATCTTGA
GGGCGTTTCTGCTATTCTTAAGTGGCTTAGTTACGTACCAC
CCTATGTCGGTGGGCCACTTCCAATAATAAAATCCTTGGAT
CCCCCAGAAAGGCCAGTGGAGTATTTTCCTGAAAATTCATG
TGATCCACGGGCCGCAATTTGCGGCATTGATGATGGCAAT
GGCAAGTGGTTAGGTGGTATGTTTGATAAAGATAGTTTTA
CGGAGACATTAGAAGGTTGGGCAAAGACGGTGGTCACCG
GAAGAGCAAAGTTGGGTGGAATTCCAGTAGGAGTTATAG
```

TABLE 1-continued

ACCase gene sequences isolated from weedy plant species

| SEQ ID NO | SPECIES | TYPE | LENGTH | SEQ |
|---|---|---|---|---|
| | | | | CTGTCGAGACACAGACTGTGATGCAAGTCATTCCTGCAGA |
| | | | | TCCTGGTCAGCTTGATTCCCATGAACGTGTTGTCCCACAAG |
| | | | | CTGGTCAAGTTTGGTTCCCTGATTCTGCCACCAAAACGGCA |
| | | | | CAAGCATTATTAGACTTCAATCGTGAAGAATTGCCACTTTT |
| | | | | CATACTAGCCAACTGGAGAGGATTCTCAGGCGGACAGAGA |
| | | | | GATCTCTTCGAAGGTATACTTCAGGCTGGTTCCACAATCGT |
| | | | | CGAAAACTTAAGGACATATAAGCAGCCTGTATTTACCTACA |
| | | | | TCCCAATGGCCGGGGAGCTTCGTGGTGGTGCATGGGTTGT |
| | | | | GGTGGACAGCAAAATCAACCCGGATCACATCGAGATGTAT |
| | | | | GCCGAAAGAACAGCAAGGGGCAACGTACTTGAGCCCGAA |
| | | | | GGAATGATTGAGATTAAGTTCAGAACTAAAGAACTTCTCG |
| | | | | AGTGCATGGGTAGACTTGATCCTGAGCTAATCAGTTTGAA |
| | | | | AACAAAGCTTAGGGAGTTGAAGGCAGCTGGACCTTCCAGA |
| | | | | GATGTGGACGTCCTCCAGAAAAGTGTAACGGCTAGAGAG |
| | | | | AAGCAGTTATTGCCTGTATATACACAAATTGCTATAAAGTT |
| | | | | TGCAGAGTTGCACGATACATCCTTGCGAATGGCTGCCAAA |
| | | | | GGTGTGATCAAGAAAGTGGTAGACTGGGAGAACTCCCGTT |
| | | | | CTTTCTTCTACAAAAGGTTAAACAGGAGAGTTTCCGAGGAT |
| | | | | GTCCTTGCAAAAACTGTTAGAGATGCTGCTGGGGAGCAGT |
| | | | | TGTCGTACAAGTCTGCTATTGAACTGCTTAAGCAGTGGTTT |
| | | | | TCATCTTCCGACAATGTGGACGTTGGAAAATGGGAGGAAG |
| | | | | ACGATGCTTTCCTTGCCTGGAAAGACAACCCTAAAAATTAT |
| | | | | GCCAAGTATCTTGAAGAGCTACGAGTTCAGAAGATATTGC |
| | | | | AGCAGCTCTCAGCTCTTGGTGAATCATCTTCGGATTTGCGA |
| | | | | GTATTGCCTCAATGTCTTGCTACAGTCCTTAGCAAGGGCAG |
| | | | | AATAACAAACTCAAGCGAATCGGAGAAGAGCAGGACCGA |
| | | | | GCACGAGATCTGGTCGACTGAGCTTGAGTGGGCCAAGCTT |
| | | | | AAGCTTGCGATGGAGAAGAAGTGCGCCAGAGAAGAGGG |
| | | | | GCACACCTGGATAAGGAAGGCGAGATACACGAGCATGAC |
| | | | | CAAATCGAAAATGAGCTGGAGGGGAAGGGAGGAGGAGA |
| | | | | ATAAGGGAGACATGAGAGGAGGGGAAGGATAA |
| 63 | Commelina diffusa | gDNA Contig | 14748 | AAAAAAAAAAAAAAAACAAAGATCTTATGATAGTCTGAAAA |
| | | | | CAAACTTTGACCAGTGTGATTTTATGTTAAGTGTATTTACCT |
| | | | | ATCTTTCAATTGACTTTTCAGGTTCACAATGACGATGAAGT |
| | | | | GAGAGCTCTCTTCAAACAAGTGCAAGGAGAAGTTCCAGGA |
| | | | | TCTCCAATATTTATAATGAAAGTGGCATCACAGGTGAGATA |
| | | | | AATGTATTTTTAAAGCTTCAGTTATGTCATGAATTTATATGG |
| | | | | CCCTGCATTAACTGAATCTAGACTATGCCCAATATGAAATT |
| | | | | ATTGCAGGTTACTTTAAGCAGAATATATGTTTGACAGTAAG |
| | | | | TAGGCTGACTTAGTACTGAACAATTGAGTGTATCAATGCAT |
| | | | | GCCCAATATAATAGTGTGTTTCATTTCAGGATAAAAAGTGA |
| | | | | GATGTAGTTTTCGGATTCAACATATGCATTCTTTTTCAACCT |
| | | | | TGATGTCATCAGTCAATGCATAGTAGTGCATGTACTTGACT |
| | | | | TTGTGTATGTAATTATTATTCTTTGGTAGTTGCAATTAAAG |
| | | | | GATGCATTGATACACCCAATTGTATCATCAGTTATTTTGCA |
| | | | | ATTCATATTCCACCCTTCTGTTTTTAGGAAATTCTAGAAACT |
| | | | | TTTAACTTGGAAGCTCTAGAATACCATATCTTGCTTTATATC |
| | | | | ATGGCAGTTACACTGAAGCTTTATGTTACATGTGCATTCAT |
| | | | | TTTTAACGCTCCAATATTGTTATCCTTTTATTTCCTCTAGAGT |
| | | | | CGTCACTTGGAAGTTCAGTTGCTTTGTGATGAATATGGCAA |
| | | | | TGTTGCTGCTCTTCACAGTCGAGATTGCAGTGTTCAAAGGC |
| | | | | GACACCAAAAGGTAAACTTTAGTAAAGCATCTATATAATTA |
| | | | | TGTTATTTGTAACCTTTCATGCTTACCTTTATATTTCATAGAC |
| | | | | CTGAACCATGTCTATGAATATATTTGTGTGCTGTTATGAGC |
| | | | | AGGTTATTTTCTCCAGATCATGTATCTTTATCCTGAACTCT |
| | | | | TGTGGACTTATCTTGAATTAACATTTTGTAAATATTTCAAGA |
| | | | | CTTTCTTCATGATGCTTATTTATTACCCAACAGATCATCGAA |
| | | | | GAAGGTCCGATCACGGTGGCCCCTCCTGAGACAGTCAAAC |
| | | | | AACTTGAGCAGGCAGCAAGAAGGCTTGCTAAGTGTGTTGG |
| | | | | TTATGTTGGTGCTGCTACTGTTAATATCTCTACAGTATGG |
| | | | | AAACTGGTGACTACTATTTCCTAGAACTGAACCCTCGATTA |
| | | | | CAGGTTTGTCTTTGCTTGTTGGCTGAAGATTCATTGTTCATC |
| | | | | AGAACTTTGTCTTCTAAGTCTTGGTCCTTTTCAGGTTGAGC |
| | | | | ATCCTGTAACTGAGTGGATAGCTGAAGTCAGCTTGCCTGC |
| | | | | GGCTCAAGTTTCAGTTGGTATGGGCATACCACTATGGCAA |
| | | | | ATTCCAGGTATGAACTTGTAAGGGAATTTTGCATAATTAAT |
| | | | | GCAAAAGCTTAAGAGAAAAAGATGTAAGTTTCTTGTGAT |
| | | | | GCTAACTCTAGTTATAATTTTGGTTTCTTTCTTTCAGAAATC |
| | | | | AGAAGATTTTATGGAAAGGAGCATGGTGGAGGATATGAT |
| | | | | GCTTGGAGGAAGACATCACTTTCTGCAAGTCCTTTTGACTT |
| | | | | TGACAAAGCAGAGTCTACAAGGCCAAGAGGTCATTGTGTA |
| | | | | GCTGTTCGTGTGACGAGTGAAGATCCAGATGATGGCTTCA |
| | | | | AGCCCACCAGTGGCAAAGTGCAGGTAAATGTTGTTGAATA |
| | | | | TAGGATATTTAGGCTTAATATTTTCTGCAGGGACACTGACC |
| | | | | AACTTTACTGAACTGGGACTTAAATATTTTCAGGAGCTAAA |

TABLE 1-continued

ACCase gene sequences isolated from weedy plant species

| SEQ ID NO | SPECIES | TYPE | LENGTH | SEQ |
|---|---|---|---|---|

```
TTTTAAAAGCAAGCCTAATGTGTGGGCATACTTCTCTGTTA
AGGTATGTTGTTTAAGTTTTTCTGGGCTGGCTGCCCTTCTTT
GGGTTATTTCTTTGATTTCTATCAATTAATGTACAACAACAA
AAAAAATCTTTTAAGAGTTAATATAAACAAATGTTGGAAAC
AAATGTTCTGGCTAAGGAGATCAAAATATAAACTTTTGTGG
AAAAAAGTTGTGTAGTTTGCAATATGAATACAGTGTGATA
CTTAGTTGATTGTGTCTTCATTTTTGTCCTAATTAAATTATAT
TTTGTAATTATTAGACTAAATGTGCTTATACAGACAAATAT
TTTGTTTGCAGTCTGGTGGTGGCATCCATGAATTTTCTGAT
TCTCAATTTGGTATCTCCTTGACAATGAAAGAAGTTAAATT
CTTTTGAATGCTGTGAAAAACTCTTCTTAATATTTCCTATTC
TTCTCAGGACATGTTTTTGCATTTGGGGAATCTAGAGCCTT
GGCGATAGCTAACATGGTTCTTGGACTGAAGGAGATCCAA
ATTCGTGGGGAAATTCGAACAAATGTTGATTACACAATTG
ATCTATTAAATGTAAGCTCTTGATCTTCTTGTTACCTCTAAT
CCAACTTATTGCAATTGCACGTCTTTGTTCTCATCCGCTGCC
TCACAGGCATCAGAATACAGAGACAACAAAATCCACACTG
GTTGGCTGGATAGCAGAATAGCAATGAGGGTCAGAGCTG
AGAGGCCTCCATGGTACCTTTCAGTTGTTGGAGGAGCTCTT
TATGTAAGAATCGAAGCATAATGTAATCTAGTTATAGTTCT
GGTAGGTTAAGTTGTTATTTATATACTTGACTTATTTTGTGT
CTTCAGAAAGCAACAACTAGCAGTGCTGCCATTGTTTCCGA
ATATGTTGGTTATCTTGGTAAAGGTCAAATCCCACCAAAGG
TATAATGCATCCCAGCTGTTTATGTCGTATTTTATTTTCTTC
GATTAGTTCATTAACAAGGAAAAGCAATGCAGCACATTTC
GCTGGTCAAAACTCTTGTGACTCTGAATATTGAAGGGAGC
AAATACACGGTAAACTTCACTATTTCCAAAAGTTTTCATTCT
TAATTTTCTTTCAAGAGACACTTCACCTAAACTCCTTGCTGA
ATGTTTCTTAGATTGAAATGGTTCGAGGTGGACCTGGTAG
TTATAAATTAAAAATGAATGGTTCAGAGATTGAAGCTGAA
ATTCATACTCTCCGTGATGGTGGACTTCTGATGCAGGTAAA
CTTTCTAAATCATCATGTTCCATTGTGTATTTTTTTATTTTA
AACAATGACTAGCTAGTTTCAGTGGCAAAGCAAGCATTCC
AATATGCTAAGCCTGTTAACAGTATTGATGCTGCTGTAAAA
TTGCCCCGTATGGTCCATGAGAGTACAAATGGTATTACCAT
AGTGATCTGATTGTTCATTTGCATTTGATCTAACTTTCCAGA
ATTTCCAGTCTTCTTCATACTCTATTTTTCTTAATAAGATAAT
GTACCGACAACTTGATGATGGAAGCTTTGTAAGTACCTGA
AAATTTTTTAGGTATTGGTTCTGATTTCAGCACTAAGGTTTA
TACCATAAACTTCAATACTAAGTGGTCAGTTAAACTTTGGA
TCTTTGCACATCAGACTTGTCAGAACTGTTTTGTTTACAATC
ATCCACAATTGGTTATGGGGTGATAATTATGGATGCTTTGT
GATTGTTGGCCATCCTGCTGCTCAGAAATTATCTTGAACTT
TATTTGCCCCCAAATTTGAATCATCTTTTTTTTGGGAATTCT
CTTTAGTTTCTTTTCTTTCTGCACCAATGTTTTTGTTCTACAT
GCCCATATTGACTGCACTTGTGCACAACTGCACGTCTGCAC
GTCTGCACGCATATATCACTCTAGGAATACAGTTGATATTC
TCAATTCTCGATCTTGTCATATGGTTAAAGTAATTTAGCAG
TTCAGATCTTGAACATATTTAATTTCTAAAACTCTATGAAAT
TCATACAGTTGGATGGAAACAGCCATGTGATATATGCTGA
AGAGGAGGCTGCTGGTACACGCCTTCTTATCGATGGAAGG
ACTTGCTTGTTACAGGTAGAAACAACTTATATATTTTTCAA
AATTTTTAGTTTCTTGAAGGAAATTAAATTTATTTATTATCT
GCTAGTAGAATTAATGTAAGGGACCTTTTATGATGTTTTGA
CATTATATATTGAAGGTTCTTTGATTTATTAAAAAATGCATA
AGATAGATAGATTGCAGTATTGCACTTTGCATCTTTCAAGT
GCGCTTATGCTCAACATGCTTAAGGTGCTTACTGCTTAGAT
TGCCCAGTGCTGCTCAAAACTTGCATAGAACTGTGAAAACC
ATTATTTCTTTTGTTCTATCCCTAATGTGAAAGCTTCTGTGC
GCCTGCTCCGGCCCTACTCTAATCTTCATTAGCTTCTTTGCA
CTGATTTATGTGATATTTCTTGGACTGTTCATGGTCCTTGC
TAAGAGTTCCTAAGTATCTGATGTTTGTTTATGTTAATTTTT
GCATTCCATTCCTTTTAGTTCTAAATGATTGTTTCTATCGG
TCAAACTAAATGCTGCAACTTAGTTATCAGTTGCACTCACC
CTATTCAAATGAAATTTAAGGTACATTTCACAAATGGGATT
AACACATTAAAAACACTTTATGTGTTAACATGCTACTATTA
GAAATCCAGATATGTTATTTCAGAATCATAAAGCAACGTTA
GATGGCTTCATAAACTGTGAATAAGTGGTAAAGAATTCCTT
CCTAGATATTATTGAAGAAAGTTTCTCTTGAACAAGTTACC
TTAAATAATTAATCATAACTGGTTTTGTCTTCAGAATGATCA
TGATCCATCGAAATTGATTGCGGAGACACCATGCAAACTTC
TTCGCTACTTGATTGCTGATGGAGAGCATCTTGATGCTGAT
GCACCATATGCAGAGGTCGAAGTAATGAAGATGTGCATGC
CCCTTTTGTTACCTGCTTCTGGAGTTATTCATTTTGTGATGT
CTGAAGGTCAGGCTATGCAGGTAAGTAAACCTTGTAAAGA
TTAGAAAGAAAGTTTCTCTTGTGTTTTCTCATAAACTACATA
```

TABLE 1-continued

ACCase gene sequences isolated from weedy plant species

| SEQ ID NO | SPECIES | TYPE | LENGTH | SEQ |
|---|---|---|---|---|

```
GAATCTTGTTTTTGCAGGCTGGTGACCTCATAGCAAGGCTC
GACTTAGACGATCCATCTGCTGTAAGAAGAGCTGAACCAT
TCAATGGTACATTCCCTAAAGTAGGTCCTCCCACTGCAGTT
TCTGACAGAGTTCACCAGAGATGTGCTGCAAGTTTGAATG
CTGCACGCATGATTCTTGCAGGATATGAACATAATATTAAT
GAAGTAAGGGCTAACGATTAAACTTTTTTTTATTCTTTGTT
ATTTTTAATTAATTCAAAGTGCTATCTACTTTTATTTCTTTAT
ACTTTAAGTGGCATTTCTATTAACTAAAACATATGTTTTTA
CTACCCTTTGCCAATGTTGATTAGACCAAAATGGGTTTAAA
CTCTTTTATGATGCATTCTAATAATCTTTATTTGCTGAACCTT
TTTAGTTACTTTCAAATTTATGTAGAGATTAAAGCTTTTATT
CGAAAACGCCACCATACATACACCTCATCCTTGGAAAATGG
AATGTATACAATTTGCTGATTTTAGTTCCATCAAATCCCAGT
TTAGTCACAAGGAATCATGCTGATAAGATGCTAAATTTGTG
CTACCATGTGCAGTGATCCATGTCTGCAGCTTTGTATATAT
GCCTTGTGGAGATTAGACGTCCATTTGTCTTATCTTTTAGT
TTCCCCACCTTCAACTTTGGTGACCGCTGCCCTTAATGTTTA
TTTTAAGGAGAAGCATCATGCTTTTGAGAAATTGGTTGCTT
CTATCAGATGACTGAACACCTTTTTATTTTTATATATCTTGT
TCTAATCATGCTAAGTTTCATTGAATTTCTCTTTATGTTTTCC
AATTTTAAACTGATGGTTATGCTATGCCAAAGTGACTAGGC
TCTATTGTAATTTTAACTGCAAAGGGACTATTTGATGATTG
ACACTTTACTTTTTGTTTTAATTCTTTTAGTTTACCATTTTAT
ATACTTGTTACTTATATGAACTGCAACTTGCATTACTGTATA
CAATTTTAAAATTGTTTCTTTCCTTTATGCATATACTGGTTT
GCATTTTTTCTCTAACGTCCCAAGTATAAATAGGTTGTTCA
AGAGTTACTACATTGTTTGGATAGTCCGGAGCTTCCTTTTC
TACAGTGGCAGGAAAGTATGTCTGTATTGGCAACTCGCCT
GCCGAAAGAACTTAAAAATGAGGTTTGTGCATAGTTCTTA
ATTTTTTGTCAGAAGCACATAGTCTAGTTTCCAGTTGGACA
GTTGGATTGTACATTTCCCAAATTTAATAATTTTATGTGCAA
TTTCTTATTTGATACAGTTGGATTCTAAATACAAAGTATTTG
AAACAAACTCAAACGTTCAAAAGAATGTGGAATTTCCTGCC
AAGCTTCTGAGTGGAGTTATTGAGGTTAGTATGTTTTAGTA
TGAATATCACTCAAATAATAAGGTTTTAAAACTTTATTTCCT
CGATCTGCAGAGCTATCTCTCATCTTGTAGTGAGAAAGATA
AGGCGGCACAGGAAAGGCTTGTGGAACCACTTCTGAGCCT
TGCGAAGTCATACGAAGGTGGAAGAGAAAGCCATGCTCG
TGTAATTGTGCATTCTCTTTTTGAAGAGTACTTATCTGTTGA
AGAGTTATTCAGTGATAGCATTCAGGTGATTGTTTATCCGA
AGTTCATTCAAACTTTTTCGACTAACTCTTCCATCAAAATAA
ATACTAAAGGAACAAAACTGATTCTCAATGTTTTTGAAAGT
TTCGTTGCTCCAGCTAGATTTTCCAAAGGCCTTAACCATGC
ATTTTTCTTGTATAGGCCGATGTCATAGAACGCCTACGACT
TCAATACCAGAAGGATCTTCTGAAAGTTGTAGACATAGTG
CTGTCTCATCAGGTATATTTGCAACGTCTGAAGTTGTTTTAT
TTTACTCCATAGAATTGACCAATTCTCCTTAAAGTAACATGA
ATGCTGATAATTCACCTTTTAGTTTCTCTGTGGATGAGATA
CATCTCGTATGCTAGTTTTTCCATTAACAATATGCCGTTTTT
GTTTACTAAAGGGTGTTAGAAGTAAAAATAAGCTGATACT
GAGGTTGATGGAAGCATTGGTCTATCCTAATCCTGCTGCCT
ATCGGGAACAACTGATTCGCTTCTCTGCTCTTAACCATACC
ACTTACTCCGAGGTCAATAATCTTACTGGATATCTTGCACC
TATCCCTTCATGTTTGTAATTCTTTTGCTCACATTGGCCTATC
CTTACTCGTGCTTGGTCAATATGGTTCCTGCAGTTAGCATT
GAAAGCCAGTCAACTCCTTGAACAAACTAAATTGAGTGAG
CTTCGAACAAGCATTGCCAGAAGCCTTTCCGAGCTAGAAAT
GTTTACAGAAGAAGGTGAACGTCTATCTACACCGAGAAGG
AAAAGTGCTATCAATGAGAGGATGGAGGATCTTGTAAGTG
CTACGCTGGCCGTTGAAGATGCACTTGTGTCTTTGTTTGAT
CACACTGATCCAACTGTTCAGAGACGAGTGATGGAAACAT
ATGTCCGAAGATTGTACCAGGTACCAAACTGAAGTAATAT
GGTAACAAACATGTAGCTGTTAAATATTTATCTGACACTGC
TTTTTTCTCAGCCCTACCTTGTGAAGGATAGTGTCCGAATG
CAGTGGCACCGTTCTGGTTTGATCGCGACATGGGAATTCA
CCGAAGAACATATTGAGAAAAGAATGATTCTTCTACACA
AGATAAGTCATTTATGGAGAAACATTGTCAAAAGAGATGG
GGAGCTATGGTTATCGTCAAATCTCTCCAGTTTCTTCCAGC
AGCAATTAGTGCAGCATTGAAGGAAACCAGTCATCTGTCA
TCTGATACTGATCATGATACAGTATCTAATGGGCTTCCTCA
ACATGCTAGTCAAGGCAATATGCTTCATGTTGCATTGGTTG
GCATTAACAATCAAATGAGTACACTTCAGGATAGGTAACTT
AATTATTCTTGAATATTTCCATCATATGGTATGTTTGGGTA
ATTTGATCATTTAGTTATGAAAGGTGCAGTCTTGTGCTTAT
CTTTGAATCTTTTTAATGGACAAATGTTCCTTGATCATATTA
CAGTGGAGATGAGGATCAGGCTCAGGAGAGGATACACAA
```

TABLE 1-continued

ACCase gene sequences isolated from weedy plant species

| SEQ ID NO | SPECIES | TYPE | LENGTH | SEQ |
|---|---|---|---|---|

```
GCTTGCCAAGATTCTAAAAGATAACAAGGTAGCGACTGAA
CTTTCCAATGCTGGAGTCCGAGTTGTTAGCTGTATTATACA
AAGAGATGAAGGACGAACACCTATGCGTCACTCCTTCCATT
GGTCTGCCGATAAGCAATGCTATGAAGAAGAACCCTTGCT
TCGTCATCTGGAACCTCCTCTGTCTACTTTCCTTGAATTGGT
TGGTGAATGTTTTTAACTTATTTTATTCACATCTTTATTGTA
ATTCCCTTTCTCTGATTAATGCCATTTGTTATTGATTCCATTG
CAGGATAAGCTGAAAGGCTACAAAAATATACAATACACAC
CATCACGGGATCGCCAGTGGCATATGTACACAGTTCAAGA
AACTAAACCACTTAATCAGAGGATGTTTCTGAGGACCCTTG
TCAGACAACCAAGGATAAATAATGGATTTTCATCAAACCA
GCTTCCCGAATTAGAAACTAGACATGATTTATCCTTTACAT
CAGTCAGCTTGTTGAGATCTTTGATGGCAGCATTGGAAGA
GTTAGAACTACATGTCCATAGCGAAACAATCAGATCTGATC
ATTCTCACATGTATCTCTGCATATTACAAGAACAACAACTCT
CCGATCTTTTACCTCGTTCAGGGTAAGTCTTGTTGTCTAGTT
AGTTTGGTGTATTCTTCTGAAAAATGTTTGTTTGTAGATTA
AAAAAAAAATGTAGTGTTTTTGGCTAAACTGATTTCTCCTT
TGCTTTGGCTAAAACATTTTTTGGAAGTTTCCATGTTTTGG
AAATTATTCTTTAAGGGCTGTTTGGATACCTATAATGAGGG
TTATAATGTGGATACTTGTAGTTAGTGATTTTAGTGTAGTT
GGAAAGTAAAACATAGGTGGTAAACTACATCTCAACATCT
CCAAATTTGGTGTTGTTGCTATGATGTAGTCACATGACGTG
CCAATTTTGGTGTAGTTCCCAAAATTTTTTTAGGTAAAATA
TATTTACAAATATCGCACAAGTTTATTCATCTATTAGTATTT
CGTGTAAAGATATCTATAAAATTAAGCAAACAATGAAGTT
GTAGTTCTTTTCAACTATAGCTACATGCACTATCAACTAGA
ACTACAAGCATCCATGTCACAATGTTCATTAAGTTAAATAA
TATAATTTTAAAATAATTTTTATTTATTTATTAAAATATAGTC
ATGAGGAGACTTTCGAAAATAAATTTCAGAACAAACAAAC
GCATTTTTTATTCCAAAATATCATATTGTTGCTTTTAGATAA
CTATTTACTGAGAATGAATTTGAACATTGTTTCAAGAAACC
CTTCAAAACAAGCAAAGTAAATTTGTGTTCTCATCTTCGTG
CTCTAGATACTTTGTTCATTTACTTCTTTCGTTAGTCATTTTT
TGAAGTTCTAACTAACTCAAGCATTCAATTTGTCCAGTACT
CTTGATCCTGATGCCTATCAGAATGAAAGTCAAGTGTCCCT
GCTTTTAAAAGATATGGCTGTCAGGATTCATGAGATAGTT
GGTGTAAGGATGCATCGTCTTACTGTTATTGAGTGGGAGG
TAAAGCTCTGGTTGGGTTCTGATGGTGTTGCTGGTGGTTCT
TGGAGGGTTGTGGTGACAAATGTTACTGGACGTACATGTA
ATGTCCATGTAAGTGCGATTGATTCACTTTGTCTAAGACTT
TACTACTATACTTGCATGGTTAGACATAATATTTCATTTCCT
TATGTAGGTAACGTTTTCTAGCATAGCTAATTGTTTGACTA
GGACTATATTAACTAATTGTAAAAATTGAACTTTTGCCATT
AGAGCAGTTAATTAATAGATATTGCTCTAGCCCGTAATTTT
GCTTTCATTTGATTGTAAAATACTCAGTAAGTTTTTGCTTCA
GATTTACCGAGAATTGGAGGACAGCAAATCACATGAAGTG
GTCTATCACTCTGCAGCTTCAGTCACAGGACCTCTCCATGG
TATGCCGTTGATTGCTAGATATCAGCCACTTAGTGTTATTG
ATAAAAAACGATGGGTGGCAAGAAGGAGCAACACTACTT
ATTGCTATGACTTTCCACTGGTATAGCTCCCAATTCCTGATT
GATATACTCCCAGTTTTCTTGTTTTGATACTTCAATACCTTA
CTAATTAATATGTGCAGGCGTTTGAGACAGCACTGAAGCA
GTCATGGGCTTCTTATAGTGATACTAAAGCACCAGAAAGC
AAAGCTCTTCTCCAAGTTCAAGAACTTATGTTTGTTGACAA
AAAGGGATCATGGGGTACTCCTGTTGAACCTGTATGCTGC
CCACCTGGTCTCAGTGATATTGGCATGGTTGCTTGGTCAAT
GGAAATGTACACACCAGAATTTCCCGAAGGAAGGAAGATT
GTTGTTGTAGCCAATGATTTGACTTTCAAAGCAGGCTCCTT
TGGGCCTCGTGAAGATGCATTTTTCCATGCTGTAACCAATT
ATGCATGTGATAAGAGGCTCCCTCTAATCTATTTGGCAGCA
AATTCTGGCGCCAGGATTGGTGCTGCTGAAGAGGTCAAGT
CTTGCTTTAAGGTTGGATGGTCTGATGAGTCGAGTCCAGA
ACGTGGTTTTCAGTATGTGTATCTGACACAGGAGGACTAT
AACCGTATTGGTTCATCTGTTATTGCACATGAACTGAAGCT
TGAAAGTGGTGAGATCAGATGGGTGATCGACACAATTGTT
GGCAAAGATGATGACTTGGGTGTTGAGAACCTCACTGGCA
GTGGTGCAATTGCCGGTGCTTATTCCAGGGCTTATAACGA
GGTATTTACTCTTACATATGTGACTGGACGTACTGTAGGAA
TCGGAGCCTATCTTGCTCGGCTTGGCATGAGGTGTATCCA
GAGGCTAGACCAGCCTATAATCCTAACAGGGTTTTCTACAC
TCAACAAGTTGCTTGGCCGTGAGGTGTACAGCTCACACAT
GCAACTAGGTGGCCCGAAGATCATGGCTACAAATGGTGTT
GTTCATCTGACGGTATCAGATGATCTTGAGGGCGTTTCTGC
TATTCTTAAGTGGCTTAGTTACGTACCACCCTATGTCGGTG
GGCCACTTCCAATAATAAAATCCTTGGATCCCCCAGAAAGG
```

TABLE 1-continued

ACCase gene sequences isolated from weedy plant species

| SEQ ID NO | SPECIES | TYPE | LENGTH | SEQ |
|---|---|---|---|---|

```
CCAGTGGAGTATTTTCCTGAAAATTCATGTGATCCACGGGC
CGCAATTTGCGGCATTGATGATGGCAATGGCAAGTGGTTA
GGTGGTATGTTTGATAAAGATAGTTTTACGGAGACATTAG
AAGGTTGGGCAAAGACGGTGGTCACCGGAAGAGCAAAGT
TGGGTGGAATTCCAGTAGGAGTTATAGCTGTCGAGACACA
GACTGTGATGCAAGTCATTCCTGCAGATCCTGGTCAGCTTG
ATTCCCATGAACGTGTTGTCCCACAAGCTGGTCAAGTTTGG
TTCCCTGATTCTGCCACCAAAACGGCACAAGCATTATTAGA
CTTCAATCGTGAAGAATTGCCACTTTTCATACTAGCCAACT
GGAGAGGATTCTCAGGCGGACAGAGAGATCTCTTCGAAG
GTATACTTCAGGCTGGTTCCACAATCGTCGAAAACTTAAGG
ACATATAAGCAGCCTGTATTTACCTACATCCCAATGGCCGG
GGAGCTTCGTGGTGGTGCATGGGTTGTGGTGGACAGCAA
AATCAACCCGGATCACATCGAGATGTATGCCGAAAGAACA
GCAAGGGGCAACGTACTTGAGCCCGAAGGAATGATTGAG
ATTAAGTTCAGAACTAAAGAACTTCTCGAGTGCATGGGTA
GACTTGATCCTGAGCTAATCAGTTTGAAAACAAAGCTTAG
GGAGTTGAAGGCAGCTGGACCTTCCAGAGATGTGGACGT
CCTCCAGAAAAGTGTAACGGCTAGAGAAGCAGTTATTG
CCTGTATATACACAAATTGCTATAAAGTTTGCAGAGTTGCA
CGATACATCCTTGCGAATGGCTGCCAAAGGTGTGATCAAG
AAAGTGGTAGACTGGGAGAACTCCCGTTCTTTCTTCTACAA
AAGGTTAAACAGGAGAGTTTCCGAGGATGTCCTTGCAAAA
ACTGTTAGAGATGCTGCTGGGGAGCAGTTGTCGTACAAGT
CTGCTATTGAACTGCTTAAGCAGTGGTTTTCATCTTCCGAC
AATGTGGACGTTGGAAAATGGGAGGAAGACGATGCTTTCC
TTGCCTGGAAAGACAACCCTAAAAATTATGCCAAGTATCTT
GAAGAGCTACGAGTTCAGAAGATATTGCAGCAGCTCTCAG
CTCTTGGTGAATCATCTTCGGATTTGCGAGTATTGCCTCAA
TGTCTTGCTACAGTCCTTAGCAAGGTACAGTTTCTTTCATTG
TGCATTCAATTTCTCTTTTCAAAATATAGACATATAGTTAGA
TTTTTACTTAGTTTTGCATCATTTTCCCTGCAACATGGTAAA
CATTTCTCTATAAGTATTTTAATATCACTGCAAAATATTCAA
TAATGTTCCTGAACTTGTTCGGAGCGCCTTGATTAGTAGCT
ACACTAGCATTGCGATCTCACAGTAAAAGCTATCATTCTCT
TTGAAATAATTCTTTTAACTCTGGGTAGATATTTTTTCTTCT
CTCAACTATATCTTGAAAATTTGTGCGATAAATTCCTAACAT
GATTATTGCTTGGCATTGATGCAGATGGACTCGTCTAGTAG
AGCTGATCTTGTCAAAGAAATCAAAGATATCCTTGGTTGAT
CAATTTGACCTTATATATGGTGCACCGCAACAAATTAATGT
GATGAACATCCCAGTAATGCCTTCTCAAGACGTTGAACGCA
AGCCAGTATATTATATCTTTTTTTTCCCCGACAGAGTATCTA
CAGCTCCTACCAATTTCAGGATATTTAATCATATTTTTCCTT
GCGTAGTTCATATAGAAACGACATTACTTCAGTTCACCTGT
AGATAAGTTGAATGTTGTCATTCAAGCAGGATGTAGCAGT
CCACAACATTTGTATTTTTTATATTTCGAGATTCAGCTGTAA
GGAATAATGGCTGTATTATTTTCTCTAGGAATGAAGAGTAC
ACTTTATTGCCCAATAAAAGAAAGAAATGTCAGGGATTGTT
TCAATGGAATTCCAAACTGATCTCAACTACATTAGGCGTGG
TTAAAAAAAACTACACTACGTCTGTTGCCAAATATAGAAA
AGTATTTTTAGGAATATTTAGGCTTTGTTTGGGAAACATAA
TGACTTAATACAATAATTGTGTAAACACAAGTAATTAATTA
CTATATTTGGATAACACTTTATAATACAAAGTCTCTCACTAC
AAATGTAATGTTTATTATCTCATAGGAGCAAAAAAAAAAA
AAAACTCTTAGGAGGTCGTGTGTAAATGTAATGTTTATTAT
CTCATAGGAGGTCGTATTCATTACACAGACATATAATCCCA
TCATAAGATATCTCTCATGTTTACTAAAAATTTTCATTTTAA
AATTTAAACATAAATGTTATTACTAATAATATATACATTCTT
TATTTATTATTTTTATTATATTACACGTATTTTAGCCAATGTT
GTAAGTCACTACATTACAAATTTTGTAAATGATTTAATTAC
GTTGCAAATCATTTTATCCTTCCCAAATAAGGCAGAATCAC
TTTGTCATTTCATGTGATTAAAAAAATAAGAGGTCAGAGAT
AATTACTTGGACTTGATATTATAGTAATTTTGCATGATATCT
TACCCATTCTATGATATTTAAACACTCATATTTGGACGTCAT
GGGATCCTATGGAATAATGGAAATAACTCAATGCTCATGA
ACTGGGCAAAACAATTAGCTCTTACCTTTTCTTTTTTTCCC
CTAACAAGATGATTCTATGATGTAAATAACTTTACTGATTTT
TTTTTATTTGCTTAACACACTCTCAATCTATATGGTAATGGG
CTAAAATCTTTTGCTCATGAGATTCAAATATTTCTCGCGAG
ATTTCGTTATTGCCAAACAGGTCTGTTCTTTTGTAGTTACTT
AAATAATCATAAACTTTAGATAAGACCAACTTAATTTAAGT
TAATCAACATCATCAACTGAATATTAACTTTACTAACACAAT
GTCCGTAATGGCATGTTTTGCTCACTTGAAATAAAAAATTA
AAAAGAATATATAAGTAGCATTCGAAATTAATACTACGTC
CAATTAGAGTTAACATTATGACAACAATACGACAATATCCA
AATTACCATCTTTGCTCCTCTGTCTCCAAAAACTAATGTTAT
```

TABLE 1-continued

ACCase gene sequences isolated from weedy plant species

| SEQ ID NO | SPECIES | TYPE | LENGTH | SEQ |
|---|---|---|---|---|
| | | | | TCATCTCGCTGCCCCCAACCATTGAACCAATTGATATTCTAA
CCTTAATCAATCAATTCTCCCACTCTCACTGACAACTGGACT
CTGACCTCAGTTGGTGGCACCTCCGTCGTGGGCTTCTTCAC
TCCTTACAACTCTAATAACTCCTAGCTTAATTTTCAGTACAA
AATCACAGTCCAAAATGTTGTATGGATAGCAAACAAAGTT
AAACCCATAATCCAAGGGCAGAATAACAAACTCAAGCGAA
TCGGAGAAGAGCAGGACCGAGCACGAGATCTGGTCGACT
GAGCTTGAGTGGGCCAAGCTTAAGCTTGCGATGGAGAAG
AAGTGCGCCAGAGAAGAGGGGCACACCTGGATAAGGAAG
GCGAGATACACGAGCATGACCAAATCGAAAATGAGCTGG
AGGGGAAGGGAGGAGGAGAATAAGGGAGACATGAGAGG
AGGGGAAGGATAACAAGAGGGAGA |
| 64 | Commelina diffusa | gDNA Contig | 3209 | CAAGTAATTATTATATAATTTTCACCCTATTCCATTTTATTTA
TTTTTAATTTATTGACTATAAAAGTTACATAATACTGTACTT
TATTTTTGTTTACTTTTATTGAAGAAAAAACAGCCCTTCTCT
CCCCTCACAAATAAATTAAAAACAATTAATTTCCAATATTA
GAGAACCAAAAGTAATTCCCCTTAATGACAATTTAAAAGA
AAGAAATAAATACAACCAACCTCTAAATCACACACATATTC
ATATATTTATACAAATAAAATAAATAGAGGGAGAGAGTAG
TTGGCCATCAGCCCCACCTAACAAAAACAAGTCTAGAGTCA
AAATTGGGACACGAAGATGTCATCTTCATTGTAAAATCAAA
TGTTAATTAAACCCCAAAAATAAATGTAAGCACAAGATGT
TTGAACAAGCACTTTGATTCCCAATTTTCACCTCAGGGGAT
CAAAAAGGCACCATCTTGACAATTATATATACACACTCT
ATACAACATTGTTGTGGTAGTTGGCAGCTGTGGCTCT
GAATTTCAATTCCTTTGTTTGCCCTTCAATTCCCTGTTGCTG
TTGTTGGTGAGGAGAAAGGAAGCTGGCGTCACGTGGTGC
TGCTGTCCATACCATTTAAGGCCCTCGCCGTCTCCCCACCCC
ATTGGTGCCCTTTTCCCCCTTTTTAAATACTGCTTTTTTGGT
GATTTGGTGAATGGTGTGGTGAGGAGTCGTCAAAATCCCG
CCTTTTTGCTGGGATTGTGCTCGTCTTAGCTCCCCTGAGCT
GTTGGTTGTGTAAAGGTGCGATCTTGGTGCGTTTTGTTGG
GTGAATTCGAGCTCTTTGTCGCTGTTTAGGGTTCAAGATTG
CGCTTTTTTTTTTTTGCCCTTGTTAGTGTTGGTAGTTGTTA
GTCCACCGGCTGATTGAATTGTAGCTCTTTGGCACTGTTTG
TGTGAGTGATCTGCTTTGCATCAGGGGACTACAAATTTCAT
TTTAGTAGTGTTATGCTGGAATTTTGGTTCTGCTGATTGGG
TTATTGCGCCTGTGTTATTTTGTCTTGTGCGTCTTAAATTCT
GTCTGTAGTTTAGTGTTGTAACGAGTGCTTCTCGCTTCTAG
ACTTTGTTTGTATCTTCTGTGTCTTGATTATTGTTACTATTAT
TATTTTATTTTATTTTTGGTTAGTGAGTCAACCTATGGGGTT
AGTAATAAGACATTGTTTCAGTTAGTTATGTGAATTGGTAA
CTCTTAATCTCGTTTAGAAGATTGGTGAGTTAGTTTTTACCT
GGTTCTGTACATTCGAATAGCTTTTACTGTTGATTTGCTGCA
TTTTTACCAAATTCTTTGTCGCTTTTTTGGTGTAAAGCAAGA
ATGAGAAAAATGATACTTGATTGAATTATGGGTTCCCAAAC
CAAGTAATAATTTGGGAATTGCTTTCTGATAACTCTTTATTG
GTGGAGCTTTGGTACTAGGATATATATGTATATATATGATT
ATATCATATGGATAGCAACTGGGTAGTTGTTCAGTTAGAAT
CTTGGTCGTTAAAAGAAAAAAGAATGAATTGAATATTCATT
TATTTGAGCCTATGAGGATAATTTGTTAACTGAAAATGGTT
TTGTTCGAGTGGTAGGGATGTCTAAGGAGCCATGTAGTTC
GTTTAGTTTGTTATTCTATTTTCATTCTTATAAAGAAATTTA
ATTTATCATGAAAGCATTGGGACCAGTTGTATAAATAGTTC
TCCTTTTTACTGCAAATGGCAGTTACATAAAGAATCTATTA
CAAGAATATGCTTATTAGGAGCTGGTTTATATTTTCAGTTT
GCACTTTTCTGTGTTTACTAAAGAAACAAGTTATTCTTGTG
CCTTTCTTACCTGACGTCAGAGAATGATATTTTCTTGAAAG
TCAAATGTTGCTTATTATATATCCCGTCACTTTGCGTGTATA
TTGATGACACTGATTAAATATCTATGTAGAACGCCTGAAGC
CCAGAAGGGAGCAGTTATGGCAGATGTCTGGCAAGATCAT
GGGATTTTAAATGGGACAGTTCAAGTCAAACATGCAGCTA
CAACGTCTGAAGTTGATGATTTCTGTTATGCACTTGGTGGA
AAGAGACCTATTCGCAGCATATTGATTGCTAATAATGGAAT
GGCTGCTGTCAAATTCATGCGTAGTATTAGAACCTGGGCTT
ACGAAACATTTGGATCAGAAAAGGCAATTTTGTTGGTTGC
GATGGCAACTCCAGAAGACTTGAGGATAAATGCCGAGCAC
ATTAGAATTGCTGATCAATTTGTAGAGGTTCCCGGTGGAA
CCAATAATAACAATTATGCAAATGTTCAACTCATTGTGGAG
GTCAGTTTTGCTTACTTTTTGGCTGACATTACTTTGATTGAG
CATTTTGATTGTTTCTTTTCTTGTTTGTGCTGATTTTGACAAC
ACACTTTGTGACAGCTGGCCGAAATAACACGTGTTTCTGCA
GTTTGGCCTGGATGGGGCCATGCATCCGAGAATCCCGAAC
TTCCAGATGCCCTGAATGCAAAGGGAATAATCTTTCTCGG
GCCTCCAGCTGCGCCAATGTCAGCACTAGGTGATAAAATT |

TABLE 1-continued

ACCase gene sequences isolated from weedy plant species

| SEQ ID NO | SPECIES | TYPE | LENGTH | SEQ |
|---|---|---|---|---|
| | | | | GGTTCTTCTCTAATTGCTCAGGCAGCAGGTGTACCAACTCT |
| | | | | TCCGTGGAGTGGCTCACATGTAATCTTACTTGCTAATTTGC |
| | | | | AAATACATTATTTCATATTTCTCATTCTTTCACCAAAATTTAC |
| | | | | ATGTGAAATTATCTTTTAGGTCAAAATTTCAGCGGAAAGTT |
| | | | | GTATGGACACAATACCCGAAGAGATATACAAGCAGGCTTG |
| | | | | TGTTTATACAACAGAAGAAGCAGTGGCCAGCTGCCAGGTA |
| | | | | GTTGGCTATCCTGCCATGATAAAGGCATCTTGGGGCGGTG |
| | | | | GTGGTAAAGGAATAAGAAAGGTATAGCATAAAAATAATCA |
| | | | | GTAGTAGTTCTTTTATTCTCTCCAACAATGCTTACAGAAAG |
| | | | | GGTGGCAAATAGATTAGTGCAATGCCTGTGGCTATATATG |
| | | | | CCAAAGAAGGTAGAGAAACGCTGAAACGGATATTGTTTCT |
| | | | | TAATATTTTTGAGGTTATGATCTTATTTTGGTGTTCAGTCAA |
| | | | | CTCCTGAAGTCCAACAATAATGATGTAGCCATATGTATTA |
| | | | | TCTAAACATGATTCATTTGTTTATTCATGGTTGTCATTACAA |
| | | | | ATGGAATTACAGTACTCGTTATGATATGCAAATTAAAAAAA |
| | | | | AAAAAA |
| 65 | Digitaria sanguinalis | cDNA Contig | 1629 | GTTGTTGCAAATGAATGTGACATTTAAAGCTGGGTCCTTT |
| | | | | GGTCCAAGAGAAGATGCGTTTTTTGATGCTGTTACCAATCT |
| | | | | TGCTTGTGAGAGGAAACTTCCTCTTATCTACCTGGCTGCAA |
| | | | | CTGCTGGTGCCAGACTTGGTGTAGCAGAGGAAATAAAGG |
| | | | | CATGCTTCCATGTCGGCTGGTCTGATGATGAGAGCCCTGA |
| | | | | ACGTGGTTTTCACTACATCTACCTAACTGAACAAGACTATT |
| | | | | CACGTCTAAGCTCTTCAGTTATAGCTCACGAGCTGAAACTA |
| | | | | GAAAATGGAGAAACCAGATGGGTGGTTGATACCATTGTTG |
| | | | | GGAAAGAGGATGGACTTGGTTGTGAGAATCTACATGGAA |
| | | | | GTGGTGCGATTGCCAGCGCGTATTCTAAGGCATACAAAGA |
| | | | | GACCTTCACCCTGACATTGTGACTGGAAGAGCTGTTGGC |
| | | | | ATTGGAGCTTACCTGGCTCGTTTAGGTATGAGGTGCATAC |
| | | | | AACGTCTTGATCAACCAATTATTTTGACTGGGTTTTCTGCAT |
| | | | | TGAACAAGCTTCTGGGACGGGAGGTATACAGTTCTCATAT |
| | | | | GCAATTGGGTGGCCCCAAAATCATGGCTACAAATGGTGTT |
| | | | | GTCCACCAGACCGTGTCAGATGATCTTGAAGGTGTTTCTGC |
| | | | | TATCCTGAAATGGCTCAGTTACGTTCCTCCCTATGTTGGTG |
| | | | | GTCCTCTTCCTATTATGAAACCCTTGGACCCACCAGAAAGA |
| | | | | CCTGTAACATACTTCCCTGAGAATGCATGTGATGCTCATGC |
| | | | | CGCTATATGCGGCATTCAGGACGGTGAAGGCAAGTGGTTG |
| | | | | GGTGGTATGTTTGACAAGGAAAGCTTCGTGGAAACATTGG |
| | | | | AAGGCTGGGCAAAAACTGTTATCACCGGGAGAGCAAAACT |
| | | | | TGGTGGAATACCAGTTGGTGTCATAGCTGTGGAAACCCAG |
| | | | | ACAGTGATGCAAGTCATCCCTGCTGATCCAGGGCAGCTTG |
| | | | | ATTCCGCTGAGCGTGTAGTCCCTCAAGCAGGACAAGTGTG |
| | | | | GTTCCCTGATTCTGCCACCAAAACGGCTCAGGCATTGATGG |
| | | | | ATTTCAACCGTGAGGAGCTTCCACTTTTCATCCTTGCAAATT |
| | | | | GGAGAGGTTTCTCTGGTGGACAAAGGGATTTGTTTGAAGG |
| | | | | GATACTTCAGGCTGGTTCAACAATTGTTGAGAATCTGAGG |
| | | | | ACATACAAGCAGCCTGCTTTCGTATATATCCCAATGGGTGG |
| | | | | AGAGCTGCGGGGAGGAGCCTGGGTTGTGGTGGACAGCAA |
| | | | | GATCAATCCGGACCACATTGAGATGTATGCGGAGAGGACT |
| | | | | GCGAAAGGCAATGTCCTTGAGCCAGAAGGATTGGTGGAG |
| | | | | ATCAAATTCAGGCCAAAGGAACTGGAAGATTGCATGCTAA |
| | | | | GGCTTGATCCAGAATTGATTGGCCTGAATGCTAGGCTGAA |
| | | | | AGAGTTGAAGAAGCAAAATGCCAGCAACTCGGAAACGGA |
| | | | | GACCATCCGTAAGAGTATGACAGTTCGGATGAAGCAGCTA |
| | | | | ATGCCTATATATACTCAGGTTGCCACACGGTTTGCTGAGTT |
| | | | | GCATGACACCTCCGCTAGAATGGCTGCAAAAGGCGTAATT |
| | | | | GGTAAGGTTGTTGATTGGGAGGAGTCTCGGGCCTTCTCTA |
| | | | | CAGGAGATTGCGAAGGAG |
| 66 | Digitaria sanguinalis | cDNA Contig | 1468 | CGTGGTGTAGATGACAGCCAAGGGAAATGGTTGGGTGGT |
| | | | | ATGTTTGACAAGGACAGCTTTGTGGAGACATTTGAGGGAT |
| | | | | GGGCAAAAACAGTGGTTACTGGCAGAGCAAAGCTTGGAG |
| | | | | GAATTCCTGTCGGTGTCATAGCTGTGGAGACACAAACCAT |
| | | | | GATGCAGCTTGTCCCTGCTGATCCAGGCCAGCTTGATTCCC |
| | | | | ATGAGCGATCTGTTCCTCGGGCTGGACAAGTGTGGTTCCC |
| | | | | AGATTCTGCAACCAAGACAGCTCAGGCATTGTTGGATTTCA |
| | | | | ACCGTGAAGGATTGCCTCTCTTCATCCTTGCCAACTGGAGA |
| | | | | GGTTTCTCCGGTGGACAAAGAGATCTGTTTGAAGGAATTC |
| | | | | TTCAAGCTGGGTCAACAATTGTTGAGAATCTTAGGACATAC |
| | | | | AATCAGCCTGCATTTGTCTACATTCCTATGGCTGGAGAGCT |
| | | | | ACGTGGAGGAGCATGGGTTGTGTTGATAGCAAAATAAAT |
| | | | | CCAGACCGCATTGAGTGTTATGCTGAGAGGACTGCAAAAG |
| | | | | GCAATGTCCTTGAACCTCAAGGGTTAATTGAAATCAAGTTC |
| | | | | AGATCAGAGGAACTCCAAGACTGTATGGGTAGGCTTGACC |
| | | | | CAGAGTTGATAAATCTGAAAGCAAAACTCCAAGGTGCAAA |
| | | | | GCTTGGAAATGGAAGTCTACCGGACATAGAATCCCTTCAG |

TABLE 1-continued

ACCase gene sequences isolated from weedy plant species

| SEQ ID NO | SPECIES | TYPE | LENGTH | SEQ |
|---|---|---|---|---|
| | | | | AAGAGTATAGAAGCTCGTACGAAACAGTTGTTGCCTTTATA<br>TACACAGATTGCAATACGTTTTGCTGAATTGCATGATACTT<br>CCCTCAGAATGGCAGCTAAAGGTGTGATTAAGAAAGTTGT<br>AGATTGGGAAGAATCACGTTCTTTCTTCTACAAAAGGCTAC<br>GGAGGAGGATCTCCGAAGATGTTCTTGCAAAAGAAGTAA<br>GAAGAATAGCTGGTGACCACTTCACTCACCAATCAGCAGTT<br>GAGCTGATCAAGGAATGGTACATGGCTGCTCAACCAACAA<br>CAGGAAGCACTGAATGGGATGACGATGATGCTTTTGTTGC<br>CTGGAAGGAGAATCCTGAAAATTATAAGGGATATATCCAG<br>GAGCTAAGGGCCCAAAAGGTGTCCCAGTCGCTCTCCGATC<br>TCGCAAACTCCACTTCAGATCTAGAAGCATTCTCTCAGGGT<br>CTTTCTGCACTATTAGATAAGATGGAACCCTCCCAGAGAGC<br>CAATTTTGTTCAGGAAGTCAAGAAGGTCCTTGGTTAATTGG<br>ATCATACCAACACAATGTGTATGCAACATGTTTTTTGTTGA<br>AGTACATACATAGAAGGCCCTTGATGAGATCTGATCTGAA<br>TCTACCATTATTTGTTAAAATTTGTTTGGTTGGACGATCATG<br>TGGTTGAGTAAGTGCTAAGTTGTCTCTGTAGTTCTGGGATG<br>TATTACCAGCAGTTCGATTGTGTAATTTTAGAGTGTATCAT<br>GCGGATATTACATTCAGTTGAGTGGTTCATTAAATTTTGAA<br>CTCGAATAATTT |
| 67 | Digitaria<br>sanguinalis | cDNA<br>Contig | 1194 | GCAAGCGAACTTCTTGAACAAACTAAACTAAGTGAACTCC<br>GTGCAAGCATCGCAAGAAGCCTTTCTGATCTGGGGATGCA<br>TAAGGGAGAAATGACTATTAAGGATAGCATGGAAGAGTT<br>AGTCTCTGCCCCATTGCCTGTTGAAGATGCACTTATTTCCTT<br>GTTTGATTACAGTGATCCAACTGTTCAGCGGAAAGTGGTT<br>GAAACATACATATCTCGATTATATCAGCCTCTTCTTGTGAA<br>GGATAGCATCCAAATGAAACTTAAGGAATCTGGTGCCGTT<br>GCTTTTTGGGAATTTTCTGATGAGCATGCTGACACTAAAAA<br>TGGACAAGAAGCTGTTCTTGGTCAAAAGAGATGGGGGGC<br>CATGGTTGTCATCAAATCACTTGAATCTGCGCAACAGCCA<br>TTGTAGATGCATTAAAGGATTCGGCATGGCAATCCAGCTCT<br>GAGGGCAACATGATGCACATTGCATTATTGAGTTCTGAAA<br>ATGAAAATAATATCAGCAGTGATGATCAAGCTCAACATAG<br>GATGGAAAAATTACCAAGATATTCAAGGATAGTGGTGTT<br>GTAAACGATCTCCGATCTGCTGGTTTGAAGGTTATAAGTTG<br>CATTGTTCAAAGAGATGAAGTACGCATGCCAATGCGCCAC<br>ACATTCCTCTGGTCAGATGAAAAGAGTTGTTATGAGGAAG<br>AACAGATTCTCCGCCATGTGGAGCCTCCCCTCTCTGCGCTT<br>CTTGAATTGGACAAGTTGAAAGTGAAAGGATACAATGAAA<br>TGAAGTATACTCCATCACGCGACCGTCAATGGCATATCTAC<br>ACACTAAGGAATACTGAAAACCCCAAAATGTTGCATAGGG<br>TATTTTTCCGAACTATTGTCAGGCAACTGAATGCAGACAAC<br>AAATTTGCATCAGCCCAAGTTAGCAACACTGAAGTTGGAG<br>GTCTGGAGGAATCTTTGTCATCTACATCAAATAGCATTTTA<br>AGATCGTTGATTACTGCTATTGAAGAATTAGAGCTTCATGC<br>GATTAGGACAGGTCATTCTCACATGTATTTATGCATATTGA<br>AAGAACAAAAGCTTCTTGATCTCATCCCCTTTTCAGGGAGC<br>ACAATTGTCGATGTTGGCCAAGATGAAGCAACTGCTTGTTC<br>ACTTCTAAAATCAATGGCTCTGAAGATACATGAACTTGTTG<br>GTGCACAGATGCATCATCTT |
| 68 | Digitaria<br>sanguinalis | cDNA<br>Contig | 586 | GAGAAGAAAAGGGGTATCATGGTTGTAATCAAGTCTCTCC<br>AGTTTCTAGCAACTGCAATTGATGCTGCACTGAAGGAGAC<br>CTCGCAATATAGAGCAGGTGCTGTAAGTGTCTCGAATGGT<br>AACCATGTAAATTCAAATCAAAGCAATATGCTGCATATTGC<br>TTTTGGTTGGTATCAGTAATCAGATGAGTACACTCCAAGACA<br>GTGGTGACGAGGATCAAGCACAGGAAAGGATCAACAAAC<br>TTTCCAAAATTTTGAAGGATAATACTATTACATCGCAGCTT<br>AATGGTGCTGGTGTTAAGGTCGTCAGCTGCATTATCCAAA<br>GAGATGAAGGCGTCCACCAATGCGACACTCCTTCCATTG<br>GTCTGCTGACAAGCTTTATTATGAGGAGGATCCAATGCTCC<br>GCCACGTGGAACCACCATTGTCTACATTCCTTGAGCTGGAC<br>AAAGTAAATTTGGAGGGTTACACTGAAGTAAAATACACCC<br>CATCACGTGATCGTCAGTGGCATATTTACACACTTATCAAG<br>AACAAGAAAGATCAGAGATTAAACGACCAGAGGATGTTCC<br>TTCGTACCATAGTCAGACAAC |
| 69 | Digitaria<br>sanguinalis | cDNA<br>Contig | 488 | CAGCCTTTGAAATTACTGGATCAGAAACGTCTTTTGGCCCG<br>TAAAAGCAATACTACTTACTGCTATGACTTTGCACTGGCAT<br>TTGAAGCAGCCCTTGAGAATATCTGGTCATCGAAACTCCCA<br>GGTGTTAACAGGCCTGGTGCTAAGCTTGTAAATGTGACAG<br>AGCTTGCGTTTGCTGACCCAAGAGGCTCATGGGGTACACC<br>ACTTGTGGAAATAAACCGTGAGCCGGGCCAGAACAATGTG<br>GGCATGGTGGCATGGACCATGGACCTCTGCACACCCGAGT<br>TTCCTCATGGAAGGACAATTTTGGTAGTTGCAAACGATGTC |

TABLE 1-continued

ACCase gene sequences isolated from weedy plant species

| SEQ ID NO | SPECIES | TYPE | LENGTH | SEQ |
|---|---|---|---|---|
| | | | | ACGTTTAAAAACGGGTCTTTCGGCCCGATTGAAGACGCGT<br>TTTTCGAGGCGGTTACCGAACTTGCTTGTTCCAAGAAACTG<br>CCACTCATCTATCTGGCAGCTAACTCAGGGGCCCGAATTG<br>GGGCGGCTGAGGAGGTCAGATCTTGCTTTAGAATCGGGT<br>GGTC |
| 70 | Digitaria sanguinalis | gDNA Contig | 10084 | TTTTCAGGTTTGTTTGTTTCGATTTTCCGATTGTGTTTTTGA<br>GTCGCTGTTGCTTGATTTCTGCTGCTGTTACTGCTGGTTGA<br>CTCTTCTAGTGTGTTGATTGAGATTTGTTTAGTTTGATTCGAC<br>TTCGATTTTGGAATCGGATTTTTGAACTTGGAGTTGTAAGT<br>GTTTTGAAGCGTGTTTTTCGGCGTTTTAGTTGCGTTTTTCTT<br>ATGGATCCGATTCTTTTATATGAATGCGGCGTTTGGCGCTG<br>AGCAACATGAATTGGAATAAACTTGTGGTATTTTGCTCTTT<br>TTCTATATATTAGTCTAATTCAACTTCGATTATGGAATCTGA<br>TTTTTGAATTTGGAGTATATGTAGTATATTTAAACATGTTTT<br>TCGGTGTTATCATTGTGTATTTTTTATGGATCCTGTGCATCG<br>GAGATGCGTTTATATGAATACTGTGTTTGGTGCTGAGCAA<br>CATAAATTGGATTATACTTGTCGAAAATAATTCTCGTAATA<br>AGGTTCAAGGTATCTAGAAGTCTACCTGAAGTGATATAGT<br>GGACCATGCGGATTTGATTCTTTGAGTTGTTTTCTTCAAGT<br>CAAAGATCCTGTTATATTTAATTATTTCTTTTGATTTATGAA<br>ATGAGTAATTAAGCAAGTGGTATGCTCAATTCGTTGAAAAT<br>ATTATGTATTGAAAAGGATTTGAAGGTTACGAACTGGATTT<br>TCAACTCGAATGAGTTTTTTTTTGTGCAGAATGTTGGAGAC<br>ACAGAGGAGGCAGCCGTTAGCAGTAGGGGTTACTCGTGG<br>GAATGATTTCACCAATGGTGTGCTTACGATGAGAAGCCCT<br>GCTACAATATCAGAAGTAGATCAATTTTGCCGTGCTCTTGG<br>AGGAAAGAGACCGATCCACAGTATATTAATTGCAAACAAT<br>GGAATGGCAGCTGTCAAGTTTATACGAAGTGTTAGGACAT<br>GGGCTTATGAAACTTTTGGCACTGAAAAGGCTATCTTGTTG<br>GTGGCCATGGCAACTCCAGAAGACATGAGGATCAATGCAG<br>AGCATATTAGAATAGCTGATCAGTTTGTGGAAGTTCCTGG<br>GGGGACAAACAATAACAATTATGCCAATGTGCAACTCATT<br>GTTGAGGTGTGTAAGTTCATAACCTTTTAGCATATTGGATA<br>GCTTATGTTGTGTTAGTCTAAAGTTCGATAATTCTAAGCAT<br>ATAATGATATTAAATGTGTTTAAGGATTTCTCAGTAATAGG<br>AATTTGTAAATCTTTTCTGTCAATGGGTTTTACAGAAATTCA<br>TAAATTATAATGTAATCTAGAAGCTTTGAAATTGTATTTTTG<br>CACATCTCAGAAGATTATGAAGTAATAGGCTGGTATACAG<br>TGAATTTCATTATTGCAAGATATTGTTGTTATGTGCTCACTC<br>AAGAGCATTCTTTTCAATTTGGCAATGTGAAAAGGTTCAGT<br>TAGAAATATCACTTGTTACCCTTGTTGTTTGCATAACTAAGT<br>TTGATTTTGTGTCCAGATGGCAGAGGTCACCCATGTTGATG<br>CAGTTTGGCCTGGTTGGGGACATGCATCTGAAAACCCAGA<br>GCTTCCAGATGCACTAACTGCAAAGGGAATCGTATTCTTG<br>GGCCCCCAGCTGCGTCCATGGGAGCTTTGGGTGATAAAAT<br>TGGATCCTCTTTGATTGCGCAAGCAGCAGATGTTCCTACTC<br>TTCCATGGAGTGGCTCTCATGTAAGTAATGCTCTTCTCAAG<br>CTGTTCTTTCATTTTCTGTAGTCATTCCAATCTAAGATATCA<br>TGATCTTCCTTATAGGTGAAAATTCCTCCAGAAAGTTGTTT<br>GATTACCATCCCCGATGACATATATAGAGAAGCATGTGTTC<br>ACACAACAGAGGAAGCTATTGCAAGCTGCCAAGTTGTTGG<br>TTACCCTGCTATGATAAAGGCATCATGGGGCGGTGGTGGT<br>AAAGGCATAAGAAAGGTTTGGCTTCGATATAACAAATTTC<br>CGAGTGTAGTGTTCAAGTCTGTAGTGTACGATGGCTGAGT<br>TTTGTTTTCTTGGATTATCTAGGTTCATAATGATGATGAAGT<br>TAGGGCATTGTTCAAGCAAGTCCAGGGTGAAGTTCCCGGT<br>TCACCCATATTTATAATGAAGGTCGCTTCACAGGTTAGGAT<br>ATTATCTAGCTTCTAATTTGATACAAGAGATTTTACTTTGTG<br>ATTCTTGACGCGTGAATCGAATTCTGATGATCTATTTGATTT<br>TCCTTATGTAGAGTCGACATTTAGAAGTCCAATTGCTCTGC<br>GATCAATATGGAAATGTAGCAGCTTTGCATAGCCGTGATT<br>GTAGTGTTCAAAGGCGGCATCAAAAGGCATGTTTATTTCTC<br>TCAAGTAATTTTGATTTTGTCTGCTTAGTGAAATTGACCAT<br>GAAAGTATAAGCTTAGTGTGAAGAGCCTGAGGCTCTGACC<br>ACATGCATGTTGAGAATGAGCCAGTGACTTTTAATCAGTG<br>GCTCAACCATTAATTTCTCCCCTTCCAAATTTCAACTGTTTG<br>TACATCTATCTAGTATCTACTACATGGGTTATGCATTTCAAA<br>AAAGGCCTAACTGTGTTGAGATGTGAAACAGATAATTGA<br>GGAGGGTCCAATTACCGTTGCACCATTGGTGACTGTAAAA<br>AAACTAGAGCAGGCAGCTCGAAGGTTAGCGAAATCTGTGA<br>ATTATGTGGGCGCTGCTACTGTTGAGTATTTGTACAGTATG<br>GAAACTGGCGAGTACTATTTTCTAGAGCTCAACCCTCGGTT<br>ACAGGTATAAATGAATATAGTTTGTAGGGATGTGAAGTTG<br>TTATGCTCTATAGTAGTAATGATATCTAAAATGCTTAAATTT<br>TATGTTGCTCAATTGATGACAATTGGATAAACCGTATTCAC |

TABLE 1-continued

ACCase gene sequences isolated from weedy plant species

| SEQ ID NO | SPECIES | TYPE | LENGTH | SEQ |
|---|---|---|---|---|

```
TTGGGAAAAACCATCCTGAATATAGTTCGTACCTCATTCAC
CTTGCGTACTACTGATATTGATCCTATGAATCTGTTTTTTAA
AATATCTTTGTTTCTGTAATAAATTGTTCTTTGACTTTTCTAA
TGATCTTTAATCTACATCCTAATCTGGATGTAGGTGGAGCA
TCCTGTCACAGAGTGGATTGCTGAAATAAATTTGCCTGCTG
CCCAAGTAGCTGTTGGGATGGGAATTCCTCTGTGGCAAAT
TCCTGGTATGACCGCAAAAGTTGGAAATTCGCATTCTCTTG
CTCATTAGACATGTTTCTTTGACATTCTGTTCATTTTTATTCA
GAGATTAGGCGATTTTATGGAATGGAACATGGTGGAGGA
TATGATGCTTGGAGGAAAACTTCAGTGGCTGCTACGCCTTT
TGATTTTGACAAGGTAGACTCTACAAAGCCAAAAGGTCATT
GTGTAGCTGTACGTGTGACAAGTGAGGATCCAGATGACG
GTTTCAAGCCTACTAGTGGAAAAGTACTGGTAAGGTTTTCA
GGTTGACTATTCTAATTTGAATTTCCTTCTATTCCAAAATTC
CTTATCCTGTAATGAACTTGTACTTTTATTGTCTTGCACAGG
AGCTGAGTTTTAAAAGCAAGCCAAATGTGTGGGCTTATTTC
TCTGTGAAGGTGACTTTTTGCTGCTCTCTTTCTTTGGAACAT
GTTTATGTTGACACAATTGGTTTCTGACTTAATAACTTCATT
CTGATTTGTAGTCTGGTGGAGGCATTCATGAATTCTCAGAT
TCACAATTTGGTAAGTAATAATTGCTAAATAATCACACTTC
ATGGATAATAATGAAAAGAAGTTTGTGAGATGAGTTATCC
AATCTGCTGCAAATTAATGGTTCTTTTTTATCTTCTTGTGAC
ATTTTTTTTAACAAAAGCTACAGTCTGCTTTTCAGTTTAGTC
TTTTCCGTTTGTTACATTTGCTATCGAAAGCACTCATGATTG
TCGTAATCTTTCCTTAGGACATGTTTTTGCATTTGGGGAGT
CCAGAGCTTTGGCAATAGCTAATATGGTTCTTGGGCTGAA
GGAAATACAGATAAGAGGAGAAATCCGCACCAATGTTGAC
TACTCTGTTGACCTTTTACATGTAAACTATCTTAGCTGTTGA
TGTTCCCTTTATACATCATGTAAACTTTCACGAGGAACATG
AACACGAGTTGACATGCTATGCAGGCTTCAGATTATAGGG
AAAATAAAATTCACACAGGTTGGTTGGACAGTAGAATAGC
TATGAGGGTTAGAGCAGAAAGACCTCCTTGGTACCTCTCT
GTTGTTGGAGGGGCACTATATGTAAGTTGTCACGATTTCAC
ATGAGAGGATGACTGTATACTTTTGGAATGCTTTATTATGT
CTTTCAGAACTTGCCACTTAAGTGTTCAATTTTTTGTTTGCA
CCAGAAAGCATCTGCTAGCAGCGCAGCTATGGTTTCTGATT
ATGTTGGTTACCTTGAAAAGGGCCAAATCCCTCCCAAGGTA
CATCAAAAGTATATTTGTACAATTGTATATGTTTCTTATTCA
GCCGATTATGTTGATGTTGATGTTGATGTTAGTTGATCTTG
TTTTCAGCACATATCACTTGTGAACTCTCAAGTTTCATTGAA
CATCGAAGGAAGCAAATATACGGTATGGTACCTTTCATATT
AGTATCTTAAATGAATAAATTTTAGTTTGGTGATGGATGCC
ATTTACGTTTGTAAAATCATTGCTAGATTGACATGGTTAGA
GGGGGGCCAGGGAGCTATAGATTGAGGATGAATGGATCG
GAGATAGAGGCAGAAATTCATACACTGCGTGATGGAGGTT
TATTGATGCAGGCAAGTTGACTCATTAACCATGGCTGTTGT
AAACTAATAATTTTCGTCCTTTTTATCATTTAATATTTGCTTT
AGTCGACCCTCCATGCTTTGGAGACCATAACAGACTCTATT
CTGTTTCTTCACAGTTAGACGGAAACAGTCATGTAATATAT
GCTGAAGAAGAAGCAGCCGGAACTCGCCTTCTAATTGACG
GGAGGACTTGCTTGCTACAGAATGATCATGATCCGTCAAA
GTTAGTGGCAGAGACACCATGCAAACTTCTGAGATATTTG
GTTTCAGATGGTAGTCATATTGAAGCTGATGCTCCATATGC
AGAGGTTGAAGTTATGAAGATGTGCATGCCTCTTCTTTCAC
CTGCTTCTGGAGTTGTCCATTTTAAAATGTCTGAAGGTCAA
GCAATGCAGGTGTGTTTGATTTCACAAACACGTGCTTTTGG
GCTTGATAAGTACTTTTTAGTTTTATATGAATAGTCAGTTTT
GATGTGAATCTAAGAAGTTTTCATGTAGGCTGGGGAGCTC
ATTGCAAGGCTTGATCTTGATGATCCTTCTGCTGTAAGAAA
GGCAGAGCCTTTTCATGGGAGATTCCCGCTACTTGGCTCTC
CGACTGCTATTTCTGGTAAAGTTCATCAGAGATGTGCTGCA
AGTTTGAATGCAGCCCGTATGATTCTTGCTGGCTATGATCA
TAATATTGATGAAGTAAGTTGCAAGCTGGCTAGTTTCAACA
TGAACTTAATTGATGAATTAATTGTTCATTCTATATTTTGTT
GATTGTGTAATTTCATAACAAAATAATGAACTATGCATTTG
GTTTATTATACTGACAATTATTTGTTGAAATCTGATGTAATA
TCTCAATGACATCTATAGGTAGTGCAAAACTTGCTCAATTG
CCTTGACAGTCCTGAACTCCCTTTCCTTCAGTGGCAAGAGT
GCTTGTCTGTTCAGCAACTCGCCTTCCCAAGGATCTTAGA
AGCGAGGTGAATAATTTTTCTGTAATTTTTTCATGACCACA
TAGTCTTCTTGCTCACAATTTGATATTGGCAATTTGTATAGT
TGGAATCAAAATACACAGAGTTTGAAGGAATTTCAAGCTC
CCAGAACATTGACTTCCCTGCCAAACTGTTAAGGGGTGTCC
TCGAGGTGGGTTCCTTATTGCATGGCTCTCTTGGAATTTCT
CATTATCTGTTTTTTTTGCTGTTTAATGAGATGTGTATGCTT
TTCCTCCAGGCACACCTGAAATCCTGTCCTGAGAAAGAAAA
```

TABLE 1-continued

ACCase gene sequences isolated from weedy plant species

| SEQ ID NO | SPECIES | TYPE | LENGTH | SEQ |
|---|---|---|---|---|

```
AGGAGCCCTGGAAAGGCTTGTTGAACCTTTGATGAGTCTT
GTAAAGTCTTATGAGGGAGGACGTGAGAGTCATGCTCGA
GTGATCGTCCAATCACTTTTTGAAGAGTATTTATCTGTAGA
AGAATTATTTAGTGACAACATCCAGGTTAGCTTCTTCCTAT
CAAACATAATATGGAATTATTTTGGATTCTGAAAGTCTTCC
CTCTTTGGCATCTTTTAGAAAATTAAGCATAATACTAGGTA
CTATATCCATTATTCTTTATAATCATGAAATTTAATTTTTACA
GAAGAAAAGTGGAATTTCTATATATATTTAAACCAAGCTG
GCAAGCTTTGAATTCAATCCTGTTGTTTATTGTTTTATCCAA
CATGCCAAAAATATTAGGAACTTCATGTGACTACTTGTATC
ATTCTTATTCTGTAATTACAGTAAAGTAACTTGTCATATCCT
AATGTTATAACTCGTAACATTCTTCTTTAGGCTGATGTGATT
GAACGTCTCAGACTTCAATATAAGAAAGACCTTTTGAAGAT
AGTGGACATTGTCCTTTCTCATCAGGTATCTGATTTTCGGTT
TTAATTTTTATCTCGGGTTTTCTAAAATAGAATTCTGAGTTT
GTGGAAATAACTACCGTATTTGTTGGTTTATAGGGTGTTAA
GAGTAAAAATAAGCTGATACTACGGCTCATGGAACAACTT
GTTTACCCCAACCCTGCTGCATATAGGGATAAACTCATTCG
GTTCTCTCAGCTTAACCACACCAGCTATTCCGAGGTTGGCA
GCTATACTTGGTCCATCTGTAATTTCATAAAGTTGTTGCTCT
GTTTCCTTTTGTTCACAAGTTCATTTTTGAGAGTTTTCCATA
GGATGGTGACTGACAGGAAGAGGATTCTAATGTTTTCTCT
TGGAGGATTTTTTCTGTATTTTCATTTCTTGTCGGTCATTGA
TTAATTCCGTTTCTGGTATCAGTATCATCAAAATGTTGTCTT
TTTCTGTATACTGATGCTGAATTATGTGAACAGTTGGCATT
GAAGGCAAGTCAACTCCTAGAACAAACCAAACTGAGTGAA
CTCCGTTCCACTATTGCTAGAAGCCTTTCGGAATTGGAGAT
GTTTACCGAGGATGGTGAAAATATGGATACTCCCAAAAGG
AAAAGTGCCATTAATGAACGTATGGAGGATCTTGTGAGTG
CTCCTTTGGCTGTTGAAGATGCTTTAGTGGGTCTTTTCGAG
CACAGTGATCACACCCTTCAAAGGCGAGTGGTGGAAACTT
ATGTTCGTAGGCTATATCAGGTACTGTGTTGTAGAAACTTA
AAACTTTTATCTGGTGATCAAACACTAGACGAAACTTGATC
TTGATCAACTGTTTGTCTACCGCACCAGCCCTATCTGGTCA
AAGGTAGTGTCAGGATGCAGTGGCATAGATTTGGTCTTAT
TGCTACATGGGAATTCTTGGGAGAGCATATCGGGAGAAAG
AATGGATCTGAAGGTCAAATGTCAGATGAACCAGAGGCTA
AAAAACAGTCTAATAAGAGATGGGGAGCAATGGTTATCAT
CAGATCTCTGCAGTTTTTGCCTTCAGTTATTGGTGCTGCATT
AAGGGAAACAAATCAAAGCCTTAATGAGTCCATTCCAAGT
GGATTAGTAAAATCAGCGAGCTTTGGTAATATGATGCACA
TAGCATTGGTAGGCATCAATAATCAGATGAGCTTACTACA
GGATAGGTAACTTCCTTCGGTACTATAATATAAGCGTTTAT
TTTAATCATAAAAATTAGTAGCATTTTACATTCTATTATTCA
TTGTAAGATCTCAAGTCTTCTTAATCATTTCTGCATTTGAAA
CCTTGATAGATCTGGATAGATTCCTTATTTTTGTTTAAAATT
TATGATAGAGTTACCTGGTCTCGAACCCTTAAAACATGCAC
ATATATTGGCTTGCCAAACATAAGTTATTTTGCGTTGTCAA
TTTCGATTATTGACGGTCAGCTTGTTAATGCTCCTAACTGG
CACCATCTATGACATTTTGCAGTGGTGATGAGGATCAGGC
ACAAGAGAGAATTAACAAGTTAGCCAAAATTCTCAAAGAA
CAGGAACTAGGTTCCAGTTTGAGCTTGTCAGGCGTTGGAG
TTATTAGCTGTATCATACAGAGGGATGAAGGGAGAGCCCC
TATGAGGCACTCCTTTCACTGGTCAGAGGAAAAGCTTTATT
ATGAGGAAGAACCTCTATTGCGACATTTGGAACCTCCACTA
TCCATCTACCTTGAACTGGTTTGTCACCTATCGCAGTGTTTC
AATACATTTTTTTGGCAGAAACCTTTATTGAGCCCCTGAAC
TTACCAGTTTTATTCTCAAGTTATTATTTGACTACATTAAAT
ACTTAATTACTATTGATTCCACATTATGACCTTGCAATATAA
TTACAAGTGTTACGTTTTATTGATAAAATTATAACTGTTGCT
ATTTTGTTTTACATATATCAAGGACTGCACTATAGTAAAAA
AATGAGGACTCGATAGGATTGGAAAGTTCAGGGGCTTACT
AATTGTTTGAGCGGAAAAAAATATATATAAATGTGAAATT
GGATAATTCTATATCATTCATCTGAAGCTTATTATGGCCTTT
TTTTGATCCAGGACAAACTTAAAGGCTATGACAATAGACA
ATATACTCAGTCAAGGGACAGACAATGGCACATGTACACT
GTTGTAGACAAACCAGTTCCAATCCAGAGGATGTTTCTAAG
AACCCTTGTGAGACAGCCCACAAGTACTTCATATCAAGGTC
TTGGCGCCGAAGCACCCAATGTGCAGTGGGCCATGTCCTT
TACGTCAAAGAGCATTTTGAGGTCCTTAGTAGCTGCAATG
GAGGAACTGGAGCTTCACGTGCACACTGTCAAATCTGACC
ATGCTCATATGTACCTCTGCATATTGAGGGAGCAACGGAT
AGAAGATCTTGTTCCATACACGAAGTAATTATATCAATCTT
TATGATTTATTGTGTACTTGGCACCATAACTTTATGTGTACT
CACTATGAGACTCCATCTCCAGGAAAACCGATGTAGATGC
CAACCAAGAAGAAGCTGCGGTAGCAAGAATCTTGGAAGA
```

TABLE 1-continued

ACCase gene sequences isolated from weedy plant species

| SEQ ID NO | SPECIES | TYPE | LENGTH | SEQ |
|---|---|---|---|---|
| | | | | ACTAGCGAGGAAGATACATGCGTCGGTTGGAGTCAGAAT<br>GCATAGGTTAAATGTTTGCGAGTGGGAAGTGAAGCTATGG<br>ATGACATCATCTGGACAGGCAAATGGTGCTTGGAGAGTTG<br>TCACAACAAATGTGACTGGGCATACCTGTGCTGTGCATGT<br>AAGTATCTGCGCATCTTATTTCAAGAAAATGTCTTTCCCTTC<br>CATGCATTCCTTATTAGTCGACTTAGTAATGGGGAATGTCG<br>AGAAGTGTTGGATGGTTACCAATGTGAGTACCATCACTGT<br>TTAGATTAAAATTGACCATTGCTTTAGCAATACAATAATGA<br>ATCTAATTGTGGCATGGGAGGCTTTTCTATGTGTGATCCAT<br>GGAAAAACTTGTATATAGTTCCTTAGTAGGTTTGAGTTGTT<br>TTCATTTTTCTTTTATCACATTGTAATTGTATTGGTGATTGAT<br>ACGAAAATTAGATATATCGGGAACTTGGGGACGAGAGCA<br>AACATGAAGTGGTGTACCATTCAATCTCTCCAAGAGGCCCA<br>CTGCATAGCATGCCAGTGAATGCTGTTTATCAGCCCTTGGG<br>AGTTCTCGATCGAAAACGTTTGTTGGCAAGGAAGAGCAAC<br>ACCACTTACTGCTATGATTTTCCACTGGTTAGTATTTCTATA<br>ATCATTAATCAAACATCAGTTTTTTTATTGGGGATAATTAA<br>AATCAAATAATTTTTCCTGGCCTCATCCTTTTCAGGCGTTCG<br>AGACAGCCATCGAACAATTATGGGAATCTCAATCACCAGG<br>GACTGAAAGAAACAAAGAAAAAGTCCTAAAAGTCTCGGA<br>GCTTGTTTTTGCCGATCAGAAAGGTACCTGGGGAACTCCA<br>CTTGTTCATGCAGAACGGCCAGCTGGGCTTAACGACGTGG<br>GCATGGTAGCATGGTGCATGGAAATGTTCACCCCGGAATG<br>CCCTTCCGGAAGGAAAATCTTGATAGTAGCGAACGACGTG<br>ACCTTCAAAGCCGGGTCTTTC |
| 71 | Digitaria<br>sanguinalis | gDNA<br>Contig | 2626 | AATCAACTTTATGCTCAAGCGAAAGAGCTTATATTTGCTGA<br>TTCAGTTGGAGCATGGGCACTCCAGTGGTTTTAGTTGAA<br>CGCCCTCCAGGCAACAATGATATTGGCATTGTTGCTTGGAA<br>CATGAAGCTGTCCACACCAGAATTTCCTAATGGCCGCGATA<br>TTATAGTTGTTGCAAATGATGTGACATTTAAAGCTGGGTCC<br>TTTGGTCCAAGAGAAGATGCGTTTTTTGATGCTGTTACCAA<br>TCTTGCTTGTGAGAGGAAACTTCCTCTTATCTACCTAGCTG<br>CAACTGCTGGTGCCAGGCTTGGTGTAGCAGAGGAAATAAA<br>GGCATGCTTCCATGTCGGCTGGTCTGATGATGAGAGCCCT<br>GAACGTGGTTTTCACTACATCTACCTAACTGAACAAGACTA<br>TTCACGTCTAAGCTCTTCAGTTATAGCTCACGAGCTGAAAC<br>TAGAAAATGGAGAAACCAGATGGGTGGTTGATACCATTGT<br>TGGGAAAGAGGATGGGCTTGGTTGTGAGAATCTACATGG<br>AAGTGGTGCAATTGCCAGTGCGTATTCTAAGGCATATAAA<br>GAGACCTTCACCCTGACATTTGTGACTGGAAGAGCTGTTG<br>GCATTGGGGCTTACCTGGCTCGTTTAGGTATGAGGTGCAT<br>ACAACGTCTTGATCAACCAATTATTTTGACTGGGTTTTCTGC<br>ATTGAACAAGCTTCTAGGACGGGAGGTATACAGTTCTCAT<br>ATGCAATTGGGTGGCCCCAAAATCATGGCTACAAATGGTG<br>TTGTCCACCAGACCGTGTCAGATGATCTTGAAGGTATTTCT<br>GCTATCCTAAAATGGCTCAGCTATGTTCCTCCCTATGTTGG<br>TGGTCCTCTTCCTATTATGAAACCCCTGGACCCACCAGAAA<br>GACCTGTAACATACTTCCCTGAGAATGCTTGTGATGCTCGT<br>GCCGCCATATGTGGTGTTCAGGACGGTGAAGGCAAGTGG<br>TTGGGTGGTATGTTTGACAAGGAAAGCTTCGTGGAAACAT<br>TGGAAGGCTGGGCAAAAACTGTTATCACCGGGAGAGCAA<br>AACTTGGTGGAATACCAGTTGGTGTCATAGCTGTGGAAAC<br>CCAGACAGTGATGCAAGTCATCCCTGCTGATCCAGGGCAG<br>CTTGATTCCGCTGAGCGTGTAGTCCCTCAAGCAGGACAGG<br>TGTGGTTCCCTGATTCTGCCACCAAAACGGCTCAGGCATTG<br>CTGGATTTCAACCGTGAGGAGCTTCCACTTTTCATCCTTGC<br>AAATTGGAGAGGTTTCTCTGGTGGGCAAAGGGATTTGTTT<br>GAAGGGATACTTCAGGCTGGTTCAACAATTGTTGAGAATC<br>TGAGGACATACAAGCAGCCTGCTTTCGTATATATCCCAATG<br>GGTGGAGAGCTGCGGGAGGGGCCTGGGTTGTGGTGGA<br>CAGCAAGATCAATCCGGACCACATTGAGATGTATGCCGAG<br>AGGACTGCGAAAGGCAATGTCCTTGAGCCAGAAGGATTG<br>GTGGAGATCAAATTCAGGCCAAAGGAACTGGAAGATTGC<br>ATGAATCGACTCGACCCAAAGCTGATATCTTTAAAAACCAA<br>ACTAACCGAAGCGAAGAATAGTGGGACCTACGGGATGGT<br>CGATTCCGTACAACAGCTGATAAAATCCCGGGAAAAGCAA<br>CTTCTGCCGCTTTACACGCAAATCGCCACACGATTCGCCGA<br>GCTTCACGACTCGGCTTTACGAATGGCGGCAAAGGGGGTG<br>ATTCGAGAAGTTGTCGACTGGGGGATTTCACGATCTTACTT<br>CTACAAAAGGTTAAGAAGGAGAATCGCCGAGGCTTCGTTG<br>GTGAACACCGTGAAAGATGCAGCGGGTGATAAGCTCCAG<br>CATAAGTCGGCTATGGAGTTGGTCAAAAACTGGTTTCTGG<br>ACTCGAAAGGCGATTGGGAAAACGATGAAGCTTTCTATGC<br>TTGGAAGGATAATCCCGCGAATTACGAGGAAAAGCTACAG<br>GAGTTACGGGTCCAGAAGGTGTTGCTTCAGTTAACTAACA |

TABLE 1-continued

ACCase gene sequences isolated from weedy plant species

| SEQ ID NO | SPECIES | TYPE | LENGTH | SEQ |
|---|---|---|---|---|
| | | | | TTGGCGAGTCTTTGTCGGATTTGAAAGCTTTACCTCAAGGT<br>CTTGCTGCCCTTCTAAATAAGGTAATTTTTTGGGTTTTTTCT<br>TCCAGGAATATTGTTTATTTAGACGATCGAGTCGGATGTTA<br>TGTAATACTTTATGTTTGATGTAGGTGGAGCCATCGAGCCG<br>AGGGGCGTTGATCGATGAGCTTCGGAAGGTGCTTAATTGA<br>TTTTCGGTAAGTGTTTCTCGGCTACTAAATATGTTTTACTTT<br>GGCTTCAGTCTCTGGGTAGTTTGAATCAATAGAAAATGCC<br>AATGTGAAAATACCCAGTAATATATTTGATAAGTGTAAATG<br>TAACTATTATTATATTTAAGTGAATAGGGGGAATTAGTTCA<br>TATGATTATTGTTGTTATAAACAAATCAGAGATAGAGAGA<br>GCTATATTTATTATTATATTTGCGAATTAAAGTTATTAGGA<br>GTAGTATAATTTGGCGGTTGTTGCATTTTACGTGTAATGAT<br>CTGAATGTTGTTTGTTCGTGATTATTGAATAAAAGGGCATC<br>AAATGCCATAATTTATCTTTCTTTGTTAACAAGATTTTAATT<br>AGTTTTTTTTAATTATTAGTATGTTTTGTATAATTTATATT |
| 72 | Digitaria<br>sanguinalis | gDNA<br>Contig | 2351 | TCTCTCTCTCTCTCTCGGCTATGTTCTTCGCTTGCTTCTCA<br>GCTCTGCACCGCTCGGGCGATCGAATTTCGCATTGCTCCGT<br>GTGCCGCCGGCCGCTCGAGGCTGTCCGCGTCCAAATCCAA<br>CTCCAAAACGCGACTTCGCGCGGCGCCGACGCTACTAAAT<br>CGCCGCTTGTACTTCTCAGCCGCGCCGGGCAACTTGCTTCG<br>GCGTTCCGTCGAGCAGGTTGTGCGCGCGCCAAGTGTGATT<br>GGGGAAATAGAGATCCTGCCTGCTGCTGGCAACCGGAATT<br>TCGTCAATCAAAGGCAGGGGGTTTCCTTTTCAGTTTGGTTA<br>GGGAGCTTGTTGTTTTGTTTGTTGGGGTGCCGGGGTTGGT<br>CCCCTCTGTTTTGGATTGGATTGTAGTGGCCTTTCGGGTTT<br>CCACTTTGGACTCGCCTCTAGTGCGGACCTTTCTGTGATCG<br>CATAACACATACTACGGTCAATATATTAGTCACCTTTGCCTA<br>GGTATAATCAAAACCTGTGTCCTGACACTTCTTATTCTGCT<br>GGCTGCTTGTACTCTAATTCAATACAATCAGCTGCTGCCTA<br>TGGATGAATCTGGTTAAATAGCCACTTCTCTGTTATCAACT<br>CTATATCATCTCAGCACACTATTTCATATACTACTAGTTGCC<br>TGTCCGAAAGTATCGTGCTTGCGATTTGTTTCTTTTGCCTGT<br>TCGATAGTCATGCAGTTTCCCCGTCACAATTGATGTACTAA<br>CAATCTGTTTCTTTTGCACTGACCAGGAAGTTTGAACTTCA<br>GAGGGTGAGATAATGGTTGAGCCTGACCAGATGAACGGC<br>ATACTGAATGGGATGCCTAATTTGAGGCACCCGTCCTCTCC<br>ATCAAAGGTCGATGAATTCTGTAAAGCACTTGGTGGCGAC<br>TCGCCAATACACAGTGTGCTAGTTGCCAACAATGGGATGG<br>CCGCGGTCAAGTTCATGCGCAGCATCCGCACATGGGCCTT<br>GGAGACCTTTGGGACAGAGAAGGCCATTCTCTTGGTTGCT<br>ATGGCCACTCCGGAGGACTTGAGGATAAACGCCGAGCACA<br>TAAGAATTGCTGACCAATTCATAGAAGTTCCTGGAGGAAC<br>AAATAATAACAACTATGCGAATGTACAGCTCATTGTCGAG<br>GTTAGCACAACTCATCATCCTGGAAGTGACTAACTTGTGTT<br>TAGTTTACATATGTTTTCACTCTGGACAATTCAGTAATTAAC<br>ACTGAATTCACATTTCACAGATAGCAGAGAGAACTCGTGTC<br>TCTGCAGTTTGGCCTGGCTGGGGTCATGCATCTGAGAATC<br>CAGAGCTTCCGGATGCTCTAAACGAAAAAGGAATAATTTT<br>CCTTGGGCCACCATCAGCTGCAATGTCTGCACTCGGTGATA<br>AGATTGGTTCTTCTCTTATTGCACAAGCAGCAGGAGTTCCA<br>ACTCTTCCATGGAGTGGATCACATGTATGCCTTCGCCTATT<br>TCTGTGTGCCTTTGCTTCTAACTTTTATCTGCTAGTTTAATAT<br>TCACTTAACATTGAACCAAACTCACTGCAGGTGAAAGTTCC<br>ACCAGAAAGCTGCCACTCGATTCCTGAGGAGATATATAAG<br>GATGCTTGTGTTTCCACTACAGAGGAAGCAGTGGCTAGTT<br>GCCAGGTGGTCGGGTATCCTGCCATGATCAAGGCATCATG<br>GGGTGGCGGTGGTAAAGGAATAAGGAAGGTTGGTTTTCT<br>TTTTCTATTTGAATCTGAGAAAAAAGAAGGGAAATGTCCA<br>GTATTCAGAAAACATGATCTGAAAGTTTCAAGGAAAAAGT<br>TAGAGTAAATTAACACTAATTTTGATATCATTTGCATGGAT<br>TCATAGGTACACAATGATGATGAGGTGAGGGCACTGTTCA<br>AGCAAGTTCAAGGAGAAGTCCCTGGCTCACCTATTTTTATT<br>ATGAAAGTGGCATCTCAGGTGAGAACTGATTCAACAAATT<br>TTGGCTATTTAATGGTTTGCTTTGGCGCCCACCTTTGTTCTT<br>TGTATCCTGAGCTCTTCTATGTGGTTGCATTTGTTTCTGAAA<br>GCTTTTGTTTGTTCTTTCTTTGTAGAGCCGACATCTGGAGGT<br>TCAGTTGCTCTGTGACAAACATGGCAATGTGGCTGCACTG<br>CACAGTCGAGATTGTAGTGTTCAAAGAAGGCACCAAAAGG<br>TTAGCTCGTAGAATTTTTTCTAAGCTTTGATTTACATTGTGA<br>TTTCTTGTAATTTGTCCCATACTTGGATTGTGTAGTGTGCTG<br>TATAGTAGTTTTATATATTTCTTGAATAAAGTTTAGGTGACC<br>TAGTGCAAGACGAAAAAAATCCATATTGCATTTTGTGAA<br>GAAAATTTTCTCACATTTACCTCTGCA |

TABLE 1-continued

ACCase gene sequences isolated from weedy plant species

| SEQ ID NO | SPECIES | TYPE | LENGTH | SEQ |
|---|---|---|---|---|
| 73 | Digitaria sanguinalis | gDNA Contig | 2088 | TTCAGTTGGATGGAAATAGCCATGTAATTTATGCGGAAGA<br>AGAAGCTGGTGGTACACGACTTCAGATTGATGGAAAGACA<br>TGCTTGTTACAGGTGCATATGCTCTTTTCCCTTTATTATCTTC<br>TTGGTGTCTGATTGGGAGTCTTCTGCCAGATTTGCCTTTTCC<br>GTTTATTACAACAATTTGTCTGTCATCCTTAACTTCAGAAAA<br>TCCTATTGTTTGCTTTCTTAGCATACTTGATTTCAGTGAAAT<br>TTGACTACAATACCTGAATTAAAAAAAAACTGTAATCGTGT<br>GATTAAAAATCAAGAAGTAGCCTTTTTAGGATTGTAATATT<br>TTGGTATTGCTACACTATGCCAGAAGTAGGTCACAAGTGT<br>GTGTTCTTGCAGAATGATTATGATCCATCAAAGTTAGTAGC<br>TGAGACACCCTGCAAGCTTCTTCGGTTCTTAGTTGCTGATG<br>GTGCTCATGTTGATGCCGATGTACCATATGCGGAAGTTGA<br>GGTTATGAAGATGTGCATGCCTCTCTTGTCCCCTGCTTCTG<br>GTGTCATACATGTTATGATGTCTGAGGGCCAGGCATTGCA<br>GGTTATTTTTGTACATCCCTCCTTGCATTGTGCTTGCATCAC<br>ATAACTGCATGTAACATTTTTAGACTTATATTTTGTTCTAGG<br>CTGGTGATCTTATAGCGAGGCTGGATCTTGATGACCCTTCT<br>GCTGTGAAAAGAGCTGAACCATTTGATGGAATATTTCCAC<br>AAATGGGTCTTCCTGTTGCTGCCTCTAGTCAAGTACACAAA<br>AGATATGCTTCAAGTTTGAATGCTGCTCGAATGGTCCTTGC<br>AGGATATGAGCATAATATCAACGAAGTAAATATTCCATCTT<br>ATTATGATTATACTCTATTTAGTTTTTTTTAATCTTTTGTTT<br>CCTTTACTTTGATTTGTGTACTCCATCCCAAAACAGTGTGAT<br>TCTAGTGTTGTCCTAAGTATCATTAGATTCATCATGAAATAT<br>ATTTTGGGACTGTTTTGAGGGTTCACACGGGTTCAATGTTT<br>TTTTTTTTGGTTCTGCTGACTTTTCGTCCAAACTTGTATAATC<br>TATGGAAAATTGTAATGGTAAGTACGTTCTGATCATGCTCA<br>CATAGTCACACTAGTGTAACTTTATATTCTAGTTTGATAATT<br>TTGAGTCGCACTTATTTAATTGAAGTTATTGCATTTTGTTTT<br>CTATCACATTGTCCTTAGCATTTATTTATCACATATTGATTG<br>ATTCGCTCGAAACTCTTTTTTTTTCCAGGTTGTGCAAGATAT<br>GATATGCTGTCTGGACAATCCGGAGCTTCCTTTCCTACAGT<br>GGGATGAACTTATGTCTGTTCTAGCAACTAGACTTCCAAGA<br>AACCTTAAGAGTGAGGTATAAGACAATTACCAAAATGTAG<br>CCAATCTGGGTTAAATGAAAGACGATTCATTTTACTGTGTA<br>TATTATCTTAATTTTACATATTGGCTTATGTTGATGACAGAA<br>AAGTTTGGTATCACCAGAGTAAAACCGTGATATTTTGTAGC<br>ACTGGTTTGCACTGTGTTACGTGCATTAAAGTCTATAGTGT<br>GCTGTAGTTTATTATGTAAAATTAAGTTGTATTCATGTGCT<br>AAAATTTAGAATCTTTCACTTTAGCATCTTAATAGATAGAA<br>GCTGAATCTTCCAGTAAGTTTTGTTTTAGTTTCTTGATTGTA<br>GGTCTCTTGTATGTCCTTGCATAACCCTTTTTCATTCTAGAT<br>CTGATGGTTCTATCTTTTATTATGCAGTTAGAGGATAAATA<br>CCAGGAATACAAGCTGAACTTTTACCATGGGAAAAATAAG<br>GACTTCCCATCCAAGTTGCTGAGAGACATAATTGAGGTCA<br>GTTTTAGATTTCTTTAGTCGTATTAATTTTAAACTGTTTGCTT<br>ATTTTAACAATTTTTTTGTAGGCAAATCTTGCATATGGTTCA<br>GAGAAGGAAAAAACTACGAACGAGAGGCTTGTTGAGCCT<br>CTTATGAGCCTGCTTAAGTCATATGAGGGTGGAAGAGAAA<br>GCCATGCTCATTTTGTTGTCAAATCCCTTTTCGAGGAGTATC<br>TTGCTGTGGAAGAACTTTTCAGTGAT |
| 74 | Digitaria sanguinalis | gDNA Contig | 1983 | GACTGAAGAACCATTATTTCTTACGTGTTTGTGAGCTTCAA<br>ATACAGGTGTCGTTGCTAACATTAAATATGTATCTCTTATTT<br>CTCAGGAAGCATCAAGCAGGAGCTCAAGCGTTGTTACTGA<br>TTATGTTGGTTATCTCAGCAAAGGTCAGATCCCACCAAAGG<br>TATACTATATGCTGAGATGCCCTTATTGCAGATTATGCTTCT<br>TGCTGTTTGACTTAAAGCAGATTGGTAACTGTGTAATTCCT<br>TTCTGATTTGCAGCACATCTCACTCGTCAATTTGACCATTGC<br>TCTAAACATAGAGGGGAGCAAATACACGGTACTCATCTAT<br>AGTTTTTCTCTTAACAGTTTTGTAACCTACCACTGAGTGTCT<br>TTGAGAAAACTAAATGTTAAAACTTTGATGTAGATCGAG<br>ACTGTGAGAGGTGGACCCCGCAGCTATAAATTAAGAATGA<br>ATGGATCCGAGATTGAAGCAGAGATACATTCCCTGCGAGA<br>TGGTGGACTTCTAATGCAGGTAAATATTGGACCCAACTGTC<br>TCCTTTGTTTTCCTGTTGAAAAAAGTTCTGATCAAACTTTGT<br>TGTATATTCTTCAGTTGGATGGAAACAGTCATGTAATATAT<br>GCAGAGACGGAGGCTGCTGGTACACGCCTTCTCATCAATG<br>GCAGAACATGTTTACTACAGGTAAACATGGTATTCTTGTTC<br>TCTTCCACATATTTTTTATGCTGAAACACACTACCTGTTACA<br>TATCTTTACTTGAAACTGAAGTTATTGGATCTGGCAATTTTT<br>TACGAATGTTTCTTTCATATGAAGGTCATAGAAATTATAGG<br>TTACATAGAGGGTAGAGAATACAATTTAGGAAGCTACTAT<br>GACGCATAGCCCTAAGTTATATAAATTTGCTTGAACGTAGA<br>TTTGCTTCGTCCTCTTTATGTTTTCAGCTTGGCATTTTCCATA |

TABLE 1-continued

ACCase gene sequences isolated from weedy plant species

| SEQ ID NO | SPECIES | TYPE | LENGTH | SEQ |
|---|---|---|---|---|
| | | | | ACGGTGGTTGTTCCATGTGTCAAAGCATCTAATGTTAGCTA |
| | | | | GTATTCTCAGTTGCCAAAGATAAAAGATATCCCAGTTACCT |
| | | | | ACTAGCCCACTAAAAGTTTGTAACAATGTGAAATTTTACTT |
| | | | | GAAGGAATAAGCAGTTTGGATTGTTTCAATTCTTAACCGTA |
| | | | | TTCTCACATCATATGGAAATACATGATATTGTTTTTTCTTCT |
| | | | | CTTGATTATATTTCACAGAAAGAACACGATCCTTCAAAGTT |
| | | | | GTTGGCTGATACACCGTGCAAACTTCTTCGGTTCTTGGTTG |
| | | | | CGGATGGCTCTCATGTGGATGCTGATACACCATATGCTGA |
| | | | | GGTGGAAGTCATGAAGATGTGCATGCCACTGCTAGTGCCT |
| | | | | GCCTCTGGTGTCATTCACTTCGTTATGCCTGAGGGTCAGGC |
| | | | | CATGCAGGTATTATTCCTCTTTATTTTTCTCCCCCTCTGCTCT |
| | | | | TGCTTCTTTCATTTTATAAAAACCTTAAATGTATGTTTTCCTT |
| | | | | TTTTTTTCAGGCGAATGACTTAATAGCAAGATTGGACCTTG |
| | | | | ATGACCCATCTTCTGTGAGGAGAGCTGAACCGTTTCATGG |
| | | | | CTCCTTCCCCAAATTGGGACCTCCTACTGCTATTTCTGGCAA |
| | | | | AGTTCATCAAAAATTTGCTGCAAGCGTGAATTCTGCACACA |
| | | | | TGATCCTTGCAGGCTATGAACATAATATCAATGAGGTAAG |
| | | | | ACATATAATTATTTTTAATTTCAAATTAATTTTCATTTTTAAC |
| | | | | TTCCCTTTCATTATCTTCATCTGCGAAGAACCCAATTTCATG |
| | | | | GTTTATAACACACCACTATCGCTGAGAGCAATTGGGATT |
| | | | | GCGTGGAATAATAGATTGATTAGGGTATACATGATACAGG |
| | | | | ATATATAGGCAGCCTTAAGAGGTTTATAGAATCACAGGGC |
| | | | | AGCCTTGAGAGGTTTATAGAATCACAACCAATCAAGGATG |
| | | | | CCTGCCTTTCCTAACCAACAGAGCACAGCCAGAGGCCAGC |
| | | | | ACAAGTCCTGGCACAAATTCCAAGGACCCTACCACATACAC |
| | | | | TTCTAACAATCC |
| 75 | Kochia scoparia | cDNA Contig | 7122 | ATGGGCGAGTCCGATTCCTGGACACCAATGTCGAATTTGA |
| | | | | CACTTCATCCAAGTCCAAATGATATTGATTCAACATATTGG |
| | | | | TGTAACAGTTATAGGAAAAGTGGGCGTATTTTTTGCCAAG |
| | | | | GGCAGGGCGGAATGTTATCTAGGGAAGACCCAAATAAGG |
| | | | | CAACTTCGGAGGGAAAAATTGATTACCCCAACAGAACAAC |
| | | | | TCTTTTGAGGAAATCTGCTACATTACCTGTTGATGAATTAC |
| | | | | CTGTTGATGAATTTTGTTATGCTCTTGGAGGGAAAAGACC |
| | | | | GATTCGTAGTATTTTGATTGCAAACAATGGAATGGCAGCT |
| | | | | GTTAAATTTATAAGAAGCATTCGGACATGGGCTTATGAGA |
| | | | | CCTTCGGAACAGAGAAGGCTATTGTATTAGTAGCAATAGC |
| | | | | TACTCCAGAAGACATGAGAATCAACGCTGAACACATTCGA |
| | | | | ATGGCTGACCAGTTTGTTGAGGTTCCTGGTGGGACTAACA |
| | | | | ACAACAACTATGCCAATGTGCAGCTCATTGTTGAGATGGC |
| | | | | AGAGATGACACGTGTTGATGCTGTTTGGCCAGGCTGGGGA |
| | | | | CATGCATCGGAGAACCCTGAGCTTCCAGATGCACTAAACG |
| | | | | CGAAGGGGATTGAATTTCTAGGGCCTCCAGCTAAATCTAT |
| | | | | GGCTGCTCTTGGAGACAAAATTGGTTCATCATTGATTGCTC |
| | | | | AGGCCGCAGATGTTCCAACTCTTCCATGGAGTGGCTCTCAT |
| | | | | GTGAAAGCTCCTGCTGAGAGTTGCCTTGATTCTATTCCTGA |
| | | | | TGACATATACAAGGCAGCCTGTGTTTTTACCACAGAGGAA |
| | | | | GCAGTTGCTAGTTGTCAGGTTGTCGGTTATCCAGCTATGAT |
| | | | | TAAAGCATCTTGGGGTGGTGGAGGGAAAGGAATAAGAAA |
| | | | | GGTGCATAATGATGATGAAGTAAGGGCATTGTTCAAGCAA |
| | | | | GTGCAGGGCGAAGTTCCTGGCTCTCCCATATTTATAATGAA |
| | | | | GGTGGCTTCACAGAGTCGACACTTAGAAGTGCAGTTAATT |
| | | | | TGTGATCAATATGGCAATGTAGCAGCATTACATAGCCGTG |
| | | | | ATTGCAGTGTCCAAAGGCGGCACCAGAAGATTATTGAAGA |
| | | | | GGGTCCAATAAATGTAGCTCCCCAAGAAACTGTGATAAAA |
| | | | | CTTGAGCAGGCAGCCAGAAGGTTAGCCAAATATGTGAATT |
| | | | | TTGTTGGAGCAGCAACTGTAGAATATCTATACAGCATGGA |
| | | | | AACTGGCGAGTTTTATTTCCTCGAGCTAAACCCTCGGCTAC |
| | | | | AGGTGGAGCACCCAGTAACTGAATGGATTGCTGGAATTAA |
| | | | | CCTTCCAGCTGCTCAGGTTGCAGTTGGCATGGGTATTCCCC |
| | | | | TCTGGCAAATTCCAGAAATTCGGCGATTCTATGGTAAGGA |
| | | | | ACATGGTGGGGTTATGATGCTTGGAGAAGAACATCAATT |
| | | | | GCTGCGACTGCTTTTAATTTTGACAAGGCACAATCTGTGAA |
| | | | | ACCGAAAGGTCACTGTATTGCCGTACGTGTGACAAGTGAG |
| | | | | GACCCTGATGATGGATTCAAGCCCACTAGTGGGAAAGTAC |
| | | | | AGGAGTTGATTTTCAAAAGTAAACCAAATATGTGGGCCTA |
| | | | | TTTCTCTATAAAGTCTGGGGGAGGCATTCATGAGTTCTCAG |
| | | | | ATTCTCAATTTGGTCATGTCTTTGCATTTGGTGAATCAAGA |
| | | | | GGGTTGGCCATAGCAAATATGGTTCTTGGCTTGAAAGAAA |
| | | | | TTCAAATTCGTGGAGAAATTCGCACTAATGTTGATTATACC |
| | | | | ATTGATCTTTTAAACTCTTCGGATTACAGAGATAATAAAAT |
| | | | | TCATACAGGTTGGTTAGATAGCAGAATTGCAATGAGAGTG |
| | | | | AAAGCGGAAAGACCCCCTGGTTCATCTCTGTTGTGGGAG |
| | | | | GAGCACTCTACAAAGCTTTTGCTAGTAGTGCAGCTACAGTT |
| | | | | TCAGAATATGTTGGCTATCTTGAGAAAGGTCAAATTCCTCC |
| | | | | AAAGGTAATTCAAGCACCAGATGCTGTTGAGCATATATCA |

TABLE 1-continued

ACCase gene sequences isolated from weedy plant species

| SEQ ID NO | SPECIES | TYPE | LENGTH | SEQ |
|---|---|---|---|---|

```
CTTGTCCACTCTGAAGTTTCTCTGAATATTGAGGGGAGCAA
GTACACTATTAAAGTGGTGAGGGGCGGTCCAGGAAACTAC
AGATTGAGATTGAATGAGTCTGAGATTGAGGCTGAAATAC
ATCCATTAAGAGATGGGGGTCTTTTGATGCAATTGGATGG
GAAAAGTCACGTGATATATGCTCAGGAAGAGGCAGCAGG
AACTCGCCTTCTTATTGATGGACGAACGTGTTTGCTTCAGA
ATGATCATGATCCTTCAAAGTTAATTGTGGAAACACCTTGT
AAGCTACTGCGGTATCTGGTTCCAGATGATAGTCATGTTGA
TCCAGATACTCCTTTTGCTGAAGTTGAGGTTATGAAGATGT
GTATGCCTTTGCTTTCCCCTGCATCTGGTAAAATAAGATTTA
AGATGTCCGAAGGACAACCCATGCAGGCTGGCGAACTCAT
AGCAAAACTTGAGTTGGATGATCCTTCAGCTGTAAGAAAA
GCTGAACCGTTCCGTGGTAGTTTTCCAACCTTGCATCCGCC
AACTGCTATCTCAGAAAAGGTTCATCAAAAATTTGTTGCAA
GTTTGAATGCAGCCCAGATGATTCTTGCTGGTTTTGAACAC
AACATAGATGAAGTTGTCCAGAGTTTGTTGAGGTGCCTTG
ATAGTCCTGAACTTCCTTTCTTGCAATGGCAAGAATGCTTG
TCTGTTCTAGCAACACGGCTTCCCAAAGATCTGAGAACTGA
ATTGGAATCAAAGTGTCGAAATTCACAGGAATTACGAAT
TCTCATAACATTGAATTTCCTGCTATGGTGTTTAAAGGTGTT
CTTGAGGCCCATTTGAATTCATGCCCTGAAAAGGAGAGAG
GAGCTCAAGAGCGGCTCATTGAACCTCTAATGAGTCTTGTT
AAATCCTATGAAGGTGGGAGAGAGAGTCATGCCCATGTTA
TTGTTCAGTCTCTGTTTGAAGAGTATTTGTCTGTTGAAGAA
TTGTTCAGTGTCAATATCCAGGCTGATGTGATTGAACGTCT
CCGCCTTCAACATAAAAATGATCTATCAAAAGTTGTTGATA
TTGTCCTATCACATCAGGGTGTTAAGAATAAAAATAAATTG
ATCCTCCGGCTCATGGAACAACTGGTTTACTCAAATCCTGC
CGCATATCGGGATAAGCTTAAACATTTTTCACAACTGAACC
ATAAAACATACTCTAAGTTGGCTCGTAAGGCAAGTCAATTG
CTTGAACAAACCCAGTTGAGTGAACTTCGTTCTAATATTGC
CAGAAACCTTTCCGAGTTAGAAATGTTTACAGAAGACGGT
GAAAGCATGGACGTTACAAAAAGGAAAAGTGTTATTAATG
AACGTATGGATGCTCTTGTTAATACTCCGCTTGCTGTTGAA
GATGCCCTTGTTGGCTTGTTCGATCACAGCGATCATACATT
ACAAAGGCGGGTTGTTGAGACTTATATCCAGAGGCTTTAT
CAACCTTATCTTGTAAAGGGAAGTGTCAAGATGCAGTGGC
ACCGATATGGCCTCATTGCTTCTTGGGAGTTCATGGAGGA
GCACATTGAAAGAGCAAATGCCGCTAATGATTTGTCCATCA
ACCAGCCTCTTGCTGAGAAACTCATTGAGAGAAAATTGGG
AGTCATGGTCATCATTAAATCTCTTCAGTTTTTGCCAAGAG
TGATTACTGCTGCATTAAAAGAGACCACGGATAATTCAGAT
GAAATGATTCCCAGAGGTTCTTTAGATTCAATCAGTCACGG
AAATAAGTTGCACATTGCACTTGTGGGTGTTAATAACCAGA
TGAGCTCGTTGCAGGATAGTGGTGATGAAGATCAAGCTAA
AGAGAGAATTAATAAGTTGGCGAAAATCCTGAGAGAGAA
AGAAGTGAGCTCAGTTCTTCTTAACAGTGGTGTTGGGGTA
ATTAGTTGCATTATACAGAGAAATGGAGGAAGAATCCCAA
TGAGGCATTCATTCTATTGGTCAGAAGAGAAACAATACTTT
AATGAAGAGCCTTTACTACGTCATTTGGAACCTCCTCTATC
AATATATCTTGAACTGGACAAGCTCAAACACTATGAAAATC
CCAGATATACTCCTTCTCGGGATCATCAGTGGCACCTGTAT
ACTGTCATGGACAAGCCATCTATTCGACGAATGTTTTTGAG
GACACTTGTCAGACAGCCCACCTCCGAGTTTAGCGGGGTT
GAACTAGAAATGCTTAAAACACAAAGGCCTATCTCCTTTAC
TTCAAGAAACATACTGAGGTCTTTAACAACTGCAATGGAA
GAATTAGAACTCAATGCGCACAATGCTACCTTGAAACCTGA
TCATGCTCATATGTACCTGTGCATTGTAAGAGAGCAACGAA
TTCAAGATCTTGTCCCATATCACAGGGAGGTGAACATTGAT
GATGAACAAGAAGAGATAACTGTTCAGATATATTTGGAAG
AGCTTGCGCGTGAAATCCACAGTTTTGCTGGTGTGAGAAT
GCATAAACTAAATGTATGTGAGTGGGAAGTAAAGCTTTGG
GTGTCATCTTCTGGCCAAGCCAATGGTTCATGGAGAATCAT
TGTTAATAATGTGACTGGTCATACATGCACTGTACATGTTT
ACCGTGAGTTGGAGGATAACAACCTTCATGAAATGATCTA
CCATTCAATATCTGTTCAAGGTCCTCTCCATGGAATACCAG
TGAATGCACCCTATCAACCACTTGGAGTCATTGCCCGTAAA
AGACTTCAGGCCAGGAAAAATAGCACAACCTATTGTTATG
ACTTCCCACTGAAAGCTGAAATCACCCTTGGGACGCATGT
GAAGCTTACCGCCATCCCCGGAGACGTCCCCAAAGTCAA
CGCCGTTCCCGGAAGTCAATGGCGTCCCGAGGACGTCCCC
AAGCCGTCCCCGGCGCGTTTCCGTCCCCGTTCTGTCCCCGG
CTTTCTCTACTGCCTTGGAGCAATCATGGGCATCCCAACCT
CCGCTGCTGAAGAAACCCACAAACAAAAAGTTTTGAAAG
TCTCAGAGCTAGTATTTGCTGATGCAAATGGCACCTGGGG
AACACAAGTTGTCCCAACAGACCGTGAACCTGGTCTTAATA
```

TABLE 1-continued

ACCase gene sequences isolated from weedy plant species

| SEQ ID NO | SPECIES | TYPE | LENGTH | SEQ |
|---|---|---|---|---|
| | | | | ATATTGGCATGGTGGCCTGGTCCATGGAGATGTCAACTCC<br>TGAATTTCCTGATGGAAGGACCATATTGGTTGTAGCAAAT<br>GATATCACCTTCATGGCTGGATCATTTGGGCCAAAAGAAG<br>ATGCTCTCTTCCGGGCAGTTACAGATCTTGCTTGTTCCAAA<br>AAAATTCCTCTGATTTACCTGGCTGCTAATTCTGGTGCCCG<br>ACTGGGTGTTGCTGAAGAGGTAAGAGCGTGCTTTAAAATT<br>GGTTGGTCTGATGAACTGAACCCTGAACGGGGGTTCCAGT<br>ATATCTACTTGACTCCTGAAGATTATGGTCGTATAGGGTCA<br>GCAGTTATAGCCCATGAGTTAGAACTCCAAAATGGAGAGA<br>CTCGGTGGGTTATAGACACTATTGTAGGGAAGGAGGATG<br>GGTTAGGTGTTGAGAACTTATCCGGAAGTGCGGCTATAGC<br>TGGTGCCTATTCAAGGGCATACAAAGAAACTTTTACACTAA<br>CTTTTGTAACAGGAAGAACAGTTGGTATTGGTGCCTATCTT<br>GCTCGCCTTGGGATGCGTTGTATCCAAAGGCTTGATCAGC<br>CCATTATTCTGACAGGCTTTTCAACATTAAATAAACTTCTTG<br>GTCGTGAGGTTTACAGCTCACAAATGCAACTTGGTGGGCC<br>CAAGATTATGGGTACAAACGGTGTTGTTCATTTAACAGTTT<br>CAGATGACCTTGAAGGCATTTCATCTATTATCAAATGGCTT<br>AGCTATGTTCCATCCTATTCAGGAGGTGAACTTCCTATTTC<br>ACGTTCTTTAGATCCTCCAGAAAGACAGGTTGAGTATTTGC<br>CTGACAATTCTTGCGATCCCCGTTCTGCCATATCTGGTACA<br>CTTGACTCTGATGGTAATTGGCTTGGTGGAATTTTCGACAA<br>AGATAGTTTTGTTGAAACCCTACAAGGCTGGGCAAGGACA<br>GTTATCACTGGCCGCGCCAAACTTGGTGGAATTCCAGTTG<br>GGATAGTTGCTGTTGAGACACAAACTGTGATGCAAGCTAT<br>CCCAGCTGATCCTGGTCAGCTTGATTCTCATGAGCGAGTTG<br>TCTCACAAGCTGGACAAGTATGGTTTCCGGATTCTGCAACT<br>AAGACAGCACAAGCTTTGATGGATTTTAACAGGGAAGGAC<br>TTCCACTTTTCATTCTAGCTAACTGGAGAGGGTTCTCTGGA<br>GGGCAAAGGGATCTCTTTGAAGGGATTCTTCAGGCAGGTT<br>CCACAATTGTCGAGAACCTTAGGACTTATAATCAACCTATT<br>TTTGTTTATATCCCCATGATGGGTGAACTTCGTGGTGGCGC<br>GTGGGTTGTCGTAGACAGTCGAATCAATTCGGACCAGATT<br>GAGATGTATGCTGACCAGACAGCAAAAGGAAATGTTCTTG<br>AGCCAGAAGGAATGATTGAGGTGAAGTTTAGAACCAAGG<br>AATTAATTGAATGTATGGAAAGGCTTGATCAACATCTTATC<br>AATCTTAATGCAAAACTTGTTGAAGCCAAAAACTCCAATTC<br>ATCGGATGACATCAAACCCCTCAAACAGCAGATAGAAGCT<br>CGGCAGAAGCAACTTTTGCCTCTATATACTCAAATAGCCAC<br>AAAATTTGCTGACTTGCATGATAGTCCTTATAGAATGGCTG<br>CGAAAGGAGTTGTCAAGGAAGTCCTGGATTGGAGCAATTC<br>TCGCTCATTCTTCCACAAAAGACTGTACAGGAGAGTAATG<br>GAGGAATCACTTGTCAAGACTGTCCGAGATGCTGCTGGTG<br>AAGCAATGACCCACAAGTCTGCCTTGGAGTTGATCAAGCA<br>ATGGCTTGCTGAGTCTGCCATGGATAGTACTACTAGAGCG<br>GGAGCTGATGCTTGGGCTGACGATGAAGCTTTCTTCAGGT<br>GGAAAGAAAATCCTGCTAATTATGAAGAAAAGCTAATTGA<br>GTTACGCATACAGAAAGTATTGCATCAGCTTTCAAATATTG<br>ACAACTCAGCTTCTGATCTGAGAGCTCTTCAGCTTCGTCAG<br>GGTCTTGTTGCCCTACTTCAGAAGGTGAATTCCTCAAGCCG<br>AGCAAATCTAGTAGAGAAACTCGAGAAAGTGCTCAATTGA |
| 76 | Kochia scoparia | gDNA Contig | 17930 | ACTTTGTAGTTTGTAGTTTGTAGTGTGCAGTGTGCAGTGTG<br>CAGTGTCGCATTAAAATTTGACTAATGCTAATGCTTCCCTA<br>AAATCTCTCCTAAACATGTGAATTTCCTTAAATTACCACCGC<br>AAACTCCATTCAATACTTAGAATTATTCCCTTGAATTCGATC<br>CTACTCTTCAGTTTCATAGTTTCAACACTCTTTTATTTAAACT<br>TCCTACAATCGTCGTTCTCTTTTTTTTTTTTGTTTTTCCTAGG<br>CTTCAAATGCAGTATTATTATTATTATTATTAGTTTTTCTTAT<br>TTTACAACTAAATTTTCATTTCAACACTCAGAAAATTTAAGA<br>TGATTCCAATTTCTGAGCGTTGTCATGTTGTTAAATTTCCTA<br>TACTCAAATCTTCTTCTCATTGCCGTCTCTTATTTCACAGTG<br>CAAATGGGACTATGAAATTTCAACTCAAAAAGAGGTATTTT<br>CATTTTCATTTCTTAGTGTCGTATTTTCGTAATTACGTTGATT<br>TTTGTGTGAATTGTATACTAGTATTACAAAGGATCCATGAT<br>TACATCGTTCAATTGGCATAGATGATGAAATTGTTAGAAAT<br>TTTCGTGCAATTTGCAATGCTTGCTTTCATGATTATTTGTGT<br>TGTTGAAGGGAAATTCTTAATCAATCTCGAGATATGTATTT<br>CGGGTGACATTTTCGTAAATGAACAAAAAACCTTCAAGGA<br>ATTTATTTTCACTTTATTTACGAGAATATACATAGCTTGAGA<br>TTGTTTAAGAAATTCCCGATTTGGAGGTATCACTTAGAATA<br>TATATATATATATATTTTATTTCATTATTTTAATCATGGAAA<br>ACGATATACTCGCTAACTCGCATTTGAATTCACAACTTTT<br>GTACATTGTAGCTTTCTTTCTAGGATGCATAAAGAACTTGA<br>CACTACCAACTAACCGGTGTTTACGATGAATCATACCCTTT<br>TCTTTGAGCTGATTTTGGGATGTGTCTTTTATATTGGGGTT |

TABLE 1-continued

ACCase gene sequences isolated from weedy plant species

| SEQ ID NO | SPECIES | TYPE | LENGTH | SEQ |
|---|---|---|---|---|

```
GGTTTTTGGTAGTGTGTAGTTGAGCTAAATTAAAGCTCTCT
TTGGTAAGAAGTAAAATTTTTTGATGCAAAGTGTTTTCGA
CAATTTTCTAATTTTATATTGTTTGGTTGACAAAGGAGTGT
AAAACCATTTTACATGGAAAACTTTTCCAACAATATTTTGTA
CACTCTTGTGGCTACCTCTTTGCACTCCTTCATTTTCGCTATT
TCCCATATTGTTTATGATGCAATCAAATAATGGAAAATTGC
TTCCATGTAAATTGCTTTCCATTCTAAATTGTTTTCCTTGAA
AATCATTTTACATTGTAAATATTTTACGCCAAACCAAAATTG
ACCCTAGGAGTAATATAGTGTGAATTTATCATATTGTTATA
TTCGGTAATGCATACTAGATAATTGTGGTTCATTTTAGTTG
TTACTTACTCTTCTAACTGTCGAGTGATTAATACAAGTATGT
GTAGTCCAAAGTATTTATATTTTTAAAATTAAAAAAAATT
GCATTAGATTGTTGGCTCTTGAATTCTACTTGACTCTTGAAT
GTATGAGTCAAAATAAAACAATTATTAGTATGTAGCTTTTA
TACCATAATAGTTCTGCATTTCAAACAACCAGTATGTTCTAT
TCCTTTTAGTATAAATTAATTCTCTCTTTCTCTGTTAATATTG
TAGTTGTGTGGTAAAATATGTTAATTACCCAATTAAAAAGC
TGCAATCTTGCAATAATATGAGTATTGCTTATGATAGTAGC
TCATGTGTTTCAAAGCTTGTATCATTTTAGTAAGACTATTTG
TTTTATGTAATACAAGGTTGTTGTAGCTTGATTACTTTTGAC
ATGTAGAATATGCATATCGTGTGAAAATTGGGAATGCTAT
TCATGTGATAAATTACTCGTACTCTTTCATTTATCTCACGTG
GGCTGTGTCGACACGACTTGTGTCGGACAACACCGACACG
CGATACTTCAATCTTTTAACTTTAAACACTACTTTTTTCAAG
AAAATGGGCGAGTCCGATTCCTGGACACCAATGTCGAATT
TGACACTTCATCCAAGTCCAAGTAACATAGTTCATGTGATA
TGATGTGATTAGCATGCTGATCAGTGTTTTATTAGATGATA
TTGATTCAACATATTGGTGTAACAGTTATAGGAAAAGTGG
GCGTATTTTTGCCAAGGGCAGGGCGGAATGTTATCTAGG
GAAGACCCAAATAAGGCAACTTCGGAGGGAAAAATTGATT
ACCCCAACAGAACAACTCTTTTGAGGAAATCTGCTACATTA
CCTGTTGATGAATTACCTGTTGATGAATTTTGTTATGCTCTT
GGAGGGAAAAGACCGATTCGTAGTATTTTGATTGCAAACA
ATGGAATGGCAGCTGTTAAATTTATAAGAAGCATTCGGAC
ATGGGCTTATGAGACCTTCGGAACAGAGAAGGCTATTGTA
TTAGTAGCAATAGCTACTCCAGAAGACATGAGAATCAACG
CTGAACACATTCGAATGGCTGACCAGTTTGTTGAGGTTCCT
GGTGGGACTAACAACAACAACTATGCCAATGTGCAGCTCA
TTGTTGAGGTAAATCCTATTTTACTAACACTGATCTTCATTG
TTTTCTCTGATAGAATATCGGTTTATAAGAAAAGTTATAAC
CTTGCTTGTTGGCCTGTTGATGTGGTTCACATTAAACAACC
TTGGTTCATCATAGGTAGTTCAAGCTCCAACAGTTCATCGT
TAACACACATTAATTCAAGTATCTGTTAATCATTGATCTCAG
AGGGTAAACCATTGTTAAAAGGACTTCAATTTATTTTCACT
GCTTTTCAGATGGCAGAGATGACACGTGTTGATGCTGTTT
GGCCAGGCTGGGGACATGCATCGGAGAACCCTGAGCTTCC
AGATGCACTAAACGCGAAGGGGATTGAATTTCTAGGGCCT
CCAGCTAAATCTATGGCTGCTCTTGGAGACAAAATTGGTTC
ATCATTGATTGCTCAGGCCGCAGATGTTCCAACTCTTCCAT
GGAGTGGCTCTCATGTATGCATTGATTTTCTTATTGACCTT
GACAAGCTTTCTTTTTCTCGAGGAGTTTGCTAATCCGTTTTC
TTAAATTTCTAATCTTTAGGTGAAAGCTCCTGCTGAGAGTT
GCCTTGATTCTATTCCTGATGACATATACAAGGCAGCCTGT
GTTTTTACCACAGAGGAAGCAGTTGCTAGTTGTCAGGTTGT
CGGTTATCCAGCTATGATTAAAGCATCTTGGGGTGGTGGA
GGGAAAGGAATAAGAAAGGTGAGCTAGTTGTTTGGGATG
ATGTCGTCAAGAAATTAAAGCACCGGCTTCAATGCTTATTT
ATCACCCTTTTCACAGCTTCCATCCTTGGACATCCTTTTAAT
TAACTGTCCATTAATATTTACTTGACTTAAATGATGGACAA
ATGCTTCAAACTTGTTAGTTAGAGACCCGTTGTGCTATTTC
AATTACAATCGTCTTTCTCTCAAAATATCACAAAGACTCAAT
AGTTATGCATTTTCAGGTGCATAATGATGATGAAGTAAGG
GCATTGTTCAAGCAAGTGCAGGGCGAAGTTCCTGGCTCTC
CCATATTTATAATGAAGGTGGCTTCACAGGTTAGTTATTCT
GCAAATTGGTGCTAGAATGTATCATATAAGTACTCACAAGT
CCATGGCACTCATGATTTTAGAACTAGTACTGTATGCAAAA
TTCTTTGATTTTGACAAGTTATTATATGTGCTTCAGAGTCGA
CACTTAGAAGTGCAGTTAATTTGTGATCAATATGGCAATGT
AGCAGCATTACATAGCCGTGATTGCAGTGTCCAAAGGCGG
CACCAGAAGGTGGGTCACTAGTGTACTATCAATAAATTTTT
AATCTTCTTGACCAGTTTTGTATTACTTAGGGTCTAAAGTTG
TTTTTTTCATAGAGAATCGTGATGCTCATTGTTCATTGAAG
GAATGTATAAATGATCTTGTTCATTGTATTAATTGATCAGA
TTATTGAAGAGGGTCCAATAAATGTAGCTCCCCAAGAAAC
TGTGATAAAACTTGAGCAGGCAGCCAGAAGGTTAGCCAAA
TATGTGAATTTTGTTGGAGCAGCAACTGTAGAATATCTATA
```

TABLE 1-continued

ACCase gene sequences isolated from weedy plant species

| SEQ ID NO | SPECIES | TYPE | LENGTH | SEQ |
|---|---|---|---|---|

```
CAGCATGGAAACTGGCGAGTTTTATTTCCTCGAGCTAAACC
CTCGGCTACAGGTATGAAGCATACACTTGCACATTGTATAT
TCATATTTACCTCGAATAATTACTCAAGAAAGAAAATGTTT
TATGTCAATATTTATGGCATTGCATCTCAATATCCTTTGGAT
TTATCGTTTTCTACCTTACGTTTGTGGCTCACTTTAATATGA
CTTGCTTTTGTTAAGGAGCCTTGGGATTCTTAGAGTGAGA
TATGACACTCTTGCCTTTCAACTTTTGTGAACCATGTCTGAT
ACTCCCTCCATTTCCTTTTGTTTGTTTGATTTATATCTTGAGG
GGTGATATTATTCATAGGTAGAGAGATTCCTCTAAATTTAT
AAGATGAGACATAGCTCTGAGGGGTCTTGTTGAATTCATC
TTGATGAGTACTTTAAATCAAAGCCTTGATGAGTACTTCAA
TAATATTAAATTTTTAGAATTTTTATTCTTATATAGTTAAAG
ATACTAACAACTAAAAATTTGCTCCAACAAATGTGTGATAA
TGAATCGGGACAAAGAAGGGAATGGAGGGAGTATTACT
AAGAATTAGCAATCCTATATGATCATGTGATGGATGAAAA
AATCTTATTGAAGACTTTTCTGATAATATTGTATATAATGTC
TGACATATGTAGGTTTTATTATATTTAATTTTAAAAAATT
CCTGTTTGGAAAATCCGGTTAATTTTATTGGTTATTTATCTA
ATTCCTTCTTTTGTTCGCGTTTGATAAATACAGGTGGAGCA
CCCAGTAACTGAATGGATTGCTGGAATTAACCTTCCAGCTG
CTCAGGTTGCAGTTGGCATGGGTATTCCCCTCTGGCAAATT
CCAGGTAGCTAGCATGTTCCCTTTCTGATTATCGAACTTAT
GTGCTTCATGTTGTTCTTGTGCATGATTGTGCTTGCTTTTGA
ATTATCAAAATAGAAATTCGGCGATTCTATGGTAAGGAAC
ATGGTGGGGTTATGATGCTTGGAGAAGAACATCAATTGC
TGCGACTGCTTTTAATTTTGACAAGGCACAATCTGTGAAAC
CGAAAGGTCACTGTATTGCCGTACGTGTGACAAGTGAGGA
CCCTGATGATGGATTCAAGCCCACTAGTGGGAAAGTACAG
GTTAGTAATACTAGTGTTTAACAGTTCAAACTACACTCTCA
ATTGACTGCCTTGTCTGTTTTGTGATTCATGTAAAATTATTT
ATTTCATTGGTTCCTTTTCTAGGAGTTGATTTTCAAAAGTAA
ACCAAATATGTGGGCCTATTTCTCTATAAAGGTATGTCTTT
ATTCTTCAATTTTCACATCATCCTTTTATGGATTCATCCACG
AGCTTAACAATGATCAACATTGTGACGCAGTCTGGGGGAG
GCATTCATGAGTTCTCAGATTCTCAATTTGGTAAGTTTAAA
GCACATTTTAAAGATGACTAGCAATGAAATGACAATTATA
GCTGCCTTTTAAGAATGAAGTTCTTCAACATCATATTAGGG
GTTCTCTAATTTAAGTCTGCTGCAAATGGATAAGGAACTAT
GCTGTTGTACATGTGAAATGAGATATATTGGTTTTTCGTAG
TGTGTCACAGCAGACGGTAAATGCTCTTGTTAATTGTTGAT
GATTAATTGGGATTTAGCATTCATGGTGTAATCTGCTCTTG
CACTATCAAGTCTCATGGAATTAACATGTCATTTTTTTTATC
GATTATTTTTGGTTTTAAAACATCCTTTATCTATTTTTTTAT
TTTTTTTATAGAAGGCTAATGTTAGTTAATTTGTTTGTAGGT
CATGTCTTTGCATTTGGTGAATCAAGAGGGTTGGCCATAG
CAAATATGGTTCTTGGCTTGAAAGAAATTCAAATTCGTGGA
GAAATTCGCACTAATGTTGATTATACCATTGATCTTTTAAAC
GTGAGCCTTGTACATGATTTTTTTTCCTCCCTACACTTTCCA
CTGTTTTTTCAATTAGAAGCTAAACTTGTCTTCGTTTTCCTT
TCTCCAGTCTTCGGATTACAGAGATAATAAAATTCATACAG
GTTGGTTAGATAGCAGAATTGCAATGAGAGTGAAAGCGG
AAAGACCCCCCTGGTTCATCTCTGTTGTGGGAGGAGCACT
CTACGTATGTACAACTTTTTTTCTCTAAAATTTGTTTCCTTCC
AAAAGATTCACATGTCATTTTTCGTCTTTTTTTATAACGAAT
AATTTTAAATGATTTCTCTCTTCTTTCTCCCTATCTTCAGAAA
GCTTTTGCTAGTAGTGCAGCTACAGTTTCAGAATATGTTGG
CTATCTTGAGAAAGGTCAAATTCCTCCAAAGGTAATTCAAG
CACCAGATGCTGTTGAGGTATACTGGTTTTTTTAAACACTA
ATTGTTTCTTTCAGTAAATTACATCAATTTTTGTGTGGATTG
CAGCATATATCACTTGTCCACTCTGAAGTTTCTCTGAATATT
GAGGGGAGCAAGTACACTGTAAGTATATTATTATAACTGA
TGTGAATTTTATATTTCATTTTTCGATTTCGTCTGTTTTCTTG
TTAATCATCATAACATGGTTAATGCTGTTCTCTAGATTAAA
GTGGTGAGGGCGGTCCAGGAAACTACAGATTGAGATTG
AATGAGTCTGAGATTGAGGCTGAAATACATCCATTAAGAG
ATGGGGGTCTTTTGATGCAAGTAAGAACTTAACTTTTATTC
ATTCATATATTCATGATTGAGGGCAATTGTCAAATTATACA
CATATAGGAGTTATAATATGTGTAGAGTTAAAATTGCGAG
TGAAAGCTGAGATATTACTCGATGTATTTAGTATATCATTC
ACCATAGAATGCTTGAGTTACTTGCGTTAAATTAAAAAAAA
AAAGGAAAGAGTAGAAATTAGAGAGTCTAAAGTTTCTGTG
GTCATAATGATATGTCTAATTGAACGCACCCCAATGTGTTT
CAGTTATTTTTTACCCCTAACTTAGGAGGGAAAACTGACT
TAGCGGCTTCCCCTCTAGCATAGGATATAAGTGCTCCAAAC
TCTTAGAGATATCTAAATTTGAAAAACTTATAATGTATTATTG
ACATTCTTTCAGAGAATGCTTTTCTGTGTGAACTCCTTAAGT
```

TABLE 1-continued

ACCase gene sequences isolated from weedy plant species

| SEQ ID NO | SPECIES | TYPE | LENGTH | SEQ |
|---|---|---|---|---|

```
ATGTTAATAGCAATCCCGCAACCCTGTTTCACATTATATAG
GTATTTGTTTCTTATTAGATGATATTCCATATCTCCATATAA
GATCTTTCTTCTTACCAATTCAAGCCATATATTTTTTGGATT
AAGAAGATGATATTCACAAAAGGTTTGCGTTATGATGATA
CTTAATATACCCACATGTTTCATATTTTCATTGACTTAAACG
CTATTTCTTAGAAAAGTTGGAGTTGTTGATCCAATGTATGT
GCTGGTTTCTCATCCCTTTGTTTTCAATTAGCTATGGATTTT
GAGCTCTTCTGTACATTTGAATGTGATGTAGTTGGATGGG
AAAAGTCACGTGATATATGCTCAGGAAGAGGCAGCAGGA
ACTCGCCTTCTTATTGATGGACGAACGTGTTTGCTTCAGGT
ACCATCATGTTATTTAATTGCATAGTATTTCTAAACATTTAC
CAAGCGTAACATGCTATTACATTTTCCACTTCTTCAATATTC
AGAATGATCATGATCCTTCAAAGTTAATTGTGGAAACACCT
TGTAAGCTACTGCGGTATCTGGTTCCAGATGATAGTCATGT
TGATCCAGATACTCCTTTTGCTGAAGTTGAGGTTATGAAGA
TGTGTATGCCTTTGCTTTCCCCTGCATCTGGTAAAATAAGA
TTTAAGATGTCCGAAGGACAACCCATGCAGGTTAGCATAG
GTTTTAGTAGATCGATATGTTAACTAAATATACTTCAAAAG
TTTCTTCTAAGTGAAGGTTCACTGTGTAGGCTGGCGAACTC
ATAGCAAAACTTGAGTTGGATGATCCTTCAGCTGTAAGAA
AAGCTGAACCGTTCCGTGGTAGTTTTCCAACCTTGCATCCG
CCAACTGCTATCTCAGAAAAGGTTCATCAAAAATTTGTTGC
AAGTTTGAATGCAGCCCAGATGATTCTTGCTGGTTTTGAAC
ACAACATAGATGAAGTAAGTATTTTAATTGTGAATTCAAAA
ATATTGAGCACTATATTATATAGATGAAGTATTTCAGTTAT
GAATTAAGCATAGATGATGTGAGTATTACTCTAAGGGGGC
TGATGCAAAAATTTGAGAGTAAATGTATATTTATATTTTGT
TTGGTTCCCTTATCTGAAAGATTCTTTACAAAAGAGTTTTCT
AATTCTCAGGTTGTCCAGAGTTTGTTGAGGTGCCTTGATAG
TCCTGAACTTCCTTTCTTGCAATGGCAAGAATGCTTGTCTGT
TCTAGCAACACGGCTTCCCAAAGATCTGAGAACTGAAGTA
TGTTACTAAAATCTGTATGCAATTTTTTTCCATATTTGATAA
ACACCTGCTGTCTTTAGCAGTCTTTATCTTCTTGGTCTTTCC
CTCTCTCTCTCTCTCTCTCTCACCCTGTGTATAATTCACAT
TATTTTTCCATGTTTCCCTGTCTTTGGTATTCTCAGTTGGAA
TCAAAGTGTCGAAAATTCACAGGAATTACGAATTCTCATAA
CATTGAATTTCCTGCTATGGTGTTTAAAGGTGTTCTTGAGG
TTAGTCTTTCTTTTTGCTACCCTTCTATATATGCTATATATTT
TAGTATTACTTACATAAGTATTTTGTTTACAGGCCCATTTGA
ATTCATGCCCTGAAAAGGAGAGAGGAGCTCAAGAGCGGC
TCATTGAACCTCTAATGAGTCTTGTTAAATCCTATGAAGGT
GGGAGAGAGAGTCATGCCCATGTTATTGTTCAGTCTCTGTT
TGAAGAGTATTTGTCTGTTGAAGAATTGTTCAGTGTCAATA
TCCAGGTTTGTTATTGCCGTGCAAATTAATCAGTTTATCGA
TGATCATTGGTCTTTATGTTTTTCCTCGATTGGTAGATTGG
TTATGATGTTATGACTCTAGAGTAAAGGTGGAACCAGAAA
AATGTTTTGGAGGGGGCCAAAATATTTGTTTTGTATTATTG
GAGGGGGCCGAATACAAAAATTAGCTTAATTTTTCCCATAT
TTAACCTATTTTTTAAAGAAAAATAAAAAATTGGCGGGAGT
CGTGGCCCCCACCCGCCCCCATGTTCTGCCATTGCCCTAGA
GGCTACAGAATCTTTGGAGTACCTTATGTCTCAGTGAATTA
TAGTAGCATCCTTTGAAGTATTACTTTGTTTTTTCAAGAAAT
AGCAGTTCATGTCTTTGGTTGTTGGCTTGTAATTTGTGCAC
TGTAATGCAAGCTTAGGACTAGAAGAAACAGTTTATTTATA
CGCTATGAATTATGATCCTGGTAGGCTGGCATCGTTCCACT
GTAATATGATTCTGATTTCAATCTATACAGGCTGATGTGAT
TGAACGTCTCCGCCTTCAACATAAAAATGATCTATCAAAAG
TTGTTGATATTGTCCTATCACATCAGGTAAGCAGGAAATTT
CAAATAATACAAAATAAAATTTTCTGAGTTTTCTTTTTATTT
TCTTTTCTTTTTTTTCCCACTTTCCCTTGTACTGTCTTCTAGA
CTTGTTTACTGTGTAGTAATAATGGTTTTCAGGGTGTTAAG
AATAAAAATAAATTGATCCTCCGGCTCATGGAACAACTGGT
TTACTCAAATCCTGCCGCATATCGGGATAAGCTTAAACATT
TTTCACAACTGAACCATAAAACATACTCTAAGGTTAGAGAT
GATTCAACTTTTTGCATTATTGTCACACTACAACATTCACAA
AAAGGTCATTAAGTTTATACACTAATTAATTCCTTCGCTATA
TGCAGTTGGCTCGTAAGGCAAGTCAATTGCTTGAACAAAC
CCAGTTGAGTGAACTTCGTTCTAATATTGCCAGAAACCTTT
CCGAGTTAGAAATGTTTACAGAAGACGGTGAAAGCATGGA
CGTTACAAAAAGGAAAGTGTTATTAATGAACGTATGGAT
GCTCTTGTTAATACTCCGCTTGCTGTTGAAGATGCCCTTGTT
GGCTTGTTCGATCACAGCGATCATACATTACAAAGGCGGG
TTGTTGAGACTTATATCCAGAGGCTTTATCAAGTAATATCT
AAGTTTCAACATTAAACTTTAACAATCATTTGATAATATTAT
GTCATTTAACTCTCTTTTTTGTGGGTAACCTCTTTTCTCAGC
CTTATCTTGTAAAGGGAAGTGTCAAGATGCAGTGGCACCG
```

TABLE 1-continued

ACCase gene sequences isolated from weedy plant species

| SEQ ID NO | SPECIES | TYPE | LENGTH | SEQ |
|---|---|---|---|---|
| | | | | ATATGGCCTCATTGCTTCTTGGGAGTTCATGGAGGAGCAC |
| | | | | ATTGAAAGAGCAAATGCCGCTAATGATTTGTCCATCAACCA |
| | | | | GCCTCTTGCTGAGAAACTCATTGAGAGAAAATTGGGAGTC |
| | | | | ATGGTCATCATTAAATCTCTTCAGTTTTTGCCAAGAGTGATT |
| | | | | ACTGCTGCATTAAAAGAGACCACGGATAATTCAGATGAAA |
| | | | | TGATTCCCAGAGGTTCTTTAGATTCAATCAGTCACGGAAAT |
| | | | | AAGTTGCACATTGCACTTGTGGGTGTTAATAACCAGATGA |
| | | | | GCTCGTTGCAGGATAGGTATAGATTCTATCCTTGTAGTTTC |
| | | | | AGCAAGATTTTAAATGTGGACATTATTGGACCATCCGGTTT |
| | | | | TTTTGAAGAAATATGCTTTGCTTCAATTATACAGTTGCTCTT |
| | | | | AATATTATCCATTCCAGCCTTTTGCTTAACCTTTTTTGTCTTT |
| | | | | GTGGTTTATGAAATTTATTTTTATACTATTCAGTGGTGATG |
| | | | | AAGATCAAGCTAAAGAGAGAATTAATAAGTTGGCGAAAAT |
| | | | | CCTGAGAGAGAAAGAAGTGAGCTCAGTTCTTCTTAACAGT |
| | | | | GGTGTTGGGGTAATTAGTTGCATTATACAGAGAAATGGAG |
| | | | | GAAGAATCCCAATGAGGCATTCATTCTATTGGTCAGAAGA |
| | | | | GAAACAATACTTTAATGAAGAGCCTTTACTACGTCATTTGG |
| | | | | AACCTCCTCTATCAATATATCTTGAACTGGTAATAAAATTCT |
| | | | | GAGCAAGAAGCTGTTGCTTTGTTTGTTCGTTCTTTTCTTGTT |
| | | | | TTTTAATATGGGCCAAATCATTATCTTTAATATTTTTATCAC |
| | | | | TATATGATATAGTTATAAGGTATTTGGCTCACAATTTTCATT |
| | | | | ATACAGGACAAGCTCAAACACTATGAAAATCCCAGATATA |
| | | | | CTCCTTCTCGGGATCATCAGTGGCACCTGTATACTGTCATG |
| | | | | GACAAGCCATCTATTCGACGAATGTTTTTGAGGACACTTGT |
| | | | | CAGACAGCCCACCTCCGAGTTTAGCGGGGTTGAACTAGAA |
| | | | | ATGCTTAAAACACAAAGGCCTATCTCCTTTACTTCAAGAAA |
| | | | | CATACTGAGGTCTTTAACAACTGCAATGGAAGAATTAGAA |
| | | | | CTCAATGCGCACAATGCTACCTTGAAACCTGATCATGCTCA |
| | | | | TATGTACCTGTGCATTGTAAGAGAGCAACGAATTCAAGAT |
| | | | | CTTGTCCCATATCACAGGTTCTAATTAATCATCTTAATTTTC |
| | | | | TGTGTTTCATTCGTGGTCATTGATGCAACTTATGCCTTAATA |
| | | | | GATATTATTTTGACCCATTGATCCAGGGAGGTGAACATTGA |
| | | | | TGATGAACAAGAAGAGATAACTGTTCAGATATATTTGGAA |
| | | | | GAGCTTGCGCGTGAAATCCACAGTTTTGCTGGTGTGAGAA |
| | | | | TGCATAAACTAAATGTATGTGAGTGGGAAGTAAAGCTTTG |
| | | | | GGTGTCATCTTCTGGCCAAGCCAATGGTTCATGGAGAATC |
| | | | | ATTGTTAATAATGTGACTGGTCATACATGCACTGTACATGT |
| | | | | AAGTTTGAATTTTGATTATTTTCCTATAACTTTCTGTACATC |
| | | | | AACCATGTTTAGTGATTTCTTTCAACACTCTGATATTTATGC |
| | | | | CAGTTTTTGTAAGAATTATAGAAATACAGTAGCAATGTTTT |
| | | | | GATAGCCCAGGTTCTCTCTTTCTCCCAAATTAATCTTTGTGT |
| | | | | CAATGCATGACTTTGCCGCATCAATATCTTAAATAATTTAT |
| | | | | GATTATAAACTATAAGAATATGATACTATGAGAAATTGAA |
| | | | | AATATACATCGAGAGAAATCTAAATACACCTTCCATAACCT |
| | | | | TTGATTTATTATTTTATTTTTTAATGGAAAAACAATGGGCAA |
| | | | | AGGTGATACATGAATCATGTAAAACACAAACTTTGATTTTA |
| | | | | CATATGGGATGAAGGGACTAGTAATGGTTTGTATATTGGC |
| | | | | ACTGACAAAGAAAAGTTTATTCATGATTAATTTACGTCTTG |
| | | | | TATACGTGTATCACATAATGTCTTCTTTAGTTTGATGACCTT |
| | | | | TTTTCTACTAATGTTATGCAGGTTTACCGTGAGTTGGAGGA |
| | | | | TAACAACCTTCATGAAATGATCTACCATTCAATATCTGTTCA |
| | | | | AGGTCCTCTCCATGGAATACCAGTGAATGCACCCTATCAAC |
| | | | | CACTTGGAGTCATTGCCCGTAAAAGACTTCAGGCCAGGAA |
| | | | | AAATAGCACAACCTATTGTTATGACTTCCCACTGGTAAGAA |
| | | | | ATATTAAACTCCACTATACCCCAATACTACAAAAGCAGAAT |
| | | | | TTTACTATATTAGGTTTCCTTCCCTCCCGAATTTTTTAAAAA |
| | | | | ATAAGAGTTAATACATGACTTGCATTCGAGTGTAACTATGT |
| | | | | TCTTATTAACGCTCAACTAGTAATGCAATGGGAATATAAAT |
| | | | | CTAAATTCTAAGAGGGAGGTGGGGTTCAGTAACTGTGGG |
| | | | | ACTAGGTTGCACCGATACGGGTACGGGGACATATACGGGT |
| | | | | ACGGGAACGGGGACGGGAAACGACAATTTTAAAAATTCTT |
| | | | | GGGTACGGGGACGGATTTGGGAACGACAATTTATTAAATA |
| | | | | TAAATTTTTATTTTAAAAAAAAATGAGCATTGTGATCATTTT |
| | | | | AATAAAAAAAATGCAACAAAATAAAAATCATAGTTAATAC |
| | | | | AAATAATTTAGTCCAAAGTAAAAGGCAAGTAGACAACATT |
| | | | | TAATTTTTTTAAACATAACCAGAAAACATAAATTTAATAG |
| | | | | GGTAAATAAAAAAATGGTGAAATCCAAAAAATTAAATAAAT |
| | | | | GACACAAATAAGCACACATTCACAACCACACATTTACAAAT |
| | | | | CACAAATTCACAACCACATAAAATGAATTAAAGTGGAATA |
| | | | | GTTTACTGACATGCTTTGGAAGACAATAGAAAAAGTGAAA |
| | | | | GAGAAGATTAGAAGAAGAAAGTGAGATTTAAGAAGCCAC |
| | | | | GAAGTGAAGCCTAGCGCCATAGTGGAATAGTCAAGCCTCA |
| | | | | ACATCGTCGAATAGTGTAGCCTTGCGCCATCGCCATTGAG |
| | | | | AGTGAGTGGCAGAACCACCGTTTGCCGTCACCGTGGTGTA |
| | | | | ATGCATCGTCGTCGAGAGGAAGAGAGAGAGACCCTAGAA |
| | | | | TTTGAAATTGGTTTGTTTTTGTTGTGCCAAGTGGTTTATTC |

TABLE 1-continued

ACCase gene sequences isolated from weedy plant species

| SEQ ID NO | SPECIES | TYPE | LENGTH | SEQ |
|---|---|---|---|---|
| | | | | AACATTCTATTGTAATTTTGTTGTTTTATAAACTAAAAGAAA |
| | | | | GCTGAAATCACCCTTGGGGACGCATGTGAAGCTTACCGCC |
| | | | | ATCCCCGGAGACGTCCCCAAAAGTCAACGCCGTTCCCGGA |
| | | | | AGTCAATGGCGTCCCGAGGACGTCCCCAAGCCGTCCCCGG |
| | | | | CGCGTTTCCGTCCCCGTTCTGTCCCCGGTACGGGGGACGCT |
| | | | | GGCTATGTGGCGTCCCCGTGCAACATAGCTGTGGGACCTT |
| | | | | GTAAAGGTTTAAAGTTTGGTGGAGATGCTGGGTTTATAAT |
| | | | | TAGTTTAGGACGAAACTGCCAAGTTTTCTATTGTATGTAAT |
| | | | | TTATTGGTTATGAAAGTAAAAAATCGTGATTGTTATGCAAA |
| | | | | TGATTGTACCTATAGTGATTGTGTGACAATGTTGTCAAATG |
| | | | | TATAAGCATTGCAATTTTTTTGAGATAAGGGAACCGTAAAT |
| | | | | AAAAATACAACGCATGGCTTGGATGTTACCGTCATTACCGA |
| | | | | TTTTTGTCCTATGTAGTGGTATCTCAAATTTTTATATTTCACT |
| | | | | TTGGAGCGATCAACTTGCTTTAGGTGCTAGTATTTATCTGT |
| | | | | TTTTCTATGGGAAAATTGACTTGTAATTGTTGGGAATGTTT |
| | | | | TTCTTAGGCTTTCTCTACTGCCTTGGAGCAATCATGGGCAT |
| | | | | CCCAACCTCCGCTGCTGAAGAAACCCACAAACAAAAAAGT |
| | | | | TTTGAAAGTCTCAGAGCTAGTATTTGCTGATGCAAATGGCA |
| | | | | CCTGGGGAACACAAGTTGTCCCAACAGACCGTGAACCTGG |
| | | | | TCTTAATAATATTGGCATGGTGGCCTGGTCCATGGAGATGT |
| | | | | CAACTCCTGAATTTCCTGATGGAAGGACCATATTGGTTGTA |
| | | | | GCAAATGATATCACCTTCATGGCTGGATCATTTGGGCCAAA |
| | | | | AGAAGATGCTCTCTTCCGGGCAGTTACAGATCTTGCTTGTT |
| | | | | CCAAAAAATTCCTCTGATTTACCTGGCTGCTAATTCTGGT |
| | | | | GCCCGACTGGGTGTTGCTGAAGAGGTAAGAGCGTGCTTTA |
| | | | | AAATTGGTTGGTCTGATGAACTGAACCCTGAACGGGGGTT |
| | | | | CCAGTATATCTACTTGACTCCTGAAGATTATGGTCGTATAG |
| | | | | GGTCAGCAGTTATAGCCCATGAGTTAGAACTCCAAAATGG |
| | | | | AGAGACTCGGTGGGTTATAGACACTATTGTAGGGAAGGA |
| | | | | GGATGGGTTAGGTGTTGAGAACTTATCCGGAAGTGCGGCT |
| | | | | ATAGCTGGTGCCTATTCAAGGGCATACAAAGAAACTTTTAC |
| | | | | ACTAACTTTTGTAACAGGAAGAACAGTTGGTATTGGTGCCT |
| | | | | ATCTTGCTCGCCTTGGGATGCGTTGTATCCAAAGGCTTGAT |
| | | | | CAGCCCATTATTCTGACAGGCTTTTCAACATTAAATAAACTT |
| | | | | CTTGGTCGTGAGGTTTACAGCTCACAAATGCAACTTGGTG |
| | | | | GGCCCAAGATTATGGGTACAAACGGTGTTGTTCATTTAAC |
| | | | | AGTTTCAGATGACCTTGAAGGCATTTCATCTATTATCAAAT |
| | | | | GGCTTAGCTATGTTCCATCCTATTCAGGAGGTGAACTTCCT |
| | | | | ATTTCACGTTCTTTAGATCCTCCAGAAAGACAGGTTGAGTA |
| | | | | TTTGCCTGACAATTCTTGCGATCCCCGTTCTGCCATATCTGG |
| | | | | TACACTTGACTCTGATGGTAATTGGCTTGGTGGAATTTTCG |
| | | | | ACAAAGATAGTTTTGTTGAAACCCTACAAGGCTGGGCAAG |
| | | | | GACAGTTATCACTGGCCGCGCCAAACTTGGTGGAATTCCA |
| | | | | GTTGGGATAGTTGCTGTTGAGACACAAACTGTGATGCAAG |
| | | | | CTATCCCAGCTGATCCTGGTCAGCTTGATTCTCATGAGCGA |
| | | | | GTTGTCTCACAAGCTGGACAAGTATGGTTTCCGGATTCTGC |
| | | | | AACTAAGACAGCACAAGCTTTGATGGATTTTAACAGGGAA |
| | | | | GGACTTCCACTTTTCATTCTAGCTAACTGGAGAGGGTTCTC |
| | | | | TGGAGGGCAAAGGGATCTCTTTGAAGGGATTCTTCAGGCA |
| | | | | GGTTCCACAATTGTCGAGAACCTTAGGACTTATAATCAACC |
| | | | | TATTTTTGTTTATATCCCCATGATGGGTGAACTTCGTGGTG |
| | | | | GCGCGTGGGTTGTCGTAGACAGTCGAATCAATTCGGACCA |
| | | | | GATTGAGATGTATGCTGACCAGACAGCAAAAGGAAATGTT |
| | | | | CTTGAGCCAGAAGGAATGATTGAGGTGAAGTTTAGAACCA |
| | | | | AGGAATTAATTGAATGTATGGAAAGGCTTGATCAACATCTT |
| | | | | ATCAATCTTAATGCAAAACTTGTTGAAGCCAAAAACTCCAA |
| | | | | TTCATCGGATGACATCAAACCCCTCAAACAGCAGATAGAA |
| | | | | GCTCGGCAGAAGCAACTTTTGCCTCTATATACTCAAATAGC |
| | | | | CACAAAATTTGCTGACTTGCATGATAGTCCTTATAGAATGG |
| | | | | CTGCGAAAGGAGTTGTCAAGGAAGTCCTGGATTGGAGCA |
| | | | | ATTCTCGCTCATTCTTCCACAAAAGACTGTACAGGAGAGTA |
| | | | | ATGGAGGAATCACTTGTCAAGACTGTCCGAGATGCTGCTG |
| | | | | GTGAAGCAATGACCCACAAGTCTGCCTTGGAGTTGATCAA |
| | | | | GCAATGGCTTGCTGAGTCTGCCATGGATAGTACTACTAGA |
| | | | | GCGGGAGCTGATGCTTGGGCTGACGATGAAGCTTTCTTCA |
| | | | | GGTGGAAAGAAAATCCTGCTAATTATGAAGAAAAGCTAAT |
| | | | | TGAGTTACGCATACAGAAAGTATTGCATCAGCTTTCAAATA |
| | | | | TTGACAACTCAGCTTCTGATCTGAGAGCTCTTCAGCTTCGT |
| | | | | CAGGGTCTTGTTGCCCTACTTCAGAAGGTATCTCTAAGGTT |
| | | | | CCTCCACACACACACACCCCACCCACCAAAAAAAACACA |
| | | | | CACACACATTCACAAGAAAAGTAGAATTGCTAGTGAAA |
| | | | | TAACTTCATCGTGTTCAATGCAGGTGAATTCCTCAAGCCGA |
| | | | | GCAAATCTAGTAGAGAAACTCGAGAAAGTGCTCAATTGAT |
| | | | | TTGGTAATGATCCTGCAGAAAAACCTCTTGGTATATGGTG |
| | | | | GTATGCAAATGCCATATCTGAAAGATTGATTAGGCAAGTT |
| | | | | GAGACAGAGACAGGCACAGTTGTAATAATGGGATCTATCA |

TABLE 1-continued

ACCase gene sequences isolated from weedy plant species

| SEQ ID NO | SPECIES | TYPE | LENGTH | SEQ |
|---|---|---|---|---|
| | | | | AACCAGAAGACGTTATAACTAAGCTCAAAGATGATGGTGA<br>TTTTGACCGTCTTCGTCTCAAAATCATTCGTAAGCTCAAACA<br>AAACGTATTTCTTTCTCCTTTTCATCTTCTACTGTATATTAAA<br>TGGTTTAAAATTTGATCTTGATTAATGGGTAATCTTTATAAT<br>TTTATCTTTTTTATTATAATACAAGAATGATATGCATATTTTT<br>ATTTTGTTATTAATTACCAAATGCACTTCAGTTTACATTGCC<br>GGTTTTGAAGTTTTGGAAGCAGAATTGGGGTTAGAATGCT<br>AGATATTATTGCTTGTTGATCATTTATTCAGTTACTTACATT<br>GTTTGGTTGAAATCGGAATTAAAAGAGCACAAATTGTATG<br>GTTTCTAACTCGACTTCACAATAAGAGTATAGATGCTCACT<br>GTTGTGTTGTGTGTTTGTTTTGTTAAGAAATATTGGTTTT<br>GATTGATGATGCTCCAAGCCTCGAGTGAGCGTGTTGATGA<br>AATAGAGTACTGAATTAAAGGTTATCATTTTATCGAATGTC<br>AGATTAATTGTTAATTGTTGCTCGGAGTCGGAGTTTAAATG<br>AGAATCATTTTATCGAATGTCTTAAGTTATCAGGGCAGATA<br>TTTTTTTTCTAGTGGGTATGGACTCTTGAGCCTCTTTTTCT<br>GTATCAAACTGTCCTGTTGGTTGTTCAAATTATGCAAATCA<br>TGAAGAGATTACTTTGGTCTCAGGTTTGCTTCGCCATCCTT<br>CCCAATGAATCGTCAGGATTCATTTTCAATTAAATCTTATGT<br>ATTCACGGGTTCCTTCGTCCCGGTCGCTTCTTAGTTAATGTT<br>CTAGCCCGGAGCCTTGTTGTTGGATGGTTTGATCTACTATA<br>GAGTTCATTTTCTGACTTGTTTGGCATTTGTTAATGGGCATT<br>GATACGAGTTGTTTACCGTATTAAATTAATTATTTATAAAAT<br>TTATCTTAGTCGTTCAAAAATATATACAAGTAATTTAAAATT<br>CAATCTAAAGTGAAGTATAAGTACATATACACATAATATTT<br>ACGCTATTTACAGAATTATACTAATAATCGAATTAAAATAA<br>GTCAATTAGAGTAGTAAAGGAATTAACAAGGTATTTAACT<br>AAAACAATTGATGAGTAAGAAGAACTGATGAATTTGTACT<br>CAAGAACACCCAAACGATACTCCGCTTCAACCTCACGACTC<br>GATGTCATTCTCGTTCGACCTTGAATTCAAGACTAAGCTAC<br>CTTTCAATTGTTGTCTCCTCTTCCAATTGCTCCAATCGAAAA<br>TCCTATCAAAACTCTTACTCTCAATTGCTCTCAAAATATCGG<br>CTAAGTTGTGTGTCAACAATAGGTCTATATGGTCCTGAGA<br>CCATGTGG |
| 77 | Kochia scoparia | gDNA Contig | 12931 | AATAGTAAAAACCTAGTGAACTTTGTAGTTTGTAGTTTGTA<br>GTGTGCAGTGTGCAGTGTGCAGTGTCGCATTAAAATTTGA<br>CTAATGCTAATGCTTCCCTAAAATCTCTCCTAAACATGTGAA<br>TTTCCTTAAATTACCACCGCAAACTCCATTCAATACTTAGAA<br>TTATTCCCTTGAATTCGATCCTACTCTTCAGTTTCATAGTTTC<br>AACACTCTTTTATTTAAACTTCCTACAATCGTCGTTCTCTTTT<br>TTTTTTTTGTTTTTCCTAGGCTTCAAATGCAGTATTATTATTA<br>TTATTATTAGTTTTTCTTATTTTACAACTAAATTTTCATTTCA<br>ACACTCAGAAAATTTAAGATGATTCCAATTTCTGAGCGTTG<br>TCATGTTGTTAAATTTCCTATACTCAAATCTTCTTCTCATTGC<br>CGTCTCTTATTTCACAGTGCAAATGGGACTATGAAATTTCA<br>ACTCAAAAGAGGTATTTTCATTTTCATTTCTTAGTGTCGTA<br>TTTTCGTAATTACGTTGATTTTTGTGTGAATTGTATACTAGT<br>ATTACAAAGGATCCATGATTACATCGTTCAATTGGCATAGA<br>TGATGAAATTGTTATAAATATCGTGCAATTTGCAATGCTTG<br>CTTTCATGATTATTTGTGTTGTTGAAGGGAAATTCTTAATCA<br>ATCTCGAGATATGTATATCGGGTGACATTTTCGTAAATGAA<br>CAAAAAACCTTCAAGGAATTTATTTTCACTTTATTTACGAGA<br>ATATACATAGCTTGAGATTGTTTAAGAAATTCTCGATTTGG<br>AGGTATCACTTAGATTGTTTAATTTCATTATTTTAATCATGG<br>AAAACGATATATTCTCGCTAACTCGCATTTGAATTCACAAC<br>TTTTGTACATTGTAGCTTTCTTTCTAGGATGCATAAAGAACT<br>TGACACTACCAACTAACCGGTGTTTACGATGAATCATACCC<br>TTTTCTTTGAGCTGATTTTGGGATGTGTCTTTTATATTGGGG<br>TTGGTTTTTGGTAGTGTGCAGTTGAGCTAAATAAAAGCTCT<br>CTTTGGTAAGACGTAAATTTTTTTGATGCAAAGTGTTTTCG<br>ACAATTTTCTAATTTTATATTGTTTGGTTGACAAAGGAGTAT<br>AAAACCATTTTACATGGTAAACTTTTCCTTCAATATTTTGTA<br>CACTCTTCTGGCTACCTCTTTGCACTCCTTCATTTTCGCTATT<br>TTCCATATTGTTTATGATGCAATCAAATAATGGAAAATTGC<br>TTCCATGTAAATTGCTTTCCATTGTAAATTGTTTTCCTTGAA<br>AATCATTTTACATTGAAATATTTTACGCCAAACCAAAATG<br>ACCCTAGGAGTAATATAGTGTGAATTTATCATATTGTTATA<br>TTCGGTAATGCATACTAGATAATTGTGGTTCATTTTAGTTG<br>TTACTTACTCTTCTAACTGTTGAGTGATTAATACAAGTATGT<br>GTGGTCCAAAGTATTTATATTTTTAAAATTAAAAAAAAATT<br>GCATTAGATTGTTGGCTCTTGAATTCTACTTGACTCTTGAAT<br>GTATGAGTCAAAATAAAACAATTATTAGTATGTAGCTTTTA<br>TACCATAATAGTTCTGCATTTCAAACAACCGTATGTTCTATT<br>CCTTTTAGTATAAATTAATTCTCTCTTTCTCTGTTAATATTGT<br>AGTTGTGTTGTAAAATATGTTAATTACCCAATTAAAAAGCT |

TABLE 1-continued

ACCase gene sequences isolated from weedy plant species

| SEQ ID NO | SPECIES | TYPE | LENGTH | SEQ |
|---|---|---|---|---|

```
GCAATCTTGCAATAATATGAGTATTGCTTATGATAGTAGCT
CATGTGTTTCAAAGCTTGTATCATTTTAGTAAGACTATTTGT
TTTATGTAATACTAGGTTGTTGTAGCTTGCTTGCTTTTGATA
TGTAGAATATGCATATCGTGTGAAAATTGGGAATGCTATTC
ATGTGATAAGTTACTCGTACTCTTTCATTTATCTCACGTGGG
CTGTGTCGACACGACTTGTGTCGGACAACACCGATACGCG
ATACTTCAATCTTTTAACTTAGAACACTACTTTTTTCAAGAA
AATGGGCGAGTCCGATTCTTGGACACCAATGTCTAATTTGA
CACTTCATCCAACTCCAAGTAACATAGTTCATGTGATATGA
TGTGATTAGCATGCTGATCAGTGTTTTATTAGATGATATTG
ATTCAACATATTGGTGTAACAGTTATAGGAAAAGTGGACG
TATTTTTTGCCAAGGGCAGGGCGGAATGTTATCTAGGGAA
GACCCAAATAAGGCAACTCCGGAGGGAAAAATTGATTACC
CCAACAGAACAACTCTTTTGAGGAAATCTGCTACATTACCC
GTTGTTGATGAATTTTGTTATGCTCTTGGAGGGAAAAAGCC
GATTCATAGTATTTTGATTGCCAACAATGGAATGGCAGCTG
TTAAATTTATCAGAAGTGTTCGGACATGGGCTTACGAAACT
TTTGGAACAGAGAAGGCTATTGTATTAGTAGCAATGGCTA
CTCCAGAAGACATGAGAATCAACGCTGAACACATTCGAAT
GGCTGACCAGTTTGTTGAGGTTCCTGGTGGGACTAACAAC
AACAACTATGCCAATGTACAGCTCATTGTTGAGGTAAATCC
TGCTTTAGTAACACTGATCTTCCGTGTTTTCTCTGTTAGATT
ACGAAATACTCACATTAGCCACAGTGTATGAGAAAAGATA
TCACCTGTCCTGTTGGCCTGTTGATGTTCATCATTGATTTCA
GAGGATAAAATTTTGTTAAAAAGACTTCAATTTATTTTCAC
TGCTCTTTCAGATGGCAGAAATTACACGCGTAGATGCAGTT
TGGCCAGGTTGGGGACATGCATCTGAGATCCCTGAGCTTC
CAGATGCACTAACCGCAAAGGGGATTGAATTTCTAGGGCC
TCCAGCTATATCTATGGCTGCTCTTGGAGACAAAATCGGTT
CATCATTGATTGCTCAGGCCGCAGATGTTCCAACTCTTCCA
TGGAGTGGCTCTCATGTATGAATTGATTTTCTTATCGACCTT
CACAAACTTTCTTTTTCTCAAGGAGTTTCCTAATCAGTTTTC
TTAAATTTCTATGCTTTAGGTGAAAGTTCCTGCTGAGAGTT
GCCTTGATACTATTCCTGATGATATATACAAGGCAGCCTGT
GTTTTTACCACAGAGGAAGCAGTTGCTAGTTGTCAGGTTGT
CGGTTATCCAGCTATGATTAAAGCATCTTGGGGTGGTGGA
GGGAAAGGAATAAGAAAGGTGAGCTAGTTGTTTGGGATG
ATGTCGTCAAGAAATTAAAGCACCGGCTTCATTGCTTATTT
ATCACCCTTTTCACAGCTTCCATCCTTGGACATCCTTTTAAT
TAACTGTCCAGTAATATTTACTAGACTTAAATGATGGACAA
ATGCTTCAAACTTGTTAGTTAGAGACCCGTTGTGCTATTTC
AATTACAATTGTCTTTCTCTCAAAATATCACAAAGACTCAAT
AGTTATGCATTTTCAGGTGCATAATGATGATGAAGTAAGG
GCATTGTTCAAGCAAGTGCAGGGCGAAGTTCCTGGCTCTC
CCATATTTATAATGAAGGTGGCTTCACAGGTTAGTTATTCT
GCAAATTGGTGCTAGAATGTATCATTTAAGTACTCACAAGT
CCATGGCACTCATGATTTTAGAACTAGTACTGTACGCAAAA
TTCTTTGATTTTGACAAGTTATTATATGTGCTTCAGAGTCGA
CACTTAGAAGTGCAGTTAATTTGTGATCAATATGGCAATGT
AGCAGCTTTGCATAGCCGTGATTGCAGTGTCCAAAGGCGG
CACCAGAAGGTGGGTCACTAGTGTACTATCAATAAATTTTT
AATCTTCTTGACCAGTTTTGTATTACTTAGGGTCTAAAGTTG
TTTTTTTCATAGAGAATCGTGATGCTCATTGTTCATTGAAG
GAATGTATAAATGATCTTGTTCATTGTATTAATTGATCAGA
TTATTGAAGAGGGTCCAATAAATGTAGCTCCCCAAGAAAC
TGTGATAAAACTTGAGCAGGCAGCCAGAAGGTTAGCCAAA
TATGTGAATTTTGTTGGAGCAGCAACTGTAGAATATCTATA
CAGCATGGAAACTGGCGAGTTTTATTTCCTCGAGCTAAACC
CTCGGCTACAGGTATGAAGCATACACTTGCACATTGTATAT
TCATATTTACCTCGAATAATTACTCAAGAAAGAAAATGTTT
TATGTCAATATTTATGGCATTGCATCTCAATATCCTTTGGAT
TTATCGTTTTCTACCTTACGTTTGTGGCTCACTTTAATATGA
CTTGCTTTTGTTAAGGAGCCTTGGGATTTCTTAGAGTGAGA
TATGACACTCTTGCCTTTCAACTTTTGTGAACCATGTCTGAT
ACTCCCTCCATTTCCTTTTGTTTGTTTGATTTATATCTTGAGG
GGTGATATTATTCATAGGTAGAGAGATTCCTCTAAATTTAT
AAGATGAGACATAGCTCTGAGGGGTCTTGTTGAATTCATC
TTGATGAGTACTTTAAATCAAAGCCTTGATGAGTACTTCAA
TAATATTAAATTTTTAGAATTTTTATTCTTATATAGTTAAAG
ATACTAACAACTAAAAATTTGCTCCAACAAATGTGTGATAA
TGAATCGGGACAAAAGAAGGGAATGGAGGGAGTATTACT
AAGAATTAGCAATCCTATATGATCATGTGATGGATGAAAA
AAAAAATTCTTATTTGACTTTTCTGACAATATTGTATATAAT
GTCTGACATATGTGTAGGTTTTATTATATTTAATTTTAAAAA
ATTCCTGTTTGGAAAATCCGGTTAATTTTATTGGTTATTTAT
CTAATTCCTTCTTTTGTTCGCGTTTGATAAATACAGGTGGA
```

TABLE 1-continued

ACCase gene sequences isolated from weedy plant species

| SEQ ID NO | SPECIES | TYPE | LENGTH | SEQ |
|---|---|---|---|---|

GCACCCAGTAACTGAATGGATTGCTGGAATTAACCTTCCAG
CTGCTCAGGTTGCAGTTGGCATGGGTATTCCCCTCTGGCAA
ATTCCAGGTAGCTAGCATGTTCCCTTTTTTTATTATATAACT
TATGTGCTTCATCTTGTTCTTGTGTATGAGTTGGCTTGCTTT
TGCAATTTCAAAATAGAAATTCGGCGATTCTATGGTAAGG
AACATGGTGGCGGTTATGATGCTTGGAGAAGAACATCAGT
TGCAGCGACTCCTTTTGATTTTGACAAGGCACAATCTGTGA
AACCAAAAGGTCACTGTACTGCCGTACGTGTGACAAGTGA
GGACCCTGATGATGGATTCAAGCCCACTAGTGGGAAAGTA
CAGGTTAATAATGCTATTGTTTTATAGTTCAAACTATTTTCT
CAATTGATTGCCTTGTCTGTTTTGTGATTCATGTAAAATTAT
TTAATTCATTGGTTTCTTTTCTAGGAGTTGAGTTTCAAAAGT
AAACCAAATGTGTGGGCCTATTTCTCTGTTAAGGTATGTCT
TTATTTTTTTAAGCTTTACATCATCCTTTTATGGATTCATCC
ACGAGCTTAACAATGGTCAACACTGTCAATTGCAGTCTGG
GGGAGGCATTCATGAATTCTCAGATTCTCAATTTGGTAAGT
TTAAAGCACATTTTAAAGATGACTAGCAATGAAATGACTAT
TATAGCTGCCTTTTAAGAATGAAGTTCTTCAACATCATAGT
ATTCATTCTCTAATTTAAGACTGCTGCAAATGGATTGAGAA
CTGTGCTGTTGTGCATGTGAAATGAGATATATTGGTTTTTC
ATAGTGTGTCATTGTAGACAGTAAATGCTCTTGTTAATTGT
TGATGATTGGAATTGGGATTTAGCATGCTTGGTGTAGTTTT
CTCTTGCACAAACAAGTCTCATGGAATTAACATGTCATTTTT
TTTATCGATTATTTTTGGTTTTAAAACATCCTTTATCTATTTT
TTTTATTTTTTTATAGAAGGCTAATGTTAGTTAATTTGTTT
GTAGGGCATGTCTTTGCATTTGGTGAATCAAGAGGGTTGG
CCATAGCAAACATGGTTCATGGCTTAAAAGAAATTCAAATT
CATGGAGAAATTCGCACGAATGTTGATTATACCATTGATCT
TTTAAACGTGAGCCTTGTACATGATTTTTTTTCCTCCCTACA
CTTTCCACTGTTTTTTCAATTAGAAGCTAAAGTTGTCTTTGT
TTTTCCTTTCTCCAGTCTTCGGATTACAGAGATAATAAAATT
CATACAGGTTGGTTAGATAGCAGAATTGCAATGAGAGTGA
GAGCGGAAAGACCCCCCTGGTTCATCTCTGTTGTGGGAGG
AGCACTCTACGTATGTACAGCTTTTTTTCTCTAAAATTTGTT
TCCTTCCAAAAGCTTCATGTGTCACTTTCGTTTATTTTTATA
ATGAATAATTTTAAATACTTCGTAATTTCTTTCTCCTTTCTCC
CTATCTTCAGAAAGCTTTTGCTAGTAGTACAGCTACAGTTT
CAGAATATGTTGGCTATCTTGAGAAAGGTCAAATTCCTCCA
AAGGTAATTCATGCACCAGACGCTGTTGAGGTATACTGGT
TTTTTTAAACACTAATTGTTTCTTTCAGTAAATTACATCAAT
ATTTGTGTGGATTGCAGCATATATCACTTGTCCACTCTGAA
GTTTCTCTGAATATTGAGGGGAGCAAGTACACTGTAAGTA
TATTATTATAACTGATGTGAATTTTATATTTCATTTTCGATTT
CTTCTGTTTTCTTGTTAATCATCATAACATGGTTGATGCTGT
TCTCTAGATCAAAGTGGTGAGGGGCGGTCCAGGAAACTAC
AGATTGAGATTGAATGAGTCTGAGATTGAGGCTGAAATAC
ATCCATTAAGAGATGGGGGTCTTTTGATGCAAGTAAGAAC
TTAACTTTTATTCATTCATATATTCATGATTGAGGGCAATTG
TCAAATTATACACATATAGGAGTGATAATATGTGTAGAGTT
AAAATTGCGAGTGAAAGCTGAGATATTACTCTATGTATTTA
GTATATCATTCACCATAGAATGCTTGAGTTACTTGCGTTAA
ATTAAAAAAAAAGGAAAGAGTAGAAATTAGAGAGTCTAAT
TTCTGTGGTCACAATGATATGTCTAATTGAACGCACCCAAT
GTGTTTCAGTTATTTTTTTACCCCTAACATAGGAGGGAAAA
CTGACTTAGCGGCTTCCCCTCTAGCATAGGATATAAGTGCT
CCAAACTCTTAGAATATCTAAATTTGAAAAACTTATAATGT
ATTATTGACATTCTTTCAGAGAATGCTTTTCTGTGTGAACTC
CTTAAGTATGTTAATAGCAATCCCGCAACCCTGTTTCACATT
ATATAGGTATTTGTTTCTTATTAGATGATATTCCATATCTCC
ATATAAGATCTTTCTTCTTACCAATTCAAGCCATATATTTTT
GGATTAAGAAGATGATATTCACAAAAGGTTTGCGTTATGA
TGATACTCAATATACCCACATGTTTCATATTTTCATTGACTT
AAACGCTATTTCTTAGAAAAGTTGGAGTTGTTGATCCAATG
TATGTGCTAGGTTCTCATCCCTTTGTTTTCAATTAGCTATGG
ATTTTGAGCTCTTCTGTACATTTGAATGTGATGTAGTTGGA
TGGGAAAAGTCACGTGATATATGCTCAGGAAGAGGCAGC
AGGAACTCGCCTTCTTATTGATGGACGAACGTGTTTGCTTC
AGGTACCATCATGTTATTTAATTGCATAGTATTTCTAAACAT
TTACCAAGCGTAACATGCTATTACATTTTCCACTTCTTCAAT
ATTCAGAATGATCATGATCCTTCAAAGTTAATTGCGGAAAC
ACCTTGTAAGCTACTGCGGTATTTGGTTCCAGATGATAGTC
ATGTTGATCCAGATACTCCATTTGCTGAAGTTGAGGTTATG
AAGATGTGTATGCCTTTGCTTTCCCCTGCATCTGGTAAAAT
AAGATTTAAGATGTCCGAAGGACAACCCATGCAGGTTAGC
ATAGGTTTTGGTAGATCTATATGTTAACTAATTATACTTCAA
AAGTTTCTTCTAAGTGAAGGTTCACTGTGTAGGCTGGCGA

TABLE 1-continued

ACCase gene sequences isolated from weedy plant species

| SEQ ID NO | SPECIES | TYPE | LENGTH | SEQ |
|---|---|---|---|---|

```
GCTCATAGCAAAACTTGAGTTGGATGATCCTTCAGCTGTAA
GAAAAGCTGAACCGTTCCGTGGTAGTTTTCCAACCTTGCAT
CCGCCAACTGCTATCTCAGAAAAGGTTCATCAAAAATTTGT
TGCAAGTTTGAATGCAGCCCAGATGATTCTTGCTGGTTTTG
AACACAACATAGATGAAGTAAGTATTTTAATAGTGAATTCA
AAAATATTGAGCACTATATTATATAGATGAAGTATTTCAGT
TATGAATTAAACATAGATGATGTAAGTATTACTCTAAGGG
GGCTGATGCAAAAATTTGAGAGTAAATGTATATTTATATTT
TGTTTGGTTCCCTTATCTGAAAGATTCTTTACAAAAGAGTTT
TCTAATTCTCAGGTTGTCCAGAGTTTGTTGAGGTGCCTTGA
TAGTCCTGAACTTCCTTTCTTGCAATGGCAAGAATGCTTGT
CTGTTCTAGCAACACGGCTTCCCAAAGATCTGAGAACTGAA
GTATGTTACTAAAATCTGTATGCAATTTTTTTCCATATTTGA
TAAACACCTGCTGTCTTTAGCAGTCTTTATCTTCTTTGGTCT
TTCTCCCTCTCTCTCTCTCTCACCCTGTGTATAATTCAC
ATTATTTTCCATGTTTCCCTGTCTTTGGTATTCTCAGTTGG
AATCAAAGTGTCGAAAATTCACAGGAATTACGAATTCTCAT
AACATTGAATTTCCTGCTAAGCTGTTTAAAGGTGTTCTTGA
GGTTAGTCTTTCTTTTTGTTACCCTTCTATATATGCTATATAT
TTTAGTATTACTTACATAAGTATTTTGTTTACAGGCCCATTT
GAATTCATGCCCTGAAAAGGAGAGAGGAGCTCAAGAGCG
GCTCATTGAACCTCTAATGAGTCTTGTTAAATCCTATGAAG
GTGGGAGAGAGAGTCATGCCCATGTTATTGTTCAGTCTCT
GTTTGAAGAGTATTTGACTGTTGAAGAATTGTTCAGTGACA
ATATCCAGGTTTGTTATTGCAGTTGCAAATTGATCAGTTTTT
TTGGTCAACCAATTTGTACCGGGACAAATTGCCACAGTCCT
AATTTATTGATGATCATCGGTCTTCGTGTTTTTTTCCCGGTT
TGGTTGATTGGTTATCATGTTATGAAGTTGTCACATAAAAA
AACCTAAATTTACTAATGCACCCATTTGACCCTAGAGGCTA
CAGAGTCTTTGGAGTACTCTGTCTCTGTGGATTTATAGTAG
CATCCTTTGAAGTATTACTTTATTTTTTCAAGAAATTGTAGT
TCATGTCTTTTGATTCTGATCTTGAAAGGAAGGCTGACATC
ATTCCACTTTATTTTCTAATTTCAATCTATACAGGCTGATGT
GATTGAACGTCTCCGCCTTCAACATAAAAAAGACCTGTTAA
AGGTTGTTGACATTGTCCTATCACATCAGGTAGGCAGGAA
ATTTCAAATAATACAAAATAAAATTTTCTGAGTTTTCTTTTT
ATTTTCTTTTCTTTTTTTCCCACTTTCCCTTGTACTGTCTTCT
AGACTTGTTTACTGTGTAGTAATAATGGTTTTCAGGGTGTT
AAGAATAAAAATAAATTGATCCTCCGGCTCATGGAACAAC
TGGTTTACTCAAATCCTGCCGCATATCGGGATAAGCTTAAA
CATTTTTCACAACTAAACCATACAATCTACTCTGAGGTTAGT
GATTATTCAATTTTTTGTTTATATTGTCACACTACAGCATTC
ACAAAAAGGTTATTAAGTTTATACACTAATCAATTCCTTCAC
TATATGCAGTTGGCACTTAAGGCAAGTCAATTGCTTGAACA
AACCAAGTTGAGTGAACTTCGTTCTAATATTGCCAGAAACC
TTTCCGAGTTAGAAATGTTTACAGAAGATGGTGAAAACAT
GGACACTCCAAAAAGGAAAAGTGCTATTAATGAGCGTATG
GAGGCTCTTGTGAATACTCCGCTTGCTGTTGAAGATGCCCT
TGTTGGCTTGTTCGATCACAGCGATCATACGTTACAAAGGC
GGGTTGTTGAGACTTATGTCCGGAGACTTTATCAAGTAATA
TCTAAGTTCCAACAGTAAACTTTAACTATCATTTAATAATGT
TATGTCATATAACTCTATTTTTTGTGGGTAATCTCTTTTCTCA
GCCTTATCTTGTAAAAGGAAGTGTCAGGATGCAGTGGCAC
AGATCTGGCCTCATTGTTTCTTGGGAGTTCATGGAGGAGC
ACATTGAAAGAGCAAATGCCTCTAATGATCTGTCCATCAAC
CAGCCCCTTGTTGAGAAACACAGTGAGAGAAAATGGGGA
GCCATGGTCATCATAAAATCTCTTCAGTTTTTGCCAACAGT
GATTACTGCTGCATTAAAAGAGACAACACATAATTCAGAT
GAAACGATTCCCAGAGGCTCTTTAGAATCAATCAGTCATG
GAAATATGTTGCACATTGCACTTGTGGGTGTTAATAACCAG
ATGAGCTTGTTGCAGGATAGGTATAGATTCTATTTTTATGG
TTTAAGCAAGATTTTAAAATGTGAACATTGGACTATCCAAT
TTTATTTATGTTTATTTATTTATTTTTTTTGACGAGGACT
ATCCAGTTTTTTTGAAGAAATATGCTTTGCTTCAATTATGCA
GTCGCTCTTTATAGTAACCATTCCGGCCTTTTGCTTAACCTT
TTTTTCTCTGTGGGGTTTATGAAATGGAATTTTATACTATGC
AGTGGTGATGAAGATCAAGCTCAAGAGAGAATTGATAAGT
TGGCAAAAATCCTGAGAGAGAAAGAAGTGAGCTCAGGTC
TTCGTGACGTTGGTGTCAGGGTAATTAGTTGCATTATACAG
AGAGATGAAGGAAGAACGCCAATGAGGCATTCATTCTATT
GGTCAGAAGAGAAACAATACTTCAATGAAGAGCCTTTACT
ACGTCATTTGGAACCTCCTCTATCAATATATCTTGAACTGGT
AATAAAATTCTGAGCAAGAAGCTGTTGCTTTGTTTGTTCGT
TCTTTTCTTGTTTTTAATATGGGCCAAATCATTATCTTTAAT
ATTTTTATCACTATATGATATAGTTATAAGGTATTTGGCTCA
CAATTTTCATTATACAGGACAAGCTCAAACACTATGAAAAT
```

TABLE 1-continued

ACCase gene sequences isolated from weedy plant species

| SEQ ID NO | SPECIES | TYPE | LENGTH | SEQ |
|---|---|---|---|---|
| | | | | CCCAGATATACTCCTTCTCGGGATCATCAGTGGCACCTGTA |
| | | | | TACTGTCATGGACAAGCCATCTATTCGACGAATGTTTTTGA |
| | | | | GGACACTTGTCAGACAGCCCACCTCCGAGTTTAGCGGGGT |
| | | | | TGAACTAGAAATGCTTAAAACACAAAGGCCTATCTCCTTTA |
| | | | | CTTCAAGAAACATACTGAGGTCTTTAACAACTGCAATGGAA |
| | | | | GAATTAGAACTCAATGCGCACAATGCTACCTTGAAACCTGA |
| | | | | TCATGCTCATATGTACCTGTGCATTGTAAGAGAGCAACGAA |
| | | | | TTCAAGATCTTGTCCCATATCACAGGTTCTAATTAATCATCT |
| | | | | TAATTTTCTGTGTTTCATTCGTGGTCATTGATGCAACTTATG |
| | | | | CCTTAATAGATATTATTTTGACCCATTGATCCAGGGAGGTG |
| | | | | AACATTGATGATGAACAAGAAGAGATAACTGTTCAGATAT |
| | | | | ATTTGGAAGAGCTTGCGCGTGAAATCCACAGTTTTGCTGG |
| | | | | TGTGAGAATGCATAAACTAAATGTATGTGAGTGGGAAGTA |
| | | | | AAGCTTTGGGTGTCATCTTCTGGCCAAGCCAATGGTTCATG |
| | | | | GAGAATCATTGTTAATAATGTGACTGGTCATACATGCACTG |
| | | | | TACATGTAAGTTTGAACTATGATAATTTTTTCCTATAATTTT |
| | | | | CTGTAAAGGTTTTTAGTATTGGCCGTGTTTAGTAATTTCTTT |
| | | | | CAACACTCAGATATTTATGCCAGTTTTTGTAAGAATTATAG |
| | | | | AAATACAGTAGCAATGTTTTGATAGCCCAGGTTCTCTCTTT |
| | | | | CTCCCAAATTAATCTTTGTGTCAATGCATGACTTTGCCGCAT |
| | | | | CAATATCTTAAATAATTTATGATTATAAACTATAAGAATAT |
| | | | | GATACTATGAGAAATTGAAAATATACATCGAGAGAAATCT |
| | | | | AAATACATCTTCCATTACAACCTTTGATTTTTTTTTTTTTTT |
| | | | | AAATTGAAAAAACAATGGGTAAAGGTGATACATGAATCTT |
| | | | | GTAAAACACAAACAATGACCATACATATGGGACGGAGGG |
| | | | | AGTAATAATGGTTTGTATATTGGCACTTATAAAGAAAAAG |
| | | | | GTTATGCACAATTAATTTATGTCTTGTAGACGTGTATCACA |
| | | | | TAATGTCTTCTTTAGTTTGCTGACCTTTTTCTACTAATGTTA |
| | | | | TGCAGGTTTACCGTGAGTTGGAGGATAACAACCTTCATGA |
| | | | | AATGATCTACCATTCAATATCTGTTCAAGGTCCTCTCCATG |
| | | | | GAATACCAGTGAATGCACCCTATCAACCACTTGGAGTCATT |
| | | | | GCCCGTAAAAGACTTCAGGCCAGGAAAAATAGCACAACCT |
| | | | | ATTGTTATGACTTCCCACTGGTAAGAAATATTAAACTCCAC |
| | | | | TATACCCCAATACTACAAAAGCAGAATTTTACTATATTAGG |
| | | | | TTTCCTTCCCTCCCGAATTTTTTTAAAAAATAAGAGTTAATA |
| | | | | CATGACTTGCATTCGAGTGTAACTATGGTTCTTGTTTACGC |
| | | | | TCAACTAGTAATGAAATAGGAATATAAATCTAATAAAGATT |
| | | | | TACAAATTTTGGAGAGAGGCGGGGTTGTGTAACTGTGGG |
| | | | | ACTTTGTAAAGGTTTAAAGTTAGTTAGGTGGAGATGCAGG |
| | | | | GTTTATATTTAGTTTATGAGGAAACTACAAGTTTTCAAGAT |
| | | | | TTTAATAGGTAATACGTGTAAAATTTTAAAAGATATCGGAA |
| | | | | TATTTGTCTTAGTATTTTGGATTATTGTAACTTTGTAAATAA |
| | | | | AAATAGTTTCACATTTTGTTAAGATTTCAAGTTTGGCTTTCG |
| | | | | CACACAATGGGTCTGTTCTTTTCACCTTATCTGTACTTATCC |
| | | | | GAACTTTTCCGAACTTCTATGAACTTGTTTTGTGAGAGAGA |
| | | | | AAA |
| 78 | Kochia scoparia | gDNA Contig | 10030 | ATGTCTTTGCATTTGGTGAATCAAGAGGGTTGGCCATAGC |
| | | | | AAATATGGTTCTTGGCTTGAAAGAAATTCAAATTCGTGGA |
| | | | | GAAATTCGCACTAATGTTGATTATACCATTGATCTTTTAAAC |
| | | | | GTGAGCCTTATACATGAATTTCCCCCCTACACTGTTCACTGT |
| | | | | TTTTTCAATTAGAAGCTAAACTTGTCTTTGTTTTTCCTTTCTC |
| | | | | CAGTCTTCGGATTACAGAGATAATAAAATTCACACAGGTTG |
| | | | | GTTAGATAGCAGAATTGCAATGAGAGTCAGAGCGGAAAG |
| | | | | GCCCCCCTGGTTCATCTCTGTGGTGGGAGGTGCACTCTACG |
| | | | | TATGTACAACTTTTCTCTTAAATTTTCTTCCTTCCTCAAGCTT |
| | | | | CATGTGTCACTTTCGTTTATTTTTATAATGAATAATTTTAAA |
| | | | | TGATTCTTTCTCCTTTCTCCCTATCTTCAGAAAGCTTCTGCTA |
| | | | | GTAGTGCGGCTACTGTTTCAGAATATATTGGCTATCTTGAG |
| | | | | AAAGGTCAAATTCCTCCAAAGGTAATCCAAATACCAGATG |
| | | | | CTGTTGAGATATACTTGTTTTTTAAACACTAATTGTTTCTTT |
| | | | | CAGTAAATTACATCAACATTTGTGTGGATTGCAGCATATAT |
| | | | | CACTTGTCCACTCGGAAGTTACTTTGAATATTGAGGGGAG |
| | | | | CAAGTACACTGTAAGTTTATTATTAACTGATGTGAATTTTAT |
| | | | | TTTTCGTTCATGGTTTCTCCTGTTTACTTGTTGTTAATCATCA |
| | | | | TAACATGGTTGATTCTGTTCTCCAGATCAAAATGGTGAGG |
| | | | | GGCGGTCCAGGAAGCTACAGATTGAGATTGAACGAGTCA |
| | | | | GAGATTGAGGCAGAAATACATACATTAAGAGATGGGGGT |
| | | | | CTTTTGATGCAAGTAAGAACTTAATTTTATTGATTCATATAT |
| | | | | TCATGATTGAGGACAATTATAAACCTCAAGCTATACGCATA |
| | | | | GGAATTATAATTTGTATAGAGAGTTAAAATTGCGAGTGAA |
| | | | | AGCTAAGATATTGCACCAACATGTATTAAGTCTATCATCCA |
| | | | | CCACATAATGCTGAAGTTACCTCCGTTAATTAAATTTAAAA |
| | | | | AACAGGAGAGTGTAGAAATTAGATAGTCTAAGTTTCTGTA |
| | | | | GTCATAATGATATGTCTTTTGGAAAGTGCCCCAATGTGTTA |
| | | | | CATTTATCTTTTACCCCTAACTTAGTTTAGGAGGGAAAGCT |

TABLE 1-continued

ACCase gene sequences isolated from weedy plant species

| SEQ ID NO | SPECIES | TYPE | LENGTH | SEQ |
|---|---|---|---|---|

```
GACTTAGCAACTTCTCCTCTAGTACAGGATATAAATGCTCA
AAACTCTTAGAATATCTAAATTTGAAAAGATTATAATGTAT
TATTGACATTGTTTCAGAGAATGATTTTCTGTATGAACTCCT
TAAGTATGTTTTTTGACAACTCCTTAAGTATGTTAATAGCA
ATGCCACAACCCTGTTCCACATTAGGTAGGTATATATGTTT
CTGATTAGAAATTATATTCCATATCTCCGTATAAGATCTTCC
TTCTTACCAACACGAGCCATATAATTTTGGGATTAAGTAGA
TGATGTTGGTTTGCATTATGATGATACTTAATATACCCACA
TGTTTCATATTTTCATTGACTTAAACGCTATCTTCTAGAAAA
GGGGTAGTTGTTGATCCAATGTATGTGCTACATTCTCATCC
CTTTGATTTCAACTAGCTATGGATTTTGAGCTATTCTGTGCA
TTTGAATGTGATGCAGTTGGATGGGAACAGTCATGTGATA
TATGCTGAGGAAGAGGCAGCAGGAACTCGCCTTCTTATTG
ATGGACGAACATGTTTGCTTCAGGTACCATCTTGTTATTTA
ATTGCATAATATTTCTAAATCTTTACCAAGCGTAACCTAGTA
TTAAATATCCCCCTTCTTTGTATCCAGAATGATCATGATCCT
TCAAAGTTAATTGCGGAAACACCTTGTAAGCTGATGCGGT
ATTTGGTCCCAGATAATAGTCACATTGATCCAGATACTCCA
TTTGCTGAAGTTGAGGTTATGAAGATGTGTATGCCTTTGCT
TTCCCCTGCATCTGGTAAAATACAATTTAAGATGTCCGAAG
GACAAGCCATGCAGGTTAGCATAGGTTTTGGAAAATCTAT
ATGTTAACTAATTATACTCTAAAAGTTTTTTCTAAGTGCGTG
TTCGCTGTGTAGGCTGGCGAGCTCATAGCAAGACTTGAGT
TGGATGATCCTTCAGCTGTAAGAAAAGCTGAACCTTTCCGT
GGCAGTTTTCCAATTTTGGGCCCCCCAACTGCTATCTCAGG
AAAAGTTCATCAAAGATGTGTTGCAAGTTTGAATGCAGCC
CAGATGATTCTTGCTGGTTATGAACACAACATAGATGAAGT
AAGTATTTCAATAGTGAATTCAAAAAATCGAGCAATATATT
ATATACATGAAGTATTCCTATTATGAATTTAACATAGATGA
TGTAAGTATTCCTCTGAGGGGCTGATGCAAAAATTTGAGA
TGTATATGTATGTCTATTTATATTTTGGTTGGTTCCCTTATC
AGAAAGATTCTTTACAAATGAGTTTTCTAATTCTCAGGTTG
TCCAGAGTTTGCTGATTTGCCTTGATAGTCCTGAACTTCCTT
TCCTGCAATGGCAAGAATGCTTGTCTGTTCTAGCAACACGG
CTTCCCAAAGATCTGAGAACTGAAGTATGCTACTAAGTTCT
GCATGCAATTCTTTTTCTATATTTGATAAACACCTGTTGTCT
TTAGCAGTCTTTATCTTCTTTTTTCTTTCTTTCTTTTTCTCTGT
AACTCACATTATTTTACCATGTTTCCTTATCTTTGGTTTTATC
AGTTGGAGTCAAAATATGGAAAATTCGAAGGAGTTACCAA
TTCTCAGAACATTGAATTTCCTGCTAAGCTGTTTAAAGGTG
TTCTTGAGGTCAGTCTTTCTTTTTGTTACCCTTCTGTATATG
ATACAGTTTGAGTGTTACTTACATAAGTATTTTGTTTACAG
GCTCATTTGAATTCATGCCCTGAAAAGGAGAGAGGAGCTC
AAGAGCGGCTCATTGAACCTCTAATGAGTCTTGTTAAATCC
TATGAAGGTGGGAGAGAGAGTCATGCCCATGTTATTGTTC
AGTCTCTGTTTGAAGAGTATTTGACTGTTGAAGAATTGTTC
AGTGACAATATCCAGGTTTGTTATTGCAGTTGCAAATTGAT
CAGTTTTTTTGGTCAACCAATTTGTACCGGGACAAATTGCC
ACAGTCCTAATTTATTGATGATCATCGGTCTTCGTGTTTTTT
TCCCGGTTTGGTTGATTGGTTATCATGTTATGAAGTTGTCA
CATAAAAAAACCTAAATTTACTAATGCACCCATTTGACCCT
AGAGGCTACAGAGTCTTTGGAGTACTCTGTCTCTGTGGATT
TATAGTAGCATCCTTTGAAGTATTACTTTATTTTTTCAAGAA
ATTGTAGTTCATGTCTTTTGATTCTGATCTTGAAAGGAAGG
CTGACATCATTCCACTTTATTTTCTAATTTCAATCTATACAG
GCTGATGTGATTGAACGTCTCCGCCTTCAACATAAAAAAGA
CCTGTTAAAGGTTGTTGACATTGTCCTATCACATCAGGTAG
GCAGGAAATTTCAAATAATTCAAATTAAGTTTGAGTTTTCT
TTTCCCTTTTCCCTTGTAATATCTTCCAGGCTTGTTTACTATG
TAGTAATAATGGCTTTCAGGGTGTTAAGAACAAAAATAAA
TTGATTCTCCGGCTCATGGAACAACTGGTTTACCCAAATCC
TGCCGCATACCGGGAGAAGCTTATCCGTTTTTCACAACTAA
ACCATACAATCTACTCTGAGGTTAGTGATTATTCAATTTTTT
GTTTATATTGTCACACTACAGCATTCACAAAAAGGTTATTA
AGTTTATACACTAATCAATTCCTTCACTATATGCAGTTGGCA
CTTAAGGCAAGTCAATTGCTTGAACAAACCAAGTTGAGTG
AACTTCGTTCTAATATTGCCAGAAACCTTTCCGAGTTAGAA
ATGTTTACGAAGATGGTGAAAACATGGACACTCCAAAAA
GGAAAAGTGCTATTAATGAGCGTATGGAGGCTCTTGTGAA
TACTCCGCTTGCTGTTGAAGATGCCCTTGTTGGCTTGTTCG
ATCACAGCGATCATACGTTACAAAGGCGGGTTGTTGAGAC
TTATGTCCGGAGACTTTATCAAGTAATATCTAAGTTCCAAC
AGTAAACTTTAACTATCATTTAATAATGTTATGTCATATAAC
TCTATTTTTTGTGGGTAATCTCTTTTCTCAGCCTTATCTTGTA
AAAGGAAGTGTCAGGATGCAGTGGCACAGATCTGGCCTCA
TTGTTTCTTGGGAGTTCATGGAGGAGCACATTGAAAGAGC
```

TABLE 1-continued

ACCase gene sequences isolated from weedy plant species

| SEQ ID NO | SPECIES | TYPE | LENGTH | SEQ |
|---|---|---|---|---|

```
AAATGCCTCTAATGATCTGTCCATCAACCAGCCCCTTGTTG
AGAAACACAGTGAGAGAAAATGGGGAGCCATGGTCATCA
TAAAATCTCTTCAGTTTTTGCCAACAGTGATTACTGCTGCAT
TAAAAGAGACAACACATAATTCAGATGAAACGATTCCCAG
AGGCTCTTTAGAATCAATCAGTCATGGAAATATGTTGCACA
TTGCACTTGTGGGTGTTAATAACCAGATGAGCTTGTTGCAG
GATAGGTATAGATTCTATTTTTATGGTTTAAGCAAGATTTT
AAAATGTGAACATTGGACTATCCAATTTTATTTATGTTTATT
TATTTATTTATTTTTTGACGAGGACTATCCAGTTTTTTTGA
AGAAATATGCTTTGCTTCAATTATGCAGTCGCTCTTTATAGT
AACCATTCCGGCCTTTTGCTTAACCTTTTTTTCTCTGTGGGG
TTTATGAAATGGAATTTTATACTATGCAGTGGTGATGAAGA
TCAAGCTCAAGAGAGAATTGATAAGTTGGCAAAAATCCTG
AGAGAGAAAGAAGTGAGCTCAGGTCTTCGTGACGTTGGT
GTCAGGGTAATTAGTTGCATTATACAGAGAGATGAAGGAA
GAACGCCAATGAGGCATTCATTCTATTGGTCAGAAGAGAA
ACAATACTTCAATGAAGAGCCTTTACTACGTCATTTGGAAC
CTCCTCTATCAATATATCTTGAATTGGTATGATATTCTGAGC
AAGAAGCTGTTTCTTGTTTATTATTTTCTTGTTTCTTAATATG
GGTCAAATCATTATCTTTAACATTTTTGTCACTATTTGATAT
AGTTATAAGGTATTTGGCTCACAACTTTCCTTACACAGGAC
AAGCTCAAGGTCTATGAAAATCCCAAATATACTCCTTCTCG
GGATCGTCAATGGCACCTGTATACTGTCATGGACAAGCCA
TCTATTCGACGAATGTTTTTGAGGACACTTGTCAGACAGCC
CACTTCCGAGTTCAGTGGGGTTGAACTAAAAATTCTTCAAA
CACAAAGGCCCATCTCCTTTACTTCAAGAAGCATTCTGAGG
TCTTTAACAACTGCAATGGAAGAATTAGAACTCAATGCGCA
CAATGCTACCTTGAAACCTGATCATGCTAATATGTACCTGT
ACATTGTAAGAGAGCAACAAATACATGATCTTGTCCCATAT
CACAGGTTCTAATTACTATTCTTAATTTTATGTGTCTCATTT
GTGGTTATTGATGCAACTTATGCTTTAAGAGGGATTATTTT
GATCCGTTAATCCAGGGAGGTGAACATTGATGACGAACAA
GAAGAGACAGCTGTTCATATGTACTTGGAAGAGCTTGCGC
TTGAAATCCACAGTTGTGCTGGTGTGAGAATGCATAAACT
AAATGTATGTGAGTGGGAAGTAAAACTTTGGATATCATCT
TCTGGTCAAGCCAATGGTTCATGGAGAATCATTGTTACTAA
TGTGACTGGTCATACATGCACTGTACATGTAAGTTTGAACT
ATGATAATTTTTTCCTATAATTTTCTGTAAAGGTTTTTAGTA
TTGGCCGTGTTTAGTAATTTCTTTCAACACTCAGATATTTAT
GCCAGTTTTTGTAAGAATTACAGAAATAGTAGCATGTTTTT
AGTGCCCAAGTTCTTTCTTTGTCCTTTTGCCCAGCAATATCT
TTAATAATTTATGTATAAACTATAAGATATTATGAGACTAT
ACATCGAGAAAAATCTAAATACATCTTCCATTACAACCTTT
GATTTTTTTTTTTTTTAAATTGAAAAAACAATGGGTAAA
GGTGATACATGAATCTTGTAAAACACAAACAATGACCATA
CATATGGGACGGAGGGAGTAATAATGGTTTGTATATTGGC
ACTTATAAAGAAAAAGGTTATGCACAATTAATTTATGTCTT
GTAGACGTGTATCACATAATGTCTTCTTTAGTTTGCTGACCT
TTTTCTACTAATGTTATGCAGGTTTACCGTGAGTTGGAGGA
TAACAACCTTCATGAAATGATCTACCATTCAGTATCTGTTCA
AGGTCCTCTTCATGGAATACCAGTGAATGCACCCTATCAAC
CACTTGGAGTCATTGCTCGTAAAAGACTGCAGGCCATGAA
AAACAGCACAACCTATTGTTATGATTTCCCACTGGTAAGAG
ATATCAAACTCCACTGTACCACAATACTACAAAAGCAGAAT
TTACAGTATTAGGTTTCCTTTCCTCCAAAAAAATCAAGGGT
TGATGCATGACTTACATTCGAGTGTAACTATGGTTCTTGTT
TACGCTCAACTAGTAATGAAATAGGAATATAAATCTAATAA
AGATTTACAAATTTTGGAGAGAGGCGGGGTTGTGTAACTG
TGGGACTTTGTAAAGGTTTAAAGTTAGTTAGGTGGAGATG
CAGGGTTTATATTTAGTTTATGAGGAAACTACAAGTTTTCA
AGATTTTAATAGGTAATACGTGTAAAATTTTAAAAGATATC
GGAATATTTGTCTTAGTATTTTGGATTATTGTAACTTTGTAA
ATAAAAATAGTTTCACATTTTGTTAAGATTTCAAGTTTGGCT
TTCGCACACAATGGGTCTGTTCTTTTCACCTTATCTGTACTT
ATCCGAACTTTTCCGAACTTCTATGAACTTGTTTGTGAGA
GAGAAAATAATAAGTTTGTTCTTTTCAACTTATTTTTATT
ATCTGAACTTATTTGAATTTATTTTTTCTGAAATTAAGTAAA
AATAAGCTCAATAGAACATACCCAATGTAGAAAAATAGAA
TTAAACAAAGAAATAGTGGGGAAAAAAAGTGGAGGTGAT
TTGTGTCTCTTGTGGGCATTAGTTTAGTAACAGCTAGAGTA
ATGGATATAGATGACTTATTTTTAATTCATTGTATGACATAC
ATCAAAAACCTGAAATTTTAGTGATATCAAATTGGCCTTAA
TTAGTAATTTAGTTGTTTGATATTGTTGGTTATACAAGTGA
AAACAGATACTTAATATGCGAATGATTGTGCCTATAGTGAT
TATGTGACTGTGTTGTTAAATATAAAAGTGTTTCAGTGTTT
TTAAGACAAGGGAAGTAGGGAACCATAAACAAAAATACG
```

TABLE 1-continued

ACCase gene sequences isolated from weedy plant species

| SEQ ID NO | SPECIES | TYPE | LENGTH | SEQ |
|---|---|---|---|---|
| | | | | AAGCATATCTTGGGTGTTACCTAGTTTTGTCCTATTTCTCAA
TTATTGATTTAGTTGTTTAATTTGTTGGTTATAAAAGAGAG
AAACCGGGATTGTTGGTGTGCAAAGATTGTACCTATAGTG
ATTATGTGACAACGTTGTCAAATGTAAAAGCATTGCAATTT
TTGTGAGGCAAAGGAACCATAAATAAAAATGCGAAGCATG
GCTTGGGTGTTACCTAGCTTTGTCCTATTTATTGAACTATGT
GATTGTACCTCAAATTTTTATATTTGATGTTGTATCGATCAA
CTTGCTTTAGCTCACGTTAGCATTTATCTGTTTTTCTATTGG
AAAATTGACCTGAAATTATTGGGAATGTTTTTCTCAGGCTT
TCTCTACTGCCTTAGAGCAATCATGGGCATCTCAAGCTCCG
CTTCTGAAGAAACCCGCTAACAAAAAGTTTTGAAAGTCTC
AGAGCTAGTATTTGCTGATTCAAATGGCACCTGGGGAACA
CCAGTTGTCCCGACAAATCGTGAACCTGGTCTTAACATAT
TGGCATGGTTGCCTGGTCCATGGAGATGTCAACTCCTGAA
TTCCCTGATGGAAGAACCATATTGGTTGTAGCAAATGATAT
CACCTTCATGGCTGGATCATTTGGGCCAAAAGAAGATGCT
CTCTTCCAGGCAGTTACAGATCTTGCTTGTTCCAAAAAAAT
TCCTCTGATTTACCTGGCTGCTAATTCTGGTGCTCGACTGG
GTGTTGCTGAAGAGGTAAGAGCATGCTTTAAAATTGGTTG
GACCGATGAGTTGAACCCTGAGCGGGGTTCCAGTATATC
TACTTGACTCCTGAAGATTATGAGCGTATAGGGTCAGCAG
TTATAGCCCATGAGTTAGAACTCCAAAATGGAGAGACTCG
GTGGGTTATAGACACTGTTGTAGGGAAGGAGGATGGGAT
AGGTGTTGAGAACTTATCTGGAAGTGGAGCTATAGCTGGT
GCCTACTCAAGGGCATACAAAGAAACTTTTACTCTAACTTT
TGTAACAGGAAGAACAGTAGGTATTGGTGCCTATCTTGCT
CGCCTTGGGATGCGTTGTATCCAAAGGCTTGATCAGCCCAT
TATTCTGACAGGCTTTTCTACGTTAAATAAACTTCTTGGTCG
TGAGGTTTACAGCTCACAAATGCAACTTGGCGGGCCCAAG
ATTATGGGTACAAATGGTGTTGTTCATTTAACAGTTTCAGA
TGACCTTGAAGGCATTTCAGCTATTGTCAAGTGGCTCAGCT
ATGTTCCATCCTACTCAGGAGGTGAACTTCCTATTTCACGTT
CTTTAGATCCTCCTGAAAGACAGGTTGATTATTTGCCTGAA
AATTCTTGTGATCCCCGTTCTGCTATATCTGGTACACTTGAC
TCTAATGGCAATTGGCTTGGTGGAATTTTTGACAAAGATA
GTTTTGTTGAAACCCTAGAAGGCTGGGCAAGGACAGTTAT
CACTGGCCGGGCCAAACTTGGTGGAATCCCAGTTGGGATA
GTTGCTGTTGAGACACAAACTGTGATGCAAGTTATCCCAG
CAGATCCTGGTCAGCTTGATTCGCATGAGCGAGTGGTCCC
ACAAGCTGGACAAGTATGGTTTCCAGATTCTGCAACTAAG
ACAGCACAAGCTTTGATGGATTTTAACAGGGAAGAACTTC
CACTTTTCATTCTAGCTAACTGGAGAGGCTTCTCTGGAGGG
CAAAGGGATCTCTTTGAAGGGATTCTTCAGGCAGGGTCCA
CAATTGTCGAGAACCTTAGGACTTATAATCAACCTGTTTTT
GTTTATATCCCCATGATGGGTGAACTTCGTGGTGGGGCAT
GGGTTGTCGTAGACAGTAAAATCAATTCGGACCATATTGA
GATGTATGCTGATCAGACAGCTAAAGGAAATGTTCTTGAG
CCAGAAGGAACGATTGAGATCAAGTTTAGAAACAAGGAAT
TAATTGAATGTATGGAAAGGCTTGATCAACATCTCATCAAT
CTTAACGCAAAACTCGTCGAAGCCAAAAACTCCAATTTATA
TGTTAATATCGAACTCCTGAAACAGCAGATAGAAGCTCGG
CAGAAGCAACTTTTGCCTCTATATACTCAAATAGCCACAAA
ATTTGCTGAATTGCATGATAGTCCTTATAGAATGGCTGCGA
AAGGAGTCGTCAAGGAAGTCCTGGATTGGAGCAATTCTCG
CTTATTCTTCCACAAAAGACTGTACAGGAGAGTTATGGAG
GAATCACTTGTCAAGACCGTCCGAGATGCTGCTGGTGAAG
CAATGACCCACAAGTCTGCCATGGAATTGATCAAGCAATG
GTTTGCTCAGTCTGATAGTACTAGTGGAGTGGGAGCTGAT
CCTTGGTCTGATGATGAAGCTTTCTTCAAGTGGAAAGAAA
ATCCTGCTAATTATGAAGAAAAGCTAATTGAGTTACGCATA
CAGAAAGTATTGCATCAGCTTTCAAATATTGACAACTCAGC
TTCTGATCTGAGAGCTCTTCAGCTTCGTCAGGGTCTTGTTG
CCCTACTTCAGAAGGTATCTCTAAGGTTCCTCCACACACAC
ACACACCCCACCCACCAAAAAAAAACACACAACACAACAGT
GAG |
| 79 | Kochia scoparia | gDNA Contig | 8717 | GATCTTGATTGATGTTGAGGATGACTTGTTCTGACGTTGTT
TTCTTGATGATCGGCCTGTAAAATGAAACAAAGATTGCTAC
CTCGGAGGTTTTCCCGAGTAAAACCTCTCCGAAGTTTAAGT
CAGTTCAATGATCTTGAATGGATTGGTATTTTAGGAATTTA
ATGTGAGTCGTTTTAGAATTAGATACCTGATTTTGTGTGGA
GAGCTTGGTATATATAGGCAATCGGGTGACCTACTAGCTT
ATCAGTCAAGCGATGTAATCCGGCACCTGGTAGCTTGTCAT
CAGTTTGACTGGGCAATTAATGGTCAAGCGGTTTGAAATG
TGTTTCTTGGACCTTAAAATATGGCTTTGGTTATAATGAGCT
AGATTTAGGTTTGGACCTTAGTTTTATGGGTTAATACTAGA |

TABLE 1-continued

ACCase gene sequences isolated from weedy plant species

| SEQ ID NO | SPECIES | TYPE | LENGTH | SEQ |
|---|---|---|---|---|
| | | | | GGCGATCAAAAAAACCCGGCCCGACCCAAAATTTTGTGGG |
| | | | | CTTTGGTCACGACTTTTTTTTGGCCCGAATACCCATACACAA |
| | | | | ACTAAAATGGCTAGTACAAAAGTACAAATATACAAAAGTT |
| | | | | GTTCTTACTAGAAAAAGCTAGTTATTGACCATCAATTATCT |
| | | | | CAAGTCCAAATAAACTTTTATAAGCACTAGAAGTAAGTTGT |
| | | | | ATGAGAAGTATTGATCAATAACTCAGCAAAATAGTACTTCG |
| | | | | TATATAATTATAAACAAGAAGTCAAATTTGGTGGAGTGTG |
| | | | | ATTGAATTGAAAAAATTGGTAGAATTCAATATGATACAACA |
| | | | | AAGAAAAGCTACATGGTCATATTAAAAGTTAAATTTTGCAT |
| | | | | AACAAGAGTAAAAGAAATGATAAATTGATTGACACGATCA |
| | | | | ATAAATCACCGGATAAATTCGTCATTTCTTATTATCAGTCCT |
| | | | | TCAAATTATAATAAATTCCCCAATCCCCCACCTACCATTATA |
| | | | | CTCGTAAGTTTTTAACAATGCTGGAACAAACAGTGCAAATG |
| | | | | TGTGATTTAAAAATCGGTGCTATTTGTTTATACTTCCTCGTT |
| | | | | GCAGTAGCATCATCACACATTCATACTAAAATCAAATCAC |
| | | | | ATTCATCATAAATCATAATAATAAATAATAGAATAATTATA |
| | | | | CAGGTAGCTGAAAGGTGGGCAGTTGCCACGTGCATCCCCA |
| | | | | AATAAATATGCAGTTAATTGAATGAGATGGAATGGAAGGC |
| | | | | ATTCTCTGCACCTCAAACCAAACCAACCCCCTTCTTCCCCTC |
| | | | | TAACACTTCTTCAATGACTTCTCTTCCTTCTTCTTATTCTCAT |
| | | | | TATATATACATTCACAAGTAGCTGATCACTACTGTTTTCTTT |
| | | | | TTTTTGTTCTGTCTAAAGTTTGATTCTTTTCCATCAAAGTTTG |
| | | | | CTTTTTTATGCAATAATTCAAATTGCCCAGATGCTAATTTAG |
| | | | | TGGAATTTCATTGAAAGGTTTGTTTTTTTCTGCTGAATTATG |
| | | | | TCCCTTTGATTTGATTTGAGTGTTTTTTAAGTTTATGATGAA |
| | | | | TCATACATGCCCTTTTATTTGAGTTGATTTTGGGATTTGTCT |
| | | | | TATGTTGGGGTTGGTTTTTGGTTGGTTTTTGGTTGGTTTTTT |
| | | | | TTGGTAGTGTGTAGTTGAGCTAATTAAGTGTAGAATAGTG |
| | | | | TGAAATAATATATTGGTTGTATTGGGTATTGCTTACTAGAA |
| | | | | AATGTGATTCATTTTGGTAGTTAGTTGGCTTTAGTTGACTG |
| | | | | ACTCTTCTAAGTTCTAACTATGATTGATTGATTGATAATACA |
| | | | | GGTATGTGTAGTCCAAATTGGACCTCATTTTATAATTATCCT |
| | | | | CATTTTATAATTATAATTTGTTTTTTTTGGCATTGGATTGTT |
| | | | | GACTCTTGAATTCTACTTCACTACTTGAATTGCATTGGATTT |
| | | | | TTTCTATTAGTATTTAGCTTTTATGCCATAATAAAAACTTCT |
| | | | | GCCTTTCATTCAGCTGGTATGTTCTATACTTCTATTCTTTTTT |
| | | | | TTTTTTTATATAAATTAATTCTTTCTTTCTCTGTTAATGTTGT |
| | | | | TGTTGTGTTGGATAATATGTTAATTACCCAATTAAAGAGCT |
| | | | | CAAATCTTGAAGTAATGTATGAGTATTGCTTATGATAGTAG |
| | | | | CTTTTGTGATTCAAAGCTTGCATCATTCATTAATTGACTATT |
| | | | | TGTTTTGTGTAATACGAGGTTGTTGTAGCTTGATTGCTTTTT |
| | | | | GACAGGTAGAATATGCTTATCATGTGAAAATTGGGAATGT |
| | | | | TATTCATGTGATTTGATGTTATTAGGATGCTGACCAGTGTT |
| | | | | TTATGAGGTGATACTGATTCAACTTGTTGATGTAACAGTTA |
| | | | | TAGGAAAATCGGGCGTATTTTTTGCTGAGGGCGGGGCGGT |
| | | | | GTGTTAACTAGGGAAGAGCCAAAGATGGCAACTCTAGTGC |
| | | | | GAAACATTGATTACCTTAATGGAACAACTCTGTTGAGGAAT |
| | | | | TCTACTACATTACCCGTTGTTGATGAATTTTGTTATGCTCTT |
| | | | | GGAGGGAAAAAGCCGATTCATAGTATTTTGATTGCCAACA |
| | | | | ATGGAATGGCAGCTGTTAAATTTATCAGAAGTGTTCGGAC |
| | | | | ATGGGCTTACGAAACTTTTGGAACAGAGAAGGCTATTGTA |
| | | | | TTAGTAGCAATGGCTACTCCAGAAGACATGAGAATCAACG |
| | | | | CTGAACACATTCGAATGGCTGACCAGTTTGTTGAGGTTCCT |
| | | | | GGTGGGACTAACAACAACAACTATGCCAATGTACAGCTCA |
| | | | | TTGTTGAGGTAAATCCTGCTTTAGTAACACTGATCTTCCGT |
| | | | | GTTTTCTCTGTTAGATTACGAAATACTCACATTAGCCACAG |
| | | | | TGTATGAGAAAAGATATCACCTGTCCTGTTGGCCTGTTGAT |
| | | | | GTTCATCATTGATTTCAGAGGATAAAATTTTGTTAAAAAGA |
| | | | | CTTCAATTTATTTTCACTGCTCTTTCAGATGGCAGAAATTAC |
| | | | | ACGCGTAGATGCAGTTTGGCCAGGTTGGGGACATGCATCT |
| | | | | GAGATCCCTGAGCTTCCAGATGCACTAACCGCAAAGGGGA |
| | | | | TTGAATTTCTAGGGCCTCCAGCTATATCTATGGCTGCTCTT |
| | | | | GGAGACAAAATCGGTTCATCATTGATTGCTCAGGCCGCAG |
| | | | | ATGTTCCAACTCTTCCATGGAGTGGCTCTCATGTATGAATT |
| | | | | GATTTTCTTATCGACCTTCACAAACTTTCTTTTTCTCAAGGA |
| | | | | GTTTCCTAATCAGTTTTCTTAAATTTCTATGCTTTAGGTGAA |
| | | | | AGTTCCTGCTGAGAGTTGCCTTGATACTATTCCTGATGATA |
| | | | | TATACAAGGCAGCCTGTGTTTTTACCACAGAGGAAGCAATT |
| | | | | GCTAGTTGTCAGGTTGTCGGTTATCCAGCTATGATTAAAGC |
| | | | | ATCTTGGGTGGTGGTGGGAAAGGAATAAGAAAGGTGAG |
| | | | | CTAGTTGTTTGGGATAATGTGGTCAAGAAATTAAAGCACC |
| | | | | ATCTTCATATATATCTCTATTGCTTATTTATCAACATTTTCAC |
| | | | | AGCTTCCATCCTTGAACATCCTTTAATTAGTCAATTGTCTAT |
| | | | | AATTATCTACTAGTCTTAAATGATGGACAAATGCTTCAAAC |
| | | | | TTGTTAGTTAGCTAGAGACCTGTTAATCTGTTATGCTACTTC |
| | | | | AATTTCAATCGTTTTCCTTTCAAAATATCAGAAAGACTCAAT |

TABLE 1-continued

ACCase gene sequences isolated from weedy plant species

| SEQ ID NO | SPECIES | TYPE | LENGTH | SEQ |
|---|---|---|---|---|

```
AGTTATGCATTTTTAGGTACATAATGATGATGAAGTAAGG
GCATTGTTCAAGCAAGTGCAGGGCGAAGTTCCTGGCTCAC
CCATATTTATAATGAAGGTGGCTTCACAGGTTAGATATTCT
GCAAATTGGTTCTATAATGAATTATATAAGCACTCAGAAGT
TCACGGCACTCGTGATCTTAGAACTTGTACTATATGCAAAA
TTCTTTGTTTTGACAAGTTGTTATATGTGCTTCATTCAGAGT
CGACACTTGGAAGTACATCTACTTTGTGATCAATATGGCAA
TGTAGCAGCTTTGCATAGCCGTGATTGCAGTGTCCAAAGG
CGGCACCAGAAGGTGGGTCCCTAGTGTACTATCAATAAAC
TTTTAATCTTCTTGACCAATTTAGTATTACTTCGGGTCTAAA
GTATATTTTTCAAAGAAAATCGTTATGTCTCATTGTTTTTG
AAGGAATGTATAAATATTTTGTCCATTGTATTAATTGATCA
GATTATTGAAGAGGGTCCAATAACTGTAGCTCCACCAGAA
ACTGTGAGAAAACTTGAGCAGGCAGCTAGAAGGTTAGCCA
AATGTGTGAATTATGTTGGAGCAGCAACTGTAGAATATCT
GTTCAGCATGGAAACTGGCGAGTTTTATTTCCTTGAGCTAA
ACCCTCGGCTACAGGTTTGAAGAATACACTTGCACATTGTA
TATTCGTATTTTCCTTAAGAAAAATATTTTATGTTGATATTT
ATGGTATTGCAACTCAATATCCTCTAGATATATCGTTTTCTA
CCGTACGTTTGTGGCTCACTTTATTATGACATGCTTTGTTAA
AAAGCCTTGGGATTTCTTAGAGTGAGACATGTCACCCTTGC
TTTTCAACTTCTGTGAATCATGTCTTATACTCCCTCCATTTCC
TTTTGTTTGTCTGATTTAAATCTTGGGTGTTGACACTATTCA
TAGGTAGAGAGATTCCTCTAAATTTATAAGATAAAACTTAG
CTCTGTGGGGCCTTGTTTAATTCATTTTGATGAGTACTTTAA
TGATATTAAATTTTTAGAATTTATATTCATATATAGTTAAAG
ATTTGTTAAATGTTTGCTGCGACAAACATGTGATAATGAAA
TGGGTCAGAAGAATGGAATGGAGGGAGTACTGCTAAGAA
TTATCAATCCTATATGATCATATGATGGATGAAAAAAAAAA
TTCTTATTTGACTTTTCTGACAATATTGTATATAATGTCCAT
ATGTGCAGGTTTTATTTTAAAAAATTTCCAGTATTGGAAAT
CCAGTTAATTTTATTGGTTATTTATTTAATTCCTTCTTTTTTC
GCATTTGATATATACAGGTGGAGCATCCAGTAACTGAATG
GATTGCTGAAATTAACCTTCCAGCTGCTCAGGTTGCAGTTG
GCATGGGTATTCCTCTTTGGCAAATTCCAGGTAGCTTGCAT
GTTCCCTTTTTTTATTATATAACTTATGTGCTTCATCTTGTTC
TTGTGTATGAGTTGGCTTGCTTTTGCAATTTCAAAATAGAA
ATTCGGCGATTCTATGGTAAGGAACATGGTGGCGGTTATG
ATGCTTGGAGAAGAACATCAGTTGCAGCGACTCCTTTTGAT
TTTGACAAGGCACAATCTGTGAAACCAAAAGGTCACTGTA
CTGCCGTACGTGTGACAAGTGAGGACCCTGATGATGGATT
CAAGCCCACTAGTGGGAAAGTACAGGTTAATAATGCTATT
GTTTTATAGTTCAAACTATTTTCTCAATTGATTGCCTTGTCT
GTTTTTGTGATTCATGTAAAATTATTTAATTCATTGGTTTCTT
TTCTAGGAGTTGAGTTTCAAAAGTAAACCAAATGTGTGGG
CCTATTTCTCTGTTAAGGTATGTCTTTATTTTTTTTAAGCTTT
ACATCATCCTTTATGGACTCATTCACGAGCTTAACAATGGT
CAACACTGTCAATTGCAGTCTGGGGGAGGCATTCATGAAT
TCTCAGATTCTCAATTTGGTAAGTTTAAAGCACATTTTAAA
GATGACTAGCAATGAAATGACTATTATAGCTGCCTTTTAAG
AATGAAGTTCTTCAACATCATAGTATTCATTCTCTAATTTAA
GACTGCTGCAAATGGATTGAGAACTGTGCTGTTGTGCATG
TGAAATGAGATATATTGGTTTTTCATAGTGTGTCATTGTAG
ACAGTAAATGCTCTTGTTAATTGTTGATGATTGGAATTGGG
ATTTAGCATGCTTGGTGTAGTTTTCTCTTGCACAAACAAGT
CTCACGGAGTTGATGTGTCATGTTTTTGTCGATTATTTTGG
TTTAAAACATCAAATTTTGTTTTCTTTTATTTATAGAAGGCT
AATGTTAATTAATTTGTTTGTAGGGCATGTCTTTGCATTTG
GTGAATCAAGAGGGTTGGCCATAGCAAACATGGTTCATGG
CTTAAAAGAAATTCAAATTCATGGAGAAATTCGCACGAAT
GTTGATTATACCATTGATTTTTTAAAAGTAAACCTTATACAT
TTTAACTTTGTAGATTTTAATTGAGCATGTGGCCTTATCCTT
TTACATACCCTTTCCGGCTGATTGAGGAATAGGAGTTTCCC
GCTATAACCAATGCACACAATGATTTCAAAATACAAGGATA
AGGATTTTGCTGTAAAATGAAGGTTGTGCCTTTCATTTATT
TTTATTTGTTGATGCATTGTGCTGTAAAATTAAGGCCTTCAT
TTTCATTTATTTTATTATTTTAAATTGGAGGTATACCACCTTC
TTCTAATTGAATTTTGCAATTGTTGCATGATTTTGCAATTGT
TGCATGATTATGCTCTACTTTTAAAGATTGAATTTGCAATT
TGTTGTGTGTGGTGTATGTCAATCAATTATATAAAGTAGAA
TGCTAGAGTGAAAATAAATGGTCAGCAGCACTATAGCAGA
AAAAAAAAACAAATATAAGGTGTCATATAACACACTCATTA
ACTCAGGACTACAACTTTACCCCAACTTGTTATCGATATTAC
CCATTTGCTACATCTCATATGTTCTTACAATTTTTTTATTCG
TCAAATTTGTAAGACAAGAGGCCTTGATTGTGAATTTCCTG
TCAATACCCTCTCAATTCTAAAAAAATATCATGACTACTA
```

TABLE 1-continued

ACCase gene sequences isolated from weedy plant species

| SEQ ID NO | SPECIES | TYPE | LENGTH | SEQ |
|---|---|---|---|---|
| | | | | GACTATGAGAGTTTTGTTAGATCTTATCAAGCATAAAGGAT<br>TCTATTAAAAAAATAAAATTATACTAGCAGTTGCTACCATT<br>GGAATGTTAATGTTTATCTTTCTTGGAGGGTTAGTAATAAC<br>TTTAATCAATGAGAGTGACCCACAAAGCTTTCATGATTCTT<br>TATATAAATGATTATTGTTCCCGCTGTAAAATTGTTCCCGTT<br>GTCTCATTTAATTGTTTAAAATGGATAAGATTTGATTAGTTT<br>TACTGTTAATGATGTTTGTGTTTGATTAGTTTTAGTATTTTG<br>CTTAATTGTTGAGATTAATTGTTGAATTAATGTGGGTGATG<br>AACTGTGCAAGGAAGTGCAGTAGCAGCAGCTATGAGAAA<br>TCAGCTACAGTAGGTCCAAGGAATGTAACAGCAGCTGCAA<br>CTGACCTGGGGGCCTGTGCAAGCTGTTCAGGTTGTCTGGA<br>CTTGTGCAGGCATCCCCGGGGCTTGTGTAGGCAAGGCAGC<br>AGCAAGTGCAACAGCATCAGGTCTTGTAGGACAGTGTCGA<br>CACCGTTTCGGTACATGTAATTTGGCTGTTCAATTGAATAT<br>TATTTGGCATGAAGAAGATCATGAGTTACATGATTATAGA<br>AAATGATTGTCTTCCAGTGGAGCTAATCAAGGTCCTCCTAG<br>ATAGCCTCAAGAAGGAAAATGATGTATCTCTTGCTTTATTG<br>CTTTCCGAATTTCCCATCTTTTACTCGGTTGTTGTGTTTTTG<br>CCCTTATAATCATGCCCGTCTCAGAAAAACTCACCTGCAGC<br>TTTTAATTTGGGTGTCTTTGGCATGCTCATTCTTTTTTTTCA<br>ACCGATTTCAAATTTTTTGATTTATTTACTGTGTTTTATTGCA<br>ACTTGAGTGATTTGTATTTACTTATGATTGTTATAGAATTTT<br>TGTTATGGTTTGGTTTTTGGCTTATTTATTAGCTTGGGTCTG<br>AAATTTGATCTTTCATATGGTCGGGTTTATGAGTTAATTAG<br>GGCGTTTTACTTTCTAGTAATTATTGAGATGATTTATTTTAA<br>AAGAATTAGTTTGACTATATGGAAGAAGTTTTAGTTGTGA<br>ATGTAATATTTGTTTTTTTACAAATACTTTAAATTTGCAATTT<br>TACGGTTGTGTTTAAGAAGAGCAGAAACAGAAGAAGGAA<br>GTGGGAAATCATAGACCACTTCAAGAGATTGGCTATTTTG<br>ATTTTTGAATGAGATTTTATGGTGCTATTGTTGCTGGTTGA<br>TTGTTAGAGGATCCTTGCATTTGAGCGAAAACAAAGCAAT<br>CCAAGTGTAAACTCATGCTAATTTCATGGTTTAAAGTTTTTC<br>ATTGTTGATTTTAGATTTCTTAGTCTTAGATATTTGTTTTTG<br>GTATTCATTTTTTAGGGGAAGGAATGTTTATATTCAATTTTC<br>ATCACATCAAGAATTAACTATGATGGAGCAGAGCACACAT<br>GGGCGAGCAGATGAGGTTGGTTTTTATCATTGATAATTGA<br>ATGCAACTAACAGGGGCAAACTAAGTACTCAACTAACTAA<br>TTAGGCAAAGTTACCTATACGACTATAATTGGACCCAATTA<br>AGGTTACTAGCTTGCTGCAATTTTACCAGTTTGCTAAGCAA<br>AATATTACATATTGTATATATAGTTAGAATTTGTCCTTTTGT<br>TCGAGGAAAGAAAAAGTAAGGGATGAAAATTTGAGACTTT<br>CTATTAGCAATTTCATTTAAATTCCAAAAAAAGGGTCTCAT<br>CTATTTTTTTATAACTTGTTGCTATAAAATTTGCAATGTGA<br>TTGATTGATTGTTAATATGAATTTGTAATATGTTTTAACAG<br>GATTCCTGTGTCATCTGTGGCTCAAAGGTACTTGACATTAA<br>GATCACAGTAAGTTCATCCAATTATTATAATTATCTTATCAC<br>TTTTGATATTTTAATTGTTTCTCAAGGATTATTGAGAAAGTT<br>TCAATTCATTTAGGCCCTTTTTAGTTAACAATAGGCTAATTC<br>TACTGCCTCTTGTTTTAGGTTGCCTCATAGGCACTCTTACTT<br>CTGAAAATAAACCTCAAATAACCATGATCGACCT |
| 80 | Kochia scoparia | gDNA Contig | 6978 | CAGTCTCTGTTTGAAGAGTATTTGACTGTTGAAGAATTGTT<br>CAGTGACAATATCCAGGTTTGTTATTGCAGTTGCAAATTCA<br>TCAGTTTTTTTGGTCAACCAATTTGTACCGGGACAAATTGC<br>CACAGTCCTAATTTATTGATGATCATCGGTCTTCGTGTTTTT<br>TTTCCCGGTTTGGTTGATTGGTTATCATGTTATGAAGTTGTC<br>ACATAAAAAAAACCTAAATTTACTAATGCACCCATTTGACC<br>CTAGAGGCTACAGAGTCTTTGGAGTACTCTGTCTCTGTGGA<br>TTATAGTAGCATCCTTTGAAGTATTACTTTATTTTTTCAAGA<br>AATTGTAGTTCATGTCTTTTGATTCTGATCTTGAAAGGAAG<br>GCTGACATCATTCCACTTTATTTTCTAATTTCAATCTATACA<br>GGCTGATGTGATTGAACGTCTCCGCCTTCAACATAAAAAA<br>GACCTGTTAAAGGTTGTTGACATTGTCCTATCACATCAGGT<br>AGGCAGGAAATTTCAAATAATTCAAATTAAGTTTGAGTTTT<br>CTTTTCCCTTTTCCCTTGTAATATCTTCCAGGCTTGTTTACTA<br>TGTAGTAATAATGGCTTTCAGGGTGTTAAGAACAAAAATA<br>AATTGATTCTCCGGCTCATGGAACAACTGGTTTACCCAAAT<br>CCTGCCGCATACCGGGAGAAGCTTATCCGTTTTTCACAACT<br>AAACCATACAATCTACTCTGAGGTTAGTGATTATTCAATTTT<br>TTGTTTATATTGTCACACTACAGCATTCACAAAAAGGTTATT<br>AAGTTTATACACTAATCAATTCCTTCACTATATGCAGTTGGC<br>ACTTAAGGCAAGTCAATTGCTTGAACAAACCAAGTTGAGT<br>GAACTTCGTTCTAATATTGCCAGAAACCTTTCCGAGTTAGA<br>AATGTTTACAGAAGATGGTGAAAACATGGACACTCCAAAA<br>AGGAAAAGTGCTATTAATGAGCGTATGGAGGCTCTTGTGA<br>ATACTCCGCTTGCTGTTGAAGATGCCCTTGTTGGCTTGTTC |

TABLE 1-continued

ACCase gene sequences isolated from weedy plant species

| SEQ ID NO | SPECIES | TYPE | LENGTH | SEQ |
|---|---|---|---|---|

```
GATCACAGCGATCATACGTTACAAAGGCGGGTTGTTGAGA
CTTATGTCCGGAGACTTTATCAAGTAATATCTAAGTTCCAA
CAGTAAACTTTAACTATCATTTAATAATGTTATGTCATATAA
CTCTATTTTTTGTGGGTAATCTCTTTTCTCAGCCTTATCTTGT
AAAAGGAAGTGTCAGGATGCAGTGGCACAGATCTGGCCTC
ATTGTTTCTTGGGAGTTCATGGAGGAGCACATTGAAAGAG
CAAATGCCTCTAATGATCTGTCCATCAACCAGCCCCTTGTT
GAGAAACACAGTGAGAGAAAATGGGGAGCCATGGTCATC
ATAAAATCTCTTCAGTTTTTGCCAACAGTGATTACTGCTGC
ATTAAAAGAGACAACACATAATTCAGATGAAACGATTCCC
AGAGGCTCTTTAGAATCAATCAGTCATGGAAATATGTTGCA
CATTGCACTTGTGGGTGTTAATAACCAGATGAGCTTGTTGC
AGGATAGGTATAGATTCTATTTTTATGGTTTAAGCAAGATT
TTAAAATGTGAACATTGGACTATCCAATTTTATTTATGTTTA
TTTATTTATTTATTTTTTTGACGAGGACTATCCAGTTTTTTTG
AAGAAATATGCTTTGCTTCAATTATGCAGTCGCTCTTTATA
GTAACCATTCCGGCCTTTTGCTTAACCTTTTTTTCTCTGTGG
GGTTTATGAAATGGAATTTTATACTATGCAGTGGTGATGA
AGATCAAGCTCAAGAGAGAATTGATAAGTTGGCAAAAATC
CTGAGAGAGAAAGAAGTGAGCTCAGGTCTTCGTGACGTTG
GTGTCAGGGTAATTAGTTGCATTATACAGAGAGATGAAGG
AAGAACGCCAATGAGGCATTCATTCTATTGGTCAGAAGAG
AAACAATACTTCAATGAAGAGCCTTTACTACGTCATTTGGA
ACCTCCTCTATCAATATATCTTGAATTGGTATGATATTCTGA
GCAAGAAGCTGTTGTTTTCTTGTTTATTATTTTCTTGTTTCT
TAATATGGGTCAAATCATTATCTTTAACATTTTTGTCACTAT
TTGATATAGTTATAAGGTATTTGGCTCACAACTTTCCTTACA
CAGGACAAGCTCAAGGTCTATGAAAATCCCAAATATACTCC
TTCTCGGGATCGTCAATGGCACCTGTATACTGTCATGGACA
AGCCATCTATTCGACGAATGTTTTTGAGGACACTTGTCAGA
CAGCCCACTTCCGAGTTCAGTGGGGTTGAACTAAAAATTCT
TCAAACACAAAGGCCCATCTCCTTTACTTCAAGAAGCATTC
TGAGGTCTTTAACAACTGCAATGGAAGAATTAGAACTCAA
TGCGCACAATGCTACCTTGAAACCTGATCATGCTAATATGT
ACCTGTACATTGTAAGAGCAACAAATACATGATCTTGTC
CCATATCACAGGTTCTAATTACTATTCTTAATTTTATGTGTC
TCATTTGTGGTTATTGATGCAACTTATGCTTTAAGAGGGAT
TATTTTGATCCGTTAATCCAGGGAGGTGAACATTGATGAC
GAACAAGAAGAGACAGCTGTTCATATGTACTTGGAAGAGC
TTGCGCTTGAAATCCACAGTTGTGCTGGTGTGAGAATGCA
TAAACTAAATGTATGTGAGTGGGAAGTAAAACTTTGGATA
TCATCTTCTGGTCAAGCCAATGGTTCATGGAGAATCATTGT
TACTAATGTGACTGGTCATACATGCACTGTACATGTAAGTT
TGAACTATGATGATTTTTTCCTATAATTTTCTGTAAAGGTTT
TTAGTATTGGCCGTGTTTAGTAATTTCTTTCAACACTCAGAT
ATTTATGCCAGTTTTTGTAAGAATTACAGAAATAGTAGCAT
GTTTTTAGTGCCCAAGTTCTTTCTTTGTCCTTTTGCCCAGCA
ATATCTTTAATAATTTATGGTTATAAACTATAAGATATTATG
AGACTATACATCGAGAAAATCTAAATACATCTTCCATTAC
AACCTTTGATTTTTTTTTTTTTTTTTTTAAATTGAAAAAACA
ATGGGTAAAGGTGATACATGAATCTTGTAAAACACAAACA
ATGACCATACATATGGGACGGAGGGAGTAATAATGGTTTG
TATATTGGCACTTATAAAGAAAAAGGTTATGCACGATTAAT
TTATGTCTTGTAGACGTGTATCACATAATGTCTTCTTTAGTT
TGCTGACCTTTTTCTACTAATGTTATGCAGGTTTACCGTGA
GTTGGAGGATAACAACCTTCATGAAATGATCTACCATTCAG
TATCTGTTCAAGGTCCTCTTCATGGAATACCAGTGAATGCA
CCCTATCAACCACTTGGAGTCATTGCTCGTAAAAGACTGCA
GGCCATGAAAAACAGCACAACCTATTGTTATGATTTCCCAC
TGGTAAGAGATATCAAACTCCACTGTACCACAATACTACAA
AAGCAGAATTTACAGTATTAGGTTTCCTTTCCTCCAAAAAA
ATCAAGGGTTGATGCATGACTTACATTCGAGTGTAACTATG
GTTCTTGTTTACGCTCAACTAGTAATGAAATAGGAATATAA
ATCTAATAAAGATTTACAAATTTTGGAGAGAGGCGGGGTT
GTGTAACTGTGGGACTTTGTAAAGGTTTAAAGTTAGTTAG
GTGGAGATGCAGGGTTTATATTTAGTTTATGAGGAAACTA
CAAGTTTACAAGATTTTAATAGGTAATACGTGTAAAATTTT
AAAAGATATCGGAAAAGTTGCTAGAATAAAGGAAGTTTAG
CTAACTTTAAAGAATATTTGTCTTAGTATTTTGGATTATTGT
AACTTTGTAAATAAAAATAGTTTCACATTTTGTTAAGATTTC
AAGTTTGGCTTTCGCACACAATGGGTCTGTTCTTTTCACCTT
ATCTGTACTTATCCGAACTTTTCCGAACTTCTATGAACTTGT
TTTGTGAGAGAGAAAATAATAAGTTTGTTCTTTTCAACTT
ATTTTTTATTATCTGAACTTATTTGAATTTATTTTTTCTGAAA
TTAAGTAAAAATAAGCTCAATAGAACATACCCAATGTAGA
AAAATAGAATTAAACAAAGAAATAGTGGGGAAAAAAAGT
```

TABLE 1-continued

ACCase gene sequences isolated from weedy plant species

| SEQ ID NO | SPECIES | TYPE | LENGTH | SEQ |
|---|---|---|---|---|
| | | | | GGAGGTGATTTGTGTCTCTTGTGGGCATTAGTTTAGTAACA |
| | | | | ACTAGAGTAATGGATATAGATGACTTATTTTTAATTCATTG |
| | | | | TATGACATACATCAAAAACCTGAAATTTTAGTGATATCAAA |
| | | | | TTGGCCTTAATTAGTAATTTAGTTGTTTGATATTGTTGGTTA |
| | | | | TACAAGTGAAAACAGATACTTAATATGCGAATGATTGTGC |
| | | | | CTATAGTGATTATGTGACTGTGTTGTTAAATATAAAAGTGT |
| | | | | TTCAGTGTTTTTAAGACAAGGGAAGTAGGGAACCATAAAC |
| | | | | AAAAATACGAAGCATATCTTGGGTGTTACCTAGTTTTGTCC |
| | | | | TATTTCTCAATTATTGATTTAGTTGTTTAATTTGTTGGTTATA |
| | | | | AAAGAGAAAAACCGGGATTGTTGGTGTGCAAAGATTGTAC |
| | | | | CTATAGTGATTATGTGACAACGTTGTCAAATGTAAAAGCAT |
| | | | | TGCAATTTTTGTGAGGCAAAGGAACCATAAATAAAAATGC |
| | | | | GAAACATGGCTTGGGTGTTACCTAGCTTTGTCCTATTTATT |
| | | | | GAACTATGTGATTGTACCTCAAATTTTTATATTTGATGTTGT |
| | | | | ATCGATCAACTTGCTTTAGCTCACGTTAGCATTTATCTGTTT |
| | | | | TTCTATTGGAAAATTGACCTGAAATTATTGGGAATGTTTTT |
| | | | | CTCAGGCTTTCTCTACTGCCTTAGAGCAATCATGGGCATCT |
| | | | | CAAGCTCCGCTTCTGAAGAAACCCGTTAACAAAAAAGTTTT |
| | | | | GAAAGTCTCAGAGCTAGTATTTGCTGATTCAAATGGCACCT |
| | | | | GGGGAACACCAGTTGTCCCGACAAATCGTGAACCTGGTCT |
| | | | | TAACAATATTGGCATGGTTGCCTGGTCCATGGAGATGTCA |
| | | | | ACTCCTGAATTCCCTGATGGAAGAACCATATTGGTTGTAGC |
| | | | | AAATGATATCACCTTCATGGCTGGATCATTTGGGCCAAAAG |
| | | | | AAGATGCTCTCTTCCAGGCAGTTACAGATCTTGCTTGTTCC |
| | | | | AAAAAAATTCCTCTGATTTACCTGGCTGCTAATTCTGGTGC |
| | | | | TCGACTGGGTGTTGCTGAAGAGGTAAGAGCATGCTTTAAA |
| | | | | ATTGGTTGGACCGATGAGTTGAACCCTGAGCGGGGGTTCC |
| | | | | AGTATATCTACTTGACTCCTGAAGATTATGAGCGTATAGGG |
| | | | | TCAGCAGTTATAGCCCATGAGTTAGAACTCCAAATGGAG |
| | | | | AGACTCGGTGGGTTATAGACACTGTTGTAGGGAAGGAGG |
| | | | | ATGGGATAGGTGTTGAGAACTTATCTGGAAGTGGAGCTAT |
| | | | | AGCTGGTGCCTACTCAAGGGCATACAAAGAAACTTTTACTC |
| | | | | TAACTTTTGTAACAGGAAGAACAGTAGGTATTGGTGCCTA |
| | | | | TCTTGCTCGCCTTGGGATGCGTTGTATCCAAAGGCTTGATC |
| | | | | AGCCCATTATTCTGACAGGCTTTTCTACGTTAAATAAACTTC |
| | | | | TTGGTCGTGAGGTTTACAGCTCACAAATGCAACTTGGCCGG |
| | | | | GCCCAAGATTATGGGTACAAATGGTGTTGTTCATTTAACAG |
| | | | | TTTCAGATGACCTTGAAGGCATTTCAGCTATTGTCAAGTGG |
| | | | | CTCAGCTATGTTCCATCCTACTCAGGAGGTGAACTTCCTAT |
| | | | | TTCACGTTCTTTAGATCCTCCTGAAAGACAGGTTGATTATTT |
| | | | | GCCTGAAAATTCTTGTGATCCCCGTTCTGCTATATCTGGTA |
| | | | | CACTTGACTCTAATGGCAATTGGCTTGGTGGAATTTTTGAC |
| | | | | AAAGATAGTTTTGTTGAAACCCTAGAAGGCTGGGCAAGGA |
| | | | | CAGTTATCACTGGCCGGGCCAAACTTGGTGGAATCCCAGT |
| | | | | TGGGATAGTTGCTGTTGAGACACAAACTGTGATGCAAGTT |
| | | | | ATCCCAGCAGATCCTGGTCAGCTTGATTCGCATGAGCGAG |
| | | | | TGGTCCCACAAGCTGGACAAGTATGGTTTCCAGATTCTGCA |
| | | | | ACTAAGCAGCACAAGCTTTGATGGATTTTAACAGGGAAG |
| | | | | AACTTCCACTTTTCATTCTAGCTAACTGGAGAGGCTTCTCTG |
| | | | | GAGGGCAAAGGGATCTCTTTGAAGGGATTCTTCAGGCAG |
| | | | | GGTCCACAATTGTCGAGAACCTTAGGACTTATAATCAACCT |
| | | | | GTTTTTGTTTATATCCCCATGATGGGTGAACTTCGTGGTGG |
| | | | | GGCATGGGTTGTCGTAGACAGTAAAATCAATTCGGACCAT |
| | | | | ATTGAGATGTATGCTGATCAGACAGCTAAAGGAAATGTTC |
| | | | | TTGAGCCAGAAGGAACGATTGAGATCAAGTTTAGAAACAA |
| | | | | GGAATTAATTGAATGTATGGAAAGGCTTGATCAACATCTC |
| | | | | ATCAATCTTAACGCAAAACTCGTCGAAGCCAAAAACTCCAA |
| | | | | TTTATATGTTAATATCGAACTCCTGAAACAGCAGATAGAAG |
| | | | | CTCGGCAGAAGCAACTTTTGCCTCTATATACTCAAATAGCC |
| | | | | ACAAAATTTGCTGAATTGCATGATAGTCCTTATAGAATGGC |
| | | | | TGCGAAAGGAGTCGTCAAGGAAGTCCTGGATTGGAGCAA |
| | | | | TTCTCGCTTATTCTTCCACAAAAGACTGTACAGGAGAGTTA |
| | | | | TGGAGGAATCACTTGTCAAGACCGTCCGAGATGCTGCTGG |
| | | | | TGAAGCAATGACCCACAAGTCTGCCATGGAATTGATCAAG |
| | | | | CAATGGTTTGCTGAGTCTGATAGTACTAGTGGAGTGGGAG |
| | | | | CTGATCCTGGTCTGATGATGAAGCTTTCTTCAAGTGGAAA |
| | | | | GAAAATCCTGCTAATTATGAAGAAAAGCTAATCGAGTTGC |
| | | | | GCATACAGAAGGTATTGCATCAGCTGTCAAATATTGGCAA |
| | | | | CTCGGCTTCTGATCTGAGAGCTCTTCCTCGGGGTCTTGCTG |
| | | | | CCCTTCTCCAGAAGGTATCTCTAAGTC |
| 81 | Kochia scoparia | gDNA Contig | 4017 | TTCTTTTCAACTTATTTTTTATTATCTGAACTTATTTGAATTT |
| | | | | ATTTTTTCTGAAATTAAGTAAAAATAAGCTCAATAGAACAT |
| | | | | ACCCAATGTAGAAAAATAGAATTAAACAAAGAAATAGTGG |
| | | | | GGAAAAAAGTGGAGGTGATTTGTGTCTCTTGTGGGCATT |
| | | | | AGTTTAGTAACAGCTAGAGTAATGGATATAGATGACTTATT |

TABLE 1-continued

ACCase gene sequences isolated from weedy plant species

| SEQ ID NO | SPECIES | TYPE | LENGTH | SEQ |
|---|---|---|---|---|

```
TTTAATTCATTGTATGACATACATCAAAAACCTGAAATTTTA
GTGATATCAAATTGGCCTTAATTAGTAATTTAGTTGTTTGA
TATTGTTGGTTATACAAGTGAAAACAGATACTTAATATGCG
AATGATTGTGCCTATAGTGATTATGTGACTGTGTTGTTAAA
TATAAAAGTGTTTCAGTGTTTTTAAGACAAGGGAAGTAGG
GAACCATAAACAAAAATACGAAGCATATCTTGGGTGTTAC
CTAGTTTTGTCCTATTTCTCAATTATTGATTTAGTTGTTTAAT
TTGTTGGTTATAAAAGAGAGAAACCGGGATTGTTGGTGTG
CAAAGATTGTACCTATAGTGATTATGTGACAACGTTGTCAA
ATGTAAAAGCATTGCAATTTTTGTGAGGCAAAGGAACCAT
AAATAAAAATGCGAAGCATGGCTTGGGTGTTACCTAGCTT
TGTCCTATTTATTGAACTATGTGATTGTACCTCAAATTTTTA
TATTTGATGTTGTATCGATCAACTTGCTTTAGCTCACGTTAG
CATTTATCTGTTTTTCTATTGGAAAATTGACCTGAAATTATT
GGGAATGTTTTTCTCAGGCTTTCTCTACTGCCTTAGAGCAA
TCATGGGCATCTCAAGCTCCGCTTCTGAAGAAACCCGCTAA
CAAAAAAGTTTTGAAAGTCTCAGAGCTAGTATTTGCTGATT
CAAATGGCACCTGGGGAACACCAGTTGTCCCGACAAATCG
TGAACCTGGTCTTAACAATATTGGCATGGTTGCCTGGTCCA
TGGAGATGTCAACTCCTGAATTCCCTGATGGAAGAACCAT
ATTGGTTGTAGCAAATGATATCACCTTCATGGCTGGATCAT
TTGGGCCAAAAGAAGATGCTCTCTTCCAGGCAGTTACAGA
TCTTGCTTGTTCCAAAAAAATTCCTCTGATTTACCTGGCTGC
TAATTCTGGTGCTCGACTGGGTGTTGCTGAAGAGGTAAGA
GCATGCTTTAAAATTGGTTGGACCGATGAGTTGAACCCTG
AGCGGGGGTTCCAGTATATCTACTTGACTCCTGAAGATTAT
GAGCGTATAGGGTCAGCAGTTATAGCCCATGAGTTAGAAC
TCCAAAATGGAGAGACTCGGTGGGTTATAGACACTGTTGT
AGGGAAGGAGGATGGGATAGGTGTTGAGAACTTATCTGG
AAGTGGAGCTATAGCTGGTGCCTACTCAAGGGCATACAAA
GAAACTTTTACTCTAACTTTTGTAACAGGAAGAACAGTAGG
TATTGGTGCCTATCTTGCTCGCCTTGGGATGCGTTGTATCC
AAAGGCTTGATCAGCCCATTATTCTGACAGGCTTTTCTACG
TTAAATAAACTTCTTGGTCGTGAGGTTTACAGCTCACAAAT
GCAACTTGGCGGGCCCAAGATTATGGGTACAAATGGTGTT
GTTCATTTAACAGTTTCAGATGACCTTGAAGGCATTTCAGC
TATTGTCAAGTGGCTCAGCTATGTTCCATCCTACTCAGGAG
GTGAACTTCCTATTTCACGTTCTTTAGATCCTCCTGAAAGAC
AGGTTGATTATTGCCTGAAAATTCTTGTGATCCCCGTTCT
GCTATATCTGGTACACTTGACTCTAATGGCAATTGGCTTGG
TGGAATTTTTGACAAAGATAGTTTTGTTGAAACCCTAGAAG
GCTGGGCAAGGACAGTTATCACTGGCCGGGCCAAACTTGG
TGGAATCCCAGTTGGGATAGTTGCTGTTGAGACACAAACT
GTGATGCAAGTTATCCCAGCAGATCCTGGTCAGCTTGATTC
GCATGAGCGAGTGGTCCCACAAGCTGGACAAGTATGGTTT
CCAGATTCTGCAACTAAGACAGCACAAGCTTTGATGGATTT
TAACAGGGAAGAACTTCCACTTTTCATTCTAGCTAACTGGA
GAGGCTTCTCTGGAGGGCAAAGGGATCTCTTTGAAGGGAT
TCTTCAGGCAGGGTCCACAATTGTCGAGAACCTTAGGACTT
ATAATCAACCTGTTTTTGTTTATATCCCCATGATGGGTGAA
CTTCGTGGTGGGGCATGGGTTGTCGTAGACAGTAAAATCA
ATTCGGACCATATTGAGATGTATGCTGATCAGACAGCTAA
AGGAAATGTTCTTGAGCCAGAAGGAACGATTGAGATCAAG
TTTAGAAACAAGGAATTAATTGAATGTATGGAAAGGCTTG
ATCAACATCTCATCAATCTTAACGCAAAACTCGTCGAAGCC
AAAAACTCCAATTTATATGTTAATATCGAACTCCTGAAACA
GCAGATAGAAGCTCGGCAGAAGCAACTTTTGCCTCTATAT
ACTCAAATAGCCACAAAATTTGCTGAATTGCATGATAGTCC
TTATAGAATGGCTGCGAAAGGAGTCGTCAAGGAAGTCCTG
GATTGGAGCAATTCTCGCTTATTCTTCCACAAAAGACTGTA
CAGGAGAGTTATGGAGGAATCACTTGTCAAGACCGTCCGA
GATGCTGCTGGTGAAGCAATGACCCACAAGTCTGCCATGG
AATTGATCAAGCAATGGCTTGCTGAGTCTGCCATGGATAG
TACTACTAGAGCGGGAGCTGATGCTTGGGCTGACGATGAA
GCTTTCTTCAGGTGGAAAGAAAATCCTGCTAATTATGAAGA
AAAGCTAATTGAGTTACGCATACAGAAAGTATTGCATCAG
CTTTCAAATATTGACAACTCAGCTTCTGATCTGAGAGCTCTT
CAGCTTCGTCAGGGTCTTGTTGCCCTACTTCAGAAGGTATC
TCTAAGGTTCCTCCACACACACACACACCCCACCCACCAAA
AAAAACACACACACACATTCACAAGAAAAGTAGAATTG
CTAGTGAAATAACTTCATCGTGTTCAATGCAGGTGAATTCC
TCAAGCCGAGCAAATCTAGTAGAGAAACTCGAGAAAGTGC
TCAATTGATTTGGTAATGATCCTGCAGAAAAACCTCTTGGT
ATATGGTGGTATGCAAATGCCATATCTGAAAGATTGATTA
GGCAAGTTGAGACAGAGACAGGCACAGTTGTAATAATGG
GATCTATCAAACCAGAAGACGTTATAACTAAGCTCAAAGA
```

TABLE 1-continued

ACCase gene sequences isolated from weedy plant species

| SEQ ID NO | SPECIES | TYPE | LENGTH | SEQ |
|---|---|---|---|---|
| | | | | TGATGGTGATTTTGACCGTCTTCGTCTCAAAATCATTCGTA<br>AGCTCAAACAAAACGTATTTCTTTCTCCTTTTCATCTTCTACT<br>GTATATTAAATGGTTTAAAATTTGATCTTGATTAATGGGTA<br>ATCTTTATAATTTTATCTTTTTTATTATAATACAAGAATGAT<br>ATGCATATTTTTATTTTGTTATTAATTACCAAATGCACTTCA<br>GTTTACATTGCCGGTTTTGAAGTTTTGGAAGCAGAATTGG<br>GGTTAGAATGCTAGATATTATTGCTTGTTGATCATTTATTCA<br>GTTACTTACATTGTTTGGTTGAAATCGGAATTAAAAGAGCA<br>CAAATTGTATGGTTTCTAACTCGACTTCACAATAAGAGTAT<br>AGATGCTCACTGTTGTGTGTGTGTTTTGTTTTTGTTAAGAA<br>ATATTGGTTTTGATTGATGATGCTCCAAGCCTCGAGTGAGC<br>GTGTTGATGAAATAGAGTACTGAATTAAAGGTTATCATTTT<br>ATCGAATGTCAGATTAATTGTTAATTGTTGCTCGGAGTCGG<br>AGTTTAAATGAGAATCATTTTATCGAATGTCTTAAGTTATC<br>AGGGCAGATATTTTTTTCTAGTGGGTATGGACTCTTGAGC<br>CTCTTTTTTCTGTATCAAACTGTCCTGTTGGTTGTTCAAATT<br>ATGCAAATCATGAAGAGATTACTTTGGTCTCAGGTTTGCTT<br>CGCCATCCTTCCCAATGAATC |
| 82 | Kochia scoparia | gDNA Contig | 2591 | ACAATGAGGCCTGGTATTTTATAAAAAAGAAAAGAATTGT<br>TAGTGCTAAAAACTCCTCGTATACAAAGTTACAAACAACAC<br>CCAGCATCCATTTTGCATATCTAACACAAAATATACAAAAC<br>ATATTAGGCAGGACAACCAAGAATTCAGAGGGAAATCTTA<br>AAATATGTTAATGCGGGCAGTACGATTCCACTGCGAAAAA<br>TTTACTCACTTAGACCAAGGTTAGGAACAACAATGTACACG<br>AATGTTGAGCAGAGAAAATATATACAAATGAAGCAGTTCA<br>TATACAATAAAAGGCAGAGAAGATGCCCAATATTCCCCTTT<br>CAATCGAAATTCACAATTGATCTTGTCATTAGAAAAGTGAA<br>ACAAGAGGGTCTCATCGTAATTAAGGGAATGAAGTATGCT<br>TCAGCCATACCCAACAGTACCTTACAATAACTGTCAAGTTT<br>CCTCACTATCTTGAGCTGCCCAAGATGGTGCAGCAAGCACT<br>TGCGCTGCTAGTCTCAGAAAAACAACTATAGGCAATCCCAT<br>CAAGATCTTGTTTTCTTCCAGGAATTAAAATAGTTCAGTTTC<br>ATCAACATCCAAACATCAAAAACAAAATGACCTGAGATAG<br>AAAAGAGCACTTACAAGCACCTTTTGATGTGCAACAAAAG<br>AACAATTTCCTCAGACGAAGCACTCTTTCTCTTACCCAAAAT<br>AGGCTACACACTCATTCAGATCTCAGGGTTGCTACACTCAT<br>ATCGATCCCAGAAATCTTTCGTTTTTAGGGAGCAGATTTCC<br>TCGCAAATGAGCATGTAAGTACTAGTTTGAAATTATCTACA<br>CTACAACTTGACATCAATATCAGACTCTGACAGCCAGGGCC<br>AAAGCCATCGGATTTGGTTACTCATCTGCTCACACAAATTG<br>AAATGTCCGGGACATAGAAGAAAAAAATACACCTATGATG<br>GTCTTGCGAAAAACTATTAAATAAAGTACTATATTTATCTTC<br>TTATTAGACCATTTTAGATCAGAGAATGTTGCTTAAAATAT<br>CCTAAGGAAAAAGCTCAGGCTATATGATTGTATTACACCAT<br>ATTATTGATATCCCAGAGTGCACTAAGGGACTGGTGAATTT<br>GGTGTTAAGCAGATGTTATCAATCCCAACTACATCATATCC<br>CATCTACTAGGCAGGCAGCGGCAAGGCAATAATGTTAGGG<br>AAAAAAATCCCATTATCTCCATTAGAAAACTATCATATTAG<br>TCTTTAAAATTTAAACAAAAAGGAATTTCAAAACAAAATGT<br>TGATTTCAATAGGCTATGTAACCTAAGCAATGTTAACAAGC<br>AGAATGCTGGTTTCACTAGAAGAGCTAGTGGGCTACAGGC<br>TACAAATTATCTAAGCCATTCTTGTTTCCTATGATTAGTTTT<br>AATAGGCATAATAGCATAAATTCTTCTATACACATCTGCCG<br>GCATTTACTGCATCACTACATTACCCGTTGTTGATGAATTTT<br>TTTTATGCTCTTGGAGGGAAAAGGTCAATTCATAGTATTTG<br>GATTGCAAACAATGGAATGACAACTGTTAAATTTATCAGA<br>AGTGTTCGGACATGGGCTTATGAAAATTTTGGAACAGAGA<br>AGGCTATTGTATTAGTAGCAATGGCTACTCCAGAAGACAT<br>GAGAATCAATGTTGAACACATTCGAATTGCTCACCAGTTTG<br>TTGAGGTTCCTGGTGGGACTAACAACAACTATGCCAATGT<br>ACAACTCATTGTTGAGGTAAATCCTGCTTTAGTAACACTGA<br>TCTTCCGTGTTTTTGCACTAATGTTGATTATACCATTTATCTT<br>TTAAACGTAAGCCTTATACATGAATTTTCCCCCTACACTGTT<br>CACTGTTTTTTCAATTAGAACCTAAATTTGTCTTTGTTTTCC<br>CTTTCTCTAGTCTTTGGATTACAAAGATAATAAAATTCATAC<br>GGGTTGGTTAGATAGTAGAATTGCAATGAGAGTCAGAGC<br>GGAAAGGCCCCCCTGGTTCATCTCTGTGGGGGAGGTGCA<br>CTCTACGTGTGTACAACTTTTCTCTTAAATTTTTTTCCTTCCA<br>AAAGCTTGATGTGTCACTTTCGTTTATTTTTATAATGAATAA<br>TTTTAAATACTTCGTAATTTCTTTCTCCTTTCTCCCTATCTTC<br>AGTAAGCTTCTTCTAGTAGTGCAGCTACTGTTTCAGAATAT<br>ATTGGCTATCTTGAGAAAGGTCAAATTCCTCCAAAGGTAAT<br>CCAAACACCAGATGCTGTTGAGATATAATTGTTTTTTAAAC<br>ACTAATTGTTTCTTTCAGTAAATTACATCAATATTTGTGTGG<br>ATTGCAGCATATTTCACTTGTCCACTTGGAAGTTACTTTGA |

TABLE 1-continued

ACCase gene sequences isolated from weedy plant species

| SEQ ID NO | SPECIES | TYPE | LENGTH | SEQ |
|---|---|---|---|---|
| | | | | ATATTGAGGGGAGCAAGTACACTATAAGTTTATTATTAAGT<br>TATGTGAATTTCATTTTTCGTTCATGGTTTCTCCTGTTTACTT<br>GATGTTAATCATCATAACATGGTTGATTCTGTTCTCCAGAT<br>CAAAATGGTGAGAGGCGGTCCAGGAAGCTACAGATTGTG<br>ATTGAATGAGTCAAAGATTGAGGCAGAAATACATACATTA<br>AGTCATTAAGAGATGGGGGTCTTTTAATGCAAGTAAGAAC<br>TTAATTTTTA |
| 83 | Kochia<br>scoparia | gDNA<br>Contig | 704 | GTGTTCGGACATGGGCTTATGAAAATTTTGGAACAGAGAA<br>GGCTATTGTATTAGTAGCAATGGCTACTCCAGAAGACATG<br>AGAATCAACGCTGAACACATTCGAATTGCTGACGAGTTTGT<br>TGAGGTTCCTGGTGGGACTAACAACAACTATGCCAATGTA<br>CAACTCATTGTTGAGGTAAATCCTGCTTTAGTAAAACTGAT<br>CTTCCGTGTTTTTGCACTAATGTTGATTATACCATTGATCTT<br>TTAAACGTGAGCCTTATACATGAATTTTCCCCCTACATTGTT<br>CACTGTTTTTTCAATTAGAAGCTAAATTTGTCTTTGTTTTTCC<br>TTTCTCCAGTCTTTGGATTACAGAGATAATAAAATTCATAC<br>GGGTTGGTTAGATAGTAGAATTGCAATGAGAGTCAGAGC<br>GGAAAGGCCCCCCTGGTTCATCTCTGTGGGGGGAGGTGCA<br>CTCTACGTGTGTACAACTTTTCTCTTAAATTTTTTTCCTTCCA<br>AAAGCTTGATGTGTCACTTTCGTTTATTTTTATAATGAATAA<br>TTTTAAATGATTTCTTTCTCCTTTCTCCCTATCTTCAGAAAGC<br>TTCTTCTAGTAGTGCAGCTACTGTTTCAGAATATATTGGCT<br>ATCTTGAGAAAGGTCAAATTCCTCCAAAGGTAATCCAAACA<br>CCAGATGCTGTTGAGATATAATTGTTTTTTAAACACTAATT<br>GTTT |
| 84 | Lolium<br>multiflorum | cDNA<br>Contig | 842 | GACATGAGGATAAATGCAGAGCACATTAGAATTGCTGATC<br>AGTTTGTTGAAGTACCTGGTGGAACAAACAATAACAACTA<br>TGCAAATGTCCAACTCATAGTGGAGATAGCAGAGAGAACA<br>GGTGTTTCGGCCGTTTGGCCTGGTTGGGGCCATGCATCTG<br>AGAATCCTGAACTTCCAGATGCACTCACTGCAAAAGGAATT<br>GTTTTTCTTGGGCCACCAGCATCATCAATGAACGCATTAGG<br>TGACAAGGTTGGTTCAGCTCTCATTGCTCAAGCAGCAGGG<br>GTTCCGACTCTTGCTTGGAGTGGATCACATGTGGAAATTCC<br>ATTAGAACTTTGCTTGGACTCTATACCTGAGGAGATGTATA<br>GGAAAGCTTGTGTTACTACCGCGGATGAAGCAGTTGCAAG<br>TTGTCAGATGATTGGTTATCCTGCCATGATCAAGGCATCCT<br>GGGGTGGTGGTGGTAAAGGGATTAGAAAGGTTAATAATG<br>ATGATGAGGTTAAAGCACTGTTTAAGCAAGTACAGGGTGA<br>AGTTCCTGGCTCCCCAATATTTATCATGAGACTTGCATCTCA<br>GAGTCGACATCTTGAAGTCCAGCTGCTTTGTGATCAATATG<br>GCAATGTAGCAGCACTTCACAGTCGTGATTGCAGTGTGCA<br>ACGACGACACCAAAAGATAATTGAGGAAGGACCAGTTACT<br>GTTGCTCCCCGTGAGACAGTGAAGGAGCTTAGAGCAAGC<br>GCAAGGAGGCTTGCTAAGGCTGTGGGATATGTTGGTGCTG<br>CTACTGTTGAATATCTCTACAGCATGGAGACTGGTGAATAC<br>TATTTTCTGGAGCTTAATCCACGGTTGCAGGTTGA |
| 85 | Lolium<br>multiflorum | cDNA<br>Contig | 732 | GCAGAGCTACGTGGAGGGGCTTGGGTCGTGATTGATAGC<br>AAGATAAATCCAGATGCGCATTGAGTGCTATGCTGAGACAA<br>CTGCAAAAGGGAATGTTCTCGAGCCTCAAGGGTTGATTGA<br>GATCAAGTTCAGGTCAGAGGAACTCCAAGAATGCATGGGT<br>AGGCTTGATCCAGAATTGATAAATCTGAAAGCACAACTCC<br>AGGGAGCAAAGCATGAAAATGGAAGTCTATCTGATGGAG<br>AATCCATTCAGAAGAGCATCGAAGCTCGAAAGAACAGTTG<br>CTGCCTTTGTACACTCAAATCGCGATACGGTTTGCTGAATT<br>GCATGATACTTCCCTCAGAATGCTTGCTAAAGGTGTGATTA<br>GGAAAATTGTAGATTGGGAAGAATCTCGGTCTTTCTTCTAC<br>AAGAGATTACGGCGGAGGATATCTGAGGATGTTCTTGCAA<br>AAGAAATAAGAAGTGTAATTGGTGTCGAGTCTTCTCACAA<br>ATCAGCAATGGAGTTGATTAAGAAGTGGTACTTGGCTTCT<br>GAGACAGCTGGAGGAAGCACTGAATGGGATGATGATGAT<br>GCTTTTGTTGCCTGGAGGGAGAACCCTGAAAACTACAAGG<br>AGCATATCAAAGAGCTTAGGGCTCAAAGGGTATCTCAGGT<br>GCTCTCAGATGTTGCAGACTCCAGTTCGGATTTACAAGCCT<br>TGCCACAGGGTCTTTCCATGCTACTAGATAAGATGGATCCC<br>TCTAGGAGAG |
| 86 | Lolium<br>multiflorum | cDNA<br>Contig | 668 | CGTTATTGATCTAAAACGATGCTCTGCCAGGGCCAACAGA<br>ACTACATACTGCTACGATTTTCCCTTGGCATTTGAAACTGC<br>AGTGACGAAGTCATGGTCTAACATTCCTAGAAACAACCAA<br>TGTTATGTTAAAGCGACAGAGCTGGTGTTTGCTGACAAGA<br>ATGGGTCGTGGGCACTCCTATAATTCCTATGCAGCGTGCT<br>GCTGGGCTCAATGACATCGGTATGGTAGCCTGGATCTTGG<br>ACATGTCCACTCCCGAATTTCCCAGTGGCAGACAGATTATT |

TABLE 1-continued

ACCase gene sequences isolated from weedy plant species

| SEQ ID NO | SPECIES | TYPE | LENGTH | SEQ |
|---|---|---|---|---|
| | | | | GTTGTCGCAAATGATATTACTTTTAGAGCTGGATCATTTGG<br>CCCAAGGGAAGATGCATTTTTTGAAGCTGTTACCAACCTG<br>GCTTGTGAGAGAAAGCTTCCTCTTATCTATTTGGCTGCAAA<br>CTCTGGTGCTCGGATTGGCATTGCCGATGAAGTTAAATCTA<br>TCTTCCGTGTTAAATGGATTGATGATAGCAACCCTGAACGT<br>GGATTTGATTACGTTTATCTGTCTGAAGAAGACTATGGCCG<br>TATTAGCTCTTCTGTTATAGCGCACAAGACACAGCTAGATA<br>GTGGCGAAATAAGGTGGGTTATCGATTCTGTTGTGGGCAA<br>GGAGGATGGGCTAGGTGTGGAGAACATACATGGAAGTGC<br>TGCTATTGCCAGTGCGTATT |
| 87 | Lolium multiflorum | cDNA Contig | 469 | AGGGCGTCCTCCAATGCGCCATTCCTTCCAATGGTCATTTG<br>ACAAGCTATATTATGAGGAGGAGCCGATGCTCCGCCATGT<br>GGAACCTCCTCTGTCCACATTCCTTGAATTGGACAAAGTGA<br>AATTAGAAGGTTACAGTGACATGAAATACAATCCATCGCG<br>TGATCGCCAGTGGCACATTTACACACTGAACAGTGAAGAT<br>CCAAAATCAAATGACCAAAGGATATTCCTTCGTACAGTTGT<br>TAGACAGCCAAGTTTAACCAATGGGTTTTTGTTTGGAAGTA<br>TCGACAATGAAGTAGGCCGTTCTCAGGCCACATCGTCATTC<br>ACATCTAACAGCATACTTAGATCATTGATTGCAGCGCTAGA<br>AGAAATAGAGTTACATGCTCATAATAAGGCCATGAGGTCA<br>CGCCATTCCCACATGTATCTGTGCATGTTGAGAGAACAACG<br>GTTGTCTGATCTAATTCCATTT |
| 88 | Lolium multiflorum | gDNA Contig | 4094 | CACTTCTAAAGCCACAAGTAGAGGATCCCATTCGCAGGCG<br>ATGGGGTGTAATGGTTGTAATCAAGTCTCTTCAGCTTCTGC<br>CAACTGCAATTGAAGCTGCATTAAAGGAGACTTCACATTAT<br>GGAGCAGGTGATGCAAATGTCTCCAATGGTAGTCCTATAA<br>GATCTAATAATAGCAATATGCTGCATATTGCTTTGGTTGGT<br>ATCAGAAATCAGATGAGTACTCTTCAAGACAGGTTCGTTTA<br>CACTCTCTACTCTTTGCGATTCTTTATTCTTGATGAAACACA<br>AAATATCATAAGAGTGATTCTATGAACTGGTTCTGAATTTC<br>ATGAAATTTTTAGTTACACCCTCCACTTTGTTTTCTCTTTTTA<br>GTGGTGATGAGGATCAAGCACAAGAAAGGATCAACAAAC<br>TTTCCAAGATTTTGAGGGATACCACTATAACATCACATCTC<br>AATGGTGCTGGTGTTAGGACTGTCAGCTGCATTATCCAAA<br>GAGATGAAGGGCGTCCTCCAATGCGCCATTCCTTCCAATG<br>GTCATTTGACAAGCTATATTATGAGGAGGAGCCGATGCTC<br>CGCCATGTGGAACCTCCTCTGTCCACATTCCTTGAATTGGT<br>ATGCAGCTTTAGTTTTGGCTTATGTTCTCTTCAACAATACCA<br>GTACCTCTAATAACTTATCTGTAAATACAGGACAAAGTGAA<br>ATTAGAAGGTTACAGTGACATGAAATACAATCCATCGCGT<br>GATCGCCAGTGGCACATTTACACACTGAACAGTGAAGATC<br>CAAAATCAAATGACCAAAGGATATTCCTTCGTACAGTTGTT<br>AGACAGCCAAGTTTAACCAATGGGTTTTTGTTTGGAAGTAT<br>CGACAATGAAGTAGGCCGTTCTCAGGCCACATCGTCATTCA<br>CATCTAACAGCATACTTAGATCATTGATTGCAGCGCTAGAA<br>GAAATAGAGTTACATGCTCATAATAAGGCCATGAGTTCAT<br>GCCATTCCCACATGTATCTGTGCATGTTGAGAGAACAACG<br>GTTGTCTGATCTAATTCCATTTTCAAGGTCAGTCAAAATAT<br>ACTTATGTTCTCAATAAAATACACTGCATTAAATGTGCTCAT<br>ATGATGCTCACTTGGTTTGTGCTTCTCATGGTGTTAGGATG<br>ATGGGTGAAGTTGGTCAAGATGAGGAGGCAGCATGCACA<br>CTTTTGAAGCATATGGTTATGAATATATATGAACATGTTGG<br>TGTCAGGATGCATCGCCTTTCTGTGTGCCAATGGGAAGTG<br>AAGCTATGGTTAGATTGTGATGGGCAAGCCAATGGTGCTT<br>GGAGAGTTGTCATTACCAATATAACTGGGCATACCTGCACT<br>GTTGATGTAAGTTACCTTAGCGATTGCTGTATTGCACTACT<br>ATGTGAACAACAGCATCTACAGTTCTGCATATCATAAAGAA<br>TGCTACCTCTGATGGCCCCATAGATCATCATATATGATTAT<br>ATTTTAGTTAGTAAATAGAACATGGTCATCATTTCCATCATT<br>CGTGTCATGGACATTCTCTCAACTGATGCCTTTAAAGGGTC<br>TATTAAAGACCACTTAAAAATAATTAAGTACTATTTTCTCTT<br>TATTCCAATACTCTTATATGCTCACATTCGTTTGACTTTCAG<br>ATTTACCGAGAAGTAGAAGACTCCAATACGCATCAGATTTT<br>CTACCGCTCTGCCACACACACAGCTGGTCCTTTGCATGGCA<br>TTGCATTGCATGAGCCATACAAACGTTTGGCTCCTATTGAC<br>ATGAAACGGTCTGCGGCTAGGAAAAACGAAACTACATACT<br>GCTATGATTTCCCATTGGTGAGTTGGTTGCGTTTGTTAATTT<br>ACTTTTTATCTAACATTAGTTCGCATGATTAACCTGATCAAC<br>TGAGTTTGCTAATAATACTCTGTCCACAGGCATTTGAAACA<br>GCATTGAAGAAATTGTGGAAATCTAGTGCTTCACATCTTGC<br>AGAAACTAACCAGCATAATCAGCAGTATGCTGAAGTGACA<br>GAGCTTTTATTTGCTGATTCAACTGGATCATGGGGTACTCC<br>TTTGGTTCCAGTTGAACGTTCTCCATGTGTCAATGATATCG<br>GCATTGTTGCTTGGAAGATGAAGCTCTCCACGCCAGAATTT |

TABLE 1-continued

ACCase gene sequences isolated from weedy plant species

| SEQ ID NO | SPECIES | TYPE | LENGTH | SEQ |
|---|---|---|---|---|
| | | | | CCAGGCGGCCGGGAGATTATAGTTGTTGCAAATGACGTGA |
| | | | | CGTTTAAAGCTGGGTCTTTTGGTCCTAGAGAAGATATATTC |
| | | | | TTTCATGCTGCTACCAATCTTGCCTGTGAGAGGAAAATTCC |
| | | | | TCTAATCTACTTGTCAGCAACTGCTGGTGCTAGGCTTGGTG |
| | | | | TGGCAGAGGAAATAAAGTCGTGCTTCCATGTTGGATGGTC |
| | | | | TGATGACCAGAGTCCTGAACGTGGTTTTCACTACATTTACC |
| | | | | TCACTGAAGAAGACTATTCACGTCTAAGCTCTTCAGTTATA |
| | | | | GCCCATGAACTGAAACTAGACAGCGGAGAAACCAGATGG |
| | | | | ATTGTTGATACCATTGTTGGGAAGAGGATGGACTTGGTT |
| | | | | GTGAGAATCTGCATGGTAGTGGTGCCATTGCCAGTGCCTT |
| | | | | TGCTAAGGCATATAGAGAGACCTTTACTCTGACATTTGTGA |
| | | | | CTGGAAACGCAGTTGGAATTGGGGCTTATCTTGCTCGGCT |
| | | | | AGGAATGCGGTGTATACAGCGACTTGATCAATCAATTCTTT |
| | | | | TAACTGGTTTTTCTGCCCTGAACAAACTTCTGGGGCGCGAG |
| | | | | GTTTATAGCTCTCAGATGCAACTGGGTGGCCCCAAAATTAT |
| | | | | GGGTACAAATGGAGTCGTCCATCTGACAGTGCCAGATGAT |
| | | | | CTTGAAGGTGTTTCTGCTATCTTGAAATGGCTCAGCTATGT |
| | | | | TCCTGCCTATGTTGGCGGTCCTCTTCCTATTCTGAAGCCTCT |
| | | | | TGATCCACCAGATAGAGCTGTAACATATTTCCCAGAGAATT |
| | | | | CATGTGATGCCCGTGCAGCCATCTGTGGGATTCAGGACAC |
| | | | | TCAAGGCAAGTGGTTGGGTGGTATGTTTGACAGAGAAAG |
| | | | | CTTTGTGGAAACATTAGAAGGATGGGCAAAAACTGTTATT |
| | | | | ACTGGAAGGGCAAAGCTGGGTGGGATTCCAGTTGGCGTC |
| | | | | ATAGCAGTGGAAACCCAGACAATGATGCAAGTAATCCCTT |
| | | | | CTGACCCTGGTCAGCTTGATTCCGCTGAGCGTGTAGTCCCT |
| | | | | CAAGCAGGACAGGTGTGGTTCCCAGATTCGGCCTCAAAAA |
| | | | | CAGCGCAGGCGTTGCTGGATTTCAACCATGAAGGGCTCCC |
| | | | | ATTGTTCATACTTGCTAACTGGAGAGGCTTCTCTGGTGGGC |
| | | | | AAAGGGATCTGTTTGAAGGAATCCTTCAGGCTGGCTCTAC |
| | | | | AATTGTTGAGAACCTGAGGACCTACAAGCAGCCAGCTTTT |
| | | | | GTGTACATCCCAAAGGCTGGAGAGCTGCGTGGAGGTGCA |
| | | | | TGGGTTGTGGTGGACAGCAAGATCAATCCTGAGCACATTG |
| | | | | AGATGTATGCGGAGAGGACTGCAAAGGGAAATGTCCTTG |
| | | | | AGCCAGAAGGGCTGATTGAGATTAAATTTAAGCCAAAAGA |
| | | | | AGTGGAAGAGAGTATGATAAGGCTTGACCCTGAGCTGGC |
| | | | | CAGCCTTGATTCTAGACTCAAAGAAATGAAGAAAGCAAAT |
| | | | | GCTAGCCTGCAGGAAACGGAGGCCATCAACAGGAGCATC |
| | | | | AACAACCGGATAAAGAAGCTGATGCCCATCTATACGCAGG |
| | | | | TTGCCACACGGTTTGCTGAATTGCACGACACCTCTTCCAGA |
| | | | | ATGACTGCCAAAGGTGTGATCAGTAAGGTGGTTGATTGGG |
| | | | | AGGAGTCTCGGAGCTTCTTCTACAGGAGGTTGCGAAGGCG |
| | | | | GGTCGCGGAGGATTCCCTTGCCCAGGAAGTTAAAGAAGCC |
| | | | | GCTGGTGAGCCGATGCCTCACAGAGCAGCACTGGAGCGT |
| | | | | ATCAAGCAGTGGTATCTGGCCTCCAAGGGTTCCGAAGGAG |
| | | | | ACGGTGAGAAGTGGAACGATGACGAGGCTTTCTTCGCCTG |
| | | | | GAAAGACGATGCCAAGAACTACGAGAACCATCTTCAGGAG |
| | | | | TTGAAGGCTGAAAGAGTATCTAGACTGTTCTCGGATCTTGC |
| | | | | TGAAAGCTCGGACGTGAAGGCCTTGCCCAACGGTCTTTCG |
| | | | | CGCCTCCTTGGCAAAGTAAGTTCTGCTTCTTCTTTTCTTA |
| 89 | Lolium multiflorum | gDNA Contig | 3198 | CTAGTTCTTGACTCGAGAAGAAGGTCTGCAGCCAGCAGCC |
| | | | | TCGTTCGTTAACTCGGCGAGCAAAGGAAACAAGGTAAACA |
| | | | | CACGATCCTGGCAAACACTTTTCTTTCTTCTCTGAATTGAAG |
| | | | | TCGTCGATATCGTGATGTTTCATCTTCGTTACAATAAGCTTG |
| | | | | GATGACGGGGAGGGTACTTGCGTTGGCTAGGCAGTCGTTT |
| | | | | CGACAAAGCTGGTGGTGGTGTGTCAACTCCAAAAGCCAAC |
| | | | | CTGCTTTTCGTTTCTGGCAACAACCCTCCCCTGTTCAAAAAC |
| | | | | CTTGTCCTGTCAAATCCCAGCTTGCCGAAACGTCCTACTGC |
| | | | | TGGCACCCCTTGTACCTCTTGTTCTAGGTTTGATCAAAGTT |
| | | | | GATCTTTGTCAAATTTTACTAGATTTTTTTTACATCTATACA |
| | | | | ACATATTTGTACAGTACATGTGCATACCGATCGATATAATT |
| | | | | TTGTTGGTGCTCGCAGAGTTTGACTAGCATGTAGCAGGAG |
| | | | | CAGTGATTTATGCTACTACTACTTATTGTACTCCAGTAGGA |
| | | | | TCTACAATAGTACTAGTATCGTAGTCGTCGAATTTAGTCAG |
| | | | | TGGTAGCAAACACCCAAACAGCGAGCAGAGAACGTCGCCTT |
| | | | | CGCCGCCGTGATGCTGCTGGGTTGGGGGTTTAGCTCAGCT |
| | | | | ACCTCCCAACTAATTCCATCCTTCCCCAAATCAAATAAAAAA |
| | | | | GAAAAGAAAATAAATAAAACCAGTCCACCCCACAGTCCAA |
| | | | | ATCCAAGTCCCAAGTCCCAACCCAGCTCCTCTCGCTCACGC |
| | | | | CTTCCGGCCTCCCTCTCTACCCCGTCCCGTGTTCCGGCCCCA |
| | | | | GCCGAGCGTCGCATGGCGGGGCCGCCGGTGGCACGGCAG |
| | | | | TTATAAGCCGCGCGCGGCCAACCATCCAGCGAGAGCACAG |
| | | | | CACAGTAGCATAGCTACCTCGCAGCACGCCCTCCCTCCCTG |
| | | | | CTAGCTACTCCTCCTCTGCAGACTGCAGCGGGTGGGGGAG |
| | | | | AGGAGGCGCGCATTTAAGCCCGGCCTCCTCACCTGTCGGC |
| | | | | CTGCCGCCGCGCCCGACGCCGAGGCCTTCCCTTCCCGGATC |

TABLE 1-continued

ACCase gene sequences isolated from weedy plant species

| SEQ ID NO | SPECIES | TYPE | LENGTH | SEQ |
|---|---|---|---|---|
| | | | | TTGATCTGCCCGCCTTCCTCCTCCTCGGCGGCATTCCGTCG |
| | | | | AACGGGCGGCGCGCGCCTACGGCAGTACGGTACCTACCCT |
| | | | | GCCTTCTCTCCCCCCATCTCCCCTGCTCGCCGTGTACGCGCC |
| | | | | AGCGTTGGGCACCCCGCACAAATCTACCACACAATTTCGCT |
| | | | | CTCCCCGGCTCAGTCAGTCGCCGCTGTGCGTAGATCGCTTC |
| | | | | CACTTCCTGCTGGGCGCTCCTGGACGTTCCGTCGAGCGGTT |
| | | | | TCTGAGATTGGGCTGAGGGGATCATACCGGCTTCCTTTTCT |
| | | | | GTCCTCTTTTCTGTTCCGTTGCGTGCAGGAATTGTTGTCTGC |
| | | | | TCCCACGCCTTTGCTTGCTCACCTATTCCGTGGACTCCCCTG |
| | | | | TGATCACAACATACTCAGCATACTTTTTCTTCACATGCCTAG |
| | | | | GATAATGAAATCGCAATCTATGTACCATCGCTGTCGCGATT |
| | | | | TCTGCTGGCTGTTGACTACTAATTTTACCCCTTCACTTGTGT |
| | | | | ACTTATCCTCGTACCGCTGCTTGAGGAATTTCATATTTGGCT |
| | | | | GCTTGAGGAATTTCATAAATCTGGCTAGACACTCTTCATGT |
| | | | | TTTTGTTCTTACATCTAGTAGTAGTTCAGAAAGAGGAAGCA |
| | | | | CAGACGAGCAACTGACGTATCCGTGCAATTGTTCGCTAGT |
| | | | | CAGAATGACAGAATCGACGTGCTCATTTATATACCTGATGT |
| | | | | AATTGTGCGCTTCTCCTCAAGCCGTAGCTTGAGGCGTTTCA |
| | | | | TTTTGTTCGTTTGCGAAAAGTTTGATGAGGAATTTCATGGT |
| | | | | CTGGCTACGTACTCACCTGTTTGTTTGCATCATTTTAGCAT |
| | | | | CAAGTTCAGAAACAATAAATACCCTACTTGTGCAATCATTC |
| | | | | GCTAACAGAATCGACAATGCTAACGGTTTTTCTGTCCGTTG |
| | | | | CTTGTCCAGCGCTGAAGGCTAGAGGGCGGCGACAATGGT |
| | | | | GGCGGAACCGGACAAGACAAATGGGACGCCCAACAGGAT |
| | | | | GTCCAGTAACAGGCACCTGTCCTCGCCGTCCGTGGTCGAC |
| | | | | GAGTTCTGCAAGGCGCTCGGGGGCGATTCGCCCATCCACA |
| | | | | GCGTCCTGGTCGCCAACAATGGAATGGCCGCCGTCAAGTT |
| | | | | CATGCGCAGCATCCGCACCTGGGCCCTCGAGACGTTTGGG |
| | | | | ACCGAGAAGGCCATTCTCCTGGTGGCCATGGCAACTCCGG |
| | | | | AGGACCTCAGGATAAACGCCGAGCACATAAGGATCGCCG |
| | | | | ACCAGTTCTTGGAAGTCCCTGGCGGAACAAACAATAACAA |
| | | | | TTATGCGAATGTGCAGCTCATTGTGGAGGTTAGCACGACG |
| | | | | ACCATTCTCCCGGTCCTTTTTACTAGCTTGTTGATTTAGCGT |
| | | | | ATCCATGTTTCTTGTGCTGGATATTTGACTAGTTACTTAATG |
| | | | | TTTCTACCTTCACTGTCACAGATAGCGGAGAGAACTCGGGT |
| | | | | TTCTGCGGTTTGGCCTGGCTGGGGCCATGCTTCTGAGAAC |
| | | | | CCGGAACTTCCAGACGCGCTCAAGGAGAAGGGAATCATTT |
| | | | | TTCTTGGGCCACCATCAGCCGCGATGGCTGCACTTGGTGAT |
| | | | | AAGATTGGTTCTTCTCTTATTGCGCAAGCAGCAGGAGTTCC |
| | | | | GACTCTTCCATGGAGTGGATCACATGTATACGTTCTTCTAT |
| | | | | TTCTGTATAGTTTTGCTCCTCTTTTTTTATCGGCTGCTATGTT |
| | | | | GCTTAAAATTAAATCCAAATCAACTGTAGGTGAAAGTTCCG |
| | | | | CAAGAAACCTGCCACTTGATACCTGAGGACATCTATAAGA |
| | | | | AAGCTTGTGTTACAACTACGGAGGAAGCGGTGGCTAGTTG |
| | | | | TCAGGTGGTGGGGTATCCTGCAATGATCAAGGCATCATGG |
| | | | | GGTGGTGGTGGTAAAGGAATAAGGAAGGTTGGTCTTCTTT |
| | | | | TTAGTTCGACTCTACCGCAATTATATGGAAAGTCTCTGTTC |
| | | | | ACAAACGATACATGGAAATGTCCACTGTCCATACAAAACG |
| | | | | AAGCTAGGTTTCGGCAAATATTGTAGAATAAACGAAAGAT |
| | | | | GATTTTGATGTCATCCAAATGCTTTTTATAGGTCCACAATG |
| | | | | ATGATGAGGTGAGAGCCTTGTTTAAGCAAGTGCAAGGAG |
| | | | | AAGTCCCCGGATCACCTATATTTATCATGAAGGTGGCATCT |
| | | | | CAGGTGATAAGTGATAACAGC |
| 90 | Lolium multiflorum | gDNA Contig | 511 | CTAATAACTTATCTGTAAATACAGGACAAAGTGAAATTAGA AGGTTACAGTGACATGAAATACAATCCATCGCGTGATCGC CAGTGGCACATTTACACACTGAACAGTGAAGATCCAAAAT CAAATGACCAAAGGATATTCCTTCGTACAGTTGTTAGACAG CCAAGTTTAACCAATGGGTTTTTGTTTGGAAGTATCGACAA TGAAGTAGGCCGTTCTCAGGCCACATCGTCATTCACATCTA ACAGCATACTTAGATCATTGATTGCAGCGCTAGAAGAAAT AGAGTTACATGCTCATAATAAGGCCATGAGTTCACGCCATT CCCACATGTATCTGTGCATGTTGAGAGAACAACGGTTGTCT GATCTAATTCCATTTTCAAGGTCAGTCAAAATATACTTATGT TCTCAATAAAATACACTGCATTAAATGTGCTCATAGATGCT CACTTGGTTTGTGCTTCTCATGGTGTTAGGATGATGGGTGA AGTTGGTCAAGATGAGGAGAT |
| 91 | Lolium multiflorum | gDNA Contig | 252 | TTCTCTGTAGAGCCGACATCTAGAGGTTCAGCTGCTCTGTG ACAAACACGGCAATGTAGCAGCACTGCACAGTCGAGACTG TAGTGTTCAAGAAGGCACCAAAAGGTTAGAAATTCTCCT GAAAAGTTATGTTGTCCAATATCAGTTTCCTTGGAGCTAAT ACATGCCGAAACATTGTATACTGAGTACTGGTAGAAGTTCT GTAGCTTTAGGGATTGGCAAAGTGCTAAACTCTGCAGAAG CTATACAAA |

TABLE 1-continued

ACCase gene sequences isolated from weedy plant species

| SEQ ID NO | SPECIES | TYPE | LENGTH | SEQ |
|---|---|---|---|---|
| 92 | Sorghum halepense | cDNA Contig | 1913 | CTCACAGATGTATCTGTGCTTACTGAGAGAACAACAATTGC ATGAACTAATTCCATTTTCAAGGATGACTGATGAAATTGAT CAGGATGAAGGAACTGCATGTACACTTTTGAAGCATATGG TATTGAATTTATATGAACATGTTGGGGTCAGGATGCATCGT CTTTCTGTGTGCCAGTGGGAAGTCAAGCTCTGGTTGGTTTG TGATGGGCAAGCTAGTGGTGCTTGGAGAGTTGTTGTTACC AATGTTACTGGTCACACCTGCACCATTGATATTTACCGAGA AGTGGAAGACCCCAGCACACATCAGCTTCTCTACCACTCTG CCACAGCCACGGCTGGTCCTTTGCATGGTGTTGCATTGAAT GAACCATACAAGCCTTTGGACGCTATTGACCTCAAACGTTA TGCTGCTAGGAAAAATGAAACCACATACTGCTACGATTTCC CCTTGGCATTTGAAACAGCGCTGAAGAGATTATGGAAATC AAGTAGCTATGGTGTTAGTGAAGCTAATGAGCGCAATCAA CTCTATGCTGAAGTGAAAGAGCTTATATTTGTTGATTCGGA TGGAGCATGGGCACTCCATTGGTTTCATTTGAACGCCCTC CAGGCATCAATGATATTGGCATTGTTGCTTGGAACATGAA GCTGTCCACGCCAGAATTCCCAAGTGGCCGGGAGATTATA GTTGTTGCCAATGATGTGACATTTAAAGCTGGGTCCTTTGG TCCAAGAGAAGATGCATTTTTTGATGCTGTTACCAATCTTG CCTGTGAGAGGAAACTTCCTCTTATCTATCTGGCAGCAACT GCTGGTGCCAGGCTTGGTGTAGCTGAGGAAATAAAGTCAT GCTTCCATGTCGGCTGGTCTGATGATGAGAGCCCTGAACG TGGTTTTCAGTACATTTACCTCACTACACAAGATTATTCACG TCTAAGCTCTTCAGTAATAGCTCACGAGCTGCAACTAGAAA ATGGAGAAACCAGATGGGTGGTTGATACCATTGTTGGTAA AGAGGATGGACTTGGTTGTGAGAATCTCCATGGAAGTGGT GCGATTGCCAGTGCATATTCCAAGGCATACAAAGAGACCT TTACTCTGACATTTGTGACTGGAAGAGCTGTTGGCATTGG GGCTTATCTGGCTCGTTTAGGTATGAGGTGTATACAACGTC TTGATCAACCAATTATTCTGACTGGGTTTTCTGCACTAAAC AAGCTTCTGGGGCGGGAGGTGTACAGTTCTCATATGCAAT TGGGTGGCCCCAAAATCATGGCTACAAATGGTGTTGTCCA CCAAACTGTGTCAGATGACCTTGAAGGTGTTTCTGCTATCC TGAAATGGCTCAGTTATGTTCCTCCATATGTTGGTGGTCCT CTTCCCATTATGAAACCCTGGACCCACCCGAAAGACCAGT AGCATACTTCCCTGAGAATGCTTGTGATGCTCGTGCAGCCA TCTGTGGCATTCAAGACGGTGAAGGGAAGTGGTTAGGTG GTATGTTTGATAGGGAAACCTTCGTGGAAACATTGGAAGG TTGGGCAAAAACAGTTATCACCGGAAGAGCAAAGCTTGGT GGAATACCAGTTGGTGTCATAGCTGTGGAAACCCAGACTG TGATGCAAGTCATCCCAGCTGATCCAGGTCAGCTTGATTCC GCTGAGCGTGTAGTCCCTCAAGCAGGTCAGGTGTGGTTCC CAGATTCTGCAGCCAAAACAGCTCAGGCATTAATGGATTTC AACCGTGAGGAGCTTCCACTGTTCATCCTTGCAAACTGGA GAGGTTTCTCTGGTGGGCAAAGGGATTTATTTGAAGGAAT CCTTCAGGCTGGTTCAACAATTGTTGAGAATCTGAGGACG TACAAGCAGCCTGCTTTTGTATATATCCCAATGGGTGGAGA GCTACGGG |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09422557B2). An electronic copy of the "Sequence Listing" will also be available from the USPTO upon request and payment of the fee set forth in 37 CFR 1.19(b)(3).

We claim:

1. A method of plant control comprising: treating a plant with a composition comprising a non-transcribable polynucleotide and a transfer agent, wherein said non-transcribable polynucleotide is from 18 to about 700 nucleotides in length and is at least 85% identical or at least 85% complementary to an ACCase gene sequence, or to an RNA transcript of said ACCase gene sequence, wherein said ACCase gene sequence is selected from the group consisting of SEQ ID NOs:1-92 and a polynucleotide fragment thereof, wherein said transfer agent conditions the surface of said plant for permeation by said non-transcribable polynucleotide, and whereby said plant's growth, development, or reproductive ability is reduced or said plant is more sensitive to an ACCase inhibitor herbicide relative to a plant not treated with said composition.

2. The method as claimed in claim 1, wherein said transfer agent is an organosilicone surfactant composition or compound contained therein.

3. The method as claimed in claim 1, wherein said non-transcribable polynucleotide is selected from the group consisting of sense ssDNA, anti-sense ssDNA, sense ssRNA, anti-sense ssRNA, dsRNA, dsDNA, and dsDNA/RNA hybrids.

4. The method as claimed in claim 1, wherein said plant is selected from the group consisting of *Amaranthus palmeri, Amaranthus rudis, Amaranthsu chlorostachys, Amaranthus thunbergii, Amaranthus graecizans, Amaranthus hybridus, Amaranthus lividus, Amanaranthus spinosus, Abutilon theophrasti, Ambrosia trifida, Commelina diffusa, Conyza candensis, Lolium multiflorum, Sorghum halepense, Xanthium strumarium, Euphorbia heterophylla, Kochia scoparia* and *Digitaria sanguinalis*.

5. The method as claimed in claim 1, wherein said composition further comprises said ACCase inhibitor herbicide and said treating comprises external application to said plant with said composition.

6. The method as claimed in claim 5, wherein said composition further comprises one or more herbicides different from said ACCase inhibitor herbicide.

7. The method as claimed in claim 1, wherein said composition comprises any combination of two or more of said non-transcribable polynucleotide or a fragment thereof and said treating comprises external application to said plant with said composition.

8. A composition comprising a non-transcribable polynucleotide and a transfer agent, wherein said non-transcribable polynucleotide is from 18 to about 700 nucleotides in length and is at least 85% identical or at least 85% complementary to an ACCase gene sequence, or to an RNA transcript of said ACCase gene sequence, wherein said ACCase gene sequence is selected from the group consisting of SEQ ID NOs:1-92 and a polynucleotide fragment thereof, wherein said transfer agent conditions the surface of a plant for permeation by said non-transcribable polynucleotide, and whereby said plant treated with said composition has its growth, development, or reproductive ability suppressed or delayed or said plant is more sensitive to an ACCase inhibitor herbicide as a result of said non-transcribable polynucleotide containing composition relative to a plant not treated with said composition.

9. The composition of claim 8, wherein said transfer agent is an organosilicone composition.

10. The composition of claim 8, wherein said non-transcribable polynucleotide is selected from the group consisting of SEQ ID NOs: 93-3900 and a fragment thereof.

11. The composition of claim 8, wherein said non-transcribable polynucleotide is selected from the group consisting of SEQ ID NOs: 3901-4530 and a fragment thereof.

12. The composition of claim 8, further comprising said ACCase inhibitor herbicide.

13. The composition of claim 12, wherein said ACCase inhibitor herbicide is selected from the group consisting of aryloxyphenoxypropionates, cyclohexanediones and phenylpyrazoline.

14. The composition of claim 12, further comprising a non-ACCase inhibitor herbicide.

15. A method of reducing expression of an ACCase gene in a plant comprising: external application to said plant of a composition comprising a non-transcribable polynucleotide and a transfer agent, wherein said non-transcribable polynucleotide is from 18 to about 700 nucleotides in length and is at least 85% identical or at least 85% complementary to an ACCase gene sequence, or to an RNA transcript of said ACCase gene sequence, wherein said ACCase gene sequence is selected from the group consisting of SEQ ID NOs:1-92 and a polynucleotide fragment thereof, wherein said transfer agent conditions the surface of said plant for permeation by said non-transcribable polynucleotide, and whereby said expression of said ACCase gene is reduced relative to a plant in which the composition was not applied.

16. The method as claimed in claim 15, wherein said transfer agent is an organosilicone compound.

17. The method as claimed in claim 15, wherein said non-transcribable polynucleotide is selected from the group consisting of sense ssDNA, anti-sense ssDNA, sense ssRNA, anti-sense ssRNA, dsRNA, dsDNA, and dsDNA/RNA hybrids.

18. A method of identifying non-transcribable polynucleotides useful in modulating ACCase gene expression when externally treating a plant comprising: a) providing a plurality of non-transcribable polynucleotides that are from 18to about 700 nucleotides in length and are at least 85 percent identical or at least 85 percent complementary to an ACCase gene sequence selected from the group consisting of SEQ ID NOs:1-92; b) externally treating said plant with one or more of said non-transcribable polynucleotides and a transfer agent; and c) analyzing said plant or extract for modulation of ACCase gene expression, wherein said transfer agent conditions the surface of said plant for permeation by said one or more of said non-transcribable polynucleotides, and whereby said plant treated with said one or more of said non-transcribable polynucleotides and said transfer agent has its growth, development, or reproductive ability suppressed or delayed or said plant is more sensitive to an ACCase inhibitor herbicide as a result of said one or more of said non-transcribable polynucleotides and said transfer agent relative to a plant not treated with said one or more of said non-transcribable polynucleotides and said transfer agent.

19. The method as claimed in claim 18, wherein said plant is selected from the group consisting of *Amaranthus palmeri, Amaranthus rudis, Amaranthsu chlorostachys, Amaranthus thunbergii, Amaranthus graecizans, Amaranthus hybridus, Amaranthus lividus, Amanaranthus spinosus, Abutilon theophrasti, Ambrosia trifida, Commelina diffusa, Conyza candensis, Lolium multiflorum, Sorghum halepense, Xanthium strumarium, Euphorbia heterophylla, Kochia scoparia* and *Digitaria sanguinalis*.

20. The method as claimed in claim 18, wherein said ACCase gene expression is reduced relative to a plant not treated with said one or more of said non-transcribable polynucleotides and said transfer agent.

21. The method as claimed in claim 18, wherein said transfer agent is an organosilicone compound.

22. An agricultural chemical composition comprising an admixture of a non-transcribable polynucleotide, an ACCase inhibitor herbicide, and a co-herbicide, wherein said non-transcribable polynucleotide is from 18 to about 700 nucleotides in length and is at least 85% identical or at least 85% complementary to a portion of an ACCase gene sequence, or to a portion of an RNA transcript of said ACCase gene sequence, wherein said ACCase gene sequence is selected from the group consisting of SEQ ID NOs:1-92and a polynucleotide fragment thereof, and whereby a plant treated with said composition has its growth, development, or reproductive ability suppressed or delayed or said plant is more sensitive to said ACCase inhibitor herbicide as a result of said non-transcribable polynucleotide containing composition relative to a plant not treated with said composition.

23. The agricultural chemical composition of claim 22, wherein said co-herbicide is selected from the group consisting of amide herbicides, arsenical herbicides, benzothiazole herbicides, benzoylcyclohexanedione herbicides, benzofuranyl alkylsulfonate herbicides, cyclohexene oxime herbicides, cyclopropylisoxazole herbicides, dicarboximide herbicides, dinitroaniline herbicides, dinitrophenol herbicides, diphenyl ether herbicides, dithiocarbamate herbicides, glycine herbicides, halogenated aliphatic herbicides, imidazolinone herbicides, inorganic herbicides, nitrile herbicides, organophosphorus herbicides, oxadiazolone herbicides, oxazole herbicides, phenoxy herbicides, phenylenediamine herbicides, pyrazole herbicides, pyridazine herbicides, pyridazinone herbicides, pyridine herbicides, pyrimidinediamine herbicides, pyrimidinyloxybenzylamine herbicides, quaternary ammonium herbicides, thiocarbamate herbicides, thiocarbonate herbicides, thiourea herbicides, triazine herbicides, triazinone herbicides, triazole herbicides, triazolone herbicides, triazolopyrimidine herbicides, uracil herbicides, and urea herbicides.

24. An agricultural chemical composition comprising an admixture of a non-transcribable polynucleotide, an ACCase inhibitor herbicide, and a pesticide, wherein said non-transcribable polynucleotide is from 18 to about 700 nucleotides in length and is at least 85% identical or at least 85% complementary to a portion of an ACCase gene sequence, or to a portion of an RNA transcript of said ACCase gene sequence, wherein said ACCase gene sequence is selected from the group consisting of SEQ ID NOs:1-92 and a polynucleotide fragment thereof, and whereby a plant treated with said composition has its growth, development, or reproductive ability suppressed or delayed or said plant is more sensitive to said ACCase inhibitor herbicide as a result of said non-transcribable polynucleotide containing composition relative to a plant not treated with said composition.

25. The agricultural chemical composition of claim 24, wherein said pesticide is selected from the group consisting of insecticides, fungicides, nematicides, bactericides, acaricides, growth regulators, chemosterilants, semiochemicals, repellents, attractants, pheromones, feeding stimulants, and biopesticides.

26. A herbicide composition comprising an ACCase inhibitor herbicide, a non-transcribable polynucleotide, and a transfer agent, wherein said non-transcribable polynucleotide is selected from the group consisting of SEQ ID NOs: 4531-4538 and a complement or a polynucleotide fragment thereof, wherein said transfer agent conditions the surface of a plant for permeation by said non-transcribable polynucleotide, and whereby said plant treated with said composition has its growth, development, or reproductive ability suppressed or delayed or said plant is more sensitive to said ACCase inhibitor herbicide as a result of said non-transcribable polynucleotide containing composition relative to a plant not treated with said composition.

27. The method of claim 1, wherein said non-transcribable polynucleotide is an RNA polynucleotide.

28. The composition of claim 8, wherein said non-transcribable polynucleotide is an RNA polynucleotide.

* * * * *